US012399179B2

(12) United States Patent
Modlin et al.

(10) Patent No.: US 12,399,179 B2
(45) Date of Patent: Aug. 26, 2025

(54) CHEMICAL COMPOSITIONS AND METHODS OF USE

(71) Applicant: Liquid Biopsy Research LLC, Charlestown (KN)

(72) Inventors: Irvin Mark Modlin, Woodbridge, CT (US); Mark Kidd, New Haven, CT (US); Ignat Drozdov, Stratford Upon Avon (GB)

(73) Assignee: Liquid Biopsy Research LLC, Charlestown (KN)

( * ) Notice: Subject to any disclaimer, the term of this patent is extended or adjusted under 35 U.S.C. 154(b) by 394 days.

(21) Appl. No.: 17/490,433

(22) Filed: Sep. 30, 2021

(65) Prior Publication Data
US 2023/0022236 A1 Jan. 26, 2023

Related U.S. Application Data

(63) Continuation of application No. 15/984,935, filed on May 21, 2018, now abandoned.

(60) Provisional application No. 62/511,058, filed on May 25, 2017.

(51) Int. Cl.
*A61K 31/435* (2006.01)
*C12Q 1/6886* (2018.01)
*G01N 33/53* (2006.01)
*G01N 33/574* (2006.01)
*G01N 33/58* (2006.01)
*A61K 39/395* (2006.01)
*A61P 17/00* (2006.01)
*A61P 35/00* (2006.01)

(52) U.S. Cl.
CPC ....... *G01N 33/5743* (2013.01); *C12Q 1/6886* (2013.01); *G01N 33/5308* (2013.01); *G01N 33/582* (2013.01); *A61K 39/3955* (2013.01); A61P 17/00 (2018.01); A61P 35/00 (2018.01); C12Q 2600/106 (2013.01); C12Q 2600/118 (2013.01); C12Q 2600/158 (2013.01); G01N 2800/52 (2013.01); G01N 2800/56 (2013.01); G01N 2800/60 (2013.01); G01N 2800/7028 (2013.01)

(58) Field of Classification Search
CPC .................................................... A61K 31/435
USPC .......................................................... 514/300
See application file for complete search history.

(56) References Cited

U.S. PATENT DOCUMENTS 9,221,815 B2 * 12/2015 Lehmann ................. A61P 43/00
2008/0113360 A1 5/2008 Riker et al.
2010/0248225 A1 9/2010 Bankaitis-Davis et al.
2011/0070582 A1 3/2011 Bankaitis-Davis et al.
2014/0045915 A1 2/2014 Skog et al.
2018/0340934 A1 11/2018 Modlin et al.

FOREIGN PATENT DOCUMENTS

AU      2006203830 A1    7/2006
WO   WO-2011047033 A2    4/2011
WO   WO-2018217627 A1   11/2018

OTHER PUBLICATIONS

Babajide Mustapha, I. and Saeed, F. (Jul. 2016) "Bioactive Molecule Prediction Using Extreme Gradient Boosting" Molecules, 21:983, doi:10.3390/molecules21080983, 11 pages.
Benner, S.A. and E.A. Gaucher (Jul. 2001) "Evolution, language and analogy in function genomics" Trends in Genetics, 17(7):414-418.
Berger, A.C. et al. (2016) "Clinical impact of a 31-gene expression profile test for cutaneous melanoma in 156 prospectively and consecutively tested patients" Curr Med Res Opin, 32:1599-1604.
Bodei, L. et al. (2016) "Measurement of circulating transcripts and gene cluster analysis predicts and defines therapeutic efficacy of peptide receptor radionuclide therapy (PRRT) in neuroendocrine tumors" Eur J Nucl Med Mol Imaging, 43:839-851.
Breiman, Leo and Adele Cutler. Random Forests. Technical Report. https://www.stat.berkeley.edu/-breiman/RandomForests/cc_papers.htm, downloaded Jun. 30, 2020, 1 page.
Brunner, G. et al. (2013) "A nine-gene signature predicting clinical outcome in cutaneous melanoma" J Cancer Res Clin Oncol, 139(2):249-258.
Chen, T. and C. Guestrin (2016) "XGBoost: A Scalable Tree Boosting System" KDD '16, Proceedings of the 22nd ACM SIGKDD International Conference on Knowledge Discovery and Data Mining, Aug. 13-17, 2016, San Francisco, CA [online]. DOI: http://dx.doi.org/10.1145/2939672.9369785, 10 pages.
Cheung, V.G. et al. (Mar. 2003) "Natural variation in human gene expression assessed in lymphoblastoid cells" Nature Genetics, 33:422-425.
Ćwikla, J.B. et al. (Nov. 2015) "Circulating Transcript Analysis (NETest) in GEP-NETs Treated With Somatostatin Analogs Defines Therapy" J Clin Endocrinol Metab, 100:E1437-1445.
Diaz-Uriarte, R. and S. Alvarez De Andres (2006) "Gene selection and classification of microarray data using random forest" BMC Bioinformatics, 7:3; doi:10.1186/1471-2105-7-3, 13 pages.
Gerami, P. et al. (2015) "Development of a Prognostic Genetic Signature to Predict the Metastatic Risk Associated with Cutaneous Melanoma" Clin Cancer Res, 21:175-183.
Gershenwald, J.E. et al. (1999) "Multi-Institutional Melanoma Lymphatic Mapping Experience: The Prognostic Value of Sentinel Lymph Node Status in 612 Stage I or II Melanoma Patients" J Clin Oncol, 17(3):976-983.

(Continued)

*Primary Examiner* — Raymond J Henley, III
(74) *Attorney, Agent, or Firm* — Fenwick & West LLP

(57) ABSTRACT

The present invention is directed to methods for detecting a melanoma, methods for determining whether a melanoma is stable or progressive, methods for evaluating the extent of surgery resection in a subject having a melanoma, and methods for determining a response by a subject having a melanoma to a therapy.

17 Claims, 6 Drawing Sheets

Specification includes a Sequence Listing.

(56) References Cited

OTHER PUBLICATIONS

Girotti, M.R. et al. (2015) "Application of Sequencing, Liquid Biopsies, and Patient-Derived Xenografts for Personalized Medicine in Melanoma" Cancer Discovery, 6(3):286-299.
GITHUB (Jun. 7, 2020) "dmlc/xgboost" [online]. Retrieved from: https://github.com/dmlc/xgboost/releases, downloaded Jun. 30, 2020, 34 printed pages.
Greenbaum, D. et al. (2003) "Comparing protein abundance and mRAN expression levels on a genomic scale" Genome Biology, 4:117, 8 pages.
Hanahan, D. et al. (2000) "The Hallmarks of Cancer" Cell, 100:57-70.
Hanahan, D. et al. (Mar. 2011) "Hallmarks of Cancer: The Next Generation" Cell, 144:646-674.
Juusola, J. and J. Ballantyne (2005) "Multiplex mRNA profiling for the identification of body fluids" Forensic Science International, 152:1-12.
Kaisaki, P.J. et al. (2016) "Targeted Next-Generation Sequencing of Plasma DNA from Cancer Patients: Factors Influencing Consistency with Tumour DNA and Prospective Investigation of Its Utility for Diagnosis" PLoS One, 11:e0162809; DOI:10.1371/journal.pone. 0162809, 13 pages.
Khoja, L. et al. (2015) "Circulating tumour cells as tumour biomarkers in melanoma: detection methods and clinical relevance" Ann Oncol, 26:33-39.
Kidd, M. et al. (2015) "Blood and tissue neuroendocrine tumor gene cluster analysis correlate, define hallmarks and predict disease status" Endocr Relat Cancer, 22(4):561-575.
Knol, A.C. et al. (2016) "Clinical significance of BRAF mutation status in circulating tumor DNA of metastatic melanoma patients at baseline" Exp Dermatol, 25:783-788.
Krauthammer, M. et al. (2015) "Exome sequencing identifies recurrent mutations in NF1 and RASopathy genes in sun-exposed melanomas" Nat Genet, 47(9):996-1002.
Li, S-C. et al. (2013) "Global microRNA profiling of well-differentiated small intestinal neuroendocrine tumors" Mod Pathol, 26:685-696.
Liu, W. et al. (Mar. 5, 2013) "A new 12-gene diagnostic biomarker signature of melanoma revealed by integrated microarray analysis" PEERJ, 1:e49; DOI: 10.7717/peerj.49, 23 pages.
Mar, V.J et al. (2013) "BRAF/NRAS Wild-Type Melanomas Have a High Mutation Load Correlating with Histologic and Molecular Signatures of UV Damage" Clin Cancer Res, 19:4589-4598.
May, Robert M. (Sep. 1988) "How Many Species are There on Earth?" Science, 241:1441-1449.
Merlino, G. et al. (Apr. 5, 2016) "The state of melanoma: challenges and opportunities" Pigment Cell Melanoma Res, 29:404-416; DOI: 10.1111/pcmr.12475.
Minor, D.R. et al. (2009) "Prognostic Factors in Metastatic Melanoma Patients Treated with Biochemotherapy and Maintenance Immunotherapy" Oncologist, 14:995-1002.
Modlin, I. et al. (2013) "The Identification of Gut Neuroendocrine Tumor Disease by Multiple Synchronous Transcript Analysis in Blood" Plos ONE, 8(5):e63364; doi: 10.1371/journal/pone/ 0063364, 12 pages.
Modlin, I. et al. (2014) "A multianalyte PCR blood test outperforms single analyte ELISAs (chromogranin A, pancreastatin, neurokinin A) for neuroendocrine tumor detection" Endocrine-Related Cancer, 21(4):615-628.
Modlin, I.M. et al. (Jan. 2016) "Blood measurement of neuroendocrine gene transcripts defines the effectiveness of operative resection and ablation strategies" Surgery, 159:336-347.
Pavel, M. (2017) "NET Blood Transcript Analysis Defines the Crossing of the Clinical Rubicon: When Stable Disease Becomes Progressive" Neuroendocrinology, 104:170-182.
Robert, C. et al. (Jan. 2015) "Improved Overall Survival in Melanoma with Combined Dabrafenib and Trametinib" The New England Journal of Medicine, 372:30-39.
Saito-Hisaminato, A. et al. (2002) "Genome-Wide Profiling of Gene Expression in 29 Normal Human Tissues with a cDNA Microarray" DNA Research, 9:35-45.
Schadendorf, D. et al. (Apr. 23, 2015) "Melanoma" Nat Rev Dis Primers, 1:15003; DOI:10.1038/nrdp.2015.3, 20 pages.
Seif, G. (May 29, 2019) "A Beginner's guide to XGBoss" [online]. Retrieved from: https://towardsdatascience.com/a-beginners-guide-to-xgboost-87f5d4c30ed7, on Jun. 30, 2020; 8 pages.
Stark, M.S. et al. (2015) "The Prognostic and Predictive Value of Melanoma-related MicroRNAs Using Tissue and Serum: A MicroRNA Expression Analysis" EBioMedicine, 2:671-680.
Svedman, F.C. et al. (2016) "Stage-specific survival and recurrence in patients with cutaneous malignant melanoma in Europe—a systematic review of the literature" Clin Epidemiol, 8:109-122.
The Cancer Genome Atlas Network (Jun. 18, 2015) "Genomic Classification of Cutaneous Melanoma" Cell, 161:1681-1696.
Wan, P.T. et al. (Mar. 19, 2004) "Mechanism of Activation of the RAF-ERK Signaling Pathway by Oncogenic Mutations of B-RAF" Cell, 116:855-867.
Daud et al. "Tumor immune profiling predicts response to anti-PD-1 therapy in human melanoma" The Journal of Clinical Investigation (2016); 126(9):3447-3452.
Weinstein et al. "Diagnostic and prognostic biomarkers in melanoma" The Journal of Clinical and Aesthetic Dermatology (2014); 7(6):13-24.

* cited by examiner

CHEMICAL COMPOSITIONS AND METHODS OF USE

CROSS-REFERENCE TO RELATED APPLICATIONS

This application is a Continuation of U.S. patent application Ser. No. 15/984,935, filed on May 21, 2018, which claims the benefit of and priority to U.S. Provisional Application No. 62/511,058, filed on May 25, 2017. The contents of each of the aforementioned patent application are hereby incorporated by reference in their entireties for all purposes.

INCORPORATION BY REFERENCE OF SEQUENCE LISTING

The instant application contains a Sequence Listing which has been submitted in ASCII format via EFS-Web and is hereby incorporated by reference in its entirety. Said ASCII copy, created on Sep. 28, 2021, is named "LBIO-001_C01US_SeqList.txt" and is about 272,331 bytes in size.

FIELD OF THE INVENTION

The present invention relates to melanoma detection.

BACKGROUND OF THE INVENTION

Melanoma is a common (~24-35/100,000 incidence—US), highly aggressive, skin cancer with an incidence that continues to rise. The most common, cutaneous melanomas, are associated with UV exposure and immune dysregulation. As a group, melanoma is known to carry the highest mutational burden (>10 mutations/Mb). Major mutations include BRAF (~50%), N-Ras (~20%) and NF-1 (~5%), which together, comprise 75% of all mutations. Melanomas are addicted to MAPK pathway activation, regardless of whether tumors exhibit mutations in genes coding for proteins in this pathway. This provides the rationale for targeted therapy e.g., BRAF v600E agents, in this tumor. Other gain-of-function and loss-of-function mutations e.g., in RASopathy genes and amplification of cyclin D1/cdk4 and/or mutation/loss of the tumor suppressor PTEN, also characterize the tumor. This makes melanoma one of the most aggressive and therapy-resistant cancers.

Five-year survival rates range from 95-100% for stage I, 65-93% for stage II, to 41-71% and 9-28% for stage III and IV, respectively. Surgery, immunotherapy and targeted therapies provide the basis for management, with chemotherapy and radiation as adjuncts. Surgery, however, has a critical role in melanoma care (diagnosis, cure and palliation). Sentinel lymph node biopsy has become widespread, as it provides prognostic information. Melanoma, however, lacks a clinically useful non-invasive e.g., blood-based biomarker of disease activity to help guide patient management by providing predictive or prognostic information.

Blood-based factors include lactate dehydrogenase (LDH), detecting mutations in circulating tumor (ct) DNA, measurements of circulating tumor cells (CTCs) and circulating mRNA. LDH is typically used to identify aggressive tumor behavior and predict recurrence but its metrics are very low e.g., 30-50% accurate. It is also non-specific for melanoma. Mutations in target genes, like BRAF, can be detected in the blood in ctDNA but its utility as an indicator of therapeutic efficacy is limited e.g., 45-70% accurate. CTCs do not appear to be an accurate marker in melanomas and there is no consensus as to their clinical utility. Circulating microNAs (miRNA) have been detected but there is no evidence yet for clinical usefulness.

For melanomas, there are no multi-mRNA circulating biomarkers that function as a diagnostic or as a prognostic for disease recurrence. A biomarker that can be used to monitor the efficacy of surgery or drug therapy in melanomas is currently lacking.

SUMMARY OF THE INVENTION

Among other things, disclosed herein is a 28-gene expression tool for melanoma. It has high sensitivity and specificity (>95%) for the detection of melanoma and can differentiate aggressive untreated disease from stable, treated disease.

One aspect of the present disclosure relates to a method for detecting a melanoma in a subject in need thereof, comprising: (1) determining the expression level of at least 29 biomarkers from a test sample from the subject by contacting the test sample with a plurality of agents specific to detect the expression of the at least 29 biomarkers, wherein the at least 29 biomarkers comprise ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, YY2, and at least one housekeeping gene; (2) normalizing the expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2 to the expression level of the at least one housekeeping gene, thereby obtaining a normalized expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2; (3) inputting each normalized expression level into an algorithm to generate a score; (4) comparing the score with a first predetermined cutoff value; and (5) producing a report, wherein the report identifies the presence of a melanoma in the subject when the score is equal to or greater than the first predetermined cutoff value or identifies the absence of a melanoma in the subject when the score is below the first predetermined cutoff value, wherein the first predetermined cutoff value is 20 on a scale of 0 to 100.

In some embodiments, the method further comprises treating the subject identified as having a melanoma with surgery or drug therapy.

Another aspect of the present disclosure relates to a method for determining whether a melanoma in a subject is stable or progressive, comprising: (1) determining the expression level of at least 29 biomarkers from a test sample from the subject by contacting the test sample with a plurality of agents specific to detect the expression of the at least 29 biomarkers, wherein the at least 29 biomarkers comprise ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, YY2, and at least one housekeeping gene; (2) normalizing the expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2 to the expression level of the at least one housekeeping gene, thereby obtaining a normalized expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2; (3) inputting each normalized expression level into an algorithm to generate a score; (4) comparing the score with a second predetermined cutoff value; and (5) producing a report, wherein the report identifies that the melanoma is progressive when the normalized expression level is equal to or greater than the second predetermined cutoff value or identifies that the melanoma is stable when the normalized expression level is below the second predetermined cutoff value, wherein the second predetermined cutoff value is 50 on a scale of 0 to 100.

Another aspect of the present disclosure relates to a method for evaluating the extent of surgical resection in a subject having a melanoma, comprising: (1) determining the expression level of at least 29 biomarkers from a test sample from the subject after the surgical resection by contacting the test sample with a plurality of agents specific to detect the expression of the at least 29 biomarkers, wherein the at least 29 biomarkers comprise ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, YY2, and at least one housekeeping gene; (2) normalizing the expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2 to the expression level of the at least one housekeeping gene, thereby obtaining a normalized expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2; (3) inputting each normalized expression level into an algorithm to generate a score; (4) comparing the score with a third predetermined cutoff value; and (5) producing a report, wherein the report identifies that the surgical resection does not remove the entire melanoma when the normalized expression level is equal to or greater than the third predetermined cutoff value or identifies that the surgical resection removes the entire melanoma when the normalized expression level is below the third predetermined cutoff value, wherein the third predetermined cutoff value is 20 on a scale of 0 to 100.

In some embodiments, the report further identifies that the risk of melanoma recurrence is high when the normalized expression level is equal to or greater than the third predetermined cutoff value or identifies that the risk of melanoma recurrence is low when the normalized expression level is below the third predetermined cutoff value.

Yet another aspect of the present disclosure relates to a method for determining a response by a subject having a melanoma to a therapy, comprising: (1) determining a first expression level of at least 28 biomarkers from a first test sample from the subject at a first time point by contacting the first test sample with a plurality of agents specific to detect the expression of the at least 28 biomarkers, wherein the 28 biomarkers comprise ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2; (2) determining a second expression level of the at least 28 biomarkers from a second test sample from the subject at a second time point by contacting the second test sample with a plurality of agents specific to detect the expression of the at least 28 biomarkers, wherein the second time point is after the first time point and after the administration of the therapy to the subject; (3) comparing the first expression level with the second expression level; and (4) producing a report, wherein the report identifies that the subject is responsive to the therapy when the second expression level is significantly decreased as compared to the first expression level.

In some embodiments, the first time point is prior to the administration of the therapy to the subject. In some embodiments, the first time point is after the administration of the therapy to the subject. In some embodiments, the therapy comprises an immunotherapy or a targeted therapy (e.g., a BRAF inhibitor).

In some embodiments, the at least one housekeeping gene is selected from the group consisting of ALG9, SEPN, YWHAQ, VPS37A, PRRC2B, DOPEY2, NDUFB11, ND4, MRPL19, PSMC4, SF3A1, PUM1, ACTB, GAPD, GUSB, RPLP0, TFRC, MORF4L1, 18S, PPIA, PGK1, RPL13A, B2M, YWHAZ, SDHA, HPRT1, TOX4, and TPT1.

In some embodiments, the at least one housekeeping gene comprises TOX4 and TPT1.

In some embodiments, the normalized expression level is obtained by: (1) normalizing the expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2 to the expression level of TOX4, thereby obtaining a first normalized expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2; (2) normalizing the expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2 to the expression level of TPT1, thereby obtaining a second normalized expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2; and (3) averaging the first normalized expression level and the second normalized expression level to obtain the normalized expression level.

In some embodiments, the method can have a specificity, sensitivity, and/or accuracy of at least 75%, 80%, 85%, 90%, 91%, 92%, 93%, 94%, 95%, 96%, 97%, 98%, or 99%. In some embodiments, the method has a sensitivity of greater than 90%. In some embodiments, the method has a specificity of greater than 90%.

In some embodiments, the biomarker is RNA, cDNA, or protein. When the biomarker is RNA, the RNA can be reverse transcribed to produce cDNA, and the produced cDNA expression level is detected. In some embodiments, the expression level of the biomarker is detected by forming a complex between the biomarker and a labeled probe or primer. When the biomarker is RNA or cDNA, the RNA or cDNA can be detected by forming a complex between the RNA or cDNA and a labeled nucleic acid probe or primer. When the biomarker is protein, the protein can be detected by forming a complex between the protein and a labeled antibody. In some embodiments, the label is a fluorescent label.

In some embodiments, the test sample is blood, serum, plasma, or neoplastic tissue.

In some embodiments, the first predetermined cutoff value can be derived from a plurality of reference samples obtained from subjects free of a neoplastic disease. The second predetermined cutoff value can be derived from a plurality of reference samples obtained from subjects whose melanomas are being adequately controlled by therapies like immune therapy. The third predetermined cutoff value can be derived from a plurality of reference samples obtained from subjects whose melanomas have been completely removed by surgery and they are considered "disease free." In some embodiments, each reference sample can be blood, serum, plasma, or non-neoplastic tissue.

In some embodiments, the subject in need thereof is a subject diagnosed with a melanoma, a subject having at least one melanoma symptom, or a subject having a predisposition or familial history for developing a melanoma. In some embodiments, the subject is a human.

In some embodiments, the algorithm is XGB, RF, glmnet, cforest, CART, treebag, knn, nnet, SVM-radial, SVM-linear, NB, NNET, or mlp.

BRIEF DESCRIPTION OF THE DRAWINGS

FIG. 6A identifies the cell lines demonstrate elevated expression—Melanomx score ranging from 40 (A375) to 95 (Hs294). FIG. 6B identifies that spiking these cells into blood from a subject that does not have a melanoma, resulted in detectable gene expression and scores. A minimum of 1 cell/ml of blood could be consistently identified.

In FIG. 7A, the Melanomx score ranged 40-97 in melanoma tumor tissue. In contrast, normal epithelium exhibited values <20. In FIG. 7B, gene expression in tumor tissue is compared to matched blood samples. This is highly concordant (correlation ~0.80).

DETAILED DESCRIPTION OF THE INVENTION

Figure 1:
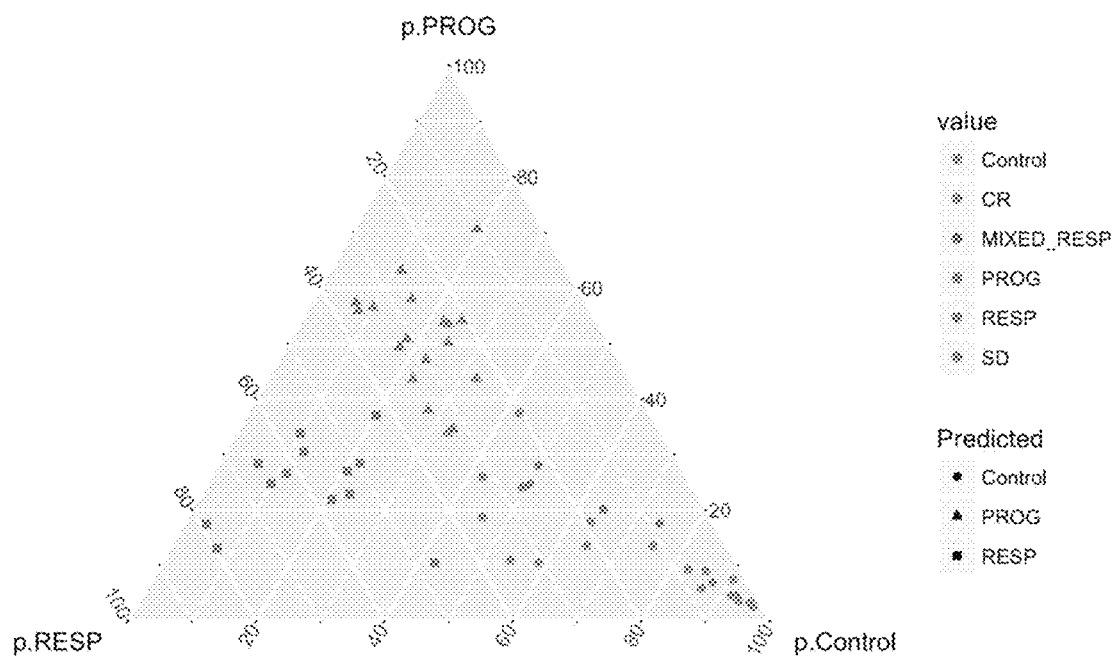
FIG. 1 is a graph showing visualization of the melanoma score as a system of three contributors to the clinical picture—Control, Response, and Progression. Samples towards each of the corner represent pure representations of each clinical group. Samples in the middle are in the area of both algorithmic and clinical uncertainty.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Early signs of melanoma include changes to the shape or color of existing moles or, in the case of nodular melanoma, the appearance of a new lump anywhere on the skin. At later stages, the mole may itch, ulcerate or bleed. Visual inspection is the most common diagnostic technique. Melanoma can be divided into the following types: lentigo maligna, lentigo maligna melanoma, superficial spreading melanoma, acral lentiginous melanoma, mucosal melanoma, nodular melanoma, polypoid melanoma, and desmoplastic melanoma.

Measurements of circulating melanoma transcripts—the Melanomx-identify melanomas and decreases in the Melanomx score correlate with the efficacy of therapeutic interventions such as immunotherapy and targeted therapy. Targeted gene expression profile of RNA can be isolated from the peripheral blood of patients with melanoma. This expression profile is evaluated in an algorithm and converted to an output (prediction). It can identify active disease, provide an assessment of treatment responses, or predict risk of relapse, in conjunction with standard clinical assessment and imaging.

In one aspect, the present disclosure provides a method for detecting a melanoma in a subject in need thereof, including: (1) determining the expression level of at least 29 biomarkers from a test sample from the subject by contacting the test sample with a plurality of agents specific to detect the expression of the at least 29 biomarkers, wherein the at least 29 biomarkers comprise ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, YY2, and at least one housekeeping gene; (2) normalizing the expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2 to the expression level of the at least one housekeeping gene, thereby obtaining a normalized expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2; (3) inputting each normalized expression level into an algorithm to generate a score; (4) comparing the score with a first predetermined cutoff value; and (5) producing a report, wherein the report identifies the presence of a melanoma in the subject when the score is equal to or greater than the first predetermined cutoff value or identifies the absence of a melanoma in the subject when the score is below the first predetermined cutoff value, wherein the first predetermined cutoff value is 20 on a scale of 0 to 100.

In some embodiments, the at least one housekeeping gene is selected from the group consisting of ALG9, SEPN, YWHAQ, VPS37A, PRRC2B, DOPEY2, NDUFB11, ND4, MRPL19, PSMC4, SF3A1, PUM1, ACTB, GAPD, GUSB, RPLP0, TFRC, MORF4L1, 18S, PPIA, PGK1, RPL13A, B2M, YWHAZ, SDHA, HPRT1, TOX4, and TPT1.

In some embodiments, the at least one housekeeping gene comprises TOX4 and TPT1. In some embodiments, the normalized expression level is obtained by: (1) normalizing the expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2 to the expression level of TOX4, thereby obtaining a first normalized expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2; (2) normalizing the expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2 to the expression level of TPT1, thereby obtaining a second normalized expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2; and (3) averaging the first normalized expression level and the second normalized expression level to obtain the normalized expression level.

Among the provided methods are those that are able to classify or detect a melanoma. In some embodiments, the provided methods can identify or classify a melanoma in a human blood sample. In some examples, the methods can provide such information with a specificity, sensitivity, and/or accuracy of at least 75%, 80%, 85%, 90%, 91%, 92%, 93%, 94%, 95%, 96%, 97%, 98%, or 99%.

The agents can be any agents for detection of the biomarkers, and typically are isolated polynucleotides or isolated polypeptides or proteins, such as antibodies, for example, those that specifically hybridize to or bind to the at least 29 biomarkers.

The biomarker can be RNA, cDNA, or protein. When the biomarker is RNA, the RNA can be reverse transcribed to produce cDNA (such as by RT-PCR), and the produced cDNA expression level is detected. The expression level of the biomarker can be detected by forming a complex between the biomarker and a labeled probe or primer. When the biomarker is RNA or cDNA, the RNA or cDNA detected by forming a complex between the RNA or cDNA and a labeled nucleic acid probe or primer. The complex between the RNA or cDNA and the labeled nucleic acid probe or primer can be a hybridization complex.

When the biomarker is protein, the protein can be detected by forming a complex between the protein and a labeled antibody. The label can be any label, for example a fluorescent label, chemiluminescence label, radioactive label, etc. The protein level can be measured by methods including, but not limited to, immunoprecipitation, ELISA, Western blot analysis, or immunohistochemistry using an agent, e.g., an antibody, that specifically detects the protein encoded by the gene.

In some embodiments, the methods are performed by contacting the test sample with one of the provided agents, more typically with a plurality of the provided agents, for example, a set of polynucleotides that specifically bind to the at least 29 biomarkers. In some embodiments, the set of polynucleotides includes DNA, RNA, cDNA, PNA, genomic DNA, or synthetic oligonucleotides. In some embodiments, the methods include the step of isolating RNA from the test sample prior to detection, such as by RT-PCR, e.g., QPCR. Thus, in some embodiments, detection of the melanoma biomarkers, such as expression levels thereof, includes detecting the presence, absence, or amount of RNA. In one example, the RNA is detected by PCR or by hybridization.

In some embodiments, the polynucleotides include sense and antisense primers, such as a pair of primers that is specific to each of the at least 29 biomarkers. In one aspect of this embodiment, the detection of the at least 29 biomarkers is carried out by PCR, typically quantitative or real-time PCR. For example, in one aspect, detection is carried out by producing cDNA from the test sample by reverse transcription; then amplifying the cDNA using the pairs of sense and antisense primers that specifically hybridize to the panel of at least 28 biomarkers, and detecting products of the amplification.

The test sample can be any biological fluid obtained from the subject. Preferably, the test sample is blood, serum, plasma or neoplastic tissue.

The first predetermined cutoff value can be derived from a plurality of reference samples obtained from subjects free of a neoplastic disease. Each reference sample can be any biological fluid obtained from a subject not having, showing symptoms of or diagnosed with a neoplastic disease. In some embodiments, the reference sample is blood, serum, plasma, or non-neoplastic tissue.

The subject in need thereof can be a subject diagnosed with a melanoma, a subject having at least one melanoma symptom or a subject having a predisposition or familial history for developing a melanoma. The subject can be any mammal. Preferably, the subject is human. The terms "subject" and "patient" are used interchangeably herein.

The score is the Melanomx score, which has a scale of 0 to 100. The Melanomx score is the product of a classifier built from predictive classification algorithms, e.g., XGB, RF, glmnet, cforest, CART, treebag, knn, nnet, SVM-radial, SVM-linear, NB, NNET, or mlp. The algorithm analyzes the data (i.e., expression levels) and then assigns a score.

The method can further include treating the subject identified as having a melanoma with surgery, drug therapy, radiation therapy, or a combination thereof. The drug therapy can be an immunotherapy, a targeted therapy, a chemotherapy, or a combination thereof. In some embodiments, the drug therapy includes an immunotherapy. Examples of immunotherapies for treating a melanoma include, but are not limited to, Imlygic (T-VEC), Yervoy in combination with Opdivo, Opdivo (nivolumab), Keytruda (pembrolizumab), Yervoy (ipilimumab), Interleukin-2 (IL-2), and Interferon alpha 2-b. In some embodiments, the drug therapy includes a targeted therapy such as a BRAF inhibitor. Examples of targeted therapies for treating a melanoma include, but are not limited to, Zelboraf in combination with Cotellic (cobimetinib), Tafinlar in combination with Mekinist, Tafinlar (dabrafenib), Mekinist (trametinib), and Zelboraf (vemurafenib). In some embodiments, the drug therapy includes a chemotherapy. In some embodiments, the chemotherapy includes dacarbazine.

Accordingly, the present disclosure provides a method of treating melanoma in a human subject in need thereof, the method comprising: a) determining the expression level of 29 biomarkers from a biological fluid sample from the subject by contacting the test sample with a plurality of agents specific to detect the expression of the 29 biomarkers, wherein the 29 biomarkers comprise each of atlastin GTPase 1 (ATL1), ATPase H+ transporting V0 subunit d1 (ATP6V0D), chromosome 1 open reading frame 21 (C1ORF21), CASP8 and FADD like apoptosis regulator (CFLAR), CFLAR antisense RNA 1 (CFLAR-AS1), calcineurin like EF-hand protein 1 (CHP1), DEAD-box helicase 55 (DDX55), dystrophin (DMD), DnaJ heat shock protein family (Hsp40) member C9 (DNAJC9), enolase superfamily member 1 (ENOSF1), Fanconi anemia complementation group L (FANCL), Holliday junction recognition protein (HJURP), major histocompatibility complex, class II, DO alpha (HLA-DOA), major histocompatibility complex, class II, DR alpha (HLA-DRA), heterogeneous nuclear ribonucleoprotein A3 pseudogene 1 (HNRNPA3P1), interleukin 23 subunit alpha (IL23A), IQ motif containing GTPase activating protein 1 (IQGAP1), NFYC pseudogene (LOC494127), uncharacterized LOC646471 (LOC646471), loss of heterozygosity, 12, chromosomal region 2 (non-protein coding) (LOH12CR), PBX homeobox interacting protein 1 (PBXIP1), ring finger protein 5 (RNF5), SERTA domain containing 2 (SERTAD2), solute carrier family 35 member G5 (SLC35G5), spermatogenesis associated serine rich 2 like (SPATS2L), tudor domain containing 7 (TDRD7), TXK tyrosine kinase (TXK), YY2 transcription factor (YY2), and at least one housekeeping gene; b) normalizing the expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2 to the expression level of the at least one housekeeping gene, thereby obtaining a normalized expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2; c) inputting each normalized expression level into an algorithm to generate a score, wherein the algorithm is the product of a trained classifier built from at least one predictive classification algorithm; d) determining that the human subject has melanoma by determining that the score is greater than or equal to a first predetermined cutoff value, wherein the first predetermining cutoff value is 20 on a scale of 0 to 100; and e) administering to the human subject at least one therapeutically effective amount of at least one of:

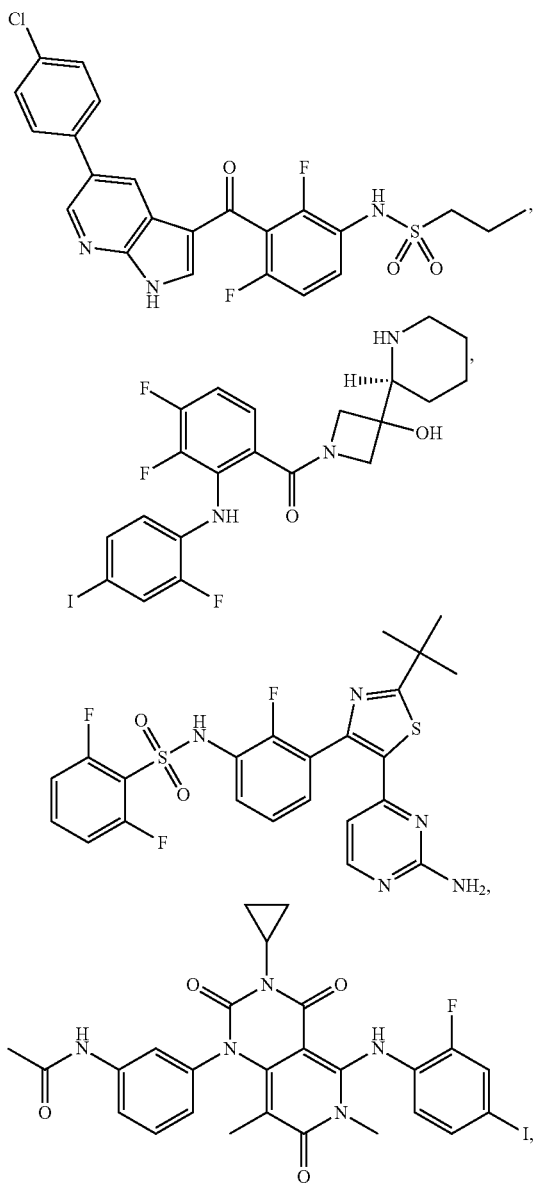

or any combination thereof.

The present disclosure also provides a method for determining whether a melanoma in a subject is stable or progressive, including: (1) determining the expression level of at least 29 biomarkers from a test sample from the subject by contacting the test sample with a plurality of agents specific to detect the expression of the at least 29 biomarkers, wherein the at least 29 biomarkers comprise ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, YY2, and at least one housekeeping gene; (2) normalizing the expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2 to the expression level of the at least one housekeeping gene, thereby obtaining a normalized expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2; (3) inputting each normalized expression level into an algorithm to generate a score; (4) comparing the score with a second predetermined cutoff value; and (5) producing a report, wherein the report identifies that the melanoma is progressive when the normalized expression level is equal to or greater than the second predetermined cutoff value or identifies that the melanoma is stable when the normalized expression level is below the second predetermined cutoff value, wherein the second predetermined cutoff value is 50 on a scale of 0 to 100.

The second predetermined cutoff value can be derived from a plurality of reference samples obtained from subjects whose melanomas are being adequately controlled by therapies like immune therapy.

Surgical resection is a procedure that removes melanoma tissues from the subject in need thereof. The present disclosure also provides a method for evaluating the extent of surgical resection in a subject having a melanoma, including: (1) determining the expression level of at least 29 biomarkers from a test sample from the subject after the surgical resection by contacting the test sample with a plurality of agents specific to detect the expression of the at least 29 biomarkers, wherein the at least 29 biomarkers comprise ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, YY2, and at least one housekeeping gene; (2) normalizing the expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2 to the expression level of the at least one housekeeping gene, thereby obtaining a normalized expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2; (3) inputting each normalized expression level into an algorithm to generate a score; (4) comparing the score with a third predetermined cutoff value; and (5) producing a report, wherein the report identifies that the surgical resection does not remove the entire melanoma when the normalized expression level is equal to or greater than the third predetermined cutoff value or identifies that the surgical resection removes the entire melanoma when the normalized expression level is below the third predetermined cutoff value, wherein the third predetermined cutoff value is 20 on a scale of 0 to 100.

The third predetermined cutoff value can be derived from a plurality of reference samples obtained from subjects whose melanoma disease has been completely removed by surgery and they are considered "disease free."

When it is determined that the surgical resection does not remove the entire melanoma, the subject is at risk of melanoma recurrence. Accordingly, in some embodiments, the report further identifies that the risk of melanoma recurrence is high when the normalized expression level is equal to or greater than the third predetermined cutoff value or identifies that the risk of melanoma recurrence is low when the normalized expression level is below the third predetermined cutoff value.

The present disclosure also provides a method for determining a response by a subject having a melanoma to a therapy, comprising: (1) determining a first expression level of at least 28 biomarkers from a first test sample from the subject at a first time point by contacting the first test sample with a plurality of agents specific to detect the expression of the at least 28 biomarkers, wherein the 28 biomarkers comprise ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2; (2) determining a second expression level of the at least 28 biomarkers from a second test sample from the subject at a second time point by contacting the second test sample with a plurality of agents specific to detect the expression of the at least 28 biomarkers, wherein the second time point is after the first time point and after the administration of the therapy to the subject; (3) comparing the first expression level with the second expression level; and (4) determining that the subject is responsive to the therapy when the second expression level is significantly decreased as compared to the first expression level.

In some embodiments, the methods can predict treatment responsiveness to, or determine whether a patient has become clinically stable following, or is responsive or non-responsive to, a melanoma treatment, such as a surgical intervention or drug therapy (for example, an immunotherapy or targeted therapy). In some cases, the methods can do so with a specificity, sensitivity, and/or accuracy of at least 75%, 80%, 85%, 90%, 91%, 92%, 93%, 94%, 95%, 96%, 97%, 98%, or 99%. In some cases, it can differentiate between treated and untreated melanoma with a specificity, sensitivity, and/or accuracy of at least 75%, 80%, 85%, 90%, 91%, 92%, 93%, 94%, 95%, 96%, 97%, 98%, or 99%.

In some embodiments, the first and second test samples can be of the same type. In some embodiments, the first and second test samples can be of different types.

In some embodiments, the therapy can be a drug therapy. The drug therapy can be an immunotherapy, a targeted therapy, a chemotherapy, or a combination thereof. In some embodiments, the therapy can be a radiation therapy.

In some embodiments, the first time point is prior to the administration of the therapy to the subject. In some embodiments, the first time point is after the administration of the therapy to the subject. The second time point can be a few days, a few weeks, or a few months after the first time point. For example, the second time point can be at least 1 day, at least 7 days, at least 14 days, at least 30 days, at least 60 days, or at least 90 days after the first time point.

In some embodiments, the second expression level is significantly decreased as compared to the first expression level when the second expression level is at least 10% less than the first expression level. In some embodiments, the second expression level is significantly decreased as compared to the first expression level when the second expression level is at least 20% less than the first expression level. In some embodiments, the second expression level is significantly decreased as compared to the first expression level when the second expression level is at least 30% less than the first expression level. In some embodiments, the second expression level is significantly decreased as compared to the first expression level when the second expression level is at least 40% less than the first expression level. In some embodiments, the second expression level is significantly decreased as compared to the first expression level when the second expression level is at least 50% less than the first expression level. In some embodiments, the second expression level is significantly decreased as compared to the first expression level when the second expression level is at least 60% less than the first expression level. In some embodiments, the second expression level is significantly decreased as compared to the first expression level when the second expression level is at least 70% less than the first expression level. In some embodiments, the second expression level is significantly decreased as compared to the first expression level when the second expression level is at least 80% less than the first expression level. In some embodiments, the second expression level is significantly decreased as compared to the first expression level when the second expression level is at least 90% less than the first expression level.

In some embodiments, the method further comprises determining a third expression level of the at least 28 biomarkers from a third test sample from the subject at a third time point by contacting the third test sample with a plurality of agents specific to detect the expression of the at least 28 biomarkers, wherein the third time point is after the second time point. The method can further comprise creating a plot showing the trend of the expression level change.

The present disclosure also provides an assay comprising: (1) determining the expression level of biomarkers consisting essentially of the following 30 biomarkers from a test sample from a patient diagnosed of a melanoma or a subject suspected of having a melanoma: ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, YY2, TOX4, and TPT1, wherein the expression level is measured by contacting the test sample with a plurality of agents specific to detect the expression of the 30 biomarkers; (2) normalizing the expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2 to the expression level of TOX4, thereby obtaining a first normalized expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2; (3) normalizing the expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2 to the expression level of TPT1, thereby obtaining a second normalized expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2; (4) averaging the first normalized expression level and the second normalized expression level to obtain a normalized expression level for each biomarker; (5) inputting each normalized expression level into an algorithm to generate a score; and (6) comparing the score with a first predetermined cutoff value.

The present disclosure also provides an assay comprising: (1) determining the expression level of biomarkers consisting of the following 30 biomarkers from a test sample from a patient diagnosed of a melanoma or a subject suspected of having a melanoma: ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, YY2, TOX4, and TPT1, wherein the expression level is measured by contacting the test sample with a plurality of agents specific to detect the expression of the 30 biomarkers; (2) normalizing the expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2 to the expression level of TOX4, thereby obtaining a first normalized expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2; (3) normalizing the expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2 to the expression level of TPT1, thereby obtaining a second normalized expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2; (4) averaging the first normalized expression level and the second normalized expression level to obtain a normalized expression level for each biomarker; (5) inputting each normalized expression level into an algorithm to generate a score; and (6) comparing the score with a first predetermined cutoff value.

The sequence information of the melanoma biomarkers and housekeepers is shown in Table 1.

TABLE 1

Melanoma Biomarker/Housekeeper Sequence Information

| Gene Name | RefSeq Accession | Sequence | SEQ ID NO: |
|---|---|---|---|
| ATL1 | NM_001127713.1 | AGTTTGAGGC TGCACTGCAC ACCTGCACAA CCTGCCTTCT ACTTAGTTCT TCTGAGACAT TTCTGAAAGT CTGAATTCCT AGGACTGCTC AATGACCTTT GTCCCTGTTG GGCACACGCA GTGTCTCATC GCTGGTATTG CACCTTTAAT GAGACCAGGA GTTCCGCAAA AGTAAAACAA AGGGGTCACA GACTGGTTCT GGTTCTACCA CTTCCTCAGT ATGTGCTCTG GGACAAAACA GCATATTTGG CAACATCTCG GTGTCCTTAT CTGCAGCTTG AAGAGGCGCC ACAGCAACAT CCTCAGAGTC TGAGCGAACT GCGCCCAGCG CGGGCACGGA GCCTCCCACC GCCAGCAACC TGCGGCCCCG GAGAAGGCAG CGAGCGCAGT GACAGCGCCT CACCGCCACC AGCTCCTGGA CCACCATGGC CAAGAACCGC AGGGACAGAA ACAGTTGGGG TGGATTTTCG GAAAAGACAT ATGAATGGAG CTCAGAAGAG GAGGAGCCAG TGAAAAAGGC AGGACCAGTC CAAGTCCTCA TTGTCAAAGA TGACCATTCC TTTGAGTTAG ATGAAACTGC ATTAAATCGG ATCCTTCTCT CGGAGGCTGT CAGAGACAAG GAGGTTGTTG CTGTATCTGT TGCTGGAGCA TTTAGAAAAG GAAAATCATT CCTGATGGAC TTCATGTTGA GATACATGTA CAACCAGGAA TCAGTTGATT GGGTTGGAGA CTACAATGAA CCATTGACTG GTTTTTCATG GAGAGGTGGA TCTGAGCGAG AGACCACAGG AATTCAGATA TGGAGTGAAA TCTTCCTTAT CAATAAACCT GATGGTAAAA AGGTTGCAGT GTTATTGATG GATACTCAGG GAACCTTTGA TAGTCAGTCA ACTTTGAGAG ATTCAGCCAC AGTATTTGCC CTTAGCACAA TGATCAGCTC AATACAGGTA TATAACTTAT CCCAAAATGT CCAGGAGGAT GATCTTCAGC ACCTCCAGCT TTTCACTGAG TATGGCAGAC TGGCAATGGA GGAAACATTC CTGAAGCCAT TTCAGAGTCT GATATTTCTT GTTCGAGACT GGAGTTTCCC ATACGAATTT TCATATGGAG CCGATGGTGG TGCCAAATTC TTGGAAAAAC GCCTCAAGGT CTCAGGGAAC CAGCATGAAG AACTACAGAA CGTCAGAAAA CACATCCATT CCTGTTTCAC CAACATTTCC TGTTTTCTGC TACCTCATCC TGGCTTAAAA GTAGCTACCA ATCCAAACTT TGATGGAAAA TTGAAAGAAA TAGATGATGA ATTCATCAAA AACTTGAAAA TACTGATTCC TTGGCTACTT AGTCCCGAGA GCCTAGATAT TAAAGAGATC AATGGGAATA AAATCACCTG CCGGGGTCTG GTGGAGTACT TCAAGGCTTA TATAAAGATC TATCAAGGTG AAGAATTACC ACATCCCAAA TCCATGTTAC AGGCCACAGC AGAAGCTAAC AATTTAGCAG CCGTGGCAAC TGCCAAGGAC ACATACAACA AAAAAATGGA AGAGATTTGT GGTGGTGACA AACCATTTCT GGCCCCAAAT GACTTGCAGA CCAAACACCT GCAACTTAAG GAAGAATCTG TGAAGCTATT CCGAGGGGTG AAGAAGATGG GTGGGGAAGA ATTTAGCCGG CGTTACCTGC AGCAGTTGGA GAGTGAAATA GATGAACTTT ACATCCAATA TATCAAGCAC AATGATAGCA AAAATATCTT CCATGCAGCT CGTACCCCAG CCACACTGTT TGTAGTCATC TTTATCACAT ATGTGATTGC TGGTGTGACT GGATTCATTG GTTTGGACAT CATAGCTAGC CTATGCAATA TGATAATGGG ACTGACCCTT ATCACCCTGT GCACTTGGGC ATATATCCGG TACTCTGGAG AATACCGAGA GCTGGGAGCT GTAATAGACC AGGTGGCTGC AGCTCTGTGG GACCAGGCTT TGTACAAGCT TTACAGTGCA GCAGCAACCC ACAGACATCT GTATCATCAA GCTTTCCCTA CACCAAAGTC GGAATCTACT GAACAATCAG AAAAGAAAAA AATGTAATGC AAATTTTAAG AAATACAGGT GCATGACCAA TTGTCAATTA AATATTCAGT TTTATGTCTC ATGCAAACA TTCAAAGTGC TTCCATCAGA ACGGAGTAAA ATACTAAACA CCTCTGAAGA CTGCAAACTG GATTAGTTCT TTTACTTCAG TGTTTAATAA GCAGATGTAT GTATGCATGG TTATACTATT TTGTTAACAT GTACAATTTC CTGATTTTTC TTCAAAAATG CTGTTATAAA GTATTTGTCT ATTTATGATA ACAGTACACG TGTTCTGCTT GAATTTACTA AATTCTACTA CTGGGTTATA ATTAAATCAT GTGATATTCC ACGTTTGGAT ATGCTCATTT AATTTCTACA GAAAAAATTT TAAATTATTT CACATTAGCC ATTTGTTAAA ACACAGCATC ATAACTCAGC AGGCTGGATT TAATCTGTAT CATCTTATAT ATATCACAAT CTTATTTTTA AGCACATTTT AGAGTTCCTT AGTTGCTTTA TCAAAACCA GATATTGCTT TTACATGGTT TAATAGAATA TAAACCTCTT GATAAAAAAT GCACAAAAAA TCACTTTGTA TATGTGAGTT TCACTGCATT GTATATTTTT TCATTTGGTA CACAAAGAAT GTATTCTTCA TAGGTTTATT CTTTTAATAT GTGAACTATT ATTAAAGTTT ACTCTGGTTC CTAAGATTAA AAACAAATGC TTACTGAATT TGAAAAAAA A | 1 |

TABLE 1-continued

Melanoma Biomarker/Housekeeper Sequence Information

| Gene Name | RefSeq Accession | Sequence | SEQ ID NO: |
|---|---|---|---|
| ATP6V0D | NM_004691.4 | ACTTGACAGC CCGCTGAGGA CGCAGCGTCA GCTGACCTGG GGAGTCGCGA TTCGTGCCGG CCGGTCCTGG TTCTCCGGTC CCGCCGCTCC CGCAGCAGCC ATGTCGTTCT TCCCGGAGCT TTACTTTAAC GTGGACAATG GCTACTTGGA GGGACTGGTG CGCGGCCTGA AGGCCGGGGT GCTCAGCCAG GCCGACTACC TCAACCTGGT GCAGTGCGAG ACGCTAGAGG ACTTGAAACT GCATCTGCAG AGCACTGATT ATGGTAACTT CCTGGCCAAC GAGGCATCAC CTCTGACGGT GTCAGTCATC GATGACCGGC TCAAGGAGAA GATGGTGGTG GAGTTCCGCC ACATGAGGAA CCATGCCTAT GAGCCACTCG CCAGCTTCCT AGACTTCATT ACTTACAGTT ACATGATCGA CAACGTGATC CTGCTCATCA CAGGCACGCT GCACCAGCGC TCCATCGCTG AGCTCGTGCC CAAGTGCCAC CCACTAGGCA GCTTCGAGCA GATGGAGGCC GTGAACATTG CTCAGACACC TGCTGAGCTC TACAATGCCA TTCTGGTGGA CACGCCTCTT GCGGCTTTTT TCCAGGACTG CATTTCAGAG CAGGACCTTG ACGAGATGAA CATCGAGATC ATCCGCAACA CCCTCTACAA GGCCTACCTG GAGTCCTTCT ACAAGTTCTG CACCCTACTG GGCGGGACTA CGGCTGATGC CATGTGCCCC ATCCTGGAGT TTGAAGCAGA CCGCCGCGCC TTCATCATCA CCATCAATTC TTTCGGCACA GAGCTGTCCA AAGAGGACCG TGCCAAGCTC TTTTCCACACT GTGGGCGGCT CTACCCTGAG GGCCTGGCGC AGCTGGCTCG GGCTGACGAC TATGAACAGG TCAAGAACGT GGCCGATTAC TACCCGGAGT ACAAGCTGCT CTTCGAGGGT GCAGGTAGCA ACCCTGGAGA CAAGACGCTG GAGGACCGAT TCTTTGAGCA CGAGGTAAAG CTGAACAAGT TGGCCTTCCT GAACCAGTTC CACTTTGGTG TCTTCTATGC CTTCGTGAAG CTCAAGGAGC AGGAGTGTCG CAACATCGTG TGGATCGCTG AATGTATCGC CCAGCGCCAC CGCGCCAAAA TCGACAACTA CATCCCTATC TTCTAGCGTC CTGGCCCAAG GCTCTCAATT GCACTCTTTG TGTGTGTGTG TGTGTGTGTG CGCGTGTGTG TGCGTGTGTG TGTATGTGGT CTGTGACAAG CCTGTGGCTC ACCTGCCTGT CCGGGGTGTA GTACGCTGTC CTAGCGGCTG CCCAGTTCTC CTGACCCTCT TAGAGACTGT TCTTAGGCCT GAAAAGGGGC TGGGCACCCC CCCCCACCAA GGATGGACGA AGACCCCCTC CAGAGCAAGG AGGCCCCCTC AGCCCTGTGG TTACAGCCGC TGATGTATCT AAGAAGCATG TCACTTTCAT GTTCCTCCCT AACTCCCTGA CCTGAGAACC CTGGGGCCTG GGGGCAGTTT GAGCCTCCTC TCCCTTCTGT GGGTCGCTCC CAGAGCCATG GCCCATGGGA AGGACAGAGT GTGTGTGTCC TTGGGGCCTG GGGGATGTT GCTCCTCAGC TCCCTCCCTC AGCCCTGCCC CTCTGAGACA ATAAAACTGC CCTCTCTAAG GCCAACTGTC AAAAAAAAA AAAAAAAA | 2 |
| C1ORF21 | NM_030806.3 | CCCTCCCTCG CTCGCTCCTC GCAAGCTCCC GCTCGCTCCC TGCCCACTCC CGGGGGGACG TTCCGTGCCG CGGCCGCCGC GGCCGCTGCT TCTTTCACAC TTTAGTTGGG AGCTGCGCGC CGCGCTCAGT TACTGGAGAG CTGGCCGCGC GCCGCCGCCT CCCGCACGCT TGCACGCGGG CCCGGCTTCG GGGTTTTGGG TTCTTACTCC AAGCGGCGGG GAGGAGGGGG AGCCCCGGAC ACACTGTGGG GAGGAGGAGG AAGAAGAGGA GGAGGGAGGA AGAAAAAAGA CGAGGAGGAC AGGGGCGGGG GGCGGGAGGG TTGCCACCTT CAGCCCCCCC GCGAACGCCC AAGGTGCACA CATCTTGACC AACTCAGCAG CAAGGTGGAT TTTCTTTGTG TTTAAAGAAA AAAAATGTCC CTGTGTCTGT AGAGATGATT TGCAGTTCAG CCCGGCTGAA GCTGACCGAA TGAGACTATG GGCTGTGCCT CCGCCAAGCA TGTTGCCACT GTTCAAAATG AAGAGGAAGC CCAGAAAGGG AAAAACTACC AGAACGGAGA TGTGTTTGGC GATGAGTATA GGATCAAACC AGTGGAAGAG GTCAAATACA TGAAAAATGG GGCAGAAGAA GAGCAGAAAA TAGCAGCCAG GAACCAAGAA AACTTGGAAA AAAGTGCCAG CTCAAATGTA AGACTTAAAA CTAATAAAGA GGTTCCGGGA TTAGTTCATC AACCCAGAGC AAACATGCAC ATCTCTGAAA GCCAACAAGA ATTCTTCAGA ATGCTGGATG AAAAAATTGA AAAGGGTCGG GATTACTGTT CGGAAGAAGA GGATATCACA TAGCACCAAT TTTACCACTC AAACCAGGAG CTACTACTGT GTAAATAGGT TACACCCCAG TTGAAATCTT GCAAAGGTC GGTTCTATTC AGCAACAGC ACTATAGCAA AAGAAGATCG TTCCATATTG TACGCCCCAT TAAATTACAG TGTTTCTTAA TGAACTTGCA AAGGAATATT GCTAAAAACA AACAAAAAAA ACTGTTATCG AACTTTCTTT GTTGCTGCTA GTTAAAACTT GTTGCAACTT TTCACTTCTC TTGTGTCCAG GTATGCAGCA AAATTCTGCA ATTTCACCTT AAAGATACTG TTGGTTTTAC AGATGCTCTC CAACCTATTT TCTATAAGAT GAGGTAGTGG | 3 |

TABLE 1-continued

Melanoma Biomarker/Housekeeper Sequence Information

| Gene Name | RefSeq Accession | Sequence | SEQ ID NO: |
|---|---|---|---|
| | | TGAACTCAGA TAACAAACTT CTCTTCTAAA CTGGTTCTGC<br>TTCTAAGACA AGCATCTCCT GCCCTCTCTC CTTCCTCCCC<br>ATCTCTCGCA CGCAGTCTAG AGATGGACTG AGCCTTGCTT<br>CTCACTGGCA GTGTTGAGCT TTGGAGATGG GATGGTTGCT<br>ATGCCAAGCC TTGTTTCTCT GCTCAGAAGA AGTAGAGAAG<br>CTATTATCAA TTAAAAGCAT GCTGTGATGT GACTCCTGGA<br>AGTGACGTAG GAGTGAGTGG CAGGTTGTTT GATTTAATAG<br>GTATCTTAAT CAAGAATTAA GCTTGCAACA TTGGCTTTGC<br>TCAGATGCAG ATGGAAGTGT GATCACAATC ATTTTGAATC<br>CCTCTTCCTC ACTTTTTTTT CTAAGAAAAT AAACATTTTA<br>CTGTTTTTAT GGATCCTTGT CTTCTCCCAT TCATCCAGCT<br>CAGTGTTTTA AGATGATCCT GGGTGCAGAA GTTGAGCCCT<br>CCTTTGCATT GACACTGATA ATTAGCCTAT AGGGCTCCCT<br>ACCCTTCCAT TAAGAATCTA CCAAGCATTA GCAAGGCTGA<br>AAGTGGTCTA AGAGGTGAGG GGACATCCTA TGACTTTTTA<br>GGAAGGCCTG AAACCACCTT GTTACCTTTC ATTTTGTTAG<br>CAAATAAACC ATCCTATTTT GTAACTCTCC CCCTTCAAAA<br>TGCTACATGA GCCTTGCCAC TTCCTTTTTC TCTTACTTCC<br>AGCACACTAG ACATAGCAAA AGTGTTTGCC TACTCAAAAA<br>CATAATACTT TTATGCTGAT GATGGTATTT GGAGATGTGA<br>AAGCCAAAAG CCCCTGGCAG TGGTGGGGAA TGTTGACTGA<br>GTGTTCAGCA GAGTTTATTT TTCCATACTA TATGAAGAGA<br>ATGATCTCTT CTCAAAGACA GAAGTGATAT TTTTAACAAA<br>TATTGTCACA AGTAAATAGC AATCAAAAGG AGAAAATAAC<br>TTTTGTATTT TTTTAATGTG TTTGATAGCT TTGACGAGGG<br>TTCTCTTTGT TACTTTCAGG GGAGGGCATC CTATTAAATG<br>CCACGCCAGC AGTCCGGGTC TGGGTTTGTC CCACAAAATC<br>ACAGGAGCAC TGTATGTTCC TCTCTTTTGG AGTTGTGACT<br>TTGAAGGGCC TCAATATTAG CCACACTGCC GCCTGCAGAA<br>GGTGGAGAGT TAAGATGTTC TATGTCAATT TGCTCTTGCC<br>GAAAAGATGA GCCTCGATTT TAAAATCTAT CCACATCCAA<br>CTGATGGCAC CATTGATGTG CAAATAATGA GATTCCCTAT<br>CTCCTTTTAG ACCTGGGACG GCAAAAGGGA AGGGAAGGAA<br>ACTTAGCAGA GTGCTATTGA CTATAGATTC ACATATTAGC<br>AACAAAATCC CGTAATTCTT TTGGCCAACA GCAGCTATTT<br>TGGGGAGCAG CTGTGGCTGT TACATAAATA GAGATGCAGC<br>CAAAATTTTA GGCCTTTTAT CCTGCTTCTA GCAGAAAAAT<br>GCAGGGAGAG TCAAGTAGTC TAGGGTTTCA GGTTGCCTCC<br>CCTCATATGG TTTTTGGCCA AGTGACTAAA ACAGTTTTCC<br>ACAACTGTAA ACAAACTGCT AAGCCCCACC TCAAACTTGT<br>TCACTGGGGA CTTTGCTTAC CGTTCTGTGG GTGACCTTTT<br>CCGGGATTTC TTGTTCTTAT CAAGCAAGAA TTAAGCACAT<br>GCTAAACGTC TTCCATTTGA CTTCTCTACT CGGTGTCTCA<br>GACAGTGTCT TCCCAGAAAA CCACCACCCT CTACCCAAAG<br>ATGAAACATG CTCATGTCAT TTTTCTCATG GTCACATTTA<br>ACAGTTTTGA CATGTTATAC TTGCGCATAG ATCCAAGCGT<br>TTCTTGGGAA CCTGACTTTT GAGTGTTTAA TAAAGCCGGA<br>AGTGGTGTTG CCCTGAACCA GCAGATTTTC ACCTGGGTTC<br>TGGCTCCGGT GTTTAACACT GGATACATCT TTGATGTGCG<br>AAAGTGAGTT CATCTTCAGA CACATTTGGT ACATCCAGAA<br>ATAGATCCAA GAAATGGGGT GGTTGAGTGG GTCCGCACGA<br>AATGCTTGAT TATGTCAGCA ACACCCAACA CTGTCTGTTT<br>TCCATTTGTT GGTTTTAATC ATAAAATTGT CAAGTGATTC<br>GTGTTTGTAC TTTATTTTTT TGTGCCTTCT GAAAGGATCT<br>AAAACAAAAA TATTTTGCCT TTTTTTCCCC ACGTGTATCT<br>GAACATTAAG CAGATTGGCT CAGACACAAT GAAAAGGATA<br>ATCCAATGTA CGTGCTGGTG CACTCTGCTA GTTGTTATCT<br>CTGTAGGGCT CAGGAAGCTG GAAGGAGGAA GGGAGGGTAA<br>GTGGCCTGGT GAGTGGAGGT AGAAAAATGA TGAGAAATGA<br>ACTGAGAGCA TTAAGCAGAG AGGGTTGATA GGCTGGCCGT<br>GTCCGGGGTG AAATTGGAAA TCCAGCTGCC TAGTGGCCAG<br>TGGGTGGGGC AAGACTGTCA ACGAGATTTA CAGCTGGCTT<br>ACACATGCCT TATGTCCTCT GAGTTGTAGA GTTGTAAAAG<br>TTCAGCAGTG TGTGCACAGC TTTCTTTTGG TTGGCAGAGA<br>TTCAGGATCA TGGAGTACTG CTCTCATAAT TGAAGACGTG<br>TTTGTTATTG GCAGAGAACC TTAAAAAAGG CCTTTACCTC<br>AGCGATGCTT CCTAGCCCCA GGCTTGCAGA GAACACAGAG<br>TGGTGTTGTG GTCTATTTAG GGACAAAGAA GGTATAAAGT<br>CCAGAGATGA GAAAACTGGG TCAGCCCTCA GAAACTGCAG<br>CAGCCACGCA CACAGAAGCC TGCTGGAAGA CAGGTCTCTC<br>TCCGTCCACA GTGCCCATCA TCTGAGCCTG GGCTGGGATG<br>ACTCAACTTA GCAAAGACGG ACCCAGGAGG AGTGCTGGTT<br>CTTCAGTCTT TGTACTGGCC CCATCCTCTC CTCACTGTAA<br>TGTGAGGAAG CACCTCTGTG TCAGGGCTCA CCTGGGCATC | |

TABLE 1-continued

Melanoma Biomarker/Housekeeper Sequence Information

| Gene Name | RefSeq Accession | Sequence | SEQ ID NO: |
|---|---|---|---|
| | | CAAAGCGGCC ACGCCCACAA TCCGACAGCC CCCAGGAGCA GGTCCAGGGA TGATGCAGCC CCCTTCTTGG TCCCATGTGA TGTCATCCTG CTTTGTTATC TTCTTATAAC TTTATCCTGC TATAACTTTA TCCTCTTCCC AGCCTCATCC CTGTTTTTCT GTTAGGGCAA GACTCTTCCA TAAGCCTGCT AAAAAACAGA GATGATACCT CTTACAAACT TTACCTCATA GCCTGTGAAG CAGGTTGGCA TGTGGATTAC AAGTCCTGCT TTGACACTGG GCAAGAATTT AAGATTGTTC TATCTCTACT AGTCATAGAA AAGAAACATT GTTAAACATG TTGAGTTTTA AAGGAAGAAA TATTTTCAAA TTCTTAATCC AAGAAAATAC TGAGTTGGAA TCTTAGACTT CGGGACTCTG ACACGTTCTT TATGAAAGGC AAAATAATTG GTATCTAAAG TTCTCTCCTT CCTGCCTCCC CTAAAGAAAA AGGATATTAG ATTGCACACT ATAATTTTAC ATAAGATCTG CCTTCCACAC TTCCCTGCTG GAAGGCATTC TCAGAGCTTT ATGTCTTCGT ACCTCTCAGA GATTGGACTT TTTCTTGTTT AAAACCCCAA CCAAAAAAAA TAATAAGGCA TGATTGGTGG GGAGGGAATG TGTATTTAGG GGCATAATAA AAAGGTGGCT CGAAGCAGGA ACTTTGGCCT CATGGTGTCA TGGGTGGATG CCTGGACTCC AGTGTGCCTG TGAGGGGCTG GGTTAGGCAG TCGGCTGTCA CACTCACATG TGCCTGCAAT AAACCTTTTG GAATTTCATG AACGAGGTCT ATGAATTGCC TTTTGCCAAT GAATGGATGT ATTTTTCCAA GGGGGGAATA GTATCCTTGA CTTTGGCAGT CACCTTTTTG TATGTCTCTA GAAAGGGGTC AAAAAACTAT GGTAAAGATG AGGCTTATGA GTGAATACCT CTGGGACAAA CCTTAGGACT CACAAGCTAT GCCATGTTTT TCAGGAGACT CTTGTACCTT ATCTGGAATC TAATCTTGGG AGAAGAGGAA AAAGGAGCTA ATATTTGTCA TTTATACTCA CTCTGTGCCA GATACTGTGC TAGGCATTTT ATAATTGTTT TGTGTCATCC TCATGATAAT CCTGTGAAGT AGATCTATTA CCCCCGTGTT CTAAATAATA GATCTTAAGT GTGGAATGCA TCTATCCAAC ATAAATGCCC ATGTTGAAAG AAGGAAAGAT GTCATTCAAG TATTTTTCAA ATTCTTTTTA TTATGACTAT GCCCTTCGCA ACACTGTGAA AACAACCCCT GGGGGCATCT GCCTTCCAGA ATCTCTCTCT GGCTTCTCAC CAGCTTGGTT TCCTCATGGG GAGTGTTTTA TTTGGCCTCC CCTATCTGAG CTGCACACAC ACCAGGGGAG GCCACTGGCT AACAGTAGGA CTTCAGTGCC CTGAGGAAAA GGCTTTGGGA ATTTAGGCAC ACGTTCTCT CCTTGGAATC CTTCTAGCAT CTGGAAAAGG AACCTGGTAT TTCTGCAGTT AGATACCAGA TGCAACCAGA ACAGGCTTTC GAGTGCTGTG ATTTCTTTCC TGGGTTCCCA AGTCTTGTTG TTTCATCACA AACTGTATCT TTTTAAGGTT AAAAGTCTTG ACCTTCATGG GGGTCTGGGA CAATCCGATC TCCAAGCATG GAGGAAAGGC AATGCCTGGA CCACTGACTT GCATTGAAAT CCTTTCTTGT GGGCTAGGGT TTGATGTCTC TTTTTCATCT TTGGACTGGG GATCTGCATC TTCCAGGTCC ATTTAAGCAC TGAAACTAGA TGCAAATCTC TTTCGAGACC TTACATGTTT TAGATAGTCA TGTAATGACT TGGATAGACA TTTAAATAAC TTGTTCCAAG GTCGGAAGAG CCCAAGAACT CCTCAGAGTT CCTCTTCTTG CTTCTTGAAT CACATCCTCT AAAGATGACT CATGTCTCCA TAGCAACTGT TAAAGGTGCT GCCTAGACGG GACCCGCTCC CACCTTTACT TACTTTGCTC GAAGGAACCA AAACAATGTC CTTGTGTAAA GGGGCTGTCA TATCCAGTTT TCCTTTGAAA TCTGGCCCCC AAGATCCTGC TTCTTTCTAA CCTGGCAGCT GTCATGTCCC TTCAAGATGA TGTGGGAAAT GGCCCTTACA ACTTGGGAAC CACAGAAATT GCTGTATTTC GGGAAGATTC ACCTCTAAAC TGAAGGCTTC ATTCTGATAG TGTCTGCCCT CTCTACCCTG ATTTCGCCCT TCTTTGCTTC CATTTTTAGC CCAAGGCTTT GAATTTGATT GAGTAAGACT TAGAGGCAGT ATAAAGAACA CCATAAACTT AGGCAGAGGT CCCTTAGGGT CTCTAGAGTT GAAAATAATT CTACAGCCTT AGGGGGACCT CTTGGCATTG ACTCTAAAGG GAGAGAATAG CCCCTGTGTC CTGGCATTTC AGTCTAGACC TTCAAGGACT GTTCTCTCTT GACAGGCAAG CAAGCAAAGA AAGTTTTGCA ATAGATTTCA AGCCAGTTTT TCCATTCAAA CCAAGATGCA AATTCATAAA ATTACTCTTT TCCTGGAATA GATCCAGGCA GCTGCCTTAT TAGAACTTTA GATTCGGATC TATTTTCTTA ACACACATAC ACATACACGC GCATACATAC ATATACAGAG AGATACGTGG AGAAAGGAAA TTTACTCTAT CATTGCAATA CTTCAAGAAA GAGCTGTATT TTGCCTTTCT GTAATCTCCA AGATAGTGTC TAGGAAAGTA ATAGTATAAC TATAGGGATA CCGAAACAGG AAAAACCAGC CATCACTCTT GAGAAAGTTT GAGTTCGACT CACATGGGAG AATCGAGGTC TGCTACTCGT CTTGCTTTGT GCCCCATCTG TGCCTGGATG CCCTACTACA TCTGCTTGAC TCGTCTGGGC | |

TABLE 1-continued

Melanoma Biomarker/Housekeeper Sequence Information

| Gene Name | RefSeq Accession | Sequence | SEQ ID NO: |
|---|---|---|---|
| | | TGCTAGCCGG GGTGTTGTGG CTGACATCCT TTCCTGGCCT TACACACATA ATAGACACAT CCCTAACGGC GTGTGCCTGG TCCAGCCACA TACAGCCACC ACATGTGTCA CACACTGTCC CCCTCATCCA TGTGGACTTG ACTGGCATTT CAGCAGCTCC ACTGGGATGC TCTAACCCCA GTGTGTGGAG TTGGGGTCCC TTCATCTAGG TTGACCCAGG TATAGCATTT TTAGCATTGC CTTTCCAGTC TTGATGATTC ATTCATTGAA CTCATTTATT TCTGGAGCCC CTGGTACACT CCAGGCACTG CGCTAATTGC CAGCAAAGCA CAACTGAACT AAATCCACCT TCAAGGAACC TAGCCATAAC GAGGGAGGCA GCATGGAAGT ACCCTACAGG GGAAAGTCCT GAGTGCTGTG GGAGCATCTC ACCGTGGCAG CCAGCCCAGT TTTGGCAATC AGGGGCTTCC TGAAAGAGGT GACATCAAAG CCCGGATGTG TCAGAGGACT GAGGGAGAGT GTTACTAAAG GACTTTCAGG CTGAGAGGAT AGCACAGGAC TCAGCCCAAA GGAGGGCCAG TGTGGACTGT CCAGGGCCAG CCTGCAGTAC AGAGGCTGGA GCTTGGACTT GTAGAGGGAG AGAGAAGAGC AAGGGACGTG GACGGGGCAG TGAGCCAGGC TAGCCACAGA GGGTTCCCGG GGCTTTGCTG GGGATTCAGG GAGCATAAAT AAGAGCTTTA GGTGGTGCTG TGTCCTCTGC AGCCCACTGC TGAGGTCCTC CAGACAGGTA AGGTGTGGTC ACAATCAGGG CCGGGTTTC CCTGCTCACT GCGGCAGTGC AGGGGTGCTT GCTGAGATGA TTCATCCCAG GGTGTCCTCT GTCCCTTACC CAGCCCCAAC TCCTCTTCCT CTGCCAAAAG CTATTTGAAT TCAAGGACTT TAACCTGGGC CGGATCTGGT TTGGAGACAA AGGGGACAGC TCTGGGTCAG CATGACCTTC TTTAGAGCCA CTAAGGCGAA AAATACCGTT TGGGACCAGG CTGGCCTAGA CCCAGGGATG AGAATGCACC CTAAAATAAA TATACGGGAA GCAGCAGAGG GCTTCCCTGT CTAGTGTGTG ATCCTAACTA AAGGCAGCTC TCTTGGACAG CCTTCCCCTG GATTAGGTCA CATACACCTG GTGGCCAAGC CTCTGCTGGG TCCCAAATAC ACACCCGAGT CCTGCCAAAG AAAGGAGATT TTTAAAAAGC ACAGACAAAT TGTATGCAAG TGGAAAATAC CCATAGGCCT AGACAGCTGT GGAGGGAAGA CCTCGTGGGT ACCTGGAGGC TGCCAGAGCT GGGAGCTCTG CAGGTATGAG TCAGGGAAGG CTCAGAGACA AGCAGAATCT CTCTATGGAG ACAACTTGCA GTGCCTTTTA GGTTTTCCAA ATAACCTCGG AGTTCAGAGC ATTGGGTTTT TTTCTCCCCT CCCCACCCCC AGAAAAATAA TTAGAAAAAT GTTTAGGAGA AAGGAAAAGA ATTAGATGCA TCAGAATACC AGCTATAAGC CAACACTGTT TCCAGAAACT CAAGAAAAAG CTCAAACAGA AGACAGTTCC CCTGAGAGGC TGGAGGCGTT GGTGCTGAAG GCAATTTTCC TAGCTAAGGG GCACTGGGCC TTGCTGCACC TTGGGGCTGA CCTTTTTTGC AAAACACCCA CCCCTGCCCT CCTGGCATAC TCAACAGCAA CGCCAGCTTT CTGGACCCTT GGAAAGATGT TAGCTCAAAC ACCCACTTTT TCCAGATCTT CCTCTTGCTC TTCACTGAGG AATTTGTAAT TCTGAGGCTA GCGATGCCCA CTCGGATATT CCGCAGGCCC AGGTGTTTAG ATTAGAATTT GTCCAGCGGT AATCCTGATG CTGGAAACCA ACAAACATTT GGCCTCATAT TCACCCATTT AAAAACTAGA GCCCCTGGCA GGTCCCCTTA GGGCCATGTG TTCATGGAAT ATAAGCCAAG TTTGCCTTAG GCTTGTTCAT GGAATATAAG CCAAGTTTAC CTCTCCCCAT TTTCTGCCCT GGCCCACTTC CCACTCACCT CCACCTCATT GCCAGGAAGG GATCAAAATG CCTCCATGCC AGTTGTTAAT GGCTACATAT TTGCCCTTCC CAAGGGTATT TGCATTTTAT TTAGGAACAT GGCCTTATAT TCAAGGAAAA TCTAGCATCA AGATTACGAG GCATCACCTC TCAATCAGGT CTGGGAGGTA TCTTGGGGCA TTGCTCTTCT GAACACCTGC AGAGGCTTCC TCAGGTGAGT GTGGGAGCCC GGAAGGGTGG CCTCCCTAAC CACTCTGCCT GCACATGAAT TCTCCAAAGC AGTGGGCCCC CATCTGTTTC AATTACACAT GCCTGTCAGC AAAAACTTCG TGAGATGCAC TCTCTCTGTG TGTTTATTAA TTTATTTAAA GCATATATCC CTTTACTTTT GTACTACTAT ATTAGGCACA TTATAAAAAG TATACAGCAT AGAAACTTTA AATGAATAAG ACACAAAATA TTATAAACAG AGGTTCTGGC ATTTTCTCTC TGAACTCCTG AGGGGGACCT TGGGCACCTC CTGGTATGTG CACACCCCAC TTTGAACACC CTTGCTTTAG TGCAAATCAG CACGCCTAAA TAGCATCCCA AACCACTGTG CGACATTTGG CCTGCAGAAT AAGAAAGTCC TAAGGCAGAA TCCCCAGGAA CTTCAAATCT GGGAGATGAG GAAAGAAAAC TCACTCACAA ACAACATAAA TGTAAATAAT TCAAAACCCT AAAGGAGAGC TGTCCCTAGA CAGTAGTGGC TACAGGTGCT AAGCAAAAGT CAGGTACACT GGACAGAGCC ATGCGATTGA TTGTTCATCT TCCCTCTCTG GGTCTCCAGA AAAGGACACT GGCAATATCC CCAGCTCTCT CCTGATTGGA ATTCTTTGAA | |

TABLE 1-continued

Melanoma Biomarker/Housekeeper Sequence Information

| Gene Name | RefSeq Accession | Sequence | SEQ ID NO: |
|---|---|---|---|
| | | CCCTCGAAGT GCTCCAGCAG TACTACCCCC CACGTAGCAG TGGGCCCATG TCGCTTGAAT ATTATTTTTG ATTTGACCAC CAAGATGTAA TGATGATTCT ATTCCATTTT GAAAAGGGTC TGAGAAAGTG TACAGGTCTA ATTATATATA CATATTTATA CATGTGTATT TTTGTTTATT GTTACATTTT GACATTGGAC TTTCTATTAA ATAATTTTTA AGAGTTGG | |
| CFLAR | NM_001127183.2 | GACCACGCAT GGAGAATTTT ACCACCCAGA GACACGCGAG TGGCCCTGTG CAAGTTTCAA CTGCGCGGGG GGCGGGGAAT TCCGCAGACA GGATTCTAGA ATTTATGTCT TGTGTGGTAA CATTTCAGCC GGTGGGTGGC GGGGATTAGG CGTGAAGCGG TTCAGCAGGC AGAGGTTCTC GGACGCCCTC CGGCGAAGCC ACCTGTTGAT GCTTTTGACT TTCTGTCCTT GTTCCTCGTC CCATCTGGAG CATTTCCAAT TCTGGTTTTG CGGAGCAGCA GGTCTGAGCT TGTCCGGCGA GGGTGGGAGT TGGTCCCGGC GGAGATCCAG TGGGAAGAGC CGGCGGCTGC CCGGGCAACT CCCCCACTGG AAAGGATTCT GAAAGAAATG AAGTCAGCCC TCAGAAATGA AGTTGACTGC CTGCTGGCTT TCTGTTGACT GGCCCGGAGC TGTACTGCAA GACCCTTGTG AGCTTCCCTA GTCTAAGAGT AGGATGTCTG CTGAAGTCAT CCATCAGGTT GAAGAAGCAC TTGATACAGA TGAGAAGGAG ATGCTGCTCT TTTTGTGCCG GGATGTTGCT ATAGATGTGG TTCCACCTAA TGTCAGGGAC CTTCTGGATA TTTTACGGGA AAGAGGTAAG CTGTCTGTCG GGGACTTGGC TGAACTGCTC TACAGAGTGA GGCGATTTGA CCTGCTCAAA CGTATCTTGA AGATGGACAG AAAAGCTGTG GAGACCCACC TGCTCAGGAA CCCTCACCTT GTTTCGGACT ATAGAGTGCT GATGGCAGAG ATTGGTGAGG ATTTGGATAA ATCTGATGTG TCCTCATTAA TTTTCCTCAT GAAGGATTAC ATGGGCCGAG GCAAGATAAG CAAGGAGAAG AGTTTCTTGG ACCTTGTGGT TGAGTTGGAG AAACTAAATC TGGTTGCCCC AGATCAACTG GATTTATTAG AAAAATGCCT AAAGAACATC CACAGAATAG ACCTGAAGAC AAAAATCCAG AAGTACAAGC AGTCTGTTCA AGGAGCAGGG ACAAGTTACA GGAATGTTCT CCAAGCAGCA ATCCAAAAGA GTCTCAAGGA TCCTTCAAAT AACTTCAGGC TCCATAATGG GAGAAGTAAA GAACAAAGAC TTAAGGAACA GCTTGGCGCT CAACAAGAAC CAGTGAAGAA ATCCATTCAG GAATCAGAAG CTTTTTTGCC TCAGAGCATA CCTGAAGAGA GATACAAGAT GAAGAGCAAG CCCCTAGGAA TCTGCCTGAT AATCGATTGC ATTGGCAATG AGACAGAGCT TCTTCGAGAC ACCTTCACTT CCCTGGGCTA TGAAGTCCAG AAATTCTTGC ATCTCAGTAT GCATGGTATA TCCCAGATTC TTGGCCAATT TGCCTGTATG CCCGAGCACC GAGACTACGA CAGCTTTGTG TGTGTCCTGG TGAGCCGAGG AGGCTCCCAG AGTGTGTATG GTGTGGATCA GACTCACTCA GGGCTCCCCC TGCATCACAT CAGGAGGATG TTCATGGGAG ATTCATGCCC TTATCTAGCA GGGAAGCCAA AGATGTTTTT TATTCAGAAC TATGTGGTGT CAGAGGGCCA GCTGGAGGAC AGCAGCCTCT TGGAGGTGGA TGGGCCAGCG ATGAAGAATG TGGAATTCAA GGCTCAGAAG CGAGGGCTGT GCACAGTTCA CCGAGAAGCT GACTTCTTCT GGAGCCTGTG TACTGCGGAC ATGTCCCTGC TGGAGCAGTC TCACAGCTCA CCATCCCTGT ACCTGCAGTG CCTCTCCCAG AAACTGAGAC AAGAAAGAAA ACGCCCACTC CTGGATCTTC ACATTGAACT CAATGGCTAC ATGTATGATT GGAACAGCAG AGTTTCTGCC AAGGAGAAAT ATTATGTCTG GCTGCAGCAC ACTCTGAGAA AGAAACTTAT CCTCTCCTAC ACATAAGAAA CCAAAAGGCT GGGCGTAGTG GCTCACACCT GTAATCCCAG CACTTTGGGA GGCCAAGGAG GGCAGATCAC TTCAGGTCAG GAGTTCGAGA CCAGCCTGGC CAACATGGTA AACGCTGTCC CTAGTAAAAA TACAAAAATT AGCTGGGTGT GGGTGTGGGT ACCTGTATTC CCAGTTACTT GGGAGGCTGA GGTGGGAGGA TCTTTTGAAC CCAGGAGTTC AGGGTCATAG CATGCTGTGA TTGTGCCTAC GAATAGCCAC TGCATACCAA CCTGGGCAAT ATAGCAAGAT CCCATCTCTT TAAAAAAAAA AAAAAGGAC AGGAACTATC TTACTCAATG TATTAGTCAT GTTTCTCTAG AGGGACAGAA CTAATAGGAT ACATGTATAT AAAAAGGGGA GTTTATTAAG GAGTATTGAC TCACATGATC ACAGGGTTAG GTCCCACAAT AGGTCATCTG CAAGCAAGGA AGCCAATTCA AGTCCCAAAG CTGAAGAACT TGGAGTCCAA TGTTTGAGGG CAGGAAGCAT TCAGCATGAG AGAAAGATGG AGGCCAGAAG ACTACACCAG TCTAGTCTTT CCATGTTTTG CCTGCTTTTA TTCTGGCAGT GCTGGCAGCT GATTAGATGG TGCCCACCCA GATTGAGGAT GGTCTGCCTT TCCCAGTCCA CTGACTCAAA TGTTAAATCT CCTTTGGCAG CACCCTCACA GATGTACCCG GGAACACTTT GCATCCTTCT | 4 |

TABLE 1-continued

Melanoma Biomarker/Housekeeper Sequence Information

| Gene Name | RefSeq Accession | Sequence | SEQ ID NO: |
|---|---|---|---|
| | | ATTCAATCAA GTTGATACTC AGTATTAACC ATCACAGTCC<br>ATTTGGGCAA CTATACCAAA TTACCATAGA CCAGGTGACT<br>TAAACAGCAG TTATTTCTCA CAGTTCCGGA GGCTGGGAAA<br>TCCAACATCT AAGTGGTAGC ATATCTGGTG TCTGGTAAGG<br>CATGCTTCCA GATCTTACCA GATGTCAGTC TTTTGATGTT<br>CTCACATGGC AGAAAAAGAG GATGCAAACT CTCAAGTATA<br>TCTTTAAGGG CACAAATTCC ATTCATGAGG GCTCTACCCT<br>CATCACCTAA TTACCTCCCA AAGGCCCCAC CTTCTGATAC<br>TGTCACTTTG GGGATACTGT CTCCCCTTTG AATTCTGGGG<br>GGAATACAAA CATTCAGTTT GTAACAATAG CCTTATGATT<br>TAGAGGTTAC TTGTTCATTC ACCTAGACCT CAAATTGCAT<br>TTTACAGCTA GTCAAGTATA TCTTTCTCTG ATTTGATAGT<br>GTGACCTAAA AGGGGACCAT TGTTTGAAAT ATCATTAGAG<br>TTGCTTATTA TTATTATTAT TATTATTATT ATTATTATTA<br>TTATTATTAT TGAGACAGAG TTTCATTCTG CTGCCCAGGC<br>TGGAGTGCAG TGGCATCATC TTGGCTCATT GCAACCTCTG<br>CCTTCTGGGT TCAAGCGATT CTCCTGCCTC AGCCTCCCGA<br>GTAGCTGGGA TTACAGGCTC CTGCCACCAC ACCCGGCTAA<br>TTTTTGTATT TTTAGTGGAG ACAGGGTTTC CACCATGTTG<br>GCCAGCGTGG TCTTGAACTC CTGACCTCAG GTGATTCACC<br>AGCCTCGGCC TCCCAAAGTG CTGGGATTAC AGGTGTGAGC<br>CACTGCACCT GGCCTATTAT TATTTTTAAA TTTTTTTTTT<br>TTAATTGATC ATTCTTGGGT GTTTCTCACA GAGGGTGATT<br>TGGCAGGGTC ACAGGACAAT AGTGGAGGGA AGGTCAGCAG<br>ATAAACAAGT GAACAAAGGT CTCTGGTTTT CCTAGGCAGA<br>GGACCCTGCG GCCTTCCGCA GTGTTTGTGT CCCTGGGTAC<br>TTGAGATTAG GGAGTGGTGA TGACTCTTAA GGAGCATGCT<br>GCCTTCAAGC ATCTGTTTAA CAAAGCACAT CTTGCACTGC<br>CCTTAATCCA TTTAACCCTG AGTGGACACA GCACATGTTT<br>CAGAGAGCAC AGGGTTGGGG GTAAGGTCAT AGATCAACAG<br>CATCCTAAGG CAGAAGAATT TTTCTTAGTA CAGAACAAAA<br>TGAAGTCTCC CATGTCTACT TCTTTCTACA CAGACACAGC<br>AACAATCTGA TTTCTCTATC TTTTCCCCAC CTTTCCCCCT<br>TTTCTATTCC ACAAAACCGC CATCGTCATC ATGGCCTGTT<br>CTCAATGAGC TGTTGGGTAC ACCTCCCAGA CGGGGTGGCG<br>GCTGGGCAGA GGGGCTCCTC ACTTCCCAGA TGGGGCGGCC<br>AGGCGGACGC GCCCCCCACC TCCCTCCCGG ACGGGATAGC<br>TGGCCGGGCG GGGGCTGACC CCCCACCTCC CTCCCCGACG<br>GGGCGGCTGG CCGGGCGGGG GCTGACCCCC ACGCCTCCCT<br>CCCCGACGGG GCGGCTGCCA GGCGGAGGGG CTCCTCACTT<br>CTCAGACGGG GTGGCTGCTG GGCGGAGACG CTCCTCACTT<br>CCCAGACAGG GTGGCTGTCG GGCGGAGGGG CTCCTCACTT<br>CTCAGACGGG GCAGCTGCGG GCGGAGGGGC TCCTCACTTC<br>TCAGACGGGG TGGCCGGGCA GAGAAGCTCC TCACATCCCA<br>GACGGGGGGG CGGGGCAGAG GCGCTCCCCA CATCTCAGAC<br>GATGGGCGGC CGGGCAGAGA CGCTCCTCAC TTCATCCCAG<br>ACGGGGTGGC GGCCGGGCAG AAGCTGTAAT CTCGGCACCC<br>TGGGGGGCCA AGGCAGGCGG CTGGGAGGCG GAGGCCGTAG<br>CCAGCTGAGA TCACACCACT GCACTCCAGC CTGGGCAACA<br>TTGAGCACTG AGTGGACGAG ACTCTGCCCG CAATCCCGGC<br>ACCTCGGGAG GCCGAGGCTG GCAGATCACT CGCAGTCAGG<br>AGCTGGAGAC CAGCCCGGCC AACACAGTGA AACCCTGTCT<br>CCACCAAAAA AATACGAAAA CCAGTCAGGC GTGGCGGCGC<br>CCGCAATGGC AGGCACGCGG CAGGCCGAGG CGGGAGAATC<br>AGGCAGGGAG GCTGCAGTGA GCCGAGATGG CAGCAGTACA<br>GTCCAGCTTC GGCTCGGCAT CAGAGGGAGA CCGTGGGGAG<br>AGGGAGAAGA GAGGGAGGGG GAGAGGGCTA TTTTTAAAAT<br>TTTTTAAAAT TGCTGAACAG GGGTACCTCT GGGCAGTGTG<br>TCAGAATACC ACTTTTTAAA TATTTTATGA TTTATTTATT<br>TTTCTATTTC TTGAGGTTTT AACTGATGTG TATCTGTATG<br>TCTATTTGTG TATATTTTGT CATGATCATG TAACAGAGTC<br>TGAAAAGTGT CGAAGAGACA GTTTTCAGGA ACAACAAGCA<br>ATTATTCCTA CTTTCCAAGT TATTTTGATG CCATGGTGGC<br>TCATACCTAT AATCTGAGTA CTTTGGGAGG CTGAGGTGGA<br>CTGATCACTT GAGCCCAGGA GTTTGAGACC AGCCTGGGCA<br>ACATAGCAAG ACTCCATCTC TACAAAAAAA GACAAAATTT<br>AGCTGAGCGT GGTGGCGTGT TCCTGTAGTC CCAGCTACTT<br>GGGAGGCTGA AGTGAGTGGA TCCCCTGAGC CCAGAGAGGT<br>CAAGGTTGTG ATGAGCTGTG ATCACACCAC TGCACTTCAG<br>CATGGGAGAC AGAGTGAGAC CCTGTTTCAG AAAAAATAAA<br>TAAATAAAAC CACCAGCACC ACAACAACA ACAAAAAGTT<br>ATTTTGTACT TGTTTTGAGC ACAGGACTCC TGAGGGTATC<br>TTTGCATTTA ATATTACATA GGGGTGCCAG TGGGAAGTAA<br>TGTGTATGCT TGGCCTCATG AGCTAAAACC CTGTGTTAAT | |

TABLE 1-continued

Melanoma Biomarker/Housekeeper Sequence Information

| Gene Name | RefSeq Accession | Sequence | SEQ ID NO: |
|---|---|---|---|
| | | TATGACAGAA GGAAAGTGTG TGAGAGAGAT CTTAACTACC TAGCAGCTCT AGCTGCCATC TTGAACCATG AAGATACGGG CCACACGTAG GGGTAGCTGG GTAGTGAGCA GCAAGAAGCC TTGTTGGATG AGGGCACGAA GGAGCAGAAT CACTGGAATC ACTGTGTCAG CCCTAATTAC CTACCTCTGG ACTTTTATGT GAGGGGAAAA AAAATTGACA GTTTATATTT ATCTCAACCT AGTTAACCCA AGTGATGCAT TGTTATGAGA TTAAAATGTT TGGAGGCCGG GTGCGGTGGC TCACGCCTAT AATCCCAGCC CTTTGGGAGG CCAAGGCGGG CGGATCACGA GGTCAGGAGA TCAAGACCAT CCTGGCTAAC ATGTAAAACC CCGTCTCTAC TAAAAATACA AAAAATTAGC CAGGCGTTGT GGCGGTCGCC TGTAGTCCCT GCTATTTGGG AGGCCGAGGC AAGAGAACGG CATGAACCTG GGAGGTGGAG CTTGCAGCGA GCTGAGATCT TGCCACTGCA CTCCAGCCTG GGCGACAGTG CGAGACTCTG TCTCAAAAAT AAATAAATAA ATAATAATA AATAAAATGT TTGGAATGTT GGCTTCATCC CTGGGATGCA AGGCTGGTTC AACATACGCA AATCAAGAAA CATAATTCAT CACATAAACA GAACTAAAGA CAAAAACCAC ATGATTATCT CAATAGATAC AGAAAAGGCC TTCAATAAAA TTCAACGTTG CTTCATGTTA AAAACTCTCA ATAAACTAGG TATTGATGGA AAATATCTCA AAATAATAAC CATTTATGAC AAACCCACAG CCATTATCAT ACTGAATGGG CAAAAGCTGG AAGCATTCCC CTTGAAAACT GGCACAAGAC AGGGATGCCG TCTCACCACT CCTATTTAAC ATAGTATTGG AAGTTCTGGC CAAGAAAATC AGGCAAGAGA AACAAATAAG GGGTATTCAA ATAGGAAAAG AGGAAGTAAA ACTGTGTTTG CAGATGACAT GATACTATAT CTAGAAAACC CCATTATCTC CACCCAAAAG TTCCTTAAGC TGATAAGCAA CTTCAGCAAA GTCTCAGGAT ACAAAATCAA TGTGCAGAAA TCACAAGCAT TCTATACACC AACAATACAC AAGCAGAGAG CCAAATCATG AATGAACTCC CATTCACAGT TGCTAGAAAG AGAATAAAAT ACCTAGGAAT ACAGCTAATA AGATGTGAAG GATCTCTTCA AGGAGAACTA CAAACCACTG CTCAAGGAAA TAAGAGAGGA CACAAATGAA AAAACATTCC ATTCTCGTGG ATAGGAAGAA TCAATATCAT GAAAATGGCC ATACTACCCA AAGTAATTTA TAGGTTCATT GCTATTCCCA TTAAACTACT ATTGACATTC TTCACAGAAT TAGAAAAAA CTACTTTAAA ATTCAAATGG AACCAAAAAA GAGCCCGTAT AACCAAGACA ACAATAAGCA AAAAGAACAA AGCTGGAAGC ATCACACTAC CCAACTTCAA AGTATACTGC AAGGCTACAG TAGCCAAAAT GGCATGGTAC TGGTACAAAA ACAGACACAT AGACCAATGG AACAGAATAG AGACCAGAGA AAGAAGACCA CACATCTACA GCCATCTGAT CATCGACAAA CCTGACAAAA ACAAGCAATG GGGAAAAGAT TCCCTATTTA ATAAATGGTG CTGGGAAAAC TGGCTAGCCA TATGCAGAAA ATTGAAACTG ACCCCTTCCT TACACCTTAT ACAAAAATTA ACTCAAGATT AAAGACTTAA TGTAAAACCT AAAACTATAA AAACCCTAGA AGAAAATCTA TTTAATACCA TTCAAGACAT AGGCACAAGC AAAGGTTTCA TGACAAAAAC ATCAAAAGCA ATTGCAACAA AAGCAAAAAT TACAAATGGG ATCTAATTAA ACTAAAGAGC TCCTGCACAG CAAAAGAAAC TATCATTAGA GTGAACAGGC AACCTACAGA ATGGGAGAAC ATTTTTGCAA TCTATCCATC TGACAAAGGT CTAATATCCA GAACCTACAA GGAACTTAAA ACAAATTTAC AAGGAAAAAA ACAACCCCAT CAAAAAGTGG ACAAAGGACA TGAACAGACA CTTCTCAAAA GAAGACATTT ATGTGGCCAA CAAACATATA AAAAAAAGCT CAACCTTACT GATCATTAGA GAAATGCAAA GGAGAACCAC AATGAGATAC CATCTCATGC CGGTCAGAAT GGTGATTATT AAAAGTCAA AAAACAACAG ATGCTGGCGA GGCTGTGGAG AAGTAGGAAC ACTTTTACAT TGTTGGTGGG AATGTAAATT AGTTCAACCG TTGTGGAAGT GTGTGTGGCT ATTCCTCAAA GATCTAGAAC TAGAAATACT ATTTGTCCCA GCAATCCCAT TACTGGGTAT ATACCCAAAG GAATATAAAC CATTTTATTA TAAAGATACA TGCACATTTT TGTTCATTGC AGCACTCTTC ACAATAGCAA AGACACAATA GCAAATGCCC ATCAAAGATA GACTGGATAA AGAAAATGTG GTACATATAC ACCATGGAAT ACTGTGCAGT GCAGCCATTA CAGCTTTTGG TGATACAGTG AATCAGATTT TTCATTAATT CTTTTAATTG GTTATTACTG AACGTGAAAA AGTAATGTTT GTATTGAAAT CTTGAGTCTG GCCATGTTTC TATTTTAAAT TCATAAAGAA TTCTAACAAG AGGAATTCCA AGAATGTCAT AAATGGATGT TTCTCCATGG ATGAAGGAAC TGTTTTATTC ACTTGCTGAT AATTCAGCCT AATCCAGTTT GACATCATAT AGATAAGTAG TTGAATTATG GATTTAAAAT ACATATCATT TTCTAACTCC AAAGGTAATA CTTATTTAAA TGGTTTTGAA AATATAGAAA GGCACAATTT CTTTTTAAAT CTGTTATTCT | |

TABLE 1-continued

Melanoma Biomarker/Housekeeper Sequence Information

| Gene Name | RefSeq Accession | Sequence | SEQ ID NO: |
|---|---|---|---|
| | | CCACCACCAC TCAATCTGTC TATCATCTAT CTCTCCATTC ATTCTTCCAT TTGTTTATAT CTGTTAATCT TTGTATGTGT TCATGTATAG CTTTTACATG ATTGGAATCA TAATGCATAT TCCATTTTGA AGTCTGCTTT TTTTTACACA AAAATATGTT GTGAATATTT TCCTATATTA TGAAATATCA TTAGCTGAGC TTTTAGAATT GACTGCATGT TTTGGTACCA TTTAGATATA GTTTAAGATA CTTAGAAGTT ATGTGGCTTT GCCACTATGG ATGAATCTTA TTTACTCAAT ATTAATTACT TACAAATAAC CTCACCTAAA CACTACTCAG CCATAAAAAG GAATGAATTA ATGACATTCA CAGCAACCTG GAGACTATTA CTCTAAAGGA AGTAACTGAG GAATGGAAAA CCAAACATTG TATGTTCTCA CTCATAAGTG GGAGATAAGC TATGAGGATG CAAAGGCATA AGAAGGATAC AATGGACTTT GGGGACTTAG GGGAAAGGGT GGGAGGGGGG TGAAGGATAA AAGAATACAA ATTGGGTTCA GTGTATACTG CTCAGGTGAT GGGTGCACCA GAATCTCACA AGTAACCACT TAATTACTTA CGCATGTAAC CAGATACCAC CTGTTCCCCA AACACCTATG GAAATAATTT TGTTTTTTTT TTTAAAAAAG GAATGAGATC ATGTCCTTTG CAGGGACATG GATGAAGCTG GAAGCCATTA TCCTCAGCAA ACTAACAGAG GAGCAGGAAA CCAAACACCA CATGTTCTCA CTTGTAAGCG GAAGCTGAAC AATGAGAACA CACGGACACA GGGATGAGAT CAACACACAC TGGGGCCTGA TGCAGGGGCC GTAGCGGGGA GAGCATCAGG ATAACTAGCT AATGCATGTG GGGCTTAATA CCTAGGTGAT AGGTTGATAG GTGCAGCAAA CCACCATGGG ACACGTTTAC CTATGTAACA AACCCGCACA TCCTGCACTT GTATCCAGAA CTTAAAATAT TTTAAAAATC TTTAGAGAAT ACAAAAAAAA AAAAAAAGAT TCTTCAATGC ATACACAATA AAATTGCAGT TCAGTCAAAC ATTGGAAGTC TTTCTCTGAC TGTCTAGTTG GTATCTTCAT TTTCAGCTTC TTCAAGATCC CACTCCAAAC ACTGTTAGCT CAGCCAAATT GAACAGCTCA TATCTCCTAC CTCTGGATCT TTGGTTCTGG TGATTGTATA TTTCTGGACC ATCTGGAACC CCAGCATATC ACCCTACCCC ACATCTCCAC ATCCCCAAAA TATAACCATA CTTCAAGGGC AGTTCAAATA CCATCTCCTT CTATCCTCCA TGAAGTCAGT TATCTCTTCC ATTGGAATTA TCGCCCCCTC TCCTGAACAG TACTATTTCG TGTGAATCTC CTCCAAGCCT TCTTTTCATT TTATATCTCA TGCTGTAATT CTTGGAAAGT ATGCTGTAGC TCAAGTGCAG AATTCTCATC AGTTTTATCT TTATATCTCT CCTAAACACT TTACCTGATG AAGAGCCTGG CATACACATA AATATATATT GAATGAATCA GTGATGGATT GAAAAGAGAA ATGATGGATC TCCTAAATTT TAACTTTTAT AAAATATTTT GATACATTCA TGACCTTACT TTAGCAAGCA ATGAACGTGA TGTAAACTAT TGTTGATATA GTTTTTATAT TGGAAGTGTA AGTAGTTTGT GGCATGGGAT TGTGACATAT CCTAGGTTTC CTCATCTTCT TTTTATTGAA ATGTAATTCA CAAGCCATAA AATTTGCCCC TTTAAAGTAA ATGATGCAGT GGATTTTAGT ATATTTACAG AGTTGTGCAA TCATCACCAC TATCTAATTC CAGAACATTT CCATCTACCT AGAAACTCCA TACCAGTGAG CTGCCACTCT AATCCTCCTC TTCCCCCAGC CTCTAGAAAC AATAATCCAT TTTCTGTCTC TATGATTTGC CTGTTCTAGA TATTTTATAA AAATAAACAT GTGGCCTTTC GTGTCTGACT TCCTTCACTT AAAAAAAAAA AAAAAAA | |
| CFLAR-AS1 | NR_040030.1 | CATGCATACA GCCCAGTCTA ACGTACAGGA TCAAAAGAG ACCTTATTTC GGCTGGCAAT TACCTTACCC GCTTGTTCAT TATCTGACTC CTGCACTCCT CCCAAGTGTT CAATGTTAAC CAGATGGCAA AGTTAACCAG ACAGAGGAAA TCCACATAAT TACTCTAGAT GAAGCCCCCT AACTGCGGAT TAGAAGGAAA AGAGATGAAG GGTGCTGCAC TAATAATAAC AACCATTTTC AACCAAGGCA GGATTCTGGG CCTAGAATCT TCAGTGACAA ATTACCAGGA GAGGAGGAGG GAAATGAAGA GCTGGAGGCC TAGGGAGATG GTGTGAGGAG AGGAGACTGT GCCTTTCCAC TTCTTAATAA TTAATGTTCT CCTGCTGCTC TGAGTCTGCA TCACCAGTGA TTCAGTTTGA GTCAGACATC CAACAACAAC TGAGCAAAAG AATCATCTCA GATCCAAGCA ATGGTGACGC GCAGATAGAA GAGACTGAGG CCAACGACCA AAGCAAAGGA CAGCAGAACT GACTGACACA GCTCAGAAAA TATCCAAAGC TCTGTATGCT CTGGAAAGGA AGACAAGAAA TGCTAAAGAC TCTGGATATT GCTCTGTTTC TATAAGGTCC CACCCATATA CCATCTCTTC TTTTGGATTT CCTTTGGCAG GGTTCCCTTG TATGGAAGTT CTCAGGAGAA CAACACTCTC AGAGTCCCAC TGTCTCAAAG AATTCTTAAT GGACAGCTAT ACTTGGCCCC AAGGTTTCAA CCTCACACTG AAGAAAGTGA CATAAGAAAA CACAAGTCCC AGTGCTATCA GGGGCTATCT GGAAAAGCTG | 5 |

TABLE 1-continued

Melanoma Biomarker/Housekeeper Sequence Information

| Gene Name | RefSeq Accession | Sequence | SEQ ID NO: |
|---|---|---|---|
| | | CTTAAACAGC AAGTGAAAGA AGGCTCTCCC CTACCCCGTT CTAGACTCAC CCTGAAGTTA TTTGAAGGAT CCTTGAGACT CTTTTGGATT GCTGCTTGGA GAACATTCCT GTAACTTGTC CCTGCTCCTT GAACTATAAA AGCAGAAGGG AGGTACTGAG TTAAAACTTA CAAATTATTA TCAAATAAAT CTTCAATAGT G | |
| CHP1 | NM_007236.4 | ACCACCCCTG GGTTCCCTCC CGGGTCCGCA GTGGAAACAC TGCCCTCTCC CTTCTTGACC CCTAGCCCTT CCTTCCCTCC CTCCTTCCCT CCTGTCGCCG TCTCTTCTGG CGCCGCTGCT CCCGGAGGAG CTCCCGGCAC GGCGATGGGT TCTCGGGCCT CCACGTTACT GCGGGACGAA GAGCTCGAGG AGATCAAGAA GGAGACCGGC TTTTCCCACA GTCAAATCAC TCGCCTCTAC AGCCGGTTCA CCAGCCTGGA CAAAGGAGAG AATGGGACTC TCAGCCGGGA AGATTTCCAG AGGATTCCAG AACTTGCCAT CAACCCACTG GGGGACCGGA TCATCAATGC CTTCTTTCCA GAGGGAGAGG ACCAGGTAAA CTTCCGTGGA TTCATGCGAA CTTTGGCTCA TTTCCGCCCC ATTGAGGATA ATGAAAAGAG CAAAGATGTG AATGGACCCG AACCACTCAA CAGCCGAAGC AACAAACTGC ACTTTGCTTT TCGACTATAT GATTTGGATA AAGATGAAAA GATCTCCCGT GATGAGCTGT TACAGGTGCT ACGCATGATG GTCGGAGTAA ATATCTCAGA TGAGCAGCTG GGCAGCATCG CAGACAGGAC CATTCAGGAG GCTGATCAGG ATGGGGACAG TGCCATATCT TTCACAGAAT TTGTTAAGGT TTTGGAGAAG GTGGATGTAG AACAGAAAAT GAGCATCCGA TTTCTTCACT AAAGGAGACC AAACTGTTCC TTGCGGTCTA GTATTTAAGA ACTGGAACTT GAAAGTCCTC CTTCTACCAA CTCCACCTCC ACCCCCTCAT TCCCCTTCTC CCAAAGTACT ACTGCTGTTG CATGACAACC CCAAATATGT TCTGTCAACA CAAACCTGCC TTTGGTGTAT AAACAGGGCA TTACAGAATG GTACACCCTA TATATTTCTG TTCAGTATCC ATTCACTAGT TCTTCATTTA TAAATATCAT CTTCCCCATT CTGCTGCTGA ATGCCACACA TCCATCCAGT CTGAGAAAGT GAGAGAGGCA ATCATGCCAA GAACAAGCCA GCAAAGCTCT TTCACCAGAT GTAGACTGTA GCCCTGCTGC CTTCCCTCCA GCGAGTCTGC CAGCATGCTT CTTCATCCTT TTTATATGTT CTTTGCTTCC TACTTCCCTG TCTTCCAACA TACTGTTCAC TTACTCTGGC AGTCTTTCTG CTTTTCATTA AGCCTCAAAA TCTCCTCTGT TCTACTTGGC ACCACAAGCT ATGTCCTATA TATGTATTTC TGACTTGGCA GGATAGTTCA GGGGTCTGGC AGTTTTTATT TACCTTCATT ATTAAATGGG CCTCTGGGAT GTTGCCTCTT CAGGAGCTTT TTGGTAATCA ATACTTCTCT CAGAAGTATG AGACCATCCT CTGCACTCTG CTCTGTCATC AAAGGCTGCT GGGTGGAGAT ACCCTTTTTG AAAGGTGGCC TTGGTGAGAG GTATGGAGCC AAGTCTTCTA GGTTGCTTGC CCACATCACT CTATCTCTGG CCTCTGATTC TCAACTTTGT ACCTGTGTGG CTCCTCTTGT TAGTGCAATG TTGACTGTTG AAAAAGCAGC AGTATGCTTA CAGGTTTGCT TAGTTTGGGG ACACCGTTAC CACCAGAATG GCTGCTCTGA CAATATGCCT AGGGACTTTC TCATGGCTTT TATTTAATAA GGAGGCTGGG CACCCTATAA AGCCTCATGC ATTCACACCT TTGCAGCATG GTTTATGCCT CAGTGTTATG TGCACTGGAA TGTTTTCCAC TTCACATTTC CAAGTAGAAA TATTAGTGTT ACGGAAGTGC CTAATATCCC AGTCCAAATT TTTTTTTTTT TTTTTTTTT TTTTTGAGAC AGAGTCTTGC TCTGTCACCC AGGCTGGAGT GCAGTGGTGC GATCGCTCAC TGCAACCTCA GCCTCCTGGA TTTAAGTGAT TCTCCTGCCT CAGCCTCCCA AGTAGCTGGG ATTACAGGTG TGCACCACCA TGCCCGGCTA ATTTTTTGTA TTTTTAGTGG AGACAGGGTT TCACCATGTT GGCCAGGCTG GTCTCGAACT CCTGACCTCG TGATCCGCCT GCCTCAGCCT CCCAAAGTGC TGGGATTACA GGTGTGAGCC ACCACGCCTG GCCCCAGTCC AAAATATTTA AAGATTGTTT CCTTAGTGTC TTGAAGTTTT GCACAAAATT CTTTTTTTTG AGATGGAGTC TCACTCTGTC ACCCAGGCTG GAGTGCAGTG GCGTGATCTT GGCTCACTGC AACCTCTGCC TCCTGGGTTC AAGCAATTCT CCCACCTCAG CCTCCCAAGT AGCTGGGATT ACAGACGTGT GCCACCATAC CTGGGTAATT TTTGCATTTT TAGTGGAGAG GGAGTTTCAC CATGTTGGCC AGGTTGGTCT TGAACTCCTG ACCTCAGGTG ATCCTCCTGC CTCGGCCTCC CAAAGTGCTG GATTACAGG CATGAGCCAC CGTGCTCAGC CGCAAAATTC TTTATGAATT TTACACTTGG CAAATGTTAA TGACGGAAGC CATAGTCTGC TCCTAATACA TGTCCAAAGC ATTGACTGTT GTGTCATTAG CTGCCTGGTT ACATTAGCTC CCTGGCTTCT TGTTTAGACC ACTGCTAATC CCTTAAAAAC AAGAGGTCTG GCACTAGTAG CACAACCTAA GGTGGCATTA CAGATCTTTG AGCGAGCCAC | 6 |

TABLE 1-continued

Melanoma Biomarker/Housekeeper Sequence Information

| Gene Name | RefSeq Accession | Sequence | SEQ ID NO: |
|---|---|---|---|
| | | AGCAACTTTT CTGCCAAGTC AGCTTAGTTT AGACTTCAGT<br>GAATCAGGCT ATTGCTATCC TAATGTATGT CTCTATGAGT<br>GTATTTAGCC ACACATCTGC CCTTGGTTGA CTTTCTGACT<br>CATTGCTTGC TTGCTTGTTT CCTTGCTTTG GAAAACTATT<br>GAAGATTGCT AAAAAATACC ACTGCAAAGT GATGGAAAAG<br>GGTGGAGAAC AGGGGAGTAG CCAGGCTGGA TGGCTCAAAT<br>ATAAATGAAT GAGGAATTCT TTATGAAGTA TCAGTCAGAT<br>TTTATGATTA AGTGATGTAA TATAGGAATT ATGTAAAAGG<br>GAAGAATGTC TGATACTGAT CTATTAGAGA GGTACTTTAG<br>AGGCTTCTTG ATTGGCATAA AGTTCCTAAG GTTATAGATT<br>TTCCCCCCTT TTGGCTGTAT AGCAAAGTGT TTTAATCCAC<br>GGTTGTGCCT TATTGTTCCA TTAAAATTGT ATCTTCGATC<br>CATCAATAAA TACTTGTGGT TGAAACAAAA | |
| DDX55 | NM_020936.2 | AGCGGAAGTG CTCGTTGGGG GTGCACAAGG CGCGTTCGAG<br>CAGCGGCGAC CGACGCGGCG AAGGAGCGCG CCATGGAGCA<br>TGTGACAGAG GGCTCCTGGG AGTCGCTGCC TGTGCCGCTG<br>CACCCGCAGG TGCTGGGCGC GCTGCGGGAG CTGGGCTTCC<br>CGTACATGAC GCCGGTGCAG TCCGCAACCA TCCCTCTGTT<br>CATGCGAAAC AAAGATGTCG CTGCAGAAGC GGTCACAGGT<br>AGTGGCAAAA CACTCGCTTT TGTCATCCCC ATCCTGGAAA<br>TTCTTCTGAG AAGAGAAGAG AAGTTAAAAA AGAGTCAGGT<br>TGGAGCCATA ATCATCACCC CCACTCGAGA GCTGGCCATT<br>CAAATAGACG AGGTCCTGTC GCATTTCACG AAGCACTTCC<br>CCGAGTTCAG CCAGATTCTT TGGATCGGAG GCAGGAATCC<br>TGGAGAAGAT GTTGAGAGGT TTAAGCAACA AGGTGGGAAC<br>ATCATTGTGG CCACTCCAGG CCGCTTGGAG GACATGTTCC<br>GGAGGAAGGC CGAAGGCTTG GATCTGGCCA GCTGTGTGCG<br>ATCCCTGGAT GTCCTGGTGT TGGATGAGGC AGACAGACTT<br>CTGGACATGG GGTTTGAGGC AAGCATCAAC ACCATTCTGG<br>AGTTTTTGCC AAAGCAGAGG AGAACAGGCC TTTTCTCTGC<br>CACTCAGACG CAGGAAGTGG AGAACCTGGT GAGAGCGGGC<br>CTCCGGAACC CTGTCCGGGT CTCAGTGAAG GAGAAGGGCG<br>TGGCAGCCAG CAGTGCCCAG AAGACCCCCT CCCGCCTGGA<br>AAACTACTAC ATGGTATGCA AGGCAGATGA GAAATTTAAT<br>CAGCTGGTCC ATTTTCTTCG CAATCATAAG CAGGAGAAAC<br>ACCTGGTCTT CTTCAGCACC TGTGCCTGTG TGGAATACTA<br>TGGGAAGGCT CTGGAAGTGC TGGTGAAGGG CGTGAAGATT<br>ATGTGCATTC ACGGAAAGAT GAAATATAAA CGCAATAAGA<br>TCTTCATGGA GTTCCGCAAA TTGCAAAGTG GGATTTTAGT<br>GTGCACTGAT GTGATGGCCC GGGGAATTGA TATTCCTGAA<br>GTCAACTGGG TTTTGCAGTA TGACCCTCCC AGCAATGCAA<br>GTGCCTTCGT GCATCGCTGC GGTCGCACAG CTCGCATTGG<br>CCACGGGGGC AGCGCTCTGG TGTTCCTCCT GCCCATGGAA<br>GAGTCATACA TCAATTTCCT TGCAATTAAC CAAAAATGCC<br>CCCTGCAGGA GATGAAGCCC CAGAGAAACA CAGCGGACCT<br>TCTGCCAAAA CTCAAGTCCA TGGCCCTGGC TGACAGAGCT<br>GTGTTTGAAA AGGGCATGAA AGCTTTTGTG TCATATGTCC<br>AAGCTTATGC AAAGCATGAA TGCAACCTGA TTTTCAGATT<br>AAAGGATCTT GATTTTGCCA GCCTTGCTCG AGGTTTTGCC<br>CTGCTGAGGA TGCCCAAGAT GCCAGAATTG AGAGGAAAGC<br>AGTTTCCAGA TTTTGTGCCC GTGGACGTTA ATACCGACAC<br>GATTCCATTT AAAGATAAAA TCAGAGAAAA GCAGAGGCAG<br>AAACTCCTGG AGCAACAAAG AAGAGAGAAA ACAGAAAATG<br>AAGGGAGAAG AAAATTCATA AAAAATAAAG CTTGGTCAAA<br>GCAGAAGGCC AAAAAAGAAA AGAAGAAAAA AATGAATGAG<br>AAAAGGAAAA GGGAAGAGGG TTCTGATATT GAAGATGAGG<br>ACATGGAAGA ACTTCTTAAT GACACAAGAC TCTTGAAAAA<br>ACTTAAGAAA GGCAAAATAA CTGAAGAAGA ATTTGAGAAG<br>GGCTTGTTGA CAACTGGCAA AGAACAATC AAGACAGTGG<br>ATTTAGGGAT CTCAGATTTG GAAGATGACT GCTGATTCCA<br>GTGCCACAGA TGAACCCACA AGGACATAGC TGTTCCCTAA<br>CTTGGTGGAT GGCTCCAGTT TGCTTTTAAC GAAAATCACA<br>ACTTCAGGAG ACATCTGAAA AGAATGATGT CTCTGAAAGC<br>TGTCCTTTCA GATGAGGGAG AAATGAAGGA TTTCACACTT<br>CAGAATATTT TACTAAAAAC ATTCCAGTCT TGGCCGGGTG<br>CGGTGGCTCC TGCCTATAAT CCCAGCACTT TGGGAGGCTG<br>AGGCAGGAGG ATCACTTGAG CCCAGGAGTT CAAGACCAGC<br>CTGGGAACAC AGCGAGACCC TCTCATTAAA AACAACAAAA<br>CAAAACAATT CCAGTCTTGG AGTAGTCTAA CAGAAGAAAA<br>TGTAAAATTA TTTGAGTGTA AATAATAGAT GTCAGTATTT<br>ATCATGATGG GTCACATATA GACATATGTA CATATTATAT<br>ATATATATAT ATATATATAT ATATATATAT ATATATATAT<br>ATAAGCTCTT TTTTCTGAGG CTATTTTATA GTTATTTTTA | 7 |

TABLE 1-continued

Melanoma Biomarker/Housekeeper Sequence Information

| Gene Name | RefSeq Accession | Sequence | SEQ ID NO: |
|---|---|---|---|
| | | AACATAAAGA TACAGAAGTC TTCTTGACTT CTGATTTTCA<br>AAACCATTCC TCAGTATCTT CAGGCATTTG ACCTCCTGAA<br>TGTGCTTGGC CCTGGGCTTC AGTTATCCTT TGATGTCCTG<br>CAGGGGTGGC TAATGTGCTG GGGTTTTTCT GTGTTAATAG<br>TCACAGTATT GTTTTATTGG TGAATAGCTG AAAAACAGAG<br>GGATTAAGTC ATATTCCGGG AAAGAGAATT ATAGTTTTTA<br>TGCCTCCTGT TGAATAAATG GTGTCCTGAT TGCCTGGG | |
| DMD | NM_000109.3 | CGTTAAATGC AAACGCTGCT CTGGCTCATG TGTTTGCTCC<br>GAGGTATAGG TTTTGTTCGA CTGACGTATC AGATAGTCAG<br>AGTGGTTACC ACACCGACGT TGTAGCAGCT GCATAATAAA<br>TGACTGAAAG AATCATGTTA GGCATGCCCA CCTAACCTAA<br>CTTGAATCAT GCGAAAGGGG AGCTGTTGGA ATTCAAATAG<br>ACTTTCTGGT TCCCAGCAGT CGGCAGTAAT AGAATGCTTT<br>CAGGAAGATG ACAGAATCAG GAGAAAGATG CTGTTTTGCA<br>CTATCTTGAT TTGTTACAGC AGCCAACTTA TTGGCATGAT<br>GGAGTGACAG GAAAAACAGC TGGCATGGAA GATGAAAGAG<br>AAGATGTTCA AAAGAAAACA TTCACAAAAT GGGTAAATGC<br>ACAATTTTCT AAGTTTGGGA AGCAGCATAT TGAGAACCTC<br>TTCAGTGACC TACAGGATGG GAGGCGCCTC CTAGACCTCC<br>TCGAAGGCCT GACAGGGCAA AAACTGCCAA AAGAAAAAGG<br>ATCCACAAGA GTTCATGCCC TGAACAATGT CAACAAGGCA<br>CTGCGGGTTT TGCAGAACAA TAATGTTGAT TTAGTGAATA<br>TTGGAAGTAC TGACATCGTA GATGGAAATC ATAAACTGAC<br>TCTTGGTTTG ATTTGGAATA TAATCCTCCA CTGGCAGGTC<br>AAAAATGTAA TGAAAAATAT CATGGCTGGA TTGCAACAAA<br>CCAACAGTGA AAAGATTCTC CTGAGCTGGG TCCGACAATC<br>AACTCGTAAT TATCCACAGG TTAATGTAAT CAACTTCACC<br>ACCAGCTGGT CTGATGGCCT GGCTTTGAAT GCTCTCATCC<br>ATAGTCATAG GCCAGACCTA TTTGACTGGA ATAGTGTGGT<br>TTGCCAGCAG TCAGCCACAC AACGACTGGA ACATGCATTC<br>AACATCGCCA GATATCAATT AGGCATAGAG AAACTACTCG<br>ATCCTGAAGA TGTTGATACC ACCTATCCAG ATAAGAAGTC<br>CATCTTAATG TACATCACAT CACTCTTCCA AGTTTTGCCT<br>CAACAAGTGA GCATTGAAGC CATCCAGGAA GTGGAAATGT<br>TGCCAAGGCC ACCTAAAGTG ACTAAAGAAG AACATTTTCA<br>GTTACATCAT CAAATGCACT ATTCTCAACA GATCACGGTC<br>AGTCTAGCAC AGGGATATGA GAGAACTTCT TCCCCTAAGC<br>CTCGATTCAA GAGCTATGCC TACACACAGG CTGCTTATGT<br>CACCCACCTCT GACCCTACAC GGAGCCCATT TCCTTCACAG<br>CATTTGGAAG CTCCTGAAGA CAAGTCATTT GGCAGTTCAT<br>TGATGGAGAG TGAAGTAAAC CTGGACCGTT ATCAAACAGC<br>TTTAGAAGAA GTATTATCGT GGCTTCTTTC TGCTGAGGAC<br>ACATTGCAAG CACAAGGAGA GATTTCTAAT GATGTGGAAG<br>TGGTGAAAGA CCAGTTTCAT ACTCATGAGG GGTACATGAT<br>GGATTTGACA GCCCATCAGG GCCGGGTTGG TAATATTCTA<br>CAATTGGGAA GTAAGCTGAT TGGAACAGGA AAATTATCAG<br>AAGATGAAGA AACTGAAGTA CAAGAGCAGA TGAATCTCCT<br>AAATTCAAGA TGGGAATGCC TCAGGGTAGC TAGCATGGAA<br>AAACAAAGCA ATTTACATAG AGTTTTAATG GATCTCCAGA<br>ATCAGAAACT GAAAGAGTTG AATGACTGGC TAACAAAAAC<br>AGAAGAAAGA ACAAGGAAAA TGGAGGAAGA GCCTCTTGGA<br>CCTGATCTTG AAGACCTAAA ACGCCAAGTA CAACAACATA<br>AGGTGCTTCA AGAAGATCTA GAACAAGAAC AAGTCAGGGT<br>CAATTCTCTC ACTCACATGG TGGTGGTAGT TGATGAATCT<br>AGTGGAGATC ACGCAACTGC TGCTTTGGAA GAACAACTTA<br>AGGTATTGGG AGATCGATGG GCAAACATCT GTAGATGGAC<br>AGAAGACCGC TGGGTTCTTT TACAAGACAT CCTTCTCAAA<br>TGGCAACGTC TTACTGAAGA ACAGTGCCTT TTTAGTGCAT<br>GGCTTTCAGA AAAAGAAGAT GCAGTGAACA AGATTCACAC<br>AACTGGCTTT AAAGATCAAA ATGAAATGTT ATCAAGTCTT<br>CAAAAACTGG CCGTTTTAAA AGCGGATCTA GAAAAGAAAA<br>AGCAATCCAT GGGCAAACTG TATTCACTCA AACAAGATCT<br>TCTTTCAACA CTGAAGAATA AGTCAGTGAC CCAGAAGACG<br>GAAGCATGGC TGGATAACTT TGCCCGGTGT TGGGATAATT<br>TAGTCCAAAA ACTTGAAAAG AGTACAGCAC AGATTTCACA<br>GGCTGTCACC ACCACTCAGC CATCACTAAC ACAGACAACT<br>GTAATGGAAA CAGTAACTAC GGTGACCACA AGGGAACAGA<br>TCCTGGTAAA GCATGCTCAA GAGGAACTTC CACCACCACC<br>TCCCCAAAAG AAGAGGCAGA TTACTGTGGA TTCTGAAATT<br>AGGAAAAGGT TGGATGTTGA TATAACTGAA CTTCACAGCT<br>GGATTACTCG CTCAGAAGCT GTGTTGCAGA GTCCTGAATT<br>TGCAATCTTT CGGAAGGAAG GCAACTTCTC AGACTTAAAA<br>GAAAAAGTCA ATGCCATAGA GCGAGAAAAA GCTGAGAAGT | 8 |

TABLE 1-continued

Melanoma Biomarker/Housekeeper Sequence Information

| Gene Name | RefSeq Accession | Sequence | SEQ ID NO: |
|---|---|---|---|
| | | TCAGAAAACT GCAAGATGCC AGCAGATCAG CTCAGGCCCT | |
| | | GGTGGAACAG ATGGTGAATG AGGGTGTTAA TGCAGATAGC | |
| | | ATCAAACAAG CCTCAGAACA ACTGAACAGC CGGTGGATCG | |
| | | AATTCTGCCA GTTGCTAAGT GAGAGACTTA ACTGGCTGGA | |
| | | GTATCAGAAC AACATCATCG CTTTCTATAA TCAGCTACAA | |
| | | CAATTGGAGC AGATGACAAC TACTGCTGAA AACTGGTTGA | |
| | | AAATCCAACC CACCACCCCA TCAGAGCCAA CAGCAATTAA | |
| | | AAGTCAGTTA AAAATTTGTA AGGATGAAGT CAACCGGCTA | |
| | | TCAGGTCTTC AACCTCAAAT TGAACGATTA AAAATTCAAA | |
| | | GCATAGCCCT GAAAGAGAAA GGACAAGGAC CCATGTTCCT | |
| | | GGATGCAGAC TTTGTGGCCT TTACAAATCA TTTTAAGCAA | |
| | | GTCTTTTCTG ATGTGCAGGC CAGAGAGAAA GAGCTACAGA | |
| | | CAATTTTTGA CACTTTGCCA CCAATGCGCT ATCAGGAGAC | |
| | | CATGAGTGCC ATCAGGACAT GGGTCCAGCA GTCAGAAACC | |
| | | AAACTCTCCA TACCTCAACT TAGTGTCACC GACTATGAAA | |
| | | TCATGGAGCA GAGACTCGGG GAATTGCAGG CTTTACAAAG | |
| | | TTCTCTGCAA GAGCAACAAA GTGGCCTATA CTATCTCAGC | |
| | | ACCACTGTGA AAGAGATGTC GAAGAAAGCG CCCTCTGAAA | |
| | | TTAGCCGGAA ATATCAATCA GAATTTGAAG AAATTGAGGG | |
| | | ACGCTGGAAG AAGCTCTCCT CCCAGCTGGT TGAGCATTGT | |
| | | CAAAAGCTAG AGGAGCAAAT GAATAAACTC CGAAAAATTC | |
| | | AGAATCACAT ACAAACCCTG AAGAAATGGA TGGCTGAAGT | |
| | | TGATGTTTTT CTGAAGGAGG AATGGCCTGC CCTTGGGGAT | |
| | | TCAGAAATTC TAAAAAAGCA GCTGAAACAG TGCAGACTTT | |
| | | TAGTCAGTGA TATTCAGACA ATTCAGCCCA GTCTAAACAG | |
| | | TGTCAATGAA GGTGGGCAGA AGATAAAGAA TGAAGCAGAG | |
| | | CCAGAGTTTG CTTCGAGACT TGAGACAGAA CTCAAAGAAC | |
| | | TTAACACTCA GTGGGATCAC ATGTGCCAAC AGGTCTATGC | |
| | | CAGAAAGGAG GCCTTGAAGG GAGGTTTGGA GAAAACTGTA | |
| | | AGCCTCCAGA AAGATCTATC AGAGATGCAC GAATGGATGA | |
| | | CACAAGCTGA AGAAGAGTAT CTTGAGAGAG ATTTTGAATA | |
| | | TAAAACTCCA GATGAATTAC AGAAAGCAGT TGAAGAGATG | |
| | | AAGAGAGCTA AAGAAGAGGC CCAACAAAAA GAAGCGAAAG | |
| | | TGAAACTCCT TACTGAGTCT GTAAATAGTG TCATAGCTCA | |
| | | AGCTCCACCT GTAGCACAAG AGGCCTTAAA AAAGGAACTT | |
| | | GAAACTCTAA CCACCAACTA CCAGTGGCTC TGCACTAGGC | |
| | | TGAATGGGAA ATGCAAGACT TTGGAAGAAG TTTGGGCATG | |
| | | TTGGCATGAG TTATTGTCAT ACTTGGAGAA AGCAAACAAG | |
| | | TGGCTAAATG AAGTAGAATT TAAACTTAAA ACCACTGAAA | |
| | | ACATTCCTGG CGGAGCTGAG GAAATCTCTG AGGTGCTAGA | |
| | | TTCACTTGAA AATTTGATGC GACATTCAGA GGATAACCCA | |
| | | AATCAGATTC GCATATTGGC ACAGACCCTA ACAGATGGCG | |
| | | GAGTCATGGA TGAGCTAATC AATGAGGAAC TTGAGACATT | |
| | | TAATTCTCGT TGGAGGGAAC TACATGAAGA GGCTGTAAGG | |
| | | AGGCAAAAGT TGCTTGAACA GAGCATCCAG TCTGCCCAGG | |
| | | AGACTGAAAA ATCCTTACAC TTAATCCAGG AGTCCCTCAC | |
| | | ATTCATTGAC AAGCAGTTGG CAGCTTATAT TGCAGACAAG | |
| | | GTGGACGCAG CTCAAATGCC TCAGGAAGCC CAGAAAATCC | |
| | | AATCTGATTT GACAAGTCAT GAGATCAGTT TAGAAGAAAT | |
| | | GAAGAAACAT AATCAGGGGA AGGAGGCTGC CCAAAGAGTC | |
| | | CTGTCTCAGA TTGATGTTGC ACAGAAAAAA TTACAAGATG | |
| | | TCTCCATGAA GTTTCGATTA TTCCAGAAAC CAGCCAATTT | |
| | | TGAGCAGCGT CTACAAGAAA GTAAGATGAT TTTAGATGAA | |
| | | GTGAAGATGC ACTTGCCTGC ATTGGAAACA AAGAGTGTGG | |
| | | AACAGGAAGT AGTACAGTCA CAGCTAAATC ATTGTGTGAA | |
| | | CTTGTATAAA AGTCTGAGTG AAGTGAAGTC TGAAGTGGAA | |
| | | ATGGTGATAA AGACTGGACG TCAGATTGTA CAGAAAAAGC | |
| | | AGACGGAAAA TCCCAAAGAA CTTGATGAAA GAGTAACAGC | |
| | | TTTGAAATTG CATTATAATG AGCTGGGAGC AAAGGTAACA | |
| | | GAAAGAAAGC AACAGTTGGA GAAATGCTTG AAATTGTCCC | |
| | | GTAAGATGCG AAAGGAAATG AATGTCTTGA CAGAATGGCT | |
| | | GGCAGCTACA GATATGGAAT TGACAAAGAG ATCAGCAGTT | |
| | | GAAGGAATGC CTAGTAATTT GGATTCTGAA GTTGCCTGGG | |
| | | GAAAGGCTAC TCAAAAAGAG ATTGAGAAAC AGAAGGTGCA | |
| | | CCTGAAGAGT ATCACAGAGG TAGGAGAGGC CTTGAAAACA | |
| | | GTTTTGGGCA AGAAGGAGAC GTTGGTGAAA GATAAACTCA | |
| | | GTCTTCTGAA TAGTAACTGG ATAGCTGTCA CCTCCCGAGC | |
| | | AGAAGAGTGG TTAAATCTTT TGTTGGAATA CCAGAAACAC | |
| | | ATGGAAACTT TTGACCAGAA TGTGGACCAC ATCACAAAGT | |
| | | GGATCATTCA GGCTGACACA CTTTTGGATG AATCAGAGAA | |
| | | AAAGAAACCC CAGCAAAAAG AAGACGTGCT TAAGCGTTTA | |
| | | AAGGCAGAAC TGAATGACAT ACGCCCAAAG GTGGACTCTA | |
| | | CACGTGACCA AGCAGCAAAC TTGATGGCAA ACCGCGGTGA | |
| | | CCACTGCAGG AAATTAGTAG AGCCCCAAAT CTCGAGAGCTC | |

TABLE 1-continued

Melanoma Biomarker/Housekeeper Sequence Information

| Gene Name | RefSeq Accession | Sequence | SEQ ID NO: |
|---|---|---|---|
| | | AACCATCGAT TTGCAGCCAT TTCACACAGA ATTAAGACTG | |
| | | GAAAGGCCTC CATTCCTTTG AAGGAATTGG AGCAGTTTAA | |
| | | CTCAGATATA CAAAAATTGC TTGAACCACT GGAGGCTGAA | |
| | | ATTCAGCAGG GGGTGAATCT GAAAGAGGAA GACTTCAATA | |
| | | AAGATATGAA TGAAGACAAT GAGGGTACTG TAAAAGAATT | |
| | | GTTGCAAAGA GGAGACAACT TACAACAAAG AATCACAGAT | |
| | | GAGAGAAAGC GAGAGGAAAT AAAGATAAAA CAGCAGCTGT | |
| | | TACAGACAAA ACATAATGCT CTCAAGGATT TGAGGTCTCA | |
| | | AAGAAGAAAA AAGGCTCTAG AAATTTCTCA TCAGTGGTAT | |
| | | CAGTACAAGA GGCAGGCTGA TGATCTCCTG AAATGCTTGG | |
| | | ATGACATTGA AAAAAAATTA GCCAGCCTAC CTGAGCCCAG | |
| | | AGATGAAAGG AAAATAAAGG AAATTGATCG GGAATTGCAG | |
| | | AAGAAGAAAG AGGAGCTGAA TGCAGTGCGT AGGCAAGCTG | |
| | | AGGGCTTGTC TGAGGATGGG GCCGCAATGG CAGTGGAGCC | |
| | | AACTCAGATC CAGCTCAGCA AGCGCTGGCG GGAAATTGAG | |
| | | AGCAAATTTG CTCAGTTTCG AAGACTCAAC TTTGCACAAA | |
| | | TTCACACTGT CCGTGAAGAA ACGATGATGG TGATGACTGA | |
| | | AGACATGCCT TTGGAAATTT CTTATGTGCC TTCTACTTAT | |
| | | TTGACTGAAA TCACTCATGT CTCACAAGCC CTATTAGAAG | |
| | | TGGAACAACT TCTCAATGCT CCTGACCTCT GTGCTAAGGA | |
| | | CTTTGAAGAT CTCTTTAAGC AAGAGGAGTC TCTGAAGAAT | |
| | | ATAAAGATA GTCTACAACA AAGCTCAGGT CGGATTGACA | |
| | | TTATTCATAG CAAGAAGACA GCAGCATTGC AAAGTGCAAC | |
| | | GCCTGTGGAA AGGGTGAAGC TACAGGAAGC TCTCTCCCAG | |
| | | CTTGATTTCC AATGGGAAAA AGTTAACAAA ATGTACAAGG | |
| | | ACCGACAAGG GCGATTTGAC AGATCTGTTG AGAAATGGCG | |
| | | GCGTTTTCAT TATGATATAA AGATATTTAA TCAGTGGCTA | |
| | | ACAGAAGCTG AACAGTTTCT CAGAAAGACA CAAATTCCTG | |
| | | AGAATTGGGA ACATGCTAAA TACAAATGGT ATCTTAAGGA | |
| | | ACTCCAGGAT GGCATTGGGC AGCGGCAAAC TGTTGTCAGA | |
| | | ACATTGAATG CAACTGGGGA AGAAATAATT CAGCAATCCT | |
| | | CAAAAACAGA TGCCAGTATT CTACAGGAAA AATTGGGAAG | |
| | | CCTGAATCTG CGGTGGCAGG AGGTCTGCAA ACAGCTGTCA | |
| | | GACAGAAAAA AGAGGCTAGA AGAACAAAAG AATATCTTGT | |
| | | CAGAATTTCA AAGAGATTTA AATGAATTTG TTTTATGGTT | |
| | | GGAGGAAGCA GATAACATTG CTAGTATCCC ACTTGAACCT | |
| | | GGAAAAGAGC AGCAACTAAA AGAAAAGCTT GAGCAAGTCA | |
| | | AGTTACTGGT GGAAGAGTTG CCCCTGCGCC AGGGAATTCT | |
| | | CAAACAATTA AATGAAACTG GAGGACCCGT GCTTGTAAGT | |
| | | GCTCCCATAA GCCCAGAAGA GCAAGATAAA CTTGAAAATA | |
| | | AGCTCAAGCA GACAAATCTC CAGTGGATAA AGGTTTCCAG | |
| | | AGCTTTACCT GAGAAACAAG GAGAAATTGA AGCTCAAATA | |
| | | AAAGACCTTG GGCAGCTTGA AAAAAAGCTT GAAGACCTTG | |
| | | AAGAGCAGTT AAATCATCTG CTGCTGTGGT TATCTCCTAT | |
| | | TAGGAATCAG TTGGAAATTT ATAACCAACC AAACCAAGAA | |
| | | GGACCATTTG ACGTTCAGGA AACTGAAATA GCAGTTCAAG | |
| | | CTAAACAACC GGATGTGGAA GAGATTTTGT CTAAAGGGCA | |
| | | GCATTTGTAC AAGGAAAAAC CAGCCACTCA GCCAGTGAAG | |
| | | AGGAAGTTAG AAGATCTGAG CTCTGAGTGG AAGGCGGTAA | |
| | | ACCGTTTACT TCAAGAGCTG AGGGCAAAGC AGCCTGACCT | |
| | | AGCTCCTGGA CTGACCACTA TTGGAGCCTC TCCTACTCAG | |
| | | ACTGTTACTC TGGTGACACA ACCTGTGGTT ACTAAGGAAA | |
| | | CTGCCATCTC CAAACTAGAA ATGCCATCTT CCTTGATGTT | |
| | | GGAGGTACCT GCTCTGGCAG ATTTCAACCG GGCTTGGACA | |
| | | GAACTTACCG ACTGGCTTTC TCTGCTTGAT CAAGTTATAA | |
| | | AATCACAGAG GGTGATGGTG GGTGACCTTG AGGATATCAA | |
| | | CGAGATGATC ATCAAGCAGA AGGCAACAAT GCAGGATTTG | |
| | | GAACAGAGGC GTCCCCAGTT GGAAGAACTC ATTACCGCTG | |
| | | CCCAAAATTT GAAAAACAAG ACCAGCAATC AAGAGGCTAG | |
| | | AACAATCATT ACGGATCGAA TTGAAAGAAT TCAGAATCAG | |
| | | TGGGATGAAG TACAAGAACA CCTTCAGAAC CGGAGGCAAC | |
| | | AGTTGAATGA AATGTTAAAG GATTCAACAC AATGGCTGGA | |
| | | AGCTAAGGAA GAAGCTGAGC AGGTCTTAGG ACAGGCCAGA | |
| | | GCCAAGCTTG AGTCATGGAA GGAGGGTCCC TATACAGTAG | |
| | | ATGCAATCCA AAAGAAAATC ACAGAAACCA AGCAGTTGGC | |
| | | CAAAGACCTC CGCCAGTGGC AGACAAATGT AGATGTGGCA | |
| | | AATGACTTGG CCCTGAAACT TCTCCGGGAT TATTCTGCAG | |
| | | ATGATACCAG AAAAGTCCAC ATGATAACAG AGAATATCAA | |
| | | TGCCTCTTGG AGAAGCATTC ATAAAAGGGT GAGTGAGCGA | |
| | | GAGGCTGCTT TGGAAGAAAC TCATAGATTA CTGCAACAGT | |
| | | TCCCCCTGGA CCTGGAAAAG TTTCTTGCCT GGCTTACAGA | |
| | | AGCTGAAACA ACTGCCAATG TCCTACAGGA TGCTACCCGT | |
| | | AAGGAAAGGC TCCTAGAAGA CTCCAAGGGA GTAAAGAGC | |
| | | TGATGAAACA ATGGCAAGAC CTCCAAGGTG AAATTGAAGC | |

TABLE 1-continued

Melanoma Biomarker/Housekeeper Sequence Information

| Gene Name | RefSeq Accession | Sequence | SEQ ID NO: |
|---|---|---|---|
| | | TCACACAGAT GTTTATCACA ACCTGGATGA AAACAGCCAA | |
| | | AAAATCCTGA GATCCCTGGA AGGTTCCGAT GATGCAGTCC | |
| | | TGTTACAAAG ACGTTTGGAT AACATGAACT TCAAGTGGAG | |
| | | TGAACTTCGG AAAAAGTCTC TCAACATTAG GTCCCATTTG | |
| | | GAAGCCAGTT CTGACCAGTG GAAGCGTCTG CACCTTTCTC | |
| | | TGCAGGAACT TCTGGTGTGG CTACAGCTGA AAGATGATGA | |
| | | ATTAAGCCGG CAGGCACCTA TTGGAGGCGA CTTTCCAGCA | |
| | | GTTCAGAAGC AGAACGATGT ACATAGGGCC TTCAAGAGGG | |
| | | AATTGAAAAC TAAAGAACCT GTAATCATGA GTACTCTTGA | |
| | | GACTGTACGA ATATTTCTGA CAGAGCAGCC TTTGGAAGGA | |
| | | CTAGAGAAAC TCTACCAGGA GCCCAGAGAG CTGCCTCCTG | |
| | | AGGAGAGAGC CCAGAATGTC ACTCGGCTTC TACGAAAGCA | |
| | | GGCTGAGGAG GTCAATACTG AGTGGGAAAA ATTGAACCTG | |
| | | CACTCCGCTG ACTGGCAGAG AAAAATAGAT GAGACCCTTG | |
| | | AAAGACTCCA GGAACTTCAA GAGGCCACGG ATGAGCTGGA | |
| | | CCTCAAGCTG CGCCAAGCTG AGGTGATCAA GGGATCCTGG | |
| | | CAGCCCGTGG GCGATCTCCT CATTGACTCT CTCCAAGATC | |
| | | ACCTCGAGAA AGTCAAGGCA CTTCGAGGAG AAATTGCGCC | |
| | | TCTGAAAGAG AACGTGAGCC ACGTCAATGA CCTTGCTCGC | |
| | | CAGCTTACCA CTTTGGGCAT TCAGCTCTCA CCGTATAACC | |
| | | TCAGCACTCT GGAAGACCTG AACACCAGAT GGAAGCTTCT | |
| | | GCAGGTGGCC GTCGAGGACC GAGTCAGGCA GCTGCATGAA | |
| | | GCCCACAGGG ACTTTGGTCC AGCATCTCAG CACTTTCTTT | |
| | | CCACGTCTGT CCAGGGTCCC TGGGAGAGAG CCATCTCGCC | |
| | | AAACAAAGTG CCCTACTATA TCAACCACGA GACTCAAACA | |
| | | ACTTGCTGGG ACCATCCCAA AATGACAGAG CTCTACCAGT | |
| | | CTTTAGCTGA CCTGAATAAT GTCAGATTCT CAGCTTATAG | |
| | | GACTGCCATG AAACTCCGAA GACTGCAGAA GGCCCTTTGC | |
| | | TTGGATCTCT TGAGCCTGTC AGCTGCATGT GATGCCTTGG | |
| | | ACCAGCACAA CCTCAAGCAA AATGACCAGC CCATGGATAT | |
| | | CCTGCAGATT ATTAATTGTT TGACCACTAT TTATGACCGC | |
| | | CTGGAGCAAG AGCACAACAA TTTGGTCAAC GTCCCTCTCT | |
| | | GCGTGGATAT GTGTCTGAAC TGGCTGCTGA ATGTTTATGA | |
| | | TACGGGACGA ACAGGGAGGA TCCGTGTCCT GTCTTTTAAA | |
| | | ACTGGCATCA TTTCCCTGTG TAAAGCACAT TTGGAAGACA | |
| | | AGTACAGATA CCTTTTCAAG CAAGTGGCAA GTTCAACAGG | |
| | | ATTTTGTGAC CAGCGCAGGC TGGGCCTCCT TCTGCATGAT | |
| | | TCTATCCAAA TTCCAAGACA GTTGGGTGAA GTTGCATCCT | |
| | | TTGGGGGCAG TAACATTGAG CCAAGTGTCC GGAGCTGCTT | |
| | | CCAATTTGCT AATAATAAGC CAGAGATCGA AGCGGCCCTC | |
| | | TTCCTAGACT GGATGAGACT GGAACCCCAG TCCATGGTGT | |
| | | GGCTGCCCGT CCTGCACAGA GTGGCTGCTG CAGAAACTGC | |
| | | CAAGCATCAG GCCAAATGTA ACATCTGCAA AGAGTGTCCA | |
| | | ATCATTGGAT TCAGGTACAG GAGTCTAAAG CACTTTAATT | |
| | | ATGACATCTG CCAAAGCTGC TTTTTTTCTG GTCGAGTTGC | |
| | | AAAAGGCCAT AAAATGCACT ATCCCATGGT GGAATATTGC | |
| | | ACTCCGACTA CATCAGGAGA AGATGTTCGA GACTTTGCCA | |
| | | AGGTACTAAA AAACAAATTT CGAACCAAAA GGTATTTTGC | |
| | | GAAGCATCCC CGAATGGGCT ACCTGCCAGT GCAGACTGTC | |
| | | TTAGAGGGGG ACAACATGGA AACTCCCGTT ACTCTGATCA | |
| | | ACTTCTGGCC AGTAGATTCT GCGCCTGCCT CGTCCCCTCA | |
| | | GCTTTCACAC GATGATACTC ATTCACGCAT TGAACATTAT | |
| | | GCTAGCAGGC TAGCAGAAAT GGAAAACAGC AATGGATCTT | |
| | | ATCTAAATGA TAGCATCTCT CCTAATGAGA GCATAGATGA | |
| | | TGAACATTTG TTAATCCAGC ATTACTGCCA AAGTTTGAAC | |
| | | CAGGACTCCC CCCTGAGCCA GCCTCGTAGT CCTGCCCAGA | |
| | | TCTTGATTTC CTTAGAGAGT GAGGAAAGAG GGGAGCTAGA | |
| | | GAGAATCCTA GCAGATCTTG AGGAAGAAAA CAGGAATCTG | |
| | | CAAGCAGAAT ATGACCGTCT AAAGCAGCAG CACGAACATA | |
| | | AAGGCCTGTC CCCACTGCCG TCCCCTCCTG AAATGATGCC | |
| | | CACCTCTCCC CAGAGTCCCC GGGATGCTGA GCTCATTGCT | |
| | | GAGGCCAAGC TACTGCGTCA ACACAAAGGC CGCCTGGAAG | |
| | | CCAGGATGCA AATCCTGGAA GACCACAATA AACAGCTGGA | |
| | | GTCACAGTTA CACAGGCTAA GGCAGCTGCT GGAGCAACCC | |
| | | CAGGCAGAGG CCAAAGTGAA TGGCACAACG GTGTCCTCTC | |
| | | CTTCTACCTC TCTACAGAGG TCCGACAGCA GTCAGCCTAT | |
| | | GCTGCTCCGA GTGGTTGGCA GTCAAACTTC GGACTCCATG | |
| | | GGTGAGGAAG ATCTTCTCAG TCCTCCCCAG GACACAAGCA | |
| | | CAGGGTTAGA GGAGGTGATG GAGCAACTCA ACAACTCCTT | |
| | | CCCTAGTTCA AGAGGAAGAA ATACCCCTGG AAAGCCAATG | |
| | | AGAGAGGACA CAATGTAGGA AGTCTTTTCC ACATGGCAGA | |
| | | TGATTTGGGC AGAGCGATGG AGTCCTTAGT ATCAGTCATG | |
| | | ACAGATGAAG AAGGAGCAGA ATAAATGTTT TACAACTCCT | |
| | | GATTCCCGCA TGGTTTTTAT AATATTCATA CAACAAAGAG | |

TABLE 1-continued

Melanoma Biomarker/Housekeeper Sequence Information

| Gene Name | RefSeq Accession | Sequence | SEQ ID NO: |
|---|---|---|---|
| | | GATTAGACAG TAAGAGTTTA CAAGAAATAA ATCTATATTT TTGTGAAGGG TAGTGGTATT ATACTGTAGA TTTCAGTAGT TTCTAAGTCT GTTATTGTTT TGTTAACAAT GGCAGGTTTT ACACGTCTAT GCAATTGTAC AAAAAAGTTA TAAGAAAACT ACATGTAAAA TCTTGATAGC TAAATAACTT GCCATTTCTT TATATGGAAC GCATTTTGGG TTGTTTAAAA ATTTATAACA GTTATAAAGA AAGATTGTAA ACTAAAGTGT GCTTTATAAA AAAAAGTTGT TTATAAAAAC CCCTAAAAAC AAAACAAACA CACACACACA CACATACACA CACACACACA AAACTTTGAG GCAGCGCATT GTTTTGCATC CTTTTGGCGT GATATCCATA TGAAATTCAT GGCTTTTTCT TTTTTTGCAT ATTAAAGATA AGACTTCCTC TACCACCACA CCAAATGACT ACTACACACT GCTCATTTGA GAACTGTCAG CTGAGTGGGG CAGGCTTGAG TTTTCATTTC ATATATCTAT ATGTCTATAA GTATATAAAT ACTATAGTTA TATAGATAAA GAGATACGAA TTTCTATAGA CTGACTTTTT CCATTTTTTA AATGTTCATG TCACATCCTA ATAGAAAGAA ATTACTTCTA GTCAGTCATC CAGGCTTACC TGCTTGGTCT AGAATGGATT TTTCCCGGAG CCGGAAGCCA GGAGGAAACT ACACCACACT AAAACATTGT CTACAGCTCC AGATGTTTCT CATTTTAAAC AACTTTCCAC TGACAACGAA AGTAAAGTAA AGTATTGGAT TTTTTTAAAG GGAACATGTG AATGAATACA CAGGACTTAT TATATCAGAG TGAGTAATCG GTTGGTTGGT TGATTGATTG ATTGATTGAT ACATTCAGCT TCCTGCTGCT AGCAATGCCA CGATTTAGAT TTAATGATGC TTCAGTGGAA ATCAATCAGA AGGTATTCTG ACCTTGTGAA CATCAGAAGG TATTTTTTAA CTCCCAAGCA GTAGCAGGAC GATGATAGGG CTGGAGGGCT ATGGATTCCC AGCCCATCCC TGTGAAGGAG TAGGCCACTC TTTAAGTGAA GGATTGGATG ATTGTTCATA ATACATAAAG TTCTCTGTAA TTACAACTAA ATTATTATGC CCTCTTCTCA CAGTCAAAAG GAACTGGGTG GTTTGGTTTT TGTTGCTTTT TTAGATTTAT TGTCCCATGT GGGATGAGTT TTTAAATGCC ACAAGACATA ATTTAAAATA AATAAACTTT GGGAAAAGGT GTAAAACAGT AGCCCCATCA CATTTGTGAT ACTGACAGGT ATCAACCCAG AAGCCCATGA ACTGTGTTTC CATCCTTTGC ATTTCTCTGC GAGTAGTTCC ACACAGGTTT GTAAGTAAGT AAGAAAGAAG GCAAATTGAT TCAAATGTTA CAAAAAAACC CTTCTTGGTG GATTAGACAG GTTAAATATA TAAACAAACA AACAAAAATT GCTCAAAAAA GAGGAGAAAA GCTCAAGAGG AAAAGCTAAG GACTGGTAGG AAAAAGCTTT ACTCTTTCAT GCCATTTTAT TTCTTTTTGA TTTTTAAATC ATTCATTCAA TAGATACCAC CGTGTGACCT ATAATTTTGC AAATCTGTTA CCTCTGACAT CAAGTGTAAT TAGCTTTTGG AGAGTGGGCT GACATCAAGT GTAATTAGCT TTTGGAGAGT GGGTTTTGTC CATTATTAAT AATTAATTAA TTAACATCAA ACACGGCTTC TCATGCTATT TCTACCTCAC TTTGGTTTTG GGGTGTTCCT GATAATTGTG CACACCTGAG TTCACAGCTT CACCACTTGT CCATTGCGTT ATTTTCTTTT TCCTTTATAA TTCTTTCTTT TTCCTTCATA ATTTTCAAAA GAAAACCCAA AGCTCTAAGG TAACAAATTA CCAAATTACA TGAAGATTTG GTTTTTGTCT TGCATTTTTT TCCTTTATGT GACGCTGGAC CTTTTCTTTA CCCAAGGATT TTTAAAACTC AGATTTAAAA CAAGGGGTTA CTTTACATCC TACTAAGAAG TTTAAGTAAG TAAGTTTCAT TCTAAAATCA GAGGTAAATA GAGTGCATAA ATAATTTTGT TTTAATCTTT TTGTTTTTCT TTTAGACACA TTAGCTCTGG AGTGAGTCTG TCATAATATT TGAACAAAAA TTGAGAGCTT TATTGCTGCA TTTTAAGCAT AATTAATTTG GACATTATTT CGTGTTGTGT TCTTTATAAC CACCAAGTAT TAAACTGTAA ATCATAATGT AACTGAAGCA TAAACATCAC ATGGCATGTT TTGTCATTGT TTTCAGGTAC TGAGTTCTTA CTTGAGTATC ATAATATATT GTGTTTTAAC ACCAACACTG TAACATTTAC GAATTATTTT TTTAAACTTC AGTTTTACTG CATTTTCACA ACATATCAGA CTTCACCAAA TATATGCCTT ACTATTGTAT TATAGTACTG CTTTACTGTG TATCTCAATA AAGCACGCAG TTATGTTAC | |
| DNAJC9 | NM_015190.4 | GGATGCGCGG CGTGGCCACG CCCCTTCAGT GCTTGTGACG CAGGCGCCCT GGGCTTTTTG GGCGCGAAAA AGAAGCAGTC CTGGGTTGTA CCCGGCGCAG CTGGGAGCGG CTGCTTCCTC CGGGGTCGTA TCTCCGCCCG GCATGGGGCT GCTGGACCTT TGCGAGGAAG TGTTCGGCAC CGCCGACCTT TACCGGGTGC TGGGCGTGCG ACGCGAGGCC TCCGACGGCG AGGTCCGACG AGGCTACCAC AAGGTGTCCC TGCAGGTACA CCCGGACCGG GTGGGTGAGG GCGACAAGGA GGACGCCACC CGCCGCTTCC AGATCCTGGG AAAAGTCTAT TCCGTTCTCA GTGACAGAGA | 9 |

TABLE 1-continued

Melanoma Biomarker/Housekeeper Sequence Information

| Gene Name | RefSeq Accession | Sequence | SEQ ID NO: |
|---|---|---|---|
| | | ACAGAGAGCA GTGTACGATG AGCAGGGAAC AGTGGACGAG GACTCTCCTG TGCTCACCCA AGACCGAGAC TGGGAGGCGT ATTGGCGGCT ACTCTTTAAA AAGATATCTT TAGAGGACAT TCAAGCTTTT GAAAAGACAT ACAAAGGTTC GGAAGAAGAG CTGGCTGATA TTAAGCAGGC CTATCTGGAC TTCAAGGGTG ACATGGATCA GATCATGGAG TCTGTGCTTT GCGTGCAGTA CACAGAGGAA CCCAGGATAA GGAATATCAT TCAGCAAGCT ATTGACGCCG GAGAGGTCCC ATCCTATAAT GCCTTTGTCA AAGAATCGAA ACAAAAGATG AATGCAAGGA AAAGGAGGGC TCAGGAAGAG GCCAAAGAAG CAGAAATGAG CAGAAAGGAG TTGGGGCTTG ATGAAGGCGT GGATAGCCTG AAGGCAGCCA TTCAGAGCAG ACAAAAGGAT CGGCAAAAGG AAATGGACAA TTTTCTGGCT CAGATGGAAG CAAAGTACTG CAAATCTTCC AAAGGAGGAG GGAAAAAATC TGCTCTCAAG AAAGAAAGA AATAATGGAA TTTTTCTCTT CAAAGGTCCT TAGGTGTAAA TTGATGCCAT CGTAGGCAAG GTGCAGGCAG GATTTGAAGG CAAAAGTCAA TTCAGCTCTT GAGAAAAGGT GTCTTTCCAG CCTGAATTTT TCAGATTGAC TAGACCAAGC AGAATCTCTC AACCTGATCT TAGTATTTCC TAGAAAGCAC TTGACATTGT GTGAGGTCTC ACCTGAAGGA ACTTGGTGGT GACATTTGGG AGGGTGGAGG GAGGCAGTGT CCTTCCTGAC AGCACTTGCC TCCATGGATC TTCTGTACAC AGAACTCTTA TCTAGGATGT GGTTCTGTTC ATGCTGCTTT CTGCGATGTG CGTGTCTGTT AGAATAGGCT CTCTACCCAG CTAGAACACC TTCCAGACAC TTGCTGGACA GCTATCTTCC ACATACTTCC CAGTTTACAT TTGGTCTTAA TGATCTTGAA TAGATCCTCT CTTCATTTTA CTCAGCCAGG TTTTGTACTG ATGTACAGGT GTTAAATTAC TTCAAGCATT TTTGTAAGAG GTGTATATAA TTCAATAAAA AAGGTAAAAC ATGATGATTA AGTTCTGGGG GCTTTGTAAA TGATCCCACT AAAATGTGAC CTAGGAAAAA TATGAATGGT GTTTAGGATG AGAGAAAAGG GGAAAACAAT AGCCCTGGTC AGCTTTATAA TAGAGAGCCT GGTTTCCCTA GCATGAAGAG ATGTATGTTG TAGTCCTGCC ACTGATTACT GAAGTCCTGC CATTAATTGC TGAATGTCTT CAGTTGGGCC ACTGAGCTTG TCTGAATCTG TTCCCTTTTA TAAAAGAGTT ACTACATCAA AACAAAGAGT GAAATCCAAA TTTGTCAAAC TGTATGTATT AAACATGTCC AGTTTTTTGG TTAAAAAAAA ATTGCACTGG CTTTGAGGGA AACACACAG GGTGAGGGAA TTGGGCTAAA TGACTTCTTA CAGGCCCCTT TCTGATTCTT TAACTTTGAA AGGCAAGCCA TATTGATCCA GTTGTTATAG TGAACTCATG GTAATGGTTT GTGAGAACAA TAGAGATTTT CATTTCTATG TAGATGAGTT GGTATGAGAA TATATGGAAT TTTTAAGGGA CTGTTTAAAT CTTTGATTTG TAGACTATTA AATATACCGT ATGCATAAAG TAAGCCTTTA GCTCTAAGGT AAAGACGACA CGTTTTCGGT TTGTGACTAC AAATAGGTTA AAAATAGATT TTAATTTTAT TAAAAATATA ATTTAATGCA GGTTGTTTGA AGCATCTGTC TTCATATGAT GGCATTAGAA CACCTTGGTA TAATAAAAAG TTACCGTAAT TTATGATTAT TTGAATTTAT CCATTCTGAA AATTAATAAG ATCTAAAACT GGCATGACAA TCAAGATTTG TATTTAGTGA AATTTAAAAT AAATGTAAGC CATAGTTAAA AAAAAAAAA AAAAA | |
| ENOSF1 | NM_001126123.3 | CGCCCTCCCG CCGCGCGCTC GGGATCCCGA CCAGTCCTGA CCGCACGGGG GCCGCGGCCA CGGGGCGCAG GGGCCATGGT GCGCGGCAGG ATCTCCCGGC TCTCGGTCCG GGACGTGCGC TTCCCCACGT CGCTTGGGGG CCACGGCGCG GACGCCATGC ACACGGACCC TGACTACTCG GCTGCCTATG TCGTCATAGA AACTGATGCA GAAGATGAA TCAAGGGGTG TGGAATTACC TTCACTCTGG GAAAAGGCAC TGAAGTTGAT TGGTCCAGAA AAGGGCGTGG TGCACCTGGC GACAGCGGCC GTCCTAAACG CGGTGTGGGA CTTGTGGGCC AAGCAGGAGG GAAAGCCTGT CTGGAAGTTA CTTGTGGACA TGGATCCCAG GATGCTGGTA TCCTGCATAG ATTTCAGGTA CATCACTGAT GTCCTGACTG AGGAGGATGC CCTAGAAATA CTGCAGAAAG GTCAAATTGG TAAAAAAGAA AGAGAGAAGC AAATGCTGGC ACAAGGATAC CCTGCTTACA CGACATCGTG CGCCTGGCTG GGGTACTCAG ATGACACGTT GAAGCAGCTC TGTGCCCAGG CGCTGAAGGA TGGCTGGACC AGGTTTAAAG TAAAGGTGGG TGCTGATCTC CAGGATGACA TGCGAAGATG CCAAATCATC CGAGACATGA TTGGACCGGA AAAGACTTTG ATGATGGATG CCAACCAGCG CTGGGATGTG CCTGAGGCGG TGGAGTGGAT GTCCAAGCTG GCCAAGTTCA AGCCATTGTG GATTGAGGAG CCAACCTCCC CTGATGACAT TCTGGGGCAC GCCACCATTT CCAAGGCACT GGTCCCCATTA GGAATTGGCA TTGCCACAGG AGAACAGTGC | 10 |

TABLE 1-continued

Melanoma Biomarker/Housekeeper Sequence Information

| Gene Name | RefSeq Accession | Sequence | SEQ ID NO: |
|---|---|---|---|
| | | CACAATAGAG TGATATTTAA GCAACTCCTA CAGGCGAAGG | |
| | | CCCTGCAGTT CCTCCAGATT GACAGTTGCA GACTGGGCAG | |
| | | TGTCAATGAG AACCTCTCAG TATTGCTGAT GGCCAAAAAG | |
| | | TTTGAAATTC CTGTTTGCCC CCATGCTGGT GGAGTTGGCC | |
| | | TCTGTGAACT GGTGCAGCAC CTGATTATAT TTGACTACAT | |
| | | ATCAGTTTCT GCAAGCCTTG AAAATAGGGT GTGTGAGTAT | |
| | | GTTGACCACC TGCATGAGCA TTTCAAGTAT CCCGTGATGA | |
| | | TCCAGCGGGC TTCCTACATG CCTCCCAAGG ATCCCGGCTA | |
| | | CTCAACAGAA ATGAAGGAGG AATCTGTAAA GAAACACCAG | |
| | | TATCCAGATG GTGAAGTTTG GAAGAAACTC CTTCCTGCTC | |
| | | AAGAAAATTA AGTGCTCAGC CCCAACAACT TTTTTCTTTC | |
| | | TGAAGTGAAA GGGCTTAAAA TTTCTTGGAA ATAGTTTTAC | |
| | | AAAAATGGAT TTAAAAAATC CTACCGATCA AGATGAGTTC | |
| | | AGCTAGAAGT CATACCACCC TCAGGAATCA GCTAAAGCAA | |
| | | AAAGAACTTT TACCTCGGCA TCCAGCCCAA CCCCTAAAGA | |
| | | CTGACAATAT CCTTCGAGCT CCTTTGAAAG CACCCTAAAC | |
| | | AGCCATTTCC ATTTTAATAG TTGGATGCGG ATTGTACCCT | |
| | | TCAATCTGAA AGTCTTCAGC TTTGAAGTCA TCAATTTTCT | |
| | | CAACTTTTCG AAGAATCCTG AGCTTTGGGA AAGGTCTGGG | |
| | | TTCTCGCTGA AGCTAAAAAC AAAATAAGGC CATTATTTTG | |
| | | CCATAATTGT ACGACCTGTT GTAATTGCTC CTCATGTCCG | |
| | | TGAAACAAGT ACACAGGATG TGATCAACAA AGTTCTATTT | |
| | | TACAGGAGTA TGATCCTGTC GATACCTTGC CGTAGGTTAT | |
| | | GTAACATGAT TGGAGCGCAA CCAGCTGTTC TCTTGCACAG | |
| | | ATCGAGAGTG AGGGGTATTT TGTGACATTA CACAGCATCA | |
| | | GGAGCCTGGT GCCTCATCAG GTGTAAGTTC TTATAACCAC | |
| | | TCTTGGCAAA TTTATTAAAG ACAGGAACAC AGTCAATCTG | |
| | | TAACTCATAG TAGCTCTACG TTTACTTGAA TTCCACAATC | |
| | | CCTAACCCAT CTGTCCCTGG CAGAAAGAAG GAAAGATGAC | |
| | | ATGCATGGAC AGTGAACAGA AAGGGATGAA AGCCAGGATT | |
| | | CCTGGGATGA ACAGACAGTG GCAATTAGGA TGTGAAGACA | |
| | | GGTCACAACC TATTACTATG TCTAAAAACG ACCAGAGCAG | |
| | | AGAGCCAGAG AGAATAAGCC TGAAGTCACC TCCACTCAAA | |
| | | AGCAGCCAAA CTCCCTCAAA GGAGTAACTT TTAAAACCTG | |
| | | GATCTAACCT GGAAGGGGCT AAAAAGTGTC TGGTTCTGAG | |
| | | TTTTTTTCCT TAAGGCTCAT GAAGCAGATG AACTTACATT | |
| | | TTTATTGCCA TTTCATATCA ATTGTTGGCT GCTATAACTT | |
| | | AGGGATTTCA ACAGACTTTT GAAGTTTGGA CCTAAATATT | |
| | | GTACTTAATG TAAAATTAAC AAAAAATATT TATGGCCAGG | |
| | | GTGGTGGCTT ATGCCTGTAA TTCCAGAATT TTCGGAGGCT | |
| | | GAGGCAGGTG GATCACTTGA AGTCAGGAGT TTGAGACTAG | |
| | | CCTGGCCAAC ATGATGAAAC CCCATCTCTA CTAATAATAC | |
| | | AAAAATTAGC TGGGTGTGGT GGCATGTGCC TGTAATCCCA | |
| | | GCTACCTGGG AGGCTGAGGC AGAAGAATTG CTTGAACCCG | |
| | | GGAGGTGGAG GTTGCAGTGA GCTGAGATCG CACCACGGCA | |
| | | CACTCCAGCC TGGCCGACAG AGAAAGACTC CATCTCAAAA | |
| | | AAAAAAGAAA AGGAAAAACA TTTGCACTTC AATTCTCCTT | |
| | | CAAGTTAAAA TGAGTTAAAA TGCCCCCTTT TGGACAATCC | |
| | | CCTGGCTTGA ATGTGGCTCT TCCCTCTCTG GTACTGGTGC | |
| | | TTAGTACCTC ACAGCACCTG ACATGTTAAG TGCCCATGGT | |
| | | TGCTGAGGCA GATGCCTGCC TTGTCCTGCC CACCTGCCCA | |
| | | CCCACTTCTCC CTAAACTGAA GCCCCACATT TGGAGCAGTC | |
| | | ATCTTTATCT TGGACACAGC ATTGAGCAGA TGCCTGTTCC | |
| | | ACAGTCAACC TTTTATCAAG AGAAGGTACC AAACCCAAAA | |
| | | GTATAACATC TAATTCTTAC CTGAATTTTC AGTGGCTCGA | |
| | | TGTGATTCAG GTAAATATGT GCATCTCCCA AAGTGTGTAT | |
| | | AAAGTCACCT GGCTATAAAC CCGGGGGAGA AAGCAGAACA | |
| | | GTATGTTAGT TTCAATTCTT TAAAACATCA TTTAAAAACA | |
| | | TTAGAATATG CAGACACCGC AAGGCTTTTT TTAAAAAAAT | |
| | | AATTTAGTGT AGCTTTTCCA TTTTTTTGTA GCAACAGCAT | |
| | | CTTGTTATGT TGCCCAGGCT GGTATTGAAC TCCAGACCTC | |
| | | AAGCAATTGC TCCTGTCTCA GTCTCCCAAA GTGCTGGGAT | |
| | | TACAGGCATG AGCCACCATA CCCAACCTCA GCATAGCTTT | |
| | | TGAGAAAATC CATAGAAGCT GTATCACAAA CAACCTGTAT | |
| | | AGATCTGTTA GTGCGTATAC CACAGGGCCA GAAAACCTTC | |
| | | CAGAAGAGGA AGGTTTCAAA GTAAAAGCTG GTTCATTTCT | |
| | | TACTTACACA TATCAAATTT AAAAGCTAAT CAGAGACTAA | |
| | | ACTCTGCAAT TTGTTTTCCC ATATTAAAGA ACTGAAGAGC | |
| | | TCAGTGTGGT AGGCTGGCAA GTCACCCTTC CCGAGACACG | |
| | | CCACCTTCAG GCCCGTGATG TGCGCAATCA TGTACGTGAG | |
| | | CAGGGCGTAG CTGGCGATGT TGAAAGGCAC ACCGAGGCCC | |
| | | ATGTCTCCCG ATCTCTGGTA CAGCTGGCAG GACAGCTCAC | |
| | | TGTTCACCAC ATAGAACTGG CAGAGGGCAT GGCATGGAGG | |
| | | CAGCGCCATC AGAGGAAGAT CTGAGGAACC AGCAGAGGAA | |

TABLE 1-continued

Melanoma Biomarker/Housekeeper Sequence Information

| Gene Name | RefSeq Accession | Sequence | SEQ ID NO: |
|---|---|---|---|
| | | GATAAGGAGG GATGGTGGTT TGAAAGACCA CAGCTAAAGG<br>CAAAGTAAAA CAGGAGAGAA ACAGAAGCCA ACTCATATGG<br>TGGAGACCAG GAGAGAGAGC CACTGGGCTG CAGTGATGTC<br>CATAACAGCC TCTGCAGCGA TGGCACGGAG CTGAGGGAGA<br>CTATCCATCG GTGCAAGGTT TCTGCAGGTG TCCATTTACG<br>GCTGAAGCAA TGCTCTTCCA TCAGAGCTGA AGGGATCTGG<br>GCTACCTCGT GGCACCAGAT TACAAATACA GCAGGAATAA<br>TTCTGTTTGC CACAGGAAAC TGGTGCTTCT GGTACACCCT<br>CCTATATTAA AAGTCTCTAT TACATGGCAA AAAAAAAAAA<br>AAAAAA | |
| FANCL | NM_001114636.1 | AGCGGACTGC GCATGTGCAG GACCCAGCAG GTCTAGAGCT<br>TTTCTGTGTT TCTCCGGACT TCGAGCCATG GCGGTGACGG<br>AAGCGAGCCT GTTGCGCCAG TGCCCCCTGC TTCTGCCCCA<br>GAACCGGTCG AAAACCGTGT ATGAGGGATT CATCTCGGCT<br>CAGGGAAGAG ACTTCCACCT TAGGATAGTG TTGCCTGAAG<br>ATTTACAACT GAAGAATGCA AGATTATTAT GTAGTTGGCA<br>GCTGAGAACA ATACTTAGTG GATACCATCG AATAGTACAA<br>CAGAGAATGC AGCACTCTCC TGATCTAATG AGCTTTATGA<br>TGGAGTTGAA GATGCTTTTG GAAGTTGCCT TAAAGAATAG<br>ACAAGAGCTG TATGCACTAC CTCCTCCTCC CCAGTTCTAC<br>TCAAGCCTTA TTGAAGAGAT AGGAACTCTT GGTTGGGATA<br>AACTTGTGTA TGCGGATACC TGCTTCAGTA CCATCAAGTT<br>AAAAGCAGAA GATGCTTCTG GTAGAGAGCA TTTAATCACT<br>CTCAAGTTGA AGGCAAAGTA TCCTGCAGAA TCACCAGATT<br>ATTTTGTGGA TTTTCCTGTT CCATTTTGTG CCTCCTGGAC<br>ACCTCAGGTA AATTCTCCTC AGAGCTCCTT AATAAGCATT<br>TATAGTCAGT TTTTGGCAGC AATAGAATCA CTAAAGGCAT<br>TCTGGGATGT TATGGATGAA ATCGATGAGA AGACCTGGGT<br>ACTTGAGCCA GAAAAACCTC CACGGAGTGC AACAGCACGC<br>AGAATTGCAT TAGGTAATAA TGTTTCCATA AATATAGAGG<br>TAGACCCCAG GCATCCTACT ATGCTTCCTG AGTGCTTCTT<br>TCTTGGAGCT GACCATGTGG TAAAACCCCT GGGAATTAAG<br>CTGAGCAGGA ACATACATTT GTGGGATCCA GAAAATAGTG<br>TGTTACAAAA TTTGAAAGAT GTTTTAGAAA TTGATTTTCC<br>AGCTCGTGCT ATCCTGGAAA AATCTGATTT TACTATGGAT<br>TGTGGAATTT GTTATGCTTA TCAACTTGAC GGTACCATTC<br>CTGATCAAGT GTGTGATAAT TCTCAGTGTG ACAACCTTT<br>CCATCAAATA TGCTTATATG AGTGGCTGAG AGGACTACTA<br>ACTAGTAGAC AGAGTTTTAA CATCATATTT GGTGAATGTC<br>CATATTGTAG TAAGCCAATT ACCTTAAAAA TGTCTGGAAG<br>GAAACACTGA ATAAGAATA CAACATTTCG GTGAAGAGCT<br>GGAAACTTAA AAAATTATCA AAAGGAATTT TGGTATCATC<br>TTCAGAGAAA AAATAAAGCA AGAAATACTA ACATCAAAAG<br>GACAGGTATG ATGATGCGAT AATAATAAAC ATCTGCGTTT<br>GTCTCTTCAC TAAGAGTAAA CTGGGAAATT GTAGGCCAAA<br>GTCCAGTTGA ACTTTCTAAG TCTGTGATCC CCGTGCTGAC<br>TGTGGAAGTG TATTTATACC AAGATGGAGA TCTTGACTTC<br>TTGAATATAT CTGGACTGGT AAAATCTTGA TGAGGCTCAT<br>AAAATGAGTT TGGGAATTGT GTATAGCTGA TTTTTTGTGG<br>GAAACTGTTT ACTTCATTCA AAGGTTCTTG AGACTCTTGA<br>TATTTCTGTC TTCTCCTTGT GCTTTCCTAT GGAAAAAATA<br>CATATATAGT TTAGTTTGTT AGACGTGAGT TATCCAAGTA<br>TTTATTTTGT GTAGTGTGTA AGAATGCTAA ATAAAATGTT<br>ATACAAGATC AAAAAAAAAA AAAAAAAAAA AAA | 11 |
| HJURP | NM_018410.4 | CTATTTGAGT TTGTGGCGCG CGAGGCCCTG CAGTCCGGGT<br>TGGCGCTTGG GTACTGGCTG GGTCCGATGC TGGGTACGCT<br>GCGCGCCATG GAGGGCGAGG ACGTGGAAGA CGACCAGCTG<br>CTGCAGAAGC TCAGGGCCAG TCGCCGCCGC TTCCAGAGGC<br>GCATGCAGCG GCTGATAGAG AAGTACAACC AGCCCTTCGA<br>GGACACCCCG GTGGTGCAAA TGGCCACGCT GACCTACGAG<br>ACGCCACAGG GATTGAGAAT TTGGGGTGGA AGACTAATAA<br>AGGAAAGAAA CGAAGGAGAG ATCCAGGACT CCTCCATGAA<br>GCCCGCGGAC AGGACAGATG GCTCCGTGCA AGCTGCAGCC<br>TGGGGTCCTG AGCTTCCCTC GCACCGCACA GTCCTGGGAG<br>CCGATTCAAA AAGCGGTGAG GTCGATGCCA CGTCAGACCA<br>GGAAGAGTCA GTTGCTTGGG CCTTAGCACC TGCAGTGCCT<br>CAAAGCCCTT TGAAAAATGA ATTAAGAAGG AAATACTTGA<br>CCCAAGTGGA TATACTGCTA CAAGGTGCAG AGTATTTTGA<br>GTGTGCAGGT AACAGAGCTG GAAGGGATGT ACGTGTGACT<br>CCGCTGCCTT CACTGGCCTC ACCTGCCGTG CCTGCCCCCG<br>GATACTGCAG TCGTATCTCC AGAAAGAGTC CTGGTGACCC<br>AGCGAAACCA GCTTCATCTC CCAGAGAATG GGATCCTTTG | 12 |

TABLE 1-continued

Melanoma Biomarker/Housekeeper Sequence Information

| Gene Name | RefSeq Accession | Sequence | SEQ ID NO: |
|---|---|---|---|
| | | CATCCTTCCT CCACAGACAT GGCCTTAGTA CCTAGAAATG ACAGCCTCTC CCTACAAGAG ACCAGTAGCA GCAGCTTCTT AAGCAGCCAG CCCTTTGAAG ATGATGACAT TTGCAATGTG ACCATCAGTG ACCTGTACGC AGGGATGCTG CACTCCATGA GCCGGCTGTT GAGCACAAAG CCATCAAGCA TCATCTCCAC CAAAACGTTC ATCATGCAAA ACTGGAACTC CAGGAGGAGG CACAGATATA AGAGCAGGAT GAACAAAACA TATTGCAAAG GAGCCAGACG TTCTCAGAGG AGCTCCAAGG AGAACTTCAT ACCCTGCTCT GAGCCTGTGA AAGGGACAGG GGCATTAAGA GATTGCAAGA ACGTATTAGA TGTTTCTTGC CGTAAGACAG GTTTAAAATT GGAAAAAGCT TTTCTTGAAG TCAACAGACC CCAAATCCAT AAGTTAGATC CAAGTTGGAA GGAGCGCAAA GTGACACCCT CGAAGTATTC TTCCTTGATT TACTTCGACT CCAGTGCAAC ATATAATCTT GATGAGGAAA ATAGATTTAG GACATTAAAA TGGTTAATTT CTCCTGTAAA AATAGTTTCC AGACCAACAA TACGACAGGG CCATGGAGAG AACCGTCAGA GGGAGATTGA AATCCGATTT GATCAGCTTC ATCGGGAATA TTGCCTGAGT CCCAGGAACC AGCCTCGCCG GATGTGCCTC CCGGACTCCT GGGCCATGAA CATGTACAGA GGGGGTCCTG CGAGTCCTGG TGGCCTTCAG GGCTTAGAAA CCCGCAGGCT GAGTTTACCT TCCAGCAAAG CAAAAGCAAA AAGTTTAAGT GAGGCTTTTG AAAACCTAGG CAAAAGATCT CTGGAAGCAG GTAGGTGCCT GCCCAAGAGC GATTCATCTT CATCACTTCC AAAGACCAAC CCCACACACA GCGCAACTCG CCCGCAGCAG ACATCTGACC TTCACGTTCA GGGAAATAGT TCTGGAATAT TTAGAAAGTC AGTGTCACCC AGCAAAACTC TTTCAGTCCC AGATAAAGAA GTGCCAGGCC ACGGAAGGAA TCGTTACGAT GAAATTAAAG AAGAATTTGA CAAGCTTCAT CAAAAGTATT GCCTCAAATC TCCTGGGCAG ATGACAGTGC CTTTATGTAT TGGAGTGTCT ACAGATAAAG CAAGTATGGA AGTTCGATAT CAAACAGAAG GCTTCTTAGG AAAATTAAAT CCAGACCCTC ACTTCCAGGG TTTCCAGAAG TTGCCATCAT CACCCCTGGG GTGCAGAAAA AGTCTACTGG GCTCAACTGC AATTGAGGCT CCTTCATCTA CATGTGTTGC TCGTGCCATC ACGAGGGATG GCACGAGGGA CCATCAGTTC CCTGCAAAAA GACCCAGGCT ATCAGAACCC CAGGGCTCCG GACGCCAGGG CAATTCCCTG GGTGCCTCAG ATGGGGTGGA CAACACCGTC AGACCGGGAG ACCAGGGCAG CTCTTCACAG CCCAACTCAG AAGAGAGAGG AGAGAACACG TCTTACAGGA TGGAAGAGAA AAGTGATTTC ATGCTAGAAA AATTGGAAAC TAAAAGTGTG TAGCTAGGTT ATTTCGGAGT GTTATTTATC TTCCCACTTG CTCTCTGTTT GTATTTTTGT TTTGTTTTTG ATTCTTGAGA CTGTGAGGAC TTGGTTGACT TCTCTGCCCT TAAAGTAAAT ATTAGTGAAA TTGGTTCCAT CAGAGATAAC CTCGAGTTCT TGGTGTAGAA ATTATGTGAA TAAAGTTGCT CAATTAGAAT TTTTAGGGTT CTCTTTGATA GGCCTGTTTT TCTGATGTGT GTGTTTTTTT TGGGGGGGGG TTATTTGTTT GTTTGTTTGT TTGTTTGTTT GTTTTTGAGA CAGTCTCTCT CTATCGCCCA GGCTGGAGTG CGGTGGCACA ATCTTGGCTC ACTGCAACTT CCGCCTCCCG GGTTCAAGCG ATTCTTCTGC CTCAGCCTCC CGAGTAGCTG GGATTACAGG CGCGCGCCAC CACGCCTGGC TAATTTTTGT AGTTTTAGTA GAGACGGGGT TTCACCATAT TGACCAGGCT GGTCTCGAGC TCCTGGCCTC GTGATCCATC TGCCTCGGCC TCCCAAAGTG CTGGGATTAT AGGCGTGAGC CACTGCTCCC AGCCGTGTGT TCTTTTTTAA ATTTAGATAT GTCCAGAGAA TCCTCTCTCC TGTTTCCCAT TTCATTCGAG AATATTGTTT GCTTGTGAGA CGTAAGTTCG AGCCCTGCAT GCAATGACCC TTGAAGGAAA ATAAACAGTC CTGGTGGTCC CAGACGCTCC TGCAGCCACA GCGCCTGTGA CTCCTCATGA TTCTTACTGA AGCTGTTGAT GACAGGATAT CATGGTGACG TTTTTGTAAT GAAATATTTC ACATATTCAG AATACATTGG TGAAACTCAT GCTGGAGTAA ATAGTTAATA TATGGCCAT | |
| HLA-DOA | NM_002119.3 | CTTCTTCTTT ACCTCCGCCT TGTTCCTGTC CTCACCACAC GGACTGAGAC TGATTTGATT AAAGCACCAG AGTGTAATGG CCCTCAGAGC AGGGCTGGTC CTGGGGTTCC ACACCCTGAT GACCCTCCTG AGCCCGCAGG AGGCAGGGGC CACCAAGGCT GACCACATGG GCTCCTACGG ACCCGCCTTC TACCAGTCTT ACGGCGCCTC GGGCCAGTTC ACCCATGAAT TTGATGAGGA ACAGCTGTTC TCTGTGGACC TGAAGAAAAG CGAGGCCGTG TGGCGTCTGC CTGAGTTTGG TGACTTTGCC CGCTTTGACC CGCAGGGCGG GCTGGCCGGC ATCGCCGCAA TCAAAGCCCA TCTGGACATC CTGGTGGAGC GCTCCAACCG CAGCAGAGCC ATCAACGTGC CTCCACGGGT GACCGTGCTC CCCAAGTCTC | 13 |

TABLE 1-continued

Melanoma Biomarker/Housekeeper Sequence Information

| Gene Name | RefSeq Accession | Sequence | SEQ ID NO: |
|---|---|---|---|
| | | GGGTGGAGCT GGGCCAGCCC AACATCCTCA TCTGCATCGT<br>GGACAACATC TTCCCCCCTG TGATCAATAT CACCTGGCTG<br>CGCAACGGCC AAACTGTCAC TGAGGGAGTG GCCCAGACCA<br>GCTTCTATTC CCAGCCTGAC CATTTGTTCC GCAAGTTCCA<br>CTACCTGCCC TTCGTGCCCT CAGCCGAGGA CGTCTATGAC<br>TGCCAGGTGG AGCACTGGGG CCTGGATGCG CCACTCCTCA<br>GGCATTGGGA GCTCCAGGTG CCTATTCCAC CACCAGATGC<br>CATGGAGACC CTGGTCTGTG CCCTGGGCCT GGCCATCGGC<br>CTGGTGGGCT TCCTCGTGGG CACCGTCCTC ATCATCATGG<br>GCACATATGT GTCCAGTGTC CCCAGGTAAT GATCCTTCTG<br>AGAGAAATGA CTTGTGGGAG ACACCCTGCA GATCCTCATG<br>GGTTTGTGAC AGCCCCTGCG TGCTCAGTGC CCTTTAAGTG<br>CATCCCGCTG TGCTGACTTT GAGTGGGATC AACATCTGTC<br>CTACGGGTCC CCTCTTTTTT GGCCCCAGTA TTCATGGCAG<br>GGTTTGTTGG ACACCTACTA GCTTCCCTTC CCATTCAACA<br>CACACACACA TTCTTGCTCT ACCCAAAGCT CTGGCTGGCA<br>GCACTAAATG CTTTGGTGGT GTTTGCACTG TGTCCTTTCC<br>AGGCCTTGGC CAGTTCTTCC AGGGGTGAGG CATGTGGTGC<br>TGGGGATTGG CAGCCATCCT GGGGCCCACA CAGGTGTGTC<br>TTGCTCCATT TGGCCCATTG TGTGTTACTT TGTGAATGAG<br>CCATTTCACA TGGACTTCAT GAAATTTGCC TCCTGAGTTC<br>AGGTTTACCC TGAAAGGGAT GCAGATTATC CTGTTCCTCA<br>CGACCCCCTC AGCTAACAAC AGTTCTGAAG GGTGCTGGGA<br>CAGGACAGGC TCATGGGGAC TCCACTCCTG CCTGGGTTTA<br>CTCTGTATGA AGAGGCCACT GGTATCCTGC CATGATGTTA<br>TCTCCTTTTT CTACTTTTCC CTAGAGTCCC ATGCATGATA<br>AAGAGAGGCC CAAGGCTTGG ATAAGGTGGC CACTTCCCTC<br>AGTGGAGTCA GTCATGTTAG GTAGGAGGTG GTAGAGTCGG<br>TCTGCGAGGT ATCTCGTAAG AGGGGAGGTC CACCTAGACA<br>CACTCTAAAT ATGTGGCCTA GAAGATTTTG GTCTACTTTT<br>CTGTGAACAG AATTTAAAAC ATACAAAGAG ATAAATCACC<br>ATACCACATA GTTTATGTCA GGACCAAAAT GAGCAATACA<br>GATTACGGTT TTCAAACCAG AATGCACATA AGAACTGCTT<br>GGGATCCTTT TAAAAGTACA GGCATTGGCC TGGTGCAGTG<br>GCTCATTCCT GTAATCCCAG CACTTTGGGA GGCCAAGGGG<br>ACAGGACTGC TTGAGGCCAA GAGGTGGAAA CCATCTTGGG<br>CTACATAGAG AGACCCCATC TCTACAAAGA AAGATTTAAA<br>AATTAACCAG GCATGGTGGC TCGCACCTGT ATTCCCAGCC<br>ACTGGGGAGG CTGAGGCCGG AGGAGTGCTT GAGCCCAGGA<br>GTTCAAGGCT GCAGTGAGCC AAGATTGCGC CACTGCACTC<br>CAGCCTAGGT GACAGAGTGA GACCCTGTCT CTAAATAAAT<br>AAATAAATAA AATATAAAAA TAACAGTCAT CACCCAGACC<br>TACTGAATTA GAATCTCGGG AGTGCAGGGG GCAGCAACAG<br>GGAGGCTGTC TTTTCTGAGA TGGGGTCTCA CTCTGTCACC<br>AGGCTGGAGT GCCATGGCAT GATCTCAGCT CACTGCAACC<br>TCCACCTCCT GAGTTCAAGC CATTCTCCTG CCTCAGCCTC<br>CTGAGTAGCT GGGACTACAG GTGTGCGCCA CTACACTCAG<br>CTAATTTTTG TATTTTAAGT AGAGACGGGG TTTCATCATG<br>TTGGCCAGGA TGGCCTCCAT CTCTTGACCT CGTGATCCAC<br>CCACCTTCCC TCCCAAAGTA CTGGAATTAC AGGCATTAGC<br>CACTGTGCCC AGCCGAGGCT GTCATTTTTA ACCGGCTCTG<br>GATGACTCTG ATGCAGCCAT CCTGGACCTT GGCTGTGGTC<br>TGGTAACTGG AACCCAGTGA CGTAATCAGG TGCCATCGGG<br>GGTCATGGGA AAGGGGGATC CCCAAGGTCT GAGGTGGACT<br>AGGAAGGCTT TCTGAAGAAC CTGGGTCTGT TAGGGCATCA<br>GCCAATCAAG GTACAAGTAA ATAGAGGCAA AATGAGGGTT<br>TGAACTGTGA GCAGTTGGTC CTGGAAAAGA AAGAAACCAA<br>GAGATTATGG GGACTCAATG GGCTTCTTAA GAGAGAATAA<br>GTTGAAATCA ATGACCAGAA GACCCTGATG GAAGTGGAGG<br>AGAATCATCT CAGGCAAACT TTTTGTGTGC CAGTAACAGA<br>AACCCTCTTT GTGTGATCAC ATGCAAAGTA TAGGATATTT<br>GCAATATAGC CATGGGGAGG AGTGCAGGGC CCAAGGGTAG<br>ATTTTAGCCA GGCCTCCCAG GAACAGAACT CGGATCCGAA<br>AAGCCCAGAG AAGCTAGAGC TGCCCCTCCA ACACTCTCGG<br>ATCCACATGG TCTGTGTTCT CTAGACCCCC CTGCATGTTA<br>GCGGTGTTCT CTCTCTGTGG ACTGACTGTC CTTCTCAGTG<br>AACATGTCCA CCCGACAGCT CCTGAGTTTA TATCATCTCA<br>ACCCTCACAA CCCACAGAGG CTGTGTCTCC TAGTCACAGC<br>TTTAAATTAC TGGAAAAATA AATGACTGGC CAAACTTGGA<br>GCAGGTGTGC ATCCCAGCCC TGTGTAGTTA GAGCAGGAAT<br>CAAGATCTCA ACACAAATGT GGCTGCCAAG CACTCAGCCC<br>CGGGGCGAGG GGTCAAGTTC TTCTCAGAGA AAGAGGAATA<br>AGTTGGTTCT CAGAAGACAT CACAAGATAC GTGTGTACCC<br>AACAATCTCT GATCTCTGCT GATCTTTTGC TTAGACGTTA | |

TABLE 1-continued

Melanoma Biomarker/Housekeeper Sequence Information

| Gene Name | RefSeq Accession | Sequence | SEQ ID NO: |
|---|---|---|---|
| | | ACTTGATGCA TCATTGGAAA GGTGTTTCTC TCATCTCTGT CCTAAGGCTT GATAAAGTCA TTAAAATTGT GTTCTTTTGA CTAAA | |
| HLA-DRA | NM_019111.4 | TTTTAATGGT CAGACTCTAT TACACCCCAC ATTCTCTTTT CTTTTATTCT TGTCTGTTCT GCCTCACTCC CGAGCTCTAC TGACTCCCAA CAGAGCGCCC AAGAAGAAAA TGGCCATAAG TGGAGTCCCT GTGCTAGGAT TTTTCATCAT AGCTGTGCTG ATGAGCGCTC AGGAATCATG GGCTATCAAA GAAGAACATG TGATCATCCA GGCCGAGTTC TATCTGAATC CTGACCAATC AGGCGAGTTT ATGTTTGACT TTGATGGTGA TGAGATTTTC CATGTGGATA TGGCAAAGAA GGAGACGGTC TGGCGGCTTG AAGAATTTGG ACGATTTGCC AGCTTTGAGG CTCAAGGTGC ATTGGCCAAC ATAGCTGTGG ACAAAGCCAA CCTGGAAATC ATGACAAAGC GCTCCAACTA TACTCCGATC ACCAATGTAC CTCCAGAGGT AACTGTGCTC ACAAACAGCC CTGTGGAACT GAGAGAGCCC AACGTCCTCA TCTGTTTCAT AGACAAGTTC ACCCCACCAG TGGTCAATGT CACGTGGCTT CGAAATGGAA AACCTGTCAC CACAGGAGTG TCAGAGACAG TCTTCCTGCC CAGGGAAGAC CACCTTTTCC GCAAGTTCCA CTATCTCCCC TTCCTGCCCT CAACTGAGGA CGTTTACGAC TGCAGGGTGG AGCACTGGGG CTTGGATGAG CCTCTTCTCA AGCACTGGGA GTTTGATGCT CCAAGCCCTC TCCCAGAGAC TACAGAGAAC GTGGTGTGTG CCCTGGGCCT GACTGTGGGT CTGGTGGGCA TCATTATTGG GACCATCTTC ATCATCAAGG GATTGCGCAA AAGCAATGCA GCAGAACGCA GGGGGCCTCT GTAAGGCACA TGGAGGTGAT GGTGTTTCTT AGAGAGAAGA TCACTGAAGA AACTTCTGCT TTAATGGCTT TACAAAGCTG GCAATATTAC AATCCTTGAC CTCAGTGAAA GCAGTCATCT TCAGCATTTT CCAGCCCTAT AGCCACCCCA AGTGTGGATA TGCCTCTTCG ATTGCTCCGT ACTCTAACAT CTAGCTGGCT TCCCTGTCTA TTGCCTTTTC CTGTATCTAT TTTCCTCTAT TTCCTATCAT TTTATTATCA CCATGCAATG CCTCTGGAAT AAAACATACA GGAGTCTGTC TCTGCTATGG AATGCCCCAT GGGGCATCTC TTGTGTACTT ATTGTTTAAG GTTTCCTCAA ACTGTGATTT TTCTGAACAC AATAAACTAT TTTGATGATC TTGGGTGGAA AAAAAAAAAA AAAAAAAAAA AAAAAAAAAA AA | 14 |
| HNRNPA3P1 | NR_002726.2 | CGAGTTGGAA GAGGTGAGTC CTGTCTCAAA ATGGAGGTAA AACCGCCGCC TGGTTGCCCC CAGCCCGACT CCGGCAGTCG CCGTCGCCAC TGGGGGGAGG AGGGCCATGA TCCAAAGGAA CCAGAGCAGC TGAGAAAACT GTTTATTGGT GGTCTGAGCT TTGAAACTAC AGATGATAGT TTAAGAGAAC ATTTTGAGAA ATGGGGCACA CTCACAGATT GTCTGGTAAT GAGAGACCCC CAAACAAAAC GTTCCAGGGG CTTTGGTTTT GTGACTTATT CTTGTGTTAC AGAGGTGGAT GCAGCAATGC GTGCTCGACC ATTCAAGGTT GATGGGCGTG TAGTGGAACC AAAGAGAGCT GTTTCTAGAG AGGATTCTGT GAAGCCTGGT GCCCATCTAA CAGTGAAGAA AATTTTTGTT GGCAGTATTA AGAAGATAC AGAAGAATAT AATTTGAGAG ACTACTTTGA AAAGTACGGC AAGATTGAAA CCATAGAAGT TATGGAAGAC AGGCAGAGTG GAAAAAAGAG AGGATTTGCT TCTGTAACTT TTGATGATCA TGATACAGTT GATAAAATTG TTGTTCAGAA ATACCACACT ATTAATGGGC ATAACTGTGA AGTGAAAAAG GCCCTTGCTA AACAAGTGAT GCAGCCGGCT GGATCACAGA GGGGTCGTGG AGGTGGATCT GGCAATTGTA TGGGTCACAG AGGAAACTTT GGAGGTGGTG GAGGTAATTT TGGCCGTGAT GGAAACTTTG GTGGAAGAGG AGGCTATGGT GGTGGAGGTG GTGGCAGCAG AGGTAGTTAT GGAGGAGGTG ATGTGGATAT AATGGATTAG GAGGTGATGG TGGCAACTAT GGCAGTGGTC CTGGTTATAG TAGTAGAGGC GGGTATGGTG GTGGTGGACC AGGATATGGA AACCAAGGTG GTGGATATGG TGGCGGTGTT GGAGGATATG ATGGTTACAA TGAAGGAGGA AATTTTGACG GTAGTAACTA TGGTGGTGGT GGGAACTATA TGGATTTTGG AAATTACAGT GGACAACAGC AATCAAATTA TGGACACATG AAAGGGGCA GTTTTGGTGG AAGAAGCTCG GGCAGTCCCT ATGGTGGTGG TTATGGATCT GGTGGTGGAA GTGGTGGATA TGGTAGCAGA AGGTTCTAAA AACAGCAGGA AAGGGCTACA GTTCTTAGCA GGAGAGAGAG TGAGGAGTTG TCAGGAAAGC TACAGGTTAC TTTGAGACAG TCGTCCCAAG TGCATTAGAG GAACTGTAAA AATCTGTCAC AGAAGGAACG ATGATCCATA ATCAGAAAAG TTACTGCAGC TTAAACAGGA AACCCTTCTT GTTCAGGACT GTCATAGCCA CAGTTTGCAG GAAGTGCAGC TATCGATTAA TGCAATGTAG CGTCAATTAG ATGTACATTC CTCAGGTCTT | 15 |

TABLE 1-continued

Melanoma Biomarker/Housekeeper Sequence Information

| Gene Name | RefSeq Accession | Sequence | SEQ ID NO: |
|---|---|---|---|
| | | TTATCTGTTG TAGCTTTGTC TTATTCTTTT TCTTTTCATT<br>ACATCAGGTA TATTGCCCTG TAAATTGTGG TAGTGGTACC<br>AGGAATAAAA AATTAAGGAA TTTTTAACTT TTCAATATCT<br>GTGTAGTTCA GTTTTTCTAC ATTTTAGTAC AGAAACTTTA<br>ACAAAATGCA GTTTTGAAGG TGTTTCCTTG TGAGTTAACA<br>AGTAAAGAAG ATCAATTGTT AATTACTATT TTGTATAAAT<br>TTTGCTAAAG TTAACTGTAA AGAAACACCT GCTGACTTGC<br>AGTTTAAGGG GAATCTATTC TCCCCATTTC CAAACCATGA<br>TATGAATGGA CGCCGACATG TGGAGAGAAC AGATAATTTG<br>TGTGTTTGCA ATGTGTGTTT TAGGTAAATA GGATTGGGTA<br>TTTAAATTAG CATTTGTGAA TTTAATAGCA TTAAGATTAC<br>CTTCAAATAA AAAAGTCTCA AAATTTCTTT TTGGTTTTTG<br>TGCACTTTCT TTTAAAATGT AATCACATGA TTTTAGTGTG<br>TTAGACTTGC TGAGTCCTAG CTGTGTTTAG AACATCTCCA<br>TTCTACATTT ACCTTGGTCA AATTTGAACT GCTGCCATAG<br>GTTTTGGGTG TAAAGAATGT TTACTGCCCT CCATTTAAAT<br>TCTGAAAAGG TATAGTGGAT GTTTTCCCTC TCCTACATTA<br>GAAACCATTC TTAAAAACTT TTCAAAATAT AGAACCATTA<br>AGCCTGCTAT ATCTGAGCAA ATTAGTGGGT ACCTTTTTTC<br>CTTTTTTAAA GCACAAGAGG CCCATAAATC TTGAGTTATT<br>TGCATTAGTT TACATTTTTT GATACAACTT TTCAGACCAA<br>GAGAATAAAA ATCATGCGTT ATTAAACCCC TAGCTGGCTG<br>GCATGCTTTC CTGTTTGTAC TGTATACATT TTGCTGGATG<br>AAACCAAGGA TAGTTTAGGT ATAATTGTCC AAAATAACCT<br>AACTGCAGCA GAAATGTAGG ACAGTTGCTT AGTACAGGCT<br>TCTCACTTCC TACAGACCTG AATTCAAATT TGGATAGTCT<br>GAGTTATTAA ATTCCCAAAG ACAAAGAACA CACTCTTATT<br>TCTTGTGTAT ATTTCAACAT AAATCATGTT GTTACCAATT<br>TGTTGGGAAG GCCCTGGTTG AGAAGAGTTT TAGATAATAA<br>GGCTGTATAT ATATAGATAT ATATAGATAT ATACCAATGT<br>CTATATATAG AGATATTTTA TATATATATA TACAGGTATA<br>TATATGTGTG TGTATATATA TAGGTATATA CATATATACA<br>TATATATATA TATATATATG GATATATACC CATGTCTACT<br>GTTTTGCTTC AGCTAGTGCT TACAATTTCA TTCAAGTCCT<br>GAGTATGTGT CCTGCTGTTA CTCCTTCTTT GGTAGTTGAA<br>CGTTGAATTC AAGTCTTTCC TTCTGTTTTA AGAAGTACTA<br>AGCAAACAAG CAATAAAAAG GGGAATGGCG CATGCTAGTG<br>TTTGAATATG CTCTCTTGTT GCTCTAATTC TGTGCCTCCG<br>TGCATTAATA TTTGGATGCA TGCAATGCCA GCATGGAAAT<br>TGGCCT | |
| IL23A | NM_016584.2 | AAAACAACAG GAAGCAGCTT ACAAACTCGG TGAACAACTG<br>AGGGAACCAA ACCAGAGACG CGCTGAACAG AGAGAATCAG<br>GCTCAAAGCA AGTGGAAGTG GGCAGAGATT CCACCAGGAC<br>TGGTGCAAGG CGCAGAGCCA GCCAGATTTG AGAAGAAGGC<br>AAAAAGATGC TGGGGAGCAG AGCTGTAATG CTGCTGTTGC<br>TGCTGCCCTG GACAGCTCAG GGCAGAGCTG TGCCTGGGGG<br>CAGCAGCCCT GCCTGGACTC AGTGCCAGCA GCTTTCACAG<br>AAGCTCTGCA CACTGGCCTG GAGTGCACAT CCACTAGTGG<br>GACACATGGA TCTAAGAGAA GAGGGAGATG AAGAGACTAC<br>AAATGATGTT CCCCATATCC AGTGTGGAGA TGGCTGTGAC<br>CCCCAAGGAC TCAGGGACAA CAGTCAGTTC TGCTTGCAAA<br>GGATCCACCA GGGTCTGATT TTTTATGAGA AGCTGCTAGG<br>ATCGGATATT TTCACAGGGG AGCCTTCTCT GCTCCCTGAT<br>AGCCCTGTGG GCCAGCTTCA TGCCTCCCTA CTGGGCCTCA<br>GCCAACTCCT GCAGCCTGAG GGTCACCACT GGGAGACTCA<br>GCAGATTCCA AGCCTCAGTC CCAGCCAGCC ATGGCAGCGT<br>CTCCTTCTCC GCTTCAAAAT CCTTCGCAGC CTCCAGGCCT<br>TTGTGGCTGT AGCCGCCCGG GTCTTTGCCC ATGGAGCAGC<br>AACCCTGAGT CCCTAAAGGC AGCAGCTCAA GGATGGCACT<br>CAGATCTCCA TGGCCCAGCA AGGCCAAGAT AAATCTACCA<br>CCCCAGGCAC CTGTGAGCCA ACAGGTTAAT TAGTCCATTA<br>ATTTTAGTGG GACCTGCATA TGTTGAAAAT TACCAATACT<br>GACTGACATG TGATGCTGAC CTATGATAAG GTTGAGTATT<br>TATTAGATGG GAAGGGAAAT TTGGGGATTA TTTATCCTCC<br>TGGGGACAGT TTGGGGAGGA TTATTTATTG TATTTATATT<br>GAATTATGTA CTTTTTTCAA TAAAGTCTTA TTTTTGTGGC<br>TAAAAAAAA | 16 |
| IQGAP1 | NM_003870.3 | GGACCCCGGC AAGCCCGCGC ACTTGGCAGG AGCTGTAGCT<br>ACCGCCGTCC GCGCCTCCAA GGTTTCACGG CTTCCTCAGC<br>AGAGACTCGG GCTCGTCCGC CATGTCCGCC GCAGACGAGG<br>TTGACGGGCT GGGCGTGGCC CGGCCGCACT ATGCTCTGT<br>CCTGGATAAT GAAAGACTTA CTGCAGAGGA GATGGATGAA | 17 |

TABLE 1-continued

Melanoma Biomarker/Housekeeper Sequence Information

| Gene Name | RefSeq Accession | Sequence | SEQ ID NO: |
|---|---|---|---|
| | | AGGAGACGTC AGAACGTGGC TTATGAGTAC CTTTGTCATT<br>TGGAAGAAGC GAAGAGGTGG ATGGAAGCAT GCCTAGGGGA<br>AGATCTGCCT CCCACCACAG AACTGGAGGA GGGGCTTAGG<br>AATGGGGTCT ACCTTGCCAA ACTGGGGAAC TTCTTCTCTC<br>CCAAAGTAGT GTCCCTGAAA AAAATCTATG ATCGAGAACA<br>GACCAGATAC AAGGCGACTG GCCTCCACTT TAGACACACT<br>GATAATGTGA TTCAGTGGTT GAATGCCATG GATGAGATTG<br>GATTGCCTAA GATTTTTTAC CCAGAAACTA CAGATATCTA<br>TGATCGAAAG AACATGCCAA GATGTATCTA CTGTATCCAT<br>GCACTCAGTT TGTACCTGTT CAAGCTAGGC CTGGCCCCTC<br>AGATTCAAGA CCTATATGGA AAGGTTGACT TCACAGAAGA<br>AGAAATCAAC AACATGAAGA CTGAGTTGGA GAAGTATGGC<br>ATCCAGATGC CTGCCTTTAG CAAGATTGGG GGCATCTTGG<br>CTAATGAACT GTCAGTGGAT GAAGCCGCAT TACATGCTGC<br>TGTTATTGCT ATTAATGAAG CTATTGACCG TAGAATTCCA<br>GCCGACACAT TTGCAGCTTT GAAAAATCCG AATGCCATGC<br>TTGTAAATCT TGAAGAGCCC TTGGCATCCA CTTACCAGGA<br>TATACTTTAC CAGGCTAAGC AGGACAAAAT GACAAATGCT<br>AAAAACAGGA CAGAAAACTC AGAGAGAGAA AGAGATGTTT<br>ATGAGGAGCT GCTCACGCAA GCTGAAATTC AAGGCAATAT<br>AAACAAAGTC AATACATTTT CTGCATTAGC AAATATCGAC<br>CTGGCTTTAG AACAAGGAGA TGCACTGGCC TTGTTCAGGG<br>CTCTGCAGTC ACCAGCCCTG GGGCTTCGAG GACTGCAGCA<br>ACAGAATAGC GACTGGTACT TGAAGCAGCT CCTGAGTGAT<br>AAACAGCAGA AGAGACAGAG TGGTCAGACT GACCCCCTGC<br>AGAAGGAGGA GCTGCAGTCT GGAGTGGATG CTGCAAACAG<br>TGCTGCCCAG CAATATCAGA GAAGATTGGC AGCAGTAGCA<br>CTGATTAATG CTGCAATCCA GAAGGGTGTT GCTGAGAAGA<br>CTGTTTTGGA ACTGATGAAT CCCGAAGCCC AGCTGCCCCA<br>GGTGTATCCA TTTGCCGCCG ATCTCTATCA GAAGGAGCTG<br>GCTACCCTGC AGCGACAAAG TCCTGAACAT AATCTCACCC<br>ACCCAGAGCT CTCTGTCGCA GTGGGAGATGT TGTCATCGGT<br>GGCCCTGATC AACAGGGCAT TGGAATCAGG AGATGTGAAT<br>ACAGTGTGGA AGCAATTGAG CAGTTCAGTT ACTGGTCTTA<br>CCAATATTGA GGAAGAAAAC TGTCAGAGGT ATCTCGATGA<br>GTTGATGAAA CTGAAGGCTC AGGCACATGC AGAGAATAAT<br>GAATTCATTA CATGGAATGA TATCCAAGCT TGCGTGGACC<br>ATGTGAACCT GGTGGTGCAA GAGGAACATG AGAGGATTTT<br>AGCCATTGGT TTAATTAATG AAGCCCTGGA TGAAGGTGAT<br>GCCCAAAAGA CTCTGCAGGC CCTACAGATT CCTGCAGCTA<br>AACTTGAGGG AGTCCTTGCA GAAGTGGCCC AGCATTACCA<br>AGACACGCTG ATTAGAGCGA AGAGAGAGAA AGCCCAGGAA<br>ATCCAGGATG AGTCAGCTGT GTTATGGTTG GATGAAATTC<br>AAGGTGGAAT CTGGCAGTCC AACAAAGACA CCCAAGAAGC<br>ACAGAAGTTT GCCTTAGGAA TCTTTGCCAT TAATGAGGCA<br>GTAGAAAGTG GTGATGTTGG CAAAACACTG AGTGCCCTTC<br>GCTCCCCTGA TGTTGGCTTG TATGGAGTCA TCCCTGAGTG<br>TGGTGAAACT TACCACAGTG ATCTTGCTGA AGCCAAGAAG<br>AAAAAACTGG CAGTAGGAGA TAATAACAGC AAGTGGGTGA<br>AGCACTGGGT AAAAGGTGGA TATTATTATT ACCACAATCT<br>GGAGACCCAG GAAGGAGGAT GGGATGAACC TCCAAATTTT<br>GTGCAAAATT CTATGCAGCT TTCTCGGGAG GAGATCCAGA<br>GTTCTATCTC TGGGGTGACT GCCGCATATA ACCGAGAACA<br>GCTGTGGCTG GCCAATGAAG GCCTGATCAC CAGGCTGCAG<br>GCTCGCTGCC GTGGATACTT AGTTCGACAG GAATTCCGAT<br>CCAGGATGAA TTTCCTGAAG AAACAAATCC CTGCCATCAC<br>CTGCATTCAG TCACAGTGGA GAGGATACAA GCAGAAGAAG<br>GCATATCAAG ATCGGTTAGC TTACCTGCGC TCCCACAAAG<br>ATGAAGTTGT AAAGATTCAG TCCCTGGCAA GGATGCACCA<br>AGCTCGAAAG CGCTATCGAG ATCGCCTGCA GTACTTCCGG<br>GACCATATAA ATGACATTAT CAAAATCCAG GCTTTTATTC<br>GGGCAAACAA AGCTCGGGAT GACTACAAGA CTCTCATCAA<br>TGCTGAGGAT CCTCCTATGG TTGTGGTCCG AAAATTTGTC<br>CACCTGCTGG ACCAAAGTGA CCAGGATTTT CAGGAGGAGC<br>TTGACCTTAT GAAGATGCGG GAAGAGGTTA TCACCCTCAT<br>TCGTTCTAAC CAGCAGCTGG AGAATGACCT CAATCTCATG<br>GATATCAAAA TTGACTGCT AGTGAAAAAT AAGATTACGT<br>TGCAGGATGT GGTTTCCCAC AGTAAAAAAC TTACCAAAAA<br>AAATAAGGAA CAGTTGTCTG ATATGATGAT GATAAATAAA<br>CAGAAGGGAG GTCTCAAGGC TTTGAGCAAG GAGAAGAGAG<br>AGAAGTTGGA AGCTTACCAG CACCTGTTTT ATTTATTGCA<br>AACCAATCCC ACCTATCTGG CCAAGCTCAT TTTTCAGATG<br>CCCCAGAACA AGTCCACCAA GTTCATGGAC TCTGTAATCT<br>TCACACTCTA CAACTACGCG TCCAACCAGC GAGAGGAGTA | |

TABLE 1-continued

Melanoma Biomarker/Housekeeper Sequence Information

| Gene Name | RefSeq Accession | Sequence | SEQ ID NO: |
|---|---|---|---|
| | | CCTGCTCCTG CGGCTCTTTA AGACAGCACT CCAAGAGGAA ATCAAGTCGA AGGTAGATCA GATTCAAGAG ATTGTGACAG GAAATCCTAC GGTTATTAAA ATGGTTGTAA GTTTCAACCG TGGTGCCCGT GGCCAGAATG CCCTGAGACA GATCTTGGCC CCAGTCGTGA AGGAAATTAT GGATGACAAA TCTCTCAACA TCAAAACTGA CCCTGTGGAT ATTTACAAAT CTTGGGTTAA TCAGATGGAG TCTCAGACAG GAGAGGCAAG CAAACTGCCC TATGATGTGA CCCCTGAGCA GGCGCTAGCT CATGAAGAAG TGAAGACACG GCTAGACAGC TCCATCAGGA ACATGCGGGC TGTGACAGAC AAGTTTCTCT CAGCCATTGT CAGCTCTGTG GACAAAATCC CTTATGGGAT GCGCTTCATT GCCAAAGTGC TGAAGGACTC GTTGCATGAG AAGTTCCCTG ATGCTGGTGA GGATGAGCTG CTGAAGATTA TTGGTAACTT GCTTTATTAT CGATACATGA ATCCAGCCAT TGTTGCTCCT GATGCCTTTG ACATCATTGA CCTGTCAGCA GGAGGCCAGC TTACCACAGA CCAACGCCGA AATCTGGGCT CCATTGCAAA AATGCTTCAG CATGCTGCTT CCAATAAGAT GTTTCTGGGA GATAATGCCC ACTTAAGCAT CATTAATGAA TATCTTTCCC AGTCCTACCA GAAATTCAGA CGGTTTTTCC AAACTGCTTG TGATGTCCCA GAGCTTCAGG ATAAATTTAA TGTGGATGAG TACTCTGATT TAGTAACCCT CACCAAACCA GTAATCTACA TTTCCATTGG TGAAATCATC AACACCCACA CTCTCCTGTT GGATCACCAG GATGCCATTG CTCCGGAGCA CAATGATCCA ATCCACGAAC TGCTGGACGA CCTCGGCGAG GTGCCCACCA TCGAGTCCCT GATAGGGGAA AGCTCTGGCA ATTTAAATGA CCCAAATAAG GAGGCACTGG CTAAGACGGA AGTGTCTCTC ACCCTGACCA ACAAGTTCGA CGTGCCTGGA GATGAGAATG CAGAAATGGA TGCTCGAACC ATCTTACTGA ATACAAAACG TTTAATTGTG GATGTCATCC GGTTCCAGCC AGGAGAGACC TTGACTGAAA TCCTAGAAAC ACCAGCCACC AGTGAACAGG AAGCAGAACA TCAGAGAGCC ATGCAGAGAC GTGCTATCCG TGATGCCAAA ACACCTGACA AGATGAAAAA GTCAAAATCT GTAAAGGAAG ACAGCAACCT CACTCTTCAA GAGAAGAAAG AGAAGATCCA GACAGGTTTA AAGAAGCTAA CAGAGCTTGG AACCGTGGAC CCAAAGAACA AATACCAGGA ACTGATCAAC GACATTGCCA GGGATATTCG GAATCAGCGG AGGTACCGAC AGAGGAGAAA GGCCGAACTA GTGAAACTGC AACAGACATA CGCTGCTCTG AACTCTAAGG CCACCTTTTA TGGGGAGCAG GTGGATTACT ATAAAAGCTA TATCAAAACC TGCTTGGATA ACTTAGCCAG CAAGGGCAAA GTCTCCAAAA AGCCTAGGGA AATGAAAGGA AAGAAAAGCA AAAAGATTTC TCTGAAATAT ACAGCAGCAA GACTACATGA AAAAGGAGTT CTTCTGGAAA TTGAGGACCT GCAAGTGAAT CAGTTTAAAA ATGTTATATT TGAAATCAGT CCAACAGAAG AAGTTGGAGA CTTCGAAGTG AAAGCCAAAT TCATGGGAGT TCAAATGGAG ACTTTTATGT TACATTATCA GGACCTGCTG CAGCTACAGT ATGAAGGAGT TGCAGTCATG AAATTATTTG ATAGAGCTAA AGTAAATGTC AACCTCCTGA TCTTCCTTCT CAACAAAAAG TTCTACGGGA AGTAATTGAT CGTTTGCTGC CAGCCCAGAA GGATGAAGGA AAGAAGCACC TCACAGCTCC TTTCTAGGTC CTTCTTTCCT CATTGGAAGC AAAGACCTAG CCAACAACAG CACCTCAATC TGATACACTC CCGATGCCAC ATTTTTAACT CCTCTCGCTC TGATGGGACA TTTGTTACCC TTTTTTCATA GTGAAATTGT GTTTCAGGCT TAGTCTGACC TTTCTGGTTT CTTCATTTTC TTCCATTACT TAGGAAAGAG TGGAAACTCC ACTAAAATTT CTCTGTGTTG TTACAGTCTT AGAGGTTGCA GTACTATATT GTAAGCTTTG GTGTTTGTTT AATTAGCAAT AGGGATGGTA GGATTCAAAT GTGTGTCATT TAGAAGTGGA AGCTATTAGC ACCAATGACA TAAATACATA CAAGACACAC AACTAAAATG TCATGTTATT AACAGTTATT AGGTTGTCAT TTAAAAATAA AGTTCCTTTA TATTTCTGTC CCATCAGGAA AACTGAAGGA TATGGGGAAT CATTGGTTAT CTTCCATTGT GTTTTTCTTT ATGGACAGGA GCTAATGGAA GTGACAGTCA TGTTCAAAGG AAGCATTTCT AGAAAAAAGG AGATAATGTT TTTAAATTTC ATTATCAAAC TTGGGCAATT CTGTTTGTGT AACTCCCCGA CTAGTGGATG GGAGAGTCCC ATTGCTAAAA TTCAGCTACT CAGATAAATT CAGAATGGGT CAAGGCACCT GCCTGTTTTT GTTGGTGCAC AGAGATTGAC TTGATTCAGA GAGACAATTC ACTCCATCCC TATGGCAGAG GAATGGGTTA GCCCTAATGT AGAATGTCAT TGTTTTTAAA ACTGTTTTAT ATCTTAAGAG TGCCTTATTA AAGTATAGAT GTATGTCTTA AAATGTGGGT GATAGGAATT TTAAAGATTT ATATAATGCA TCAAAAGCCT TAGAATAAGA AAAGCTTTTT TTAAATTGCT TTATCTGTAT ATCTGAACTC TTGAAACTTA TAGCTAAAAC ACTAGGATTT ATCTGCAGTG | |

TABLE 1-continued

Melanoma Biomarker/Housekeeper Sequence Information

| Gene Name | RefSeq Accession | Sequence | SEQ ID NO: |
|---|---|---|---|
| | | TTCAGGGAGA TAATTCTGCC TTTAATTGTC TAAAACAAAA ACAAAACCAG CCAACCTATG TTACACGTGA GATTAAAACC AATTTTTTCC CCATTTTTTC TCCTTTTTTC TCTTGCTGCC CACATTGTGC CTTTATTTTA TGAGCCCCAG TTTTCTGGGC TTAGTTTAAA AAAAAAATCA AGTCTAAACA TTGCATTTAG AAAGCTTTTG TTCTTGGATA AAAAGTCATA CACTTTAAAA AAAAAAAAAA CTTTTTCCAG GAAAATATAT TGAAATCATG CTGCTGAGCC TCTATTTTCT TTCTTTGATG TTTTGATTCA GTATTCTTTT ATCATAAATT TTTAGCATTT AAAAATTCAC TGATGTACAT TAAGCCAATA AACTGCTTTA ATGAATAACA AACTATGTAG TGTGTCCCTA TTATAAATGC ATTGGAGAAG TATTTTTATG AGACTCTTTA CTCAGGTGCA TGGTTACAGC CCACAGGGAG GCATGGAGTG CCATGGAAGG ATTCGCCACT ACCCAGACCT TGTTTTTTGT TGTATTTTGG AAGACAGGTT TTTTAAAGAA ACATTTTCCT CAGATTAAAA GATGATGCTA TTACAACTAG CATTGCCTCA AAAACTGGGA CCAACCAAAG TGTGTCAACC CTGTTTCCTT AAAAGAGGCT ATGAATCCCA AAGGCCACAT CCAAGACAGG CAATAATGAG CAGAGTTTAC AGCTCCTTTA ATAAAATGTG TCAGTAATTT TAAGGTTTAT AGTTCCCTCA ACACAATTGC TAATGCAGAA TAGTGTAAAA TGCGCTTCAA GAATGTTGAT GATGATGATA TAGAATTGTG GCTTTAGTAG CACAGAGGAT GCCCCAACAA ACTCATGGCG TTGAAACCAC ACAGTTCTCA TTACTGTTAT TTATTAGCTG TAGCATTCTC TGTCTCCTCT CTCTCCTCCT TTGACCTTCT CCTCGACCAG CCATCATGAC ATTTACCATG AATTTACTTC CTCCCAAGAG TTTGGACTGC CCGTCAGATT GTTGCTGCAC ATAGTTGCCT TTGTATCTCT GTATGAAATA AAAGGTCATT TGTTCATGTT AAAAAAAA | |
| LOC494127 | NR_036691.1 | GCAGTGCCCG ACTCCGCAGG AGCGCCAGGG CGGCTCCTGC TCTTCCTGGA CTCCCTGAAG AGGCGTTTGT CGAAATGTCC ACAGAAGGAG GATTTGGTGG TACTAGCCGC AGTGATGCCC AGCAAAGCCT AAAGTCCTTC TGGCTTCGGG TCATGGAAGA AATCTGGAAT TTAGCAGTGA AAGATTTCTG AATGCAGGAA CTCCCACTGG CTCGTATTAA GAAGATTATG AAACTGGATG AAGATGTGAA GATGATCAGT GCAGAGGCCC CTGTGCTCTT TGCCAGGGCA GCCCAGATTT TTTATCACAG AGTTGACTCT TCGAGCCTGG ATTCACACAG AGGATAACAA CTGCCGGACT TATGTCGCCA TGGCAATTAC GAAATTTGAT CAATTGGATT TTCTCATCGA TATTGTTCTA AGAGATGAAC TGAAACCTCC AAAGTGTCAG GAGGAGGTGC TGCAGTCTGT AACTCCTGCT GAGCCAGTCC AATACTATTT CACGCTGGCT CAGCAGCCCA CCGCCCGTCC AAGTCCAGGG ACAGCAGCAA GGCCAGACCA CCGCCAGCTC CATGACCACC ATGCAGCCTG GGCAGATCAT CATCGCACAG CTTCAGCAGG GCCAGACCAC GCCCGTGACG ACGCAGGTTG GAGAAGGTCA GCAGGTCAG ATTGTCCAGG CCCAGCCACA GGGTCAAGCC CAGTAGGCCC AGAGTGGTAC TGGATGGACC GTGCAGGTGA TGTAGCAGAT CCTCACTAAC ACAGGAGAGA TCCAGCAGAT CCCGGTGCAG CTGAAGGCTG GCCAGCTGCA GTGTATCCGC TTAGCCCAGT CTGTATCAGG CACCCACGTT CTGCAGGGAC AGATCCGAC ACTTGCCACC AGCGCTCAAC CGATTACACA GACAGAGGTC CAGCAAAGAC AGCAGTAGTT CAGCCAGTTC ACAGATGGAC AGCAGCTCTA CCAGATCCAG CAAGTATCCA TACCTGCGGG CCAGGACCTG CCCAGCCCAT GTTTTTCCAG TCAGTCAACC AGCCCTCTGA TGGGCAGGCC CCCCGGGTGA CTGGCGGCTG AGGGCCGGAG CTGGCAAGGC CGAGGACACT CAACACAATT TTTGCCGTAC AGCCCCAGGT CATGAACACA GCCTTCTTCC CCAGAGGACC CGGCCGACCT CAGCTCCTCC TGCAGGCTAG GACAATGGCG CACTAGGCCT CATGCCTGGG GGCCGAGATT CTCCAACAGA AAGATGCAAT ATTTTTTGTT TCCTTTTTTC TCCAAGGAAT CAATATTTCA ATATGTTGAG CTGTGTGTCC AATGCTATGA AATTAAAATA TTAAATCACA AAAAAAAAAA AAAA | 18 |
| LOC646471 | NR_024498.1 | AATGAATCCA ACTACTGTCC TTGTCCTCTC CTCTCTAGGT TTGTGGAGAC TGAATTCCAC AAACCTAGGG ACAGGGCACT CTCTAGGGGC AAGTCAACTC TCAATTATAG TGAGGGCAGG TTCCCCAGTT GCCAGCCTAC ACCCTGGCCA GCCACCCAAG GGAATACCTG CTGCTGCTAA GGCAGTCAAT GTTGGGAGGG TCAGGGAAGG GGAGAGGAAG TAGCTGAGTG TAGAGATTAT CCAGGCTTTC CTTCCCGTCC TCTGTACAGA AAGGCAGACA TACACTGACT CCTGAAGTGC CCCAGGATCA TAGTTGGTTC TTCTTAGGGG GAGGGAGTGA AACGGTGGCC TTGCTCCAAT TCCAGGCCTC TGGAGAAAGG AGTGCTCAAC TGGAGAGTCT | 19 |

TABLE 1-continued

Melanoma Biomarker/Housekeeper Sequence Information

| Gene Name | RefSeq Accession | Sequence | SEQ ID NO: |
|---|---|---|---|
| | | CAGAACCTTT TACAGTACTT CAGCAGGCCC AGCACCCAAC CTTCCCCACC ATACCCCTGC CCTGGGAATG CCCCTTACCA CAGTGGCTTC CATTCCTGAC ATTTGAACCA GCTCCTGCAC TTGAAGGACA AGGCAGCCAC TGGGCAGCTC CGGGAGGCGG GAGGCGTGAC TCCTTCATAT CAGGCCATCT GGAGGAGCAC CAGATTTCCC TCTTGTGAAA CAACCCCCCA CAGTGGGGAT TTAATGGTCA CCACACAAGC CCCAAAAAAC CAGGCCCTGC AGAGCCATGA CTTCACAGGG GAGAAAACCA GCCCAAGAGG CTGCCCTCAC CCAACACTTA GCTCTAAGTC CAGACTCTTA AAGGTTCTGT TAAAGATCTG CGGCCAGGCG CAGTGGCTCA CATCTGTAAT CCCAGCACTT TGGGAGGCCG AGGTGGGCGG ATCACGAGGT CAGGAGAGCG AGACCATCCT GGCTAACACA GTGAAGCCCT GTCTCTACTA AAAATACAAA AAATTAGCCA GGTGTGGTGG CGGGCACCTG TAGTACCAGC TACTTGGGAG GCTGAGGCAG GAGAATGGCG TGAACCCAGG AGGCAGAGCT TGCAGTGAGC CGAGATCACG CCACTGCACT CCAACCTGGG TGACAGAGCG AGACTCCGTC TCAAAAAAAA AAAAAAAAA AAAAGATTTG CCTAGTGAGC TTGGCCAACC CAAGAGCCTT CCTGGGCTCT CAGGTTTCTT GAGGCAAAAC TTCTAAAGAT GCAAATAGAA TCCTTGGTAG CTACAAAGCT CATCTAGCCA AATTATAAGT ACTATCCAAG CCCAGGATTC ATTCTTGAAG ATGAGATGTA AAAGCACTGC TGGGCCCTTG CAAAGGGAGA GATCAGAGAA AATAGGAGAA CGAACACCAG CTCATGCCAA TCTCAGTCTC ATGAGCTACA GAGAAAAAGA GCCAAAAAAG TTTATCCTGG CTCAGCCACC TTCTGGCTTT GTAGCTACAG GCAAGTTATT TAACTTTTCT GAATGTTGGT TTTTCCATCT GGAAAAAGGA GACAGGAAAA GCTGCCACTG GAGGCTACCT TAAGGGTCAA TGAGTGAAAT GGGGTTGAGT GCTTAATGAA CTGTTAAAAC ATGACACAGA TGGGTGAGGT GACATCTGAC TGCTCTTCAC AGCAGTCCTT GCATGGTGAG CAGATGCAAT CAGTGTGCTC GTTCATTCAC TTGTTCATCA AACACCAACA GTACCCACTT GTGCCAGGCC TTGTGCTGGG CACCGTAGGG GCTATGGAAG GAGTAAGACA CAGTCATGCT CTCAAGGAAC TCGCTGTCCA GCAGAGTGAT AGGACATGAA TACATACTTC TAGCAAAGGC TGAGTAGCAT TAGGCAGGTG GCCAGATGAG GTCAGAGCTC TGGCCCTAGT GCCCTGTAGT AAGTTGCGAG GGAGTAGGAA ATGAAGACAA AACAGCAAGA GCACAGGTCC AGCACAAGAA GGTGAAGGAC ATGGAAAGAG GAGCAGAGCA TGATAAAGCT ACAAAAGTAG GGGGCAAGTC ATGAGGTCCG GGTCACTGGG GAGCCCTGGA CAGGCTCTGA ATGGGAGATA GACTAGACTG ACAAAGCAGC TCTTTCTGGA GACCTCCTGT GGAGGGTCCC CTCTTCTACC CTTGGGAGAC GAGGTGTCAT TCACTTCACG ATACACATGG GGAAAGGAAG TTGGACAGGG GAAGGCACTT GTCTAAGGTC ACTCAGTGGT CATGCCAGTG CAAAGCACCC AAAGCCTGGT CCAGGTCCTG CCACCTCCTG CGTGGGCTCC ATCTTCTCGG CTCAGTTCAA GCCTTTATTA TCAGAGTCCC TCTGTGTGCC AGGCTCTGTG CTGAATGTCC GTGTCGGCCA CAAATTGCAC TAACGGTGCT TACTGCCACT TCCTCTCCGA CCTTACCTCC AAAGACCCAG CCGGGCCTAA CCCTCACACA CAGCCAGAGG AATCCTTCCC AAACACAGTT AATCACATCG CTCATCCGTT TAAAACTGGC TTACTAGAGC CAACACAGGA TAAAATCCAC AATCAGTCCC AAACCCATCT TTCTCTGCCG TCTCTAGACC ACATTCACTG AGCACCAAGG CCTGCACGCT TCGCAGCCAG CCCTCCTGCT CTCCCCCTTG CCCTCCAGCC ACACTGGCCC TCAACCCCCA ACACTGGGCC CACCTCTGAG CCCTGCATCA AACACCAGCA CCCCCTTCGC CGAGCTCATT CTTCATCATT CCTCAGAGCT CAGCTTAAGC ATCACCTTCC TTCCCTGCGA CAGGGTCAGG TCCTTTCCTG TGCGCTCCGC AGCACCCTGC CTGTCCCTCG GAGTCCTCGC GAGAGGAACT AGATAACTGT GATCCCCGCG CACAGCACGG TGTCTGCCTA GGACACAGTG AGCGCTTCAA CGCGCTGAAC TAAACGAATG AAGGGGAACA CCAACTCAGC TGTCACCCCC GCCCCCAAGT GTCACTGGCT AGAAGATCTT CCCCCGGTTC GCCGGCAGCA CCGGTGGGTC TTGTCACCTC TGCGCCCCGC AGCCCTCCGG AGGCTGCAGT TGCTGTCTGC TGACAGGCGT CCCCTCAGGA GAACGGGAGC TCCTCCAGCG CAGGGCCCTG CTCAGCACCC CTGGTCCCGG GGGCCCCAC GGAGGCCGCC GCGCTCAGTG AAACTTTGCC GCGCGCAGCA GTGGCCGGAG ACCCGCGCGG ACCCTCTCCC CGCGGGGACC CGCCAGGGCG AGTCGCCCCT CCCCCGCGGC AGACGACCCG ACCTGGGCCA AGGTCGGCCA AGTGCTCGCC GCCTGCCCAG CGGCCCTTGG ACCCACAGGA CCCGGACCCG AGTGCGCGGA AGCCTCCGAG CCGCGGCCAG GTCTCAGAAT GCGCGGCGGG GCAGCCCGGC CCGTCAAGCA GCGAAGCCGA AACTAGAAGC CTGAGGTCTG | |

TABLE 1-continued

Melanoma Biomarker/Housekeeper Sequence Information

| Gene Name | RefSeq Accession | Sequence | SEQ ID NO: |
|---|---|---|---|
| | | GCTTGGTCAC TGTTTGCTGG GGAACTCCGA CGAGCAACTA CCCCTTCGGGG ACTCAGTTTC CCCCGGGCCA AGTGAGACGG ACAGCTGCGG CTCCCGCGAG AACTCGCGCG GGAACAGGAG CTGCGGGCTC CGCACAGCGC CCGGCACGTA GACCCAGTCT ACTAACGGGC TGGAAGGTCG CGCTCCCGCC TCCGCGCCTC CCTAGAACCT TTCTCACCTC AAGCTCGGGC TCCCGGACTC TCTCACCTCA CGGCCCCTCC TTCCACCTTG GGCCGCCCAG CCTCAACCGC CCT | |
| LOH12CR | NR_024061.1 | GGCTACGCAA GACCTTCAGT TCCGGATTAG GAGGCCCCGC CCCCCGGCCC GAGGGAGGGG CGGAGAGACC CGCTCCTGCG ACTTAGGGCG ATGCCACCTT AAAGGGCTTG ACCTCCTCGA AGCCAGAACT GCGGAAGAGG ATGGAGAAAG AAACGCTAGA TAGACCCAGG ATTCGAACCC ACAACAGCTT GGATGCAAAG CTCATTTTGA ATTCTGAAGA GCTGGGAGTT TAGCAGTGGA CGACCAAACA AAAAAATACC AGAAGACGGT GAAAGCAGCA GCTGGAAATG AGAGAAAAAT TAAGAAATAG AAAATGCTGT TTCATGTATT AGGGAGTGCA CATCTTTAAA GAGAAGTGAA GAACCTTTTT GGCTAGGCGC TTTCTGGGGA CCTTGGCAGT TATCAACAAG TCACTCTGAA ACTAACAGAA GGTGAGGAGG GAGTAATCCA GAAAGGAAAC TGCCATTTTT GCTAGGGCAA GAAAGTAGAC CTAGCAATGC AATGCCATCA AGGAGTTAGC TGGCTCTAGC GTTCTCCGAA CTTTGCAACT CATTTTATAT TACATTGTCT GCGTCAAGAA ATTTCAAGTA AATGCCTTGA GATTTTATAT GTATAAAATG TAGTCTCTGG CCAGGCGGGG TGGCTCACGC CTGTAATCCC AGCACTTTGG GAGGCTGAGG CGAGTAGATC ACGATGTCAG GAGATCAAGA CCATCCTGGC TAACATGGTG AAACCCCGTC TCTACTAAAA AATACAAAAA ATTAGCCGGG CATGATGGTG GGCGCCTGTA GTCCCAGCTA CTCGGGAGGC TGAGACAGGA GAATGGTGTG AACCCGGGAG GCAGAGCTTG CAGTGAGCCG AGATCGCGCC ACTGCACTCC AGCCTGGGCG ACAGAGCGAG ACTCCGTCTC AAAAAAAAAA AAAAAAAAAA AAGTCTCAGA AGAAGTGTCA AGTTGACTAA ATGATTTTTA AGTCCCTTCC ACTCTACTAT ATCACAATAA TTTCCCCTAT TTTACCTTAT TTAATTTTCA CAACAACCCT GCAGCCTGTA AGTAGGTGAC TCCTCCATGG TCAGCAGGTG GTCAGTGGTC GAACTATTTA GGACTATCTG ATGCTCTTTC CTCTGCTCAC CATTGCAATA CAATGAGAAA AATGCAAATG AATCTAAGTA CAGTGTTCTC TGGGAATATG AAGATAGAAC TAAAAACTGC CTGAGAGATC AGGGCAGGCT TCTAGAAAGT TGTGTCTAAC TAGTCTTGAG GTTTACATAA ACCACACCAG GCTGATGGGA CTGGGAAGGG CCCACTAAGC AGTGAGACCA TTCCCTTTTG GAGAGTCCTT GCATCCCCTC CCAGATTTCC TCTTTGAGGG GAAGGTGAGA GAGGAGGTAA AAGGGGTGAG GAATGGAGAA TAACTCATTC TGGTTCTTGT TTCCCCTTTT CCACATAAAA GTATATTTGT CTTGTGTTCC ATACACCAGT CCATACTGAT GTGATGGTGT TTTTTATGCT TCCTTTTGAA TAAACATTTC ATTCTTAA | 20 |
| PBXIP1 | NM_020524.3 | GGTCAGTTTC TGGTCACATG ATTTTCTTCT CGGGCTGCAA ACAAAGGGAA GCCTGCAACA AGTTAAGCTG AAGACCGAAG CAAGAGCTGG TTCAGGTGGC AGCCACAGCA GCCTCAGGGA CCTCAGCAAC TATGGCCTCC TGCCCAGACT CTGATAATAG CTGGGTGCTT GCTGGCTCCG AGAGCCTGCC AGTGGAGACA CTGGGCCCGG CATCCAGGAT GGACCCAGAA TCTGAGAGAG CCCTGCAGGC CCCTCACAGC CCCTCCAAGA CAGATGGGAA AGAATTAGCT GGGACCATGG ATGGAGAAGG GACGCTCTTC CAGACTGAAA GCCCTCAGTC TGGCAGCATT CTAACAGAGG AGACTGAGGT CAAGGGCACC CTGGAAGGTG ATGTTTGTGG TGTGGAGCCT CCTGGCCCAG GAGACACAGT AGTCCAGGGA GACCTGCAGG AGACCACCGT GGTGACAGGC CTGGGACCAG ACACACAGGA CCTGGAAGGC CAGAGCCCTC CACAGAGCCT GCCTTCAACC CCCAAAGCAG CTTGGATCAG GGAGGAGGGC CGCTGCTCCA GCAGTGACGA TGACACCGAC GTGGACATGG AGGGTCTGCG GAGACGGCGG GGCCGGGAGG CCGGCCCACC TCAGCCCATG GTGCCCCTGG CTGTGGAGAA CCAGGCTGGG GGTGAGGGTG CAGGCGGGGA GCTGGGCATC TCCCTCAACA TGTGCCTCCT TGGGGCCCTG GTTCTGCTTG GCCTGGGGGT CCTCCTCTTC TCAGGTGGCC TCTCAGAGTC TGAGACTGGG CCCATGGAGG AAGTGGAGCG GCAGGTCCTC CCAGACCCCG AGGTGCTGGA AGCTGTGGGG GACAGGCAGG ATGGGCTAAG GGAACAGCTG CAGGCCCCAG TGCCTCCTGA CAGTGTCCCC AGCCTGCAAA ACATGGGTCT TCTGCTGGAC AAGCTGGCCA AGGAGAACCA GGACATCCGG CTGCTGCAGG CCCAGCTGCA | 21 |

TABLE 1-continued

Melanoma Biomarker/Housekeeper Sequence Information

| Gene Name | RefSeq Accession | Sequence | SEQ ID NO: |
|---|---|---|---|
| | | GGCCCAAAAG GAAGAGCTTC AGAGCCTGAT GCACCAGCCC AAAGGGCTAG AGGAGGAGAA TGCCCAGCTC CGGGGGGCTC TGCAGCAGGG CGAAGCCTTC CAGCGGGCTC TGGAGTCAGA GCTGCAGCAG CTGCGGGCCC GGCTCCAGGG GCTGGAGGCC GACTGTGTCC GGGGCCCAGA TGGGGTGTGC CTCAGTGGGG GTAGAGGCCC ACAGGGTGAC AAGGCCATCA GGGAGCAAGG CCCCAGGGAG CAGGAGCCAG AACTCAGCTT CCTGAAGCAG AAGGAACAGC TGGAGGCTGA GGCACAGGCA TTAAGGCAAG AGTTAGAGAG GCAGCGACGG CTGCTGGGGT CTGTACAGCA GGATCTGGAG AGGAGCTTGC AGGATGCCAG CCGCGGGGAC CCAGCTCATG CTGGCTTGGC TGAGCTGGGC CACAGATTGG CCCAGAAACT GCAGGGCCTG GAGAACTGGG GCCAGGACCC TGGGGTCTCT GCCAATGCCT CAAAGGCCTG GCACCAGAAG TCCCACTTCC AGAATTCTAG GGAGTGGAGT GGAAAGGAAA AGTGGTGGGA TGGGCAGAGA GACCGGAAGG CTGAGCACTG GAAACATAAG AAGGAAGAAT CTGGCCGGGA AAGGAAGAAG AACTGGGGAG GTCAGGAGGA CAGGGAGCCA GCAGGAAGGT GGAAGGAGGG CAGGCCAAGG GTGGAGGAGT CGGGGAGCAA GAAGGAGGGC AAGCGACAGG GCCCGAAGGA ACCCCCAAGG AAAAGTGGTA GCTTCCACTC CTCTGGAGAA AAGCAGAAGC AACCTCGGTG GAGGGAAGGG ACTAAGGACA GCCATGACCC CCTGCCATCC TGGGCAGAGC TGTTGAGGCC CAAGTACCGG GCACCCCAGG GCTGCTCAGG TGTGGACGAG TGTGCCCGGC AGGAGGGCCT GACTTTCTTT GGCACAGAGC TAGCCCCAGT GCGGCAACAG GAGCTGGCCT CTCTGCTAAG AACATACTTG GCACGGCTGC CCTGGGCTGG GCAGCTGACC AAGGAGCTAC CCCTCTCACC TGCTTTCTTT GGTGAGGATG GCATCTTCCG TCATGACCGC CTCCGCTTCC GGGATTTTGT GGATGCCCTG GAGGACAGCT TGGAGGAGGT GGCTGTGCAA CAGACAGGTG ATGATGATGA AGTAGATGAC TTTGAGGACT TCATCTTCAG CCACTTCTTT GGAGACAAAG CACTGAAGAA GAGGTCAGGG AAGAAGGACA AGCACTCACA GAGCCCAAGA GCTGCGGGGC CCAGGGAGGG GCACAGCCAT AGCCACCACC ACCACCACCG GGGCTGACAC CCTGCCCCAC AGGGAATGGC CTTGGCCTGG CCCAGCCCAA GATCCCAGCG TTATCTAACT CCTGGAGGGT GGACTCTGTC CTGGCTTGTT TGGTGTCCTC AGATATCTTT CACACAGTAG AGCAAAATCA CCAGCCCTGC ACTGATGTCA CTTTATGTAG AAAAAGGCCT TAGCTGGACC TGCGTTGCCG TCTATGCAAA TGCATGCAAA TACTCCAGGC CCTGGGATGT GGGCTTGTGT TTTGTCACTG TGAAGGGGGA GATGGGAGAG GAGCCTGTTT TGGGGTGGGG TCTGGGGAAG GCAATCTGAT TCTGAAGCTA AAGAGCTTTC ATCCTCTTGA GTGTATGTCC CCATAGTGGG CCCCTTGACC CACATGCTGA CCGGTGCCTT GGGATTTGAC TAGAGTTGCT GGCTCGAGGC CCAGCACGAG GACTTACCCT GGGGTTTTGT TAGGTTTGGA AGCAGCTGTC CCTAGGGGGT GAAGTCCCCC CCCTTTTTTT TTTTACCCCT GCTTCTCCCA CGGCTTCACC TCCCTATGTG AACTGTAGAC TCAGATCCCA ATAAAGTGCT GTTGCAGCTA TGATGCTAGG TGGTTTCTAA GCACAGGGGA CACCCCACAC CCCCTGCCTG AATGGATGGG TCCATCCCAG GCACTGGTAC TTGCCCCCTT GTTCTGTATC CCCCTTTGCC CTTGCCTTGC CCTTCCAACA AACCCTAGGC CCTTGAGAAG CTGATACTTC TCCTTTTGCT CACAGCTGCC TTGGCCCCAC CCCTGGGAGA TGTAGCAAAT TGAGTGTGGG TTTTGGAGTC TGAGCCTCAG GCTCAAATCC AGGCCAAGTG ATCTTGGGCA AGTTAATCTC TGGGAACTTT GGGTTTCTTA TCCTCAAAAA AGGCGATGGA AGGGCTGGGG AAGTGATTAA ATAAAAGCAA CGCAAGAAAA AAAAAAAAAA AAAAA | |
| RNF5 | NM_006913.3 | AATAGTGATT AGGAAACCTT GAAGCCTGCC CAACGATCGT GGGCAGGAGG TGGTTTCTGG TTTGTTGGGG CGTGTGTATG TGTATTTGGG GGGACTGAAG GGTACGTGGG GCGAAACAAA ACCGGCCATG GCAGCAGCGG AGGAGGAGGA CGGGGGCCCC GAAGGGCCAA ATCGCGAGCG GGGCGGGGCG GGCGCGACCT TCGAATGTAA TATATGTTTG GAGACTGCTC GGGAAGCTGT GGTCAGTGTG TGTGGCCACC TGTACTGTTG GCCATGTCTT CATCAGTGGC TGGAGACACG GCCAGAACGG CAAGAGTGTC CAGTATGTAA AGCTGGGATC AGCAGAGAGA AGGTTGTCCC GCTTTATGGG CGAGGGAGCC AGAAGCCCCA GGATCCCAGA TTAAAAACTC CACCCCGCCC CCAGGGCCAG AGACCAGCTC CGGAGAGCAG AGGGGGATTC CAGCCATTTG GTGATACCGG GGGCTTCCAC TTCTCATTTG GTGTTGGTGC TTTTCCCTTT GGCTTTTTCA CCACCGTCTT CAATGCCCAT GAGCCTTTCC GCCGGGGTAC AGGTGTGGAT CTGGGACAGG GTCACCCAGC | 22 |

TABLE 1-continued

Melanoma Biomarker/Housekeeper Sequence Information

| Gene Name | RefSeq Accession | Sequence | SEQ ID NO: |
|---|---|---|---|
| | | CTCCAGCTGG CAGGATTCCC TCTTCCTGTT TCTCGCCATC<br>TTCTTCTTTT TTTGGCTGCT CAGTATTTGA GCTATGTCTG<br>CTTCCTGCCC ACCTCCAGCC AGAGAAGAAT CAGTATTGAG<br>GGTCCCTGCT GACCCTTCCG TACTCCTGGA CCCCCTTGAC<br>CCCTCTATTT CTGTTGGCTA AGGCCAGCCC TGGACATTGT<br>CCAGGAAGGC CTGGGGAGGA GGAGTGAAGT CTGTGCATAG<br>ATGGAGAGC CTTCTGCTCA GAGGCTCACT CAGTAACGTT<br>GTTTAATTCT CTGCCCTGGG AAGGAGGAT GGATTGAGAG<br>AATGTCTTTC TCCTCTCCTA AGTCTTTGCT TTCCCTGATT<br>TCTTGATTTG ATCTTCAAAG GTGGGCAAAG TTCCCTCTGA<br>CTCTTCCCCC ACTCCCCATC TTACTGATTT AATTTAATTT<br>TTCACTCCCC AGAGTCTAAT ATGGATTCTG ACTCTTAAGT<br>GCTTCCGCCC CCTCACTACC TCCTTTAATA CAAATTCAAT<br>AAAAAAGGTG AAATATAAAA AAAAAAAAAA AAAAAAAAA<br>AAAAAAAAAA AAAAAA | |
| SERTAD2 | NM_014755.2 | CTCCTGCACG GCGAGTGCTG GAGCACGACG TACCGCTCGC<br>TCGGTCAGGG CGCCCCCTCC GCCCGCCTCC TGCTTCCTCC<br>TCCGCTGCCT GCCGCCGCCG CCTCCACCAT TGTATAATGC<br>TCGGGGCGCG CAGGCAGAGA ACGGCGGAGT CTTAGCTTCA<br>GCCTCGCCTG CTGCCCGCTC CCCGGCGCCA CCCTCGGGCC<br>CCTGGAGCGG GGCACTCCGC ATGGAGCGGG AGTAGCTGAG<br>GAGTGGGCGG AAACCCCTCC TGATGCGTTA GTTCCCAGGT<br>GGAGCTGCAT GTGATATATG TTGGGTAAAG GAGGAAAACG<br>GAAGTTTGAT GAGCATGAAG ATGGGCTGGA AGGCAAAATC<br>GTGTCTCCCT GTGACGGTCC ATCCAAGGTG TCTTACACCT<br>TACAGCGCCA GACTATCTTC AACATTTCCC TTATGAACT<br>CTATAACCAC AGGCCCCTGA CAGAGCCCAG CTTGCAAAAG<br>ACCGTTTTAA TTAACAACAT GTTGAGGCGG ATCCAGGAGG<br>AACTCAAACA GGAAGGCAGC CTGAGGCCCA TGTTCACCCC<br>CTCCTCCCAG CCCACCACCG AGCCCAGCGA CAGCTACCGA<br>GAGGCCCCGC CGGCCTTCAG CCACCTGGCG TCCCCGTCCT<br>CCCACCCCTG CGACCTCGGA AGCACTACGC CCCTGGAGGC<br>CTGCCTCACC CCGGCCTCAC TGCTCGAGGA CGACGATGAC<br>ACGTTTTGCA CCTCCCAGGC CATGCAGCCC ACGGCTCCCA<br>CCAAACTGTC ACCTCCAGCC CTCTTGCCAG AAAAGGACAG<br>TTTCTCCTCT GCCTTGGACG AGATCGAGGA GCTCTGTCCC<br>ACATCTACCT CCACAGAGGC GGCCACGGCT GCGACTGACA<br>GTGTGAAAGG GACCTCCAGC GAGGCTGGCA CCCAGAAACT<br>CGACGGTCCT CAAGAGAGCC GCGCAGATGA CTCAAAACTG<br>ATGGACTCTC TGCCTGGGAA TTTTGAAATA ACGACGTCCA<br>CGGGTTTCCT GACAGACTTG ACCCTGGATG ACATCCTGTT<br>TGCTGACATT GATACGTCCA TGTATGATTT TGACCCCTGC<br>ACTTCCTCAT CAGGGACAGC CTCAAAAATG GCCCCTGTGT<br>CTGCCGACGA CCTCCTCAAA ACTCTGGCTC CTTACAGCAG<br>TCAGCCTGTC ACCCCAAGTC AGCCTTTCAA AATGGACCTC<br>ACAGAGCTGG ACCACATCAT GGAGGTGCTT GTTGGGTCCT<br>AAGACCCAGG GACCCAGCGA CTATGCCCAC CCAGACCCCA<br>GAGCGTTCCC ATAACCCTGA CAGTTCTCCA CACTGTGCAT<br>GCACCCTTGC TTGCCTTTTT CAGAGAAAAA GAAAATTTTA<br>CAACAGGATC ACACTAGTTT TTGCTTTGAG CAGAGTTGGA<br>GTGCCTTCAT CCAAGTATGA CCACTTTTAA TACACTTTTT<br>TGAGTGGTTC CTCAGAGACC TACTACCCTG GTATAGGAAA<br>GAATCCATTT GAAGACAATG TTGCAATGTT GAATGACAAA<br>AATAAACAGT TCAAGTGAAG CACAAGGATT AAGTTGGAAA<br>AGCTGTAAAT TGCATGTGCA TATTTGTCTA TTTTTTCTAT<br>AAGTTTTATT GCAAGAGGTA AAGAAGAAAA CTATATATAT<br>ATATCTTATT TAGATAATCT CAGTACCTTT TCTGGCATTT<br>TTGCCCTGTA TAGGTTGACT TGGCAATTCG GCCTTTTTAG<br>AGGCATTAAC TACTCCTCGT AAGTGTTGCA TTTACATGGC<br>TGTTTAGAAA ACTGCTGCCC AAATTTATTT TATATTTTTG<br>TACAGATTCT GCAGTTTATG ATATTGTTTT TCTAAAAACA<br>AATGCTGTTT ATACATATGA GATAGCTATT TTGATAGGAT<br>TTGCTCACAT AGTTCCTGCA AACTTCAGAT GTACAAGTTG<br>CACTTGTACT TTTATAGAGT TGTAATGTTT TATATGTGTA<br>TGGTGCAAGA GAAAATTGGA TCAAATCAAT CTGCAGTTGA<br>TGTCCCCAAA TGCAAACACA GGCACACACA TGCACACACC<br>CATAAACACA CACACAGTGC TTTAAGAAAG GGCCAGGTGA<br>TATCACACCC AAATTTCACA AGCACTGACC CCCTGGCACC<br>AACACCCGCC AGTACTGTGA CTTCCAAAGC CAGAGCCACA<br>TGTGCTCATC AAACTTGCAT TAAGCAGTTG GCGGGAGATG<br>GCTGTGGAGC TGGGGGTTTA AGTGATGGTT CTCTTTTGCT<br>CCCTCTTTTG AGGGTAAAGC TACTGTCTTT CTTAAGAGTG<br>TATTTATGCC AAGTTTGCGC TTTTAATTGT TTTTATTTTG | 23 |

TABLE 1-continued

Melanoma Biomarker/Housekeeper Sequence Information

| Gene Name | RefSeq Accession | Sequence | SEQ ID NO: |
|---|---|---|---|
| | | TTTTTTAATG AAAACCCAGA TCTTTCCTTT TTGGCATAAT TTTTATGATG ACCTGAAATT TTACATCCGA ACAAAATTTT ACATCCGAAA AGCAACCAAC TTCTTCATGG AACTCAGCCC TGTTGCAATG CTTAGGGCCC TTAAAGAAGA AAATCTCCCC AGAAGGCATC CATCATGTTG CTTAATTGTC TTCTGCAGCT TCCTTTCCCT AGAGCTTTCC CTGTGTTGCT AAGAGCTGAA AATGGCATCT TCGTGATCAC CACAGTGAGC TTGGCTCGCC TCGGCCGGCC CGGGATGCAC TCTTACAACA TGTGTGACTC TTGAACCTGG AGTTCATCAC ATTACGTCAC AGCTTCCCAT CTGGTTGCTT TCCTGAGTCA GCTACTTCAC ACTTGTCAAG GCTGTTTTAC CCCAAAACTC AGACAGGACT TTCTATGCAT GTTTTCCCTC CTCCCCCCAA TTCCCCCCCC CATCACCTTA TCTCCCAGGA CACACTTGAG AAGTAGCTTT TTATTCCTAG TGGTGTACAT TTAATTTTAA AAAGGTTGCA ATGTATCATG CTTGTTGCCG AAACTGTTTA TGGCCTTCTT GTTTCAGTTT TTTCTTTTCT TCCAATGGTA CTTTAGCTGT TGAGTGCAGG TTACAACCTA TATTGTTATG CAGATGGCTT CTTTAGGAAT AACTTTTATA TTTATTTAAA AATTTTTAAA TTATGGGATG TTTTGTTGTT GTTGTTGTCT TTGTTGTTGG TCATTTGTCA ATATTCAGTC ACCAATTCTG CTCACTTCTT GCCATGGATA AAATTGGGTC TTTCTGGCTA ATTAAAAAAG ACAACTTTAT AAAATGGCAC TTTAAGCAAG CCATAGTTAG TTTTATTTTT GTAATGCACA TGGCAAAGCA AAGACGTTTG TGATGAAGGA ACTGCTCATC TAAGCAAAAG ATTTGAGTAT GATATGATAA AGGCTTTCTA CATTCTAATT TACTTTTTCC CCCCACTTGA ATGTGTTTTA AAGGCTAATT ATCAGCTCAG TAGAGCAGTG AGAAACTGAT CAAATTGCAC TTGTTCTCCT ACAAGCAACC TCCACGCAGA CACCTCGTAC TGCTACAGGT GTGTCATTTC CTTTAATAGG ACCAGGGACC ATGTAACTGA GGTGAGGGTT GTAGTAGATG CTTCCAGTGT CAGTATGCCT GTTAATTTTA AGAGCTTCCC TTTCTTGCAG AGAACAAGTC TGCCCAGATT CCATGCTTTC TATAACTGGA GGACCTGGCA AACCTGCCGC ATGCTGCACA CATCTACCTA CGTACACATA TACAATAGTA TTGATGATTC TGAACAATAA CAGGGTAAAA CAGTTGGTTT GCCATTGTTA AAAACTGATT TACAGTAACT TACAACAACT GTACTTTTGT TGGATTAGCA AATCATGTGT TTAAACAAAT CCCATATGTT GGGCAACAGT TCAAATAAGC ACGGAGAAGT GTTGCCCAAA CTTGGTTCTC TGACTCTTAT GTATTTGTAA GGCTGGGCTT CAAAATCAAA ACAAAACCC CAAAACAGC AGGCAAATGC TTTTTAACTC TGACACCGTT GCCATAAATC CCTGATACTC AAAGTCTAAC AAGAAAGACA TGGAAAATTA GCAGCCCATT TTCAGAAAGA TCAAAATGAT CTAGGGTTCT AATTGCTTTT GCATCCTATT CTTACAAAGT GATGTCCCAA CAGGGAACAG TAGGAGCTGG AGTGGGATCT CCAAGTCCCA GTTTGAGTGT GGGATGTGCT TCCAGCAGTG CCTTCCCTTT ATGAAAGACA TCACATGGCA TCCAGGGCCA GGCAGGCAGC TTGAGGTGCC TTTACGAGAA AACCGAGCTG GGGCTGGGAG AGGACAGTTA TTGACACTGA TGTGCAATGA AGTGACAAGA TGAGAGCAGA ATCGTAAGAG CTTTGAATTT GAAGTGAGTT TTTTTCCCCC CATAAGTTAT TTATTCCTTT TTTCTGTGTA AATATATTTA TTTTACTGTG GAGCGCTAAC ATCTGGATCG TAACATGTGC AGAATGTATG GTAGGAATGT ATTCTCTTGT AGGAATGTAA ATCTGTATTA AAAGGGGTC CAAGCCAGGC CCCCAGGTCT TCTCATTGTA TGCACAGTCC GCATTCATTT TTACTCTTCT CTAATATGGG TCTATTTGAA ATATGCAAAA GGTATGAGGA ATGTTTTAAT ACCTCCAAAT TTTTAAGAAA AGCATCAAAG GGTTGATATT TTTTAAAGTT TTTTTAGTAG CACTTTCTCT GGATGACAGA AGGAGCAACC ACATGGGCAC CCTTGTTCAT ACCAAAGGGT GAGCAGTGGC CAGAGCCTCC TCTGCACCTC TCGAGTGTCT TTACCAATTG AGCTTTTTAT CGCCATAGCC CCTTGGAGTG CCCCAGCTGC CCTGAGGTCA ATCAAGGAAA ATTTCTTAAT GAAATAAGCT CCAAAGAGCC AAAGTATCAA CTTACAGATC GTTTTTAAAG CTTAAATTTA TGAACCACCT TTGTGGTAAA CAATGAATTA TGAATACCGC AGGGCAGCCT TCTTAAATGA CAAATGTAAA AAAAAAAAA AAAAAGACTC TACTTCGTGC AGCAATTGCT ACTCTATACG AATTGTCTTA ATTGAAAAC CTTGCTGTTA CAAATTGGAC CTTTATACAT TTTCTGAAAA CAATGAAAAG AGTATATTTA ACCTTTTCTG GCTGTAAATG GTTACCTTCC TGTAACTGCC CCGCACCTGG AGGCATGGAG TTGTGTGCAT CCTGCTTATG TACAATTGTT TCAGTGTTT CTAAGAATGA GTCTGAATGG TTCTTGAAAA TTAGCCAGGA TCAAATGCTA TTGCAGACAA AGCCAATAAA AAGTTGGACT TCTTTTGGGG ATAACAAGTT TTGGAAGAGA AATGCAGGCC ATATGTGCGC ATGACCGAGA | |

TABLE 1-continued

Melanoma Biomarker/Housekeeper Sequence Information

| Gene Name | RefSeq Accession | Sequence | SEQ ID NO: |
|---|---|---|---|
| | | TTTTGAAAAA AGATGTACAT AGTGACATGT TTGGTGCATG GTTTTTGAGG AGGGCTTTTG TCAAAAAGGA GGTATAACCT TTCCCCCACA GACCTGAGAG CTGTGCCTTT TCTATGCAAT ATTACAGACG TTACATCGGA ACCCAGATGG CTGTATTCAC ATGTAGGTTT GGGCTGTAAT CTAAACAATT GGACAGATTA AATGTACATG GAAATGAGCA GTCTTACTTT TGTAGTTTTA TATTATACAA TAAACAGTTA AAAGATGAAA AAAAAAAAAA AAAAA | |
| SLC35G5 | NM_054028.1 | TACCACCTCA GGAGAGTTCC AGGGAAGAAC CCCACCCGCA CTCCAATGAG GTCACAATGG CTGGAGCTCT GAGGGGCCCA GGCTCCCTGA GCCAGGAGGA GAGGAGAAAG TCCAAGGAAA GATGGCTGGC AGTCACCCCT ACTTCAACCT GCCTGACTCC ACACACCCAT CGCCGCCCTC CGCTCCACCC AGCCTCCGCT GGCACCAGCG CTGCCAGCCC TCTGGTGCCA CCAATGGGCT GCTGGTGGCC CTGCTGGGTG GGGGCCTGCC TGCTGGCTTC GTGGGCCCCC TTTCTCGTAT GGCTTACCAG GGTTCCAACC TGCCCTCGCT GGAGCTGCTC ATCTGTCGAT GCCTCTTCCA CCTCCCTATT GCCCTGCTAC TTAAACTGCG TGGCGACCCC CTTCTGGGAC CTCCTGACAT CCGAGGCTGG GCCTGCTTCT GTGCCCTGCT CAACGTCCTC AGCATTGGAT GTGCCTACAG TGCAGTTCAG GTGGTGCCCG CTGGCAACGC TGCCACTGTT CGCAAAGGTT CTTCCACCGT ATGCTCCGCT GTCCTCACCC TCTGCCTTGA GAGCCAGGGT CTCGGTGGCT ACGAGTGGTG TGGACTGTTG GGCAGCATCC TAGGACTAAT CATCATTCTG GGACCTGGAC TCTGGACACT ACAGGAGGGG ACCACAGGTG TCTACACCAC CCTGGGCTAT GTGCAGGCTT TCCTGGGAGG CCTGGCGCTG TCCCTGGGGC TTCTGGTCTA TCGTTCTCTG CACTTTCCCT CCTGCCTCCC AACAGTGGCC TTCCTATCTG GCTTGGTGGG GCTGCTGGGC TGTGTGCCAG GCCTCTTTGT GCTGCAGACC CCCGTGTTGC CCAGTGACCT CCTGAGTTGG AGTTGTGTGG GGGCAGAGGG GATCCTCGCC TTGGTCTCCT TCACATGTGT GGGCTATGCG GTCACCAAGG CCCACCCTGC CCTGGTGTGC GCTGTCCTGC ATTCCGAGGT GGTTGTGGCC CTTATACTGC AGTATTATAT GCTCCATGAG ACTGTGGCAC TTTCTGACAT CATGGGGGCA GGGGTTGTGC TGGGCAGCAT TGCCATCATT ACAGCCCGGA ACCTCAGCTG TGAGAGGACA GGGAAGGTGG AGGAGTGAGA TAGAACTTGG GAGCCCGGGG GTTGGGAGGG ACAGGGATAA ATAAAGACAA AGACTGAAGA C | 24 |
| SPATS2L | NM_001100422.1 | AGTGCTGAGG GAGCAAAGTT CATTTTCTCG GGTAGGAGAA GATGATTCTC TTGCAACACG TGCGGATTGT GACAAAATCT TTCATTAACA AGGGGAGTTT CGGTGAAGTG GAGGTTTGGG GAAAGGCGAG GAAGTCGGTC TGGAGCAAGC AAGCAAAGTG CGGAAGCTGT ACTGGGATTC TTCTAGAAAG TGGGGTGGGA AAGGAGCTAG GGAGGGCGTG TGGAGGGACG AGATCTGTGT CAGAACGTGC GTGTGAGCGG ATACAAAACC CGAGAGAGGC GTGAGCAGCG CTGTGTTTGC GAGCGGGAGC GAGGGGCGCC GGCTGGGGTG TGTGCTCCTG AGCTCTTCAG AAACCAGGCT GCTTTCAGGA ACATTGCTGT GGATTCCCAG GGCCTATTCC ACTAGAAGCA AGATGGCTGA ACTCAATACT CATGTGAATG TCAAGGAAAA GATCTATGCA GTTAGATCAG TTGTTCCCAA CAAAAGCAAT AATGAAATAG TCCTGGTGCT CCAACAGTTT GATTTTAATG TGGATAAAGC CGTGCAAGCC TTTGTGGATG GCAGTGCAAT TCAAGTTCTA AAAGAATGGA ATATGACAGG AAAAAAGAAG AACAATAAAA GAAAAAGAAG CAAGTCCAAG CAGCATCAAG GCAACAAAGA TGCTAAAGAC AAGGTGGAGA GGCCTGAGGC AGGGCCCCTG CAGCCGCAGC CACCACAGAT TCAAAACGGC CCCATGAATG GCTGCGAGAA GGACAGCTCG TCCACAGATT CTGCTAACGA AAAACCAGCC CTTATCCCTC GTGAGAAAAA GATCTCGATA CTTGAGGAAC CTTCAAAGGC ACTTCGTGGG GTCACAGAAG GCAACAGACT ACTGCAACAG AAACTATCCT TAGATGGGAA CCCCAAACCT ATACATGGAA CAACAGAGAG GTCAGATGGC CTACAGTGGT CAGCTGAGCA GCCTTGTAAC CCAAGCAAGC CTAAGGCAAA AACATCTCCT GTTAAGTCCA ATACCCCTGC AGCTCATCTT GAAATAAAGC CAGATGAGTT GGCAAAGAAA AGAGGCCCAA ATATTGAGAA ATCAGTGAAG GATTTGCAAC GCTGCACCGT TTCTCTAACT AGATATCGCG TCATGATTAA GGAAGAAGTG GATAGTTCCG TGAAGAAGAT CAAAGCTGCC TTTGCTGAAT TACACAACTG CATCATTGAC AAAGAAGTTT CATTAATGGC AGAAATGGAT AAAGTTAAAG AAGAAGCCAT GGAAATCCTG ACTGCTCGTC AGAAGAAAGC AGAAGAACTA AAGAGACTCA CTGACCTTGC CAGTCAGATG GCAGAGATGC AGCTGGCCGA ACTCAGGGCA | 25 |

TABLE 1-continued

Melanoma Biomarker/Housekeeper Sequence Information

| Gene Name | RefSeq Accession | Sequence | SEQ ID NO: |
|---|---|---|---|
| | | GAAATTAAGC ACTTTGTCAG CGAGCGTAAA TATGACGAGG AGCTCGGGAA AGCTGCCCGG TTTTCCTGTG ACATCGAACA GCTGAAGGCC CAAATCATGC TCTGCGGAGA AATTACACAT CCAAAGAACA ACTATTCCTC AAGAACTCCC TGCAGCTCCC TGCTGCCTCT GCTGAATGCG CACGCAGCAA CCTCTGGGAA ACAGAGTAAC TTTTCCCGAA AATCATCCAC TCACAATAAG CCCTCTGAAG GCAAAGCGGC AAACCCCAAA ATGGTGAGCA GTCTCCCCAG CACCGCCGAC CCCTCTCACC AGACCATGCC GGCCAACAAG CAGAATGGAT CTTCTAACCA AAGACGGAGA TTTAATCCAC AGTATCATAA CAACAGGCTA AATGGGCCTG CCAAGTCGCA GGGCAGTGGG AATGAAGCCG AGCCACTGGG AAAGGGCAAC AGCCGCCACG AACACAGAAG ACAGCCGCAC AACGGCTTCC GGCCCAAAAA CAAAGGCGGT GCCAAAAATC AAGAGGCTTC CTTGGGGATG AAGACCCCCG AGGCCCCGGC CCATTCTGAA AAGCCCCGGC GAAGGCAGCA CGCTGCAGAC ACCTCGGAGG CCAGGCCCTT CCGGGGTAGT GTCGGTAGGG TTTCACAGTG CAATCTCTGC CCCACGAGAA TAGAAGTTTC CACAGATGCA GCAGTTCTCT CAGTCCCGGC TGTGACGTTG GTGGCCTGAG CTAGGAGGAA AAAGAGCAGT TTTCACTCAG TTTTGGTTCC CTGCCCGAGG TGCTGACCCA ATTCGCTGCC AAAAGAGTGT CAATCAGAAT ATACAAATCC CGTATGGTTG TGTCATCCTC TCTTAATCAT TTTTACTAAT TCTAATAATC AGCTCTAGCT TGCTTCATAA TTTTCATGGC TTTGCTTGAT CTGTTGATGC TTTCTCTCAT CAAGACTTTG CAGCATTTTA GCCAGGCAGT ATTTACTCAT TATTAGGAAA ATCAAGATGT GGCTGAAGAT CAGAGGCTCA GTTAGCAACC TGTGTTGTAG CAGTGATGTC AGTCCATTGA TTGTCTTTAG AGAGTTAATG TTACAAAAAA GAATTCTTAA TAATCAGACA AACATGATCT GCTGAGGACA CATGCGCTTT TGTAGAATTT AACATCTGGT GTTTTTCTGA AAAAATATAT ATACATATAT TGCTTTATTT GAAACAAATT AAAATATGCT GCATTTGACA CCTGGCTAGT TTCTTTTATT GATACCCACC TAGTTATTGA ATGTACTGTT TAGTGCTTTC AAAAAAAACT TTAGAGACTA GAGGTTGTGG TGCAAAGCTG TGTACAATAA ATACTGTTTC TGTTGAGACA AGTACTCTTT CAGGAAAATA TATATATGCC CTTTCAATTA GATTACACAA ATAGATGGAT ATGCACCCTG ATCATCTTAG ACACACCATG TGGCAGTTGG GCAGTTGAA ACATTGGTTG CAAGTACTAC AAACCTCAGC TGAGCCTAGC TTCAACAATA AGAATTTATT GGTTCAGTGA GTGAAAAGTC CAGTTGGTCC AATTTGATCA GGATTTCAGC TCCCATCTCT TTTTTTTTT TCTTTTTCT TTTTCTTTTT TTGAGACAGT CTTGCTTTGT CACCCAGGTG GAGTGCAATG GCATGATCTC GGCTCACTGC AACCTCCGCC TCCTGGGTTC AAGCCATTCT CCTGCCCGGC CTTCCGAGTA GCTGGGATTA CAGGCATGTG CCACCACGCG CTGCTAATTT TTATATTATT AGTACAGACA GGATTTCACC ATGTTGTCCA GGCTGGTCTC AAACCCCTGA CCTCAGGTGA TCCACCTGCT TTGGCCTCCG AAACTGCCGG AATTACAGGC ATGAGCCACC GTACCCGGCC AGCTCCCATC TCTTAATTAT CTTAGCTCTC CTTTCCTCCT TGGGTTGACA TTGCATTCAG AATTGTGGCA AAGGGCCACC ATGCTCTTAA GACTCAAGTC TATTTTCCAC ACTGTCCAGA GGAGAGAAGT TATCCTAGTA GCTTCTACAC AGAGCAAGTG TCTTTCTCAG AAATCCCAGC AAAGGTCTTG CATACCATTG CTGGTAGGCC TGTCTCTTAA ACCAATCATG AAAGGGGGGA GAGAAGTGAA TGGGATGAAC TAATTTGCAT AGACTAATTA GAGCCCACCC CTGGAGCCTG GGTGTGGCCA TCTTCCCAGA GTTCCTGAGC TAGATGGAGA AGGGGTACTT CTCAGAAAGG GAAAATGGAT ACCCAATGGC CCAAACCCAA AATAGCCCCA GTTCCCCTAA CTTTGACTAC AGGGCAGTCC AGTTTGGGTG CCGCTTCCGT TGCACTCACA TGTCCTACAT ATCTGTTGAC TACTCACAAG TGCAAATGCT TATTCTCAAC TCAACATTAA CATTTTTTCT GGCAACCCAG GTTCACTGGT TCTCTTCCAC AGAGCGGCCC TGAGCAGCTG AGCCTGCAAG CCACGCAAGC ATCTGTTTCT TCTTTTGCCA AGTACAGGAG GATGTTTGCT CTCTCTGTAG AGAGCTTTCT GAGGTCTCTG GGTGTACCCA GAGATTTAAT AGAAATTCTT AACGTTAAGT CACATTCCAG GAAGGAAGGA AGAGTTGTTC GTTCAAATAA GAAAGATAAA TGTTCGGCAC TGTAGGCCCT GTTTACCCCA TCTGAGGCCC TGAATTCATA TATTACAAGA CGGAAGGATT TGCACAGTT TTTTATGTAG CAAGATTTTG CTCACCACTG AAAAATGTCA GTGTAAATGT GACCGCTTTA AAGATGAGTC AAGTAATTCT TGGAACAGGG AAAAAAATGA ATTTGCCAGG TCAGGAGTTC ACCTGCCTTT GTCAGAGTTG AACCCAACCA CTCTTGACCT CGACTCACTC CCTTAGGGTT AAGAAAGCCC AAACACATTC CTGAGCACAG AGCAAACACT | |

TABLE 1-continued

Melanoma Biomarker/Housekeeper Sequence Information

| Gene Name | RefSeq Accession | Sequence | SEQ ID NO: |
|---|---|---|---|
| | | CCCATGTCAC TGAAAAGAAA CAAAAGAATG CTAAAAAGTG CTCAGACCTG ATCACATTTT TTCCAATATT TTTTCCTTTT TTTTTTTTTT TTTGAGACAG GGTCTTGCTC TATCACCTAG GCTGGAGTGC ATGTTTTTGA GACAGGGTCT TGCTCTATCA CCTAGGCTGG AGTGCATGAT CATGGCTCAC TATAGCCTTG AACTCCTGGG CTCAAGCCAT CCTCAGCCTC CCAAGTTGCG AGGACTACAG GTGTGCACCA CAACGTCCCA GCTACTTTTT AAATTTTTAG TAGAAACGAG GTCTCACTAT GGTGCCCAGA CTGGTCTCGA ACTCCGGAGC TCAAGTGATC TTCCTGCTTT GGCCTCCCAA AGTGTTAGAA TTACAGGCAT GAGCCACCTC GCCTGGCTGG TTTTTGCCTT TCTTATAGAC CCTGGGCATG TAAGCATTTA TTAGTTTGCA TTTTTGAAAC AGTAATTTCA ATATTTTAGT GCCAATGTCA GGCCGCTTAA ACACTGTATT ACATATCTTC ATCTGTCTGG TGGAACTATT GGTGTGATCC TAGAGAACTG AGTCCTATTC TGCCATTCAT TTAAAGTGTT TTAAACTCTA ATCTCTCTAC TTAATGCACA GTAGTCAGAT TATTCTCTTA AACATTTGCC TAGTAGAGGT TAAAATAGTT TAATCCTTAT GAAGATGGAA TAACTTCAAA CTCACATTGT GGCACTTAGA TCTTCCACCA AGACTTCATC CGTGAAATCC ACACCTCCCT GTTGGGTTCC CAATTACATT CCAAATTTAC ATTTCTTTTG AGAATCTCTG CATACTCCAG CTCTGTCCTG TTGATCCTAT TCTAGAAGTG CTTAATGCAG CAAGACACAG AAAGTTAAAC GCAAATTGCT GCAAAATTCA CCCTCAGTGG AGGACTAGAA ACACAACATG TCCAATTTAA AGCTCAGTTC ACAAGCAGTT CAATTCTGCT GGCATCAGAA AAGGAGATTC TAATTAAACA TTCTTAGGGA AGGACATCAA ATGAGGTTAA TGGGAAACGT TACCAGATTA AAAGCAGTTT TTTGACAAAG TAACAGATTT GGAAATTCTG ACTCTCTGAA AGCCTTGATT TGAACCTCAA ACTTGATTTC ACCATGAGAA GTGGGGATCA AGGGCCTGCG CAGTTCTTTT CCTAAATCGA TTCGGTGCTC CCCACCCCGA CGCAGGCACA GGTCCGCAAC CAGATAGGGA GATGCTGAA TTTCAGGCTA CCTTTGACAA AGCTTTCTTC CTCCCTCCCT CCCTTTGCAC GCTGCATCCC ACGCTGCCTG CTTAAAGCGC CCTCATGTGT CTACAGATGG TAAAACGTTT ATTTCTCAAC AGACATTCCA GTGATAGCAT CCAATGACCT ATGTAACGGC ACCCTTTTTT GCTGTACGCG TTTTTTGAGA TGGAGTCTCG CTCTGTCGCC CAGGCTGGAG TGCAGTGGCG CGGTCTCGGC TCACTGCAAG CTCCGCCTCC CGGGTTCACG CCATTCTCCT GCCTCAGCCT CCCGAGTAGC TGGGACTACA GGCACCCGCC ACCACACCTG GCTAATTTTT TGTATTTTTA GTAGATACAG GGTTTCACCG TGTTAGCCAG GATGGTTTTG ATCTCCTGAC CTCGTGATCC ACCCCCCTCG GCCTCCCAAA GTGCTGGGAT TACAGGGGTG AGCCACTGCG CCCGGCCCCA GTCACTTGTT CTTAAGTTTC TTAAGCAAAC TATAAAATAG CAAAAGACCA AAAAAAAAGG AAAAAAAGCA GTTCGCCTAA TACATTGTTC CAGCATTTCC TTGAAAGTAC TGAGCCATCT CAATTGCTCT GATTTTGTGA GAAAATTATG AAGAGTTGCA AAGTCCCAGT GATTCTCTTG TTACTTAGCT AAGAATTTGA AATGTAATTT AAATACTATT CTTTACAATC CATTATAAGG ATTTTAAAAT CTTTTTGCTT CTTTAATAAA TTCTAACAAA GAAAAAAAAA AAAAA | |
| TDRD7 | NM_001302884.1 | AGAGCCGAGG CCAGGCTGCC CTCGAAGCGG GGCGGGGCGA AGCGGGGCGG GGCCGAGCAG GGCGGGGCGG GGGCTTGAGG TGATTCCCAA GCCGCGGGGC GGCTCCGGTG GTGCGGGGAA ACCGAAAGTG GGCGGCGGCC GCGGCGGGGC CCCTGGCGGA GACGCGGCA GGAGCTGGGC CCAGAGACGC GGGGACGGGC CGTGGGCCCC CGGAACGAGA TTACCTGCTA TGCCATGGCC TGCACAGAAA CTGCAAGAAT TGCTCAGCTT GTGGCTCGTC AAAGGAGTTC TAAAAGGAAA ACCGGGCGTC AAGTTAATTG TCAGATGAGA GTGAAGAAAA CCATGCCATT TTTTCTAGAA GGAAAACCAA AAGCAACCCT CAGACAACCA GGATTTGCTT CAAATTTTTC TGTTGGCAAA AAACCTAATC CAGCACCGTT AAGAGACAAA GGAAACTCTG TTGGAGTTAA GCCTGATGCT GAAATGTCTC CTTATATGCT ACACACAACT CTTGGAAATG AAGCATTCAA AGACATTCCA GTGCAAAGGC ATGTGACCAT GTCCACCAAC AACAGGTTTA GCCCAAAGGC GTCCCTTCAA CCACCTTTGC AGATGCATCT CTCAAGAACC TCTACTAAGG AAATGAGTGA TAATTTAAAT CAGACTGTTG AAAAACCCAA TGTCAAGCCT CCTGCCTCTT ACACTTATAA AATGGATGAG GTTCAAAATC GCATAAAGGA AATACTAAAC AAGCATAACA ATGGCATTTG GATATCTAAG CTTCCACATT TTTACAAAGA GTTATATAAA GAAGACCTTA ATCAAGGAAT TTACAACAG TTTGAACACT GGCCTCATAT TTGCACGGTG GAGAAACCTT | 26 |

TABLE 1-continued

Melanoma Biomarker/Housekeeper Sequence Information

| Gene Name | RefSeq Accession | Sequence | SEQ ID NO: |
|---|---|---|---|
| | | GCAGTGGTGG CCAAGATTTA CTTCTTTATC CAGCTAAGAG<br>AAAGCAGCTT TTGAGAAGTG AACTGGATAC TGAGAAAGTA<br>CCTCTATCCC CACTACCTGG TCCCAAACAA ACACCACCGT<br>TGAAAGGGTG TCCAACAGTT ATGGCAGGAG ACTTTAAAGA<br>AAAAGTGGCA GACCTGCTGG TGAAATACAC AAGTGGCCTT<br>TGGGCCAGTG CACTTCCGAA AGCATTTGAG GAAATGTACA<br>AAGTGAAATT CCCTGAGGAT GCCTTAAAAA ATCTTGCCTC<br>ACTTTCTGAT GTATGCAGCA TAGACTACAT TTCTGGAAAT<br>CCCCAGAAGG CCATTCTCTA TGCTAAACTT CCATTGCCCA<br>CTGACAAAAT CCAAAAGGAT GCAGGGCAAG CACATGGTGA<br>TAATGATATC AAGGCTATGG TTGAACAAGA GTATTTGCAG<br>GTAGAAGAAA GCATTGCTGA AAGTGCTAAT ACCTTTATGG<br>AGGACATAAC AGTTCCTCCT TTAATGATTC CAACTGAAGC<br>ATCACCATCT GTATTGGTGG TTGAACTGAG CAACACAAAT<br>GAAGTGGTTA TCAGGTATGT GGGCAAAGAC TATTCTGCTG<br>CTCAGGAATT AATGGAAGAT GAGATGAAGG AATATTACAG<br>TAAGAATCCT AAGATCACAC CAGTCCAGGC TGTGAATGTT<br>GGGCAGTTGC TGGCCGTAAA TGCCGAGGAG GACGCCTGGT<br>TACGGGCACA GGTCATCTCA ACAGAAGAGA ACAAATAAA<br>GGTATGCTAT GTTGACTATG GTTTTAGTGA AAATGTTGAA<br>AAAAGCAAAG CATACAAATT AAACCCGAAG TTTTGTTCAC<br>TCTCATTTCA AGCTACAAAA TGTAAGCTTG CAGGCTTGGA<br>AGTCCTAAGC GATGACCCTG ATCTAGTGAA GGTGGTTGAA<br>TCTTTAACTT GTGGAAAGAT CTTTGCAGTG GAAATACTTG<br>ACAAAGCTGA CATTCCACTT GTTGTTCTGT ACGATACCTC<br>AGGAGAAGAT GATATCAATA TCAATGCCAC CTGCTTGAAG<br>GCTATATGTG ACAAGTCACT AGAGGTTCAC CTGCAGGTTG<br>ACGCCATGTA CACAAATGTC AAAGTAACTA ATATTTGCTC<br>TGATGGGACA CTCTACTGCC AGGTGCCTTG TAAGGGTCTG<br>AACAAGCTCA GTGACCTTCT ACGTAAGATA GAGGACTACT<br>TCCATTGCAA GCACATGACC TCTGAGTGCT TTGTTTCATT<br>ACCCTTCTGT GGGAAAATCT GCCTCTTCCA TTGCAAAGGA<br>AAATGGTTAC GAGTAGAGAT CACAAATGTT CACAGCAGCC<br>GGGCTCTTGA TGTTCAGTTC CTGGACTCTG GCACTGTGAC<br>ATCTGTAAAA GTGTCAGAGC TCAGGGAAAT TCCACCTCGG<br>TTTCTACAAG AAATGATTGC AATACCACCT CAGGCCATTA<br>AGTGCTGTTT AGCAGATCTT CCACAATCTA TTGGCATGTG<br>GACACCAGAT GCAGTGCTGT GGTTAAGAGA TTCTGTTTTG<br>AATTGCTCGG ACTGTAGCAT TAAGGTTACA AAAGTGGATG<br>AAACCAGAGG GATCGCACAT GTTTATTTAT TTACCCCTAA<br>GAACTTCCCT GACCCTCATC GCAGTATTAA TCGCCAGATT<br>ACAAATGCAG ACTTGTGGAA GCATCAGAAG GATGTGTTTT<br>TGAGTGCCAT ATCCAGTGGA GCTGACTCTC CCAACAGCAA<br>AAATGGCAAC ATGCCCATGT CGGGCAACAC TGGAGAGAAT<br>TTCAGAAAGA ACCTCACAGA TGTCATCAAA AAGTCCATGG<br>TGGACCATAC GAGCGCTTTC TCCACAGAGG AACTGCCACC<br>TCCTGTCCAC TTATCAAAGC CAGGGGAACA CATGGATGTG<br>TATGTGCCTG TGGCCTGTCA CCCAGGCTAC TTCGTCATCC<br>AGCCTTGGCA GGAGATACAT AAGTTGGAAG TTCTGATGGA<br>AGAGATGATT CTATATTACA GCGTGTCTGA AGAGCGCCAC<br>ATAGCAGTGG AGAAAGACCA AGTGTATGCT GCAAAAGTGG<br>AAAATAAGTG GCACAGGGTG CTTTTAAAAG GAATCCTGAC<br>CAATGGACTG GTATCTGTGT ATGAGCTGGA TTATGGCAAA<br>CACGAATTAG TCAACATAAG AAAAGTACAG CCCCTAGTGG<br>ACATGTTCCG AAAGCTGCCC TTCCAAGCAG TCACAGCTCA<br>ACTTGCAGGA GTGAAGTGCA ACCAGTGGTC TGAGGAGGCT<br>TCTATGGTGT TTCGAAATCA TGTGGAGAAG AAACCTCTGG<br>TGGCACTGGT GCAGACAGTC ATTGAAAATG CTAACCCTTG<br>GGACCGGAAA GTAGTGGTCT ACTTAGTGGA CACATCGTTG<br>CCAGACACCG ATACCTGGAT TCATGATTTT ATGTCAGAGT<br>ATCTGATAGA GCTTTCAAAA GTTAATTAAT GACTGCCTCT<br>GAAACCTTGA CAACTAATTC AGATTTTTTA GCAATAACAA<br>AATGTAGTAG GCTTAAAAAA AATCTTAACT CTGCTACATG<br>GCTCTGACTG CTGTGGGGGA TTGAAAAGAA TATGCTTATG<br>TTTGATGAAA GATATTTAAC AAGTTTTGTT TTAACAGAGT<br>TGACTTTTCA AGAAAATTG TACTTGAATT ATTACTATAA<br>TATTAGAATA AAAATGTTTA TCAATATAAA AAAAAAAAA<br>AAAAAAAAAA AA | |

TABLE 1-continued

Melanoma Biomarker/Housekeeper Sequence Information

| Gene Name | RefSeq Accession | Sequence | SEQ ID NO: |
|---|---|---|---|
| TOX4 (house-keeping gene) | NM_001303523.1 | AGCAGAGAGA ACACACGTCC TTGCGGAAGT GACGGCAGTT CCGAGTCCAG TGGGGCGGT GGGAGCGATG AGGGTCTGAG ACGGTGGGAG CGGTTGTGTG AAGATGGAGA CATTCCATAC ACCAAGCTTG GGTGATGAGG AATTTGAAAT CCCACCTATC TCCTTGGATT CTGATCCCTC ATTGGCTGTC TCAGATGTGG TTGGCCACTT TGATGACCTG GCAGACCCTT CCTCTTCACA GGATGGCAGT TTTTCAGCCC AGTATGGGGT CCAGACATTG GACATGCCTG TGGGCATGAC CCATGGCTTG ATGGAGCAGG GCGGGGGGCT CCTGAGTGGG GGCTTGACCA TGGACTTGGA CCACTCTATA GGAACTCAGT ATAGTGCCAA CCCCACCTGTT ACAATTGATG TACCAATGAC AGACATGACA TCTGGCTTGA TGGGGCATAG CCAGTTGACC ACCATTGATC AGTCAGAACT GAGTTCCCAG CTGGGTTTGA GCCTAGGGGG TGGCACCATC CTGCCACCTG CCCAGTCACC TGAAGATCGT CTTTCAACCA CCCCTTCACC TACTAGTTCA CTTCACGAGG ATGGTGTTGA GGATTTCCGG AGGCAACTTC CCAGCCAGAA GACAGTCGTG GTGGAAGCAG GGAAAAAGCA GAAGGCCCCA AGAAGAGAA AAAAGAAAGA TCCTAATGAA CCTCAGAAAC CAGTTTCAGC ATATGCTTTA TTCTTTCGTG ATACACAGGC TGCCATCAAG GGACAGAATC CTAATGCCAC TTTTGGTGAG GTTTCAAAAA TTGTGGCCTC CATGTGGGAT AGTCTTGGAG AGGAGCAAAA ACAGGTATAT AAGAGGAAAA CTGAGGCTGC CAAGAAAGAG TATCTGAAGG CACTGGCTGC TTACAAAGAC AACCAGGAGT GTCAGGCCAC TGTGGAAACA GTGGAATTGG ATCCAGCACC ACCATCACAA ACTCCTTCTC CACCTCCTAT GGCTACTGTT GACCCAGCAT CTCCAGCACC AGCTTCAATA GAGCCCCCTG CCCTGTCCCC ATCCATTGTT GTTAACTCCA CCCTTTCATC CTATGTGGCA AACCAGGCAT CTTCTGGAGC TGGGGGTCAG CCCAATATCA CCAAGTTGAT TATTACCAAA CAAATGTTGC CCTCTTCTAT TACTATGTCT CAAGGAGGGA TGGTTACTGT TATCCCAGCC ACAGTGGTGA CCTCCCGGGG GCTCCAACTA GGCCAAACCA GTACAGCTAC TATCCAGCCC AGTCAACAAG CCCAGATTGT CACTCGGTCA GTGTTGCAGG CAGCAGCAGC TGCTGCTGCT GCTGCTTCTA TGCAACTGCC TCCACCCCGA CTACAGCCCC CTCCATTACA ACAGATGCCA CAGCCCCCGA CTCAGCAGCA AGTTACCATT CTGCAGCAGC CTCCTCCACT CCAGGCCATG CAACAGCCTC CACCTCAGAA AGTTCGAATC AATTTACAGC AACAGCCTCC TCCTCTGCAG ATCAAGAGTG TGCCTCTACC CACTTTGAAA ATGCAGACTA CCTTAGTCCC ACCAACTGTG GAAAGTAGTC CTGAGCGGCC TATGAACAAC AGCCCTGAGG CCCATACAGT GGAGGCACCT TCTCCTGAGA CTATCTGTGA GATGATCACA GATGTAGTTC CTGAGGTTGA GTCTCCTTCT CAGATGGATG TTGAATTGGT GAGTGGGTCT CCTGTGGCAC TCTCACCCCA GCCTCGATGT GTGAGGTCTG GTTGTGAGAA CCCTCCCATT GTGAGTAAGG ACTGGGACAA TGAATACTGC AGCAATGAGT GTGTGGTGAA GCACTGCAGG GATGTATTCT TGGCCTGGGT AGCCTCTAGA AATTCAAACA CAGTGGTGTT TGTGAAATAG TCCTTCCTGT TCTCCAAGCC AGTGAAGAGT TATCTGCTGG GAAAGTGTCC AAGAGCCTGT TTTTGAAACA CAAGCTGGGC TTCTGGTAGT GCCTCATCAC AACCCATGAT GGCTGTTCAT GTTTCACCCC TTTTCTTCCT TCAGCAGAGG CCAGGCTATG GAGCAGGGCC ACTGAATTTG CTGTAATCTG GAGATGCTTT TTACTTTCAA CCATAAGCGG TAATAGCAGA GGAAAGGGTG AAGGGAGTCT GGGCAAGCAA AGCATAGAGA TGGTGGGGTG GTGGTGGGGT TGAAGAAACT TGTTGGTATA ATTGTCATAG GACTTGCCTA AAATATTATT AAAATTACGG GAGTGTACTC AGCTTTGAGC CTAGGAGAAA ATGCCACTGT GTGCATCCAT TTTAAAGGGT TCCCTCATAA AAAAATGTTA TTCCCCATTA TCACATCAGT ACACTGCTTT GAAAACAAAA CTTTTCAACA TGGGCATACT GGGCTACATG GAAAATGACA TCACCCAGGA GTGATTTCTC TTTATATATA TTATTTCTGC AGTTACCATC CTTATCTGAG TTATACAGT TCATGAATCT AAGAGGCGGA ACTCTACATC ATTAGTAAGA GGTTCCACCA AAGTCTAAAG TTGTATTCAC TTGTGTTTGA TGAACTATCT TTAAAAGACC ATAGGTCTAT CATTATTTCT TAGACATAAT CTAAAGAAAA ACAGACTAGA GAAGCCACCT GGTTGTAACA GAATAAGCAG AAGTTTACAG CATGATAGTC CAAGTGGTGA TAACTTTAAA TAAAACTCAA ATTTTTACTG TTTGTAGACA GGAATGCTGT CCTAGAGAAC CTCCTCCTCA ACCAGCTACG TACATAGTTT TATCCTATGC ATTCCTGTTT TCTGTGTGTT TTTTGTTTTT TTTTTTTTT TTTTTTTTG AGACAGAGTC TCGCTCTGTC ACCCAGGCTG GAGTGCAGTG GTGCGACCTC AGCTCACTGA AACCTCTGCC TCCCGGGTTC | 27 |

TABLE 1-continued

Melanoma Biomarker/Housekeeper Sequence Information

| Gene Name | RefSeq Accession | Sequence | SEQ ID NO: |
|---|---|---|---|
| | | AAGCGATTCT CCTGCATCAG CCTCCCGAGT AGCTAGGATT<br>ACAGGCGCCC GCCACTACGC CCAGCTAATT TGTGGTATTT<br>TTAGTAGAGA CAGGGTTTCA CCATGTTGGC CAGGCTGGTC<br>TCGAACTCCT GACCTCATGA TCCGCCCGCC TTGACCTCCC<br>AAAGTGCTGG GATTACAGGC ATGAGCCACC GCACCCAGCC<br>TGCATTCCTG TTTTTTTAAT GGTTTTGGAG GGTAGCAGTA<br>GAGATGGGGT CTCACTATGT TGCCCAGTCT AGTCTTGAAC<br>TCCTGGGCTA CAGTTACCCT CCTACCTCGG CTTCCCAAAG<br>TGCTCGGATT ACAGGTGTGA GCCACTGTGC CTAGCCTATA<br>ATGATCATTT TAATGTTTCC CATGCACTCA TTTAGTTTGA<br>ACCTTCACAG CAACCCAATG AGGTAATACT CCCATTTCAC<br>ATATAATACT GAGAGATGAG TTGCACAAGA TTATACACTG<br>TTAAGTAGCA GAGCCAGAAT GGACTTCAGA ATCCCAACTA<br>CAATACAAAT GTTTATTTAA ATAAAGAAGA AAGCTATTGT<br>ACAAATATCA CTCTTCAGGT TTAGCTTACA GAGCCATGGC<br>TATGGATTCT TAGCTCTGTA AGGAAGTGCT TCTATAAATT<br>CTTAGGTTTA GAGATGATAC CATCTGGGTA CCTTTGCTTG<br>AACCGTGCAA CCACATCTGG GTCTAGTAGG TGGATCCCAT<br>CCAGTTGGTT TCCAAGGGTG ATCCTGAAAC AGTGTAAAAG<br>GAGGGGCAAA CCAGAAATCC TGGAATTAGA GGGTTTAATA<br>TTGTTAAAAA ATGCATACCA AATGAAGACT GCCTATCATC<br>ATATCAAATA TGCCAATTCT AAAAAGAGCT TAACATTAGA<br>ATAGTATATG GTAGAATTAC TAGTTCAGAA TTGGCATAGA<br>TTCTGGTGTT AAAATAGACT GGATCTGTAT TATCTGAGGG<br>TTAGTAACTA ATGCTTAGCC AGGCCTGCTT CACAGAGTTG<br>CTACCAGGGA GTATTCTTTG GATAAGCAAA ATGCTAGCAG<br>CATGTGTTTT AAGCTCTGTT AAGGGGTGAA AGATGTAATT<br>ATTGACAGAT TAAATAGATA ACTTCGTAAC CACCAGGGGG<br>CAGATTCAAT ACATCACAGA ATGGCTGAGG AAGATCCTTG<br>GGTTGTGAAG AGAGTAGAAA CCCTAGGGAG CAGTGCTTTT<br>GGGTCCTAGA ACCTGTTGAG TTTCTAATGA ATATTTGTAG<br>AATCTCATAA AACAGTTTAA ATACAAGCTT AAGTGGCTTA<br>TGAATCCTGT GAAGCTCATT TATGGACTAG TGTAAAACAA<br>TGTGAAGCTC TACTAAGTTC TGTCCTTAAT CATAAATAAT<br>AGCCCCTTGA GGACTAGCCT GTTCTCTGGT CACCTTACCA<br>GTTGGGTTGC ACATTGTGTG GTCGTCCAAA TAACTCAATC<br>TTGCGAGTGC CAGGAGATAG TCTTTCAATC ATGCCATAGA<br>TTTCATCTGG TTTATGACTG GTGGAACGAA CCTAGGAAAT<br>AAAAACTAGC TGCTTTTTAA GTTACACAAG AAAAAA | |
| TPT1<br>(house-<br>keeping<br>gene) | NM_001286272.1 | CTTCGTGCCA CGTCACCGCC TGCGTCGCTT CCGGAGGCGC<br>AGCGGGCGAT GACGTAGAGG GACGTGCCCT CTATATGAGG<br>TTGGGGAGCG GCTGAGTCGG CCTTTTCCGC CCGCTCCCCC<br>CTCCCCCCGA GCGCCGCTCC GGCTGCACCG CGCTCGCTCC<br>GAGTTTCAGG CTCGTGCTAA GCTAGCGCCG TCGTCGTCTC<br>CCTTCAGTCG CCATCATGAT TATCTACCGG GACCTCATCA<br>GCCACGATGA GATGTTCTCC GACATCTACA AGATCCGGGA<br>GATCGCGGAC GGGTTGTGCC TGGAGGTGGA GGGGAAGATG<br>GTCAGTAGGA CAGAAGGTAA CATTGATGAC TCGCTCATTG<br>GTGGAAATGC CTCCGCTGAA GGCCCCGAGG GCGAAGGTAC<br>CGAAAGCACA GTAATCACTG GTGTCGATAT TGTCATGAAC<br>CATCACCTGC AGGAAACAAG TTTCACAAAA GAAGCCTACA<br>AGAAGTACAT CAAAGATTAC ATGAAATCAA TCAAAGGGAA<br>ACTTGAAGAA CAGAGACCAG AAAGAGTAAA ACCTTTTATG<br>ACAGGGGCTG CAGAACAAAT CAAGCACATC CTTGCTAATT<br>TCAAAAACTA CCAGTTCTTT ATTGGTGAAA ACATGAATCC<br>AGATGGCATG GTTGCTCTAT TGGACTACCG TGAGGATGGT<br>GTGACCCCAT ATATGATTTT CTTTAAGGAT GGTTTAGAAA<br>TGGAAAAATG TGATGCAAAA GAAAGAAATC CCTGCGCTTT<br>CTGTCTGTCT TTGTGGCGGC CCAGATTGAA TTGGGGAATA<br>CATCTTTAGC CTGGAAATGT AGGCTGCATG TTAATGCTAA<br>TGTAACTTTT GCAGTGTAAT GTTTGAAAAA TATTAATGTA<br>GTTTTTGCTT TTACAGTAAC AAATGTGGCA ATTATTTTGG<br>ATCTATCACC TGTCATCATA ACTGGCTTCT GCTTGTCATC<br>CACACAACAC CAGGACTTAA GACAAATGGG ACTGATGTCA<br>TCTTGAGCTC TTCATTTATT TTGACTGTGA TTTATTTGGA<br>GTGGAGGCAT TGTTTTTAAG AAAAACATGT CATGTAGGTT<br>GTCTAAAAAT AAAATGCATT TAAACTCATT TGAGAGAATG<br>CCTTTTAGTT TAATGCATAT TTAAACTAAA TTGATCCTGT<br>AGTGTTCCTG GAGAAGCTAG AGCCTGATTG TAGGCTACTA<br>CTCATCAATT AACTTCTACA GTGGAGACTA CTTCTGGGAC<br>TGGAATATAA AAAAGAATCA AAGGTTCTGA TTTTGAGTTG<br>CAATAAAGGG AAAGACCATG CTCATAGCAG TGCCAACATC<br>TGAAGTGTGG AGCCTTACCC ATTTCATCAC CTACAACGGA | 28 |

TABLE 1-continued

Melanoma Biomarker/Housekeeper Sequence Information

| Gene Name | RefSeq Accession | Sequence | SEQ ID NO: |
|---|---|---|---|
| | | AGTAGTTAAC TGGAAGAGAT TACCAAGAGA ATAAAAAGAG ACTCATTCAG TGGAAGCAAC TTTGTCTCAG CTTATTTCAC ATAAAGAGAG CGAAGTCTTT TGGGATGAAT GTTAATTAAA CTCCCTGGTA ACTAGAACAG GGACTGGCAA ACTAGCCTAT CTGACCACCT GTTTTGTACA CTTTAAGGTG GTTGGTTGCC TTTTTAAATG GTTGAGGGGA AAAGAATACC TTGTGGGATA TGGAATTTAA GTTCGAGTCC AGTTTTATTG GAACGTGGCT ATGCTTATTC ATTTATGGAT TGACTGTGGC TGTTGTCAGT GCATGAGCAG AGTTGTGTCT AACAGACTAG AGCCTGCAAG TTTGCCAGCC CCTGATTTAA AAGATGAAGG TACACAGAAT GTGGGCTGGC TGGTGGGCAA AGGGGTAAAA ATGTTCTCTA TATTGTATCT GAAAAGATGG GGTGTCTGAA TAAGAAAATG CATCTATTTG ACAGACCTGG AGCAGTTGCT ATCTGCTGCT ATGGTTTCCA CCACAGATGC AAGAAGAACA TGTCCTTGCG CTTTCCGTCT GTCTAATTGT GGCAGCTGAG ATTGAATAGA GGAATACAGG AGGAAAAAAA GCGGGAAGAG TTTTTGAGGC AGGTCGGTCA CCCAGGCTTG TAGTGCAGTG GCACAAGCAA CTCACTGCAT TCTCTGCATC CTGTGCTCAA GCCATTTTCC CACCTCAGTC TCACTAGTTG CTGGGACTGC AGGCATGCAC CCCTATGCCC AGCTAATTTT TGTAGAGACC GAGTATCGCT TAGTTGCCCA GGGTGGTCTC AACTCCTGGG CTCAAGGAGA TCTGCCCACC TCAGCCTCCC AAAGTGCAGG CCTAGCCTGG GAGGGGAATT TTCAAAACGT GAGTTTTGGG AAATAGTCTA TCAGCCTTAC CTGGTTGATT ACACTTGTAA AAGAAAGATT AAAAGCAGGC CAGTGACTCT GGTCTGCTTG AACATGTGAA TGTAGTGGTT TGAGCAATCT GGAGTTTGCC CTAGTGTCAA ATTCCAGACT GTCCATAGTG TCCAAAACCT GAGGCAGATA CTAATGTTAA CCCCCAGCAC CCCGTGATTG GAAACAAACC TAAATACGTA TTGGGAACTT AATAGCAATT TTAAGCATTC TGATAGATTT TTTGTAGGGA TGGGGTCATG CCATGTGGCC CAGGCTGGTC TGAAAACTCT GGCCTCAAGT GATCTCAAGC TTTGGCCTTC TAAAGTGTTG GGATTACAGG TGTGAGGCAT TGCACCTGGC TTAGCGTTCT GATTTGACAT TGTAATGAAA AGTGTGAGTC TCATCTACAG GGCCTTTTGT CCTCTGAAAT GATAGCAGGA AGGGAATTTT CAGGCAGTGG TCAAAGCTGG GGAAACCAGG ATAGTGAAGA AGGCCTTGAG GTGAGAGATG GAAGCTAATT GGTGAACTAG CCTTGGAAGC CTGAAACAGA CAAGTAGCAA TTCAGAGACT TTGTGGGCTC CACTGCTCCA ACTTGTTTTG AAGATTTTCA GTTCTGCAGA AGAGGTATTT CCCCAGTTGT CCTTTCAGTG CTCTTAGCTG TTTTCCCAAC ATCCAGATCC AATCAAGGCT GGGACATAGC ATTTTATCAT GTCTATTTAA GTCAGAAGTG ATGAACCCCA GCTGTTTACC TCATGGTAAA CCTTTGAAGA TTCCAGGTAG AATCTTCTCA GACTTTGAAG ACTGTCTCAT TTTATATCTT TTTCTCGTTA TTCCTAGGGT CAAGACGTTT TGGGCAAGAA TAAGGATGTG AACATCAGAA AGCTCATAAC ATTTTGTTTT TGATGCTAAG TTTAACAAAG GCATGCTTTA GTAGCCTGTG GGCCCTAGGG TTTGTTAAAG TGTGGAGAAC AACTGAGTGG AGCAAGAGGA CTTTTCTAGG AAGGTCCTTG TAATGTGACA TTTGAAAACA AATGAAGGTG TGGAAGTAGG CCATGTGGAT ATCAGGACAA ACCATTCCAG GCCAAGACAA CAGCAGTTAG TCTGGAGTGT GATGTGTTCT GGGAAAAAAG TGGCCACTTT GCTAACCCAA GAAGACAGGA AGGGTTGTAA AGCAGTGGGA GTGTGCAAGG AAGGAAGACC AGACCTCAAG GAAACCACAG GCGCTCTGAG CAGAAGAGTT ACATGATATG ACTCAAATTT TAAAGGATC ACTTTGGCTG CCAGGTGGCA GGGTAAAAGC ATAGAATAAT TGTGTATAAT GTGTTTTTAA GGCAAAGATA GTGGCTTAGT CTAGGGTAGT AGACTGAGGT GGTAGGAAAT GAAGATAGAG ACAACAGGAT ATGCTGGTGG GTGAGGATGG ATTTAATGTT GATACAAGTA TTTTGGTCTG AGCGTTTGGA AGAAAGTTGG CACTGAGGTG GGAAGTCGAG TTTAGTTTTG TTAGTTTTGG ATGTGTTAAG TTTGAGATGC TGATTCTTCA GAGAAGTCTA AGCTGGAGAA CTATATAGAG AGTGGAAAGA TAACAATAGA CATTGAAAGC CATGATACAG GATAAGGTCA TTTGGAGAGA GGATAGACTG CATTCCAACA TGAGATTGGT TGACAAAGAG AAACCAACAA AGGTAATTAA GAGGTGCTCC CACTGCACTT GTACTCAGAA GGCTGAGGTA GGATTGTTAG AGGCCAGCCT GGGCACCACA GGGAGACCCC ATCTCTAAAA TTTAGCCAGG AACCATGGCT CATGCCTGTA GCCCCAGGAA TTTGGAGGGC TGAGTGGGGA GGATCGCTTG AGGTCAGGAG TTTGAGACCA GCCTGGGCAA CATAGGGAGA CCTAAAAAAA TTAATTGGGC ATCTGTAGTC CCAGCTACTC AGGCGGCTGA GCTGAGAGGA TGGCTTGAGT CCGAGAGATT GAGGGTGCAG TGAGCTGTGA TCATACCACT GCACTCCAGC CTGGGCGGCA GTGAGACACT | |

TABLE 1-continued

Melanoma Biomarker/Housekeeper Sequence Information

| Gene Name | RefSeq Accession | Sequence | SEQ ID NO: |
|---|---|---|---|
| | | ATCTGAAAAA AGTTTAAAAA TTTTAAAAAA GAAGGAACTG<br>CCCCTGAGGT AAGAACCAAG GGAGGGCCTC CCAGAGGTCA<br>GGTGGAAAAA GTTTTAGGAA GGAGGAAGTA GTCAACAGGG<br>TTACCTGTTG CAAAGTACTT AAGTAATATG AGGCCTGATA<br>GTGGTAAACT TGACTACCGT TGGATTTCAC TAGTGGGAAA<br>GGAAGTCTAA TTAAAATGCA CTCAAGAGAC TAACAGTCGC<br>AGGCATGAAA TACAATACAG GTACATGGTT TTTTATTATG<br>TGTGCATCTG CTTCAGTAAT AGGTGTGAAT TACTCATTTG<br>GATCATTAGG AGTTTCAAAA TCTAGTTAAA TGACTAGATT<br>TTTGTTGATG TAAATTCTGT CATTCTGAAC TGCAGGGATT<br>GTCAGTAACT TAACTGCAAA CTAAACTGGT GATAATTATG<br>GTAAATTGC AAGACGAGCA ATAAATCTCA ACCAACTTGA<br>GAGAACACTG ATAA | |
| TXK | NM_003328.2 | GATTTCAGTT GAAAGATGTG TTTTTGTGAG TAGAGCACCG<br>CAGAAGAACT GAAGACTGTT GTGTGCTCCC CGCAGAAGGG<br>GCTACCATGA TCCTTTCCTC CTATAACACC ATCCAGTCGG<br>TTTTTCTGTTG CTGCTGTTGC TGTTCAGTGC AGAAGCGACA<br>AATGAGAACA CAGATAAGCC TGAGCACAGA TGAAGAGCTT<br>CCAGAAAAAT ACACCCAGCG TCGCAGGCCG TGGCTCAGCC<br>AATTGTCAAA TAAGAAGCAA TCCAACACGG GCCGTGTGCA<br>GCCGTCAAAA CGAAAGCCAC TGCCTCCCCT CCCACCCTCT<br>GAGGTTGCTG AAGAGAAGAT CCAAGTCAAG GCACTTTATG<br>ATTTTCTGCC CAGAGAACCC TGTAATTTAG CCTTAAGGAG<br>AGCAGAAGAA TACCTGATAC TGGAGAAATA CAATCCTCAC<br>TGGTGGAAGG CAAGAGACCG TTTGGGGAAT GAAGGCTTAA<br>TCCCAAGCAA CTATGTGACT GAAAACAAAA TAACTAATTT<br>AGAAATATAT GAGTGGTACC ATAGAAACAT TACCAGAAAT<br>CAGGCAGAAC ATCTATTGAG ACAAGAGTCT AAAGAAGGTG<br>CATTTATTGT CAGAGATTCA AGACATTTAG GATCCTACAC<br>AATTTCCGTA TTTATGGGAG CTAGAAGAAG TACGGAGGCT<br>GCCATAAAAC ATTATCAGAT AAAAAAGAAT GACTCAGGAC<br>AGTGGTATGT GGCTGAAAGA CACGCCTTTC AATCAATCCC<br>TGAGTTAATC TGGTATCACC AGCACAATGC AGCCGGTCTC<br>ATGACTCGTC TCCGATATCC AGTTGGGCTG ATGGGCAGTT<br>GTTTACCAGC CACAGCTGGG TTTAGCTACG AAAAGTGGGA<br>GATAGATCCA TCTGAGTTGG CTTTTATAAA GGAGATTGGA<br>AGCGGTCAGT TTGGAGTGGT CCATTTAGGT AATGGCGGT<br>CACATATCCA GGTAGCTATC AAGGCCATCA ATGAAGGCTC<br>CATGTCTGAA GAGGATTTCA TTGAAGAGGC CAAAGTGATG<br>ATGAAATTAT CTCATTCAAA GCTAGTGCAA CTTTATGGAG<br>TCTGTATACA GCGGAAGCCC CTTTACATTG TGACAGAGTT<br>CATGGAAAAT GGCTGCCTGC TTAACTATCT CAGGGAGAAT<br>AAAGGAAAGC TTAGGAAGGA AATGCTACTG AGTGTATGCC<br>AGGATATATG TGAAGGAATG GAATATCTGG AGAGGAATGG<br>CTATATTCAT AGGGATTTGG CGGCAAGGAA TTGTTTGGTC<br>AGTTCAACAT GCATAGTAAA AATTTCAGAC TTTGGAATGA<br>CAAGGTACGT TTTGGATGAT GAGTATGTCA GTTCTTTTGG<br>AGCCAAGTTC CCAATCAAGT GGTCCCCTCC TGAAGTTTTT<br>CTTTTCAATA AGTACAGCAG TAAATCTGAT GTCTGGTCAT<br>TTGGAGTTTT AATGTGGGAA GTTTTTACAG AAGGAAAAAT<br>GCCTTTTGAA AATAAGTCAA ATTTGCAAGT CGTGGAAGCT<br>ATTTCTGAAG GCTTCAGGCT ATATCGCCCT CACCTGGCAC<br>CAATGTCCAT ATATGAAGTC ATGTACAGCT GCTGGCATGA<br>GAAACCTGAA GGCCGCCCTA CATTTGCCGA GCTGCTGCGG<br>GCTGTCACAG AGATTGCGGA AACCTGGTGA CCGGAAACAG<br>AATGCCAACC CAAAGAGTCA TCTTGCAAAA CTGTCATTTA<br>TTGTGAATAT CTTCACCATA TGGGGTCACT TATGGTGAAT<br>ATCTTTCTTC AGAGTTGCTG ACTCTTGAAA ACAGTGCAAA<br>GATCACAGTT TTTAAAAGTT TTAAAAATTT AAGAATATTC<br>ACACAATCGT TTTTCTATGT GTGAGAGGGA TTTGCACACT<br>CTTATTTTTC TGTAAAATAT TTCACATCCC AAATGTGAAG<br>AAGTGAAAAA GACTTGCAG CAGTCTTCAT TGTGGTGCTC<br>TTCATGATCA TAGCCCCAGG AACCCTTGAG GTTCTTCTTC<br>ACAAGGCTGA GAGTGCTTCC TTCTTGAAGA CGAGTGACAT<br>TCATCACTTC AGTGATCCAT GCATAGAATA TGAAAATAAA<br>TTCTTCCAAC TCATGGGATA AAGGGGACTC CCTTGAAGAA<br>TTTCATGTTT TTGGGCTGTA TAGCTCTTTA CAGAAAATGC<br>ACCTTTATAA ATCACATGAA TGTTAGTATT CTGGAAATGT<br>CTTTTGTTAA TATAATCTTC CCATGTTATT TAACAAATTG<br>TTTTTGCACA TATCTGATTA TATTGAAAGC AGTTTTTTGC<br>ATTCGAGTTT TAAACACTGT TATAAAATGT AGCCAAAGCT<br>CACCTTTGAA CAGATCCCGG TGACATTCTA TTTCCAGGAA<br>AATCCGGAAC CTGATTTTAG TTCTGTGATT TTACACTTTT | 29 |

TABLE 1-continued

Melanoma Biomarker/Housekeeper Sequence Information

| Gene Name | RefSeq Accession | Sequence | SEQ ID NO: |
|---|---|---|---|
| | | TACATGTGAG ATTGGACAGT TTCAGAGGCC TTATTTTGTC<br>ATACTAAGTG TCTCCTGTAA TTTTCAGGAA GATGATTTGT<br>TCTTTCCAGA AGAGGAGACA AAAGCAAGAT AGCCAAATGT<br>GACATCAAGC TCCATTGTTT CGGAAATCCA GGATTTTGAA<br>TTCGAGATGA AACAACCAGC AATCACAGTT AAATCTTAAC<br>TTTGCCTGCA CTCTTTGTAG GAATGATCAG AAATTTATCT<br>TTATCATTCT GAGTGCTTCA GGAGTACAAT AGGAAGAAAG<br>ATACTGGAGA AAGCACTAAT GTAATCACCA TGAAGTCTGA<br>CAACAGGAGC CCATTATTTG CGTACTGTCC CACCCTGTAT<br>CATGGTTCTC TGGGAACAAG CTTTATGATT CTCATTAGAG<br>TTTATTTGTT GATTGTCAGT AGTTGCGACT TTTAAATTAT<br>ATTTCCCCCA CTCAAAGAAT GGTATCTTTA TATATCAATG<br>ACATTCAATA AATGTGTATT ATTTCTAATG AGAA | |
| YY2 | NM_206923.3 | ATTAAATAAG AGAAAAAAGC ATAAAAGGAG TAGGCTTTTT<br>TGGCAGATAC TGTTATATGG GATGGACAGG AGGGGAAGAC<br>ATGAAAATCA ACTAAAATGA AATACATAAA AAATCAGTAA<br>AGAGCCTGCT TACGAAAGTG GAAAAACAAC AGCTGGGCGG<br>GGTCGCAGGG TGGCAAACGT ACGCGGGCAC GTGCACGTGC<br>TTTTGGGGCC GACAGACGCG CCAGTTGCCT AGGCGCATGC<br>GTCTGGCTAT CCCAGAAGCA CCTGCGCCTT CCGGCTCGTG<br>CTTTCCTCAG TCTCGCGCCT TTCTCTGCAG CTCGCGCCTT<br>TCTCTGCAGC TCGCGCCTTT CTCTGCAGCT CGCGCCTTTC<br>TCTGCAGCTC GCGCCTTTCT CTGCAGCTCG CCCCTTCCTC<br>TGCAGCTCGC CCCTTCCTCT GCAGCTCCCA CCTCACTCCC<br>CTCAGCGTTC TTTTTCCCAC GGTCTTCCCG TTGCCGCTAA<br>CCTAACTAAC TCTCAGCCAT GGCCTCCAAC GAAGATTTCT<br>CCATCACACA AGACCTGGAG ATCCCGGCAG ATATTGTGGA<br>GCTCCACGAC ATCAATGTGG AGCCCCTTCC TATGGAGGAC<br>ATTCCGACGG AAAGCGTCCA GTACGAGGAT GTGGATGGCA<br>ATTGGATCTA CGGTGGCCAC AACCATCCGC CATTGATGGT<br>GTTGCAGCCG CTCTTCACGA ACACGGGCTA TGGCGACCAC<br>GACCAGGAAA TGCTTATGTT GCAGACACAA GAGGAAGTGG<br>TGGGCTATTG CGACTCAGAC AACCAGCTAG CAACGACTT<br>GGAGGACCAG TTGGCCCTCC CGGATAGCAT TGAAGACGAG<br>CACTTCCAGA TGACCCTGGC CTCTCTGTCG GCCTCGGCGG<br>CATCAACATC AACATCAACC CAGAGCCGCA GCAAAAAGCC<br>CAGCAAAAAG CCCAGCGGCA AGAGTGCCAC CAGCACTGAG<br>GCCAACCCGG CAGGCAGCAG CTCCAGCCTG GGCACGAGGA<br>AGTGGGAGCA GAAGCAAATG CAGGTCAAAA CGCTGGAGGG<br>TGAGTTTTCC GTGACTATGT GGTCCCCTAA CGATAACAAT<br>GACCAAGGGG CAGTGGGTGA AGGCCAGGCT GAAAACCCAC<br>CTGATTATTC CGAGTACTTG AAAGGGAAGA AACTTCCTCC<br>TGGGGGGTTA CCAGGCATTG ATCTCTCAGA TCCTAAACAG<br>CTGGCAGAAT TTACTAAAGT GAAGCCCAAA AGGTCCAAAG<br>GAGAACCTCC CAAAACAGTC CCTTGCTCTT ATAGCGGCTG<br>CGAAAAGATG TTCCGGGATT ACGCCGCCAT GAGAAAACAT<br>CTCCACATCC ACGGGCCCAG AGTCCACGTA TGTGCAGAAT<br>GTGGCAAAGC TTTTCTTGAG AGCTCAAAGC TGAGACGACA<br>CCAGCTGGTC CACACCGGCG AGAAGCCCTT TCAGTGCACA<br>TTCGAAGGCT GCGGGAAACG CTTTTCCCTT GATTTCAATT<br>TGCGCACACA CTTGCGCATC CACACCGGCG ATAAGCCCTT<br>CGTGTGCCCC TTCGATGTTT GCAACAGGAA GTTCGCTCAG<br>TCAACCAACC TGAAAACCCA CATATTAACG CATGTGAAGA<br>CCAAAAACAA CCCGTGAAAA GGAGAAGACC CCTCTCAGAC<br>TTGGGAATTA TCTTCCAGGA CTGCGGTAGG GAATAAATAT<br>GCCTCTCAAA GCTTTGTATG TTGTTTCTAA GAGTTTTAAA<br>AAAAAATGAA TCCTGCACAT TTAAGGTTCG TGTTTTGTTA<br>GAGTAGTAAA AATAGAATTT AAACGTTTTT AAAAAGGTAA<br>ACCTTGACAT AAGATAATAG TGCTAAGATG CCATAGCTTG<br>TTCTGTAACT ATTTTTGTAA AGTTTGGTCC CAACAGGAGA<br>AAAATTCGTA GACTTCACAT CAAGAGACGG TTCTTACAAA<br>CTGTTTAAAA TGGGACTTTT CACATTCTTA GAAATAGGAA<br>GTTCATTTAT TGTTTACAAT GTTTTTAAAA AACTTGTTAA<br>AAAATTCAAA GTGTTCATGT TTATACTTTT AGGAATATGC<br>TTAATAAGTC TATGTATGGT TTTTCTGGAG GTTGATAACT<br>TTGGGAAAGA TTTACTTTAA AAGAGTGAAC AATTATATGC<br>ATACGTGAAG TATTTTCCTG CTTAAAAAAG TTATATAGGT<br>GTTATTTGTT TTAATCTTGG TTGTAGTCTT GGATGTTAAC<br>ACATCTTGCA TTTTAGCTGT ATTAGGTCAT GTAGTATTGA<br>TATTAGGTGA TTTAATAGTA CTAGTTTAAA CCTATTTTAG<br>TCATTTTATT TTCCCCAAAA TACTACCAGA TGCTGTTGTT<br>TAGTGTAATT TCTTTGCCTG TTCAGTTAAA GTAGTGCTTG<br>CTTGTAGAAT ATATTGTGTA TATGTTGACT TTAACACTTA | 30 |

TABLE 1-continued

Melanoma Biomarker/Housekeeper Sequence Information

| Gene Name | RefSeq Accession | Sequence | SEQ ID NO: |
|---|---|---|---|
| | | AGAAGTACAT CCTGTGTAAT AGAAAAAGCA AAATAAAACA CCTCTTCTAA AGAAGGAAAA AAGTAGTTTG CCTATATCGA TACAGAAGTT AGAACTAAAG AAAAGGGGGA GGGTGCTACT GGCATCTGGT GAGTGGAGGG AGATCAGGAA TGCCACTAAA CATCCTACAA TGCACAGACA GCCCCACGAA ACACATAATT ATTTGGCTAA AATGCCAATA GTGTCAGGTG CAGGGGCTCA GGCCTGTAAT GTCAACACTT TGGGAGGCCG AGGTGGGTGG ATCGTTTGAG CTCAGGAATT GAACATCAGC CTGGGCAACA TGGCATAACT CGGTCTCTAC C | |
| ALG9 | NM_001077690.1 | GTCTTTTGTC CCTCGGCGGA CACCGTTTGC CAGCCAAAGC TATGTCTGCG CGCTCACCGA CTTCATAGGG TGCCGAATTC TTTTTTCCCC AGGCTTGCCA TGGCTAGTCG AGGGGCTCGG CAGCGCCTGA AGGGCAGCGG GGCCAGCAGT GGGGATACGG CCCCGGCTGC GGACAAGCTG CGGGAGCTGC TGGGCAGCCG AGAGGCGGGC GGCGCGGAGC ACCGGACCGA GTTATCTGGG AACAAAGCAG GACAAGTCTG GGCACCTGAA GGATCTACTG CTTTCAAGTG TCTGCTTTCA GCAAGGTTAT GTGCTGCTCT CCTGAGCAAC ATCTCTGACT GTGATGAAAC ATTCAACTAC TGGGAGCCAA CACACTACCT CATCTATGGG GAAGGGTTTC AGACTTGGGA ATATTCCCCA GCATATGCCA TTCGCTCCTA TGCTTACCTG TTGCTTCATG CCTGGCCAGC TGCATTTCAT GCAAGAATTC TACAAACTAA TAAGATTCTT GTGTTTTACT TTTTGCGATG TCTTCTGGCT TTTGTGAGCT GTATTTGTGA ACTTTACTTT TACAAGGCTG TGTGCAAGAA GTTTGGGTTG CACGTGAGTC GAATGATGCT AGCCTTCTTG GTTCTCAGCA CTGGCATGTT TTGCTCATCA TCAGCATTCC TTCCTAGTAG CTTCTGTATG TACACTACGT TGATAGCCAT GACTGGATGG TATATGGACA AGACTTCCAT TGCTGTGCTG GGAGTAGCAG CTGGGGCTAT CTTAGGCTGG CCATTCAGTG CAGCTCTTGG TTTACCCATT GCCTTTGATT TGCTGGTCAT GAAACACAGG TGGAAGAGTT TCTTTCATTG GTCGCTGATG GCCCTCATAC TATTTCTGGT GCCTGTGGTG GTCATTGACA GCTACTATTA TGGGAAGTTG GTGATTGCAC CACTCAACAT TGTTTTGTAT AATGTCTTTA CTCCTCATGG ACCTGATCTT TATGGTACAG AACCCTGGTA TTTCTATTTA ATTAATGGAT TTCTGAATTT CAATGTAGCC TTTGCTTTGG CTCTCCTAGT CCTACCACTG ACTTCTCTTA TGGAATACCT GCTGCAGAGA TTTTCATGTTC AGAATTTAGG CCACCCGTAT TGGCTTACCT TGGCTCCAAT GTATATTTGG TTTATAATTT TCTTCATCCA GCCTCACAAA GAGGAGAGAT TTCTTTTCCC TGTGTATCCA CTTATATGTC TCTGTGGCGC TGTGGCTCTC TCTGCACTTC AGAAATGTTA CCACTTTGTG TTTCAACGAT ATCGCCTGGA GCACTATACT GTGACATCGA ATTGGCTGGC ATTAGGAACT GTCTTCCTGT TTGGGCTCTT GTCATTTTCT CGCTCTGTGG CACTGTTCAG AGGATATCAC GGGCCCCTTG ATTTGTATCC AGAATTTTAC CGAATTGCTA CAGACCCAAC CATCCACACT GTCCCAGAAG GCAGACCTGT GAATGTCTGT GTGGGAAAAG AGTGGTATCG ATTTCCCAGC AGCTTCCTTC TTCCTGACAA TTGGCAGCTT CAGTTCATTC CATCAGAGTT CAGAGGTCAG TTACCAAAAC CTTTTGCAGA AGGACCTCTG GCCACCCGGA TTGTTCCTAC TGACATGAAT GACCAGAATC TAGAAGAGCC ATCCAGATAT ATTGATATCA GTAAATGCCA TTATTTAGTG GATTTGGACA CCATGAGAGA AACACCCCGG GAGCCAAAAT ATTCATCCAA TAAAGAAGAA TGGATCAGCT TGGCCTATAG ACCATTCCTT GATGCTTCTA GATCTTCAAA GCTGCTGCGG GCATTCTATG TCCCCTTCCT GTCAGATCAG TATACAGTGT ACGTAAACTA CACCATCCTC AAACCCCGGA AGCAAAGCA AATCAGGAAG AAAAGTGGAG GTTAGCAACA CACCTGTGGC CCCAAAGGAC AACCATCTTG TTAACTATTG ATTCCAGTGA CCTGACTCCC TGCAAGTCAT CGCCTGTAAC ATTTGTAATA AAGGTCTTCT GACATGAATA CTGGAATCTG GGTGCTCTGG GCTAGTCAAA GTCTATTTCA AAGTCTAATC AAAGTCACAT TTGCTCCCTG TGTGTGTCTC TGTTCTGCAT GTAAACTTTT TGCAGCTAGG CAGAGAAAGG CCCTAAAGCA CAGATAGATA TATTGCTCCA CATCTCATTG TTTTTCCTCT GTTCAATTAT TTACTAGACC GGAGAAGAGC AGAACCAACT TACAGGAAGA ATTGAAAATC CTGGTACTGG ATGGCTGTGA TAAGCTGTTC TCCACACTCT GGCCTGGCAT CTGAGAACTA GCAAGCCTCT CTTAGGCCAT ATGGGCTTCT CCACCAAAGC TGTTTGGCAG CTCCTAGCAG ACCTTCTTAT TGAAATCCTC ATGCTGAAAA TGAACACAGC CTAGTTGCCA ACCCACATGT CCTTTTCACC TCCAGCAAGA CTAAGCTTCT TTAAAGCACT TCACAGGACT AGGACCCTGT CCTGGAGCTA TCTCAGGAAA AAGGTGACCA TTTGAGGAAC | 31 |

TABLE 1-continued

Melanoma Biomarker/Housekeeper Sequence Information

| Gene Name | RefSeq Accession | Sequence | SEQ ID NO: |
|---|---|---|---|
| | | TGTGACCTAA TTTTATTATA ATGATGCCTC TAATTTTCAT <br> TTCCTTTACA ACCAACTGTA ACTATAAGGT TGTATTGCTT <br> TTTTGTTCAG TTTTAGCATG CTATTTTTTG AATTCTAGAC <br> TCCTCCATGT GAAGATATCA ACAGACAAAA CTACAACTGT <br> ATAGGACATA TTTGGAGAAA ATTCTATCAA TTGATACATT <br> TGGATGACAT CACATTTTTA AGTAATGTAA TCTGAGGCCA <br> TTGCTGAGGA AATTAAGAAT TTTCCTTTTT TTTTAACCAC <br> CCCCAGTGAA AAGGATCAGT GTATATTTAT AGCACCTATT <br> TTTTAGTTCT GTCTGTTGTG AGGCACATCC TGCATGGGGC <br> ACTTCTAGTC AAATAGGCAA TGATAAGGAC CTAATTAAAA <br> TGTGATAAGT GTATACTATT ACTTTAAAAG CCTTTACAGT <br> CAGTACTTCA GTTTACAAGG CACTTTCACA GCATCTCGTT <br> TGATCCTCAC AGTCACAACA TGTGGTAGAC AAGGCAGGTG <br> ATTTTTATCC CCATTTTACA GATAAGGAAA CAGGCTGCGG <br> GTGGGGAGTG AGGGGAGGTA AAGATAGTTA GTTGCCTAAG <br> GTCACACAGC CAGTAAGTAA TAGAGCTGGG ACTGGAACCC <br> AGGTTTCCTT ACTCTCATCT ATTGCTCCTC CATATTCCTC <br> ACTCAACCAT GAAAACATTA CTTGAAAGGA CTGATGAGGT <br> TAACCAGAGA CCTAACTGAT ATTGTAACTT TCTATTTTAA <br> GGAAGAATTG TGTCTGTATT TGAGTTCTTT GGAGCCTCCA <br> GTCTGCCTGT GTGTTAGACC AGCACAGCAG TGCTGTGTGA <br> TGCAGCCTGA CCTGTGGCAG GAAAGTAGTG CTTCTGTTTG <br> GAAGTCATGT TCTTTTGCAG CCACACAGGA TCCAAATATC <br> AGTACTATTC CTGTAGTCAA TCTGGGGTCA CATTATAGGT <br> GCCTTATTTC CCTAAGGGTA ACTGATCTGA ATATCTGCAA <br> ATAGGATGAA TCTATTTTTC AGAAGTTCCA TCTTTCATTT <br> TTCTTTTTTT TTTTGAGACA GAGTCTCATT CTGTCGCCCA <br> TGCTGGAGTG CAGTGGCGCG ATCTCGGCTC GCTGCAACCT <br> CTGCCTCCCA GGTTGAAGCA ATTCTCATGC CTCAGCCACC <br> CGAGTAGCTG GGATTACAGG CATGCGCCAT CATGCCCAGC <br> TAATTTATGT ATTTTTAGTA GAGTTGGAGT TTCACCATGT <br> TGGCCAGGCT GGTCTTGGAC TCCTGACCTC AGGTCATCCA <br> CCCGCCTCAG CCTCCCAAAG TGCTGGTATT ACAGGCGTGA <br> GCCACCGCAC CCAGCCCCAT CTTTCATTTT CAAAGAGAAG <br> GGCATTCTAA TAGGAACTGG TGCCAAGAGA GAAGAAAAGA <br> AGTGATAACA GAAGAAATGG CTAGTTACAA TATTAAAAAG <br> CTCCTCTTTG AGATCTCCTC TGCAGGAATA TCAGAGACGG <br> AGTTGAAGCG CTGGAGAGGT AATAGGTCTA GACAGTACAG <br> AACAATAACT GGGGAGTGTG TGAGGATAGA CTGGGCTCCC <br> CCTTGCTTGA AAGATCTCTG GCATTTAATT CTCAATTCTT <br> GATTACTATT TTCCAGTGTA AAACTAGCAC ATATGATCTG <br> ACTACAGGAC AGAGAATTTT AAGTGAAACA TTTGCCTTAC <br> TTGCAGTAAT AATGTGCTGT TCTTCACAGT AGCTAAGGCC <br> CTCTATGTTT CCCAGAGGTA AATAAGAATC CAGGAATGGA <br> GGTCCATCTG TGATGAATGG CTTTTTTCTA ATCAAAGTAG <br> TATAATGCTG TTTTATCTGT TTTGTCATCT TGTTTTTTTT <br> TTTTTTTAAA AAAACAAAAC CTTAATTATA ATATAGCGCA <br> AAGAAAGGCC AGGACTGATG CAGGGATTCC TTGGAAATAT <br> CAGTTCCTAT CACTTTTAAA ACCTGATTTT GGATCTCTCT <br> GTTCTATGTA TGTCTTTAGT GAGAGCACAA TACATGGCAG <br> AACGCTGTGC CAAATGTTAT AGGTAAGGAA TATAGAAATG <br> AATGTTTTTT GTTGTGAAGG TGTTTTCATG TGATATTTTA <br> TAAACACATT TTAAAAAATC TCCATCACTT TTTAGTATAG <br> GAAGGATAGC TTTGCCTGGG AAAAACAGTT TCAACACACC <br> TGCTCAGAGT AGCAGTTCTC CCTCAAAAAA GCAGTGTTCA <br> GCCTGCACTG ACTGTTCTGC TTGCCAAAAG GAGGAAGCAT <br> GCAAGATACT TATTTCTCCA TAGATTGTGG AGTATAGAGG <br> GATGTGGGAC TACAGATTAT TATTTTTTTT CCCCGAGACA <br> GAGTCTTGCT CTGTCGCCCA GGTTGGAACA CAATGGCACG <br> ACCTCAGCTC ACTGCAACCT CTGTCTCCCG GGTTCAAGCA <br> ATTCTCCTGC TTCAGCCTCC TGAGTAGCTG GGATTACAGG <br> CACACACCAC CACCGCACTC AGCTAATTTT TGTATTTTTA <br> GTAGAGGTGG GGTTTTACCA TGTTGGCCAG GCTGGTCTTA <br> AACTCCTGAC CTTGTAATCA TCCCGCCTCG GCCTCCTAAA <br> GTGCTAGGAT TACAGGCATG AGCCACCGCA CCCGGCCCAG <br> ATAATTTTTA ATAGCCTTTG ATCATGGGGT GAGTGAGGGA <br> GTAGGTATAC TTGGCAAATG CATGGTTCTC TGATTTCTAG <br> CTCTAAAGCA GCCTTATCTG AATCCCCAAA TCTTGTGATG <br> CTGAGTACCA TTACTGAACC AGTCTGCACG GTAGGCATCT <br> GCTACCAAAA TTTACCTCCT ACCTGGTAGG TGTCATCTGA <br> TAAGAAAGAA GACAGGTTAT TTTAATTTTT TGAGATAATC <br> ACAGAAAATT GCAGCCCATA CTCTTTATTA CCGAATTCAA <br> GTTTGGAAAT AGACCCTTTG TTTTAAATCA TGATGGGTCT <br> TTATCCCAAT CATTTATCTG GGTCATTTTT CCAACTTTGG | |

TABLE 1-continued

Melanoma Biomarker/Housekeeper Sequence Information

| Gene Name | RefSeq Accession | Sequence | SEQ ID NO: |
|---|---|---|---|
| | | AGTTCTAGGA AAGAACCTTG AAAACCTGAT ATGATTCTGC AGCATGAGGT CTACGGTGAC CATTTGGGCA AAGCTCCAGT GGCAATCATT TATTGTGTTT TGCATTTCCT GGGATTTATT GAAATAAGAA TTCACTGTGA TTATGTAGTC TTCTGGCTAG TATCAGGCAG CTCTGCTTTT AATTTGGTTA ATTTTATTTT CTCTGAAGAG GGAGAAGAGG TACAATTTAA TCTTGGCCTC CACAAGCATA TTAAAGCTCA CGTGTTAATC AGTGCATTCT TATGCTCCTA CATTAAATGC CTTGGGTAAA TGGATAAATG GACATGTGCC CAGCTTTAAT TTTTTTTGCA ACAGAAAGAT CAGACTTCCG TATGGCATCG TTGGATTTCA GAGGCTTTCT GGTGTATCTG TAAATCTGAA TGTTGCCTTC TGCCAGTCTG TATAACCAGG TGATTCATGC TGCAAATGAA ATCAGGAAGC AGTAAAGTGT TAAAGCAAGA GTATTGTCCA ATTCACTTGT CTTCCTGATC CTTGTACTTT ATTTCACGTG TCGGTGTTTA CATTACATAC TTATATTTCC TGTGAAAGAA AGAGTTAAAT AAATTGTAGC AGTTTGA | |
| SEPN | NM_031475.2 | AGCGGAGCGC CAGGCAGCGC GGAGCGGAGG CCAGGCCCAC AGCCGCTCCG CCTCCCGGCC CGCAGATCCC CGACGGCCGC ACCGCGGGCT CCTCTGGCCC GCAAGAACAC GTGCATGGCG TCCTGGGGAA GGCGCTGAGT GCGGAGTCGC GGCGCCGCAC GCGGCACCAT GGCCCTGGAG CAGGCGCTGC AGGCGGCGCG GCAGGGCGAG CTGGACGTGC TGAGGTCGCT GCACGCCGCA GGCCTCCTGG GGCCCTCGCT GCGCGACCCG CTGGACGCGC TGCCCGTGCA CCACGCGGCC CGCGCTGGGA AGCTGCACTG TCTGCGCTTC CTGGTGGAGG AAGCCGCCCT CCCCGCCGCG GCCCGCGCCC GCAACGGCGC CACACCGGCC CACGACGCCT CCGCCACCGG CCACCTCGCC TGCCTGCAGT GGCTGCTGTC GCAGGGCGGC TGCAGAGTGC AGGACAAAGA CAATTCTGGT GCCACAGTCT TGCATCTGGC TGCCCGCTTC GGCCACCCCG AGGTGGTGAA CTGGCTCTTG CATCATGGCG GTGGGGACCC CACCGCGGCC ACAGACATGG GCGCCCTGCC TATCCACTAC GCTGCCGCCA AAGGAGACTT CCCCTCCCTG AGGCTTCTCG TCAGCACTA CCCTGAGGGA GTGAATGCCC AAACCAAGAA CGGTGCCACG CCCCTGTACC TGGCGTGCCA GGAGGGCCAC CTGGAGGTGA CCCAGTACCT GGTGCAGGAA TGCGGCGCAG ACCCGCACGC GCGCGCCCAC GACGGCATGA CCCCGCTGCA CGCCGCGGCG CAGATGGGCC ACAGCCCAGT CATCGTGTGG TTGGTGAGCT GCACCGACGT GAGCCTGTCC GAGCAGGACA AAGACGGCGC CACCGCCATG CACTTCGCGG CGAGCCGCGG CCACACCAAG GTGCTCAGCT GGCTGCTGCT GCACGGCGGG GAGATCTCGG CTGACCTGTG GGGCGGGACC CCGCTGCACG ACGCCGCCGA GAACGGGGAG CTAGAGTGCT GCCAGATCCT GGTAGTGAAC GGCGCGGAGC TGGACGTCCG CGACCGCGAC GGGTACACGG CCGCCGACCT GTCGGACTTC AACGGCCACA GCCACTGCAC CCGCTACCTG CGCACGGTGG AGAACCTGAG CGTGGAGCAC CGCGTGCTTT CCCGGGATCC ATCCGCAGAG CTGGAGGCTA AGCAGCCGGA TTCAGGCATG TCCTCACCCA ATACCACGGT GTCGGTCCAG CCGCTGAACT TGACCTCAG CTCGCCTACC AGCACCCTCT CCAACTACGA CTCCTGCTCC TCCAGCCACT CCAGCATCAA GGGCCAGCAC CCTCCATGTG GGCTTTCCAG CGCTAGAGCT GCAGACATAC AGAGCTACAT GGACATGCTG AACCCGGAGC TGGGCCTGCC TCGGGGCACG ATTGGGAAGC CCACACCCCC ACCACCCCCA CCCAGCTTCC CCCCGCCACC CCCGCCCCCA GGCACCCAAC TGCCCCCACC CCCACCTGGC TACCCAGCTC CCAAGCCTCC TGTAGGACCA CAGGCAGCTG ACATCTACAT GCAGACCAAG AACAAACTCC GCCACGTGGA GACAGAGGCC CTCAAGAAGG AGCTGAGCTC CTGTGACGGC CACGACGGGC TGCGGAGGCA GGACTCCAGC CGCAAGCCCC GCGCCTTCAG CAAGCAGCCC AGCACGGGGG ACTACTACCG GCAGCTGGGC CGCTGCCCCG GCGAGACGCT GGCCGCACGC CCGGGCATGG CGCACAGCGA GGAGGTGCGT GCCCGCCAGC CCGCGCGCGC CGGCTGCCCG CGCCTCGGCC CTGCCGCCCG CGGCTCACTC GAAGGCCCCT CCGCTCCCCC GCAGGCGGCG CTGCTTCCTG GGAACCATGT TCCTAACGGC TGCGCCGCGG ACCCCAAGGC GTCCAGGGAG CTGCCACCGC CGCCCCCACC GCCGCCGCCG CCCCTGCCGG AGGCCGCGAG TTCGCCACCG CCGGCCCCGC CTCTGCCCCT CGAGAGCGCT GGCCCTGGCT GCGGGCAGCG CCGCTCCTCC TCGTCCACCG GCAGCACCAA GTCTTTCAAC ATGATGTCCC CGACGGGCGA CAACTCGGAG CTACTGGCTG AGATTAAGGC AGGCAAGAGC CTGAAGCCGA CGCCCCAGAG CAAGGGGCTG ACCACAGTGT TCTCAGGCAT CGGGCAGCCG GCCTTCCAGC CCGATTCGCC GCTGCCTTCT GTGTCACCTG CACTGTCACC AGTCCGGAGC | 32 |

TABLE 1-continued

Melanoma Biomarker/Housekeeper Sequence Information

| Gene Name | RefSeq Accession | Sequence | SEQ ID NO: |
|---|---|---|---|
| | | CCCACACCGC CAGCTGCGGG GTTTCAGCCG CTGCTCAATG<br>GAAGCTTGGT TCCCGTGCCG CCCACTACTC CTGCGCCGGG<br>AGTGCAGCTG GACGTGGAGG CTCTCATCCC CACGCACGAT<br>GAGCAGGGCC GGCCCATCCC CGAGTGGAAG CGCCAGGTGA<br>TGGTGCGCAA GATGCAGCTG AAGATGCAGG AGGAGGAGGA<br>GCAGAGGCGG AAGGAGGAGG AGGAGGAGGC CCGGCTGGCC<br>AGCATGCCCG CCTGGAGGCG GGACCTCCTG CGGAAGAAGC<br>TGGAAGAAGA GAGGGAGCAG AAGCGGAAAG AGGAGGAGCG<br>ACAGAAGCAG GAGGAGCTGC GGCGGGAGAA GGAACAGTCA<br>GAGAAGCTGC GGACGCTGGG CTACGATGAG AGCAAGCTGG<br>CGCCCTGGCA GCGACAGGTC ATCCTGAAGA AGGGGACAT<br>CGCTAAGTAC TAGAGGCCGC AGACTCCTGT CCGCAGCCTC<br>GCAGCTCCGT GGGGCCCTCC GCCCCAGCCC CAGCCAGCCA<br>GGCCCTGGTG GAAAGGCTGG GAGCCGCACA GCCCTCCCCT<br>CCTCGCCTGG AAACCCTCCC TGACCCCCAC CCTGGCCCCC<br>CGTATCCCCA GCCCTTGGCA ACACTGGAGT GCACACGCCG<br>CCACGGTTGC CCAGAAAAAG TGCCCAAGCT GCTGACGCAA<br>ACAACAACAA ATGCTGCTTA TTTGCATGCC GACTTACATA<br>TATTTGCATG TTCGTTGACT ATCAAAGAGT GCAGAGCTCT<br>CCCCAGCCCC GTGGGTGGTG ACTTTGTTTT CCTGCGGGGC<br>TCAGCCCCCT CCAGGATGCA GCCCCCTCCC CCGCACCCCG<br>GAACCGGCGT CGCTGGCGCA TCCTGGGTGG AGGCAGGCCC<br>CGAGCTCGGG GAAGGGGTTT TCCCTTCCTC TCTGACCCAG<br>ATCTGCGCGC GGCCTAGCCC GGGCCTCATT TCTTATCCCC<br>GCCAAGGGTT TCCTCTCAGT CATTTGTTTA CCAGAAACAT<br>GAAAACTGCC TGTCTGGCCG GGCCGCACTT GTGGCCCCCG<br>GGACCCCACC TCTGGCCCCA CCTCCCTCAA GTCTGCGCCC<br>CGTCCCCAGC CAGACCCACT CGCTGCCGGG ACCCTTTCAC<br>TGCCCCGGTG GAGTGAATAG AGGATGAGGG GCCCTGACCC<br>TGTGTCTCCA ACTGCTGCAC CCCATCCCGA CCCTGTCTCC<br>GCCACCTCGC AGCCCCATTA AAGCGCTCTC ATCTGGGCTC<br>CGGTTCACTC A | |
| YWHAQ | NM_006826.3 | TTGGGCGGTG GACCGCCCCT CGGCCCCGGG GTAGGCTGAC<br>ACGGGAGGGT CCTCAGCTAA AGCCAAAAGC AGATCAAAGT<br>GGTGGGACTC GCGTCGCGGC CGCGGAGACG TGAAGCTCTC<br>GAGGCTCCTC CCGCTGCGGG TCGGCGCTCG CCCTCGCTCT<br>CCTCGCCCTC CGCCCCGGCC CCGGCCCCGC GCCCGCCATG<br>GAGAAGACTG AGCTGATCCA GAAGGCCAAG CTGGCCGAGC<br>AGGCCGAGCG CTACGACGAC ATGGCCACCT GCATGAAGGC<br>AGTGACCGAG CAGGGCGCCG AGCTGTCCAA CGAGGAGCGC<br>AACCTGCTCT CCGTGGCCTA CAAGAACGTG GTCGGGGGCC<br>GCAGGTCCGC CTGGAGGGTC ATCTCTAGCA TCGAGCAGAA<br>GACCGACACC TCCGACAAGA AGTTGCAGCT GATTAAGGAC<br>TATCGGGAGA AAGTGGAGTC CGAGCTGAGA TCCATCTGCA<br>CCACGGTGCT GGAATTGTTG GATAAATATT TAATAGCCAA<br>TGCAACTAAT CCAGAGAGTA AGGTCTTCTA TCTGAAAATG<br>AAGGGTGATT ACTTCCGGTA CCTTGCTGAA GTTGCGTGTG<br>GTGATGATCG AAAACAAACG ATAGATAATT CCCAAGGAGC<br>TTACCAAGAG GCATTTGATA TAAGCAAGAA AGAGATGCAA<br>CCCACACACC CAATCCGCCT GGGGCTTGCT CTTAACTTTT<br>CTGTATTTTA CTATGAGATT CTTAATAACC CAGAGCTTGC<br>CTGCACGCTG GCTAAAACGG CTTTTGATGA GGCCATTGCT<br>GAACTTGATA CACTGAATGA AGACTCATAC AAAGACAGCA<br>CCCTCATCAT GCAGTTGCTT AGAGACAACC TAACACTTTG<br>GACATCAGAC AGTGCAGGAG AAGAATGTGA TGCGGCAGAA<br>GGGGCTGAAA ACTAAATCCA TACAGGGTGT CATCCTTCTT<br>TCCTTCAAGA AACCTTTTTA CACATCTCCA TTCCTTATTC<br>CACTTGGATT TCCTATAGCA AAGAAACCCA TTCATGTGTA<br>TGGAATCAAC TGTTTATAGT CTTTTCACAC TGCAGCTTTG<br>GGAAAACTTC ATTCCTTGAT TTGTGTTTGT CTTGGCCTTC<br>CTGGTGTGCA GTACTGCTGT AGAAAAGTAT TAATAGCTTC<br>ATTTCATATA AACATAAGTA ACTCCCAAAC ACTTATGTAG<br>AGGACTAAAA ATGTATCTGG TATTTAAGTA ATCTGAACCA<br>GTTCTGCAAG TGACTGTGTT TTGTATTACT GTGAAAATAA<br>GAAAATGTAG TTAATTACAA TTTAAAGAGT ATTCCACATA<br>ACTTCTTAAT TTCTACATTC CCTCCCTTAC TCTTCGGGGG<br>TTTCCTTTCA GTAAGCAACT TTTCCATGCT CTTAATGTAT<br>TCCTTTTTAG TAGGAATCCG GAAGTATTAG ATTGAATGGA<br>AAAGCACTTG CCATCTCTGT CTAGGGGTCA CAAATTGAAA<br>TGGCTCCTGT ATCACATACG GAGGTCTTGT GTATCTGTGG<br>CAACAGGGAG TTTCCTTATT CACTCTTTAT TTGCTGCTGT<br>TTAAGTTGCC AACCTCCCCT CCCAATAAAA ATTCACTTAC<br>ACCTCCTGCC TTTGTAGTTC TGGTATTCAC TTTACTATGT | 33 |

TABLE 1-continued

Melanoma Biomarker/Housekeeper Sequence Information

| Gene Name | RefSeq Accession | Sequence | SEQ ID NO: |
|---|---|---|---|
| | | GATAGAAGTA GCATGTTGCT GCCAGAATAC AAGCATTGCT TTTGGCAAAT TAAAGTGCAT GTCATTTCTT AATACACTAG AAAGGGGAAA TAAATTAAAG TACACAAGTC CAAGTCTAAA ACTTTAGTAC TTTTCCATGC AGATTTGTGC ACATGTGAGA GGGTGTCCAG TTTGTCTAGT GATTGTTATT TAGAGAGTTG GACCACTATT GTGTGTTGCT AATCATTGAC TGTAGTCCCA AAAAAGCCTT GTGAAAATGT TATGCCCTAT GTAACAGCAG AGTAACATAA AATAAAGTA CATTTTATAA ACCATTTACT ATGGCTTTGT AACAATTGCA TACCCATATT TTAAGGGACA GGTGAATTTA CTACTTTCTA AAGTTTATTG ATACTTCCCT TTTATGTAAA ATGTAGTAGT GATACCTATA TTTCCACATT GTGCATTGTG ACACACTTGT CTAGGGATGC CTGGAAGTGT ATAAAATTGG ACTGCATTTC TTAGAGTGTT TTACTATAGA TCAGTCTCAT GGGCCATCTC TTCCTCAGAT GTAAATGATA TCTGGTTAAG TGTTATATGG AATAAAGTGG ACATTTTAAA ACTAGCAAAG TTAAAAAAAA AAAAAAAAA AA | |
| VPS37A | NM_001145152.1 | GCAGAGGGGG CGGAGAGCGC CCCCGGGGGC GGGGCACGCA AGTGACGGCG GCGCGGGTGG TGGAGCGCTG GGCGGCCAGG CTCCCTGGCT GGCCGGTTTG GGCGTCTGGG CCGTGAAGGT GGGACCTCCT GTTCCGGGCC GCAAGTTTCC CTCTCCAGCC GCCCGCCGTT CGTAGCATGT CCCCCAGAAC TCGGGGAGCG CAGGCAGGAC AGGCTTAGAG AAGACGCGGT CCCCAGCGCT TGGGCCACGG ACGTCCCACC CCGCTCCTCT GTCGCTGGAG AACCGCCGGG CCGAGCCACT GGGAGAAGCA GGCCAGAGCC TTCCAGGGCC TCCGGCCCGT GGACCCGAGG AGGATGAGCT GGCTTTTTCC CCTGACCAAG AGCGCCTCCT CCTCCGCGGC TGGGTCCCCC GGTGGCCTCA CCAGCCTCCA GCAGCAGAAG CAGCGCCTGA TCGAGTCCCT CCGGAACTCA CACTCCAGAT TGCTTCCTCC ACAGTTTCCT CAGGAAAAAC CAGTGATCAG TGTTTATCCA CCAATACGAC ATCACTTAAT GGATAAACAA GGAGTGTATG TTACCTCTCC ATTAGTAAAC AATTTTACAA TGCACTCAGA TCTTGGAAAA ATTATTCAGA GTCTGTTGGA TGAGTTTTGG AAGAATCCTC CAGTTTTAGC TCCTACTTCA ACAGCATTTC CTTATCTATA CAGTAACCCA AGTGGGATGT CTCCTTATGC TTCTCAGGGT TTTCCATTTC TTCCTCCATA TCCTCCACAA GAAGCAAACA GGAGTATCAC TTCTTTATCT GTTGCTGACA CTGTTTCTTC TTCAACAACA AGTCATACCA CAGCCAAGCC TGCCGCTCCT TCATTTGGTG TCCTTTCAAA TCTGCCATTA CCCATTCCCA CAGTGGATGC TTCAATACCG ACAAGCCAAA ATGGTTTTGG GTACAAGATG CCAGATGTCC CTGATGCATT TCCAGAACTC TCAGAACTAA GTGTGTCACA ACTCACAGAT ATGAATGAAC AAGAGGAGGT ATTACTAGAA CAGTTTCTGA CTTTGCCTCA ACTAAAACAA ATTATTACCG ACAAAGATGA CTTAGTAAAA AGTATTGAGG AACTAGCAAG AAAAAATCTC CTTTTGGAGC CCAGCTTGGA AGCCAAAAGA CAAACTGTTT TAGATAAGTA TGAATTACTT ACACAGATGA AGTCCACTTT CGAAAAGAAG ATGCAAAGGC AGCATGAACT TAGTGAGAGC TGTAGTGCAA GTGCCCTTCA GGCAAGATTG AAAGTAGCTG CACATGAAGC TGAGGAAGAA TCTGATAATA TTGCAGAAGA CTTCTTGGAG GGAAAGATGG AAATAGATGA TTTTCTCAGT AGCTTCATGG AAAAGAGAAC AATTTGCCAC TGTAGAAGAG CCAAGGAAGA GAAACTTCAG CAGGCGATAG CAATGCACAG CCAATTTCAT GCTCCACTAT AGATTTTCCT GGAAACATGA ACTGCCAAGA GAGGAATGGG ACACAAAACC AAACACTGTT TTATATTTAT GGTTTGCAAA CTGGCATTTC ATCAGTGGCT AAATTCACAG ATATCCTATA TAGATTGTAT ACAGAACTGA GACTGATTTT GTACCGATTA GAATGATTGC TATGATCTTT GAGAAATTTT TCTGCACTAT TTGCACTGAA ATGTTTATTT ATTGTTGATA AATTGTATCA TATTTAAGTT CCACTGCTGT TCCTCTTACC TTGATTAAAT GCCTATGCAT GTACTTTTAG CTAGTTTTTA ATATTTTATA AAACTTCATT TAAATTTGTA TTTTTAACTT GAAGTTCCAT TTCTTTTATCA AGGATGGTAT TTAGATTTTT TTCCTCTTAA CCTTTTTTCA AAAACTATTT TCAACTGTGA GGAAACCCTT ATTTTTCTTT CTTTGTGGAT AAAACTTTCA AAAGCAATTT AAGATATTCA TAGTGTTAGG AAACACCAAA CCTGCCTATG TGCCATCTCA CAAAAGAAAC TTTTAATACC TACAATAAAT CAAAAGAATA AACCAGCTGT TCTTATATAT TGTTTCATTT TTAAAACTAA AGATGCATTT AAGAAGCAAT ACAAGTAAAT ATTTTACCTA ATAGGAAAAA AAAAGTTGC CTTTCATTTA AACCATTCCA ACAGAAATTC TTATGCTAAT TTAAAACATA TATATATCTG GTAGGTTTGT GGTTGGATAG GTTTTCTAAA TTCCTAATGT TAAAAACAAT CTTTATGTTA ATATACACTA AATCTATACA | 34 |

TABLE 1-continued

Melanoma Biomarker/Housekeeper Sequence Information

| Gene Name | RefSeq Accession | Sequence | SEQ ID NO: |
|---|---|---|---|
| | | CAAAAAAAGT CAGTGAACTT TTCTGACCTT TACTGTGAGT TACCTTTTCC TAAGAGGAAA GCTATAGTAA TAAGTAAAAT TTAATTTTTA GGCAATCCTG ATTTTTAATG AATTTAATTG AGTGTTCTTG TATACTACAT TGAGCAGTTT GCTTCTATAC CGTGTCACAA AATTCATGTA TTTCTTGAGA AGCCCTAAAA GCTCATAAAG GAAAATGCCG TGAACTATGT AGCTCAGGCT TGGTAAGGTG CCATCTAAAT TACAAAACAA ACTAATGCAT AATTTTGCTT AAATTTCATC CCAGTATGAT TGTCTTCCCA ACACCAGCAT ATAGTATAGA TTGTCTGTCT TTTTTATATT TTTTAGTTCT TCCTGTACAT GTTTTTGGCA ATAAAGTTAT AGGAAGAACA AAATTATTTT GTTAGAATTA AAACATGCTT AATATTTAGT CTGTTTGTGG AGGGCAGGTA TTCACGTGGA CTGAGATACA ATGTTGGATA CAGAAAATAA CTTTCATTGT CTTCCTGACA CTGTGCTAAG GACATGCTGT TAAAGCTTCA AAGTGACCAG ATGAGGAAGG AATAATTAAT TATTACTCCT GATTTGTAGA TAACTGAGGT AAGAGTGTTT CAAATTTATG ATAGTCTTTT GGGTATTCAG AAACCTTTCC TTATACTGCA CTGGCCACCA GAGCTTAATT TTCCCAGCAG TTACAGCAAT GGGAGATAGA ACAGTCTCAA TCTTTTGCCA ACCATCAGGT TCCTAGAAAC CAGGTAGGTG TATCCCATAA CAAGGGAGGA GCATACCACA GCCCCTCATT TGATTAATTC ATTTGATCTA TCTATGTTAT TAAGTACCTA CTAGGAATAA GGCATTGTGG AAATACTATA CAAAGATAAA CATTGTTTAG ATGCTTATCT ACTTTCCTTT TCACCAGAAA AACAGAAAAA AAAGAAACAT TTTCTTACAG AGTAAAAATG TTCTACATAA TCACATGAGT AGTTCATCTC AGTGTTTTTT ATTCTTTAAA GTTGAACTAT CCCAGTTTCA TTCTATACCA TTCATTGGAT AACCTTGTTA CAACCCAGTC ATGAAACAGA GCAGTGTGAT CAGTTATCTG CATTTAACAA ATAGACAAAT CAGTTTACAT AAAGGTTATG TATGTCACCC ACGATGAAAA GAATCTGCAT TTGAATATGC CCGTATGAAT GTGGGTTCTG TTTTTGCAAC AGAGATTAAG TGACCATTTT TTCTAATTTT ATGGCTATAT ATTTTCTTCA TAAAAATTGG TCACATCGGA GAAGCAGTGC CACAGGAAAA ATGAAATGCA TGTGAAAGTT TGTATTCTGA TTTTACAAGA TGAGATAGAA ATCAGAATTA AAGAGGAATA CTTAGGAGTT ACTAGGCTAA TCAGTGTACG AATTTGTCAT AGGTAGAGAT TTAAAGGTTA ATATCTTAAA ATAGAAGAAA ATTCTAAATC AATCAATCAG TGAGATATAA ACTAAACAGA CCCCACTTCA AGTTGAAAGA AATTTCTAGG CATAAATTGA GACTAGGAAA TTTATATCAG AATAGAGGGT GCTTGACACA TATATATGCT TAAATTGAAG GACAGCTCAG ATTCATTTTT AGGAGAAGAA AGTAAACTAA TGTGCTCTTA AAGAATAAAA ATTTATTCTA TGGTTTCTGT CTCTGATCAT CACCTTCCAT TCTATAAAAA GCTCAGTTAC TGATTTGCTG GGTCATGGTC AAAATTCTTA CCTATTTATT TCATATCAAC TTTAAAAAAT AAATTACTTG CATTCTATAT ATTACTAATT GGGAAGTAAT ATGCCTCAAA TCAGTTTTAT ACTGGATTAT TCCCTATGCT TTAAACCACT GCTCTCAATA AAACACTTCC TGATTAATGT TTGATTATTA GATATTTTAG TCTTGTTGGG GATATTTTAG TCTTGTTGGG TTAGCCATGC TCTGAAGAAT CTGTGAAAGT ACAGTAAAGT TTTAATAAGC AATAAATGTA ACCTTTTATA TAAATCTCAG TGCTAGGTTA ACTTCTAATA AGCAGACGAA CATGTTACAT AAATTATAAT GTCTGTCTTG TAAAAAAGTT GAGGGGACTA AAAGTTTATG ACTCTGATAT GGAAGTTGTC ATATTAAAAA ACTACATTTT AAAACATCAA ATATTTATAC TATTTGCTTT TCAAATAAAA GCATAGTGCT GTTTGGCATA | |
| PRRC2B | NM_013318.3 | GCAGATCGGG AGCGGTGCCG AGAAAAATTT CCTTACTAGA TGACATTTCA TCGCAATGTC CGATCGTTTG GGGCAAATTA CCAAGGGCAA GGATGGGAAA AGCAAGTACT CGACTCTCAG CCTGTTTGAT AAGTATAAAG GAAAATCAGT AGACGCGATT AGATCCTCAG TTATTCCTAG ACATGGCTTA CAGAGTCTTG GGAAAGTTGC TGCAGCCCGG CGCATGCCAC CGCCTGCAAA CCTGCCAAGC TTGAAGTCTG AAAACAAAGG AAACGACCCC AACATCGTGA TAGTACCCAA GGACGGGACG GGATGGGCAA ACAAGCAGGA TCAGCAAGAC CCAAAGAGTT CCAGTGCGAC GGCCTCTCAG CCGCCGGAGT CGCTGCCGCA GCCGGGTTTG CAGAAATCTG TCTCCAATTT GCAGAAACCG ACACAGTCAA TCAGTCAGGA GAATACAAAT TCAGTGCCAG GTGGACCAAA GTCATGGGCA CAGCTGAATG AAAGCCAGT AGGACACGAA GGTGGTTTAA GGGGCTCAAG CCGACTGTTA TCCTTCTCTC CCGAGGAATT TCCGACGCTG AAAGCAGCTG GAGGGCAGGA CAAGGCTGGC AAAGAAAAGG GCGTCTTAGA TCTGTCGTAT GGGCCAGGAC CAAGCCTCCG CCCTCAGAAT GTGACAAGCT | 35 |

TABLE 1-continued

Melanoma Biomarker/Housekeeper Sequence Information

| Gene Name | RefSeq Accession | Sequence | SEQ ID NO: |
|---|---|---|---|
| | | GGAGGGAGGG CGGTGGGCGA CACATAATTT CTGCCACGTC<br>TCTGAGCACC TCCCCAACTG AGCTGGGCAG CAGGAACTCG<br>AGTACGGGAG ATGGAGCCCC CTCCTCGGCA TGTACCAGCG<br>ATTCTAAGGA CCCCTCTCTC CGCCCGGCTC AGCCTGTCCG<br>AAAAGGGGCT TCACAGTTCA TGGGAAATGT ATACCACCCA<br>CCTACATACC ATGACATGCT TCCTGCTTTT ATGTGTTCGC<br>CGAAGTCATC AGAAAACCAG GGTACAGTGG AACGAGGCTC<br>TTTTCCCCTT CCTCAGCTCC GCCTTGAACC TCGAGTTCCT<br>TTTAGACAGT TCCAGATGAA TGACCAAGAC GGAAAAGAAA<br>ACAGGCTGGG ATTGTCTCGC CCACTCCGCC CACTAAGGCA<br>GCTGGTGGAG CGGGCACCAC GGCCCACCAT TATCAATGCG<br>GAAAACCTGA AGGGCCTTGA CGATCTGGAC GCCGATGCCG<br>ATGATGGCTG GGCAGGCCTC CATGAAGAAG TGGACTATTC<br>TGAGAAACTG AAGTTCAGTG ATGATGAAGA GGAGGAAGAA<br>GTTGTGAAGG ACGGCAGGCC AAAGTGGAAC AGTTGGGACC<br>CTAGGAGGCA GCGGCAGTTG TCAATGAGCT CTGCAGACAG<br>TGCGGACGCT AAGCGGACTC GAGAGGAAGG GAAGGACTGG<br>GCTGAAGCAG TGGGTGCGTC CCGTGTGGTC CGAAAGGCGC<br>CAGACCCTCA GCCACCGCCC AGGAAGCTTC ATGGCTGGGC<br>ACCAGGCCCT GACTACCAGA AGTCATCAAT GGGCAGCATG<br>TTCCGGCAAC AGTCCATCGA GGACAAGGAG GACAAGCCCC<br>CACCAAGGCA GAAGTTCATT CAGTCAGAGA TGTCCGAGGC<br>GGTGGAGCGA GCCCGAAAGC GCCGGGAAGA AGAGGAGCGC<br>CGAGCCCGGG AGGAGAGGCT GGCCGCCTGT GCTGCCAAAC<br>TCAAGCAGCT GGACCAGAAG TGTAAGCAGG CACGAAAGGC<br>AGGTGAGGCC CGGAAGCAGG CAGAGAAGGA AGTGCCCTGG<br>TCTCCAAGTG CTGAGAAGGC ATCTCCCCAG GAAAACGGCC<br>CTGCTGTCCA CAAAGGCTCC CCAGAATTCC CTGCCCAAGA<br>GACCCCCACC ACATTCCCAG AAGAGGCACC CACAGTGTCC<br>CCAGCAGTGG CACAGAGCAA CAGCAGTGAG GAAGAGGCCA<br>GAGAGGCTGG GTCCCCTGCA CAGGAGTTCA AGTATCAGAA<br>GTCCCTTCCT CCCCGATTCC AGCGCCAGCA GCAGCAACAA<br>CAGCAGGAGC AGCTGTACAA GATGCAGCAC TGGCAGCCGG<br>TGTACCCCCC GCCGTCCCAC CCCCAGCGCA CCTTTTACCC<br>ACACCACCCC CAGATGTTGG GCTTCGATCC CAGGTGGATG<br>ATGATGCCTT CCTACATGGA CCCACGTATC ACGCCCACTC<br>GGACCCCGGT GGACTTCTAC CCCTCCGCCC TGCATCCCTC<br>AGGACTGATG AAGCCCATGA TGCCCCAGGA GTCCCTCAAT<br>GGGACAGGCT GTCGCTCTGA GGATCAGAAC TGTGTGCCCC<br>CACTCCAAGA AAGAAAAGTG ACCCCCATCG ACTCACCCCC<br>TGTGTGGAGC CCAGAGGGCT ACATGGCACT GCAGAGCAAG<br>GGCTACCCGC TCCCGCACCC GAAGTCGAGT GACACCTTGG<br>CTATGGACAT GCGTGTCAGG AATGAAAGCT CTTTCTCTGC<br>CTCACTCGGA AGGGCAGGGG GCGTAAGTGC TCAGCGCGAT<br>CTCTTTGAGG AGAGAGGGGA GGAGTACTTG AGTGCTTTTG<br>ACAAGAAGGC CCAAGCAGAC TTTGACAGCT GTATCTCTTC<br>TCAAAGAATA GGCCAGGAGC TTTTGTTTCC ACCCCAAGAA<br>AATGTTCAGG ATGCAGGTGC TCCTGGGGGT CACACCCAAA<br>ACCTCAGGTG TTCCCCATTG GAGCCTGACT TTGTCCCAGA<br>TGAGAAAAAG CCAGAGTGTG GCAGTTGGGA TGTTAGCCAC<br>CAGCCAGAGA CCGCTGACAC AGCCCATGGT GTTGAGCGGG<br>AGACACCCCG GGAGGGGACG GCCTTTAACA TCTCCTCCTG<br>GGACAAGAAC GGGAGCCCCA ACAAACAGCC ATCCTCGGAG<br>CCTGAATGGA CTCCCGAGCC CCGGAGCTCC AGCAGCCAGC<br>ACCCGGAGCA GACGGGCAGG ACCCGGAGGT CGGGACCCAT<br>CAAGAAACCA GTCCTGAAAG CCCTCAAGGT GGAAGACAAG<br>GAGAAGGAGC TTGAGAAGAT TAAGCAGGAG CTAGGGGAGG<br>AGAGTACCCG GCTGGCCAAG GAGAAGGAGC AGAGCCCCAC<br>GGCAGAAAAG GATGAGGACG AAGAGAACGA TGCCTCTCTG<br>GCCAACTCCT CCACCACCAC TTTGGAGGAC AAAGGCCCTG<br>GCCATGCCAC TTTTGGCCGC GAGGCCACCA AATTTGAAGA<br>GGAGGAGAAA CCTGACAAGG CCTGGGAAGC CAGACCCCCA<br>CGAGAGTCCA GCGATGTTCC CCCCATGAAG AGAAATAACT<br>GGATCTTTAT TGATGAGGAG CAAGCCTTTG GGGTCAGAGG<br>ACAGGCCCGG GGCCGGGGCC GTGGTTTCAG AGAGTTCACT<br>TTTCGTGGTC GGCCTGCTGG CGGAAATGGG AGCGGCCTCT<br>GTGGTGGGGG GGTCCTGGGG GCCCGCAGCA TCTACTGCAG<br>CAGTCAGCGC AGCGGCCGTG GCCGGGGCCT GCGAGAGTTT<br>GCGCGGCCAG AGGACTGCCC CAGAGCCAAG CCCCGACGGA<br>GAGTTGCCAG TGAGACCCAT AGCGAGGGCT CAGAGTATGA<br>AGAACTTCCC AAGCGCCGCC GGCAGAGGGG CTCCGAGAAC<br>GGGAATGAAG GCTCGCTCCT GGAGAGGGAG GAGAGCACCT<br>TGAAGAAGGG CGACTGCAGA GATTCTTGGC GGTCCAACAA<br>GGGGTGCTCT GAGGACCACA GCGGTCTAGA TGCCAAGAGC | |

TABLE 1-continued

Melanoma Biomarker/Housekeeper Sequence Information

| Gene Name | RefSeq Accession | Sequence | SEQ ID NO: |
|---|---|---|---|
| | | CGAGGCCCTC GGGCCTTTGG GCGAGCCCTC CCTCCCCGGC<br>TGAGCAATTG CGGGTATGGA CGGAGAACCT TCGTCTCCAA<br>AGAGTCACCC CACTGGCAGA GCAAAAGTCC AGGCAGCTCT<br>TGGCAGGAAT ATGGCCCTTC CGACACATGC GGATCCCGGC<br>GACCTACAGA CAGAGACTAT GTCCCAGATT CCTACAGACA<br>CCCTGACGCA TTTGGTGGCC GGGGCTTTGA GGACAGCCGC<br>GCGGAGGACA AGAGATCCTT CTTCCAAGAT GAACACGTGG<br>CAGATTCTGA AAATGCAGAG AACCGGCCCT TCAGGAGAAG<br>GCGCCCCCCA CGCCAAGATA AGCCCCCTCG ATTCCGGCGC<br>CTCCGGCAAG AGCGGGAGTC CCTGGGCCTG TGGGGACCCG<br>AGGAGGAGCC CCACCTGCTG GCAGGTCAGT GGCCAGGCAG<br>GCCCAAACTG TGTTCTGGGG ACAAGAGTGG CACTGTGGGC<br>CGCAGGTCCC CTGAGCTCTC CTACCAGAAC TCCTCCGATC<br>ACGCCAATGA GGAGTGGGAG ACGGCCTCCG AAAGCAGCGA<br>CTTCAGCGAG CGGCGGGAGC GGCGGGAAGG CCCTGGGTCC<br>GAGCCCGACT CCCAGGTGGA TGGTGGCCTG TCGGGGCTA<br>GTTTGGGTGA GAAGAGGAG CTGGCCAAGA GGAGCTTCTC<br>CAGTCAGAGA CCCGTGGTTG ACAGACAGAG CCGAAAGCTG<br>GAGCCGGGAG GGTTTGGGGA GAAGCCCGTT AGGCCAGGTG<br>GTGGTGACAC CTCCCCTCGC TATGAGAGCC AACAGAATGG<br>GACGCCTTTG AAAGTGAAAA GATCCCCAGA CGAGGCCTTG<br>CCTGGAGGTC TTAGTGGCTG CAGCAGTGGG AGTGGCCACT<br>CCCCCTATGC CCTGGAGCGG GCAGCCCATG CCAGTGCTGA<br>CCTTCCCGAA GCCTCCAGTA AAAAGGCAGA GAAGGAGGCC<br>AAGTTGGCTG CTCCGAGGGC AGGTGAACAG GGAGAGGCCA<br>TGAAACAGTT TGACCTGAAC TATGGAAGTG CCATCATTGA<br>AAATTGCGGG TCCAGCCCCG GGGAGGAGAG TGAGGTGGGT<br>TCTATGGTGG GCGAAGGCTT CATCGAAGTC CTGACCAAGA<br>AGCAGCGCCG CCTGCTGGAG GAAGAGAGAA GAAAGAAGGA<br>GCAGGCCGTG CAGGTGCCTG TCAAAGGTCG AGGCCTTTCC<br>TCCCGTATTC CTCCTCGATT TGCAAAAAAG CAGAACAACT<br>TATGTCTGGA GCAAGGTGAC GTGACCGTGC CTGGCAGCAG<br>CCTGGGCACT GAGATCTGGG AGAGCAGCAG CCAGGCTCTC<br>CCTGTGCAGG CCCCAGCCAA CGACTCCTGG AGGAAAGCTG<br>TCACTGCCTT CAGCAGCACC GAGACTGGCT CTGCGGAGCA<br>GGGTTTTAAG AGCAGCCAGG GAGATAGTGG CGTTGACTTG<br>AGTGCCGAGT CTCGGGAGTC GTCTGCGACC TCCTCGCAGC<br>GCAGCTCCCC ATATGGGACT CTGAAGCCAG AGGAGATGAG<br>CGGGCCCGGC CTGGCGGAAC CCAAGGCCGA CAGCCACAAG<br>GAGCAGGCTC CAAAGCCATC TGAGCAGAAG GATTCAGAAC<br>AAGGCTCTGG ACAGAGCAAG GAGCACAGAC CAGGACCCAT<br>CGGCAACGAG CGTTCTCTGA AAAACAGAAA GGGCTCGGAG<br>GGGGCCGAGC GGCTGCAAGG GGCTGTCGTC CCGCCTGTTA<br>ACGGGGTGGA GATTCACGTG GACTCCGTGC TGCCTGTGCC<br>ACCCATTGAA TTTGGAGTCA GTCCAAAAGA CTCCGATTTC<br>AGCTTGCCAC CTGGTTCTGC CTCTGGTCCT ACTGGGAGTC<br>CAGTTGTTAA ACTTCAGGAT GCCTTGGCCA GTAATGCAGG<br>GTTAACACAG AGTATCCCCA TCCTGCGGCG GGACCATCAC<br>ATCCAGAGGG CCATCGGTCT CTCCCCAATG TCCTTCCCCA<br>CCGCCGACCT TACTCTGAAG ATGGAGTCTG CGCGCAAGGC<br>TTGGGAAAAC TCCCCCAGTT TGCCGGAGCA GAGCTCTCCA<br>GGCGGCGCTG GCTCAGGCAT CCAGCCTCCA TCCTCTGTGG<br>GTGCCTCCAG CGGGGTCAAC TACAGCTCCT TCGGTGGAGT<br>GTCCATGCCA CCCATGCCTG TGGCCTCTGT AGCACCTTCT<br>GCTTCTATGC CAGGCAGCCA CCTCCCGCCC CTGTACCTGG<br>ATGGCCATGT GTTTGCAAGT CAGCCCCGGC TGGTTCCTCA<br>AACGATACCT CAGCAGCAGA GTTACCAACA GGCCGCCGCT<br>GCCCAGCAGA TCCCGATCTC CCTTCACACA TCTCTGCAGG<br>CACAAGCTCA GCTTGGACTG AGGGGTGGGC TTCCTGTGTC<br>CCAGTCCCAG GAGATCTTCA GCTCCTTGCA GCCCTTCAGA<br>TCTCAGGTGT ACATGCACCC CAGCCTGTCA CCGCCCAGCA<br>CCATGATCCT CTCTGGGGGC ACAGCCTTGA AGCCTCCATA<br>CTCGGCGTTC CCAGGCATGC AGCCCTTGGA GATGGTGAAG<br>CCGCAGTCTG GCTCACCCTA CCAGCCCATG AGCGGGAACC<br>AAGCCCTGGT CTACGAGGGC CAGCTCAGCC AGGCTGCTGG<br>CCTGGGTGCC TCCCAGATGT TGGACTCCCA GCTCCCACAG<br>CTGACCATGC CACTGCCTCG GTACGGCTCC GGGCAGCAGC<br>CACTGATCCT GCCCCAGTCT ATTCAGCTGC CACCTGGGCA<br>GAGCCTCTCC GTTGGGGCCC CCCGAAGGAT TCCTCCGCCC<br>GGGTCCCAGC CGCCAGTCCT GAACACCAGC AGAGAGCCCT<br>CTCAGATGGA GATGAAGGC TTCCACTTTG CCGACAGTAA<br>ACAGAATGTC CCTTCAGGAG GCCCCGTGCC ATCGCCACAG<br>ACCTACAGGC CTAGCTCTGC TAGCCCCAGT GGGAAGCCCT<br>CTGGATCAGC AGTTAACATG GGCTCTGTGC AGGGACACTA | |

TABLE 1-continued

Melanoma Biomarker/Housekeeper Sequence Information

| Gene Name | RefSeq Accession | Sequence | SEQ ID NO: |
|---|---|---|---|
| | | CGTGCAACAG GCAAAACAAC GAGTGGATGA GAAACCCAGC | |
| | | CTGGGAGCCG TGAAGCTGCA GGAGGCCCCC TCGGCTGCCT | |
| | | CCCAGATGAA GCGAACCGGA GCGATCAAGC CTCGGGCTGT | |
| | | CAAAGTGGAG GAGAGTAAGG CCTGACAGTG CCTGGCTGCC | |
| | | ACCTCGCCTC TCCCTACTGA GGACGGTGCC GCCATGCGGC | |
| | | CTCGACACAG CCGACACTCG GGAGCCTCAC CAGATCCACC | |
| | | GTCCAAATGC GTGGCCCAGA CTGAGAGACC TCCCTCCTCT | |
| | | CCACTCCCGA AAGCTCCGTT GTCAACCAGC TTGCACCCGT | |
| | | GGATATATGG CATTGACCCG CTTGCTTTGA TACGAAACAA | |
| | | AAAAGCAGAC GACTCCTTCA TCCCATCTGC TCCTACCGTG | |
| | | ACTGTGGAGT GACGCCTCCT GTGCAGTGCA GATTTGCCCT | |
| | | CCCTGCCTCC TCCCTGTCCT GCCGCGCAGC CAGGGCGCCT | |
| | | TCTCAGCAGT GCTTCCGGCC CAGCCGCCCA TCCCTAGGCA | |
| | | CAGTGATTTG GCAGCAGGGT CATTTTACTT TGAGGCTTTT | |
| | | TGTTTTAAAA TGTAGCCAAG GTTTTTACAA AGGGGAAAGG | |
| | | AAAAGAAAAC AAAAACGCAA GCTCCATGTG TATAGCTGAA | |
| | | CTTTTATATG TTTCTTGCCA GCCCCTCCGC TCCCTTCCAT | |
| | | CTCTAGCCTC TGTCCTGTTT AGTTTGATAC GTCACTGCAG | |
| | | TACCTTAAGA GGTGACTCTT AAGAATGCAT CCCCTCCTGA | |
| | | TTCCTCAGCT GGTTCACCCT TGAGGTTATT TGCAAAAAGA | |
| | | AAAGGAGGTT CTTGAGGGCA CCGATTGCGA GCATTCTGGT | |
| | | GCCTGGCTCC CCGCCTGGGA AGCGATGGGG TGCTCAGAGC | |
| | | AGCAGGCAGG TTGGGGGAGG GGGGGGGTCA TAGTTGGGTT | |
| | | CCAGCTCCTG GCTTGATGAG CCCAGGGCGC TTACAGGCAG | |
| | | CCCATGAAGT TGATGACAGT TTTAGCATGA GAATCACACA | |
| | | GGGTCCCTGT CCTGGGCTCC TCTAAAGCCA GTGGATGTGC | |
| | | TGGGCACCAG AGACAAATCA TGGAGATGGC TGCTGGTGGC | |
| | | TCCCAGGTTG GCCCAGATGG GGTGAGCTGA CATACCACAG | |
| | | GCCCATCCCA GGCCCCGTGG GCTCTGCTTC TGGGGCTCCA | |
| | | TACCCTGCCC TGCAGGGGTG CTGTGTTTTT CACACATTTC | |
| | | TTTCCCTGAA GCCTTCTGTA ACCTGTCATT TTCCTTCCTT | |
| | | CCTCTTCCGG AGCCTGCTGC TTTCTCTGGA CCTGTCTCCA | |
| | | CCTCCCACAC AGCTCATCGT GAACACCACT TGGTGATGGA | |
| | | GGGAGTGGAC CCGTGTGTGG TCCCCAAGTG AGGCCACTGG | |
| | | GAGTTTGTCC TTTTCCTCCT TTGCTTCACT CCCAGCAGCA | |
| | | GACCCAGGTT GTCAGGACAG GAGGGCCTGA GCTAAGCAGT | |
| | | AGGCATCAGT CTCGTTTGTC TTCAGACGGC GGGGGCAGGT | |
| | | CCAGGGTGAG GCTGGGTGGA GGGCTGACCA AGGTCCAAAG | |
| | | GGCCTGCGCA GCCTCCGGGA GGGCAGCTTC TCCAGCCAGA | |
| | | GGCTTGTGTG AGCCATCGTG TGCTGGGCTT GTTTTTAAGT | |
| | | AAGAAACAAG GAAATCACTC CAGATTCTGT CATTCCAAGG | |
| | | AAAGGGAAGG GGACAGTTCA GGTTTCTCAG CTGTTCTTAG | |
| | | GGGTCACTGA GCGTCTACCT CCTCCTCCAG AGGAGGCTGG | |
| | | CTCAGAACAC CTAGAGGAGG GGGCCGGGGA TGCACCCCCC | |
| | | ACCAGAGGCT GCCTTCAGCG TCTCACGGGT GCAGGACAGC | |
| | | GCTCAGGCTT GGGCTCTAAG CTCTGTGTCT AGTGTAGAAC | |
| | | ATGGGGAAGG AGCATCTTAG GAACTGCTGA AGTAACTTCT | |
| | | TACTGCTCTC ACAATTCTAA GGAAGCGGGA GAACGGCCTC | |
| | | CTACCAACAG CGCCCACCCC AGAGCTGCCT GGGAAAGGGC | |
| | | AGTTTTACTG AAAGGTGCTT TACTGTTCAC CTGCATCTTT | |
| | | CAGCAGCTCC CCTCCTGCCC TCACCTGGTC TTTTCCCTCT | |
| | | TTATCCCAAG CCTTTATGCT TGAGTCCCTT CCCCAGGGGC | |
| | | TGCCCACCCG ACAGTTCCAG GCATTCCCTA CCTGAGCTTC | |
| | | TTGTCTGCTT TTCCTTCTCC CACTGCAAGC GGCTGCTTGT | |
| | | GGGGCCTGGG ATGAGCCCTC TCTGTCCCCA CCGGCCCTCC | |
| | | TTGCCAAGCC ATTCCTGGGT GAGTTCAGGC CTGCGGGAGC | |
| | | CACACATTCA TCTCCACCTG GACACTTGAG CCGCATGGCC | |
| | | AGACCCCTCC CACCTGATGC GGTGGTGCGT GTGATTTGTC | |
| | | AAAAGAAAGC CTTCTGGATG CTGTTAAGAT GTACCCTTCA | |
| | | GGTGAACCTG GTATCAGACC CACAGTACTT GCTGTTTGAG | |
| | | AAAAAATAAA AACAAAAAGG TCACCTGTTC TCCAGCCCTT | |
| | | TTCTCTTACC TGGTATTTCC TTCCTTTCTC CTCCCCCACC | |
| | | CCAAATAAAA AAACAAAAAA CACTAGAATT TATTTATATG | |
| | | TATTGATGTT GTAGGTCTAG GTGAAAAAAA AAGAAGTAAA | |
| | | TGTTTCACTG CTCTATTTAT ATATAATGTC TGAATTAATT | |
| | | CTGTGCAGGA AAGGCCAGGA AATTGCATGT GAAGTTCGGT | |
| | | GCAGTCACCA CCTGTGTGTG ACCTGAGCTG CAGTCTCTTC | |
| | | GCTGAGATGC AGGTTTTAAA TGAGACTTGG GGGGCTGAGG | |
| | | GCAGGCCTCA GGCCTCCCAG CGCCCCAACC CCTCCTTGGT | |
| | | CTAATGAAAT GCAGTTCTTA GTGCAGAGAT GTTTTAAGGT | |
| | | GCAATATATC TCTTCCTTTC CCGTGGTTTT AGAGCCAAGC | |
| | | TCAAGGTAGT AGGACGTAGG GTCTTATTTT GTTTTCAAAC | |
| | | CCCCATCCTC AGAGCGCAGA TACATGCAGA GGCTTCTGCC | |
| | | AGGATACCAC GGGGCCTTAG TGGGAACAGG TGGAGACCAG | |

TABLE 1-continued

Melanoma Biomarker/Housekeeper Sequence Information

| Gene Name | RefSeq Accession | Sequence | SEQ ID NO: |
|---|---|---|---|
| | | CACTTCCCTT TCCTGCTGCT GAGGTAGGGA TTGGGGGGTC<br>AGAACCCACT CACTTTTGCC TGTTAAAGTT GCCCTCCTGA<br>CGCTGGCAGC TCTGCCTTGG TCACTGGGGA TGCGGCTCGT<br>TGCTCAGCCA CCAGTGGCCT TGCGGTATTG TCCACCATCC<br>ACTAGAGTGG GATGAAGTCC AGAGTGTGGG TATACATCTC<br>AGATGCCCAT CTACCCACTG GGGACTTCAA TGCCAGCTGC<br>ATTTGGTTTG GTTTTCTTAA CTGTTGGCTT CTCCCCACAG<br>CGTTTTTTGT TTTTTTTTAA ACATTCATAT TGTTTTCAAA<br>CTTGGAATTC ATAGACACTC TGGCTCTAGG TTCCTTAAGG<br>GGGAAAACAA AAGATGACTT TATTTCACAT TCAAGAAAAT<br>CAGTTCAGTT CCAAAGCTGT GGTCCTTCCA GCCACTTCTA<br>GGGACACTGG GGAACCTTGT TAAACGTTGA CATCAGTGCT<br>CTCCAGCCGT GCTGTCACCC TCCTATCTTC TGGATCTGCC<br>TTCGCGATGG TCAGTGACAG CTTCTGGAAG CTGAGCACAC<br>ACAGGTGCAC AGCCATGCTG TGGTCTGGCC TGCTACGGCA<br>GCATGGCAGC TCTGGTGGAG CCTTCTCCCT TGCCATTTGG<br>TTCCCCTGTG CCAAGTAGCT GCAGGCTGCC CCTCAAATCT<br>TCATTTGTCC CTTTTCACTT CCTGCAGAAC AAGCCTGGGT<br>TAGAGGGTCT GCTGGAAATG GCCTTTGAAG ACCAAGGATA<br>CCAGGATGTG TGCACTCTGT CGTGTTCTGT GATGAATGGG<br>AAACGTAGGC TTCCAGAAAG CCAGCTCTCT TCTGAAATGT<br>GACGGACCTA AGCAGGAAGT CATCCAGGAC AGGAGTGGCT<br>CAGTGTTGGG GATGGACGCT GTCGCCCAGC CATGCTCCAC<br>CAGGGCCACC AATGTGTAGT TGGCTGGTGG TCTTCGGGCA<br>TGTGAGACCT GCTCTTCACT GTTTCCACCC CACTTGGTGG<br>CCTCCAGGAT GGTAGTGGCA CCCTCAGAGC CCCATCTTCA<br>GCATGTTCTG AAGCCTCAGA GTGGAAATTC CTGCTAAGGC<br>TCTGTGTGGA CGCCTTTCTC CCGTGATCTA AAGGGGACAC<br>TGTACTCAAG CTTTTGACCT CATGCCTTGT GTAGTAAAAA<br>AGGATTTGGG GGTTTTGTTT GGTTCCTGAG AGGGTTGTGT<br>TTTGTTTTTG TTTCCTTTTG TTTATGTTTT GGCCTTTCCT<br>CTTTGTCTTT CCATGTAGAC CAGATATTTG AAAGGGCAGA<br>CGATGGCTAG AGGTGTAATG TGCAGCTTGT TTATACGGTA<br>TTTTGGGAAA CTTACCTTGG ATGGGAAATC GAATCGTGGA<br>TTCACCAGGC CGGTGCTGGC ACACTCACCC TCGCCCTTTC<br>CCTCCGGTTC AGTACCTATT GTTTCTCCTT TCAAATATGT<br>GATTGTACTA GCTCTTTCCA TATGAAAGAA TTCTCCTTAT<br>TTAAATAAAA AAAGTTTAAA AA | |
| DOPEY2 | NM_005128.3 | TCCCACAGTG CCTGGCCCAG AAGCCTTGCT AAATATTTGA<br>ACAGGATTGC CCAATACTTT TCTGCTGTGA GAATGTAAGA<br>TGGATCCAGA AGAGCAGGAG CTCTTAAATG ATTACAGATA<br>CAGAAGCTAC TCTTCAGTGA TTGAAAAGGC TTTGAGAAAT<br>TTTGAGTCCT CGAGTGAATG GGCGGATCTC ATATCTTCAC<br>TTGGCAAACT CAACAAGGCT CTTCAGAGTA ACCTGAGGTA<br>CTCCTTGTTG CCAAGACGGC TCCTCATCAG CAAAAGATTA<br>GCTCAGTGTT TGCACCCTGC CCTGCCCAGT GGTGTCCACT<br>TAAAAGCTCT GGAAACCTAC GAGATTATCT TTAAAATCGT<br>GGGGACCAAA TGGCTGGCCA AGGACTTGTT TCTGTACAGC<br>TGCGGGTTAT TTCCTCTCCT GGCACACGCG GCGGTGTCGG<br>TGAGGCCGGT GCTGCTCACC CTGTACGAGA AGTACTTCCT<br>CCCACTGCAG AAGCTGCTCC TGCCCAGTCT GCAGGCCTTC<br>ATCGTGGGCC TGCTGCCCGG CCTTGAAGAG GGCTCCGAGA<br>TCTCCGACAG AACGGATGCT CTGCTCCTGA GACTGTCGCT<br>GGTGGTTGGC AAAGAGGTGT TTTACACCGC CCTCTGGGGG<br>AGCGTCCTGG CCAGCCCGTC CATCCGCCTC CCTGCCTCAG<br>TCTTCGTGGT GGGCCACATC AACAGGGATG CCCCCGGCCG<br>GGAGCAGAAG TACATGCTGG GGACCAATCA CCAACTCACG<br>GTGAAGTCTT TGCGTGCCTC CCTGTTGGAC TCAAATGTTC<br>TTGTGCAAAG AAATAATCTG GAAATCGTTC TGTTTTTCTT<br>CCCATTTTAT ACCTGTCTGG ATTCCAATGA GAGAGCCATC<br>CCCCTCCTCA GATCTGACAT CGTGCGCATT CTCTCAGCCG<br>CCACCCAGAC CCTACTGAGA AGGGACATGT CCCTGAACAG<br>AAGACTGTAT GCATGGTTAC TAGGCTCAGA CATAAAAGGA<br>AATACCGTTG TGCCAGAATC TGAAATCTCA AATTCTTATG<br>AAGACCAGTC GTCTTATTTT TTTGAAAAAT ACTCCAAGGA<br>TCTTTTAGTT GAGGGTTTGG CTGAGATATT GCATCAGAAG<br>TTCATAGATG CTGACGTGGA GGAACGCCAT CATGCATACC<br>TGAAGCCTTT TCGCGTCCTC ATCAGTCTGC TTGACAAGCC<br>AGAAATAGGG CCTCAAGTGG TTGGGAATTT GTTTCTCGAA<br>GTCATCAGGG CCTTTTATTC TTACTGCAGA GATGCCCTTG<br>GCTCTGATCT TAAACTTAGC TACACCCAGA GTGGAAATTC<br>GCTGATAAGT GCAATCAAGG AAAACAGAAA TGCCTCTGAG<br>ATTGTCAAAA CGGTAAATTT GCTGATAACT TCTCTAAGCA | 36 |

TABLE 1-continued

Melanoma Biomarker/Housekeeper Sequence Information

| Gene Name | RefSeq Accession | Sequence | SEQ ID NO: |
|---|---|---|---|
| | | CAGACTTTCT CTGGGATTAT ATGACAAGGT GTTTTGAGGA ATGCTTTAGA CCAGTGAAGC AGCGTTACAG CGTGAGGAAC AGCGTCAGCC CTCCCCCCAC GGTCTCGGAG CTCTGCGCCC TCCTGGTCTT CCTGCTGGAT GTCATTCCTT TGGAACTTTA CTCTGAGGTG CAAACCCAGT ATCTCCCTCA GGTGCTCGGC TGCCTGGTGC AGCCTCTTGC TGAGGACATG GAGGCCTTAA GTTTACCTGA ACTCACGCAT GCCTTGAAGA CGTGTTTCAA GGTGCTCAGC AAAGTCCAGA TGCCTCCTTC CTACCTCGAC ACGGAGTCCA CCAGCGGAAC CTCGAGTCCA GTAAAAGGTG AAAACGGCAA AATAATTTTG GAAACAAAGG CAGTGATTCC CGGTGACGAA GATGCTTCGT TTCCCCCTCT GAAGTCTGAG GACAGTGGGA TCGGGCTCAG TGCCTCGTCA CCGGAGCTCT CTGAGCACTT GAGGGTTCCT CGAGTTTCTC TGGAAAGGGA CGACGTTTGG AAGAAGGGCG GGAGCATGCA GAGGACGTTT CTTTGCATCC AAGAGCTAAT CGCCAACTTT GCCAGCAAGA ACATTTTTGG AGTACAGCTG ACAGCGTCAG GAGAAGAAAG CAAGTCCGAG GAGCCTGCAG GGAAGAGGGA CAGGGATGGG ACGCAGAGCC TGGCAGCCAA TGATTCCAGC AGGAAGAACT CTTGGGAGCC CAAGCCCATC ACTGTGCCTC AGTTCAAGCA GATGCTGTCA GACTTGTTCA CAGCACGAGG GTCTCCATTC AAGACAAAAA GTTCAGAGTC ACCATCGTCT TCGCCCAGCA GCCCTGCCAG GAAAAACGGG GGAGAATGGG ATGTTGAGAA GGTGGTCATT GACCTGGGGG GTTCCAGGGA GGAACGCAGG GAGGCCTTTG CCGCCGCCTG CCACCTGCTG CTGGATTGTG CCACTTTCCC TGTCTACCTG TCCGAGGAAG AGACCGAGCA GCTCTGTGCA ACGCTCTTCC AGCTGCCAGG AGCCGGTGAT TCCAGTTTTC CATCTTGGCT GAAGTCCCTC ATGACTATTT GCTGCTGTGT GACTGACTGC TACCTCCAGA ACGTGGCCAT TTCCACTCTG CTGGAAGTGA TAAACCATTC CCAGTCCCTG GCGCTTGTCA TTGAAGACAA GATGAAACGC TATAAGAGCT CTGGACACAA CCCTTTTTTT GGCAAGCTGC AGATGGTGAC GGTTCCTCCC ATTGCTCCAG GGATATTGAA AGTCATTGCA GAGAAAACAG ATTTCTATCA GAGGGTGGCT CGTGTGCTTT GGAATCAGCT GAACAAAGAG ACCCGGGAGC ATCACGTCAC CTGCGTAGAA TTGTTCTACC GGCTGCACTG CCTGGCCCCT ACGGCCAACA TCTGCGAGGA CATCATCTGC CATGCCCTCC TGGACCCTGA CAAGGGAACA AGGCTGGAAG CTCTGTTTAG ATTTTCCGTG ATCTGGCATC TGACAAGAGA GATCCAAGGC AGTCGAGTAA CATCTCACAA TCGCTCCTTT GATAGGTCCT TGTTTGTCGT GCTGGACAGC CTGGCCTGCA CGGATGGTGC CATCGGTGCG GCAGCCCAGG GCTGGCTGGT GCGTGCGCTC TCCCTCGGGG ACGTGGCTCG CATCCTCGAA CCCGTGCTCC TGCTGCTGCT GCAGCCAAAA ACCCAGAGAA CCTCCATCCA CTGCCTCAAG CAGGAGAACT CGGCCGATGA CTTGCACCGT TGGTTTAACA GGAAGAAAAC CTCTTTCAGA GAGGCATGCG CAGTGCCCGA GCCTCAGGAG AGCGGCTCTG AAGAGCACCT GCCTCTGAGC CAGTTCACCA CAGTGGACCG TGAAGCCATT TGGGCCGAAG TGGAGAAGGA GCCCGAGAAG TACCCGCTGC GAGGCGAGCT GAGCGAGGAA GAGCTGCCCT ACTACGTGGA GCTTCCAGAC AGGACGGCCC ACGGCGCCCC GGACAGCAGC GAGCACACCG AGTCTGCAGA TACAAGCTCC TGCCACACGG ACAGCGAGAA CACGTCCTCC TTCTCCTCCC CTTCCCACGA CCTGCAGGAG CTGAGCAACG AAGAGAACTG CTGTGCACCC ATCCCCATGG GGGGCAGGGC GTACCCCAAG CGCTCGGCCC TGCTGGCGGC CTTCCAGTCA GAAAGCTTCA AGGCTGGGGC CAAGTTAAGC CTGGTGCGGG TGGACTCGGA CAAGACGCAG GCTTCTGAGT CGTTCTCCAG CGACGAGGAG GCGGACTTGG AGCTCCAGGC CCTCACCACA TCCAGGCTGC TAAAGCAGCA GCGGGAAAGG CAGGAGGCCG TCGAGGCCTT GTTCAAGCAC ATCCTGCTCT ACCTGCAGCC CTACGACTCT CGGCGGGTCC TCTATGCCTT CTCGGTGCTG GAGGCTGTGC TCAAAACCAA CCCTAAGGAA TTCATCGAGG CTGTGTCCAG GACTAGCATG GATACCAGCT CCACCGCGCA CCTCAACCTC ATCTCCAACC TCCTCGCTCG CCACCAGGAG GCCCTCATTG GCCAGAGTTT CTACGGAAAG CTCCAGACCC AGGTCCCCAA CGTGTGCCCC CACTCTCTGC TCCTGGAGCT GCTCACCTAC CTCTGCCTGA GCTTCCTGCG CTCCTACTAC CCTTGCTATT TGAAGGTCTC GCACCGAGAC ATTCTCGGCA ACCGGGACGT GCAGGTCAAA AGTGTCGAGG TTTTGATCAG GATAATGATG CAGCTGGTCT CAGTGGCCAA GTCTTCGGAA GGGAAGAACG TGGAGTTCAT CCACAGCTTG CTGCAGAGGT GCAAAGTTCA GGAGTTTGTC CTGCTCTCCC TGTCGGCGTC CATGTACACG AGCCAGAAGC GCTACGGGCT GGCCACCGCC CACCACGGCA GGGCCCTGCC AGAGGACAGC CTCTTTGAGG AGAGTCTCAT TAACTTGGGT | |

TABLE 1-continued

Melanoma Biomarker/Housekeeper Sequence Information

| Gene Name | RefSeq Accession | Sequence | SEQ ID NO: |
|---|---|---|---|
| | | CAGGACCAGA TCTGGAGTGA GCACCCGCTG CAGATTGAGC TGCTGAAGCT GCTGCAGGTG CTGATTGTCT TGGAACACCA CCTGGGTCGG GCCCATGAGG AGGCGGAAAA CCAGCCCGAC CTGTCCCGGG AGTGGCAGAG AGCCCTGAAC TTCCAGCAGG CCATCAGCGC CCTGCAGTAC GTGCAGCCCC ACCCCCTCAC CTCCCAGGGT CTTCTGGTCT CTGCGGTGGT GAGGGGTCTG CAGCCCGCCT ACGGTTACGG CATGCATCCG GCCTGGGTGA GCTTGGTCAC GCATTCCTTG CCCTACTTCG GAAAGTCCCT GGGCTGGACG GTGACACCCT TTGTTGTCCA GATTTGCAAA AACTTGGATG ACTTGGTCAA GCAGTATGAA AGCGAATCTG TGAAGCTCTC TGTCAGCACA ACCTCCAAGA GGGAAAACAT TTCTCCAGAT TATCCACTCA CCCTTCTAGA AGGTCTAACG ACCATTAGTC ATTTTTGTCT TTTGGAACAA GCCAACCAAA ACAAAAAGAC CATGGCTGCA GGTGATCCTG CCAACTTGAG GAATGCCAGA AATGCCATTT TGGAAGAGCT GCCTCGAACT GTTAACACCA TGGCCCTTCT CTGGAATGTT CTCAGAAAGG AGGAGACTCA AAAGAGACCT GTCGATCTCC TAGGGGCCAC GAAGGGATCC TCTTCCGTTT ACTTTAAAAC CACCAAAACC ATAAGACAAA AAATTTTAGA CTTCTTAAAC CCCTTGACGG CCCATCTTGG GGTTCAGTTG ACAGCGGCTG TTGCGGCAGT GTGGAGCAGA AAGAAAGCCC AGCGTCACAG TAAGATGAAG ATTATCCCAA CGGCAAGTGC ATCCCAGCTA ACCCTTGTCG ACTTGGTGTG TGCACTCAGC ACCCTGCAGA CTGACACGCT GCTGCACCTG GTGAAGGAGG TGGTGAAGAG GCCACCCCAA GTCAAAGGGG GTGATGAGAA ATCGCCCCTA GTGGACATTC CTGTGTTGCA GTTTTGCTAT GCTTTTCTCC AAAGGCTCCC AGTACCAGCC TTGCAAGAGA ACTTTTCTTC ACTGTTGGGA GTATTGAAAG AGTCTGTACA GTTGAATCTA GCCCCACCTG GGTATTTTCT GCTTCTCAGC ATGCTGAATG ACTTTGTAAC AAGAACTCCC AACCTGGAAA ACAAGAAGGA CCAAAAAGAC CTGCAGGAAA TCACTCAGAA AATCCTAGAA GCTGTGGGGA ACATTGCCGG CTCTTCCTTG GAGCAAACCA GCTGGCTAAG CAGAAACCTG GAAGTGAAGG CCCAACCTCA GGCCTCTCTA GAAGAATCTG ATGCTGAGGA GGACCTGTAT GATGCTGCTG CAGCTTCAGC AATGGTGTCT TCATCCGCCC CGTCGGTGTA CAGCGTGCAA GCCCTCTCTC TCCTGGCAGA GGTACTGGCT TCCCTCCTGG ACATGGTTTA TCGAAGTGAT GAGAAGGAGA AAGCTGTGCC GTTAATCTCC CGTCTGCTTT ACTATGTTTT TCCATACTTA CGCAACCACA GTGCCTACAA TGCTCCCAGC TTCCGGGCTG GCGCTCAGCT GCTGAGCTCC CTGAGTGGCT ATGCCTACAC AAAGCGAGCC TGGAGGAAGG AGGTCCTGGA GCTGTTTCTC GACCCCGCTT TCTTTCAGAT GGATACTTCC TGTGTTCATT GGAAGTCCAT TATTGACCAT CTTTTGACTC ATGAGAAAAC AATGTTTAAG GATTTAATGA ACATGCAGAG CAGTTCTTTG AAACTATTCT CAAGTTTTGA ACAGAAAGCC ATGCTGTTAA AGCGCCAGGC TTTTGCTGTC TTCAGTGGAG AACTTGATCA ATACCACCTT TACCTTCCAC TGATACAAGA ACGCCTGACA GACAATCTCA GAGTTGGACA GACATCCATA GTTGCTGCTC AGATGTTTCT TTTTTTCAGA GTTTTGCTGC TAAGAATATC TCCTCAACAT TTGACTTCAT TGTGGCCAAT AATGGTCTCT GAATTGATTC AGACATTCAC ACAGCTTGAA GAAGATCTAA AAGATGAAGA TGAGTCATTG AGAAGCACCA ACAAAGTAAA CAGAACGAAA GTTTCAGTCC CGGATGCAAA TGGACCCTCA GTGGGGGAGA TACCCCAGAG TGAACTCATC TTGTATTTAT CAGCTTGCAA ATTCTTGGAC ACAGCGCTTT CTTTTCCACC TGACAAGATG CCATTATTTC AAATTTATAG GTGGGCATTT ATTCCAGAAG TGGACACAGA GGGCCCTGCC TTCCTGTCGG ATGTAGAGGA GAATCACCAA GAATGCAAAC CCCACACTGT CAGGATTCTA GAACTTCTAA AATTAAAGTT TGGGGAAATC AGTAGCTCTG ATGAGATCAC CATGAAGAGT GAATTCCCGC TTCTGCGCCA ACATTCTGTT TCCAGCATCA GGCAGTTGAT GCCATTCTTC ATGACTCTAA ATGGTGCATT TAAGACCCAG AGACAGCTGC CTGCTGATAG CCCAGGAACT CCATTCTTGG ACTTTCCTGT CACAGATAGC CAAGGATCT TAAAACAACT GGAAGAATGC ATCGAATATG ATTTTCTGGA ACATCCAGAA TGTTAACCAT GTGAGAGAGA ATATGTTTAA TCCATGTATT GGTACTTTAC TGAAAACCAG GTTATATTCT AAAGAAGAAA GAAGGCAGGA TAGTGCTTTT GAACAAGCCT ATTTCCATTT TGAAAGTAGA TTTCAGGCTA GGTGCGGTGG CTCACACCTG TAATCTCAGC ACTTTGGGAG GCCAAGGCAG GCAGATCACT TGAGGTCAGG AGTTCGAGAC CAGCCTGACC AACATGGTGA GACCCTGTCT CTACTAAAAA TACAAAAATT AGCTGGGTGT GGTGGCGGCG CCTGTAATCC CAGCTACTTG GGAGGCTAAG GCATAGGAAT TGCTTGAACC CAGGAGGTGG | |

TABLE 1-continued

Melanoma Biomarker/Housekeeper Sequence Information

| Gene Name | RefSeq Accession | Sequence | SEQ ID NO: |
|---|---|---|---|
| | | AGGCTGCAGT GAGCCGAGAT CACGACACTG CACTCCAGCT GTGTGACAGA ATGAGACCAT CTCCAAAAAA AAAAAAAAGT AGATTTCAGA TAATTTACTG TTCAGCAACA GGACACACCT CCCTAAATGC CTTGTAATAT ATTTGAATCT GATTCTGCAT TTCTTCCTCA ATTTATGTAA TGAAAATAAA ATTAATATAT CATCTAACAG TAGCACAAAA TTTGTAATAT GAAGTAAAGT ATGAAGATAA TGAAGAAGTT GTTTTCTTTG TTGAAGCAGT TATATGGGTC TTTCTCAGTA TATTTCTCTT TTCTCTAAAA GTTTAAACTT ATTAAAGAA TGTTATTTTT AACCTTTCAA AAAAAAAA | |
| NDUFB11 | NM_019056.6 | GCTCTGGCCG GCCCCGGCGA TTGGTCACCG CCCGCTAGGG GACAGCCCTG GCCTCCTCTG ATTGGCAAGC GCTGGCCACC TCCCCACACC CCTTGCGAAC GCTCCCCTAG TGGAGAAAAG GAGTAGCTAT TAGCCAATTC GGCAGGGCCC GCTTTTTAGA AGCTTGATTT CCTTTGAAGA TGAAAGACTA GCGGAAGCTC TGCCTCTTTC CCCAGTGGGC GAGGGAACTC GGGGCGATTG GCTGGGAACT GTATCCACCC AAATGTCACC GATTTCTTCC TATGCAGGAA ATGAGCAGAC CCATCAATAA GAAATTTCTC AGCCTGGCCG AAAATGGTTG GCCCCACGAA GCCACGACAA CTGGAGGCAA AGAGGGTTGC TCAACGCCCC GCCTCATTGG AAAACCAAAT CAGATCTGGG ACCTATATAG CGTGGCGGAG GCGGGGCGAT GATTGTCGCG CTCGCACCCA CTGCAGCTGC GCACAGTCGC ATTTCTTTCC CCGCCCCTGA GACCCTGCAG CACCATCTGT CATGGCGGCT GGGCTGTTTG GTTTGAGCGC TCGCCGTCTT TTGGCGGCAG CGGCGACGCG AGGGCTCCCG GCCGCCCGCG TCCGCTGGGA ATCTAGCTTC TCCAGGACTG TGGTCGCCCC GTCCGCTGTG GCGGGAAAGC GGCCCCCAGA ACCGACCACA CCGTGGCAAG AGGACCCAGA ACCCGAGGAC GAAAACTTGT ATGAGAAGAA CCCAGACTCC CATGGTTATG ACAAGGACCC CGTTTTGGAC GTCTGGAACA TGCGACTTGT CTTCTTCTTT GGCGTCTCCA TCATCCTGGT CCTTGGCAGC ACCTTTGTGG CCTATCTGCC TGACTACAGG TGCACAGGGT GTCCAAGAGC GTGGGATGGG ATGAAAGAGT GGTCCCGCCG CGAAGCTGAG AGGCTTGTGA ATACCGAGA GGCCAATGGC CTTCCCATCA TGGAATCCAA CTGCTTCGAC CCCAGCAAGA TCCAGCTGCC AGAGGATGAG TGACCAGTTG CTAAGTGGGG CTCAAGAAGC ACCGCCTTCC CCACCCCCTG CCTGCCATTC TGACCTCTTC TCAGAGCACC TAATTAAAGG GGCTGAAAGT CTGAAAAAAA AAAAAAAA | 37 |
| ND4 | NC_012920.1 | ATGCTAAAACTAATCGTCCCAACAATTATATTACTACCACTGAC ATGACTTTCCAAAAAACACATAATTTGAATCAACACAACCACCC ACAGCCTAATTATTAGCATCATCCCTCTACTATTTTTTAACCAAA TCAACAACAACCTATTTAGCTGTTCCCCAACCTTTTCCTCCGACC CCCTAACAACCCCCCTCCTAATACTAACTACCTGACTCCTACCC CTCACAATCATGGCAAGCCAACGCCACTTATCCAGTGAACCACT ATCACGAAAAAAACTCTACCTCTCTATACTAATCTCCCTACAAA TCTCCTTAATTATAACATTCACAGCCACAGAACTAATCATATTT TATATCTTCTTCGAAACCACACTTATCCCCACCTTGGCTATCATC ACCCGATGAGGCAACCAGCCAGAACGCCTGAACGCAGGCACAT ACTTCCTATTCTACACCCTAGTAGGCTCCCTTCCCCTACTCATCG CACTAATTTACACTCACAACACCCTAGGCTCACTAAACATTCTA CTACTCACTCTCACTGCCCAAGAACTATCAAACTCCTGAGCCAA CAACTTAATATGACTAGCTTACACAATAGCTTTTATAGTAAAGA TACCTCTTTACGGACTCCACTTATGACTCCCTAAAGCCCATGTC GAAGCCCCCATCGCTGGGTCAATAGTACTTGCCGCAGTACTCTT AAAACTAGGCGGCTATGGTATAATACGCCTCACACTCATTCTCA ACCCCCTGACAAAACACATAGCCTACCCCTTCCTTGTACTATCC CTATGAGGCATAATTATAACAAGCTCCATCTGCCTACGACAAAC AGACCTAAAATCGCTCATTGCATACTCTTCAATCAGCCACATAG CCCTCGTAGTAACAGCCATTCTCATCCAAACCCCCTGAAGCTTC ACCGGCGCAGTCATTCTCATAATCGCCCACGGGCTTACATCCTC ATTACTATTCTGCCTAGCAAACTCAAACTACGAACGCACTCACA GTCGCATCATAATCCTCTCTCAAGGACTTCAAACTTACTCCCAC TAATAGCTTTTGATGACTTCTAGCAAGCCTCGCTAACCTCGCC TTACCCCCCACTATTAACCTACTGGGAGAACTCTCTGTGCTAGT AACCACGTTCTCCTGATCAAATATCACTCTCCTACTTACAGGAC TCAACATACTAGTCACAGCCCTATACTCCCTCTACATATTTACC ACAACACAATGGGGCTCACTCACCCACCACATTAACAACATAA AACCCTCATTCACACGAGAAAACACCCTCATGTTCATACACCTA TCCCCCATTCTCCTCCTATCCCTCAACCCCGACATCATTACCGGG TTTTCCTCTT | 38 |

TABLE 1-continued

Melanoma Biomarker/Housekeeper Sequence Information

| Gene Name | RefSeq Accession | Sequence | SEQ ID NO: |
|---|---|---|---|
| MORF4L1 | NM_001265603.1 | CGGCGTGCCC TGGGGCGGCG CGGGCGCAGG GGCGCGTGCG CGGCGGGCTG TCGTTGGCTG GAGCAGCGGC TGCGCGGGTC GCGGTGCTGT GAGGTCTGCG GGCGCTGGCA AATCCGGCCC AGGATGTAGA GCTGGCAGTG CCTGACGGCG CGTCTGACGC GGAGTTGGGT GGGGTAGAGA GTAGGGGCG GTAGTCGGGG GTGGTGGGAG AAGGAGGAGG CGGCGAATCA CTTATAAATG GCGCCGAAGC AGGACCCGAA GCCTAAATTC CAGGAGGTTG GGATGAATGG GTTCCGGAGA GCAGAGTACT CAAATACGTG GACACCAATT TGCAGAAACA GCGAGAACTT CAAAAAGCCA ATCAGGAGCA GTATGCAGAG GGGAAGATGA GAGGGGCTGC CCCAGGAAAG AAGACATCTG GTCTGCAACA GAAAAATGTT GAAGTGAAAA CGAAAAAGAA CAAACAGAAA ACACCTGGAA ATGGAGATGG TGGCAGTACC AGTGAGACCC CTCAGCCTCC TCGGAAGAAA AGGGCCCGGG TAGATCCTAC TGTTGAAAAT GAGGAAACAT TCATGAACAG AGTTGAAGTT AAAGTAAAGA TTCCTGAAGA GCTAAAACCG TGGCTTGTTG ATGACTGGGA CTTAATTACC AGGCAAAAAC AGCTCTTTTA TCTTCCTGCC AAGAAGAATG TGGATTCCAT TCTTGAGGAT TATGCAAATT ACAAGAAATC TCGTGGAAAC ACAGATAATA GGGAGTATGC GGTTAATGAA GTTGTGGCAG GGATAAAAGA ATACTTCAAC GTAATGTTGG GTACCCAGCT ACTCTATAAA TTTGAGAGAC CACAGTATGC TGAAATTCTT GCAGATCATC CCGATGCACC CATGTCCCAG GTGTATGGAG CGCCACATCT CCTGAGATTA TTTGTACGAA TTGGAGCAAT GTTGGCTTAT ACACCTCTGG ATGAGAAGAG CCTTGCTTTA TTACTCAATT ATCTTCACGA TTTCCTAAAG TACCTGGCAA AGAATTCTGC AACTTTGTTC AGTGCCAGCG ATTATGAAGT GGCTCCTCCT GAGTACCATC GGAAAGCTGT GTGAGAGGCA CTCTCACTCA CTTATGTTTG GATCTCCGTA AACACATTTT TGTTCTTAGT CTATCTCTTG TACAAACGAT GTGCTTTGAA GATGTTAGTG TATAACAATT GATGTTTGTT TTCTGTTTGA TTTTAAACAG AGAAAAAATA AAAGGGGGTA ATAGCTCCTT TTTTCTTCTT TCTTTTTTTT TTTCATTTCA AAATTGCTGC CAGTGTTTTC AATGATGGAC AACAGAGGGA TATGCTGTAG AGTGTTTTAT TGCCTAGTTG ACAAAGCTGC TTTTGAATGC TGGTGGTTCT ATTCCTTTGA CACTACGCAC TTTTATAATA CATGTTAATG CTATATGACA AAATGCTCTG ATTCCTAGTG CCAAAGGTTC AATTCAGTGT ATATAACTGA ACACACTCAT CCATTTGTGC TTTTGTTTTT TTTTATGGTG CTTAAAGTAA AGAGCCCATC CTTTGCAAGT CATCCATGTT GTTACTTAGG CATTTTATCT TGGCTCAAAT TGTTGAAGAA TGGTGGCTTG TTTCATGGTT TTTGTATTTG TGTCTAATGC ACGTTTTAAC ATGATAGACG CAATGCATTG TGTAGCTAGT TTTCTGGAAA AGTCAATCTT TTAGGAATTG TTTTTCAGAT CTTCAATAAA TTTTTTCTTT AAATTTCAAA GAACAAAAAA AAAAAAAA | 39 |
| MRPL19 | NM_014763.3 | GTAGTCTTGA CGTGAGCTAG CTGGCATGGC GGCCTGCATT GCAGCGGGGC ACTGGGCTGC AATGGGCCTA GGCCGGAGTT TCCAAGCCGC CAGGACTCTG CTCCCCCCGC CGGCCTCTAT CGCCTGCAGG GTCCACGCGG GGCCTGTCCG GCAGCAGAGC ACTGGGCCTT CCGAGCCCGG TGCGTTCCAA CCGCCGCCGA AACCGGTCAT CGTGGACAAG CACCGCCCCG TGGAACCGGA ACGCAGGTTC TTGAGTCCTG AATTCATTCC TCGAAGGGGA AGAACAGATC CTCTGAAATT TCAAATAGAA AGAAAAGATA TGTTAGAAAG GAGAAAAGTA CTCCACATTC AGAGTTCTA TGTTGGAAGT ATTCTTCGTG TTACTACAGC TGACCCATAT GCCAGTGGAA AAATCAGCCA GTTTCTGGGG ATTTGCATTC AGAGATCAGG AAGAGGACTT GGAGCTACTT TCATCCTTAG GAATGTTATC GAAGGACAAG GTGTCGAGAT TTGCTTTGAA CTTTATAATC CTCGGGTCCA GGAGATTCAG GTGGTCAAAT TAGAGAAACG GCTGGATGAT AGCTTGCTAT ACTTACGAGA TGCCCTTCCT GAATATAGCA CTTTTGATGT GAATATGAAG CCAGTAGTAC AAGAGCCTAA CCAAAAAGTT CCTGTTAATG AGCTGAAAGT AAAAATGAAG CCTAAGCCCT GGTCTAAACG CTGGGAACGT CCAAATTTTA ATATTAAAGG AATCAGATTT GATCTTTGTT TAACTGAACA GCAAATGAAA GAAGCTCAGA AGTGGAATCA GCCATGGCTT GAATTTGATA TGATGAGGGA ATATGATACT TCAAAAATTG AAGCTGCAAT ATGGAAGGAA ATTGAAGCGT CGAAAAGGTC TTGATTCTGA GAATGAATTT GGTTAGTTGC AGAAGATACA TTGGCTCTAA GAGGATATAT TTTGAGACCA ATTTAATTTC ATTTATAAGA ACATAGTAAT TAAGTGAACT AAGCATTCAT TGTTTTATTA ATACTTTTTT TCTAAAATAA AACTTGTACA CCAGTTTATT ACTCTAAAAA GAGAATTACA CATGCCAAAT GGACCAATGT CCATTTGCTT | 40 |

TABLE 1-continued

Melanoma Biomarker/Housekeeper Sequence Information

| Gene Name | RefSeq Accession | Sequence | SEQ ID NO: |
|---|---|---|---|
| | | ATTGGAGGCA AAGCTACAAT AGAAGTCAGA GCATCACCAG | |
| | | AATGGTCTTT AATGAGCATG GAACCTGAGC AAAGGGAATA | |
| | | GGTGGGATGA ATTTTTTTTT TAATTGTGAA ACAATTCATA | |
| | | AGCACAATAT GATTTACAGA ATAATAAACA TTCATGTACC | |
| | | CACTATCAGG TTAAGAAATA GAACATTTAT TAATATGTAG | |
| | | GAATGTTAAG AAATAAAACA TTTAATAAGA TCTCAGAAGA | |
| | | CTCCAGTAAA TCTGCAATTG TATCTCTCTC CTTTTTAAAT | |
| | | GTAAATATCA TCTTGACTTG TTAATTATTC CCTTGCATTT | |
| | | CTTTTAGTTT ACTGCCAACA CATATATTCT TCAACAATAT | |
| | | ATTTAATTTT GAAAAACCTG AAAAAAAAAA CCTGTTAGCA | |
| | | AGTATAAAGG GGCAGTATTA CTATTATTGC ATGAAGGCTT | |
| | | CAAGGGAAAC GTTACAGTCT TTGGGTCATA GTCTGGCTTC | |
| | | AGCTTCCTCT GAGAGTTTAC AGAGGCCAAT TTTGAGCAAA | |
| | | TTCATGGCTA AGGTTATGAG TGAGTTCTGC TAAACAGAAG | |
| | | GCTCACCACA AGGTATCTGG CAGGATTATA CTGGGTAGCT | |
| | | GGATGTTGCA GAAATGTGGT TAGAGGAAGT AAACTGTTTT | |
| | | TTGATGCTCA CAGCATGATG AATCAAACTC TGTATCTTAG | |
| | | GATTAGGTTA AACAATACC TTTGGTATGA TATGAGTGTT | |
| | | GTTGCTGATC CATGCAGCAT GGATTGGAAA GCTGGGGTAT | |
| | | AAGCACACAT GCTAAAGAAA AACATGTAAT TTGGTCCATA | |
| | | CTCACCTGGA TATACTGTTC CTCAGGTTAA AAAATACAGT | |
| | | ACTATCCTAA ATCTTGAAGG CAACTCTCAG CCTATCCATT | |
| | | GAGTTACCTT CAGATCTGCC CTCTGGTTCC TAGCTGTCTT | |
| | | GGGACTAACT TCTTTCCTGC GCTCAGCTGT TTTCTGGATT | |
| | | CCATGTTTTC CATTTTATTG AGTACTAACT TGTTTTGCTG | |
| | | CAGCACATCC TTTGGTAGCT TCTAGAGGAA GTTTGTGTGG | |
| | | AGGTAAAATT TTTGAGACCT TGCATGTCTC ATGTTTGATT | |
| | | GATACTTTAT ACGTTAGGT AGGAGGTAAT TTTCCTTCAG | |
| | | GACTTTAAAA ATATTGTTGC TCCATTTTCT TTGTTTCTAT | |
| | | TGTTGTATTG AGAAATCCAA TGCCATTTTG ATTTCCCCAT | |
| | | CATAAATTTC ATGATGATGT GTCTTGGTGT GGGTCTATAT | |
| | | TTATCCATTG TATTGGGTTT TAGGTGAACC CTTCCAGATA | |
| | | GTAACTCATT TCTGTCAGTT CTGGGAAACA CTTAGCATTG | |
| | | GTTGATGATT TATTCTCTGC TGCTTTGTTC TCCCAACTAT | |
| | | TATTTGGATG TTGGATATCC AGCACTGGGT ATCTATTTTC | |
| | | TTACCTCCCT CCCTTGACCC CAGTCTCTGT TTTTTAGCTC | |
| | | TTTAGCTCAA TCTTCCAACT CTTTGCTATT GTATTTTAAA | |
| | | ATCTTAAGAC CCCTTCTTGA TTTGTAGAAG TTCCTTTTCT | |
| | | TACAACCAAA AAGCCTTTAT CTATGGATTT GTTCACAGAT | |
| | | AAGGGGTATT CAATATATGC TATTTTTTTT TCATTTAAAA | |
| | | TTGTTTGCGC ATCTATTTCC TCCAAATTTC TTTCTGTATT | |
| | | TATTTTTTGT TGTCTATATT TCAGACTTTT CCAGGATATC | |
| | | TGATAATCTT TGGCTGTCTT CTTATGGTTG AAAGAGGGAC | |
| | | TAAAAAGCTT GGAAAGCCTT TGGGTTGTGG GAAGGGGCTG | |
| | | TCTTTAGGAT TATCTGAATG GGCTTTTTTG GGAGTCCCCT | |
| | | CCTCCACATG AATATTTTGG TTTTGTCAGA TTCCCTAGAA | |
| | | TAGAGGCTTC CAATCTCCTT CCTGGAGGGG TCTGTCCAGG | |
| | | AAGGAGATTG TCTAGGGGTC TGTCAGACAG CAGCTTTCAG | |
| | | CTACTTCCTT GATCTTTTTC ACTAATGATT ATATAGTCAT | |
| | | CTAACTACTG TCAACAAGTA ATAGATATCC TATCCTTCAC | |
| | | TTGTTTAGAT TATTTGCTGA GATAACCTCT CAAAAGAACC | |
| | | TCTCAAAATA AAAGGTTAAC AAGAGCCTAT ATCTTATATT | |
| | | TTTCTTCTCT TTATCTTGTT AGAAGATAGC TATTAAAACC | |
| | | TGTTCTTTTT CTGTCTTGAT AAACACACTT CAATCTTGGT | |
| | | AGAATGGTAG ATGGGACAGT ATATTTAGG ACCTAAAGCT | |
| | | CTGCAAATGT ATGATCAGCT TGTAAGTACA GGTGCTCAAA | |
| | | AACATGTAAA CAATCATGCT TTTTACTCTG TAGGAATATC | |
| | | TTTAAAATTC TTGTGAATTT TTCCCCAGAA GTAAAGCAAA | |
| | | TCTTCCCCCA GAAATAAAAT TAAATGTGCA TAATCTAAAG | |
| | | CTTTTTTTTT TTATTGTGGT AGGATATATA TATAAAACAT | |
| | | AATTTGCCAT TGTAAACATT TTAAATTTAC AAGTCAGAGG | |
| | | CATTAATTAC ATCACAATGT TGTGAAATTA TTACTACTAT | |
| | | TTCCAAAATT TTCTCATCAC CCCAAACTGA AACTCTGTAA | |
| | | CTGTTGAGCA ATAACCTCAT TCCTGTATCT CTCCCAACCC | |
| | | CAGGTAACCT CAAATCTTTC TTTTTATCTT TGAGACAAGG | |
| | | TCTCATTCTA TCACTCAGGT AGGAGTGCAG TGGTGTGATC | |
| | | ATAGCTCATT GCAGCCTCAA AATCCTGGGC TCAAGCAATC | |
| | | CTCCTTGAGT AGCTAAGACT ATAGGCACAC ATTAACTGCG | |
| | | CCTGGCTGAT TTTGTTTTTT GTAGAGATGT GGTCTTGCTA | |
| | | TGTTTCCCAT GCTGGTCTTG AGTTCCTGGC CTCAAGCAGT | |
| | | CCTTAAGATT CATCCATGTT GTGGCATGTG TCAGAATTTC | |
| | | ATTTGTTTTT ATGACTAAAT AATATTCCAT TGTATGTATA | |
| | | TACATTTTGT TCATCCATCT TCTGATGAAC ACTGGGATAT | |
| | | GTCTACCTTT TGGCTATTGT GAATAATGCT GCAGTAAACA | |

TABLE 1-continued

Melanoma Biomarker/Housekeeper Sequence Information

| Gene Name | RefSeq Accession | Sequence | SEQ ID NO: |
|---|---|---|---|
| | | TTGACATAAC AAGTATGTAT TTGATTGCCT GTTTCTAAGT | |
| | | TCTTTTGGGT ATACATCTTG AGTAGAATTG CTAGATAATG | |
| | | TCATGTTTTA TTTCTCTTGT GATTTCTTCT TCGATCCCCT | |
| | | GGTTGAGTGT GTTAATTTCT ACATGTTTAT GAATTTCCCA | |
| | | CTGTTTTTTT GTTATTGATT TCCAAGTTCA TTCCATTGTG | |
| | | ATTAGAGAAG ATACTTAGTA TGATTTTAAT GTTTTTGAGA | |
| | | ATTGGTGTGT GGCCTGATAG ATGGTCTGTC CTGGAGAATG | |
| | | TTCCTCATAC ACTTGAGCAA AATATTTATC ATGCTATTGT | |
| | | TGACTGTAGT TTTCTATATG TCTCTTAGGT CAAGGTGGTT | |
| | | TACAATGTGT TAAGGTTCTC TTTTTTTAAA AAAATTTTTG | |
| | | CACAGAGTAT CTTTTTCTAT GTGTTCCATG TATTTGTGTC | |
| | | TTTGGAGCTA TAGTCTCTTG TAGACAGCAT ATCACTATCT | |
| | | TGTTTTGTTT TGTTTTTTCT GTCCATTCTG CCAATTTCTG | |
| | | CCTTTTGATT GGAAAATTTA ATCCATTTGC ATTTAAAGTA | |
| | | ATTAAGGAAG GACTTTCTTC TACCATTTAA CACTTCTTCT | |
| | | ATATGTCATA TACTTTTTTG GCCCCTCATT TCCTCTTTAT | |
| | | GGCCTTCTTT TCTGTTTTTT TGTAGTGAAC TAGTCTGATT | |
| | | CTCTTTCCAC TCCCCTTTGT GTATATTTGT TAGATGTTTT | |
| | | ATTTGTGGTT GCTATGGGGA TTATAGTTAA CATCCTACAC | |
| | | TTAAAACAAT CTAATTTAAA CTGATACCAA TTTACCTTCA | |
| | | ATAGCATACA AAATCTCTAC TCCTGTAAAG CTCTGCCCCT | |
| | | GCCCCCCTTA TGTTATTGAT GGCACAAATT GCCTAATAAA | |
| | | TAATTTATAG TTATTTGTAT GAGTTTGTCT TTTAAATCAT | |
| | | TTAGGAAATA AAAAGTGGAG TTAGAAAACA GTATGATAGT | |
| | | AATACTGACT TTTATATTTG TCAATATATT TATCTTATTT | |
| | | TGGATCCTTA TTTCATTATA TAGATTTGAG TTACTGTCTA | |
| | | GTGCCCTTCC ATTTCGGCCC AAAGGATTCC CTTATGCATT | |
| | | TCTTGCAGGG CAAGTCTAAT TGTAATAAAC TCCCTCAGCT | |
| | | TTTGTTTTAT CTGAGAATGT CTTGATTTCT CCCTTATTTT | |
| | | TGATGGATAA TTTTGCCAGA TACATGAATT TTTGGTAACA | |
| | | GTATTTTTCT TTCAGCACTT TAAATATGTC ATCCCACTAC | |
| | | CTTCTGACTT CATGGTTTCT CATGAGATAT TAGATGTTAT | |
| | | AAAATTTGAG GATTCCTCAT TCTTGATGAG TCAGTTCTGT | |
| | | CTTATTGCTT TTCGGATTTG CTCAGCTTTT GTCTTTTGAC | |
| | | AGTTTGATTA TAACGCGGCT CAGTGTGGGT CTCTGAGTTT | |
| | | ATCCCACTTA GAGTTTGTTG AGTTTCTTGG AGTCATAGAT | |
| | | TTATGTCTTT TATCAAATTT TGGACATATT TGGCTATTAT | |
| | | TTCTTCAATT TTTTTCACTG CTTCTTTCTT TTCCTTCTGA | |
| | | AATATTCTTA ATGTATATGT TGGTCTGTTT GATGCTGTCT | |
| | | CACCAGTTTC TTAGGCTGTG TTCTCTTTTG TTCCTCAGAC | |
| | | TTGATTATTG CAGTTGCCCT TCTTTTTATT TTTTTCAAGT | |
| | | TTGTTGATTC TTCTCCCTGT TCAGATCAAC TGTTGAACTC | |
| | | CTCTAGTGAA TTTATTTCAG TTACTGTACT TTTCAGCTCC | |
| | | AAGATTTATC TTTGGTTCCT TTTTATAACG TCTGTGTCTT | |
| | | TATTGATATT CTCATTTTGT TCATATGTCT CTTTCTTCCT | |
| | | TTAGTTCTTT GTCCATGTTT TCCTTTAGCT CTTTGGGCTT | |
| | | ATTTAAGACA ATTGTTTAAA GTCTTTGCAT AGTAAGTCCA | |
| | | ATGTCTGTGT TTCTTCAGGG ATGGTTTTCA TTATTTTGTT | |
| | | TTCAATGAGC CATACTTTCC TGTGTCTTTG TATGCTGTCT | |
| | | TTTTGTTGTT GAAAACTGTA TGTTTGAACA TCATAACGTG | |
| | | GTGGCCCTGA AAATCAGATA TTCCCCCCTT CCTGAGAGTT | |
| | | AGTTTTATTT TTATTATTGA AGATTGTAGC AGTCTATTGC | |
| | | TACATGTGCA GTCATTTCCA AACTATTTTT GCAAAGACTG | |
| | | TATTCCTTCT GTGTGTCATC ACTGAAGTCT CTGTTCCTTA | |
| | | GTTTGTGTTT AATAGTTTGA CATAGATTTC CTTGAAAGGA | |
| | | GTTAAAACTA GCAGAAAAAT CTCTCTCCCA GTCTTTCCAG | |
| | | TCTTTGTAGA TTGGTTCTGT GCTGGGCTTT TCCATTAATA | |
| | | CTTAGCCAGG CTTGTACTGA GCCTAACAAT CAGGCCCAAA | |
| | | AGCGTAGGGT CTTTGCAGAT CTTGTCTGAG CATGCTTCTT | |
| | | GCTGTGTATG CACGTAGTTT TCTAAATCTC CCTGTATGTG | |
| | | CTGTTGAATA TTCTAATTTC CCAAAGAAAC TCCTTTGCAG | |
| | | CTTTTTCTCA CAGAACATAG ATGGTTTTTT GGATATCTTG | |
| | | ACCATATGTCT TTCGACCCAG GTGTTTGCGG TTGTTAGTTC | |
| | | ACCTTACACT TTTTTCAAGC ATTGCCTACT GCTTACGATG | |
| | | AGTGCTCTGT CAATCCTTTA AGTAGCCCCA GACAGGCTAC | |
| | | CAGAGACTTA AACAAGAATT TGTAAGTTCT GCTCAGCTTC | |
| | | CTCTAGAAAT GGGGATCAGG GTCCAAGACA GAATGCAGTT | |
| | | GCTGATTTCA AGACTGCTGC AACACCAGGG AGCTTGTGGG | |
| | | GGAAGGGCAA GCAGAAATGT CACAAAGCTT TCTTGCCATT | |
| | | TTAAAGTTGC CTGTTCTTGA CTCAGCATTT GCTTCATTGC | |
| | | TATAAACTTT TTACTGTTTT TCAGAGTTCT GATAAAATTG | |
| | | GCTATGCCTG TTCCTGCTTT AAAAAATATA TATATATTTT | |
| | | TTAGGGATTG GGGTCTCACT ATACTGACCA GGCTGGTCTT | |
| | | GAACTTCTGG CCTCAAGCCA TCCTCTCATT TCAGCTTCCC | |

TABLE 1-continued

Melanoma Biomarker/Housekeeper Sequence Information

| Gene Name | RefSeq Accession | Sequence | SEQ ID NO: |
|---|---|---|---|
| | | AAAGTGCTGC AATTACACGC GTGAACCACC ACACCCAGCC CCTGCTTGTT TTTCAATGTG CCTACTCCAC CATGTTGCTC AAGTATGTAT ATTTTCTAAA CTACCTTGTA GTGTTGTGAT GGGAAATAAA TCCCTGAGCC TTTTGAATAA CTCAGAGAGA TCAAAAACTT AGTTTATCCT ATTCGAAGGA TTAGAAAAAT GATATATCTT TCACTTTTTC AGGGATAGGC TCCTCATTAG AAGGCTCCTA TGTGCCGATG CTGTACAAGA CATTTCATTT CTCTTAATGT TTACAACAAG CTTGTTGCCA AGGCTGATCT TGAACTCCTG GCCTCAAACG ATCCTCCCAG CTCAGTCTCA CAAAGTGTTG GGATGTCTGG CCAACTAATG ACTATCTTAA CTCTTGTGTT TCAATGTTTA TGCCTTCTTT TATCTTGACT GATTGTATGA CTATGTCTTC TAGAACAATG TTGAACAGAA ATGGTGAGAG CAGACATCCT TGCTTTAATA TTTCACCATT ATATATGATG TTAGGTATAG ATTTTTCTCA CAGATGCCTT TTATCAGATT GAGGAATTTA TATTCCTACT TTGCCGAAAG GTTTTTGTAG TATGAGGGGG TGCTGAATTT TGTCAAACAC TTTTTCGGTA ATAATTGAGA TGATTGGTTC TGCAGTCATC GAGATGTGGA TTTTCTCCTT TATTCTGTTC GTGAGTGATT ACACTGGTTG ACTAATGTTA AAACAACCTT ACTTTCCAGG AATAAACCCT ATTATCTTTT TTATACA | |
| PSMC4 | NM_153001.2 | TGCGGGTACG DACAGCGCAT GAGCTTATGT TGAGGGCGGA GCCCAGACCA GCCCTTCGTC CTATCCTGCC CTTCCAGCAC CTCTCAGCCG TAACTTAAAC TACACTTCCC AGAAGCCTCC TCAGCCAGGG ACTTCCGTTG TCGTCAGCGG AAGCGGTGAC AGATCATCCC AGGCCACACA GAGGCCGGCT TGGTCACTAT GGAGGAGATA GGCATCTTGG TGGAGAAGGC TCAGGATGAG ATCCCAGCAC TGTCCGTGTC CCGGCCCCAG ACCGGCCTGT CCTTCCTGGG CCCTGAGCCT GAGGACCTGG AGGACCTGTA CAGCCGCTAC AAGGAGGAGG TGAAGCGAAT CCAAAGCATC CCGCTGGTCA TCGGACAATT TCTGGAGGCT GTGGATCAGA ATACAGCCAT CGTGGGCTCT ACCACAGGCT CCAACTATTA TGTGCGCATC CTGAGCACCA TCGATCGGGA GCTGCTCAAG CCCAACGCCT CAGTGGCCCT CCACAAGCAC AGCAATGCAC TGGTGGACGT GCTGCCCCCC GAAGCCGACA GCAGCATCAT GATGCTCACC TCAGACCAGA AGCCAGATGT GATGTACGCG GACATCGGAG GCATGGACAT CCAGAAGCAG GAGGTGCGGG AGGCCGTGGA GCTCCCGCTC ACGCATTTCG AGCTCTACAA GCAGATCGGC ATCGATCCCC CCCGAGGCGT CCTCATGTAT GGCCCACCTG GCTGTGGGAA GACCATGTTG GCAAAGGCGG TGGCACATCA CACAACAGCT GCATTCATCC GGGTCGTGGG CTCGGAGTTT GTACAGAAGT ATCTGGGTGA GGGCCCCCGC ATGGTCCGGG ATGTGTTCCG CCTGGCCAAG GAGAATGCAC CTGCCATCAT CTTCATAGAC GAGATTGATG CCATCGCCAC CAAGAGATTC GATGCTCAGA CAGGGGCCGA CAGGGAGGTT CAGAGGATCC TGCTGGAGCT GCTGAATCAG ATGGATGGAT TTGATCAGAA TGTCAATGTC AAGGTAATCA TGGCCACAAA CAGAGCAGAC ACCCTGGATC CGGCCCTGCT ACGGCCAGGA CGGCTGGACC GTAAAATTGA ATTTCCACTT CCTGACCGCC GCCAGAAGAG ATTGATTTTC TCCACTATCA CTAGCAAGAT GAACCTCTCT GAGGAGGTTG ACTTGGAAGA CTATGTGGCC CGGCCAGATA AGATTTCAGG AGCTGATATT AACTCCATCT GTCAGGAGAG TGGAATGTTG GCTGTCCGTG AAAACCGCTA CATTGTCCTG GCCAAGGACT TCGAGAAAGC ATACAAGACT GTCATCAAGA AGGACGAGCA GGAGCATGAG TTTTACAAGT GACCCTTCCC TTCCCTCCAC CACACCACTC AGGGGCTGGG GCTTCTCTCG CACCCCCAGC ACCTCTGTCC CAAAACCTCA TTCCCTTTTT TCTTTACCCA GGATTGGTTT CTTCAATAAA TAGATAAGAT CGAATCCATT TAATTTCTTC TTAGAAGTTT AACTCCTTTG GAGAATGTGG GCCTTGAATA GGATCCTCTG GGTCCCTCTT AATCTGACAG ATGAGCAGAC GAGGTGCATG GCCTGGGTTG CAGCTTGAGA GAACCAAAAT ATTCAAACCA GATGACTTCC AAAATGTGGG GAAAGGGATG GAAAATGAAC CTGAGATGGA GTCCTTAATC ACGGGATAAA GCCCTGTGCA TCTCCCTCAT TTCCTACAGG TAAAAGACAG TAAAGAAATT CAGGTCACAG GCCTTGGGAG TTCATAGGAA GGAGATGTCC AGTGCTGTCC AGTAGAACTT T | 41 |
| SF3A1 | NM_005877.5 | GGTCCCGGAA GTGCGCCAGT CGTACCTTCG CGGCCGCAAC TCGCTCGGCC GCCGCCATCT TGCGAGCTCG TCGTACTGAC CGAGCGGGGA GGCTGTCTTG AGGCGGCACC GCTCACCGAC ACCGAGGCGG ACTGGCAGCC CTGAGCGTCG CAGTCATGCC GGCCGGACCC GTGCAGGCGG TGCCCCCGCC GCCGCCCGTG CCCACGGAGC CCAAACAGCC CACAGAAGAA GAAGCATCTT | 42 |

TABLE 1-continued

Melanoma Biomarker/Housekeeper Sequence Information

| Gene Name | RefSeq Accession | Sequence | SEQ ID NO: |
|---|---|---|---|
| | | CAAAGGAGGA TTCTGCACCT TCTAAGCCAG TTGTGGGGAT<br>TATTTACCCT CCTCCAGAGG TCAGAAATAT TGTTGACAAG<br>ACTGCCAGCT TTGTGGCCAG AAACGGGCCT GAATTTGAAG<br>CTAGGATCCG ACAGAACGAG ATCAACAACC CCAAGTTCAA<br>CTTTCTGAAC CCCAATGACC CTTACCATGC CTACTACCGC<br>CACAAGGTCA GCGAGTTCAA GGAAGGGAAG GCTCAGGAGC<br>CGTCCGCCGC CATCCCCAAG GTCATGCAGC AGCAGCAGCA<br>GACCACCCAG CAGCAGCTGC CCCAGAAGGT CCAAGCCCAA<br>GTAATCCAAG AGACCATCGT GCCCAAAGAG CCTCCTCCTG<br>AGTTTGAGTT CATTGCTGAT CCTCCCTCTA TCTCAGCCTT<br>CGACTTGGAT GTGGTGAAGC TGACGGCTCA GTTTGTGGCC<br>AGGAATGGGC GCCAGTTTCT GACCCAGCTG ATGCAGAAAG<br>AGCAGCGCAA CTACCAGTTT GACTTTCTCC GCCCACAGCA<br>CAGCCTCTTC AACTACTTCA CGAAGCTAGT GGAACAGTAC<br>ACCAAGATCT TGATTCCACC CAAAGGTTTA TTTTCAAAGC<br>TCAAGAAAGA GGCTGAAAAC CCCCGAGAAG TTTTGGATCA<br>GGTGTGTTAC CGAGTGGAAT GGGCCAAATT CCAGGAACGT<br>GAGAGGAAGA AGGAAGAAGA GGAGAAGGAG AAGGAGCGGG<br>TGGCCTATGC TCAGATCGAC TGGCATGATT TTGTGGTGGT<br>GGAAACAGTG GACTTCCAAC CCAATGAGCA AGGGAACTTC<br>CCTCCCCCCA CCACGCCAGA GGAGCTGGGG GCCCGAATCC<br>TCATTCAGGA GCGCTATGAA AAGTTTGGGG AGAGTGAGGA<br>AGTTGAGATG GAGGTCGAGT CTGATGAGGA GGATGACAAA<br>CAGGAGAAGG CGGAGGAGCC TCCTTCCCAG CTGGACCAGG<br>ACACCCAAGT ACAAGATATG GATGAGGGTT CAGATGATGA<br>AGAAGAAGGG CAGAAAGTGC CCCCACCCCC AGAGACACCC<br>ATGCCTCCAC CTCTGCCCCC AACTCCAGAC CAAGTCATTG<br>TCCGCAAGGA TTATGATCCC AAAGCCTCCA AGCCCTTGCC<br>TCCAGCCCCT GCTCCAGATG AGTATCTTGT GTCCCCCATT<br>ACTGGGGAGA AGATCCCCGC CAGCAAAATG CAGGAACACA<br>TGCGCATTGG ACTTCTTGAC CCTCGCTGGC TGGAGCAGCG<br>GGATCGCTCC ATCCGTGAGA AGCAGAGCGA TGATGAGGTG<br>TACGCACCAG GTCTGGATAT TGAGAGCAGC TTGAAGCAGT<br>TGGCTGAGCG GCGTACTGAC ATCTTCGGTG TAGAGGAAAC<br>AGCCATTGGT AAGAAGATCG GTGAGGAGGA GATCCAGAAG<br>CCAGAGGAAA AGGTGACCTG GGATGGCCAC TCAGGCAGCA<br>TGGCCCGGAC CCAGCAGGCT GCCCAGGCCA ACATCACCCT<br>CCAGGAGCAG ATTGAGGCCA TTCACAAGGC CAAAGGCCTG<br>GTGCCAGAGG ATGACACTAA AGAGAAGATT GGCCCCAGCA<br>AGCCCAATGA AATCCCTCAA CAGCCACCGC CACCATCTTC<br>AGCCACCAAC ATCCCCAGCT CGGCTCCACC CATCACTTCA<br>GTGCCCCGAC CACCCACAAT GCCACCTCCA GTTCGTACTA<br>CAGTTGTCTC CGCAGTACCC GTCATGCCCC GGCCCCCAAT<br>GGCATCTGTG GTCCGGCTGC CCCCAGGCTC AGTGATCGCC<br>CCCATGCCGC CCATCATCCA CGCGCCCAGA ATCAACGTGG<br>TGCCCATGCC TCCCTCGGCC CCTCCTATTA TGGCCCCCCG<br>CCCACCCCCC ATGATTGTGC CAACAGCCTT TGTGCCTGCT<br>CCACCTGTGG CACCTGTCCC AGCTCCAGCC CCAATGCCCC<br>CTGTGCATCC CCCACCTCCC ATGGAAGATG AGCCCACCTC<br>CAAAAAACTG AAGACAGAGG ACAGCCTCAT GCCAGAGGAG<br>GAGTTCCTGC GCAGAAACAA GGGTCCAGTG TCCATCAAAG<br>TCCAGGTGCC CAACATGCAG GATAAGACGG AATGGAAACT<br>GAATGGGCAG GTGCTGGTCT TCACCCTCCC ACTCACGGAC<br>CAGGTCTCTG TCATTAAGGT GAAGATTCAT GAAGCCACAG<br>GCATGCCTGC AGGGAAACAG AAGCTACAGT ATGAGGGTAT<br>CTTCATCAAA GATTCCAACT CACTGGCTTA CTACAACATG<br>GCCAATGGCG CAGTCATCCA CCTGGCCCTC AAGGAGAGAG<br>GCGGGAGGAA GAAGTAGACA AGAGGAACCT GCTGTCAAGT<br>CCCTGCCATT TTGCCTCTCC TGTCTCCCAC CCCCTGCCCC<br>AGACCCAGGA GCCCCCCTGA GGCTTTGCCT TGCCTGCATA<br>TTTGTTTCGC TCTTACTCAG TTTGGGAATT CAAATTGTCC<br>TGCAGAGGTT CATTCCCCTG ACCCTTTCCC CACATTGGTA<br>AGAGTAGCTG GGTTTTCTAA GCCACTCTCT GGAATCTCTT<br>TGTGTTAGGG TCTCGATTTG AGGACATTCA TTTCTTCAGC<br>AGCCCATTAG CAACTGAGAG CCCAGGGATG TCCTACAGGA<br>TAGTTTCATA GTGACAGGTG GCACTTGGCT AATAGAATAT<br>GGCTGATATT GTCATTAATC ATTTTGTACC TTGACATGGG<br>TTGTCTAATA AAACTCGGAC CCTTCTTGTG AAATCAGTTA<br>AATAAGACTT GTCTCGGTCA CCTGTGCCCT GTCCAGACTC<br>GAGGCAGTGG TAACACTGCA CAGTGCTATG TGGCTTCTCT<br>TTGAGGATTT TTGGGTTTTG TAACTAAATT CTTGCTGCCC<br>TCATACTTTT TATGTATTAG AATCATATTC GTATTGCCCT<br>TTTAAAACAT TGGGATCCTC CAAAGGCCTG CCCCATGTAT<br>TTAACAGTAA TACAGGAAGC ATGGCAGGCA CCATGCAAAC | |

TABLE 1-continued

Melanoma Biomarker/Housekeeper Sequence Information

| Gene Name | RefSeq Accession | Sequence | SEQ ID NO: |
|---|---|---|---|
| | | CAAGGATGGA TGGTGCAGTC CCTGTGTCAG TGGGCGGTGG<br>TTTCCTGCTG GCCTGGAATC ACTCATCACC TGATTGATTG<br>GCTCTGTGGT CCTGGGCAGG TGCCTCATAG GTGTGTGGAT<br>ATGATGACGT TTCTTTAAAA TGTATGTATT AACAAATAC<br>TTAATTGTAT TAAGGTCATG TACCAAGGAT TTGATAAAGT<br>TTAAATAATT TACTCTCTAC TTTTATCCAT TTTATCCATT<br>TTAACTCATG TAATCCTCAT GTGAGTATTC CTGTTTAACA<br>CTTGAGTAAA CTGAGGCACA GAGAACATAA GTTGCATGCC<br>ATAGTCACAC ACTGTGAAAG TGAAAAGAGA ATGTGTGCAA<br>AACACGTCAC AGTCCTGGTT TCTGAGTAAA GGCAGGCTGT<br>TATCTTTAGA ATCAAGCTAT CACAGGGAGA TAGGCAATGC<br>TGTGGGTGTT GGAGGAAGGT GAGAGCCTGT TGCTAACAAT<br>TTCCTGGTTT TAAAGCTAAG GCTGATTTTA TTGGGAAGAT<br>CTCACATGTG TGTGGCCCCT GAGAGTTCCC AGTGCCTTTT<br>ATTTGCAGTC CTTCCATTTG GACCTCCTAG CTGCCCCATC<br>AGGTCATCTC CAGGGCTCAG AGGGGTGAGA CCATTTCCCA<br>AGGTCACAGA ACCAGCTCTC TAGTCACCAC CCTGCCTCTC<br>CCTCTCACCC AGAGTCAGTA CCAGTTTTAT GGCTTTATTA<br>CAAACTGCTG GGTCCCTCCC ATTTTCAACT TGATTGATGG<br>GATGTCATCC CTTATCCTGT CTGACATTTG CCTCTGGCCT<br>GGTTGCTAGA AGTTTGCCCC AGGGGCAAGA GTTGAAATTT<br>GGCTTCCTGA GGTGGGCTTT GTGGTTTGCG TCCCTAAAGT<br>GAGCCCACTA CTGGTTGCTT GTCCATGGCC AACACCAGAA<br>ATCCCCTGAG CACTACCTGG GTCTCATTCC AAGAAGGAAG<br>AGGGTCAGGA GACCTGGGGA GTCTCATATT CCAAGTTCTT<br>CTTTCTTTCT GGGAGCAGTG GGCAGTTCAT GGTGTTAGGG<br>CACTCACCCC CACAGACTGG CAAACCCTGC AGGACTTCCG<br>TGGCTGAGGC TGTGACCGGA GGCCAGGAAT GCCGTTGGGT<br>GGATTGTGAG TGAATGGGCC CTTTGAGCTG CCCTCTAGAG<br>AGCAAATCCA GTTTCCTGGA GCTCCTGAAT GAATATCTGT<br>ACTGGCTCGC TCAGATGCAG AAGCTCCATT GACCATGAGG<br>CCTTGTGAAC ATCAGTGGCC ACAGGCCCAG TGTGCTGCTT<br>GGCACTGCAC TAGTTTAGGA CCTGCAGCAT GTAGGTAGCG<br>TCCTAGTGTT TATAATACAA AGCTGCTCTG CACAGCTTTT<br>CTGATTCTTC TTGCAATCTC CTGAGGATTA TCTGCCCCAT<br>TTTTAAAACG AGGTGGAATA CCCAAGGTCA TGTAGCCAGT<br>GAGTGCTCTG GAAAGCCAAA GCAGCTCATC CCTTCCTGGG<br>GACCACACTG CTCTGCTCCA CCAGACCACA CTATGAAATA<br>GGAATAAGTG CTCCTGTTGC AGGACTGCTG GGAAAACAGG<br>TGGTGTGGGA CTTAAGTCAC CATAATTTTG AAGCTTGCA<br>TGCAGAGGGC TCCAGGAATT GTAGACATTA AGGAATTTCA<br>CTTTCAGTTC TACCCACTAC TTAAGTACTT GTCATGTACT<br>CTTAGAGGAG GCCAGTAATG ATCAGAACCA TTTTACTTTA<br>AAATTAATAA TATTGTATTA GAGAATATAT TAAATGGTTA<br>TATTGGGTTA TGTTAGGATA TATACTTGAA TGGAAATACA<br>TGTACTATTA GCAATCATAT TTCATTTATC CCTGTAATTA<br>GACAAGAAAG CATAATATAG CTCTACTCAT GGGTACACAT<br>ACCAGTGTAT AAGATTTTTA GAAGTTTACT TTTTAAAAAT<br>AAAAGCAAAA TGTAAGATCT TAAAAAAAAA AAAAAAAA | |
| PUM1 | NM_001020658.1 | AGTGGGCCGC CATGTTGTCG GAGTGAAAGG TAAGGGGGAG<br>CGAGAGCGCC AGAGAGAGAA GATCGGGGGG CTGAAATCCA<br>TCTTCATCCT ACCGCTCCGC CCGTGTTGGT GGAATGAGCG<br>TTGCATGTGT CTTGAAGAGA AAAGCAGTGC TTTGGCAGGA<br>CTCTTTCAGC CCCCACCTGA AACATCACCC TCAAGAACCA<br>GCTAATCCCA ACATGCCTGT TGTTTTGACA TCTGGAACAG<br>GGTCGCAAGC GCAGCCACAA CCAGCTGCAA ATCAGGCTCT<br>TGCAGCTGGG ACTCACTCCA GCCCTGTCCC AGGATCTATA<br>GGAGTTGCAG GCCGTTCCCA GGACGACGCT ATGGTGGACT<br>ACTTCTTTCA GAGGCAGCAT GGTGAGCAGC TTGGGGGAGG<br>AGGAAGTGGA GGAGGCGGCT ATAATAATAG CAAACATCGA<br>TGGCCTACTG GGGATAACAT TCATGCAGAA CATCAGGTGC<br>GTTCCATGGA TGAACTGAAT CATGATTTTC AAGCACTTGC<br>TCTGGAGGGA AGAGCGATGG GAGAGCAGCT CTTGCCAGGT<br>AAAAAGTTTT GGGAAACAGA TGAATCCAGC AAAGATGGAC<br>CAAAAGGAAT ATTCCTGGGT GATCAATGGC GAGACAGTGC<br>CTGGGGAACA TCAGATCATT CAGTTTCCCA GCCAATCATG<br>GTGCAGAGAA GACCTGGTCA GAGTTTCCAT GTGAACAGTG<br>AGGTCAATTC TGTACTGTCC CCACGATCGG AGAGTGGGGG<br>ACTAGGCGTT AGCATGGTGG AGTATGTGTT GAGCTCATCC<br>CCGGGCGATT CCTGTCTAAG AAAAGGAGGA TTTGGCCCAA<br>GGGATGCAGA CAGTGATGAA AACGACAAAG GTGAAAGAA<br>GAACAAGGGT ACGTTTGATG GAGATAAGCT AGGGAGATTTG<br>AAGGAGGAGG GTGATGTGAT GGACAAGACC AATGGTTTAC | 43 |

TABLE 1-continued

Melanoma Biomarker/Housekeeper Sequence Information

| Gene Name | RefSeq Accession | Sequence | SEQ ID NO: |
|---|---|---|---|
| | | CAGTGCAGAA TGGGATTGAT GCAGACGTCA AAGATTTTAG CCGTACCCCT GGTAATTGCC AGAACTCTGC TAATGAAGTG GATCTTCTGG GTCCAAACCA GAATGGTTCT GAGGGCTTAG CCCAGCTGAC CAGCACCAAT GGTGCCAAGC CTGTGGAGGA TTTCTCCAAC ATGGAGTCCC AGAGTGTCCC CTTGGACCCC ATGGAACATG TGGGCATGGA GCCTCTTCAG TTTGATTATT CAGGCACGCA GGTACCTGTG GACTCAGCAG CAGCAACTGT GGGACTTTTT GACTACAATT CTCAACAACA GCTGTTCCAA AGACCTAATG CGCTTGCTGT CCAGCAGTTG ACAGCTGCTC AGCAGCAGCA GTATGCACTG GCAGCTGCTC ATCAGCCGCA CATCGGTTTA GCTCCCGCTG CGTTTGTCCC CAATCCATAC ATCATCAGCG CTGCTCCCCC AGGGACGGAC CCCTACACAG CTGGATTGGC TGCAGCAGCG ACACTAGGCC AGCTGTGGT CCCTCACCAG TATTATGGAG TTACTCCCTG GGGAGTCTAC CCTGCCAGTC TTTTCCAGCA GCAAGCTGCC GCTGCCGCTG CAGCAACTAA TTCAGCTAAT CAACAGACCA CCCCACAGGC TCAGCAAGGA CAGCAGCAGG TTCTCCGTGG AGGAGCCAGC CAACGTCCTT TGACCCCAAA CCAGAACCAG CAGGGACAGC AAACGGATCC CCTTGTGGCA GCTGCAGCAG TGAATTCTGC CCTTGCATTT GGACAAGGTC TGGCAGCAGG CATGCCAGGT TATCCGGTGT TGGCTCCTGC TGCTTACTAT GACCAAACTG GTGCCCTTGT AGTGAATGCA GGCGCGAGAA ATGGTCTTGG AGCTCCTGTT CGACTTGTAG CTCCTGCCCC AGTCATCATT AGTTCCTCAG CTGCACAAGC AGCTGTTGCA GCAGCCGCAG CTTCAGCAAA TGGAGCAGCT GGTGGTCTTG CTGGAACAAC AAATGGACCA TTTCGCCCTT TAGGAACACA GCAGCCTCAG CCCCAGCCCC AGCAGCAGCC CAATAACAAC CTGGCATCCA GTTCTTTCTA CGGCAACAAC TCTCTGAACA GCAATTCACA GAGCAGCTCC CTCTTCTCCC AGGGCTCTGC CCAGCCTGCC AACACATCCT TGGGATTCGG AAGTAGCAGT TCTCTCGGCG CCACCCTGGG ATCCGCCCTT GGAGGGTTTG GAACAGCAGT TGCAAACTCC AACACTGGCA GTGGCTCCCG CCGTGACTCC CTGACTGGCA GCAGTGACCT TTATAAGAGG ACATCGAGCA GCTTGACCCC CATTGGACAC AGTTTTTATA ACGGCCTTAG CTTTTCCTCC TCTCCTGGAC CCGTGGGCAT GCCTCTCCCT AGTCAGGGAC CAGGACATTC ACAGACACCA CCTCCTTCCC TCTCTTCACA TGGATCCTCT TCAAGCTTAA ACCTGGGAGG ACTCACGAAT GGCAGTGGAA GATACATCTC TGCTGCTCCA GGCGCTGAAG CCAAGTACCG CAGTGCAAGC AGCGCCTCCA GCCTCTTCAG CCCGAGCAGC ACTCTTTTCT CTTCCTCTCG TTTGCGATAT GGAATGTCTG ATGTCATGCC TTCTGGCAGG AGCAGGCTTT TGGAAGATTT TCGAAACAAC CGGTACCCCA ATTTACAACT GCGGGAGATT GCTGGACATA TAATGGAATT TTCCCAAGAC CAGCATGGGT CCAGATTCAT TCAGCTGAAA CTGGAGCGTG CCACACCAGC TGAGCGCCAG CTTGTCTTCA ATGAAATCCT CCAGGCTGCC TACCAACTCA TGGTGGATGT GTTTGGTAAT TACGTCATTC AGAAGTTCTT TGAATTTGGC AGTCTTGAAC AGAAGCTGGC TTTGGCAGAA CGGATTCGAG GCCACGTCCT GTCATTGGCA CTACAGATGT ATGGCTGCCG TGTTATCCAG AAAGCTCTTG AGTTTATTCC TTCAGACCAG CAGGTAATTA ATGAGATGGT TCGGGAACTA GATGGCCATG TCTTGAAGTG TGTGAAAGAT CAGAATGGCA ATCACGTGGT TCAGAAATGC ATTGAATGTG TACAGCCCCA GTCTTTGCAA TTTATCATCG ATGCGTTTAA GGGACAGGTA TTTGCCTTAT CCACACATCC TTATGGCTGC CGAGTGATTC AGAGAATCCT GGAGCACTGT CTCCCTGACC AGACACTCCC TATTTTAGAG GAGCTTCACC AGCACACAGA GCAGCTTGTA CAGGATCAAT ATGGAAATTA TGTAATCCAA CATGTACTGG AGCACGGTCG TCCTGAGGAT AAAAGCAAAA TTGTAGCAGA AATCCGAGGC AATGTACTTG TATTGAGTCA GCACAAATTT GCAAGCAATG TTGTGGAGAA GTGTGTTACT CACGCCTCAC GTACGGAGCG CGCTGTGCTC ATCGATGAGG TGTGCACCAT GAACGACGGT CCCCACAGTG CCTTATACAC CATGATGAAG GACCAGTATG CCAACTACGT GGTCCAGAAG ATGATTGACG TGGCGGAGCC AGGCCAGCGG AAGATCGTCA TGCATAAGAT CCGGCCCCAC ATCGCAACTC TTCGTAAGTA CACCTATGGC AAGCACATTC TGGCCAAGCT GGAGAAGTAC TACATGAAGA ACGGTGTTGA CTTAGGGCCC ATCTGTGGCC CCCTAATGG TATCATCTGA GGCAGTGTCA CCCGCTGTTC CCTCATTCCC GCTGACCTCA CTGGCCCACT GGCAAATCCA ACCAGCAACC AGAAATGTTC TAGTGTAGAG TCTGAGACGG GCAAGTGGTT GCTCCAGGAT TACTCCCTCC TCCAAAAAAG GAATCAAATC CACGAGTGGA AAAGCCTTTG TAAATTTAAT TTTATTACAC ATAACATGTA CTATTTTTTT TAATTGACTA ATTGCCCTGC TGTTTTACTG | |

TABLE 1-continued

Melanoma Biomarker/Housekeeper Sequence Information

| Gene Name | RefSeq Accession | Sequence | SEQ ID NO: |
|---|---|---|---|
| | | GTGTATAGGA TACTTGTACA TAGGTAACCA ATGTACATGG GAGGCCACAT ATTTTGTTCA CTGTTGTATC TATATTTCAC ATGTGGAAAC TTTCAGGGTG GTTGGTTTAA CAAAAAAAAA AAGCTTTAAA AAAAAAAGAA AAAAAGGAAA AGGTTTTTAG CTCATTTGCC TGGCCGGCAA GTTTTGCAAA TAGCTCTTCC CCACCTCCTC ATTTTAGTAA AAAACAAACA AAAACAAAAA AACCTGAGAA GTTTGAATTG TAGTTAAATG ACCCCAAACT GGCATTTAAC ACTGTTTATA AAAATATAT ATATATATAT ATATATATAT AATGAAAAAG GTTTCAGAGT TGCTAAAGCT TCAGTTTGTG ACATTAAGTT TATGAAATTC TAAAAAATGC CTTTTTTGGA GACTATATTA TGCTGAAGAA GGCTGTTCGT GAGGAGGAGA TGCGAGCACC CAGAACGTCT TTTGAGGCTG GGCGGGTGTG ATTGTTTACT GCCTACTGGA TTTTTTTCTA TTAACATTGA AAGGTAAAAT CTGATTATTT AGCATGAGAA AAAAAAATCC AACTCTGCTT TTGGTCTTGC TTCTATAAAT ATATAGTGTA TACTTGGTGT AGACTTTGCA TATATACAAA TTTGTAGTAT TTTCTTGTTT TGATGTCTAA TCTGTATCTA TAATGTACCC TAGTAGTCGA ACATACTTTT GATTGTACAA TTGTACATTT GTATACCTGT AATGTAAATG TGGAGAAGTT TGAATCAACA TAAACACGTT TTTTGGTAAG AAAAGAGAAT TAGCCAGCCC TGTGCATTCA GTGTATATTC TCACCTTTTA TGGTCGTAGC ATATAGTGTT GTATATTGTA AATTGTAATT TCAACCAGAA GTAAATTTTT TTCTTTTGAA GGAATAAATG TTCTTTATAC AGCCTAGTTA ATGTTTAAAA AGAAAAAAAT AGCTTGGTTT TATTTGTCAT CTAGTCTCAA GTATAGCGAG ATTCTTTCTA AATGTTATTC AAGATTGAGT TCTCACTAGT GTTTTTTTAA TCCTAAAAAA GTAATGTTTT GATTTTGTGA CAGTCAAAAG GACGTGCAAA AGTCTAGCCT TGCCCGAGCT TTCCTTACAA TCAGAGCCCC TCTCACCTTG TAAAGTGTGA ATCGCCCTTC CCTTTTGTAC AGAAGATGAA CTGTATTTTG CATTTTGTCT ACTTGTAAGT GAATGTAACA TACTGTCAAT TTTCCTTGTT TGAATATAGA ATTGTAACAC TACACGGTGT ACATTTCCAG AGCCTTGTGT ATATTTCCAA TGAACTTTTT TGCAAGCACA CTTGTAACCA TATGTGTATA ATTAACAAAC CTGTGTATGC TTATGCCTGG GCAACTATTT TTTGTAACTC TTGTGTAGAT TGTCTCTAAA CAATGTGTGA TCTTTATTTT GAAAATACA GAACTTTGGA ATCTGAAAAA AAAAAAAAAA AAAAAAAAAA AAAAAA | |
| ACTB | NM_001101.4 | GAGTGAGCGG CGCGGGGCCA ATCAGCGTGC GCCGTTCCGA AAGTTGCCTT TTATGGCTCG AGCGGCCGCG GCGGCGCCCT ATAAAACCCA GCGGCGCGAC GCGCCACCAC CGCCGAGACC GCGTCCGCCC CGCGAGCACA GAGCCTCGCC TTTGCCGATC CGCCGCCCGT CCACACCCGC CGCCAGCTCA CCATGGATGA TGATATCGCC GCGCTCGTCG TCGACAACGG CTCCGGCATG TGCAAGGCCG GCTTCGCGGG CGACGATGCC CCCCGGGCCG TCTTCCCCTC CATCGTGGGG CGCCCCAGGC ACCAGGGCGT GATGGTGGGC ATGGGTCAGA AGGATTCCTA TGTGGGCGAC GAGGCCCAGA GCAAGAGAGG CATCCTCACC CTGAAGTACC CCATCGAGCA CGGCATCGTC ACCAACTGGG ACGACATGGA GAAAATCTGG CACCACACCT TCTACAATGA GCTGCGTGTG GCTCCCGAGG AGCACCCCGT GCTGCTGACC GAGGCCCCCC TGAACCCCAA GGCCAACCGC GAGAAGATGA CCCAGATCAT GTTTGAGACC TTCAACACCC CAGCCATGTA CGTTGCTATC CAGGCTGTGC TATCCCTGTA CGCCTCTGGC CGTACCACTG GCATCGTGAT GGACTCCGGT GACGGGGTCA CCCACACTGT GCCCATCTAC GAGGGGTATG CCCTCCCCCA TGCCATCCTG CGTCTGGACC TGGCTGGCCG GGACCTGACT GACTACCTCA TGAAGATCCT CACCGAGCGC GGCTACAGCT TCACCACCAC GGCCGAGCGG GAAATCGTGC GTGACATTAA GGAGAAGCTG TGCTACGTCG CCCTGGACTT CGAGCAAGAG ATGGCCACGG CTGCTTCCAG CTCCTCCCTG GAGAAGAGCT ACGAGCTGCC TGACGGCCAG GTCATCACCA TTGGCAATGA GCGGTTCCGC TGCCCTGAGG CACTCTTCCA GCCTTCCTTC CTGGGCATGG AGTCCTGTGG CATCCACGAA ACTACCTTCA ACTCCATCAT GAAGTGTGAC GTGGACATCC GCAAAGACCT GTACGCCAAC ACAGTGCTGT CTGGCGGCAC CACCATGTAC CCTGGCATTG CCGACAGGAT GCAGAAGGAG ATCACTGCCC TGGCACCCAG CACAATGAAG ATCAAGATCA TTGCTCCTCC TGAGCGCAAG TACTCCGTGT GGATCGGCGG CTCCATCCTG GCCTCGCTGT CCACCTTCCA GCAGATGTGG ATCAGCAAGC AGGAGTATGA CGAGTCCGGC CCCTCCATCG TCCACCGCAA ATGCTTCTAG GCGGACTATG ACTTAGTTGC GTTACACCCT TTCTTGACAA AACCTAACTT GCGCAGAAAA CAAGATGAGA TTGGCATGGC | 44 |

TABLE 1-continued

Melanoma Biomarker/Housekeeper Sequence Information

| Gene Name | RefSeq Accession | Sequence | SEQ ID NO: |
|---|---|---|---|
| | | TTTATTTGTT TTTTTTGTTT TGTTTTGGTT TTTTTTTTTT<br>TTTTGGCTTG ACTCAGGATT TAAAAACTGG AACGGTGAAG<br>GTGACAGCAG TCGGTTGGAG CGAGCATCCC CCAAAGTTCA<br>CAATGTGGCC GAGGACTTTG ATTGCACATT GTTGTTTTTT<br>TAATAGTCAT TCCAAATATG AGATGCGTTG TTACAGGAAG<br>TCCCTTGCCA TCCTAAAAGC CACCCCACTT CTCTCTAAGG<br>AGAATGGCCC AGTCCTCTCC CAAGTCCACA CAGGGGAGGT<br>GATAGCATTG CTTTCGTGTA AATTATGTAA TGCAAAATTT<br>TTTTAATCTT CGCCTTAATA CTTTTTTATT TTGTTTTATT<br>TTGAATGATG AGCCTTCGTG CCCCCCCTTC CCCCTTTTTT<br>GTCCCCCAAC TTGAGATGTA TGAAGGCTTT TGGTCTCCCT<br>GGGAGTGGGT GGAGGCAGCC AGGGCTTACC TGTACACTGA<br>CTTGAGACCA GTTGAATAAA AGTGCACACC TTAAAAATGA<br>GGAAAAAAAA AAAAAAAAA | |
| GAPD | NM_002046.6 | GCTCTCTGCT CCTCCTGTTC GACAGTCAGC CGCATCTTCT<br>TTTGCGTCGC CAGCCGAGCC ACATCGCTCA GACACCATGG<br>GGAAGGTGAA GGTCGGAGTC AACGGATTTG GTCGTATTGG<br>GCGCCTGGTC ACCAGGGCTG CTTTTAACTC TGGTAAAGTG<br>GATATTGTTG CCATCAATGA CCCCTTCATT GACCTCAACT<br>ACATGGTTTA CATGTTCCAA TATGATTCCA CCCATGGCAA<br>ATTCCATGGC ACCGTCAAGG CTGAGAACGG GAAGCTTGTC<br>ATCAATGGAA ATCCCATCAC CATCTTCCAG GAGCGAGATC<br>CCTCCAAAAT CAAGTGGGGC GATGCTGGCG CTGAGTACGT<br>CGTGGAGTCC ACTGGCGTCT TCACCACCAT GGAGAAGGCT<br>GGGGCTCATT TGCAGGGGGG AGCCAAAAGG GTCATCATCT<br>CTGCCCCCTC TGCTGATGCC CCCATGTTCG TCATGGGTGT<br>GAACCATGAG AAGTATGACA ACAGCCTCAA GATCATCAGC<br>AATGCCTCCT GCACCACCAA CTGCTTAGCA CCCCTGGCCA<br>AGGTCATCCA TGACAACTTT GGTATCGTGG AAGGACTCAT<br>GACCACAGTC CATGCCATCA CTGCCACCCA GAAGACTGTG<br>GATGGCCCCT CCGGGAAACT GTGGCGTGAT GGCCGCGGGG<br>CTCTCCAGAA CATCATCCCT GCCTCTACTG GCGCTGCCAA<br>GGCTGTGGGC AAGGTCATCC CTGAGCTGAA CGGGAAGCTC<br>ACTGGCATGG CCTTCCGTGT CCCCACTGCC AACGTGTCAG<br>TGGTGGACCT GACCTGCCGT CTAGAAAAAC CTGCCAAATA<br>TGATGACATC AAGAAGGTGG TGAAGCAGGC GTCGGAGGGC<br>CCCCTCAAGG GCATCCTGGG CTACACTGAG CACCAGGTGG<br>TCTCCTCTGA CTTCAACAGC GACACCCACT CCTCCACCTT<br>TGACGCTGGG GCTGGCATTG CCCTCAACGA CCACTTTGTC<br>AAGCTCATTT CCTGGTATGA CAACGAATTT GGCTACAGCA<br>ACAGGGTGGT GGACCTCATG GCCCACATGG CCTCCAAGGA<br>GTAAGACCCC TGGACCACCA GCCCCAGCAA GAGCACAAGA<br>GGAAGAGAGA GACCCTCACT GCTGGGGAGT CCCTGCCACA<br>CTCAGTCCCC CACCACACTG AATCTCCCCT CCTCACAGTT<br>GCCATGTAGA CCCCTTGAAG AGGGGAGGGG CCTAGGGAGC<br>CGCACCTTGT CATGTACCAT CAATAAAGTA CCCTGTGCTC<br>AACCAGTTAA AAAAAAAAA AAAAAAAA | 45 |
| GUSB | NM_000181.3 | GTCCTCAACC AAGATGGCGC GGATGGCTTC AGGCGCATCA<br>CGACACCGGC GCGTCACGCG ACCCGCCCTA CGGGCACCTC<br>CCGCGCTTTT CTTAGCGCCG CAGACGGTGG CCGAGCGGGG<br>GACCGGGAAG CATGGCCCGG GGGTCGGCGG TTGCCTGGGC<br>GGCGCTCGGG CCGTTGTTGT GGGGCTGCGC GCTGGGGCTG<br>CAGGGCGGGA TGCTGTACCC CCAGGAGAGC CCGTCGCGGG<br>AGTGCAAGGA GCTGGACGGC CTCTGGAGCT TCCGCGCCGA<br>CTTCTCTGAC AACCGACGCC GGGGCTTCGA GGAGCAGTGG<br>TACCGGCGGC CGCTGTGGGA GTCAGGCCCC ACCGTGGACA<br>TGCCAGTTCC CTCCAGCTTC AATGACATCA GCCAGGACTG<br>GCGTCTGCGG CATTTTGTCG GCTGGGTGTG GTACGAACGG<br>GAGGTGATCC TGCCGGAGCG ATGGACCCAG GACCTGCGCA<br>CAAGAGTGGT GCTGAGGATT GGCAGTGCCC ATTCCTATGC<br>CATCGTGTGG GTGAATGGGG TCGACACGCT AGAGCATGAG<br>GGGGGCTACC TCCCCTTCGA GGCCGACATC AGCAACCTGG<br>TCCAGGTGGG GCCCCTGCCC TCCCGGCTCC GAATCACTAT<br>CGCCATCAAC AACACACTCA CCCCCACCAC CCTGCCACCA<br>GGGACCATCC AATACCTGAC TGACACCTCC AAGTATCCCA<br>AGGGTTACTT TGTCCAGAAC ACATATTTTG ACTTTTTCAA<br>CTACGCTGGA CTGCAGCGGT CTGTACTTCT GTACACGACA<br>CCCACCACCT ACATCGATGA CATCACCGTC ACCACCAGCG<br>TGGAGCAAGA CAGTGGGCTG GTGAATTACC AGATCTCTGT<br>CAAGGGCAGT AACCTGTTCA AGTTGGAAGT GCGTCTTTTG<br>GATGCAGAAA ACAAAGTCGT GGCGAATGGG ACTGGGACCC<br>AGGGCCAACT TAAGGTGCCA GGTGTCAGCC TCTGGTGGCC | 46 |

TABLE 1-continued

Melanoma Biomarker/Housekeeper Sequence Information

| Gene Name | RefSeq Accession | Sequence | SEQ ID NO: |
|---|---|---|---|
| | | GTACCTGATG CACGAACGCC CTGCCTATCT GTATTCATTG<br>GAGGTGCAGC TGACTGCACA GACGTCACTG GGGCCTGTGT<br>CTGACTTCTA CACACTCCCT GTGGGGATCC GCACTGTGGC<br>TGTCACCAAG AGCCAGTTCC TCATCAATGG GAAACCTTTC<br>TATTTCCACG GTGTCAACAA GCATGAGGAT GCGGACATCC<br>GAGGGAAGGG CTTCGACTGG CCGCTGCTGG TGAAGGACTT<br>CAACCTGCTT CGCTGGCTTG GTGCCAACGC TTTCCGTACC<br>AGCCACTACC CCTATGCAGA GGAAGTGATG CAGATGTGTG<br>ACCGCTATGG GATTGTGGTC ATCGATGAGT GTCCCGGCGT<br>GGGCCTGGCG CTGCCGCAGT TCTTCAACAA CGTTTCTCTG<br>CATCACCACA TGCAGGTGAT GGAAGAAGTG GTGCGTAGGG<br>ACAAGAACCA CCCCGCGGTC GTGATGTGGT CTGTGGCCAA<br>CGAGCCTGCG TCCCACCTAG AATCTGCTGG CTACTACTTG<br>AAGATGGTGA TCGCTCACAC CAAATCCTTG GACCCCTCCC<br>GGCCTGTGAC CTTTGTGAGC AACTCTAACT ATGCAGCAGA<br>CAAGGGGGCT CCGTATGTGG ATGTGATCTG TTTGAACAGC<br>TACTACTCTT GGTATCACGA CTACGGGCAC CTGGAGTTGA<br>TTCAGCTGCA GCTGGCCACC CAGTTTGAGA ACTGGTATAA<br>GAAGTATCAG AAGCCCATTA TTCAGAGCGA GTATGGAGCA<br>GAAACGATTG CAGGGTTTCA CCAGGATCCA CCTCTGATGT<br>TCACTGAAGA GTACCAGAAA AGTCTGCTAG AGCAGTACCA<br>TCTGGGTCTG GATCAAAAAC GCAGAAAATA CGTGGTTGGA<br>GAGCTCATTT GGAATTTTGC CGATTTCATG ACTGAACAGT<br>CACCGACGAG AGTGCTGGGG AATAAAAAGG GGATCTTCAC<br>TCGGCAGAGA CAACCAAAAA GTGCAGCGTT CCTTTTGCGA<br>GAGAGATACT GGAAGATTGC CAATGAAACC AGGTATCCCC<br>ACTCAGTAGC CAAGTCACAA TGTTTGGAAA ACAGCCTGTT<br>TACTTGAGCA AGACTGATAC CACCTGCGTG TCCCTTCCTC<br>CCCGAGTCAG GGCGACTTCC ACAGCAGCAG AACAAGTGCC<br>TCCTGGACTG TTCACGGCAG ACCAGAACGT TTCTGGCCTG<br>GGTTTTGTGG TCATCTATTC TAGCAGGGAA CACTAAAGGT<br>GGAAATAAAA GATTTTCTAT TATGGAAATA AAGAGTTGGC<br>ATGAAAGTGG CTACTGAAAA AAAAAAAAAA AAAAAAAAA A | |
| RPLP0 | NM_001002.3 | GTCTGACGGG CGATGGCGCA GCCAATAGAC AGGAGCGCTA<br>TCCGCGGTTT CTGATTGGCT ACTTTGTTCG CATTATAAAA<br>GGCACGCGCG GGCGCGAGGC CCTTCTCTCG CCAGGCGTCC<br>TCGTGGAAGT GACATCGTCT TTAAACCCTG CGTGGCAATC<br>CCTGACGCAC CGCCGTGATG CCCAGGGAAG ACAGGGCGAC<br>CTGGAAGTCC AACTACTTCC TTAAGATCAT CCAACTATTG<br>GATGATTATC CGAAATGTTT CATTGTGGGA GCAGACAATG<br>TGGGCTCCAA GCAGATGCAG CAGATCCGCA TGTCCCTTCG<br>CGGGAAGGCT GTGGTGCTGA TGGGCAAGAA CACCATGATG<br>CGCAAGGCCA TCCGAGGGCA CCTGGAAAAC AACCCAGCTC<br>TGGAGAAACT GCTGCCTCAT ATCCGGGGGA ATGTGGGCTT<br>TGTGTTCACC AAGGAGGACC TCACTGAGAT CAGGGACATG<br>TTGCTGGCCA ATAAGGTGCC AGCTGCTGCC CGTGCTGGTG<br>CCATTGCCCC ATGTGAAGTC ACTGTGCCAG CCCAGAACAC<br>TGGTCTCGGG CCCGAGAAGA CCTCCTTTTT CCAGGCTTTA<br>GGTATCACCA CTAAAATCTC CAGGGGCACC ATTGAAATCC<br>TGAGTGATGT GCAGCTGATC AAGACTGGAG ACAAAGTGGG<br>AGCCAGCGAA GCCACGCTGC TGAACATGCT CAACATCTCC<br>CCCTTCTCCT TTGGGCTGGT CATCCAGCAG GTGTTCGACA<br>ATGGCAGCAT CTACAACCCT GAAGTGCTTG ATATCACAGA<br>GGAAACTCTG CATTCTCGCT TCCTGGAGGG TGTCCGCAAT<br>GTTGCCAGTG TCTGTCTGCA GATTGGCTAC CCAACTGTTG<br>CATCAGTACC CCATTCTATC ATCAACGGGT ACAAACGAGT<br>CCTGGCCTTG TCTGTGGAGA CGGATTACAC CTTCCCACTT<br>GCTGAAAAGG TCAAGGCCTT CTTGGCTGAT CCATCTGCCT<br>TTGTGGCTGC TGCCCCTGTG GCTGCTGCCA CCACAGCTGC<br>TCCTGCTGCT GCTGCAGCCC CAGCTAAGGT TGAAGCCAAG<br>GAAGAGTCGG AGGAGTCGGA CGAGGATATG GGATTTGGTC<br>TCTTTGACTA ATCACCAAAA AGCAACCAAC TTAGCCAGTT<br>TTATTTGCAA AACAAGGAAA TAAAGGCTTA CTTCTTTAAA<br>AAGTAAAAAA AAAAAAAAAA AAAAAAAA | 47 |
| TFRC | NM_003234.3 | AGAGCGTCGG GATATCGGGT GGCGGCTCGG GACGGAGGAC<br>GCGCTAGTGT GAGTGCGGGC TTCTAGAACT ACACCGACCC<br>TCGTGTCCTC CCTTCATCCT GCGGGGCTGG CTGGAGCGGC<br>CGCTCCGGTG CTGTCCAGCA GCCATAGGGA GCCGCACGGG<br>GAGCGGGAAA GCGGTCGCGG CCCCAGGCGG GCGCGGCCGG<br>ATGGAGCGGG GCCGCGAGCC TGTGGGGAAG GGGCTGTGGC<br>GGCGCCTCGA GCGGCTGCAG GTTCTTCTGT GTGGCAGTTC<br>AGAATGATGG ATCAAGCTAG ATCAGCATTC TCTAACTTGT | 48 |

TABLE 1-continued

Melanoma Biomarker/Housekeeper Sequence Information

| Gene Name | RefSeq Accession | Sequence | SEQ ID NO: |
|---|---|---|---|
| | | TTGGTGGAGA ACCATTGTCA TATACCCGGT TCAGCCTGGC | |
| | | TCGGCAAGTA GATGGCGATA ACAGTCATGT GGAGATGAAA | |
| | | CTTGCTGTAG ATGAAGAAGA AAATGCTGAC AATAACACAA | |
| | | AGGCCAATGT CACAAAACCA AAAAGGTGTA GTGGAAGTAT | |
| | | CTGCTATGGG ACTATTGCTG TGATCGTCTT TTTCTTGATT | |
| | | GGATTTATGA TTGGCTACTT GGGCTATTGT AAAGGGGTAG | |
| | | AACCAAAAAC TGAGTGTGAG AGACTGGCAG GAACCGAGTC | |
| | | TCCAGTGAGG GAGGAGCCAG GAGAGGACTT CCCTGCAGCA | |
| | | CGTCGCTTAT ATTGGGATGA CCTGAAGAGA AAGTTGTCGG | |
| | | AGAAACTGGA CAGCACAGAC TTCACCGGCA CCATCAAGCT | |
| | | GCTGAATGAA AATTCATATG TCCCTCGTGA GGCTGGATCT | |
| | | CAAAAAGATG AAAATCTTGC GTTGTATGTT GAAAATCAAT | |
| | | TTCGTGAATT TAAACTCAGC AAAGTCTGGC GTGATCAACA | |
| | | TTTTGTTAAG ATTCAGGTCA AAGACAGCGC TCAAAACTCG | |
| | | GTGATCATAG TTGATAAGAA CGGTAGACTT GTTTACCTGG | |
| | | TGGAGAATCC TGGGGGTTAT GTGGCGTATA GTAAGGCTGC | |
| | | AACAGTTACT GGTAAACTGG TCCATGCTAA TTTTGGTACT | |
| | | AAAAAAGATT TTGAGGATTT ATACACTCCT GTGAATGGAT | |
| | | CTATAGTGAT TGTCAGAGCA GGGAAAATCA CCTTTGCGAA | |
| | | AAAGGTTGCA AATGCTGAAA GCTTAAATGC AATTGGTGTG | |
| | | TTGATATACA TGGACCAGAC TAAATTTCCC ATTGTTAACG | |
| | | CAGAACTTTC ATTCTTTGGA CATGCTCATC TGGGGACAGG | |
| | | TGACCCTTAC ACACCTGGAT TCCCTTCCTT CAATCACACT | |
| | | CAGTTTCCAC CATCTCGGTC ATCAGGATTG CCTAATATAC | |
| | | CTGTCCAGAC AATCTCCAGA GCTGCTGCAG AAAAGCTGTT | |
| | | TGGGAATATG GAAGGAGACT GTCCCTCTGA CTGGAAAACA | |
| | | GACTCTACAT GTAGGATGGT AACCTCAGAA AGCAAGAATG | |
| | | TGAAGCTCAC TGTGAGCAAT GTGCTGAAAG AGATAAAAAT | |
| | | TCTTAACATC TTTGGAGTTA TTAAAGGCTT TGTAGAACCA | |
| | | GATCACTATG TTGTAGTTGG GGCCCAGAGA GATGCATGGG | |
| | | GCCCTGGAGC TGCAAAATCC GGTGTAGGCA CAGCTCTCCT | |
| | | ATTGAAACTT GCCCAGATGT TCTCAGATAT GGTCTTAAAA | |
| | | GATGGGTTTC AGCCCAGCAG AAGCATTATC TTTGCCAGTT | |
| | | GGAGTGCTGG AGACTTTGGA TCGGTTGGTG CCACTGAATG | |
| | | GCTAGAGGGA TACCTTTCGT CCCTGCATTT AAAGGCTTTC | |
| | | ACTTATATTA ATCTGGATAA AGCGGTTCTT GGTACCAGCA | |
| | | ACTTCAAGGT TTCTGCCAGC CCACTGTTGT ATACGCTTAT | |
| | | TGAGAAAACA ATGCAAAATG TGAAGCATCC GGTTACTGGG | |
| | | CAATTTCTAT ATCAGGACAG CAACTGGGCC AGCAAAGTTG | |
| | | AGAAACTCAC TTTAGACAAT GCTGCTTTCC CTTTCCTTGC | |
| | | ATATTCTGGA ATCCCAGCAG TTTCTTTCTG TTTTTGCGAG | |
| | | GACACAGATT ATCCTTATTT GGGTACCACC ATGGACACCT | |
| | | ATAAGGAACT GATTGAGAGG ATTCCTGAGT TGAACAAAGT | |
| | | GGCACGAGCA GCTGCAGAGG TCGCTGGTCA GTTCGTGATT | |
| | | AAACTAACCC ATGATGTTGA ATTGAACCTG GACTATGAGA | |
| | | GGTACAACAG CCAACTGCTT TCATTTGTGA GGGATCTGAA | |
| | | CCAATACAGA GCAGACATAA AGGAAATGGG CCTGAGTTTA | |
| | | CAGTGGCTGT ATTCTGCTCG TGGAGACTTC TTCCGTGCTA | |
| | | CTTCCAGACT AACAACAGAT TTCGGGAATG CTGAGAAAAC | |
| | | AGACAGATTT GTCATGAAGA AACTCAATGA TCGTGTCATG | |
| | | AGAGTGGAGT ATCACTTCCT CTCTCCCTAC GTATCTCCAA | |
| | | AAGAGTCTCC TTTCCGACAT GTCTTCTGGG GCTCCGGCTC | |
| | | TCACACGCTG CCAGCTTTAC TGGAGAACTT GAAACTGCGT | |
| | | AAACAAAATA ACGGTGCTTT TAATGAAACG CTGTTCAGAA | |
| | | ACCAGTTGGC TCTAGCTACT TGGACTATTC AGGGAGCTGC | |
| | | AAATGCCCTC TCTGGTGACG TTTGGGACAT TGACAATGAG | |
| | | TTTTAAATGT GATACCCATA GCTTCCATGA GAACAGCAGG | |
| | | GTAGTCTGGT TTCTAGACTT GTGCTGATCG TGCTAAATTT | |
| | | TCAGTAGGGC TACAAAACCT GATGTTAAAA TTCCATCCCA | |
| | | TCATCTTGGT ACTACTAGAT GTCTTTAGGC AGCAGCTTTT | |
| | | AATACAGGGT AGATAACCTG TACTTCAAGT TAAAGTGAAT | |
| | | AACCACTTAA AAAATGTCCA TGATGGAATA TTCCCCTATC | |
| | | TCTAGAATTT TAAGTGCTTT GTAATGGGAA CTGCCTCTTT | |
| | | CCTGTTGTTG TTAATGAAAA TGTCAGAAAC CAGTTATGTG | |
| | | AATGATCTCT CTGAATCCTA AGGGCTGGTC TCTGCTGAAG | |
| | | GTTGTAAGTG GTCGCTTACT TTGAGTGATC CTCCAACTTC | |
| | | ATTTGATGCT AAATAGGAGA TACCAGGTTG AAAGACCTTC | |
| | | TCCAAATGAG ATCAAGCCT TTCCATAAGG AATGTAGCTG | |
| | | GTTTCCTCAT TCCTGAAAGA AACAGTTAAC TTTCAGAAGA | |
| | | GATGGGCTTG TTTTCTTGCC AATGAGGTCT GAAATGGAGG | |
| | | TCCTTCTGCT GGATAAAATG AGGTTCAACT GTTGATTGCA | |
| | | GGAATAAGGC CTTAATATGT TAACCTCAGT GTCATTTATG | |
| | | AAAAGAGGGG ACCAGAAGCC AAAGACTTAG TATATTTTCT | |
| | | TTTCCTCTGT CCCTTCCCCC ATAAGCCTCC ATTTAGTTCT | |

TABLE 1-continued

Melanoma Biomarker/Housekeeper Sequence Information

| Gene Name | RefSeq Accession | Sequence | SEQ ID NO: |
|---|---|---|---|
| | | TTGTTATTTT TGTTTCTTCC AAAGCACATT GAAAGAGAAC CAGTTTCAGG TGTTTAGTTG CAGACTCAGT TTGTCAGACT TTAAAGAATA ATATGCTGCC AAATTTTGGC CAAAGTGTTA ATCTTAGGGG AGAGCTTTCT GTCCTTTTGG CACTGAGATA TTTATTGTTT ATTTATCAGT GACAGAGTTC ACTATAAATG GTGTTTTTTT AATAGAATAT AATTATCGGA AGCAGTGCCT TCCATAATTA TGACAGTTAT ACTGTCGGTT TTTTTTAAAT AAAAGCAGCA TCTGCTAATA AAACCCAACA GATACTGGAA GTTTTGCATT TATGGTCAAC ACTTAAGGGT TTTAGAAAAC AGCCGTCAGC CAAATGTAAT TGAATAAAGT TGAAGCTAAG ATTTAGAGAT GAATTAAATT TAATTAGGGG TTGCTAAGAA GCGAGCACTG ACCAGATAAG AATGCTGGTT TTCCTAAATG CAGTGAATTG TGACCAAGTT ATAAATCAAT GTCACTTAAA GGCTGTGGTA GTACTCCTGC AAAATTTTAT AGCTCAGTTT ATCCAAGGTG TAACTCTAAT TCCCATTTTG CAAAATTTCC AGTACCTTTG TCACAATCCT AACACATTAT CGGGAGCAGT GTCTTCCATA ATGTATAAAG AACAAGGTAG TTTTTACCTA CCACAGTGTC TGTATCGGAG ACAGTGATCT CCATATGTTA CACTAAGGGT GTAAGTAATT ATCGGGAACA GTGTTTCCCA TAATTTTCTT CATGCAATGA CATCTTCAAA GCTTGAAGAT CGTTAGTATC TAACATGTAT CCCAACTCCT ATAATTCCCT ATCTTTTAGT TTTAGTTGCA GAAACATTTT GTGGTCATTA AGCATTGGGT GGGTAAATTC AACCACTGTA AAATGAAATT ACTACAAAAT TTGAAATTTA GCTTGGGTTT TTGTTACCTT TATGGTTTCT CCAGGTCCTC TACTTAATGA GATAGTAGCA TACATTTATA ATGTTTGCTA TTGACAAGTC ATTTTAACTT TATCACATTA TTTGCATGTT ACCTCCTATA AACTTAGTGC GGACAAGTTT TAATCCAGAA TTGACCTTTT GACTTAAAGC AGAGGGACTT TGTATAGAAG GTTTGGGGGC TGTGGGGAAG GAGAGTCCCC TGAAGGTCTG ACACGTCTGC CTACCCATTC GTGGTGATCA ATTAAATGTA GGTATGAATA AGTTCGAAGC TCCGTGAGTG AACCATCATT ATAAACGTGA TGATCAGCTG TTTGTCATAG GGCAGTTGGA AACGGCCTCC TAGGGAAAAG TTCATAGGGT CTCTTCAGGT TCTTAGTGTC ACTTACCTAG ATTTACAGCC TCACTTGAAT GTGTCACTAC TCACAGTCTC TTTAATCTTC AGTTTTATCT TTAATCTCCT CTTTTATCTT GGACTGACAT TTAGCGTAGC TAAGTGAAAA GGTCATAGCT GAGATTCCTG GTTCGGGTGT TACGCACACG TACTTAAATG AAAGCATGTG GCATGTTCAT CGTATAACAC AATATGAATA CAGGGCATGC ATTTTGCAGC AGTGAGTCTC TTCAGAAAAC CCTTTTCTAC AGTTAGGGTT GAGTTACTTC CTATCAAGCC AGTACGTGCT AACAGGCTCA ATATTCCTGA ATGAAATATC AGACTAGTGA CAAGCTCCTG GTCTTGAGAT GTCTTCTCGT TAAGGAGATG GGCCTTTTGG AGGTAAAGGA TAAAATGAAT GAGTTCTGTC ATGATTCACT ATTCTAGAAC TTGCATGACC TTTACTGTGT TAGCTCTTTG AATGTTCTTG AAATTTTAGA CTTTCTTTGT AAACAAATGA TATGTCCTTA TCATTGTATA AAAGCTGTTA TGTGCAACAG TGTGGAGATT CCTTGTCTGA TTTAATAAAA TACTTAAACA CTGAAAAAAA AAAA | |
| 18S | X03205.1 | TACCTGGTTG ATCCTGCCAG TAGCATATGC TTGTCTCAAA GATTAAGCCA TGCATGTCTA AGTACGCACG GCCGGTACAG TGAAACTGCG AATGGCTCAT TAAATCAGTT ATGGTTCCTT TGGTCGCTCG CTCCTCTCCC ACTTGGATAA CTGTGGTAAT TCTAGAGCTA ATACATGCCG ACGGGCGCTG ACCCCCTTCG CGGGGGGGAT GCGTGCATTT ATCAGATCAA AACCAACCCG GTCAGCCCCT CTCCGGCCCC GGCCGGGGGG CGGGCGCCGG CGGCTTTGGT GACTCTAGAT AACCTCGGGC CGATCGCACG CCCCCCGTGG CGGCGACGAC CCATTCGAAC GTCTGCCCTA TCAACTTTCG ATGGTAGTCG CCGTGCCTAC CATGGTGACC ACGGGTGACG GGGAATCAGG GTTCGATTCC GGAGAGGGAG CCTGAGAAAC GGCTACCACA TCCAAGGAAG GCAGCAGGCG CGCAAATTAC CCACTCCCGA CCCGGGGAGG TAGTGACGAA AAATAACAAT ACAGGACTCT TTCGAGGCCC TGTAATTGGA ATGAGTCCAC TTTAAATCCT TTAACGAGGA TCCATTGGAG GGCAAGTCTG GTGCCAGCAG CCGCGGTAAT TCCAGCTCCA ATAGCGTATA TTAAAGTTGC TGCAGTTAAA AAGCTCGTAG TTGGATCTTG GGAGCGGGCG GGCGGTCCGC CGCGAGGCGA GCCACCGCCC GTCCCCGCCC CTTGCCTCTC GGCGCCCCCT CGATGCTCTT AGCTGAGTGT CCCGCGGGGC CCGAAGCGTT TACTTTGAAA AAATTAGAGT GTTCAAAGCA GGCCCGAGCC GCCTGGATAC CGCAGCTAGG AATAATGGAA TAGGACCGCG GTTCTATTTT GTTGGTTTTC GGAACTGAGG CCATGATTAA GAGGGACGGC CGGGGGCATT CGTATTGCGC CGCTAGAGGT | 49 |

TABLE 1-continued

Melanoma Biomarker/Housekeeper Sequence Information

| Gene Name | RefSeq Accession | Sequence | SEQ ID NO: |
|---|---|---|---|
| | | GAAATTCTTG GACCGGCGCA AGACGGACCA GAGCGAAAGC ATTTGCCAAG AATGTTTTCA TTAATCAAGA ACGAAAGTCG GAGGTTCGAA GACGATCAGA TACCGTCGTA GTTCCGACCA TAAACGATGC CGACCGGCGA TGCGGCGGCG TTATTCCCAT GACCCGCCGG GCAGCTTCCG GGAAACCAAA GTCTTTGGGT TCCGGGGGA GTATGGTTGC AAAGCTGAAA CTTAAAGGAA TTGACGGAAG GGCACCACCA GGAGTGGAGC CTGCGGCTTA ATTTGACTCA ACACGGGAAA CCTCACCCGG CCCGGACACG GACAGGATTG ACAGATTGAT AGCTCTTTCT CGATTCCGTG GGTGGTGGTG CATGGCCGTT CTTAGTTGGT GGAGCGATTT GTCTGGTTAA TTCCGATAAC GAACGAGACT CTGGCATGCT AACTAGTTAC GCGACCCCCG AGCGGTCGGC GTCCCCCAAC TTCTTAGAGG GACAAGTGGC GTTCAGCCAC CCGAGATTGA GCAATAACAG GTCTGTGATG CCCTTAGATG TCCGGGGCTG CACGCGCGCT ACACTGACTG GCTCAGCGTG TGCCTACCCT ACGCCGGCAG GCGCGGGTAA CCCGTTGAAC CCCATTCGTG ATGGGGATCG GGGATTGCAA TTATTCCCCA TGAACGAGGA ATTCCCAGTA AGTGCGGGTC ATAAGCTTGC GTTGATTAAG TCCCTGCCCT TTGTACACAC CGCCCGTCGC TACTACCGAT TGGATGGTTT AGTGAGGCCC TCGGATCGGC CCCGCCGGGG TCGGCCCACG GCCCTGGCGG AGCGCTGAGA AGACGGTCGA ACTTGACTAT CTAGAGGAAG TAAAAGTCGT AACAAGGTTT CCGTAGGTGA ACCTGCGGAA GGATCATTA | |
| PPIA | NM_021130.4 | GGGGCCGAAC GTGGTATAAA AGGGGCGGGA GGCCAGGCTC GTGCCGTTTT GCAGACGCCA CCGCCGAGGA AAACCGTGTA CTATTAGCCA TGGTCAACCC CACCGTGTTC TTCGACATTG CCGTCGACGG CGAGCCCTTG GGCCGCGTCT CCTTTGAGCT GTTTGCAGAC AAGGTCCCAA AGACAGCAGA AAATTTTCGT GCTCTGAGCA CTGGAGAGAA AGGATTTGGT TATAAGGGTT CCTGCTTTCA CAGAATTATT CCAGGGTTTA TGTGTCAGGG TGGTGACTTC ACACGCCATA ATGGCACTGG TGGCAAGTCC ATCTATGGGG AGAAATTTGA AGATGAGAAC TTCATCCTAA AGCATACGGG TCCTGGCATC TTGTCCATGG CAAATGCTGG ACCCAACACA AATGGTTCCC AGTTTTTCAT CTGCACTGCC AAGACTGAGT GGTTGGATGG CAAGCATGTG GTGTTTGGCA AAGTGAAAGA AGGCATGAAT ATTGTGGAGG CCATGGAGCG CTTTGGGTCC AGGAATGGCA AGACCAGCAA GAAGATCACC ATTGCTGACT GTGGACAACT CGAATAAGTT TGACTTGTGT TTTATCTTAA CCACCAGATC ATTCCTTCTG TAGCTCAGGA GAGCACCCCT CCACCCCATT TGCTCGCAGT ATCCTAGAAT CTTTGTGCTC TCGCTGCAGT TCCCTTTGGG TTCCATGTTT TCCTTGTTCC CTCCCATGCC TAGCTGGATT GCAGAGTTAA GTTTATGATT ATGAAATAAA AACTAAATAA CAATTGTCCT CGTTTGAGTT AAGAGTGTTG ATGTAGGCTT TATTTTAAGC AGTAATGGGT TACTTCTGAA ACATCACTTG TTTGCTTAAT TCTACACAGT ACTTAGATTT TTTTTACTTT CCAGTCCCAG GAAGTGTCAA TGTTTGTTGA GTGGAATATT GAAAATGTAG GCAGCAACTG GGCATGGTGG CTCACTGTCT GTAATGTATT ACCTGAGGCA GAAGACCACC TGAGGGTAGG AGTCAAGATC AGCCTGGGCA ACATAGTGAG ACGCTGTCTC TACAAAAAAT AATTAGCCTG GCCTGGTGGT GCATGCCTAG TCCTAGCTGA TCTGGAGGCT GACGTGGGAG GATTGCTTGA GCCTAGAGTG AGCTATTATC ATGCCACTGT ACAGCCTGGG TGTTCACAGA TCTTGTGTCT CAAAGGTAGG CAGAGGCAGG AAAAGCAAGG AGCCAGAATT AAGAGGTTGG GTCAGTCTGC AGTGAGTTCA TGCATTTAGA GGTGTTCTTC AAGATGACTA ATGTCAAAAA TTGAGACATC TGTTGCGGTT TTTTTTTTTT TTTTTTCCCC TGGAATGCAG TGGCGTGATC TCAGCTCACT GCAGCCTCCG CCTCCTGGGT TCAAGTGATT CTAGTGCCTC AGCCTCCTGA GTAGCTGGGA TAATGGGCGT GTGCCACCAT GCCCAGCTAA TTTTTGTATT TTTAGTATAG ATGGGGTTTC ATCATTTTGA CCAGGCTGGT CTCAAACTCT TGACCTCAGC TGATGCGCCT GCCTTGGCCT CCCAAACTGC TGAGATTACA GATGTGAGCC ACCGCACCCT ACCTCATTTT CTGTAACAAA GCTAAGCTTG AACACTGTTG ATGTTCTTGA GGGAAGCATA TTGGGCTTTA GGCTGTAGGT CAAGTTTATA CATCTTAATT ATGGTGGAAT TCCTATGTAG AGTCTAAAAA GCCAGGTACT TGGTGCTACA GTCAGTCTCC CTGCAGAGGG TTAAGGCGCA GACTACCTGC AGTGAGGAGG TACTCTTGT AGCATATAGA GCCTCTCCCT AGCTTTGGTT ATGGAGGCTT TGAGGTTTTG CAAACCTGAC CAATTTAAGC CATAAGATCT GGTCAAAGGG ATACCCTTCC CACTAAGGAC TTGGTTTCTC AGGAAATTAT ATGTACAGTG CTTGCTGGCA GTTAGATGTC AGGACAATCT AAGCTGAGAA | 50 |

TABLE 1-continued

Melanoma Biomarker/Housekeeper Sequence Information

| Gene Name | RefSeq Accession | Sequence | SEQ ID NO: |
|---|---|---|---|
| | | AACCCCTTCT CTGCCCACCT TAACAGACCT CTAGGGTTCT TAACCCAGCA ATCAAGTTTG CCTATCCTAG AGGTGGCGGA TTTGATCATT TGGTGTGTTG GGCAATTTTT GTTTTACTGT CTGGTTCCTT CTGCGTGAAT TACCACCACC ACCACTTGTG CATCTCAGTC TTGTGTGTTG TCTGGTTACG TATTCCCTGG GTGATACCAT TCAATGTCTT AATGTACTTG TGGCTCAGAC CTGAGTGCAA GGTGGAAATA AACATCAAAC ATCTTTTCAT TATCCCTA | |
| PGK1 | NM_000291.3 | GAGAGCAGCG GCCGGGAAGG GGCGGTGCGG GAGGCGGGGT GTGGGGCGGT AGTGTGGGCC CTGTTCCTGC CCGCGCGGTG TTCCGCATTC TGCAAGCCTC CGGAGCGCAC GTCGGCAGTC GGCTCCCTCG TTGACCGAAT CACCGACCTC TCTCCCCAGC TGTATTTCCA AAATGTCGCT TTCTAACAAG CTGACGCTGG ACAAGCTGGA CGTTAAAGGG AAGCGGGTCG TTATGAGAGT CGACTTCAAT GTTCCTATGA AGAACAACCA GATAACAAAC AACCAGAGGA TTAAGGCTGC TGTCCCAAGC ATCAAATTCT GCTTGGACAA TGGAGCCAAG TCGGTAGTCC TTATGAGCCA CCTAGGCCGG CCTGATGGTG TGCCCATGCC TGACAAGTAC TCCTTAGAGC CAGTTGCTGT AGAACTCAAA TCTCTGCTGG GCAAGGATGT TCTGTTCTTG AAGGACTGTG TAGGCCCAGA AGTGGAGAAA GCCTGTGCCA ACCCAGCTGC TGGGTCTGTC ATCCTGCTGG AGAACCTCCG CTTTCATGTG GAGGAAGAAG GGAAGGGAAA AGATGCTTCT GGGAACAAGG TTAAAGCCGA GCCAGCCAAA ATAGAAGCTT TCCGAGCTTC ACTTTCCAAG CTAGGGGATG TCTATGTCAA TGATGCTTTT GGCACTGCTC ACAGAGCCCA CAGCTCCATG GTAGGAGTCA ATCTGCCACA GAAGGCTGGT GGGTTTTTGA TGAAGAAGGA GCTGAACTAC TTTGCAAAGG CCTTGGAGAG CCCAGAGCGA CCCTTCCTGG CCATCCTGGG CGGAGCTAAA GTTGCAGACA AGATCCAGCT CATCAATAAT ATGCTGGACA AAGTCAATGA GATGATTATT GGTGGTGGAA TGGCTTTTAC CTTCCTTAAG GTGCTCAACA ACATGGAGAT TGGCACTTCT CTGTTTGATG AAGAGGGAGC CAAGATTGTC AAAGACCTAA TGTCCAAAGC TGAGAAGAAT GGTGTGAAGA TTACCTTGCC TGTTGACTTT GTCACTGCTG ACAAGTTTGA TGAGAATGCC AAGACTGGCC AAGCCACTGT GGCTTCTGGC ATACCTGCTG GCTGGATGGG CTTGGACTGT GGTCCTGAAA GCAGCAAGAA GTATGCTGAG GCTGTCACTC GGGCTAAGCA GATTGTGTGG AATGGTCCTG TGGGGGTATT TGAATGGGAA GCTTTTGCCC GGGGAACCAA AGCTCTCATG GATGAGGTGG TGAAAGCCAC TTCTAGGGGC TGCATCACCA TCATAGGTGG TGGAGACACT GCCACTTGCT GTGCCAAATG GAACACGGAG GATAAAGTCA GCCATGTGAG CACTGGGGGT GGTGCCAGTT TGGAGCTCCT GGAAGGTAAA GTCCTTCCTG GGGTGGATGC TCTCAGCAAT ATTTAGTACT TTCCTGCCTT TTAGTTCCTG TGCACAGCCC CTAAGTCAAC TTAGCATTTT CTGCATCTCC ACTTGGCATT AGCTAAAACC TTCCATGTCA AGATTCAGCT AGTGGCCAAG AGATGCAGTG CCAGGAACCC TTAAACAGTT GCACAGCATC TCAGCTCATC TTCACTGCAC CCTGGATTTG CATACATTCT TCAAGATCCC ATTTGAATTT TTTAGTGACT AAACCATTGT GCATTCTAGA GTGCATATAT TTATATTTTG CCTGTTAAAA AGAAAGTGAG CAGTGTTAGC TTAGTTCTCT TTTGATGTAG GTTATTATGA TTAGCTTTGT CACTGTTTCA CTACTCAGCA TGGAAACAAG ATGAAATTCC ATTTGTAGGT AGTGAGACAA AATTGATGAT CCATTAAGTA AACAATAAAA GTGTCCATTG AAACCGTGAT TTTTTTTTTT TTCCTGTCAT ACTTTGTTAG GAAGGGTGAG AATAGAATCT TGAGGAACGG ATCAGATGTC TATATTGCTG AATGCAAGAA GTGGGGCAGC AGCAGTGGAG AGATGGGACA ATTAGATAAA TGTCCATTCT TTATCAAGGG CCTACTTTAT GGCAGACATT GTGCTAGTGC TTTTATTCTA ACTTTTATTT TTATCAGTTA CACATGATCA TAATTTAAAA AGTCAAGGCT TATAACAAAA AAGCCCCAGC CCATTCCTCC CATTCAAGAT TCCCACTCCC CAGAGGTGAC CACTTTCAAC TCTTGAGTTT TTCAGGTATA TACCTCCATG TTTCTAAGTA ATATGCTTAT ATTGTTCACT TCTTTTTTTT TTATTTTTTA AAGAAATCTA TTTCATACCA TGGAGGAAGG CTCTGTTCCA CATATATTTC CACTTCTTCA TTCTCTCGGT ATAGTTTTGT CACAATTATA GATTAGATCA AAAGTCTACA TAACTAATAC AGCTGAGCTA TGTAGTATGC TATGATTAAA TTTACTTATG TAAAAAAAAA AAAAAAAA | 51 |
| RPL13A | NM_012423.3 | CACTTCTGCC GCCCCTGTTT CAAGGGATAA GAAACCCTGC GACAAAACCT CCTCCTTTTC CAAGCGGCTG CCGAAGATGG CGGAGGTGCA GGTCCTGGTG CTTGATGGTC GAGGCCATCT | 52 |

TABLE 1-continued

Melanoma Biomarker/Housekeeper Sequence Information

| Gene Name | RefSeq Accession | Sequence | SEQ ID NO: |
|---|---|---|---|
| | | CCTGGGCCGC CTGGCGGCCA TCGTGGCTAA ACAGGTACTG<br>CTGGGCCGGA AGGTGGTGGT CGTACGCTGT GAAGGCATCA<br>ACATTTCTGG CAATTTCTAC AGAAACAAGT TGAAGTACCT<br>GGCTTTCCTC CGCAAGCGGA TGAACACCAA CCCTTCCCGA<br>GGCCCCTACC ACTTCCGGGC CCCCAGCCGC ATCTTCTGGC<br>GGACCGTGCG AGGTATGCTG CCCCACAAAA CCAAGCGAGG<br>CCAGGCCGCT CTGGACCGTC TCAAGGTGTT TGACGGCATC<br>CCACCGCCCT ACGACAAGAA AAAGCGGATG GTGGTTCCTG<br>CTGCCCTCAA GGTCGTGCGT CTGAAGCCTA CAAGAAAGTT<br>TGCCTATCTG GGGCGCCTGG CTCACGAGGT TGGCTGGAAG<br>TACCAGGCAG TGACAGCCAC CCTGGAGGAG AAGAGGAAAG<br>AGAAAGCCAA GATCCACTAC CGGAAGAAGA AACAGCTCAT<br>GAGGCTACGG AAACAGGCCG AGAAGAACGT GGAGAAGAAA<br>ATTGACAAAT ACACAGAGGT CCTCAAGACC CACGGACTCC<br>TGGTCTGAGC CCAATAAAGA CTGTTAATTC CTCATGCGTT<br>GCCTGCCCTT CCTCCATTGT TGCCCTGGAA TGTACGGGAC<br>CCAGGGGCAG CAGCAGTCCA GGTGCCACAG GCAGCCCTGG<br>GACATAGGAA GCTGGGAGCA AGGAAAGGGT CTTAGTCACT<br>GCCTCCCGAA GTTGCTTGAA AGCACTCGGA GAATTGTGCA<br>GGTGTCATTT ATCTATGACC AATAGGAAGA GCAACCAGTT<br>ACTATGAGTG AAAGGGAGCC AGAAGACTGA TTGGAGGGCC<br>CTATCTTGTG AGTGGGGCAT CTGTTGGACT TTCCACCTGG<br>TCATATACTC TGCAGCTGTT AGAATGTGCA AGCACTTGGG<br>GACAGCATGA GCTTGCTGTT GTACACAGGG TATTTCTAGA<br>AGCAGAAATA GACTGGGAAG ATGCACAACC AAGGGGTTAC<br>AGGCATCGCC CATGCTCCTC ACCTGTATTT TGTAATCAGA<br>AATAAATTGC TTTTAAAGAA AAAAAAAAA AAAAAA | |
| B2M | NM_004048.2 | AATATAAGTG GAGGCGTCGC GCTGGCGGGC ATTCCTGAAG<br>CTGACAGCAT TCGGGCCGAG ATGTCTCGCT CCGTGGCCTT<br>AGCTGTGCTC GCGCTACTCT CTCTTTCTGG CCTGGAGGCT<br>ATCCAGCGTA CTCCAAAGAT TCAGGTTTAC TCACGTCATC<br>CAGCAGAGAA TGGAAAGTCA AATTTCCTGA ATTGCTATGT<br>GTCTGGGTTT CATCCATCCG ACATTGAAGT TGACTTACTG<br>AAGAATGGAG AGAGAATTGA AAAAGTGGAG CATTCAGACT<br>TGTCTTTCAG CAAGGACTGG TCTTTCTATC TCTTGTACTA<br>CACTGAATTC ACCCCCACTG AAAAAGATGA GTATGCCTGC<br>CGTGTGAACC ATGTGACTTT GTCACAGCCC AAGATAGTTA<br>AGTGGGATCG AGACATGTAA GCAGCATCAT GGAGGTTTGA<br>AGATGCCGCA TTTGGATTGG ATGAATTCCA AATTCTGCTT<br>GCTTGCTTTT TAATATTGAT ATGCTTATAC ACTTACACTT<br>TATGCACAAA ATGTAGGGTT ATAATAATGT TAACATGGAC<br>ATGATCTTCT TTATAATTCT ACTTTGAGTG CTGTCTCCAT<br>GTTTGATGTA TCTGAGCAGG TTGCTCCACA GGTAGCTCTA<br>GGAGGGCTGG CAACTTAGAG GTGGGGAGCA GAGAATTCTC<br>TTATCCAACA TCAACATCTT GGTCAGATTT GAACTCTTCA<br>ATCTCTTGCA CTCAAAGCTT GTTAAGATAG TTAAGCGTGC<br>ATAAGTTAAC TTCCAATTTA CATACTCTGC TTAGAATTTG<br>GGGGAAAATT TAGAAATATA ATTGACAGGA TTATTGGAAA<br>TTTGTTATAA TGAATGAAAC ATTTTGTCAT ATAAGATTCA<br>TATTTACTTC TTATACATTT GATAAAGTAA GGCATGGTTG<br>TGGTTAATCT GGTTTATTTT TGTTCCACAA GTTAAATAAA<br>TCATAAAACT TGATGTGTTA TCTCTTA | 53 |
| YWHAZ | NM_003406.3 | CTTTCTCCTT CCCCTTCTTC CGGGCTCCCG TCCCGGCTCA<br>TCACCCGGCC TGTGGCCCAC TCCCACCGCC AGCTGGAACC<br>CTGGGGACTA CGACGTCCCT CAAACCTTGC TTCTAGGAGA<br>TAAAAGAAC ATCCAGTCAT GGATAAAAAT GAGCTGGTTC<br>AGAAGGCCAA ACTGGCCGAG CAGGCTGAGC GATATGATGA<br>CATGGCAGCC TGCATGAAGT CTGTAACTGA GCAAGGAGCT<br>GAATTATCCA ATGAGGAGAG GAATCTTCTC TCAGTTGCTT<br>ATAAAAATGT TGTAGGAGCC CGTAGGTCAT CTTGGAGGGT<br>CGTCTCAAGT ATTGAACAAA AGACGGAAGG TGCTGAGAAA<br>AAACAGCAGA TGGCTCGAGA ATACAGAGAG AAAATTGAGA<br>CGGAGCTAAG AGATATCTGC AATGATGTAC TGTCTCTTTT<br>GGAAAAGTTC TTGATCCCCA ATGCTTCACA AGCAGAGAGC<br>AAAGTCTTCT ATTTGAAAAT GAAAGGAGAT TACTACCGTT<br>ACTTGGCTGA GGTTGCCGCT GGTGATGACA AGAAAGGGAT<br>TGTCGATCAG TCACAACAAG CATACCAAGA AGCTTTTGAA<br>ATCAGCAAAA AGGAAATGCA ACCAACACAT CCTATCAGAC<br>TGGGTCTGGC CCTTAACTTC TCTGTGTTCT ATTATGAGAT<br>TCTGAACTCC CCAGAGAAAG CCTGCTCTCT TGCAAAGACA<br>GCTTTTGATG AAGCCATTGC TGAACTTGAT ACATTAAGTG<br>AAGAGTCATA CAAAGACAGC ACGCTAATAA TGCAATTACT | 54 |

TABLE 1-continued

Melanoma Biomarker/Housekeeper Sequence Information

| Gene Name | RefSeq Accession | Sequence | SEQ ID NO: |
|---|---|---|---|
| | | GAGAGACAAC TTGACATTGT GGACATCGGA TACCCAAGGA GACGAAGCTG AAGCAGGAGA AGGAGGGGAA AATTAACCGG CCTTCCAACT TTTGTCTGCC TCATTCTAAA ATTTACACAG TAGACCATTT GTCATCCATG CTGTCCCACA AATAGTTTTT TGTTTACGAT TTATGACAGG TTTATGTTAC TTCTATTTGA ATTTCTATAT TTCCCATGTG GTTTTTATGT TTAATATTAG GGGAGTAGAG CCAGTTAACA TTTAGGGAGT TATCTGTTTT CATCTTGAGG TGGCCAATAT GGGGATGTGG AATTTTTATA CAAGTTATAA GTGTTTGGCA TAGTACTTTT GGTACATTGT GGCTTCAAAA GGGCCAGTGT AAAACTGCTT CCATGTCTAA GCAAAGAAAA CTGCCTACAT ACTGGTTTGT CCTGGCGGGG AATAAAAGGG ATCATTGGTT CCAGTCACAG GTGTAGTAAT TGTGGGTACT TTAAGGTTTG GAGCACTTAC AAGGCTGTGG TAGAATCATA CCCCATGGAT ACCACATATT AAACCATGTA TATCTGTGGA ATACTCAATG TGTACACCTT TGACTACAGC TGCAGAAGTG TTCCTTTAGA CAAAGTTGTG ACCCATTTTA CTCTGGATAA GGGCAGAAAC GGTTCACATT CCATTATTTG TAAAGTTACC TGCTGTTAGC TTTCATTATT TTTGCTACAC TCATTTTATT TGTATTTAAA TGTTTTAGGC AACCTAAGAA CAAATGTAAA AGTAAAGATG CAGGAAAAAT GAATTGCTTG GTATTCATTA CTTCATGTAT ATCAAGCACA GCAGTAAAAC AAAAACCCAT GTATTTAACT TTTTTTTAGG ATTTTTGCTT TTGTGATTTT TTTTTTTTTG ATACTTGCCT AACATGCATG TGCTGTAAAA ATAGTTAACA GGGAAATAAC TTGAGATGAT GGCTAGCTTT GTTTAATGTC TTATGAAATT TTCATGAACA ATCCAAGCAT AATTGTTAAG AACACGTGTA TTAAATTCAT GTAAGTGGAA TAAAAGTTTT ATGAATGGAC TTTTCAACTA CTTTCTCTAC AGCTTTTCAT GTAAATTAGT CTTGGTTCTG AAACTTCTCT AAAGGAAATT GTACATTTTT TGAAATTTAT TCCTTATTCC CTCTTGGCAG CTAATGGGCT CTTACCAAGT TTAAACACAA AATTTATCAT AACAAAAATA CTACTAATAT AACTACTGTT TCCATGTCCC ATGATCCCCT CTCTTCCTCC CCACCCTGAA AAAATGAGT TCCTATTTTT TCTGGGAGAG GGGGGGATTG ATTAGAAAAA AATGTAGTGT GTTCCATTTA AAATTTTGGC ATATGGCATT TTCTAACTTA GGAAGCCACA ATGTTCTTGG CCCATCATGA CATTGGGTAG CATTAACTGT AAGTTTTGTG CTTCCAAATC ACTTTTTGGT TTTTAAGAAT TTCTTGATAC TCTTATAGCC TGCCTTCAAT TTTGATCCTT TATTCTTTCT ATTTGTCAGG TGCACAAGAT TACCTTCCTG TTTTAGCCTT CTGTCTTGTC ACCAACCATT CTTACTTGGT GGCCATGTAC TTGGAAAAAG GCCGCATGAT CTTTCTGGCT CCACTCAGTG TCTAAGGCAC CCTGCTTCCT TTGCTTGCAT CCCACAGACT ATTTCCCTCA TCCTATTTAC TGCAGCAAAT CTCTCCTTAG TTGATGAGAC TGTGTTTATC TCCCTTTAAA ACCCTACCTA TCCTGAATGG TCTGTCATTG TCTGCCTTTA AAATCCTTCC TCTTTCTTCC TCCTCTATTC TCTAAATAAT GATGGGCTA AGTTATACCC AAAGCTCACT TTACAAAATA TTTCCTCAGT ACTTTGCAGA AAACACCAAA CAAAATGCC ATTTTAAAAA AGGTGTATTT TTTCTTTTAG AATGTAAGCT CCTCAAGAGC AGGGACAATG TTTTCTGTAT GTTCTATTGT GCCTAGTACA CTGTAAATGC TCAATAAATA TTGATGATGG GAGGCAGTGA GTCTTGATGA TAAGGGTGAG AAACTGAAAT CCCAAACACT GTTTTGTTGC TTGTTTTATT ATGACCTCAG ATTAAATTGG GAAATATTGG CCCTTTTGAA TAATTGTCCC AAATATTACA TTCAAATAAA AGTGCAATGG AGAAAAAAAA AAA | |
| SDHA | NM_004168.3 | ACTGCAGCCC CGCTCGACTC CGGCGTGGTG CGCAGGCGCG GTATCCCCCC TCCCCCGCCA GCTCGACCCC GGTGTGGTGC GCAGGCGCAG TCTGCGCAGG GACTGGCGGG ACTGCGCGGC GGCAACAGCA GACATGTCGG GGGTCCGGGG CCTGTCGCGG CTGCTGAGCG CTCGGCGCCT GGCGCTGGCC AAGGCGTGGC CAACAGTGTT GCAAACAGGA ACCCGAGGTT TTCACTTCAC TGTTGATGGG AACAAGAGGG CATCTGCTAA AGTTTCAGAT TCCATTTCTG CTCAGTATCC AGTAGTGGAT CATGAATTTG ATGCAGTGGT GGTAGGCGCT GGAGGGGCAG GCTTGCGAGC TGCATTTGGC CTTTCTGAGG CAGGGTTTAA TACAGCATGT GTTACCAAGC TGTTTCCTAC CAGGTCACAC ACTGTTGCAG CACAGGGAGG AATCAATGCT GCTCTGGGGA ACATGGAGGA GGACAACTGG AGGTGGCATT TCTACGACAC CGTGAAGGGC TCCGACTGGC TGGGGGACCA GGATGCCATC CACTACATGA CGGAGCAGGC CCCCGCCGCC GTGGTCGAGC TAGAAAATTA TGGCATGCCG TTTAGCAGAA CTGAAGATGG AAGATTTAT CAGCGTGTCAT TTGGTGGACA GAGCCTCAAG TTTGGAAAGG | 55 |

TABLE 1-continued

Melanoma Biomarker/Housekeeper Sequence Information

| Gene Name | RefSeq Accession | Sequence | SEQ ID NO: |
|---|---|---|---|
| | | GCGGGCAGGC CCATCGGTGC TGCTGTGTGG CTGATCGGAC<br>TGGCCACTCG CTATTGCACA CCTTATATGG AAGGTCTCTG<br>CGATATGATA CCAGCTATTT TGTGGAGTAT TTTGCCTTGG<br>ATCTCCTGAT GGAGAATGGG GAGTGCCGTG GTGTCATCGC<br>ACTGTGCATA GAGGACGGGT CCATCCATCG CATAAGAGCA<br>AAGAACACTG TTGTTGCCAC AGGAGGCTAC GGGCGCACCT<br>ACTTCAGCTG CACGTCTGCC CACACCAGCA CTGGCGACGG<br>CACGGCCATG ATCACCAGGG CAGGCCTTCC TTGCCAGGAC<br>CTAGAGTTTG TTCAGTTCCA CCCTACAGGC ATATATGGTG<br>CTGGTTGTCT CATTACGGAA GGATGTCGTG GAGAGGGAGG<br>CATTCTCATT AACAGTCAAG GCGAAAGGTT TATGGAGCGA<br>TACGCCCCTG TCGCGAAGGA CCTGGCGTCT AGAGATGTGG<br>TGTCTCGGTC CATGACTCTG GAGATCCGAG AAGGAAGAGG<br>CTGTGGCCCT GAGAAAGATC ACGTCTACCT GCAGCTGCAC<br>CACCTACCTC CAGAGCAGCT GGCCACGCGC CTGCCTGGCA<br>TTTCAGAGAC AGCCATGATC TTCGCTGGCG TGGACGTCAC<br>GAAGGAGCCG ATCCCTGTCC TCCCCACCGT GCATTATAAC<br>ATGGGCGGCA TTCCCACCAA CTACAAGGGG CAGGTCCTGA<br>GGCACGTGAA TGGCCAGGAT CAGATTGTGC CCGGCCTGTA<br>CGCCTGTGGG GAGGCCGCCT GTGCCTCGGT ACATGGTGCC<br>AACCGCCTCG GGGCAAACTC GCTCTTGGAC CTGGTTGTCT<br>TTGGTCGGGC ATGTGCCCTG AGCATCGAAG AGTCATGCAG<br>GCCTGGAGAT AAAGTCCCTC CAATTAAACC AAACGCTGGG<br>GAAGAATCTG TCATGAATCT TGACAAATTG AGATTTGCTG<br>ATGGAAGCAT AAGAACATCG GAACTGCGAC TCAGCATGCA<br>GAAGTCAATG CAAAATCATG CTGCCGTGTT CCGTGTGGGA<br>AGCGTGTTGC AAGAAGGTTG TGGGAAAATC AGCAAGCTCT<br>ATGGAGACCT AAAGCACCTG AAGACGTTCG ACCGGGGAAT<br>GGTCTGGAAC ACGGACCTGG TGGAGACCCT GGAGCTGCAG<br>AACCTGATGC TGTGTGCGCT GCAGACCATC TACGGAGCAG<br>AGGCACGGAA GGAGTCACGG GGCGCGCATG CCAGGGAAGA<br>CTACAAGGTG CGGATTGATG AGTACGATTA CTCCAAGCCC<br>ATCCAGGGGC AACAGAAGAA GCCCTTTGAG GAGCACTGGA<br>GGAAGCACAC CCTGTCCTAT GTGGACGTTG GCACTGGGAA<br>GGTCACTCTG GAATATAGAC CCGTGATCGA CAAAACTTTG<br>AACGAGGCTG ACTGTGCCAC CGTCCCGCCA GCCATTCGCT<br>CCTACTGATG AGACAAGATG TGGTGATGAC AGAATCAGCT<br>TTTGTAATTA TGTATAATAG CTCATGCATG TGTCCATGTC<br>ATAACTGTCT TCATACGCTT CTGCACTCTG GGGAAGAAGG<br>AGTACATTGA AGGGAGATTG GCACCTAGTG GCTGGGAGCT<br>TGCCAGGAAC CCAGTGGCCA GGGAGCGTGG CACTTACCTT<br>TGTCCCTTGC TTCATTCTTG TGAGATGATA AAACTGGGCA<br>CAGCTCTTAA ATAAAATATA AATGAACAAA CTTTCTTTTA<br>TTTCCAAATC CATTTGAAAT ATTTTACTGT TGTGACTTTA<br>GTCATATTTG TTGACCTAAA AATCAAATGT AATCTTTGTA<br>TTGTGTTACA TCAAAATCCA GATATTTTGT ATAGTTTCTT<br>TTTTCTTTTT CTTTTCTTTT TTTTTTTGA GACAGGATCG<br>GTGCAGTAGT ACAATCACAG CTCACTGCAG CCTCAAACTC<br>CTGGGCAGCT CAGGTGATCT TCCTGACTCA GCCTTCTGAG<br>TAGTTGGGGC TACAGGTGTG CACCACCATG CCCAGCTCAT<br>TTATTTTGTA ATTGTAGGGA CAGGGTCTCA CTGTGTTGCC<br>TAGGCTGGTC TCAAGTGATC CTCCCTCCTT GGCCTCCCAA<br>GGTGCTGGAA TTATAGGTGT GAACAAACCA AAAAAAAAAA<br>AAA | |
| HPRT1 | NM_000194.2 | GGCGGGGCCT GCTTCTCCTC AGCTTCAGGC GGCTGCGACG<br>AGCCCTCAGG CGAACCTCTC GGCTTTCCCG CGCGGCGCCG<br>CCTCTTGCTG CGCCTCCGCC TCCTCCTCTG CTCCGCCACC<br>GGCTTCCTCC TCCTGAGCAG TCAGCCCGCG CGCCGGCCGG<br>CTCCGTTATG GCGACCCGCA GCCCTGGCGT CGTGATTAGT<br>GATGATGAAC CAGGTTATGA CCTTGATTTA TTTTGCATAC<br>CTAATCATTA TGCTGAGGAT TTGGAAAGGG TGTTTATTCC<br>TCATGGACTA ATTATGGACA GGACTGAACG TCTTGCTCGA<br>GATGTGATGA AGGAGATGGG AGGCCATCAC ATTGTAGCCC<br>TCTGTGTGCT CAAGGGGGGC TATAAATTCT TTGCTGACCT<br>GCTGGATTAC ATCAAAGCAC TGAATAGAAA TAGTGATAGA<br>TCCATTCCTA TGACTGTAGA TTTTATCAGA CTGAAGAGCT<br>ATTGTAATGA CCAGTCAACA GGGGACATAA AAGTAATTGG<br>TGGAGATGAT CTCTCAACTT TAACTGGAAA GAATGTCTTG<br>ATTGTGGAAG ATATAATTGA CACTGGCAAA ACAATGCAGA<br>CTTTGCTTTC CTTGGTCAGG CAGTATAATC CAAAGATGGT<br>CAAGGTCGCA AGCTTGCTGG TGAAAAGGAC CCCACGAAGT<br>GTTGGATATA AGCCAGACTT TGTTGGATTT GAAATTCCAG<br>ACAAGTTTGT TGTAGGATAT GCCCTTGACT ATAATGAATA | 56 |

TABLE 1-continued

Melanoma Biomarker/Housekeeper Sequence Information

| Gene Name | RefSeq Accession | Sequence | SEQ ID NO: |
|---|---|---|---|
| | | CTTCAGGGAT TTGAATCATG TTTGTGTCAT TAGTGAAACT | |
| | | GGAAAAGCAA AATACAAAGC CTAAGATGAG AGTTCAAGTT | |
| | | GAGTTTGGAA ACATCTGGAG TCCTATTGAC ATCGCCAGTA | |
| | | AAATTATCAA TGTTCTAGTT CTGTGGCCAT CTGCTTAGTA | |
| | | GAGCTTTTTG CATGTATCTT CTAAGAATTT TATCTGTTTT | |
| | | GTACTTTAGA AATGTCAGTT GCTGCATTCC TAAACTGTTT | |
| | | ATTTGCACTA TGAGCCTATA GACTATCAGT TCCCTTTGGG | |
| | | CGGATTGTTG TTTAACTTGT AAATGAAAAA ATTCTCTTAA | |
| | | ACCACAGCAC TATTGAGTGA AACATTGAAC TCATATCTGT | |
| | | AAGAAATAAA GAGAAGATAT ATTAGTTTTT TAATTGGTAT | |
| | | TTTAATTTTT ATATATGCAG GAAAGAATAG AAGTGATTGA | |
| | | ATATTGTTAA TTATACCACC GTGTGTTAGA AAAGTAAGAA | |
| | | GCAGTCAATT TTCACATCAA AGACAGCATC TAAGAAGTTT | |
| | | TGTTCTGTCC TGGAATTATT TTAGTAGTGT TTCAGTAATG | |
| | | TTGACTGTAT TTTCCAACTT GTTCAAATTA TTACCAGTGA | |
| | | ATCTTTGTCA GCAGTTCCCT TTTAAATGCA AATCAATAAA | |
| | | TTCCCAAAAA TTTAAAAAAA AAAAAAAAA AAAAA | |

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

As used herein, the terms "polynucleotide" and "nucleic acid molecule" are used interchangeably to mean a polymeric form of nucleotides of at least 10 bases or base pairs in length, either ribonucleotides or deoxynucleotides or a modified form of either type of nucleotide, and is meant to include single and double stranded forms of DNA. As used herein, a nucleic acid molecule or nucleic acid sequence that serves as a probe in a microarray analysis preferably comprises a chain of nucleotides, more preferably DNA and/or RNA. In other embodiments, a nucleic acid molecule or nucleic acid sequence comprises other kinds of nucleic acid structures such a for instance a DNA/RNA helix, peptide nucleic acid (PNA), locked nucleic acid (LNA) and/or a ribozyme. Hence, as used herein the term "nucleic acid molecule" also encompasses a chain comprising non-natural nucleotides, modified nucleotides and/or non-nucleotide building blocks which exhibit the same function as natural nucleotides.

As used herein, the terms "hybridize," "hybridizing", "hybridizes," and the like, used in the context of polynucleotides, are meant to refer to conventional hybridization conditions, such as hybridization in 50% formamide/6×SSC/0.1% SDS/100 µg/ml ssDNA, in which temperatures for hybridization are above 37 degrees and temperatures for washing in 0.1×SSC/0.1% SDS are above 55 degrees C., and preferably to stringent hybridization conditions.

As used herein, the term "normalization" or "normalizer" refers to the expression of a differential value in terms of a standard value to adjust for effects which arise from technical variation due to sample handling, sample preparation, and measurement methods rather than biological variation of biomarker concentration in a sample. For example, when measuring the expression of a differentially expressed protein, the absolute value for the expression of the protein can be expressed in terms of an absolute value for the expression of a standard protein that is substantially constant in expression.

The terms "diagnosis" and "diagnostics" also encompass the terms "prognosis" and "prognostics", respectively, as well as the applications of such procedures over two or more time points to monitor the diagnosis and/or prognosis over time, and statistical modeling based thereupon. Furthermore, the term diagnosis includes: a. prediction (determining if a patient will likely develop aggressive disease (hyperproliferative/invasive)), b. prognosis (predicting whether a patient will likely have a better or worse outcome at a pre-selected time in the future), c. therapy selection, d. therapeutic drug monitoring, and e. relapse monitoring.

The term "providing" as used herein with regard to a biological sample refers to directly or indirectly obtaining the biological sample from a subject. For example, "providing" may refer to the act of directly obtaining the biological sample from a subject (e.g., by a blood draw, tissue biopsy, lavage and the like). Likewise, "providing" may refer to the act of indirectly obtaining the biological sample. For example, providing may refer to the act of a laboratory receiving the sample from the party that directly obtained the sample, or to the act of obtaining the sample from an archive.

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), or as a likelihood, odds ratio, among other measures.

The term "biological sample" as used herein refers to any sample of biological origin potentially containing one or more biomarkers. Examples of biological samples include tissue, organs, or bodily fluids such as whole blood, plasma, serum, tissue, lavage or any other specimen used for detection of disease.

The term "subject" as used herein refers to a mammal, preferably a human.

"Treating" or "treatment" as used herein with regard to a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

Biomarker levels may change due to treatment of the disease. The changes in biomarker levels may be measured by the present disclosure. Changes in biomarker levels may be used to monitor the progression of disease or therapy.

"Altered", "changed" or "significantly different" refer to a detectable change or difference from a reasonably comparable state, profile, measurement, or the like. Such changes may be all or none. They may be incremental and need not be linear. They may be by orders of magnitude. A change may be an increase or decrease by 1%, 5%, 10%, 20%, 30%, 40%, 50%, 60%, 70%, 80%, 90%, 95%, 99%, 100%, or more, or any value in between 0% and 100%. Alternatively, the change may be 1-fold, 1.5-fold, 2-fold, 3-fold, 4-fold, 5-fold or more, or any values in between 1-fold and five-fold. The change may be statistically significant with a p value of 0.1, 0.05, 0.001, or 0.0001.

The term "stable disease" refers to a diagnosis for the presence of a melanoma, however the melanoma has been treated and remains in a stable condition, i.e. one that that is not progressive, as determined by imaging data and/or best clinical judgment.

The term "progressive disease" refers to a diagnosis for the presence of a highly active state of a melanoma, i.e. one has not been treated and is not stable or has been treated and has not responded to therapy, or has been treated and active disease remains, as determined by imaging data and/or best clinical judgment.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1

Derivation of a 28-Marker Gene Panel

Raw probe intensities (n=6,892,960 features) from n=49 whole blood samples were used to identify genes that best discriminated between different types of melanoma samples e.g., treated versus untreated, simultaneously. A total of 28 transcripts were identified in an unbiased manner as potential markers of melanoma behavior (Table 2).

An artificial intelligence model of melanoma disease dynamics was built using normalized gene expression of these 28 markers in whole blood from Controls (n=90), Responders/Stable (n=68), and Progressive (n=66) samples. The dataset was randomly split into training (n=169) and testing (n=55) partitions for model creation and validation respectively. Five algorithms (XGB, RF, TreeBag, SVM, NNET) were identified that best predicted the training data. In the test set, each algorithm produced probability scores that predicted the sample. Each probability score reflects the "certainty" of an algorithm that an unknown sample belongs to Control, Responder/Stable or Progressive class. For example, an unknown sample 51 can have the following probability vector {Control=20, Responder=50, Progressive=30}. This sample would be considered a responder, given a score of 50, but there may be potential of progression (probability of 30) (FIG. 1).

TABLE 2

| Melanoma Biomarker or Housekeeping Gene | | Chromosome location | UniGene | | Amplicon produced using forward and reverse primers | Assay Loca- | Exon Bound- |
|---|---|---|---|---|---|---|---|
| Symbol | Name | [Cytogenetic band] | ID | RefSeq | Length (bp) | tion | ary |
| ATL1 | atlastin GTPase 1 | Chr.14: 50533082-50633068 [14q22.1] | Hs.584905 | NM_001127713.1 | 65 | 1544 | 12-13 |
| ATP6V0D | ATPase H+ transporting V0 subunit d1 | Chr.16: 67438014-67481186 [16q22.1] | Hs.106876 | NM_004691.4 | 72 | 224 | 1-2 |
| C1ORF21 | chromosome 1 open reading frame 21 | Chr.1: 184387016-184629021 [1q25.3] | Hs.497159 | NM_030806.3 | 84 | 805 | 5-6 |
| CFLAR | CASP8 and FADD like apoptosis regulator | Chr.2: 201116015-201172688 [2q33.1] | Hs.390736 | NM_001127183.2 | 59 | 874 | 3-4 |
| CFLAR-AS1 | CFLAR antisense RNA 1 | Chr.2: 201140289-201157792 [2q33.1] | Hs.664613 | NR_040030.1 | 103 | 883 | 6-7 |
| CHP1 | calcineurin like EF-hand protein 1 | Chr.15: 41231149-41281887 [15q15.1 ] | Hs.406234 | NM_007236.4 | 120 | 212 | 1-2 |
| DDX55 | DEAD-box helicase 55 | Chr.12: 123602077-123620943 [12q24.31] | Hs.286173 | NM_020936.2 | 74 | 183 | 1-2 |
| DMD | dystrophin | Chr.X: 31119219-33339609 [Xp21.1] | Hs.495912 | NM_000109.3 | 76 | 9607 | 63-64 |
| DNAJC9 | DnaJ heat shock protein family (Hsp40) member C9 | Chr.10: 73241954-73247331 [10q22.2] | Hs.408577 | NM_015190.4 | 102 | 198 | 1-1 |

TABLE 2-continued

| Melanoma Biomarker or Housekeeping Gene | | Chromosome location | UniGene | | Amplicon produced using forward and reverse primers | Assay Location | Exon Boundary |
|---|---|---|---|---|---|---|---|
| Symbol | Name | [Cytogenetic band] | ID | RefSeq | Length (bp) | | |
| ENOSF1 | enolase superfamily member 1 | Chr.18: 670012-712664 [18p11.32] | Hs.658550 | NM_001126123.3 | 110 | X | 13-14 |
| FANCL | Fanconi anemia complementation group L | Chr.2: 58159243-58241380 [2p16.1] | Hs.631890 | NM_001114636.1 | 138 | 540 | 6-7 |
| HJURP | Holliday junction recognition protein | Chr.2: 233836701-233854566 [2q37.1] | Hs.532968 | NM_018410.4 | 52 | 399 | 4-5 |
| HLA-DOA | major histocompatibility complex, class II, DO alpha | Chr.6: 33004182-33009612 [6p21.32] | Hs.631991 | NM_002119.3 | 124 | 160 | 1-2 |
| HLA-DRA | major histocompatibility complex, class II, DR alpha | Chr.6: 32439842-32445046 [6p21.32] | Hs.520048 | NM_019111.4 | 129 | 884 | 4-5 |
| HNRNPA3P1 | heterogeneous nuclear ribonucleoprotein A3 pseudogene 1 | Chr.10: 43787412-43790417 [10q11.21] | Hs.632956 | NR_002726.2 | 99 | 2455 | 1-1 |
| IL23A | interleukin 23 subunit alpha | Chr.12: 56334159-56340410 [12q13.3] | Hs.382212 | NM_016584.2 | 107 | 323 | 1-2 |
| IQGAP1 | IQ motif containing GTPase activating protein 1 | Chr.15: 90388241-90502243 [15q26.1] | Hs.430551 | NM_003870.3 | 69 | 4562 | 34-35 |
| LOC494127 | NFYC pseudogene | Chr.9: 87083886-87085225 [9q21.33] | Hs.626316 | NR_036691.1 | 86 | 150 | 1-1 |
| LOC646471 | uncharacterized LOC646471 | Chr.1: 25819954-25823606 [1p36.11] | Hs.727271 | NR_024498.1 | 80 | 2858 | 1-1 |
| LOH12CR | loss of heterozygosity, 12, chromosomal region 2 (non-protein coding) | Chr.12: 12355408-12357067 [12p13.2] | Hs.67553 | NR_024061.1 | 69 | 140 | 1-2 |
| MTRNR2L2_MTO1 | CUSTOM PRIMER | | | | | | |
| PBXIP1 | PBX homeobox interacting protein 1 | Chr.1: 154944080-154956163 [1q21.3] | Hs.505806 | NM_020524.3 | 60 | 189 | 2-3 |
| RNF5 | ring finger protein 5 | Chr.6: 32178385-32180793 [6p21.32] | Hs.731774 | NM_006913.3 | 67 | 273 | 1-2 |
| SERTAD2 | SERTA domain containing 2 | Chr.2: 64631621-64751091 [2p14] | Hs.591569 | NM_014755.2 | 91 | 288 | 1-2 |
| SLC35G5 | solute carrier family 35 member G5 | Chr.8: 11330986-11332186 [8p23.1] | Hs.458397 | NM_054028.1 | 144 | 541 | 1-1 |
| SPATS2L | spermatogenesis associated serine rich 2 like | Chr.2: 200305881-200482263 [2q33.1] | Hs.120323 | NM_001100422.1 | 89 | 1364 | 10-11 |
| TDRD7 | tudor domain containing 7 | Chr.9: 97412020-97496125 [9q22.33] | Hs.193842 | NM_001302884.1 | 59 | 3084 | 15-16 |
| TOX4 (housekeeping gene) | TOX high mobility group box family member 4 | Chr.14: 21477176-21499177 [14q11.2] | Hs.555910 | NM_001303523.1 | 145 | 447 | 3-3 |
| TPT1 (housekeeping gene) | tumor protein, translationally-controlled 1 | Chr.13: 45333471-45341284 [13q14.13] | Hs.374596 | NM_001286272.1 | 131 | 377 | 3-3 |
| TXK | TXK tyrosine kinase | Chr.4: 48066393-48135322 [4p12] | Hs.479669 | NM_003328.2 | 113 | 1265 | 11-12 |
| YY2 | YY2 transcription factor | Chr.X: 21855987-21858727 [Xp22.12] | Hs.673601 | NM_206923.3 | 110 | 552 | 1-1 |

Diagnosis: Identification of Samples as Melanoma

Figure 2:
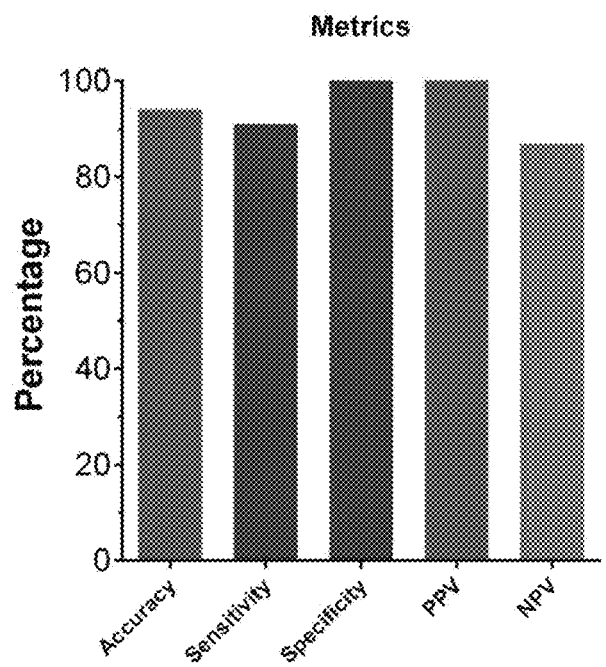
FIG. 2 is a graph showing the metrics for the test in the test set ranged from 87-100%.

In the test set 1, the data for the utility of the test to differentiate melanoma from controls are included in Table 3. The metrics are included in FIG. 2. These are: sensitivity >90%, specificity 100%, PPV 100%, NPV 87%. The overall accuracy is 94%. The tool can therefore differentiate between controls and aggressive and stable melanoma disease.

TABLE 3

Confusion matrix showing classification accuracy of the 5-model algorithm that determines whether a sample is a melanoma or a control in blood samples

| Predicted/Reference | Melanoma | Control |
|---|---|---|
| Control | 3 | 20 |
| Melanoma | 30 | 0 |
| Sensitivity | | 91% |
| Specificity | | 100% |
| Positive Predictive Value | | 100% |
| Negative Predictive Value | | 87% |
| Accuracy | | 94% |

Figure 3A:
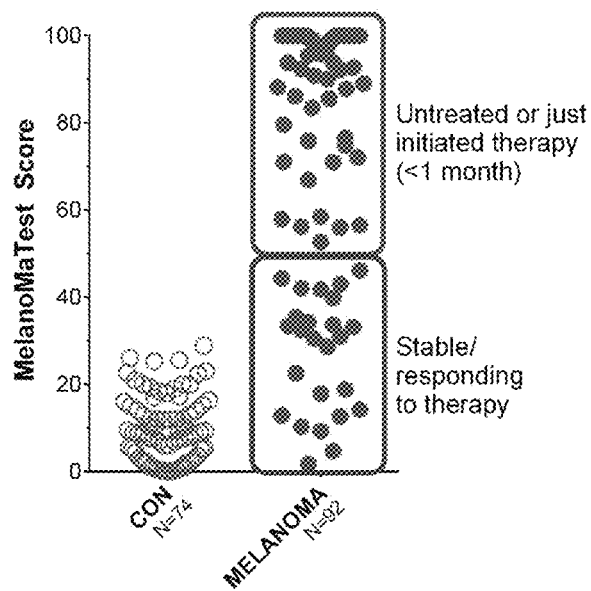
FIGS. 3A-3C are a set of graphs showing the evaluation of the circulating melanoma gene test (Melanomx) in test set 2. Values were significantly higher in melanoma samples than in controls (FIG. 3A). Patients who were responding to therapy had values similar to controls. Receiver operator curve analysis of test set 2 identifying the AUC for differentiating melanoma from controls was >0.95 (FIG. 3B). The metrics for the test ranged from 78-92% (FIG. 3C).
Figure 3B:
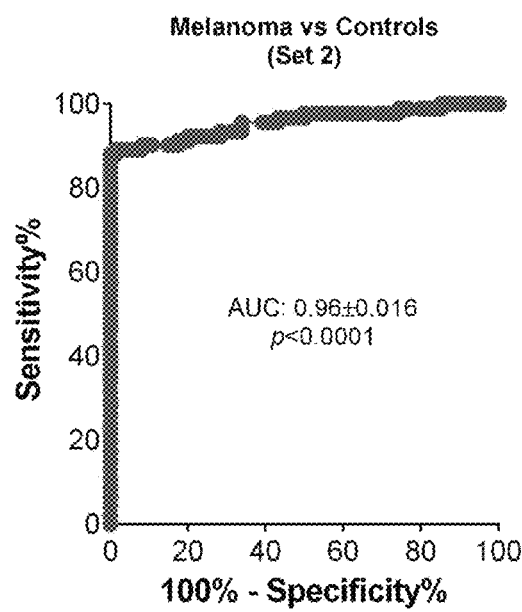
Figure 3C:
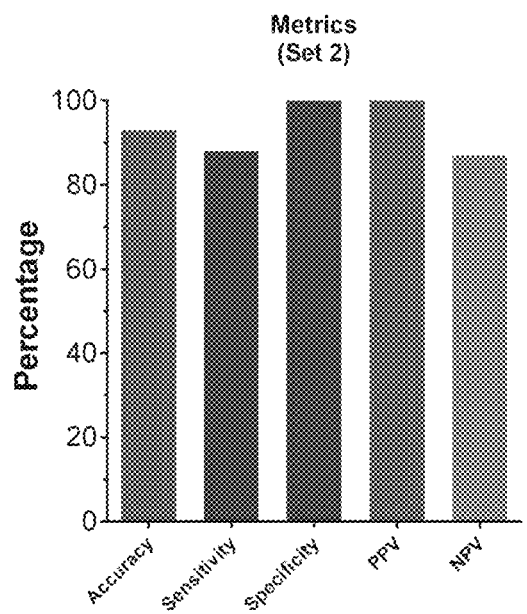

The test was evaluated in a second test set (test set 2) that included 74 controls and 92 melanoma patients. The mean Melanomx score in the melanoma group was 73±31 versus 10±8 in the control group (FIG. 3A). The receiver operator curve analysis demonstrated the score exhibited an area under the curve (AUC) of 0.96 (FIG. 3B) and the metrics were 88-100% (FIG. 3C).

Correlation with Surgical Removal of Melanoma.

Figure 4A:
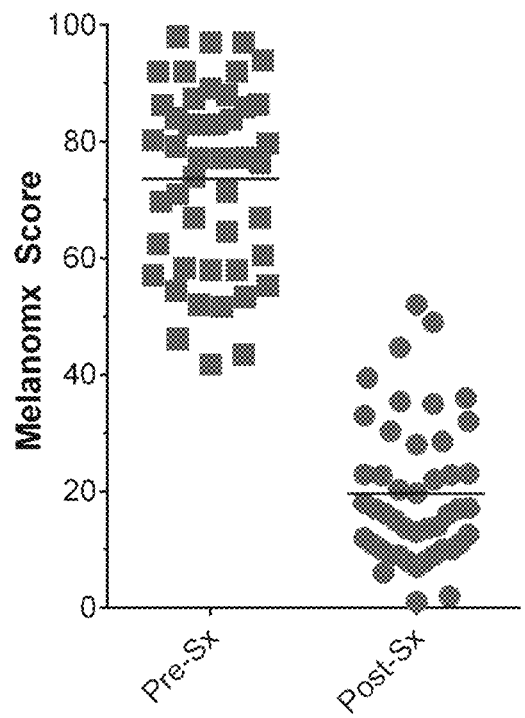
FIGS. 4A-4B are a set of graphs showing the effect of surgery on the Melanomx. Levels were significantly decreased by surgery (p<0.0001) (FIG. 4A). Values in the NED (no evidence of disease after surgery) group were significantly lower than in those with residual disease after surgery (p=0.0007) (FIG. 4B).
Figure 4B:
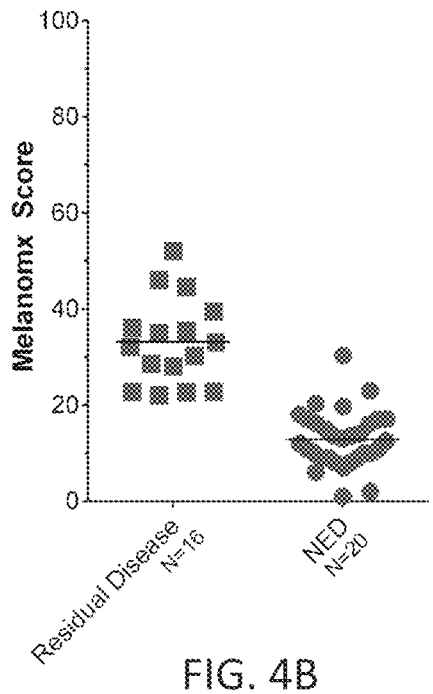

In the surgical series (n=46), removal of melanoma decreased the score from 74±16 to 20±12 (FIG. 4A). Evaluation of the post-surgical group identified the score was significantly different between patients with no evidence of disease 13±6 (not different to the control group) and those with residual disease (33±9) (FIG. 4B). The Melanomx score can therefore define the extent of surgery and identify those who are surgical cures.

Evaluation of Immune-Therapy and Targeted (BRAF Inhibitor) Therapy.

Figure 5:
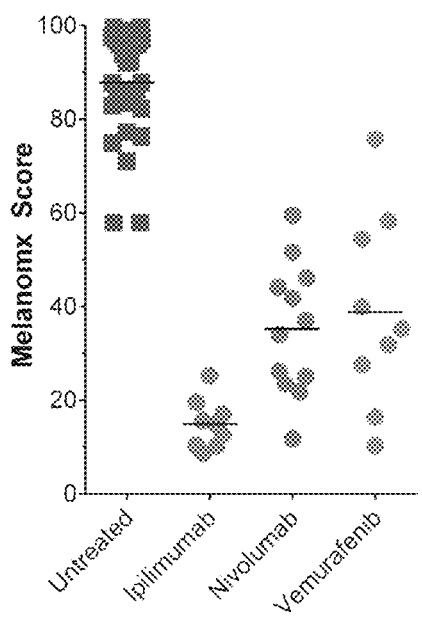
FIG. 5 is a graph showing the effect of therapy on the Melanomx score. Levels were significantly decreased by immunotherapy (ipilimumab) or a BRAF inhibitor (Vemurafenib).

In the therapy series (n=30), treatment with ipilimumab (immune therapy targeting CTLA-4), nivolumab (immune therapy targeting PD-1) or a BRAF inhibitor (vemurafenib) for 5 months significantly decreased the Melanomx scores from 88±12 to 15±5 (p<0.0001), 35±14 (p<0.001) and 38±21 (p<0.0001), respectively (FIG. 5). All patients in the treated groups were stable. This indicates that the Melanomx score can therefore be used to measure the efficacy of both immune and targeted-therapy in melanoma and that a decrease in score correlated with response to therapeutic intervention.

Confirmation that Gene Expression is Melanoma Derived.

We confirmed that melanoma was the source for the blood-based gene expression assay by evaluating expression in different melanoma cell lines, in tumor tissue and by comparing expression in blood with tumor tissue collected at the same time-point during surgery.

Figure 6A:
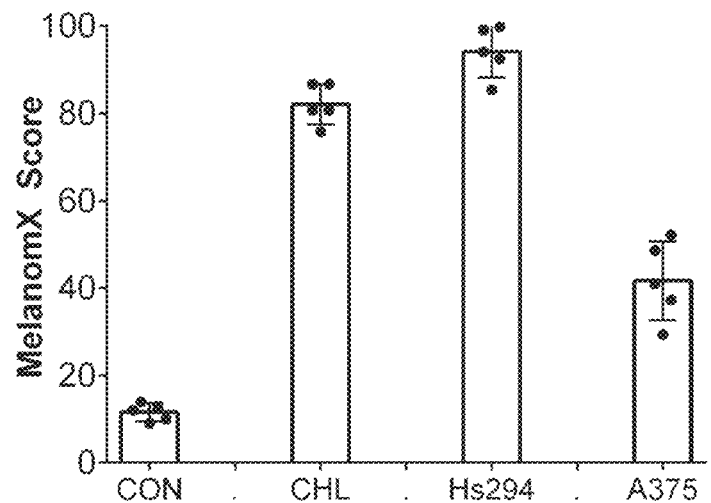
FIGS. 6A-6B are a set of graphs showing Melanomx score in 3 different melanoma cell lines.

All 28 genes were highly expressed in all 3 melanoma cell lines. Scores ranged from 94±6 (Hs294T) to 82±5 (CHL) to 42±9 (A375) (FIG. 6A).

Figure 6B:
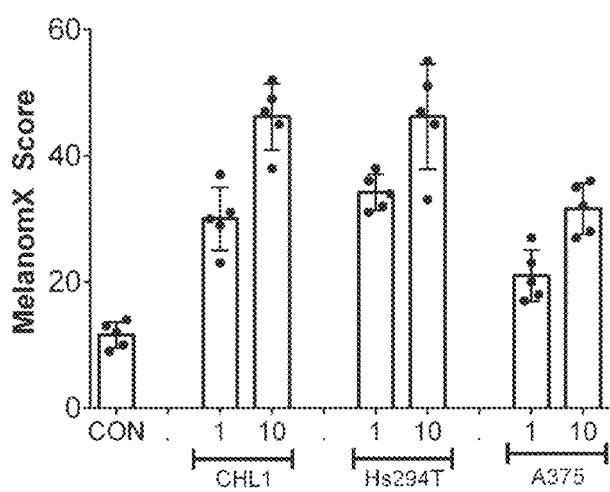

Spike-in experiments using these 3 cell lines and normal whole blood demonstrated that gene expression scores were detected when as few as 1 cell was spiked into 1 ml of blood. One single melanoma cell was detectable. Scores ranged from 21±4 (A375) to 30±5 (CHL) to 34±2 (H2294) (FIG. 6B). Scores were significantly elevated compared to control blood (no spike-in; p<0.0001).

Figure 7A:
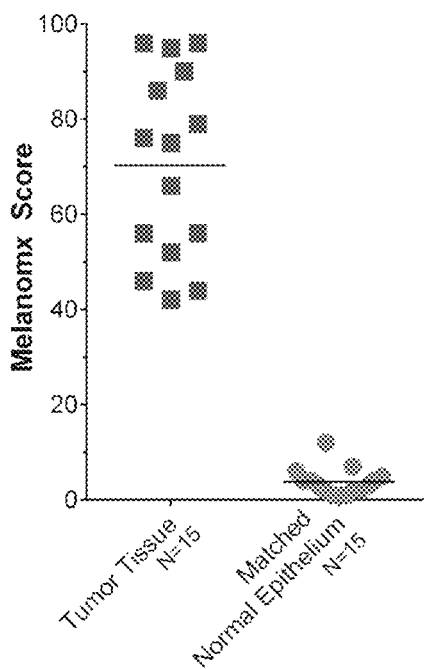
FIGS. 7A-7B are a set of graphs showing expression in tumor tissue and its correlation with blood samples collected at the same time.

We then evaluated gene expression in tumor tissue. All 28 genes were highly expressed in melanoma compared to matched normal tissue and scores were significantly elevated 70±20 versus 4±3 (p<0.0001) (FIG. 7A).

Figure 7B:
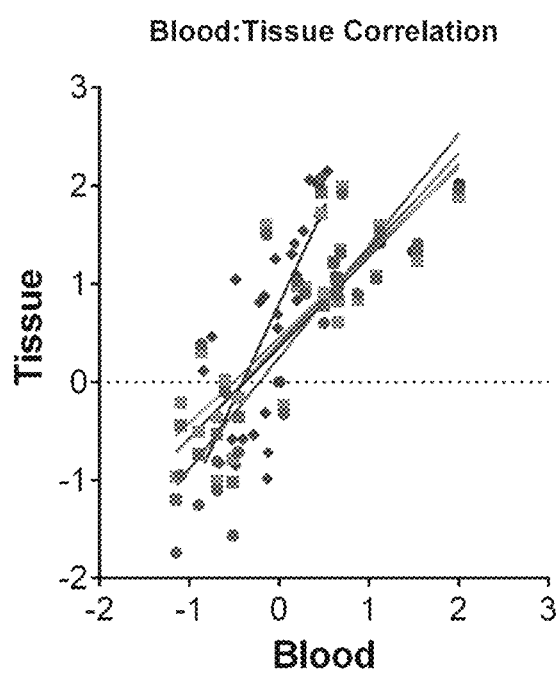

We also compared gene expression in tumor tissue and blood collected at the same time point. Gene expression was highly concordant (Pearson r: 0.74-0.83, median: 0.819) identifying gene expression in tumor tissue and blood was concordant (FIG. 7B).

REFERENCES

1. Schadendorf D, Fisher D E, Garbe C, et al. Melanoma. Nat Rev Dis Primers. 2015; 1:15003.: 10.1038/nrdp.2015.1033.
2. Mar V J, Wong S Q, Li J, et al. BRAF/NRAS wild-type melanomas have a high mutation load correlating with histologic and molecular signatures of UV damage. Clin Cancer Res. 2013; 19: 4589-4598. doi: 4510.1158/1078-0432.CCR-4513-0398. Epub 213 July 4585.
3. Genomic Classification of Cutaneous Melanoma. Cell. 2015; 161: 1681-1696. doi: 1610.1016/j.cell.2015.1605.1044.
4. Wan P T, Garnett M J, Roe S M, et al. Mechanism of activation of the RAF-ERK signaling pathway by oncogenic mutations of B-RAF. Cell. 2004; 116: 855-867.
5. Krauthammer M, Kong Y, Bacchiocchi A, et al. Exome sequencing identifies recurrent mutations in NF1 and RASopathy genes in sun-exposed melanomas. Nat Genet. 2015; 47: 996-1002. doi: 1010.1038/ng.3361. Epub 215 July 1027.
6. Svedman F C, Pillas D, Taylor A, Kaur M, Linder R, Hansson J. Stage-specific survival and recurrence in patients with cutaneous malignant melanoma in Europe—a systematic review of the literature. Clin Epidemiol. 2016; 8:109-22.: 10.2147/CLEP.S99021. eCollection 92016.
7. Gershenwald J E, Thompson W, Mansfield P F, et al. Multi-institutional melanoma lymphatic mapping experience: the prognostic value of sentinel lymph node status in 612 stage I or II melanoma patients. J Clin Oncol. 1999; 17: 976-983.
8. Minor D R, Moore D, Kim C, et al. Prognostic factors in metastatic melanoma patients treated with biochemotherapy and maintenance immunotherapy. Oncologist. 2009; 14: 995-1002. doi: 1010.1634/theoncologist.2009-0083. Epub 29 Sep. 1023.
9. Kaisaki P J, Cutts A, Popitsch N, et al. Targeted Next-Generation Sequencing of Plasma DNA from Cancer Patients: Factors Influencing Consistency with Tumour DNA and Prospective Investigation of Its Utility for Diagnosis. PLoS One. 2016; 11: e0162809. doi: 0162810.0161371/journal.pone.0162809. eCollection 0162016.
10. Knol A C, Vallee A, Herbreteau G, et al. Clinical significance of BRAF mutation status in circulating tumor DNA of metastatic melanoma patients at baseline. Exp Dermatol. 2016; 25: 783-788. doi: 710.1111/exd.13065.
11. Khoja L, Lorigan P, Dive C, Keilholz U, Fusi A. Circulating tumour cells as tumour biomarkers in melanoma: detection methods and clinical relevance. Ann Oncol. 2015; 26: 33-39. doi: 10.1093/annonc/mdu1207. Epub 214 June 1096.
12. Stark M S, Klein K, Weide B, et al. The Prognostic and Predictive Value of Melanoma-related MicroRNAs Using Tissue and Serum: A MicroRNA Expression Analysis. EBioMedicine. 2015; 2: 671-680. doi: 610.1016/j.ebiom.2015.1005.1011. eCollection 2015 July.
13. Gerami P, Cook R W, Wilkinson J, et al. Development of a prognostic genetic signature to predict the metastatic risk associated with cutaneous melanoma. Clin Cancer Res. 2015; 21: 175-183. doi: 110.1158/1078-0432.CCR-1113-3316.
14. Berger A C, Davidson R S, Poitras J K, et al. Clinical impact of a 31-gene expression profile test for cutaneous melanoma in 156 prospectively and consecutively tested patients. Curr Med Res Opin. 2016; 32: 1599-1604. doi: 1510.1080/03007995.03002016.01192997. Epub 0300216 June 03007993.
15. Hanahan D, Weinberg R A. The hallmarks of cancer. Cell. 2000; 100: 57-70.
16. Hanahan D, Weinberg R A. Hallmarks of cancer: the next generation. Cell. 2011; 144: 646-674. doi: 610.1016/j.cell.2011.1002.1013.
17. Kidd M, Drozdov I, Modlin I. Blood and tissue neuroendocrine tumor gene cluster analysis correlate, define hallmarks and predict disease status. Endocr Relat Cancer. 2015; 22: 561-575. doi: 510.1530/ERC-1515-0092. Epub 215 June 1532.
18. Modlin I, Drozdov I, Kidd M. The Identification of gut neuroendocrine tumor disease by multiple synchronous transcript analysis in blood. Plos One. 2013; e63364.
19. Li S C, Essaghir A, Martijn C, et al. Global microRNA profiling of well-differentiated small intestinal neuroendocrine tumors. Mod Pathol. 2013; 26: 685-696. doi: 610.1038/modpathol.2012.1216. Epub 213 January 1018.
20. Modlin I, Drozdov I, Alaimo D, et al. A multianalyte PCR blood test outperforms single analyte ELISAs for neuroendocrine tumor detection Endocr Relat Cancer. 2014; 21: 615-628.
21. Modlin I M, Frilling A, Salem R R, et al. Blood measurement of neuroendocrine gene transcripts defines the effectiveness of operative resection and ablation strategies. Surgery. 2016; 159: 336-347. doi: 310.1016/j.surg.2015.1006.1056. Epub 215 October 1019.
22. Cwikla J B, Bodei L, Kolasinska-Cwikla A, Sankowski A, Modlin I M, Kidd M. Circulating transcript analysis (NETest) in GEP-NETs treated with Somatostatin Analogs defines Therapy. J Clin Endocrinol Metab. 2015; 100: E1437-1445.
23. Bodei L, Kidd M, Modlin I M, et al. Measurement of circulating transcripts and gene cluster analysis predicts and defines therapeutic efficacy of peptide receptor radionuclide therapy (PRRT) in neuroendocrine tumors. Eur J Nucl Med Mol Imaging. 2015; 23: 23.
24. Pavel M, Jann H, Prasad V, Drozdov I, Modlin I M, Kidd M. NET Blood Transcript Analysis defines the Crossing of the Clinical Rubicon: When Stable Disease becomes Progressive. Neuroendocrinology. 2017; 104: 170-182.
25. Merlino G, Herlyn M, Fisher D E, et al. The state of melanoma: challenges and opportunities. Pigment Cell Melanoma Res. 2016; 29: 404-416. doi: 410.1111/pcmr.12475. Epub 1216 April 12417.
26. Diaz-Uriarte R, Alvarez de Andres S. Gene selection and classification of microarray data using random forest. BMC Bioinformatics. 2006; 7: 3.

EQUIVALENTS

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A method of treating a melanoma in a human subject in need thereof, the method comprising:

a) determining the expression level of 29 biomarkers from a biological fluid sample from the subject by contacting the test sample with a plurality of agents specific to detect the expression of the 29 biomarkers, wherein the 29 biomarkers comprise each of atlastin GTPase 1 (ATL1), ATPase H+ transporting V0 subunit d1 (ATP6V0D), chromosome 1 open reading frame 21 (C1ORF21), CASP8 and FADD like apoptosis regulator (CFLAR), CFLAR antisense RNA 1 (CFLAR-AS1), calcineurin like EF-hand protein 1 (CHP1), DEAD-box helicase 55 (DDX55), dystrophin (DMD), DnaJ heat shock protein family (Hsp40) member C9 (DNAJC9), enolase superfamily member 1 (ENOSF1), Fanconi anemia complementation group L (FANCL), Holliday junction recognition protein (HJURP), major histocompatibility complex, class II, DO alpha (HLA-DOA), major histocompatibility complex, class II, DR alpha (HLA-DRA), heterogeneous nuclear ribonucleoprotein A3 pseudogene 1 (HNRNPA3P1), interleukin 23 subunit alpha (IL23A), IQ motif containing GTPase activating protein 1 (IQGAP1), NFYC pseudogene (LOC494127), uncharacterized LOC646471 (LOC646471), loss of heterozygosity, 12, chromosomal region 2 (non-protein coding) (LOH12CR), PBX homeobox interacting protein 1 (PBXIP1), ring finger protein 5 (RNF5), SERTA domain containing 2 (SERTAD2), solute carrier family 35 member G5 (SLC35G5), spermatogenesis associated serine rich 2 like (SPATS2L), tudor domain containing 7 (TDRD7), TXK tyrosine kinase (TXK), YY2 transcription factor (YY2), and at least one housekeeping gene;

b) normalizing the expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2 to the expression level of the at least one housekeeping gene, thereby obtaining a normalized expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2;

c) inputting each normalized expression level into an algorithm to generate a score, wherein the algorithm is the product of a trained classifier built from at least one predictive classification algorithm;

d) determining that the human subject has melanoma by determining that the score is greater than or equal to a first predetermined cutoff value, wherein the first predetermining cutoff value is 20 on a scale of 0 to 100; and e) administering to the human subject at least one therapeutically effective amount of at least one of:

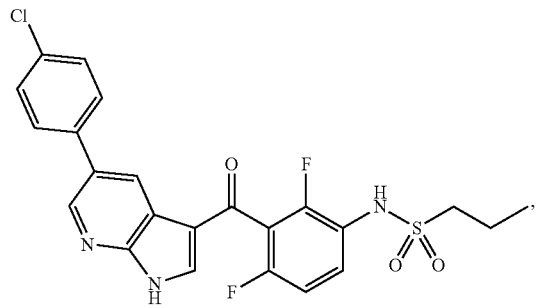 [SMILES: CCCS(=O)(=O)Nc1ccc(F)c(C(=O)c2c[nH]c3ncc(-c4ccc(Cl)cc4)cc23)c1F]

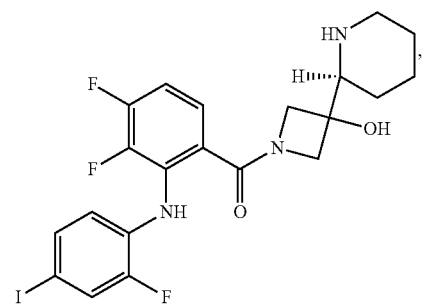 [SMILES: O=C(c1ccc(F)c(F)c1Nc1ccc(I)cc1F)N1CC(O)([C@@H]2CCCCN2)C1]

-continued

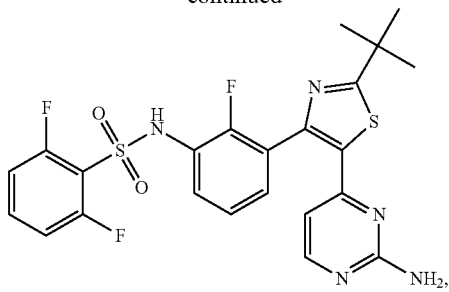

or any combination thereof.

2. The method of claim 1, wherein the method comprises administering at least one therapeutically effective amount of:

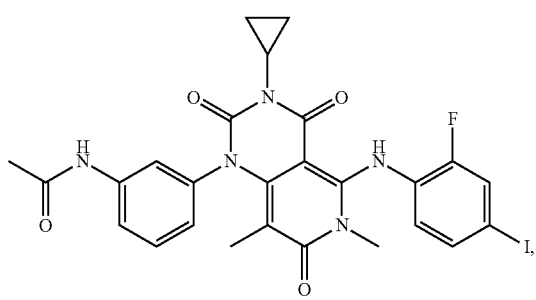

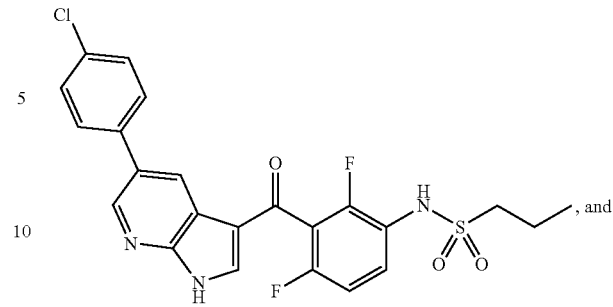

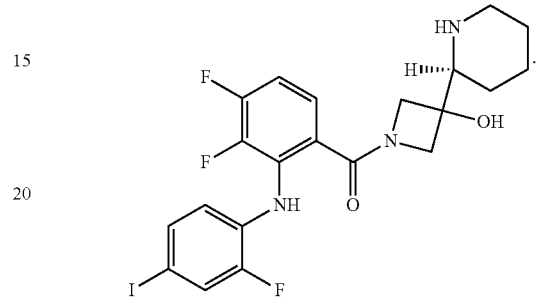

, and

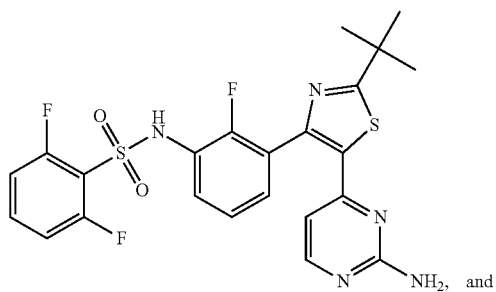 and

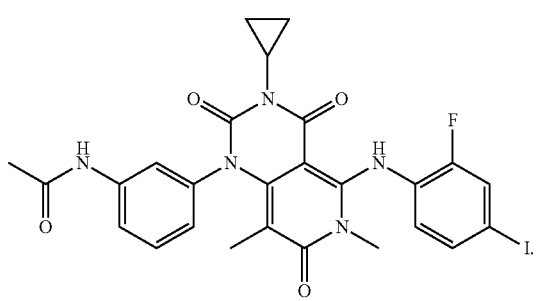

3. The method of claim 1, wherein the method comprises administering at least one therapeutically effective amount of:

4. The method of claim 1, wherein the method comprises administering at least one therapeutically effective amount of:

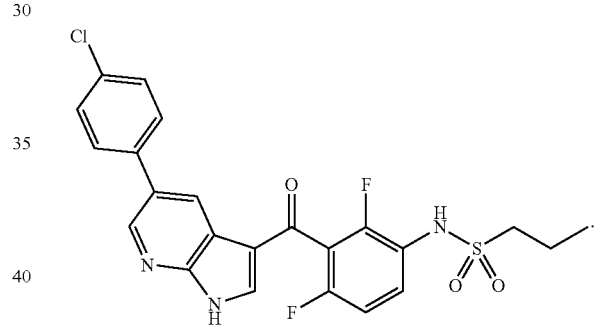

5. The method of claim 1, wherein the method comprises administering at least one therapeutically effective amount of:

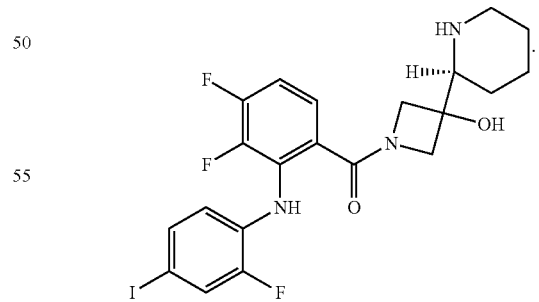

6. The method of claim 1, wherein the at least one housekeeping gene comprises TOX high mobility group box family member 4 (TOX4), tumor protein, translationally-controlled 1 (TPT1), or any combination thereof.

7. The method of claim 6, wherein the at least one housekeeping gene comprises TOX4 and TPT1.

8. The method of claim 7, wherein step (b) comprises:
i) normalizing the expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2 to the expression level of TOX4, thereby obtaining a first normalized expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2;
ii) normalizing the expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2 to the expression level of TPT1, thereby obtaining a second normalized expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2; and
iii) averaging the first normalized expression level and the second normalized expression level, thereby obtaining a normalized expression level of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2.

9. The method of claim 1, wherein at least one of the 32 biomarkers is RNA, cDNA, or protein.

10. The method of claim 9, wherein when the biomarker is RNA, the RNA is reverse transcribed to produce cDNA, and the produced cDNA expression level is detected.

11. The method of claim 1, wherein the expression level of the biomarker is detected by forming a complex between the biomarker and a labeled probe or primer.

12. The method of claim 9, wherein when the biomarker is protein, the protein is detected by forming a complex between the protein and a labeled antibody.

13. The method of claim 10, wherein when the biomarker is RNA or cDNA, the RNA or cDNA is detected by forming a complex between the RNA or cDNA and a labeled nucleic acid probe or primer.

14. The method of claim 13, wherein the label is a fluorescent label.

15. The method of claim 13, wherein the complex between the RNA or cDNA and the labeled nucleic acid probe or primer is a hybridization complex.

16. The method of claim 1, wherein the algorithm is XGB, RF, glmnet, cforest, CART, treebag, knn, nnet, SVM-radial, SVM-linear, NB, NNET, mlp, or logistic regression modeling.

17. The method of claim 1, wherein the algorithm comprises a model of melanoma disease dynamics built using the expression levels of each of ATL1, ATP6V0D, C1ORF21, CFLAR, CFLAR-AS1, CHP1, DDX55, DMD, DNAJC9, ENOSF1, FANCL, HJURP, HLA-DOA, HLA-DRA, HNRNPA3P1, IL23A, IQGAP1, LOC494127, LOC646471, LOH12CR, PBXIP1, RNF5, SERTAD2, SLC35G5, SPATS2L, TDRD7, TXK, and YY2 from reference blood samples from a plurality of subjects having melanoma and a plurality of subjects not having melanoma.

\* \* \* \* \*

SEQUENCE LISTING

```
<160> NUMBER OF SEQ ID NOS: 56

<210> SEQ ID NO 1
<211> LENGTH: 2821
<212> TYPE: DNA
<213> ORGANISM: Homo sapiens

<400> SEQUENCE: 1
agtttgaggc tgcactgcac acctgcacaa cctgccttct acttagttct tctgagacat      60
ttctgaaagt ctgaattcct aggactgctc aatgaccttt gtccctgttg ggcacacgca     120
gtgtctcatc gctggtattg cacctttaat gagaccagga gttccgcaaa agtaaaacaa     180
aggggtcaca gactggttct ggttctacca cttcctcagt atgtgctctg ggacaaaaca     240
gcatatttgg caacatctcg gtgtccttat ctgcagcttg aagaggcgcc acagcaacat     300
cctcagagtc tgagcgaact gcgcccagcg cgggcacgga gcctcccacc gccagcaacc     360
tgcggccccg gagaaggcag cgagcgcagt gacagcgcct caccgccacc agctcctgga     420
ccaccatggc caagaaccgc agggacagaa acagttgggg tggattttcg gaaaagacat     480
atgaatggag ctcagaagag gaggagccag tgaaaaaggc aggaccagtc caagtcctca     540
ttgtcaaaga tgaccattcc tttgagttag atgaaactgc attaaatcgg atccttctct     600
cggaggctgt cagagacaag gaggttgttg ctgtatctgt tgctggagca tttagaaaag     660
gaaaatcatt cctgatggac ttcatgttga gatacatgta caaccaggaa tcagttgatt     720
```

```
gggttggaga ctacaatgaa ccattgactg gtttttcatg gagaggtgga tctgagcgag      780
agaccacagg aattcagata tggagtgaaa tcttccttat caataaacct gatggtaaaa      840
aggttgcagt gttattgatg gatactcagg gaacctttga tagtcagtca actttgagag      900
attcagccac agtatttgcc cttagcacaa tgatcagctc aatacaggta tataacttat      960
cccaaaatgt ccaggaggat gatcttcagc acctccagct tttcactgag tatggcagac     1020
tggcaatgga ggaaacattc ctgaagccat tcagagtct gatatttctt gttcgagact      1080
ggagtttccc atacgaattt tcatatggag ccgatggtgg tgccaaattc ttggaaaaac     1140
gcctcaaggt ctcagggaac cagcatgaag aactacagaa cgtcagaaaa cacatccatt     1200
cctgtttcac caacatttcc tgttttctgc tacctcatcc tggcttaaaa gtagctacca     1260
atccaaactt tgatggaaaa ttgaaagaaa tagatgatga attcatcaaa aacttgaaaa     1320
tactgattcc ttggctactt agtcccgaga gcctagatat taaagagatc aatgggaata     1380
aaatcacctg ccggggtctg gtggagtact tcaaggctta tataaagatc tatcaaggtg     1440
aagaattacc acatcccaaa tccatgttac aggccacagc agaagctaac aatttagcag     1500
ccgtggcaac tgccaaggac acatacaaca aaaaaatgga agagatttgt ggtggtgaca     1560
aaccatttct ggccccaaat gacttgcaga ccaaacacct gcaacttaag gaagaatctg     1620
tgaagctatt ccgaggggtg aagaagatgg gtggggaaga atttagccgg cgttacctgc     1680
agcagttgga gagtgaaata gatgaacttt acatccaata tatcaagcac aatgatagca     1740
aaaatatctt ccatgcagct cgtaccccag ccacactgtt tgtagtcatc tttatcacat     1800
atgtgattgc tggtgtgact ggattcattg gtttggacat catagctagc ctatgcaata     1860
tgataatggg actgacccct atcaccctgt gcacttgggc atatatccgg tactctggag     1920
aataccgaga gctgggagct gtaatagacc aggtggctgc agctctgtgg gaccaggctt     1980
tgtacaagct ttacagtgca gcagcaaccc acagacatct gtatcatcaa gctttcccta     2040
caccaaagtc ggaatctact gaacaatcag aaaagaaaaa aatgtaatgc aaattttaag     2100
aaatacaggt gcatgaccaa ttgtcaatta atatattcagt tttatgtctc catgcaaaca    2160
ttcaaagtgc ttccatcaga acggagtaaa atactaaaca cctctgaaga ctgcaaactg     2220
gattagttct tttacttcag tgtttaataa gcagatgtat gtatgcatgg ttatactatt     2280
ttgttaacat gtacaatttc ctgatttttc ttcaaaaatg ctgttataaa gtatttgtct     2340
atttatgata acagtacacg tgttctgctt gaatttacta aattctacta ctgggttata     2400
attaaatcat gtgatattcc acgtttggat atgctcattt aatttctaca gaaaaaattt     2460
taaattattt cacattagcc atttgttaaa acacagcatc ataactcagc aggctggatt     2520
taatctgtat catcttatat atatcacaat cttattttta agcacatttt agagttcctt     2580 agttgctttta tcaaaaacca gatattgctt ttacatggtt aatagaata taaacctctt     2640 gataaaaaat gcacaaaaaa tcactttgta tatgtgagtt tcactgcatt gtatattttt     2700
tcatttggta cacaaagaat gtattcttca taggtttatt cttttaatat gtgaactatt     2760
attaaagttt actctggttc ctaagattaa aaacaaatgc ttactgaatt tgaaaaaaaa     2820
a                                                                    2821
```

<210> SEQ ID NO 2
<211> LENGTH: 1688
<212> TYPE: DNA
<213> ORGANISM: Homo sapiens

<400> SEQUENCE: 2

```
acttgacagc cgctgagga cgcagcgtca gctgacctgg ggagtcgcga ttcgtgccgg      60
ccggtcctgg ttctccggtc ccgccgctcc cgcagcagcc atgtcgttct ccccggagct    120
ttactttaac gtggacaatg ctacttgga gggactggtg cgcggcctga aggccggggt    180
gctcagccag gccgactacc tcaacctggt gcagtgcgag acgctagagg acttgaaact    240
gcatctgcag agcactgatt atggtaactt cctggccaac gaggcatcac ctctgacggt    300
gtcagtcatc gatgaccggc tcaaggagaa gatggtggtg gagttccgcc acatgaggaa    360
ccatgcctat gagccactcg ccagcttcct agacttcatt acttacagtt acatgatcga    420
caacgtgatc ctgctcatca caggcacgct gcaccagcgc tccatcgctg agctcgtgcc    480
caagtgccac ccactaggca gcttcgagca gatggaggcc gtgaacattg ctcagacacc    540
tgctgagctc tacaatgcca ttctggtgga cacgcctctt gcggcttttt tccaggactg    600
catttcagag caggaccttg acgagatgaa catcgagatc atccgcaaca ccctctacaa    660
ggcctacctg gagtccttct acaagttctg cacccctactg gcgggactaa cggctgatgc    720
catgtgcccc atcctggagt ttgaagcaga ccgccgcgcc ttcatcatca ccatcaattc    780
tttcggcaca gagctgtcca agaggaccg tgccaagctc tttccacact gtgggcggct    840
ctaccctgag ggcctggcgc agctggctcg ggctgacgac tatgaacagg tcaagaacgt    900
ggccgattac tacccggagt acaagctgct cttcgagggt gcaggtagca accctggaga    960
caagacgctg gaggaccgat tctttgagca cgaggtaaag ctgaacaagt tggccttcct   1020
gaaccagttc cactttggtg tcttctatgc cttcgtgaag ctcaaggagc aggagtgtcg   1080
caacatcgtg tggatcgctg aatgtatcgc ccagcgccac cgcgccaaaa tcgacaacta   1140
catccctatc ttctagcgtc ctggcccaag gctctcaatt gcactctttg tgtgtgtgtg   1200
tgtgtgtgtg cgcgtgtgtg tgcgtgtgtg tgtatgtggt ctgtgacaag cctgtggctc   1260
acctgcctgt ccggggtgta gtacgctgtc ctagcggctg cccagttctc ctgaccctct   1320
tagagactgt tcttaggcct gaaaaggggc tgggcacccc ccccaccaa ggatggacga    1380
agaccccctc cagagcaagg aggccccctc agccctgtgg ttacagccgc tgatgtatct   1440
aagaagcatg tcactttcat gttcctccct aactccctga cctgagaacc ctggggcctg   1500
ggggcagttt gagcctcctc tcccttctgt gggtcgctcc cagagccatg gcccatggga   1560
aggacagagt gtgtgtgtcc ttggggcctg ggggatgtt gctcctcagc tccctccctc    1620
agccctgccc ctctgagaca ataaaactgc cctctctaag gccaactgtc aaaaaaaaa   1680
aaaaaaaa                                                          1688

<210> SEQ ID NO 3
<211> LENGTH: 10308
<212> TYPE: DNA
<213> ORGANISM: Homo sapiens

<400> SEQUENCE: 3
ccctccctcg ctcgctcctc gcaagctccc gctcgctccc tgcccactcc cggggggacg      60
ttccgtgccg cggccgccgc ggccgctgct tctttcacac tttagttggg agctgcgcgc    120
cgcgctcagt tactggagag ctggccgcgc gccgccgcct cccgcacgct tgcacgcggg    180
cccggcttcg gggttttggg ttcttactcc aagcggcggg gaggaggggg agccccggac    240
acactgtggg gaggaggagg aagaagagga ggagggagga agaaaaaaga cgaggaggac    300
aggggcgggg ggcgggaggc ttgccacctt cagcccccccgc gcaacgccc aaggtgcaca    360
```

| | |
|---|---|
| catcttgacc aactcagcag caaggtggat tttctttgtg tttaaagaaa aaaaatgtcc | 420 |
| ctgtgtctgt agagatgatt tgcagttcag cccggctgaa gctgaccgaa tgagactatg | 480 |
| ggctgtgcct ccgccaagca tgttgccact gttcaaaatg aagaggaagc cagaaaggg | 540 |
| aaaaactacc agaacggaga tgtgtttggc gatgagtata ggatcaaacc agtggaagag | 600 |
| gtcaaataca tgaaaaatgg ggcagaagaa gagcagaaaa tagcagccag gaaccaagaa | 660 |
| aacttggaaa aaagtgccag ctcaaatgta agacttaaaa ctaataaaga ggttccggga | 720 |
| ttagttcatc aacccagagc aaacatgcac atctctgaaa gccaacaaga attcttcaga | 780 |
| atgctggatg aaaaaattga aagggtcgg gattactgtt cggaagaaga ggatatcaca | 840 |
| tagcaccaat tttaccactc aaaccaggag ctactactgt gtaaataggt tacaccccag | 900 |
| ttgaaatctt tgcaaaggtc ggttctattc agcgaacagc actatagcaa agaagatcg | 960 |
| ttccatattg tacgccccat taaattacag tgtttcttaa tgaacttgca aaggaatatt | 1020 |
| gctaaaaaca aacaaaaaaa actgttatcg aactttcttt gttgctgcta gttaaaactt | 1080 |
| gttgcaactt ttcacttctc ttgtgtccag gtatgcagca aaattctgca atttcacctt | 1140 |
| aaagatactg ttggttttac agatgctctc caacctattt tctataagat gaggtagtgg | 1200 |
| tgaactcaga taacaaactt ctcttctaaa ctggttctgc ttctaagaca agcatctcct | 1260 |
| gccctctctc cttcctcccc atctctcgca cgcagtctag agatggactg agccttgctt | 1320 |
| ctcactggca gtgttgagct ttggagatgg gatggttgct atgccaagcc ttgtttctct | 1380 |
| gctcagaaga agtagagaag ctattatcaa ttaaaagcat gctgtgatgt gactcctgga | 1440 |
| agtgacgtag gagtgagtgg caggttgttt gatttaatag gtatcttaat caagaattaa | 1500 |
| gcttgcaaca ttggctttgc tcagatgcag atggaagtgt gatcacaatc attttgaatc | 1560 |
| cctcttcctc acttttttttt ctaagaaaat aaacatttta ctgtttttat ggatccttgt | 1620 |
| cttctcccat tcatccagct cagtgtttta agatgatcct gggtgcagaa gttgagccct | 1680 |
| cctttgcatt gacactgata attagcctat agggctccct accttccat taagaatcta | 1740 |
| ccaagcatta gcaaggctga aagtggtcta agaggtgagg ggacatccta tgactttta | 1800 |
| ggaaggcctg aaaccacctt gttaccttc attttgttag caaataaacc atcctatttt | 1860 |
| gtaactctcc cccttcaaaa tgctacatga gccttgccac ttcctttttc tcttacttcc | 1920 |
| agcacactag acatagcaaa agtgtttgcc tactcaaaaa cataatactt ttatgctgat | 1980 |
| gatggtattt ggagatgtga agccaaaag cccctggcag tggtggggaa tgttgactga | 2040 |
| gtgttcagca gagtttattt ttccatacta tatgaagaga atgatctctt ctcaaagaca | 2100 |
| gaagtgatat ttttaacaaa tattgtcaca agtaaatagc aatcaaaagg agaaaataac | 2160 |
| ttttgtattt tttaatgtg tttgatagct ttgacgaggg ttctctttgt tactttcagg | 2220 |
| ggagggcatc ctattaaatg ccacgccagc agtccgggtc tgggtttgtc ccacaaaatc | 2280 |
| acaggagcac tgtatgttcc tctcttttgg agttgtgact ttgaagggcc tcaatattag | 2340 |
| ccacactgcc gcctgcagaa ggtggagagt taagatgttc tatgtcaatt tgctcttgcc | 2400 |
| gaaaagatga gcctcgattt taaaatctat ccacatccaa ctgatggcac cattgatgtg | 2460 |
| caaataatga gattccctat ctcctttag acctgggacg gcaaaaggga agggaaggaa | 2520 |
| acttagcaga gtgctattga ctatagattc acatattagc aacaaaatcc cgtaattctt | 2580 |
| ttggccaaca gcagctattt tggggagcag ctgtggctgt tacataaata gagatgcagc | 2640 |
| caaaatttta ggccttttat cctgcttcta gcagaaaaat gcaggagag tcaagtagtc | 2700 |
| tagggtttca ggttgcctcc cctcatatgg tttttggcca agtgactaaa acagttttcc | 2760 |

```
acaactgtaa acaaactgct aagccccacc tcaaacttgt tcactggga ctttgcttac      2820 cgttctgtgg gtgaccttt ccgggatttc ttgttcttat caagcaagaa ttaagcacat      2880
gctaaacgtc ttccatttga cttctctact cggtgtctca gacagtgtct tcccagaaaa     2940
ccaccaccct ctacccaaag atgaaacatg ctcatgtcat ttttctcatg gtcacattta     3000
acagttttga catgttatac ttgcgcatag atccaagcgt ttcttgggaa cctgactttt     3060
gagtgtttaa taaagccgga agtggtgttg ccctgaacca gcagattttc acctgggttc     3120
tggctccggt gtttaacact ggatacatct ttgatgtgcg aaagtgagtt catcttcaga     3180
cacatttggt acatccagaa atagatccaa gaaatggggg ggttgagtgg gtccgcacga     3240
aatgcttgat tatgtcagca acacccaaca ctgtctgttt tccatttgtt ggttttaatc     3300
ataaaattgt caagtgattc gtgttttgtac tttattttt tgtgccttct gaaaggatct     3360
aaaacaaaaa tattttgcct tttttttcccc acgtgtatct gaacattaag cagattggct     3420
cagacacaat gaaaaggata atccaatgta cgtgctggtg cactctgcta gttgttatct     3480
ctgtagggct caggaagctg aaggaggaa gggagggtaa gtggcctggt gagtggaggt      3540
agaaaaatga tgagaaatga actgagagca ttaagcagag agggttgata ggctggccgt     3600
gtccggggtg aaattggaaa tccagctgcc tagtggccag tgggtggggc aagactgtca     3660
acgagattta cagctggctt acacatgcct tatgtcctct gagttgtaga gttgtaaaag     3720
ttcagcagtg tgtgcacagc tttctttttgg ttggcagaga ttcaggatca tggagtactg     3780
ctctcataat tgaagacgtg tttgttattg gcagagaacc ttaaaaaagg ccttttacctc    3840 agcgatgctt cctagcccca ggcttgcaga gaacacagag tggtgttgtg gtctatttag     3900
ggacaaagaa ggtataaagt ccagagatga gaaaactggg tcagccctca gaaactgcag     3960
cagccacgca cacagaagcc tgctggaaga caggtctctc tccgtccaca gtgcccatca     4020
tctgagcctg ggctgggatg actcaactta gcaaagacgg acccaggagg agtgctggtt     4080
cttcagtctt tgtactggcc ccatcctctc ctcactgtaa tgtgaggaag cacctctgtg     4140
tcagggctca cctgggcatc caaagcggcc acgcccacaa tccgacagcc cccaggagca     4200
ggtccaggga tgatgcagcc cccttcttgg tcccatgtga tgtcatcctg ctttgttatc     4260
ttcttataac tttatcctgc tataaacttta tcctcttccc agcctcatcc ctgttttttct   4320 gttagggcaa gactcttcca taagcctgct aaaaaaacaga gatgatacct cttacaaact    4380
ttacctcata gcctgtgaag caggttggca tgtggattac aagtcctgct ttgacactgg     4440
gcaagaattt aagattgttc tatctctact agtcatagaa aagaaacatt gttaaacatg     4500
ttgagtttta aggaagaaa tattttcaaa ttcttaatcc aagaaaatac tgagttggaa      4560
tcttagactt cgggactctg acacgttctt tatgaaaggc aaaataattg gtatctaaag     4620
ttctctcctt cctgcctccc ctaaagaaaa aggatattag attgcacact ataatttac     4680 ataagatctg ccttccacac ttccctgctg gaaggcattc tcagagcttt atgtcttcgt     4740
acctctcaga gattggactt tttcttgttt aaaaccccaa ccaaaaaaaa taataaggca     4800
tgattggtgg ggagggaatg tgtatttagg ggcataataa aaaggtggct cgaagcagga     4860
actttggcct catggtgtca tgggtggatg cctggactcc agtgtgcctg tgaggggctg     4920
ggttaggcag tcggctgtca cactcacatg tgcctgcaat aaacctttg gaatttcatg      4980 aacgaggtct atgaattgcc ttttgccaat gaatggatgt attttccaa ggggggaata      5040 gtatccttga cttttggcagt caccttttg tatgtctcta gaaaggggtc aaaaaactat     5100
```

```
ggtaaagatg aggcttatga gtgaatacct ctgggacaaa ccttaggact cacaagctat    5160
gccatgtttt tcaggagact cttgtacctt atctggaatc taatcttggg agaagaggaa    5220
aaaggagcta atatttgtca tttatactca ctctgtgcca gatactgtgc taggcatttt    5280
ataattgttt tgtgtcatcc tcatgataat cctgtgaagt agatctatta cccccgtgtt    5340
ctaaataata gatcttaagt gtggaatgca tctatccaac ataaatgccc atgttgaaag    5400
aaggaaagat gtcattcaag tattttttcaa attcttttta ttatgactat gcccttcgca    5460
acactgtgaa acaaccect ggggcatct gccttccaga atctctctct ggcttctcac    5520
cagcttggtt tcctcatggg gagtgtttta tttggcctcc cctatctgag ctgcacacac    5580
accaggggag gccactggct aacagtagga cttcagtgcc ctgaggaaaa ggctttggga    5640
atttaggcac acgtttctct ccttggaatc cttctagcat ctggaaaagg aacctggtat    5700
ttctgcagtt agataccaga tgcaaccaga acaggctttc gagtgctgtg atttctttcc    5760
tgggttccca agtcttgttg tttcatcaca aactgtatct ttttaaggtt aaaagtcttg    5820
accttcatgg gggtctggga caatccgatc tccaagcatg gaggaaaggc aatgcctgga    5880
ccactgactt gcattgaaat cctttcttgt gggctagggt ttgatgtctc ttttcatct    5940 ttggactggg gatctgcatc ttccaggtcc atttaagcac tgaaactaga tgcaaatctc    6000
tttcgagacc ttacatgttt tagatagtca tgtaatgact tggatagaca tttaaataac    6060
ttgttccaag gtcggaagag cccaagaact cctcagagtt cctcttcttg cttcttgaat    6120
cacatcctct aaagatgact catgtctcca tagcaactgt taaaggtgct gcctagacgg    6180
gacccgctcc cacctttact tactttgctc gaaggaacca aaacaatgtc cttgtgtaaa    6240
ggggctgtca tatccagttt tcctttgaaa tctggccccc aagatcctgc ttctttctaa    6300
cctggcagct gtcatgtccc ttcaagatga tgtgggaaat ggcccttaca acttgggaac    6360
cacagaaatt gctgtatttc gggaagattc acctctaaac tgaaggcttc attctgatag    6420
tgtctgccct ctctaccctg atttcgccct tctttgcttc cattttttagc ccaaggctt    6480 gaatttgatt gagtaagact tagaggcagt ataagaaca ccataaactt aggcagaggt    6540
cccttagggt ctctagagtt gaaaataatt ctacagcctt aggggacct cttggcattg    6600 actctaaagg gagagaatag cccctgtgtc ctggcatttc agtctagacc ttcaaggact    6660
gttctctctt gacaggcaag caagcaaaga aagttttgca atagatttca agccagtttt    6720
tccattcaaa ccaagatgca aattcataaa attactcttt tcctggaata gatccaggca    6780
gctgccttat tagaaccttta gattcggatc tatttcctta acacacatac acatacacgc    6840
gcatacatac atatacagag agatacgtgg agaaggaaa tttactctat cattgcaata    6900
cttcaagaaa gagctgtatt ttgcctttct gtaatctcca agatagtgtc taggaaagta    6960
atagtataac tatagggata ccgaaacagg aaaaccagc catcactctt gagaaagttt    7020
gagttcgact cacatgggag aatcgaggtc tgctactcgt cttgctttgt gccccatctg    7080
tgcctggatg ccctactaca tctgcttgac tcgtctgggc tgctagccgg ggtgttgtgg    7140
ctgacatcct ttcctggcct tacacacata atagacacat cctaacggc gtgtgcctgg    7200 tccagccaca tacagccacc acatgtgtca cacactgtcc ccctcatcca tgtgacttg    7260 actggcattt cagcagctcc actgggatgc tctaaccca gtgtgtggag ttggggtccc    7320
ttcatctagg ttgacccagg tatagcattt ttagcattgc ctttccagtc ttgatgattc    7380
attcattgaa ctcattttatt tctggagccc ctggtacact ccaggcactg cgctaattgc    7440
cagcaaagca caactgaact aaatccacct tcaaggaacc tagccataac gagggaggca    7500
```

```
gcatggaagt accctacagg ggaaagtcct gagtgctgtg ggagcatctc accgtggcag    7560
ccagcccagt tttggcaatc aggggcttcc tgaaagaggt gacatcaaag cccggatgtg    7620
tcagaggact gagggagagt gttactaaag gactttcagg ctgagaggat agcacaggac    7680
tcagcccaaa ggagggccag tgtggactgt ccagggccag cctgcagtac agaggctgga    7740
gcttggactt gtagagggag agagaagagc aagggacgtg gacggggcag tgagccaggc    7800
tagccacaga gggttcccgg ggctttgctg gggattcagg gagcataaat aagagcttta    7860
ggtggtgctg tgtcctctgc agcccactgc tgaggtcctc cagacaggta aggtgtggtc    7920
acaatcaggg ccggggtttc cctgctcact gcggcagtgc aggggtgctt gctgagatga    7980
ttcatcccag ggtgtcctct gtcccttacc cagccccaac tcctcttcct ctgccaaaag    8040
ctatttgaat tcaaggactt taacctgggc cggatctggt ttggagacaa aggggacagc    8100
tctgggtcag catgaccttc tttagagcca ctaaggcgaa aaataccgtt tgggaccagg    8160
ctggcctaga cccagggatg agaatgcacc ctaaaataaa tatacgggaa gcagcagagg    8220
gcttccctgt ctagtgtgtg atcctaacta aaggcagctc tcttggacag ccttcccctg    8280
gattaggtca catacacctg gtggccaagc ctctgctggg tcccaaatac acacccgagt    8340
cctgccaaag aaaggagatt tttaaaaagc acagacaaat tgtatgcaag tggaaaatac    8400
ccataggcct agacagctgt ggagggaaga cctcgtgggt acctggaggc tgccagagct    8460
gggagctctg caggtatgag tcagggaagg ctcagagaca agcagaatct ctctatggag    8520
acaacttgca gtgcctttta ggttttccaa ataacctcgg agttcagagc attgggtttt    8580
tttctcccct ccccaccccc agaaaaataa ttagaaaaat gtttaggaga aggaaaaga    8640 attagatgca tcagaatacc agctataagc caacactgtt tccagaaact caagaaaaag    8700
ctcaaacaga agacagttcc cctgagaggc tggaggcgtt ggtgctgaag gcaattttcc    8760
tagctaaggg gcactgggcc ttgctgcacc ttggggctga cctttttgc aaaacaccca    8820 cccctgccct cctggcatac tcaacagcaa cgccagcttt ctggacccct ggaaagatgt    8880
tagctcaaac acccactttt tccagatctt cctcttgctc ttcactgagg aatttgtaat    8940
tctgaggcta gcgatgccca ctcggatatt ccgcaggccc aggtgtttag attagaattt    9000
gtccagcggt aatcctgatg ctggaaacca acaaacattt ggcctcatat tcacccattt    9060
aaaaactaga gccctggca ggtccccta gggccatgtg ttcatggaat ataagccaag    9120
tttgccttag gcttgttcat ggaatataag ccaagtttac ctctccccat tttctgccct    9180
ggcccacttc ccactcacct ccacctcatt gccaggaagg gatcaaaatg cctccatgcc    9240
agttgttaat ggctacatat ttgcccttcc caagggtatt tgcatttat ttaggaacat    9300 ggccttatat tcaaggaaaa tctagcatca agattacgag gcatcacctc tcaatcaggt    9360
ctgggaggta tcttggggca ttgctcttct gaacacctgc agaggcttcc tcaggtgagt    9420
gtgggagccc ggaagggtgg cctccctaac cactctgcct gcacatgaat tctccaaagc    9480
agtgggcccc catctgtttc aattacacat gcctgtcagc aaaaacttcg tgagatgcac    9540
tctctctgtg tgtttattaa tttatttaaa gcatatatcc ctttactttt gtactactat    9600
attaggcaca ttataaaaag tatacagcat agaaactttta aatgaataag acacaaaata    9660
ttataaacag aggttctggc attttctctc tgaactcctg aggggggacct tgggcacctc    9720 ctggtatgtg cacaccccac tttgaacacc cttgctttag tgcaaatcag cacgcctaaa    9780
tagcatccca aaccactgtg cgacatttgg cctgcagaat aagaaagtcc taaggcagaa    9840
```

| | |
|---|---|
| tccccaggaa cttcaaatct gggagatgag gaaagaaaac tcactcacaa acaacataaa | 9900 |
| tgtaaataat tcaaaaccct aaaggagagc tgtccctaga cagtagtggc tacaggtgct | 9960 |
| aagcaaaagt caggtacact ggacagagcc atgcgattga ttgttcatct tccctctctg | 10020 |
| ggtctccaga aaaggacact ggcaatatcc ccagctctct cctgattgga attctttgaa | 10080 |
| ccctcgaagt gctccagcag tactaccccc cacgtagcag tgggcccatg tcgcttgaat | 10140 |
| attattttg atttgaccac caagatgtaa tgatgattct attccatttt gaaaagggtc | 10200 |
| tgagaaagtg tacaggtcta attatatata catatttata catgtgtatt tttgtttatt | 10260 |
| gttacatttt gacattggac tttctattaa ataattttta agagttgg | 10308 |

<210> SEQ ID NO 4
<211> LENGTH: 10668
<212> TYPE: DNA
<213> ORGANISM: Homo sapiens

<400> SEQUENCE: 4

| | |
|---|---|
| gaccacgcat ggagaatttt accacccaga gacacgcgag tggccctgtg caagtttcaa | 60 |
| ctgcgcgggg ggcggggaat tccgcagaca ggattctaga atttatgtct tgtgtggtaa | 120 |
| catttcagcc ggtgggtggc ggggattagg cgtgaagcgg ttcagcaggc agaggttctc | 180 |
| ggacgccctc cggcgaagcc acctgttgat gcttttgact ttctgtcctt gttcctcgtc | 240 |
| ccatctggag catttccaat tctggttttg cggagcagca ggtctgagct tgtccggcga | 300 |
| gggtgggagt tggtcccggc ggagatccag tgggaagagc cggcggctgc ccgggcaact | 360 |
| cccccactgg aaaggattct gaaagaaatg aagtcagccc tcagaaatga agttgactgc | 420 |
| ctgctggctt tctgttgact ggcccggagc tgtactgcaa gacccttgtg agcttcccta | 480 |
| gtctaagagt aggatgtctg ctgaagtcat ccatcaggtt gaagaagcac ttgatacaga | 540 |
| tgagaaggag atgctgctct ttttgtgccg ggatgttgct atagatgtgg ttccacctaa | 600 |
| tgtcagggac cttctggata ttttacggga aagaggtaag ctgtctgtcg ggacttggc | 660 |
| tgaactgctc tacagagtga ggcgatttga cctgctcaaa cgtatcttga agatggacag | 720 |
| aaaagctgtg gagacccacc tgctcaggaa ccctcacctt gtttcggact atagagtgct | 780 |
| gatggcagag attggtgagg atttggataa atctgatgtg tcctcattaa ttttcctcat | 840 |
| gaaggattac atgggccgag caagataag caaggagaag agtttcttgg accttgtggt | 900 |
| tgagttggag aaactaaatc tggttgcccc agatcaactg gatttattag aaaaatgcct | 960 |
| aaagaacatc cacagaatag acctgaagac aaaaatccag aagtacaagc agtctgttca | 1020 |
| aggagcaggg acaagttaca ggaatgttct ccaagcagca atccaaaaga gtctcaagga | 1080 |
| tccttcaaat aacttcaggc tccataatgg gagaagtaaa gaacaaagac ttaaggaaca | 1140 |
| gcttggcgct caacaagaac cagtgaagaa atccattcag gaatcagaag cttttttgcc | 1200 |
| tcagagcata cctgaagaga gatacaagat gaagagcaag ccctaggaa tctgcctgat | 1260 |
| aatcgattgc attggcaatg agacagagct tcttcgagac accttcactt ccctgggcta | 1320 |
| tgaagtccag aaattcttgc atctcagtat gcatggtata tcccagattc ttggccaatt | 1380 |
| tgcctgtatg cccgagcacc gagactacga cagctttgtg tgtgtcctgg tgagccgagg | 1440 |
| aggctcccag agtgtgtatg tgtggatca gactcactca gggctcccc tgcatcacat | 1500 |
| caggaggatg ttcatgggag attcatgccc ttatctagca gggaagccaa agatgttttt | 1560 |
| tattcagaac tatgtggtgt cagagggcca gctggaggac agcagcctct ggaggtgga | 1620 |
| tgggccagcg atgaagaatg tggaattcaa ggctcagaag cgagggctgt gcacagttca | 1680 |

```
ccgagaagct gacttcttct ggagcctgtg tactgcggac atgtccctgc tggagcagtc    1740
tcacagctca ccatccctgt acctgcagtg cctctcccag aaactgagac aagaaagaaa    1800
acgcccactc ctggatcttc acattgaact caatggctac atgtatgatt ggaacagcag    1860
agtttctgcc aaggagaaat attatgtctg gctgcagcac actctgagaa agaaacttat    1920
cctctcctac acataagaaa ccaaaaggct gggcgtagtg gctcacacct gtaatcccag    1980
cactttggga ggccaaggag ggcagatcac ttcaggtcag gagttcgaga ccagcctggc    2040
caacatggta aacgctgtcc ctagtaaaaa tacaaaaatt agctgggtgt gggtgtgggt    2100
acctgtattc ccagttactt gggaggctga ggtgggagga tcttttgaac ccaggagttc    2160
agggtcatag catgctgtga ttgtgcctac gaatagccac tgcataccaa cctgggcaat    2220
atagcaagat cccatctctt taaaaaaaaa aaaaaggac aggaactatc ttactcaatg    2280
tattagtcat gtttctctag agggacagaa ctaataggat acatgtatat aaaaagggga    2340
gtttattaag gagtattgac tcacatgatc acagggttag gtcccacaat aggtcatctg    2400
caagcaagga agccaattca gtcccaaag ctgaagaact tggagtccaa tgtttgaggg    2460
caggaagcat tcagcatgag agaaagatgg aggccagaag actacaccag tctagtctttt   2520 ccatgttttg cctgctttta ttctggcagt gctggcagct gattagatgg tgcccaccca    2580
gattgaggat ggtctgcctt cccagtcca ctgactcaaa tgttaaatct cctttggcag     2640
caccctcaca gatgtacccg ggaacacttt gcatccttct attcaatcaa gttgatactc    2700
agtattaacc atcacagtcc atttgggcaa ctataccaaa ttaccataga ccaggtgact    2760
taaacagcag ttatttctca cagttccgga ggctgggaaa tccaacatct aagtggtagc    2820
atatctggtg tctggtaagg catgcttcca gatcttacca gatgtcagtc ttttgatgtt    2880
ctcacatggc agaaaaagag gatgcaaact ctcaagtata tctttaaggg cacaaattcc    2940
attcatgagg gctctaccct catcacctaa ttacctccca aaggcccac cttctgatac     3000 tgtcactttg gggatactgt ctccccttttg aattctgggg ggaatacaaa cattcagttt   3060
gtaacaatag ccttatgatt tagaggttac ttgttcattc acctagacct caaattgcat    3120
tttacagcta gtcaagtata tctttctctg atttgatagt gtgacctaaa aggggaccat    3180
tgtttgaaat atcattagag ttgcttatta ttattattat tattattatt attattatta   3240
ttattattat tgagacagag tttcattctg ctgcccaggc tggagtgcag tggcatcatc    3300
ttggctcatt gcaacctctg ccttctgggt tcaagcgatt ctcctgcctc agcctcccga    3360
gtagctggga ttacaggctc ctgccaccac acccggctaa ttttttgtatt tttagtggag  3420 acagggtttc caccatgttg gccagcgtgg tcttgaactc ctgacctcag gtgattcacc    3480
agcctcggcc tcccaaagtg ctgggattac aggtgtgagc cactgcacct ggcctattat    3540 tattttttaaa tttttttttt ttaattgatc attcttgggt gtttctcaca gagggtgatt    3600
tggcagggtc acaggacaat agtggaggga aggtcagcag ataaacaagt gaacaaaggt    3660
ctctggtttt cctaggcaga ggaccctgcg gccttccgca gtgtttgtgt ccctgggtac    3720
ttgagattag ggagtggtga tgactcttaa ggagcatgct gccttcaagc atctgtttaa    3780
caaagcacat cttgcactgc ccttaatcca tttaaccctg agtggacaca gcacatgttt    3840
cagagagcac agggttgggg gtaaggtcat agatcaacag catcctaagg cagaagaatt    3900
tttcttagta cagaacaaaa tgaagtctcc catgtctact tctttctaca cagacacagc    3960
aacaatctga tttctctatc ttttccccac ctttccccct tttctattcc acaaaaccgc    4020
```

```
catcgtcatc atggcctgtt ctcaatgagc tgttgggtac acctcccaga cggggtggcg    4080
gctgggcaga ggggctcctc acttcccaga tggggcggcc aggcggacgc gcccccacc     4140 tccctcccgg acgggatagc tggccggggcg ggggctgacc ccccacctcc ctccccgacg   4200
gggcggctgg ccggggcgggg gctgaccccc acgcctccct cccggacggg gcggctgcca   4260
ggcggagggg ctcctcactt ctcagacggg gtggctgctg ggcggagacg ctcctcactt    4320
cccagacagg gtggctgtcg ggcggagggg ctcctcactt ctcagacggg gcagctgcgg    4380 gcggagggggc tcctcacttc tcagacgggg tggccgggca gagaagctcc tcacatccca   4440
gacggggggg cggggcagag cgctccccca catctcagac gatgggcggc cgggcagaga    4500
cgctcctcac ttcatcccag acggggtggc ggccgggcag aagctgtaat ctcggcaccc    4560 tgggggggcca aggcaggcgg ctgggaggcg gaggccgtag ccagctgaga tcacaccact   4620
gcactccagc ctgggcaaca ttgagcactg agtggacgag actctgcccg caatcccggc    4680
acctcgggag gccgaggctg gcagatcact cgcagtcagg agctggagac cagcccggcc    4740
aacacagtga aaccctgtct ccaccaaaaa aatacgaaaa ccagtcaggc gtggcggcgc    4800
ccgcaatggc aggcacgcgg caggccgagg cgggagaatc aggcagggag gctgcagtga    4860
gccgagatgg cagcagtaca gtccagcttc ggctcggcat cagagggaga ccgtggggag    4920
agggagaaga gagggagggg gagagggcta tttttaaaat tttttaaaat tgctgaacag    4980
gggtacctct gggcagtgtg tcagaatacc acttttaaa tattttatga tttatttatt     5040
tttctatttc ttgaggtttt aactgatgtg tatctgtatg tctatttgtg tatattttgt    5100
catgatcatg taacagagtc tgaaaagtgt cgaagagaca gttttcagga acaacaagca    5160
attattccta ctttccaagt tattttgatg ccatggtggc tcatacctat aatctgagta    5220
ctttgggagg ctgaggtgga ctgatcactt gagcccagga gtttgagacc agcctgggca    5280
acatagcaag actccatctc tacaaaaaaa gacaaaattt agctgagcgt ggtggcgtgt    5340
tcctgtagtc ccagctactt gggaggctga agtgagtgga tccctgagc ccagagaggt     5400 caaggttgtg atgagctgtg atcacaccac tgcacttcag catgggagac agagtgagac    5460
cctgtttcag aaaaaataaa taaataaaac caccagcacc acaaacaaca caaaaagtt     5520 attttgtact tgttttgagc acaggactcc tgagggtatc tttgcattta atattacata    5580 gggggtgccca tgggaagtaa tgtgtatgct tggcctcatg agctaaaacc ctgtgttaat   5640
tatgacagaa ggaaagtgtg tgagagagat cttaactacc tagcagctct agctgccatc    5700
ttgaaccatg aagatacggg ccacacgtag gggtagctgg gtagtgagca gcaagaagcc    5760
ttgttggatg agggcacgaa ggagcagaat cactggaatc actgtgtcag ccctaattac    5820
ctacctctgg acttttatgt gagggggaaaa aaaattgaca gtttatattt atctcaacct   5880
agttaaccca agtgatgcat tgttatgaga ttaaaatgtt tggaggccgg gtgcggtggc    5940
tcacgcctat aatcccagcc ctttgggagg ccaaggcggg cggatcacga ggtcaggaga    6000
tcaagaccat cctggctaac atgtaaaacc ccgtctctac taaaaataca aaaaattagc    6060
caggcgttgt ggcggtcgcc tgtagtccct gctatttggg aggccgaggc aagagaacgg    6120
catgaacctg ggaggtggag cttgcagcga gctgagatct tgccactgca ctccagcctg    6180
ggcgacagtg cgagactctg tctcaaaaat aaataaataa ataaataata aataaatgt     6240 ttggaatgtt ggcttcatcc ctgggatgca aggctggttc aacatacgca aatcaagaaa    6300
cataattcat cacataaaca gaactaaaga caaaaaccac atgattatct caatagatac    6360
agaaaaggcc ttcaataaaa ttcaacgttg cttcatgtta aaaactctca ataaactagg    6420
```

```
tattgatgga aaatatctca aaataataac catttatgac aaacccacag ccattatcat    6480
actgaatggg caaaagctgg aagcattccc cttgaaaact ggcacaagac agggatgccg    6540
tctcaccact cctatttaac atagtattgg aagttctggc caagaaaatc aggcaagaga    6600
aacaaataag gggtattcaa ataggaaaag aggaagtaaa actgtgtttg cagatgacat    6660
gatactatat ctagaaaacc ccattatctc cacccaaaag ttccttaagc tgataagcaa    6720
cttcagcaaa gtctcaggat acaaaatcaa tgtgcagaaa tcacaagcat tctatacacc    6780
aacaatacac aagcagagag ccaaatcatg aatgaactcc cattcacagt tgctagaaag    6840
agaataaaat acctaggaat acagctaata agatgtgaag gatctcttca aggagaacta    6900
caaaccactg ctcaaggaaa taagagagga cacaaatgaa aaaacattcc attctcgtgg    6960
ataggaagaa tcaatatcat gaaaatggcc atactaccca agtaattta taggttcatt    7020 gctattccca ttaaactact attgacattc ttcacagaat tagaaaaaaa ctactttaaa    7080
attcaaatgg aaccaaaaaa gagcccgtat aaccaagaca acaataagca aaaagaacaa    7140
agctggaagc atcacactac ccaacttcaa agtatactgc aaggctacag tagccaaaat    7200
ggcatggtac tggtacaaaa acagacacat agaccaatgg aacagaatag agaccagaga    7260
aagaagacca cacatctaca gccatctgat catcgacaaa cctgacaaaa acaagcaatg    7320
gggaaaagat tccctatttta ataaatggtg ctgggaaaac tggctagcca tatgcagaaa    7380
attgaaactg acccccttcct tacaccttat acaaaaatta actcaagatt aaagacttaa    7440
tgtaaaacct aaaactataa aaaccctaga agaaaatcta tttaataacc attcaagacat    7500 aggcacaagc aaaggtttca tgacaaaaac atcaaaagca attgcaacaa aagcaaaaat    7560
tacaaatggg atctaattaa actaaagagc tcctgcacag caaaagaaac tatcattaga    7620
gtgaacaggc aacctacaga atgggagaac atttttgcaa tctatccatc tgacaaaggt    7680
ctaatatcca gaacctacaa ggaacttaaa acaaatttac aaggaaaaaa acaaccccat    7740
caaaaagtgg acaaaggaca tgaacagaca cttctcaaaa gaagacattt atgtggccaa    7800
caaacatata aaaaaaagct caaccttact gatcattaga gaaatgcaaa ggagaaccac    7860
aatgagatac catctcatgc cggtcagaat ggtgattatt aaaaagtcaa aaaacaacag    7920
atgctggcga ggctgtggag aagtaggaac acttttacat tgttggtggg aatgtaaatt    7980
agttcaaccg ttgtggaagt gtgtgtggct attcctcaaa gatctagaac tagaaatact    8040
atttgtccca gcaatcccat tactgggtat atacccaaag aatataaac cattttatta    8100 taaagataca tgcacatttt tgttcattgc agcactcttc acaatagcaa agacacaata    8160
gcaaatgccc atcaaagata gactggataa agaaaatgtg gtacatatac accatggaat    8220
actgtgcagt gcagccatta cagcttttgg tgatacagtg aatcagattt ttcattaatt    8280
cttttaattg gttattactg aacgtgaaaa agtaatgttt gtattgaaat cttgagtctg    8340
gccatgtttc tattttaaat tcataaagaa ttctaacaag aggaattcca agaatgtcat    8400
aaatggatgt ttctccatgg atgaaggaac tgttttattc acttgctgat aattcagcct    8460
aatccagttt gacatcatat agataagtag ttgaattatg gatttaaaat acatatcatt    8520
ttctaactcc aaaggtaata cttatttaaa tggttttgaa aatatagaaa ggcacaattt    8580
ctttttaaat ctgttattct ccaccaccac tcaatctgtc tatcatctat ctctccattc    8640
attcttccat ttgtttatat ctgttaatct ttgtatgtgt tcatgtatag cttttacatg    8700
attggaatca taatgcatat tccatttga agtctgcttt tttttacaca aaaatatgtt    8760
```

| | |
|---|---|
| gtgaatattt tcctatatta tgaaatatca ttagctgagc ttttagaatt gactgcatgt | 8820 |
| tttggtacca tttagatata gtttaagata cttagaagtt atgtggcttt gccactatgg | 8880 |
| atgaatctta tttactcaat attaattact tacaaataac ctcacctaaa cactactcag | 8940 |
| ccataaaaag gaatgaatta atgacattca cagcaacctg gagactatta ctctaaagga | 9000 |
| agtaactgag gaatggaaaa ccaaacattg tatgttctca ctcataagtg ggagataagc | 9060 |
| tatgaggatg caaaggcata agaaggatac aatggacttt ggggacttag gggaaagggt | 9120 |
| gggagggggg tgaaggataa aagaatacaa attgggttca gtgtatactg ctcaggtgat | 9180 |
| gggtgcacca gaatctcaca agtaaccact taattactta cgcatgtaac cagataccac | 9240 |
| ctgttcccca aacacctatg gaaataattt tgttttttt tttaaaaaag gaatgagatc | 9300 |
| atgtcctttg cagggacatg gatgaagctg gaagccatta tcctcagcaa actaacagag | 9360 |
| gagcaggaaa ccaaacacca catgttctca cttgtaagcg gaagctgaac aatgagaaca | 9420 |
| cacggacaca gggatgagat caacacacac tggggcctga tgcaggggcc gtagcgggga | 9480 |
| gagcatcagg ataactagct aatgcatgtg gggcttaata cctaggtgat aggttgatag | 9540 |
| gtgcagcaaa ccaccatggg acacgtttac ctatgtaaca aacccgcaca tcctgcactt | 9600 |
| gtatccagaa cttaaaatat tttaaaaatc tttagagaat acaaaaaaaa aaaaaaagat | 9660 |
| tcttcaatgc atacacaata aaattgcagt tcagtcaaac attggaagtc tttctctgac | 9720 |
| tgtctagttg gtatcttcat tttcagcttc ttcaagatcc cactccaaac actgttagct | 9780 |
| cagccaaatt gaacagctca tatctcctac ctctggatct ttggttctgg tgattgtata | 9840 |
| tttctggacc atctggaacc ccagcatatc accctacccc acatctccac atccccaaaa | 9900 |
| tataaccata cttcaagggc agttcaaata ccatctcctt ctatcctcca tgaagtcagt | 9960 |
| tatctcttcc attggaatta tcgcccccct tcctgaacag tactatttcg tgtgaatctc | 10020 |
| ctccaagcct tcttttcatt ttatatctca tgctgtaatt cttggaaagt atgctgtagc | 10080 |
| tcaagtgcag aattctcatc agttttatct ttatatctct cctaaacact ttacctgatg | 10140 |
| aagagcctgg catacacata aatatatatt gaatgaatca gtgatggatt gaaaagagaa | 10200 |
| atgatggatc tcctaaattt taacttttat aaaatatttt gatacattca tgaccttact | 10260 |
| ttagcaagca atgaacgtga tgtaaactat tgttgatata gtttttatat tggaagtgta | 10320 |
| agtagtttgt ggcatgggat tgtgacatat cctaggtttc ctcatcttct ttttattgaa | 10380 |
| atgtaattca caagccataa aatttgcccc tttaaagtaa atgatgcagt ggattttagt | 10440 |
| atatttacag agttgtgcaa tcatcaccac tatctaattc cagaacattt ccatctacct | 10500 |
| agaaactcca taccagtgag ctgccactct aatcctcctc ttcccccagc ctctagaaac | 10560 |
| aataatccat tttctgtctc tatgatttgc ctgttctaga tattttataa aaataaacat | 10620 |
| gtggcctttc gtgtctgact tccttcactt aaaaaaaaaa aaaaaaaa | 10668 |

<210> SEQ ID NO 5
<211> LENGTH: 1041
<212> TYPE: DNA
<213> ORGANISM: Homo sapiens

<400> SEQUENCE: 5

| | |
|---|---|
| catgcataca gcccagtcta acgtacagga tcaaaaagag accttatttc ggctggcaat | 60 |
| taccttaccc gcttgttcat tatctgactc ctgcactcct cccaagtgtt caatgttaac | 120 |
| cagatggcaa agttaaccag acagaggaaa tccacataat tactctagat gaagcccct | 180 |
| aactgcggat tagaaggaaa agagatgaag ggtgctgcac taataataac aaccatttc | 240 |

```
aaccaaggca ggattctggg cctagaatct tcagtgacaa attaccagga gaggaggagg    300
gaaatgaaga gctggaggcc tagggagatg gtgtgaggag aggagactgt gcctttccac    360
ttcttaataa ttaatgttct cctgctgctc tgagtctgca tcaccagtga ttcagtttga    420
gtcagacatc caacaacaac tgagcaaaag aatcatctca gatccaagca atggtgacgc    480
gcagatagaa gagactgagg ccaacgacca aagcaaagga cagcagaact gactgacaca    540
gctcagaaaa tatccaaagc tctgtatgct ctggaaagga agacaagaaa tgctaaagac    600
tctggatatt gctctgtttc tataaggtcc cacccatata ccatctcttc ttttggattt    660
cctttggcag ggttcccttg tatggaagtt ctcaggagaa caacactctc agagtcccac    720
tgtctcaaag aattcttaat ggacagctat acttggcccc aaggtttcaa cctcacactg    780
aagaaagtga cataagaaaa cacaagtccc agtgctatca ggggctatct ggaaaagctg    840
cttaaacagc aagtgaaaga aggctctccc ctaccccgtt ctagactcac cctgaagtta    900
tttgaaggat ccttgagact cttttggatt gctgcttgga gaacattcct gtaacttgtc    960
cctgctcctt gaactataaa agcagaaggg aggtactgag ttaaaactta caaattatta   1020
tcaaataaat cttcaatagt g                                             1041

<210> SEQ ID NO 6
<211> LENGTH: 3230
<212> TYPE: DNA
<213> ORGANISM: Homo sapiens

<400> SEQUENCE: 6 accaccctg ggttccctcc cgggtccgca gtggaaacac tgccctctcc cttcttgacc      60
cctagccctt ccttccctcc ctccttccct cctgtcgccg tctcttctgg cgccgctgct    120
cccggaggag ctcccggcac ggcgatgggt tctcgggcct ccacgttact gcgggacgaa    180
gagctcgagg agatcaagaa ggagaccggc ttttcccaca gtcaaatcac tcgcctctac    240
agccggttca ccagcctgga caaggagag aatgggactc tcagccggga agatttccag     300
aggattccag aacttgccat caacccactg ggggaccgga tcatcaatgc cttctttcca    360
gagggagagg accaggtaaa cttccgtgga ttcatgcgaa ctttggctca tttccgcccc    420
attgaggata tgaaaagag caaagatgtg aatggacccg aaccactcaa cagccgaagc    480
aacaaactgc actttgcttt tcgactatat gatttggata agatgaaaa gatctcccgt     540 gatgagctgt tacaggtgct acgcatgatg gtcggagtaa atatctcaga tgagcagctg    600
ggcagcatcg cagacaggac cattcaggag gctgatcagg atggggacag tgccatatct    660
ttcacagaat tgttaaggt tttggagaag gtggatgtag aacagaaaat gagcatccga    720
tttcttcact aaaggagacc aaactgttcc ttgcggtcta gtatttaaga actggaactt    780
gaaagtcctc cttctaccaa ctccacctcc accccctcat tcccttctc ccaaagtact     840 actgctgttg catgacaacc ccaaatatgt tctgtcaaca caaacctgcc tttggtgtat    900
aaacagggca ttacagaatg gtacacccta tatttctg ttcagtatcc attcactagt      960
tcttcattta taaatatcat cttccccatt ctgctgctga atgccacaca tccatccagt   1020
ctgagaaagt gagagaggca atcatgccaa gaacaagcca gcaaagctct tcaccagat    1080 gtagactgta gccctgctgc cttccctcca gcgagtctgc cagcatgctt cttcatcctt   1140
tttatatgtt ctttgcttcc tacttccctg tcttccaaca tactgttcac ttactctggc   1200
agtctttctg cttttcatta agcctcaaaa tctcctctgt tctacttggc accacaagct   1260
```

```
atgtcctata tatgtatttc tgacttggca ggatagttca ggggtctggc agttttatt      1320 taccttcatt attaaatggg cctctgggat gttgcctctt caggagcttt ttggtaatca      1380
atacttctct cagaagtatg agaccatcct ctgcactctg ctctgtcatc aaaggctgct     1440
gggtggagat acccttttg aaaggtggcc ttggtgagag gtatggagcc aagtcttcta      1500
ggttgcttgc ccacatcact ctatctctgg cctctgattc tcaactttgt acctgtgtgg    1560
ctcctcttgt tagtgcaatg ttgactgttg aaaaagcagc agtatgctta caggtttgct    1620
tagtttgggg acaccgttac caccagaatg gctgctctga caatatgcct agggactttc    1680
tcatggcttt tatttaataa ggaggctggg caccctataa agcctcatgc attcacacct    1740
ttgcagcatg gtttatgcct cagtgttatg tgcactggaa tgtttccac ttcacatttc     1800 caagtagaaa tattagtgtt acggaagtgc ctaatatccc agtccaaatt tttttttttt    1860
tttttttttt tttttgagac agagtcttgc tctgtcaccc aggctggagt gcagtggtgc    1920
gatcgctcac tgcaacctca gcctcctgga tttaagtgat tctcctgcct cagcctccca    1980
agtagctggg attacaggtg tgcaccacca tgcccggcta attttttgta tttttagtgg   2040
agacagggtt tcaccatgtt ggccaggctg tctcgaact cctgacctcg tgatccgcct    2100
gcctcagcct cccaaagtgc tgggattaca ggtgtgagcc accacgcctg gccccagtcc   2160
aaaatattta aagattgttt ccttagtgtc ttgaagtttt gcacaaaatt ctttttttg    2220 agatggagtc tcactctgtc acccaggctg gagtgcagtg gcgtgatctt ggctcactgc   2280
aacctctgcc tcctgggttc aagcaattct cccacctcag cctcccaagt agctgggatt   2340
acagacgtgt gccaccatac ctgggtaatt tttgcatttt tagtgagag ggagtttcac    2400 catgttggcc aggttggtct tgaactcctg acctcaggtg atcctcctgc ctcggcctcc   2460
caaagtgctg gattacagg catgagccac cgtgctcagc cgcaaaattc tttatgaatt     2520
ttacacttgg caaatgttaa tgacggaagc catagtctgc tcctaataca tgtccaaagc   2580
attgactgtt gtgtcattag ctgcctggtt acattagctc cctggcttct tgtttagacc   2640
actgctaatc ccttaaaaac aagaggtctg gcactagtag cacaacctaa ggtggcatta   2700
cagatctttg agcgagccac agcaactttt ctgccaagtc agcttagttt agacttcagt   2760
gaatcaggct attgctatcc taatgtatgt ctctatgagt gtatttagcc acacatctgc   2820
ccttggttga ctttctgact cattgcttgc ttgcttgttt ccttgctttg gaaaactatt   2880
gaagattgct aaaaaatacc actgcaaagt gatggaaaag ggtggagaac aggggagtag   2940
ccaggctgga tggctcaaat ataaatgaat gaggaattct ttatgaagta tcagtcagat   3000
tttatgatta agtgatgtaa tataggaatt atgtaaaagg gaagaatgtc tgatactgat   3060
ctattagaga ggtactttag aggcttcttg attggcataa agttcctaag gttatagatt   3120 ttccccccctt ttggctgtat agcaaagtgt tttaatccac ggttgtgcct tattgttcca   3180
ttaaaattgt atcttcgatc catcaataaa tacttgtggt tgaaacaaaa                3230
```

<210> SEQ ID NO 7
<211> LENGTH: 2678
<212> TYPE: DNA
<213> ORGANISM: Homo sapiens

<400> SEQUENCE: 7

```
agcggaagtg ctcgttgggg gtgcacaagg cgcgttcgag cagcggcgac cgacgcggcg       60
aaggagcgcg ccatggagca tgtgacagag ggctcctggg agtcgctgcc tgtgccgctg      120
cacccgcagg tgctgggcgc gctgcgggag ctgggcttcc cgtacatgac gccggtgcag      180
```

```
tccgcaacca tccctctgtt catgcgaaac aaagatgtcg ctgcagaagc ggtcacaggt    240
agtggcaaaa cactcgcttt tgtcatcccc atcctggaaa ttcttctgag aagagaagag    300
aagttaaaaa agagtcaggt tggagccata atcatcaccc ccactcgaga gctggccatt    360
caaatagacg aaggtcctgt cgcatttcacg aagcacttcc ccgagttcag ccagattctt    420
tggatcggag gcaggaatcc tggagaagat gttgagaggt ttaagcaaca aggtgggaac    480
atcattgtgg ccactccagg ccgcttggag gacatgttcc ggaggaaggc cgaaggcttg    540
gatctggcca gctgtgtgcg atccctggat gtcctggtgt tggatgaggc agacagactt    600
ctggacatgg ggtttgaggc aagcatcaac accattctgg agttttttgcc aaagcagagg    660 agaacaggcc ttttctctgc cactcagacg caggaagtgg agaacctggt gagagcgggc    720
ctccggaacc ctgtccgggt ctcagtgaag gagaagggcg tggcagccag cagtgcccag    780
aagaccccct cccgcctgga aaactactac atggtatgca aggcagatga gaaatttaat    840
cagctggtcc atttcttcg caatcataag caggagaaac acctggtctt cttcagcacc    900
tgtgcctgtg tggaatacta tgggaaggct ctggaagtgc tggtgaaggg cgtgaagatt    960
atgtgcattc acggaaagat gaaatataaa cgcaataaga tcttcatgga gttccgcaaa   1020
ttgcaaagtg ggattttagt gtgcactgat gtgatggccc ggggaattga tattcctgaa   1080
gtcaactggg ttttgcagta tgaccctccc agcaatgcaa gtgccttcgt gcatcgctgc   1140
ggtcgcacag ctcgcattgg ccacgggggc agcgctctgg tgttcctcct gcccatggaa   1200
gagtcataca tcaatttcct tgcaattaac caaaaatgcc ccctgcagga gatgaagccc   1260
cagagaaaca cagcggacct tctgccaaaa ctcaagtcca tggccctggc tgacagagct   1320
gtgtttgaaa agggcatgaa agcttttgtg tcatatgtcc aagcttatgc aaagcatgaa   1380
tgcaacctga ttttcagatt aaaggatctt gattttgcca gccttgctcg aggttttgcc   1440
ctgctgagga tgcccaagat gccagaattg agaggaaagc agtttccaga ttttgtgccc   1500
gtggacgtta ataccgacac gattccattt aaagataaaa tcagagaaaa gcagaggcag   1560
aaactcctgg agcaacaaag aagagagaaa acagaaaatg aagggagaag aaaattcata   1620
aaaaataaag cttggtcaaa gcagaaggcc aaaaaagaaa agaagaaaaa aatgaatgag   1680
aaaaggaaaa gggaagaggg ttctgatatt gaagatgagg acatggaaga acttcttaat   1740
gacacaagac tcttgaaaaa acttaagaaa ggcaaaataa ctgaagaaga atttgagaag   1800
ggcttgttga caactggcaa aagaacaatc aagacagtgg atttagggat ctcagatttg   1860
gaagatgact gctgattcca gtgccacaga tgaacccaca aggacatagc tgttccctaa   1920
cttggtggat ggctccagtt tgcttttaac gaaaatcaca acttcaggag acatctgaaa   1980
agaatgatgt ctctgaaagc tgtccttca gatgagggaa aaatgaagga tttcacactt   2040
cagaatattt tactaaaaac attccagtct tggccgggtg cggtggctcc tgcctataat   2100
cccagcactt tgggaggctg aggcaggagg atcacttgag cccaggagtt caagaccagc   2160
ctgggaacac agcgagaccc tctcattaaa aacaacaaaa caaacaatt ccagtcttgg   2220 agtagtctaa cagaagaaaa tgtaaaatta tttgagtgta aataatagat gtcagtattt   2280
atcatgatgg gtcacatata gacatatgta catattatat atatatatat atatatatat   2340
atatatatat atatatatat ataagctctt ttttctgagg ctattttata gttattttta   2400
aacataaaga tacagaagtc ttcttgactt ctgattttca aaaccattcc tcagtatctt   2460
caggcatttg acctcctgaa tgtgcttggc cctgggcttc agttatcctt tgatgtcctg   2520
```

```
cagggggtggc taatgtgctg ggttttttct gtgttaatag tcacagtatt gttttattgg    2580
tgaatagctg aaaaacagag ggattaagtc atattccggg aaagagaatt atagttttta    2640
tgcctcctgt tgaataaatg gtgtcctgat tgcctggg                             2678

<210> SEQ ID NO 8
<211> LENGTH: 14069
<212> TYPE: DNA
<213> ORGANISM: Homo sapiens

<400> SEQUENCE: 8
cgttaaatgc aaacgctgct ctggctcatg tgtttgctcc gaggtatagg ttttgttcga      60
ctgacgtatc agatagtcag agtggttacc acaccgacgt tgtagcagct gcataataaa     120
tgactgaaag aatcatgtta ggcatgccca cctaacctaa cttgaatcat gcgaaagggg     180
agctgttgga attcaaatag actttctggt tcccagcagt cggcagtaat agaatgcttt     240
caggaagatg acagaatcag gagaaagatg ctgttttgca ctatcttgat ttgttacagc     300
agccaactta ttggcatgat ggagtgacag gaaaacagc tggcatggaa gatgaaagag      360
aagatgttca aaagaaaaca ttcacaaaat gggtaaatgc acaattttct aagtttggga     420
agcagcatat tgagaacctc ttcagtgacc tacaggatgg gaggcgcctc ctagacctcc     480
tcgaaggcct gacagggcaa aaactgccaa agaaaaagg atccacaaga gttcatgccc      540
tgaacaatgt caacaaggca ctgcgggttt tgcagaacaa taatgttgat ttagtgaata     600
ttggaagtac tgacatcgta gatggaaatc ataaactgac tcttggtttg atttggaata     660
taatcctcca ctggcaggtc aaaaatgtaa tgaaaaatat catggctgga ttgcaacaaa     720
ccaacagtga aaagattctc ctgagctggg tccgacaatc aactcgtaat tatccacagg     780
ttaatgtaat caacttcacc accagctggt ctgatggcct ggctttgaat gctctcatcc     840
atagtcatag gccagaccta tttgactgga atagtgtggt ttgccagcag tcagccacac     900
aacgactgga acatgcattc aacatcgcca gatatcaatt aggcatagag aaactactcg     960
atcctgaaga tgttgatacc acctatccag ataagaagtc catcttaatg tacatcacat    1020
cactcttcca gttttgcct caacaagtga gcattgaagc catccaggaa gtggaaatgt      1080
tgccaaggcc acctaaagtg actaaagaag aacattttca gttacatcat caaatgcact    1140
attctcaaca gatcacggtc agtctagcac agggatatga gagaacttct tcccctaagc    1200
ctcgattcaa gagctatgcc tacacacagg ctgcttatgt caccacctct gaccctacac    1260
ggagcccatt tccttcacag catttggaag ctcctgaaga caagtcattt ggcagttcat    1320
tgatggagag tgaagtaaac ctggaccgtt atcaaacagc tttagaagaa gtattatcgt    1380
ggcttctttc tgctgaggac acattgcaag cacaaggaga gatttctaat gatgtggaag    1440
tggtgaaaga ccagtttcat actcatgagg ggtacatgat ggatttgaca gcccatcagg    1500
gccgggttgg taatattcta caattgggaa gtaagctgat tggaacagga aaattatcag    1560
aagatgaaga aactgaagta caagagcaga tgaatctcct aaattcaaga tgggaatgcc    1620
tcagggtagc tagcatggaa aaacaaagca atttacatag agttttaatg gatctccaga    1680
atcagaaact gaaagagttg aatgactggc taacaaaaac agaagaaaga acaaggaaaa    1740
tggaggaaga gcctcttgga cctgatcttg aagacctaaa acgccaagta caacaacata    1800
aggtgcttca agaagatcta gaacaagaac aagtcagggt caattctctc actcacatgg    1860
tggtggtagt tgatgaatct agtggagatc acgcaactgc tgctttggaa gaacaactta    1920
aggtattggg agatcgatgg gcaaacatct gtagatggac agaagaccgc tgggttcttt    1980
```

| | |
|---|---|
| tacaagacat ccttctcaaa tggcaacgtc ttactgaaga acagtgcctt tttagtgcat | 2040 |
| ggctttcaga aaagaagat gcagtgaaca agattcacac aactggcttt aaagatcaaa | 2100 |
| atgaaatgtt atcaagtctt caaaaactgg ccgttttaaa agcggatcta gaaaagaaaa | 2160 |
| agcaatccat gggcaaactg tattcactca aacaagatct tctttcaaca ctgaagaata | 2220 |
| agtcagtgac ccagaagacg gaagcatggc tggataactt tgcccggtgt tgggataatt | 2280 |
| tagtccaaaa acttgaaaag agtacagcac agatttcaca ggctgtcacc accactcagc | 2340 |
| catcactaac acagacaact gtaatggaaa cagtaactac ggtgaccaca agggaacaga | 2400 |
| tcctggtaaa gcatgctcaa gaggaacttc caccaccacc tccccaaaag aagaggcaga | 2460 |
| ttactgtgga ttctgaaatt aggaaaaggt tggatgttga tataactgaa cttcacagct | 2520 |
| ggattactcg ctcagaagct gtgttgcaga gtcctgaatt tgcaatcttt cggaaggaag | 2580 |
| gcaacttctc agacttaaaa gaaaaagtca atgccataga gcgagaaaaa gctgagaagt | 2640 |
| tcagaaaact gcaagatgcc agcagatcag ctcaggccct ggtggaacag atggtgaatg | 2700 |
| agggtgttaa tgcagatagc atcaaacaag cctcagaaca actgaacagc cggtggatcg | 2760 |
| aattctgcca gttgctaagt gagagactta actggctgga gtatcagaac aacatcatcg | 2820 |
| ctttctataa tcagctacaa caattggagc agatgacaac tactgctgaa aactggttga | 2880 |
| aaatccaacc caccaccca tcagagccaa cagcaattaa aagtcagtta aaaatttgta | 2940 |
| aggatgaagt caaccggcta tcaggtcttc aacctcaaat tgaacgatta aaaattcaaa | 3000 |
| gcatagccct gaaagagaaa ggacaaggac ccatgttcct ggatgcagac tttgtggcct | 3060 |
| ttacaaatca ttttaagcaa gtcttttctg atgtgcaggc cagagagaaa gagctacaga | 3120 |
| caattttga cactttgcca ccaatgcgct atcaggagac catgagtgcc atcaggacat | 3180 |
| gggtccagca gtcagaaacc aaactctcca tacctcaact tagtgtcacc gactatgaaa | 3240 |
| tcatggagca gagactcggg gaattgcagg ctttacaaag ttctctgcaa gagcaacaaa | 3300 |
| gtggcctata ctatctcagc accactgtga agagatgtc gaagaaagcg ccctctgaaa | 3360 |
| ttagccggaa atatcaatca gaatttgaag aaattgaggg acgctggaag aagctctcct | 3420 |
| cccagctggt tgagcattgt caaaagctag aggagcaaat gaataaactc cgaaaaattc | 3480 |
| agaatcacat acaaaccctg aagaaatgga tggctgaagt tgatgttttt ctgaaggagg | 3540 |
| aatggcctgc ccttgggat tcagaaattc taaaaaagca gctgaaacag tgcagacttt | 3600 |
| tagtcagtga tattcagaca attcagccca gtctaaacag tgtcaatgaa ggtgggcaga | 3660 |
| agataaagaa tgaagcagag ccagagtttg cttcgagact tgagacagaa ctcaaagaac | 3720 |
| ttaacactca gtgggatcac atgtgccaac aggtctatgc cagaaaggag gccttgaagg | 3780 |
| gaggtttgga gaaaactgta agcctccaga aagatctatc agagatgcac gaatggatga | 3840 |
| cacaagctga agaagagtat cttgagagag attttgaata taaaactcca gatgaattac | 3900 |
| agaaagcagt tgaagagatg aagagagcta agaagaggc ccaacaaaaa gaagcgaaag | 3960 |
| tgaaactcct tactgagtct gtaaatagtg tcatagctca agctccacct gtagcacaag | 4020 |
| aggccttaaa aaaggaactt gaaactctaa ccaccaacta ccagtggctc tgcactaggc | 4080 |
| tgaatgggaa atgcaagact ttggaagaag tttgggcatg ttggcatgag ttattgtcat | 4140 |
| acttggagaa agcaaacaag tggctaaatg aagtagaatt taaacttaaa accactgaaa | 4200 |
| acattcctgg cggagctgag gaaatctctg aggtgctaga ttcacttgaa aatttgatgc | 4260 |
| gacattcaga ggataaccca aatcagattc gcatattggc acagacccta acagatggcg | 4320 |

```
gagtcatgga tgagctaatc aatgaggaac ttgagacatt taattctcgt tggagggaac    4380
tacatgaaga ggctgtaagg aggcaaaagt tgcttgaaca gagcatccag tctgcccagg    4440
agactgaaaa atccttacac ttaatccagg agtccctcac attcattgac aagcagttgg    4500
cagcttatat tgcagacaag gtggacgcag ctcaaatgcc tcaggaagcc cagaaaatcc    4560
aatctgattt gacaagtcat gagatcagtt tagaagaaat gaagaaacat aatcagggga    4620
aggaggctgc ccaaagagtc ctgtctcaga ttgatgttgc acagaaaaaa ttacaagatg    4680
tctccatgaa gtttcgatta ttccagaaac cagccaattt tgagcagcgt ctacaagaaa    4740
gtaagatgat tttagatgaa gtgaagatgc acttgcctgc attggaaaca aagagtgtgg    4800
aacaggaagt agtacagtca cagctaaatc attgtgtgaa cttgtataaa agtctgagtg    4860
aagtgaagtc tgaagtggaa atggtgataa agactggacg tcagattgta cagaaaaagc    4920
agacggaaaa tcccaaagaa cttgatgaaa gagtaacagc tttgaaattg cattataatg    4980
agctgggagc aaaggtaaca gaaagaaagc aacagttgga gaaatgcttg aaattgtccc    5040
gtaagatgcg aaaggaaatg aatgtcttga cagaatggct ggcagctaca gatatggaat    5100
tgacaaagag atcagcagtt gaaggaatgc ctagtaattt ggattctgaa gttgcctggg    5160
gaaaggctac tcaaaaagag attgagaaac agaaggtgca cctgaagagt atcacagagg    5220
taggagaggc cttgaaaaca gttttgggca agaaggagac gttggtggaa gataaactca    5280
gtcttctgaa tagtaactgg atagctgtca cctcccgagc agaagagtgg ttaaatcttt    5340
tgttggaata ccagaaacac atggaaactt tgaccagaa tgtggaccac atcacaaagt    5400
ggatcattca ggctgacaca cttttggatg aatcagagaa aaagaaaccc cagcaaaaag    5460
aagacgtgct taagcgttta aaggcagaac tgaatgacat acgcccaaag gtggactcta    5520
cacgtgacca agcagcaaac ttgatggcaa accgcggtga ccactgcagg aaattagtag    5580
agccccaaat ctcagagctc aaccatcgat tgcagccat tcacacaga attaagactg    5640 gaaaggcctc cattcctttg aaggaattgg agcagtttaa ctcagatata caaaaattgc    5700
ttgaaccact ggaggctgaa attcagcagg gggtgaatct gaaagaggaa gacttcaata    5760
aagatatgaa tgaagacaat gagggtactg taaaagaatt gttgcaaaga ggagacaact    5820
tacaacaaag aatcacagat gagagaaagc gagaggaaat aaagataaaa cagcagctgt    5880
tacagacaaa acataatgct ctcaaggatt tgaggtctca aagaagaaaa aaggctctag    5940
aaatttctca tcagtggtat cagtacaaga ggcaggctga tgatctcctg aaatgcttgg    6000
atgacattga aaaaaaatta gccagcctac ctgagcccag agatgaaagg aaaataaagg    6060
aaattgatcg ggaattgcag aagaagaaag aggagctgaa tgcagtgcgt aggcaagctg    6120
agggcttgtc tgaggatggg gccgcaatgg cagtggagcc aactcagatc cagctcagca    6180
agcgctggcg ggaaattgag agcaaatttg ctcagtttcg aagactcaac tttgcacaaa    6240
ttcacactgt ccgtgaagaa acgatgatgg tgatgactga agacatgcct ttggaaattt    6300
cttatgtgcc ttctacttat ttgactgaaa tcactcatgt ctcacaagcc ctattagaag    6360
tggaacaact tctcaatgct cctgacctct gtgctaagga ctttgaagat ctctttaagc    6420
aagaggagtc tctgaagaat ataaaagata gtctacaaca aagctcaggt cggattgaca    6480
ttattcatag caagaagaca gcagcattgc aaagtgcaac gcctgtggaa agggtgaagc    6540
tacaggaagc tctctcccag cttgatttcc aatgggaaaa agttaacaaa atgtacaagg    6600
accgacaagg gcgatttgac agatctgttg agaaatggcg gcgttttcat tatgatataa    6660
agatatttaa tcagtggcta acagaagctg aacagttcct cagaaagaca caaattcctg    6720
```

```
agaattggga acatgctaaa tacaaatggt atcttaagga actccaggat ggcattgggc    6780
agcggcaaac tgttgtcaga acattgaatg caactgggga agaaataatt cagcaatcct    6840
caaaaacaga tgccagtatt ctacaggaaa aattgggaag cctgaatctg cggtggcagg    6900
aggtctgcaa acagctgtca gacagaaaaa agaggctaga agaacaaaag aatatcttgt    6960
cagaatttca aagagattta aatgaatttg ttttatggtt ggaggaagca gataacattg    7020
ctagtatccc acttgaacct ggaaaagagc agcaactaaa agaaaagctt gagcaagtca    7080
agttactggt ggaagagttg cccctgcgcc agggaattct caaacaatta aatgaaactg    7140
gaggacccgt gcttgtaagt gctcccataa gcccagaaga gcaagataaa cttgaaaata    7200
agctcaagca gacaaatctc cagtggataa aggtttccag agctttacct gagaaacaag    7260
gagaaattga agctcaaata aaagaccttg ggcagcttga aaaaagctt gaagaccttg     7320 aagagcagtt aaatcatctg ctgctgtggt tatctcctat taggaatcag ttggaaattt    7380
ataaccaacc aaaccaagaa ggaccatttg acgttcagga aactgaaata gcagttcaag    7440
ctaaacaacc ggatgtggaa gagattttgt ctaaagggca gcatttgtac aaggaaaaac    7500
cagccactca gccagtgaag aggaagttag aagatctgag ctctgagtgg aaggcggtaa    7560
accgtttact tcaagagctg agggcaaagc agcctgacct agctcctgga ctgaccacta    7620
ttggagcctc tcctactcag actgttactc tggtgacaca acctgtggtt actaaggaaa    7680
ctgccatctc caaactagaa atgccatctt ccttgatgtt ggaggtacct gctctggcag    7740
atttcaaccg ggcttggaca gaacttaccg actggctttc tctgcttgat caagttataa    7800
aatcacagag ggtgatggtg ggtgaccttg aggatatcaa cgagatgatc atcaagcaga    7860
aggcaacaat gcaggatttg gaacagaggc gtccccagtt ggaagaactc attaccgctg    7920
cccaaaattt gaaaaacaag accagcaatc aagaggctag aacaatcatt acggatcgaa    7980
ttgaaagaat tcagaatcag tgggatgaag tacaagaaca ccttcagaac cggaggcaac    8040
agttgaatga aatgttaaag gattcaacac aatggctgga agctaaggaa gaagctgagc    8100
aggtcttagg acaggccaga gccaagcttg agtcatggaa ggagggtccc tatacagtag    8160
atgcaatcca aaagaaaatc acagaaacca agcagttggc caaagacctc cgccagtggc    8220
agacaaatgt agatgtggca aatgacttgg ccctgaaact tctccgggat tattctgcag    8280
atgataccag aaaagtccac atgataacag agaatatcaa tgcctcttgg agaagcattc    8340
ataaaagggt gagtgagcga gaggctgctt tggaagaaac tcatagatta ctgcaacagt    8400 tcccccctgga cctggaaaag tttcttgcct ggcttacaga agctgaaaca actgccaatg    8460
tcctacagga tgctacccgt aaggaaaggc tcctagaaga ctccaaggga gtaaaagagc    8520
tgatgaaaca atggcaagac ctccaaggtg aaattgaagc tcacacagat gtttatcaca    8580
acctggatga aacagccaa aaaatcctga tccctggaa aggttccgat gatgcagtcc      8640
tgttacaaag acgtttggat aacatgaact tcaagtggag tgaacttcgg aaaaagtctc    8700
tcaacattag gtcccatttg aagccagtt ctgaccagtg gaagcgtctg cacctttctc     8760
tgcaggaact tctggtgtgg ctacagctga aagatgatga attaagccgg caggcaccta    8820
ttggaggcga ctttccagca gttcagaagc agaacgatgt acatagggcc ttcaagaggg    8880
aattgaaaac taaagaacct gtaatcatga gtactcttga gactgtacga atatttctga    8940
cagagcagcc tttggaagga ctagagaaac tctaccagga gcccagagag ctgcctcctg    9000
aggagagagc ccagaatgtc actcggcttc tacgaaagca ggctgaggag gtcaatactg    9060
```

```
agtgggaaaa attgaacctg cactccgctg actggcagag aaaaatagat gagacccttg    9120
aaagactcca ggaacttcaa gaggccacgg atgagctgga cctcaagctg cgccaagctg    9180
aggtgatcaa gggatcctgg cagcccgtgg gcgatctcct cattgactct ctccaagatc    9240
acctcgagaa agtcaaggca cttcgaggag aaattgcgcc tctgaaagag aacgtgagcc    9300
acgtcaatga ccttgctcgc cagcttacca ctttgggcat tcagctctca ccgtataacc    9360
tcagcactct ggaagacctg aacaccagat ggaagcttct gcaggtggcc gtcgaggacc    9420
gagtcaggca gctgcatgaa gcccacaggg actttggtcc agcatctcag cactttcttt    9480
ccacgtctgt ccagggtccc tgggagagag ccatctcgcc aaacaaagtg ccctactata    9540
tcaaccacga gactcaaaca acttgctggg accatcccaa aatgacagag ctctaccagt    9600
ctttagctga cctgaataat gtcagattct cagcttatag gactgccatg aaactccgaa    9660
gactgcagaa ggccctttgc ttggatctct tgagcctgtc agctgcatgt gatgccttgg    9720
accagcacaa cctcaagcaa aatgaccagc ccatggatat cctgcagatt attaattgtt    9780
tgaccactat ttatgaccgc ctggagcaag agcacaacaa tttggtcaac gtccctctct    9840
gcgtggatat gtgtctgaac tggctgctga atgtttatga tacgggacga acagggagga    9900
tccgtgtcct gtcttttaaa actggcatca tttccctgtg taaagcacat ttggaagaca    9960
agtacagata ccttttcaag caagtggcaa gttcaacagg attttgtgac cagcgcaggc   10020
tgggcctcct tctgcatgat tctatccaaa ttccaagaca gttgggtgaa gttgcatcct   10080
ttggggggcag taacattgag ccaagtgtcc ggagctgctt ccaatttgct aataataagc   10140
cagagatcga agcggccctc ttcctagact ggatgagact ggaaccccag tccatggtgt   10200
ggctgcccgt cctgcacaga gtggctgctg cagaaactgc caagcatcag gccaaatgta   10260
acatctgcaa agagtgtcca atcattggat tcaggtacag gagtctaaag cactttaatt   10320
atgacatctg ccaaagctgc tttttttctg gtcgagttgc aaaaggccat aaaatgcact   10380
atcccatggt ggaatattgc actccgacta catcaggaga gatgttcga gacttttgcca   10440
aggtactaaa aaacaaattt cgaaccaaaa ggtattttgc gaagcatccc cgaatgggct   10500
acctgccagt gcagactgtc ttagaggggg acaacatgga aactcccgtt actctgatca   10560
acttctggcc agtagattct gcgcctgcct cgtcccctca gctttcacac gatgatactc   10620
attcacgcat tgaacattat gctagcaggc tagcagaaat ggaaaacagc aatgatcttt   10680
atctaaatga tagcatctct cctaatgaga gcatagatga tgaacatttg ttaatccagc   10740
attactgcca aagtttgaac caggactccc ccctgagcca gcctcgtagt cctgcccaga   10800
tcttgatttc cttagagagt gaggaaagag gggagctaga gagaatccta gcagatcttg   10860
aggaagaaaa caggaatctg caagcagaat atgaccgtct aaagcagcag cacgaacata   10920
aaggcctgtc cccactgccg tcccctcctg aaatgatgcc cacctctccc cagagtcccc   10980
gggatgctga gctcattgct gaggccaagc tactgcgtca acacaaaggc cgcctggaag   11040
ccaggatgca aatcctggaa gaccacaata acagctgga gtcacagtta cacaggctaa   11100
ggcagctgct ggagcaaccc caggcagagg ccaaagtgaa tggcacaacg gtgtcctctc   11160
cttctacctc tctacagagg tccgacagca gtcagcctat gctgctccga gtggttggca   11220
gtcaaacttc ggactccatg ggtgaggaag atcttctcag tcctccccag gacacaagca   11280
cagggttaga ggaggtgatg gagcaactca acaactcctt ccctagttca agaggaagaa   11340
ataccctgg aaagccaatg agagaggaca caatgtagga agtctttcc acatggcaga   11400
tgatttgggc agagcgatgg agtccttagt atcagtcatg acagatgaag aaggagcaga   11460
```

```
ataaatgttt tacaactcct gattcccgca tggtttttat aatattcata caacaaagag   11520
gattagacag taagagttta caagaaataa atctatattt ttgtgaaggg tagtggtatt   11580
atactgtaga tttcagtagt ttctaagtct gttattgttt tgttaacaat ggcaggtttt   11640
acacgtctat gcaattgtac aaaaaagtta taagaaaact acatgtaaaa tcttgatagc   11700
taaataactt gccatttctt tatatggaac gcattttggg ttgtttaaaa atttataaca   11760
gttataaaga aagattgtaa actaaagtgt gctttataaa aaaagttgt ttataaaaac    11820 ccctaaaaac aaaacaaaca cacacacaca cacatacaca cacacacaca aaactttgag   11880
gcagcgcatt gttttgcatc cttttggcgt gatatccata tgaaattcat ggcttttct    11940 tttttgcat attaaagata agacttcctc taccaccaca ccaaatgact actacacact    12000
gctcatttga gaactgtcag ctgagtgggg caggcttgag ttttcatttc atatatctat   12060
atgtctataa gtatataaat actatagtta tatagataaa gagatacgaa tttctataga   12120
ctgacttttt ccattttta aatgttcatg tcacatccta atagaaagaa attacttcta    12180
gtcagtcatc caggcttacc tgcttggtct agaatggatt tttcccggag ccggaagcca   12240
ggaggaaact acaccacact aaaacattgt ctacagctcc agatgtttct cattttaaac   12300
aactttccac tgacaacgaa agtaaagtaa agtattggat tttttaaag ggaacatgtg    12360 aatgaataca caggacttat tatatcagag tgagtaatcg gttggttggt tgattgattg   12420
attgattgat acattcagct tcctgctgct agcaatgcca cgatttagat ttaatgatgc   12480
ttcagtggaa atcaatcaga aggtattctg accttgtgaa catcagaagg tatttttaa    12540 ctcccaagca gtagcaggac gatgataggg ctggagggct atggattccc agcccatccc   12600
tgtgaaggag taggccactc tttaagtgaa ggattggatg attgttcata atacataaag   12660
ttctctgtaa ttacaactaa attattatgc cctcttctca cagtcaaaag gaactgggtg   12720
gtttggtttt tgttgctttt ttagatttat tgtcccatgt gggatgagtt tttaaatgcc   12780
acaagacata atttaaaata aataaacttt gggaaaaggt gtaaacagt agccccatca    12840 catttgtgat actgacaggt atcaacccag aagcccatga actgtgtttc catcctttgc   12900
atttctctgc gagtagttcc acacaggttt gtaagtaagt aagaaagaag gcaaattgat   12960
tcaaatgtta caaaaaaacc cttcttggtg gattagacag gttaaatata taaacaaaca   13020
aacaaaaatt gctcaaaaaa gaggagaaaa gctcaagagg aaaagctaag gactggtagg   13080
aaaaagcttt actctttcat gccatttat ttcttttga tttttaaatc attcattcaa     13140
tagataccac cgtgtgacct ataatttgc aaatctgtta cctctgacat caagtgtaat    13200
tagcttttgg agagtgggct gacatcaagt gtaattagct tttggagagt gggttttgtc   13260
cattattaat aattaattaa ttaacatcaa acacggcttc tcatgctatt tctacctcac   13320
tttggttttg gggtgttcct gataattgtg cacacctgag ttcacagctt caccacttgt   13380
ccattgcgtt attttctttt tcctttataa ttcctttcttt ttccttcata attttcaaaa   13440 gaaacccaa agctctaagg taacaaatta ccaaattaca tgaagatttg gttttgtct     13500 tgcattttt tcctttatgt gacgctggac cttttcttta cccaaggatt tttaaaactc    13560
agatttaaaa caagggggtta ctttacatcc tactaagaag tttaagtaag taagtttcat  13620
tctaaaatca gaggtaaata gagtgcataa ataattttgt tttaatctttt tgttttttct  13680 tttagacaca ttagctctgg agtgagtctg tcataatatt tgaacaaaaa ttgagagctt   13740
tattgctgca ttttaagcat aattaatttg gacattattt cgtgttgtgt tctttataac   13800
```

-continued

| | |
|---|---|
| caccaagtat taaactgtaa atcataatgt aactgaagca taaacatcac atggcatgtt | 13860 |
| ttgtcattgt tttcaggtac tgagttctta cttgagtatc ataatatatt gtgttttaac | 13920 |
| accaacactg taacatttac gaattatttt tttaaacttc agttttactg cattttcaca | 13980 |
| acatatcaga cttcaccaaa tatatgcctt actattgtat tatagtactg ctttactgtg | 14040 |
| tatctcaata aagcacgcag ttatgttac | 14069 |

<210> SEQ ID NO 9
<211> LENGTH: 2385
<212> TYPE: DNA
<213> ORGANISM: Homo sapiens

<400> SEQUENCE: 9

| | |
|---|---|
| ggatgcgcgg cgtggccacg ccccttcagt gcttgtgacg caggcgccct gggcttttg | 60 |
| ggcgcgaaaa agaagcagtc ctgggttgta cccggcgcag ctgggagcgg ctgcttcctc | 120 |
| cggggtcgta tctccgcccg gcatggggct gctggacctt tgcgaggaag tgttcggcac | 180 |
| cgccgacctt taccgggtgc tgggcgtgcg acgcgaggcc tccgacggcg aggtccgacg | 240 |
| aggctaccac aaggtgtccc tgcaggtaca cccggaccgg gtgggtgagg gcgacaagga | 300 |
| ggacgccacc cgccgcttcc agatcctggg aaaagtctat tccgttctca gtgacagaga | 360 |
| acagagagca gtgtacgatg agcagggaac agtggacgag gactctcctg tgctcaccca | 420 |
| agaccgagac tgggaggcgt attggcggct actctttaaa aagatatctt tagaggacat | 480 |
| tcaagctttt gaaaagacat acaaaggttc ggaagaagag ctggctgata ttaagcaggc | 540 |
| ctatctggac ttcaagggtg acatggatca gatcatggag tctgtgcttt gcgtgcagta | 600 |
| cacagaggaa cccaggataa ggaatatcat tcagcaagct attgacgccg agaggtccc | 660 |
| atcctataat gcctttgtca agaatcgaa acaaaagatg aatgcaagga aaggagggc | 720 |
| tcaggaagag gccaagaag cagaaatgag cagaaaggag ttggggcttg atgaaggcgt | 780 |
| ggatagcctg aaggcagcca ttcagagcag acaaaaggat cggcaaaagg aaatggacaa | 840 |
| ttttctggct cagatggaag caaagtactg caaatcttcc aaaggaggag ggaaaaaatc | 900 |
| tgctctcaag aaagaaaaga aataatgaaa ttttctctt caaaggtcct taggtgtaaa | 960 |
| ttgatgccat cgtaggcaag gtgcaggcag gatttgaagg caaaagtcaa ttcagctctt | 1020 |
| gagaaaaggt gtcttttccag cctgaatttt tcagattgac tagaccaagc agaatctctc | 1080 |
| aacctgatct tagtatttcc tagaaagcac ttgacattgt gtgaggtctc acctgaagga | 1140 |
| acttggtggt gacatttggg agggtggagg gaggcagtgt ccttcctgac agcacttgcc | 1200 |
| tccatggatc ttctgtacac agaactctta tctaggatgt ggttctgttc atgctgcttt | 1260 |
| ctgcgatgtg cgtgtctgtt agaataggct ctctacccag ctagaacacc ttccagacac | 1320 |
| tgctggaca gctatcttcc acatacttcc cagtttacat ttggtcttaa tgatcttgaa | 1380 |
| tagatcctct cttcatttta ctcagccagg ttttgtactg atgtacaggt gttaaattac | 1440 |
| ttcaagcatt tttgtaagag gtgtatataa ttcaataaaa aaggtaaaac atgatgatta | 1500 |
| agttctgggg gctttgtaaa tgatcccact aaaatgtgac ctaggaaaaa tatgaatggt | 1560 |
| gtttaggatg agagaaaagg ggaaaacaat agccctggtc agctttataa tagagagcct | 1620 |
| ggtttcccta gcatgaagag atgtatgttg tagtcctgcc actgattact gaagtcctgc | 1680 |
| cattaattgc tgaatgtctt cagttgggcc actgagcttg tctgaatctg ttccctttta | 1740 |
| taaaagagtt actacatcaa aacaaagagt gaaatccaaa tttgtcaaac tgtatgtatt | 1800 |
| aaacatgtcc agtttttggg ttaaaaaaaa attgcactgg ctttgaggga aaacacacag | 1860 |

-continued

| | |
|---|---|
| ggtgagggaa ttgggctaaa tgacttctta caggcccctt tctgattctt aactttgaa | 1920 |
| aggcaagcca tattgatcca gttgttatag tgaactcatg gtaatggttt gtgagaacaa | 1980 |
| tagagatttt catttctatg tagatgagtt ggtatgagaa tatatggaat ttttaaggga | 2040 |
| ctgtttaaat ctttgatttg tagactatta aatataccgt atgcataaag taagccttta | 2100 |
| gctctaaggt aaagacgaca cgttttcggt ttgtgactac aaataggtta aaaatagatt | 2160 |
| ttaattttat taaaaatata atttaatgca ggttgtttga agcatctgtc ttcatatgat | 2220 |
| ggcattagaa caccttggta taataaaaag ttaccgtaat ttatgattat ttgaatttat | 2280 |
| ccattctgaa aattaataag atctaaaact ggcatgacaa tcaagatttg tatttagtga | 2340 |
| aatttaaaat aaatgtaagc catagttaaa aaaaaaaaaa aaaaa | 2385 |

<210> SEQ ID NO 10
<211> LENGTH: 4206
<212> TYPE: DNA
<213> ORGANISM: Homo sapiens

<400> SEQUENCE: 10

| | |
|---|---|
| cgccctcccg ccgcgcgctc gggatcccga ccagtcctga ccgcacgggg gccgcggcca | 60 |
| cggggcgcag gggccatggt gcgcggcagg atctcccggc tctcggtccg ggacgtgcgc | 120 |
| ttccccacgt cgcttggggg ccacggcgcg gacgccatgc acacggaccc tgactactcg | 180 |
| gctgcctatg tcgtcataga aactgatgca gaagatggaa tcaaggggtg tggaattacc | 240 |
| ttcactctgg gaaaaggcac tgaagttgat tggtccagaa aagggcgtgg tgcacctggc | 300 |
| gacagcggcc gtcctaaacg cggtgtggga cttgtgggcc aagcaggagg gaaagcctgt | 360 |
| ctggaagtta cttgtggaca tggatcccag gatgctggta tcctgcatag atttcaggta | 420 |
| catcactgat gtcctgactg aggaggatgc cctagaaata ctgcagaaag gtcaaattgg | 480 |
| taaaaaagaa agagagaagc aaatgctggc acaaggatac cctgcttaca cgacatcgtg | 540 |
| cgcctggctg gggtactcag atgacacgtt gaagcagctc tgtgcccagg cgctgaagga | 600 |
| tggctggacc aggtttaaag taaaggtggg tgctgatctc caggatgaca tgcgaagatg | 660 |
| ccaaatcatc cgagacatga ttggaccgga aaagactttg atgatggatg ccaaccagcg | 720 |
| ctgggatgtg cctgaggcgg tggagtggat gtccaagctg gccaagttca agccattgtg | 780 |
| gattgaggag ccaacctccc ctgatgacat tctggggcac gccaccattt ccaaggcact | 840 |
| ggtcccatta ggaattggca ttgccacagg agaacagtgc cacaatagag tgatatttaa | 900 |
| gcaactccta caggcgaagg ccctgcagtt cctccagatt gacagttgca gactgggcag | 960 |
| tgtcaatgag aacctctcag tattgctgat ggccaaaaag tttgaaattc ctgtttgccc | 1020 |
| ccatgctggt ggagttggcc tctgtgaact ggtgcagcac ctgattatat ttgactacat | 1080 |
| atcagtttct gcaagccttg aaaatagggt gtgtgagtat gttgaccacc tgcatgagca | 1140 |
| tttcaagtat cccgtgatga tccagcgggc ttcctacatg cctcccaagg atcccggcta | 1200 |
| ctcaacagaa atgaaggagg aatctgtaaa gaaacaccag tatccagatg gtgaagtttg | 1260 |
| gaagaaactc cttcctgctc aagaaaatta agtgctcagc cccaacaact tttttctttc | 1320 |
| tgaagtgaaa gggcttaaaa tttcttggaa atagttttac aaaaatggat ttaaaaaatc | 1380 |
| ctaccgatca agatgagttc agctagaagt cataccaccc tcaggaatca gctaaagcaa | 1440 |
| aaagaacttt tacctcggca tccagcccaa cccctaaaga ctgacaatat ccttcgagct | 1500 |
| cctttgaaag caccctaaac agccatttcc attttaatag ttggatgcgg attgtaccct | 1560 |

-continued

```
tcaatctgaa agtcttcagc tttgaagtca tcaattttct caacttttcg aagaatcctg    1620
agctttggga aaggtctggg ttctcgctga agctaaaaac aaaataaggc cattattttg    1680
ccataattgt acgacctgtt gtaattgctc ctcatgtccg tgaaacaagt acacaggatg    1740
tgatcaacaa agttctattt tacaggagta tgatcctgtc gataccttgc cgtaggttat    1800
gtaacatgat tggagcgcaa ccagctgttc tcttgcacag atcgagagtg aggggtattt    1860
tgtgacatta cacagcatca ggagcctggt gcctcatcag gtgtaagttc ttataaccac    1920
tcttggcaaa tttattaaag acaggaacac agtcaatctg taactcatag tagctctacg    1980
tttacttgaa ttccacaatc cctaacccat ctgtccctgg cagaaagaag gaaagatgac    2040
atgcatggac agtgaacaga aagggatgaa agccaggatt cctgggatga acagacagtg    2100
gcaattagga tgtgaagaca ggtcacaacc tattactatg tctaaaaacg accagagcag    2160
agagccagag agaataagcc tgaagtcacc tccactcaaa agcagccaaa ctccctcaaa    2220
ggagtaactt ttaaaacctg gatctaacct ggaagggggct aaaaagtgtc tggttctgag    2280 ttttttttcct taaggctcat gaagcagatg aacttacatt tttattgcca tttcatatca    2340
attgttggct gctataactt agggatttca acagacttt gaagtttgga cctaaatatt    2400
gtacttaatg taaaattaac aaaaaatatt tatggccagg gtggtggctt atgcctgtaa    2460
ttccagaatt ttcggaggct gaggcaggtg gatcacttga agtcaggagt ttgagactag    2520
cctggccaac atgatgaaac cccatctcta ctaataatac aaaaattagc tgggtgtggt    2580
ggcatgtgcc tgtaatccca gctacctggg aggctgaggc agaagaattg cttgaacccg    2640
ggaggtggag gttgcagtga gctgagatcg caccacggca cactccagcc tggccgacag    2700
agaaagactc catctcaaaa aaaaagaaa aggaaaaaca tttgcacttc aattctcctt    2760
caagttaaaa tgagttaaaa tgccccctttt tggacaatcc cctggcttga atgtggctct    2820
tccctctctg gtactggtgc ttagtacctc acagcacctg acatgttaag tgcccatggt    2880
tgctgaggca gatgcctgcc ttgtcctgcc cacctgccca ccacttctcc ctaaactgaa    2940
gccccacatt tggagcagtc atctttatct tggacacagc attgagcaga tgcctgttcc    3000
acagtcaacc ttttatcaag agaaggtacc aaacccaaaa gtataacatc taattcttac    3060
ctgaattttc agtggctcga tgtgattcag gtaaatatgt gcatctccca aagtgtgtat    3120
aaagtcacct ggctataaac ccggggggaga aagcagaaca gtatgttagt ttcaattctt    3180
taaaacatca tttaaaaaca ttagaatatg cagacaccgc aaggcttttt ttaaaaaaat    3240
aatttagtgt agcttttcca tttttttgta gcaacagcat cttgttatgt tgcccaggct    3300
ggtattgaac tccagacctc aagcaattgc tcctgtctca gtctcccaaa gtgctgggat    3360
tacaggcatg agccaccata cccaacctca gcatagcttt tgagaaaatc catagaagct    3420
gtatcacaaa caacctgtat agatctgtta gtgcgtatac cacagggcca gaaaaccttc    3480
cagaagagga aggtttcaaa gtaaaagctg gttcatttct tacttacaca tatcaaattt    3540
aaaagctaat cagagactaa actctgcaat ttgttttccc atattaaaga actgaagagc    3600
tcagtgtggt aggctggcaa gtcacccttc ccgagacagc ccaccttcag gcccgtgatg    3660
tgcgcaatca tgtacgtgag cagggcgtag ctggcgatgt gaaaggcac accgaggccc    3720 atgtctcccg atctctggta cagctggcag gacagctcac tgttcaccac atagaactgg    3780
cagagggcat ggcatggagg cagcgccatc agaggaagat ctgaggaacc agcagaggaa    3840
gataaggagg gatggtggtt tgaaagacca cagctaaagg caaagtaaaa caggagagaa    3900
acagaagcca actcatatgg tggagaccag gagagagagc cactgggctg cagtgatgtc    3960
```

| cataacagcc | tctgcagcga | tggcacggag | ctgagggaga | ctatccatcg | gtgcaaggtt | 4020 |
| tctgcaggtg | tccatttacg | gctgaagcaa | tgctcttcca | tcagagctga | agggatctgg | 4080 |
| gctacctcgt | ggcaccagat | tacaaataca | gcaggaataa | ttctgttttgc | cacaggaaac | 4140 |
| tggtgcttct | ggtacaccct | cctatattaa | aagtctctat | tacatggcaa | aaaaaaaaa | 4200 |
| aaaaaa | | | | | | 4206 |

<210> SEQ ID NO 11
<211> LENGTH: 1753
<212> TYPE: DNA
<213> ORGANISM: Homo sapiens

<400> SEQUENCE: 11

| agcggactgc | gcatgtgcag | gacccagcag | gtctagagct | tttctgtgtt | tctccggact | 60 |
| tcgagccatg | gcggtgacgg | aagcgagcct | gttgcgccag | tgcccccctgc | ttctgcccca | 120 |
| gaaccggtcg | aaaaccgtgt | atgagggatt | catctcggct | cagggaagag | acttccacct | 180 |
| taggatagtg | ttgcctgaag | atttacaact | gaagaatgca | agattattat | gtagttggca | 240 |
| gctgagaaca | atacttagtg | gataccatcg | aatagtacaa | cagagaatgc | agcactctcc | 300 |
| tgatctaatg | agctttatga | tggagttgaa | gatgcttttg | gaagttgcct | taagaatag | 360 |
| acaagagctg | tatgcactac | ctcctcctcc | ccagttctac | tcaagcctta | ttgaagagat | 420 |
| aggaactctt | ggttgggata | aacttgtgta | tgcggatacc | tgcttcagta | ccatcaagtt | 480 |
| aaaagcagaa | gatgcttctg | gtagagagca | tttaatcact | ctcaagttga | aggcaaagta | 540 |
| tcctgcagaa | tcaccagatt | attttgtgga | ttttcctgtt | ccattttgtg | cctcctggac | 600 |
| acctcaggta | aattctcctc | agagctcctt | aataagcatt | tatagtcagt | ttttggcagc | 660 |
| aatagaatca | ctaaaggcat | tctgggatgt | tatggatgaa | atcgatgaga | agacctgggt | 720 |
| acttgagcca | gaaaaacctc | cacggagtgc | aacagcacgc | agaattgcat | taggtaataa | 780 |
| tgtttccata | aatatagagg | tagaccccag | gcatcctact | atgcttcctg | agtgcttctt | 840 |
| tcttggagct | gaccatgtgg | taaaacccct | gggaattaag | ctgagcagga | acatacattt | 900 |
| gtgggatcca | gaaaatagtg | tgttacaaaa | tttgaaagat | gttttagaaa | ttgattttcc | 960 |
| agctcgtgct | atcctggaaa | aatctgattt | tactatggat | tgtggaattt | gttatgctta | 1020 |
| tcaacttgac | ggtaccattc | ctgatcaagt | gtgtgataat | tctcagtgtg | acaacctttc | 1080 |
| ccatcaaata | tgcttatatg | agtggctgag | aggactacta | actagtagac | agagttttaa | 1140 |
| catcatattt | ggtgaatgtc | catattgtag | taagccaatt | accttaaaaa | tgtctggaag | 1200 |
| gaaacactga | aataagaata | caacatttcg | gtgaagagct | ggaaacttaa | aaaattatca | 1260 |
| aaaggaattt | tggtatcatc | ttcagagaaa | aaataaagca | agaaatacta | acatcaaaag | 1320 |
| gacaggtatg | atgatgcgat | aataataaac | atctgcgttt | gtctcttcac | taagagtaaa | 1380 |
| ctgggaaatt | gtaggccaaa | gtccagttga | actttctaag | tctgtgatcc | ccgtgctgac | 1440 |
| tgtggaagtg | tatttatacc | aagatggaga | tcttgacttc | ttgaatatat | ctggactggt | 1500 |
| aaaatcttga | tgaggctcat | aaaatgagtt | tgggaattgt | gtatagctga | tttttttgtgg | 1560 |
| gaaactgttt | acttcattca | aaggttcttg | agactcttga | tatttctgtc | ttctccttgt | 1620 |
| gctttcctat | ggaaaaaata | catatatagt | ttagtttgtt | agacgtgagt | tatccaagta | 1680 |
| tttattttgt | gtagtgtgta | agaatgctaa | ataaaatgtt | atacaagatc | aaaaaaaaaa | 1740 |
| aaaaaaaaaa | aaa | | | | | 1753 |

<210> SEQ ID NO 12
<211> LENGTH: 3189
<212> TYPE: DNA
<213> ORGANISM: Homo sapiens

<400> SEQUENCE: 12

```
ctatttgagt ttgtggcgcg cgaggccctg cagtccgggt tggcgcttgg gtactggctg      60
ggtccgatgc tgggtacgct gcgcgccatg gagggcgagg acgtggaaga cgaccagctg     120
ctgcagaagc tcagggccag tcgccgccgc ttccagaggc gcatgcagcg gctgatagag     180
aagtacaacc agcccttcga ggacaccccg gtggtgcaaa tggccacgct gacctacgag     240
acgccacagg gattgagaat tggggtgga agactaataa aggaaagaaa cgaaggagag     300
atccaggact cctccatgaa gcccgcggac aggacagatg ctccgtgca agctgcagcc     360
tggggtcctg agcttccctc gcaccgcaca gtcctgggag ccgattcaaa aagcggtgag     420
gtcgatgcca cgtcagacca ggaagagtca gttgcttggg ccttagcacc tgcagtgcct     480
caaagccctt tgaaaaatga attaagaagg aaatacttga cccaagtgga tatactgcta     540
caaggtgcag agtattttga gtgtgcaggt aacagagctg aagggatgt acgtgtgact     600
ccgctgcctt cactggcctc acctgccgtg cctgccccg gatactgcag tcgtatctcc     660
agaaagagtc ctggtgaccc agcgaaacca gcttcatctc ccagagaatg gatcctttg     720
catccttcct ccacagacat ggccttagta cctagaaatg acagcctctc cctacaagag     780
accagtagca gcagcttctt aagcagccag cccttgaag atgatgacat ttgcaatgtg     840
accatcagtg acctgtacgc agggatgctg cactccatga ccggctgtt gagcacaaag     900
ccatcaagca tcatctccac caaaacgttc atcatgcaaa actggaactc caggaggagg     960
cacagatata agagcaggat gaacaaaaca tattgcaaag gagccagacg ttctcagagg    1020
agctccaagg agaacttcat accctgctct gagcctgtga agggacagg gcattaaga    1080
gattgcaaga acgtattaga tgtttcttgc cgtaagacag gtttaaaatt ggaaaaagct    1140
tttcttgaag tcaacagacc ccaaatccat aagttagatc caagttggaa ggagcgcaaa    1200
gtgacaccct cgaagtattc ttccttgatt tacttcgact ccagtgcaac atataatctt    1260
gatgaggaaa atagatttag gacattaaaa tggttaattt ctcctgtaaa aatagtttcc    1320
agaccaacaa tacgcaaggg ccatggagag aaccgtcaga gggagattga aatccgattt    1380
gatcagcttc atcgggaata ttgcctgagt cccaggaacc agcctcgccg gatgtgcctc    1440
ccggactcct gggccatgaa catgtacaga ggggtcctg cgagtcctgg tggccttcag    1500
ggcttagaaa cccgcaggct gagtttacct tccagcaaag caaaagcaaa aagtttaagt    1560
gaggcttttg aaaacctagg caaaagatct ctggaagcag gtaggtgcct gcccaagagc    1620
gattcatctt catcacttcc aaagaccaac cccacacaca gcgcaactcg cccgcagcag    1680
acatctgacc ttcacgttca gggaaatagt tctggaatat ttagaaagtc agtgtcaccc    1740
agcaaaactc tttcagtccc agataaagaa gtgccaggcc acggaaggaa tcgttacgat    1800
gaaattaaag aagaatttga caagcttcat caaaagtatt gcctcaaatc tcctgggcag    1860
atgacagtgc ctttatgtat tggagtgtct acagataaag caagtatgga agttcgatat    1920
caaacagaag gcttcttagg aaaattaaat ccagaccctc acttccaggg tttccagaag    1980
ttgccatcat caccctggg gtgcagaaaa agtctactgg gctcaactgc aattgaggct    2040
ccttcatcta catgtgttgc tcgtgccatc acgaggatg gcacgaggga ccatcagttc    2100
cctgcaaaaa gacccaggct atcagaaccc caggggctccg gacgccaggg caattccctg    2160
```

| | |
|---|---|
| ggtgcctcag atggggtgga caacaccgtc agaccgggag accagggcag ctcttcacag | 2220 |
| cccaactcag aagagagagg agagaacacg tcttacagga tggaagagaa aagtgatttc | 2280 |
| atgctagaaa aattggaaac taaaagtgtg tagctaggtt atttcggagt gttatttatc | 2340 |
| ttcccacttg ctctctgttt gtattttttgt tttgttttgt attcttgaga ctgtgaggac | 2400 |
| ttggttgact tctctgccct taaagtaaat attagtgaaa ttggttccat cagagataac | 2460 |
| ctcgagttct tggtgtagaa attatgtgaa taaagttgct caattagaat ttttaggggtt | 2520 |
| ctctttgata ggcctgtttt tctgatgtgt gtgttttttt tggggggggg ttatttgttt | 2580 |
| gtttgtttgt ttgtttgttt gttttttgaga cagtctctct ctatcgccca ggctggagtg | 2640 |
| cggtggcaca atcttggctc actgcaactt ccgcctcccg ggttcaagcg attcttctgc | 2700 |
| ctcagcctcc cgagtagctg ggattacagg cgcgcgccac cacgcctggc taattttttgt | 2760 |
| agttttagta gagacggggt ttcaccatat tgaccaggct ggtctcgagc tcctggcctc | 2820 |
| gtgatccatc tgcctcggcc tcccaaagtg ctgggattat aggcgtgagc cactgctccc | 2880 |
| agccgtgtgt tcttttttaa atttagatat gtccagagaa tcctctctcc tgtttcccat | 2940 |
| ttcattcgag aatattgttt gcttgtgaga cgtaagttcg agccctgcat gcaatgaccc | 3000 |
| ttgaaggaaa ataaacagtc ctggtggtcc cagacgctcc tgcagccaca gcgcctgtga | 3060 |
| ctcctcatga ttcttactga agctgttgat gacaggatat catggtgacg tttttgtaat | 3120 |
| gaaatatttc acatattcag aatacattgg tgaaactcat gctggagtaa atagttaata | 3180 |
| tatggccat | 3189 |

<210> SEQ ID NO 13
<211> LENGTH: 3485
<212> TYPE: DNA
<213> ORGANISM: Homo sapiens

<400> SEQUENCE: 13

| | |
|---|---|
| cttcttctttt acctccgcct tgttcctgtc ctcaccacac ggactgagac tgatttgatt | 60 |
| aaagcaccag agtgtaatgg ccctcagagc agggctggtc ctggggttcc acaccctgat | 120 |
| gacccctcctg agcccgcagg aggcagggc caccaaggct gaccacatgg gctcctacgg | 180 |
| acccgccttc taccagtctt acggcgcctc gggccagttc acccatgaat tgatgagga | 240 |
| acagctgttc tctgtggacc tgaagaaaag cgaggccgtg tggcgtctgc ctgagtttgg | 300 |
| tgactttgcc cgctttgacc cgcagggcgg gctggccggc atcgccgcaa tcaaagccca | 360 |
| tctggacatc ctggtggagc gctccaaccg cagcagagcc atcaacgtgc ctccacgggt | 420 |
| gaccgtgctc cccaagtctc gggtggagct gggccagccc aacatcctca tctgcatcgt | 480 |
| ggacaacatc ttccccccctg tgatcaatat cacctggctg cgcaacgcc aaactgtcac | 540 |
| tgagggagtg gcccagacca gcttctatt ccagcctgac catttgttcc gcaagttcca | 600 |
| ctacctgccc ttcgtgccct cagccgagga cgtctatgac tgccaggtgg agcactgggg | 660 |
| cctggatgcg ccactcctca ggcattggga gctccaggtg cctattccac caccagatgc | 720 |
| catggagacc ctggtctgtg ccctgggcct ggccatcggc ctggtgggct tcctcgtggg | 780 |
| caccgtcctc atcatcatgg gcacatatgt gtccagtgtc cccaggtaat gatccttctg | 840 |
| agagaaatga cttgtgggag acaccctgca gatcctcatg ggtttgtgac agcccctgcg | 900 |
| tgctcagtgc cctttaagtg catcccgctg tgctgacttt gagtgggatc aacatctgtc | 960 |
| ctacggggtcc cctcttttttt ggccccagta ttcatggcag ggtttgttgg acacctacta | 1020 |

```
gcttcccttc ccattcaaca cacacacaca ttcttgctct acccaaagct ctggctggca   1080
gcactaaatg ctttggtggt gtttgcactg tgtcctttcc aggccttggc cagttcttcc   1140
aggggtgagg catgtggtgc tggggattgg cagccatcct ggggcccaca caggtgtgtc   1200
ttgctccatt tggcccattg tgtgttactt tgtgaatgag ccatttcaca tggacttcat   1260
gaaatttgcc tcctgagttc aggtttaccc tgaaagggat gcagattatc ctgttcctca   1320
cgacccctc agctaacaac agttctgaag ggtgctggga caggacaggc tcatggggac   1380
tccactcctg cctgggttta ctctgtatga agaggccact ggtatcctgc catgatgtta   1440
tctccttttt ctactttcc ctagagtccc atgcatgata agagaggcc caaggcttgg    1500
ataaggtggc cacttccctc agtggagtca gtcatgttag gtaggaggtg gtagagtcgg   1560
tctgcgaggt atctcgtaag aggggaggtc cacctagaca cactctaaat atgtggccta   1620
gaagattttg gtctactttt ctgtgaacag aatttaaaac atacaaagag ataaatcacc   1680
ataccacata gtttatgtca ggaccaaaat gagcaataca gattacggtt ttcaaaccag   1740
aatgcacata agaactgctt gggatccttt taaaagtaca ggcattggcc tggtgcagtg   1800
gctcattcct gtaatcccag cactttggga ggccaagggg acaggactgc ttgaggccaa   1860
gaggtggaaa ccatcttggg ctacatagag agacccatc tctacaaaga aagatttaaa    1920
aattaaccag gcatggtggc tcgcacctgt attcccagcc actggggagg ctgaggccgg   1980
aggagtgctt gagcccagga gttcaaggct gcagtgagcc aagattgcgc cactgcactc   2040
cagcctaggt gacagagtga gaccctgtct ctaaataaat aaataaataa aatataaaaa   2100
taacagtcat cacccagacc tactgaatta gaatctcggg agtgcagggg gcagcaacag   2160
ggaggctgtc ttttctgaga tggggtctca ctctgtcacc aggctggagt gccatggcat   2220
gatctcagct cactgcaacc tccacctcct gagttcaagc cattctcctg cctcagcctc   2280
ctgagtagct gggactacag gtgtgcgcca ctacactcag ctaattttg tatttttaagt   2340
agagacgggg tttcatcatg ttggccagga tggcctccat ctcttgacct cgtgatccac   2400
ccaccttccc tcccaaagta ctggaattac aggcattagc cactgtgccc agccgaggct   2460
gtcattttta accggctctg gatgactctg atgcagccat cctggacctt ggctgtggtc   2520
tggtaactgg aacccagtga cgtaatcagg tgccatcggg ggtcatggga aaggggatc    2580
cccaaggtct gaggtggact aggaaggctt tctgaagaac ctgggtctgt tagggcatca   2640
gccaatcaag gtacaagtaa atagaggcaa aatgagggtt tgaactgtga gcagttggtc   2700
ctggaaaaga aagaaaccaa gagattatgg ggactcaatg ggcttcttaa gagagaataa   2760
gttgaaatca atgaccagaa gaccctgatg gaagtggagg agaatcatct caggcaaact   2820
ttttgtgtgc cagtaacaga aaccctcttt gtgtgatcac atgcaaagta taggatattt   2880
gcaatatagc catggggagg agtgcagggc ccaagggtag atttagcca ggcctcccag    2940
gaacagaact cggatccgaa aagcccgag aagctagagc tgcccctcca acactctcgg    3000
atccacatgg tctgtgttct ctagaccccc ctgcatgtta gcggtgttct ctctctgtgg   3060
actgactgtc cttctcagtg aacatgtcca cccgacagct cctgagttta tatcatctca   3120
accctcacaa cccacagagg ctgtgtctcc tagtcacagg tttaaattac tggaaaaata   3180
aatgactggc caaacttgga gcaggtgtcc atcccagccc tgtgtagtta gagcaggaat   3240
caagatctca acacaaatgt ggctgccaag cactcagccc cggggcgagg ggtcaagttc   3300
ttctcagaga aagaggaata agttggttct cagaagacat cacaagatac gtgtgtaccc   3360
aacaatctct gatctctgct gatcttttgc ttagacgtta acttgatgca tcattggaaa   3420
```

```
ggtgtttctc tcatctctgt cctaaggctt gataaagtca ttaaaattgt gttcttttga    3480
ctaaa                                                                3485
```

<210> SEQ ID NO 14
<211> LENGTH: 1312
<212> TYPE: DNA
<213> ORGANISM: Homo sapiens

<400> SEQUENCE: 14

```
ttttaatggt cagactctat tacacccccac attctctttt cttttattct tgtctgttct     60
gcctcactcc cgagctctac tgactcccaa cagagcgccc aagaagaaaa tggccataag    120
tggagtccct gtgctaggat ttttcatcat agctgtgctg atgagcgctc aggaatcatg    180
ggctatcaaa gaagaacatg tgatcatcca ggccgagttc tatctgaatc ctgaccaatc    240
aggcgagttt atgtttgact ttgatggtga tgagattttc catgtggata tggcaaagaa    300
ggagacggtc tggcggcttg aagaatttgg acgatttgcc agctttgagg ctcaaggtgc    360
attggccaac atagctgtgg acaaagccaa cctggaaatc atgacaaagc gctccaacta    420
tactccgatc accaatgtac ctccagaggt aactgtgctc acaaacagcc ctgtggaact    480
gagagagccc aacgtcctca tctgtttcat agacaagttc acccccaccag tggtcaatgt    540 cacgtggctt cgaaatggaa aacctgtcac cacaggagtg tcagacagt cttcctgcc     600 cagggaagac caccttttcc gcaagttcca ctatctcccc ttcctgccct caactgagga    660
cgtttacgac tgcagggtgg agcactgggg cttggatgag cctcttctca agcactggga    720
gtttgatgct ccaagccctc tcccagagac tacagagaac gtggtgtgtg ccctgggcct    780
gactgtgggt ctggtgggca tcattattgg gaccatcttc atcatcaagg gattgcgcaa    840
aagcaatgca gcagaacgca ggggggcctct gtaaggcaca tggaggtgat ggtgtttctt    900
agagagaaga tcactgaaga aacttctgct ttaatggctt tacaaagctg gcaatattac    960
aatccttgac ctcagtgaaa gcagtcatct tcagcatttt ccagccctat agccacccca   1020
agtgtggata tgcctcttcg attgctccgt actctaacat ctagctggct tccctgtcta   1080
ttgccttttc ctgtatctat tttcctctat ttccatcat tttattatca ccatgcaatg   1140
cctctggaat aaaacataca ggagtctgtc tctgctatgg aatgccccat ggggcatctc   1200
ttgtgtactt attgtttaag gtttcctcaa actgtgattt ttctgaacac aataaactat   1260
tttgatgatc ttgggtggaa aaaaaaaaaa aaaaaaaaaa aaaaaaaaa aa             1312
```

<210> SEQ ID NO 15
<211> LENGTH: 3006
<212> TYPE: DNA
<213> ORGANISM: Homo sapiens

<400> SEQUENCE: 15

```
cgagttggaa gaggtgagtc ctgtctcaaa atggaggtaa aaccgccgcc tggttgcccc     60
cagcccgact ccggcagtcg ccgtcgccac tgggggagg agggccatga tccaaaggaa    120
ccagagcagc tgagaaaact gtttattggt ggtctgagct ttgaaactac agatgatagt    180
ttaagagaac attttgagaa atggggcaca ctcacagatt gtctggtaat gagagacccc    240
caaacaaaac gttccagggg ctttggtttt gtgacttatt cttgtgttac agaggtggat    300
gcagcaatgc gtgctcgacc attcaaggtt gatgggcgtg tagtggaacc aaagagagct    360
gtttctagag aggattctgt gaagcctggt gcccatctaa cagtgaagaa aatttttgtt    420
```

```
ggcagtatta aagaagatac agaagaatat aatttgagag actactttga aaagtacggc    480
aagattgaaa ccatagaagt tatggaagac aggcagagtg gaaaaaagag aggatttgct    540
tctgtaactt ttgatgatca tgatacagtt gataaaattg ttgttcagaa ataccacact    600
attaatgggc ataactgtga agtgaaaaag gcccttgcta acaagtgat gcagccggct     660
ggatcacaga ggggtcgtgg aggtggatct ggcaattgta tgggtcacag aggaaacttt    720
ggaggtggtg gaggtaattt tggccgtgat ggaaactttg gtggaagagg aggctatggt    780
ggtggaggtg gtggcagcag aggtagttat ggaggaggtg atgtggatat aatggattag    840
gaggtgatgg tggcaactat ggcagtggtc ctggttatag tagtagaggc gggtatggtg    900
gtggtggacc aggatatgga accaaggtg gtggatatgg tggcggtgtt ggaggatatg     960
atggttacaa tgaaggagga aattttgacg gtagtaacta tggtggtggt gggaactata   1020
atgattttgg aaattacagt ggacaacagc aatcaaatta tggacacatg aaaggggca    1080
gttttggtgg aagaagctcg ggcagtccct atggtggtgg ttatggatct ggtggtggaa   1140
gtggtggata tggtagcaga aggttctaaa acagcagga aagggctaca gttcttagca    1200
ggagagagag tgaggagttg tcaggaaagc tacaggttac tttgagacag tcgtcccaag    1260
tgcattagag gaactgtaaa aatctgtcac agaaggaacg atgatccata atcagaaaag    1320
ttactgcagc ttaaacagga aacccttctt gttcaggact gtcatagcca cagtttgcag    1380
gaagtgcagc tatcgattaa tgcaatgtag cgtcaattag atgtacattc ctcaggtctt    1440
ttatctgttg tagctttgtc ttattctttt tcttttcatt acatcaggta tattgccctg    1500
taaattgtgg tagtggtacc aggaataaaa aattaaggaa ttttttaactt ttcaatatct    1560
gtgtagttca gttttttctac attttagtac agaaacttta acaaaatgca gttttgaagg    1620
tgtttccttg tgagttaaca agtaaagaag atcaattgtt aattactatt ttgtataaat    1680
tttgctaaag ttaactgtaa agaaacacct gctgacttgc agtttaaggg gaatctattc    1740
tccccatttc caaaccatga tatgaatgga cgccgacatg tggagagaac agataatttg    1800
tgtgtttgca atgtgtgttt taggtaaata ggattgggta tttaaattag catttgtgaa    1860
tttaatagca ttaagattac cttcaaataa aaaagtctca aaatttcttt ttggtttttg    1920
tgcactttct tttaaaatgt aatcacatga ttttagtgtg ttagacttgc tgagtcctag    1980
ctgtgtttag aacatctcca ttctacattt accttggtca aatttgaact gctgccatag    2040
gttttgggtg taaagaatgt ttactgccct ccatttaaat tctgaaaagg tatagtggat    2100
gttttccctc tcctacatta gaaaccattc ttaaaaactt ttcaaaatat agaaccatta    2160
agcctgctat atctgagcaa attagtgggt acctttttc ctttttttaaa gcacaagagg    2220
cccataaatc ttgagttatt tgcattagtt tacattttt gatacaactt ttcagaccaa     2280
gagaataaaa atcatgcgtt attaaacccc tagctggctg gcatgctttc ctgtttgtac    2340
tgtatacatt ttgctggatg aaaccaagga tagtttaggt ataattgtcc aaaataacct    2400
aactgcagca gaaatgtagg acagttgctt agtacaggct tctcacttcc tacagacctg    2460
aattcaaatt tggatagtct gagttattaa attcccaaag acaaagaaca cactcttatt    2520
tcttgtgtat atttcaacat aaatcatgtt gttaccaatt tgttgggaag gcccctggttg    2580
agaagagttt tagataataa ggctgtatat atatagatat atatagatat ataccaatgt    2640
ctatatatag agatattta tatatatata tacaggtata tatatgtgtg tgtatatata    2700
taggtatata catatataca tatatatata tatatatatg gatatatacc catgtctact    2760
gttttgcttc agctagtgct tacaatttca ttcaagtcct gagtatgtgt cctgctgtta    2820
```

| | |
|---|---|
| ctccttctttt ggtagttgaa cgttgaattc aagtctttcc ttctgtttta agaagtacta | 2880 |
| agcaaacaag caataaaaag gggaatggcg catgctagtg tttgaatatg ctctcttgtt | 2940 |
| gctctaattc tgtgcctccg tgcattaata tttggatgca tgcaatgcca gcatggaaat | 3000 |
| tggcct | 3006 |

<210> SEQ ID NO 16
<211> LENGTH: 1049
<212> TYPE: DNA
<213> ORGANISM: Homo sapiens

<400> SEQUENCE: 16

| | |
|---|---|
| aaaacaacag gaagcagctt acaaactcgg tgaacaactg agggaaccaa accagagacg | 60 |
| cgctgaacag agagaatcag gctcaaagca agtggaagtg gcagagatt ccaccaggac | 120 |
| tggtgcaagg cgcagagcca gccagatttg aagaaggc aaaaagatgc tggggagcag | 180 |
| agctgtaatg ctgctgttgc tgctgccctg gacagctcag gcagagctg tgcctggggg | 240 |
| cagcagccct gcctggactc agtgccagca gctttcacag aagctctgca cactggcctg | 300 |
| gagtgcacat ccactagtgg gacacatgga tctaagagaa gagggagatg aagagactac | 360 |
| aaatgatgtt ccccatatcc agtgtggaga tggctgtgac ccccaaggac tcagggacaa | 420 |
| cagtcagttc tgcttgcaaa ggatccacca gggtctgatt ttttatgaga agctgctagg | 480 |
| atcggatatt ttcacagggg agccttctct gctccctgat agccctgtgg ccagcttca | 540 |
| tgcctcccta ctgggcctca gccaactcct gcagcctgag ggtcaccact gggagactca | 600 |
| gcagattcca agcctcagtc ccagccagcc atggcagcgt ctccttctcc gcttcaaaat | 660 |
| ccttcgcagc ctccaggcct tgtggctgt agccgcccgg gtctttgccc atggagcagc | 720 |
| aaccctgagt ccctaaaggc agcagctcaa ggatggcact cagatctcca tggcccagca | 780 |
| aggccaagat aaatctacca ccccaggcac ctgtgagcca acaggttaat tagtccatta | 840 |
| attttagtgg gacctgcata tgttgaaaat taccaatact gactgacatg tgatgctgac | 900 |
| ctatgataag gttgagtatt tattagatgg gaagggaaat ttggggatta tttatcctcc | 960 |
| tggggacagt ttggggagga ttatttattg tatttatatt gaattatgta ctttttttcaa | 1020 |
| taaagtctta tttttgtggc taaaaaaaa | 1049 |

<210> SEQ ID NO 17
<211> LENGTH: 7219
<212> TYPE: DNA
<213> ORGANISM: Homo sapiens

<400> SEQUENCE: 17

| | |
|---|---|
| ggaccccggc aagcccgcgc acttggcagg agctgtagct accgccgtcc gcgcctccaa | 60 |
| ggtttcacgg cttcctcagc agagactcgg gctcgtccgc catgtccgcc gcagacgagg | 120 |
| ttgacgggct gggcgtggcc cggccgcact atggctctgt cctggataat gaaagactta | 180 |
| ctgcagagga gatggatgaa aggagacgtc agaacgtggc ttatgagtac ctttgtcatt | 240 |
| tggaagaagc gaagaggtgg atggaagcat gcctagggga agatctgcct cccaccacag | 300 |
| aactggagga ggggcttagg aatggggtct accttgccaa actggggaac ttcttctctc | 360 |
| ccaaagtagt gtccctgaaa aaaatctatg atcgagaaca gaccagatac aaggcgactg | 420 |
| gcctccactt tagacacact gataatgtga ttcagtggtt gaatgccatg gatgagattg | 480 |
| gattgcctaa gatttttttac ccagaaacta cagatatcta tgatcgaaag aacatgccaa | 540 |

```
gatgtatcta ctgtatccat gcactcagtt tgtacctgtt caagctaggc ctggcccctc      600
agattcaaga cctatatgga aaggttgact tcacagaaga agaaatcaac aacatgaaga      660
ctgagttgga gaagtatggc atccagatgc ctgcctttag caagattggg ggcatcttgg      720
ctaatgaact gtcagtggat gaagccgcat tacatgctgc tgttattgct attaatgaag      780
ctattgaccg tagaattcca gccgacacat ttgcagcttt gaaaaatccg aatgccatgc      840
ttgtaaatct tgaagagccc ttggcatcca cttaccagga tatactttac caggctaagc      900
aggacaaaat gacaaatgct aaaaacagga cagaaaactc agagagagaa agagatgttt      960
atgaggagct gctcacgcaa gctgaaattc aaggcaatat aaacaaagtc aatacatttt     1020
ctgcattagc aaatatcgac ctggctttag aacaaggaga tgcactggcc ttgttcaggg     1080
ctctgcagtc accagccctg gggcttcgag gactgcagca acagaatagc gactggtact     1140
tgaagcagct cctgagtgat aaacagcaga agagacagag tggtcagact gaccccctgc     1200
agaaggagga gctgcagtct ggagtggatg ctgcaaacag tgctgcccag caatatcaga     1260
gaagattggc agcagtagca ctgattaatg ctgcaatcca gaagggtgtt gctgagaaga     1320
ctgttttgga actgatgaat cccgaagccc agctgcccca ggtgtatcca tttgccgccg     1380
atctctatca gaaggagctg gctaccctgc agcgacaaag tcctgaacat aatctcaccc     1440
acccagagct ctctgtcgca gtggagatgt tgtcatcggt ggccctgatc aacagggcat     1500
tggaatcagg agatgtgaat acagtgtgga gcaattgag cagttcagtt actggtctta     1560
ccaatattga ggaagaaaac tgtcagaggt atctcgatga gttgatgaaa ctgaaggctc     1620
aggcacatgc agagaataat gaattcatta catggaatga tatccaagct tgcgtggacc     1680
atgtgaacct ggtggtgcaa gaggaacatg agaggatttt agccattggt ttaattaatg     1740 aagcccctgga tgaaggtgat gcccaaaaga ctctgcaggc cctacagatt cctgcagcta     1800
aacttgaggg agtccttgca gaagtggccc agcattacca agacacgctg attagagcga     1860
agagagagaa agcccaggaa atccaggatg agtcagctgt gttatggttg gatgaaattc     1920
aaggtggaat ctggcagtcc aacaaagaca cccaagaagc acagaagttt gccttaggaa     1980
tctttgccat taatgaggca gtagaaagtg gtgatgttgg caaaacactg agtgcccttc     2040 gctccccctga tgttggcttg tatggagtca tccctgagtg tggtgaaact taccacagtg     2100
atcttgctga agccaagaag aaaaaactgg cagtaggaga taataacagc aagtgggtga     2160
agcactgggt aaaaggtgga tattattatt accacaatct ggagacccag gaaggaggat     2220
gggatgaacc tccaaatttt gtgcaaaatt ctatgcagct ttctcgggag agatccagga     2280
gttctatctc tggggtgact gccgcatata accgagaaca gctgtggctg gccaatgaag     2340
gcctgatcac caggctgcag gctcgctgcc gtggatactt agttcgacag gaattccgat     2400
ccaggatgaa tttcctgaag aaacaaatcc ctgccatcac ctgcattcag tcacagtgga     2460
gaggatacaa gcagaagaag gcatatcaag atcggttagc ttacctgcgc tcccacaaag     2520
atgaagttgt aaagattcag tccctggcaa ggatgcacca agctcgaaag cgctatcgag     2580
atcgcctgca gtacttccgg gaccatataa atgacattat caaaatccag gcttttattc     2640
gggcaaacaa agctcgggat gactacaaga ctctcatcaa tgctgaggat cctcctatgg     2700
ttgtggtccg aaaatttgtc cacctgctgg accaaagtga ccaggatttt caggaggagc     2760 ttgacccttat gaagatgcgg gaagaggtta tcaccctcat tcgttctaac cagcagctgg     2820
agaatgacct caatctcatg gatatcaaaa ttggactgct agtgaaaaat aagattacgt     2880
tgcaggatgt ggtttcccac agtaaaaaac ttaccaaaaa aaataaggaa cagttgtctg     2940
```

```
atatgatgat gataaataaa cagaagggag gtctcaaggc tttgagcaag gagaagagag    3000
agaagttgga agcttaccag cacctgtttt atttattgca aaccaatccc acctatctgg    3060
ccaagctcat ttttcagatg ccccagaaca agtccaccaa gttcatggac tctgtaatct    3120
tcacactcta caactacgcg tccaaccagc gagaggagta cctgctcctg cggctcttta    3180
agacagcact ccaagaggaa atcaagtcga aggtagatca gattcaagag attgtgacag    3240
gaaatcctac ggttattaaa atggttgtaa gtttcaaccg tggtgcccgt ggccagaatg    3300
ccctgagaca gatcttggcc ccagtcgtga aggaaattat ggatgacaaa tctctcaaca    3360
tcaaaactga ccctgtggat atttacaaat cttgggttaa tcagatggag tctcagacag    3420
gagaggcaag caaactgccc tatgatgtga cccctgagca ggcgctagct catgaagaag    3480
tgaagacacg gctagacagc tccatcagga acatgcgggc tgtgacagac aagtttctct    3540
cagccattgt cagctctgtg acaaaatcc cttatgggat gcgcttcatt gccaaagtgc    3600
tgaaggactc gttgcatgag aagttccctg atgctggtga ggatgagctg ctgaagatta    3660
ttggtaactt gctttattat cgatacatga atccagccat tgttgctcct gatgcctttg    3720
acatcattga cctgtcagca ggaggccagc ttaccacaga ccaacgccga aatctgggct    3780
ccattgcaaa aatgcttcag catgctgctt ccaataagat gtttctggga gataatgccc    3840
acttaagcat cattaatgaa tatctttccc agtcctacca gaaattcaga cggttttccc    3900
aaactgcttg tgatgtccca gagcttcagg ataaatttaa tgtggatgag tactctgatt    3960
tagtaaccct caccaaaacca gtaatctaca tttccattgg tgaaatcatc aacacccaca    4020
ctctcctgtt ggatcaccag gatgccattg ctccggagca caatgatcca atccacgaac    4080
tgctggacga cctcggcgag gtgcccacca tcgagtccct gatagggga agctctggca    4140 atttaaatga cccaaataag gaggcactgg ctaagacgga agtgtctctc accctgacca    4200
acaagttcga cgtgcctgga gatgagaatg cagaaatgga tgctcgaacc atcttactga    4260
atacaaaacg tttaattgtg gatgtcatcc ggttccagcc aggagagacc ttgactgaaa    4320
tcctagaaac accagccacc agtgaacagg aagcagaaca tcagagagcc atgcagagac    4380
gtgctatccg tgatgccaaa acacctgaca agatgaaaaa gtcaaaatct gtaaaggaag    4440
acagcaacct cactcttcaa gagaagaaag agaagatcca gacaggttta aagaagctaa    4500
cagagcttgg aaccgtggac ccaaagaaca ataccagga actgatcaac gacattgcca    4560
gggatattcg gaatcagcgg aggtaccgac agaggagaaa ggccgaacta gtgaaactgc    4620
aacagacata cgctgctctg aactctaagg ccacctttta tgggggagcag gtggattact    4680 ataaaagcta tatcaaaacc tgcttggata acttagccag caagggcaaa gtctccaaaa    4740
agcctaggga aatgaaagga aagaaaagca aaaagatttc tctgaaatat acagcagcaa    4800
gactacatga aaaggagtt cttctggaaa ttgaggacct gcaagtgaat cagtttaaaa    4860
atgttatatt tgaaatcagt ccaacagaag aagttggaga cttcgaagtg aaagccaaat    4920
tcatgggagt tcaaatggag acttttatgt tacattatca ggacctgctg cagctacagt    4980
atgaaggagt tgcagtcatg aaattatttg atagagctaa agtaaatgtc aacctcctga    5040
tcttccttct caacaaaaag ttctacggga agtaattgat cgtttgctgc cagcccagaa    5100
ggatgaagga aagaagcacc tcacagctcc tttctaggtc cttcttcct cattggaagc    5160 aaagacctag ccaacaacag cacctcaatc tgatacactc ccgatgccac attttaact    5220 cctctcgctc tgatgggaca tttgttaccc ttttttcata gtgaaattgt gtttcaggct    5280
```

| | |
|---|---|
| tagtctgacc tttctggttt cttcattttc ttccattact taggaaagag tggaaactcc | 5340 |
| actaaaattt ctctgtgttg ttacagtctt agaggttgca gtactatatt gtaagctttg | 5400 |
| gtgtttgttt aattagcaat agggatggta ggattcaaat gtgtgtcatt tagaagtgga | 5460 |
| agctattagc accaatgaca taaatacata caagacacac aactaaaatg tcatgttatt | 5520 |
| aacagttatt aggttgtcat ttaaaaataa agttccttta tatttctgtc ccatcaggaa | 5580 |
| aactgaagga tatggggaat cattggttat cttccattgt gttttctttt atggacagga | 5640 |
| gctaatggaa gtgacagtca tgttcaaagg aagcatttct agaaaaaagg agataatgtt | 5700 |
| tttaaatttc attatcaaac ttgggcaatt ctgtttgtgt aactccccga ctagtggatg | 5760 |
| ggagagtccc attgctaaaa ttcagctact cagataaatt cagaatgggt caaggcacct | 5820 |
| gcctgttttt gttggtgcac agagattgac ttgattcaga gagacaattc actccatccc | 5880 |
| tatggcagag gaatgggtta gccctaatgt agaatgtcat tgttttttaaa actgttttat | 5940 |
| atcttaagag tgccttatta aagtatagat gtatgtctta aaatgtgggt gataggaatt | 6000 |
| ttaaagattt atataatgca tcaaaagcct tagaataaga aaagcttttt ttaaattgct | 6060 |
| ttatctgtat atctgaactc ttgaaactta tagctaaaac actaggattt atctgcagtg | 6120 |
| ttcagggaga taattctgcc tttaattgtc taaaacaaaa acaaaaccag ccaacctatg | 6180 |
| ttacacgtga gattaaaacc aatttttttcc ccattttttc tccttttttc tcttgctgcc | 6240 |
| cacattgtgc ctttatttta tgagccccag ttttctgggc ttagtttaaa aaaaaaatca | 6300 |
| agtctaaaca ttgcatttag aaagcttttg ttcttggata aaaagtcata cactttaaaa | 6360 |
| aaaaaaaaaa cttttttccag gaaaatatat tgaaatcatg ctgctgagcc tctattttct | 6420 |
| ttctttgatg ttttgattca gtattctttt atcataaatt tttagcattt aaaaattcac | 6480 |
| tgatgtacat taagccaata aactgcttta atgaataaca aactatgtag tgtgtccta | 6540 |
| ttataaatgc attggagaag tatttttatg agactcttta ctcaggtgca tggttacagc | 6600 |
| ccacagggag gcatggagtg ccatggaagg attcgccact acccagacct tgttttttgt | 6660 |
| tgtatttttgg aagacaggtt ttttaaagaa acattttcct cagattaaaa gatgatgcta | 6720 |
| ttacaactag cattgcctca aaaactggga ccaaccaaag tgtgtcaacc ctgttttcctt | 6780 |
| aaaagaggct atgaatccca aaggccacat ccaagacagg caataatgag cagagtttac | 6840 |
| agctcccttta ataaaatgtg tcagtaattt taaggtttat agttccctca acacaattgc | 6900 |
| taatgcagaa tagtgtaaaa tgcgcttcaa gaatgttgat gatgatgata tagaattgtg | 6960 |
| gctttagtag cacagaggat gccccaacaa actcatggcg ttgaaaccac acagttctca | 7020 |
| ttactgttat ttattagctg tagcattctc tgtctcctct ctctcctcct ttgaccttct | 7080 |
| cctcgaccag ccatcatgac atttaccatg aatttacttc ctcccaagag tttggactgc | 7140 |
| ccgtcagatt gttgctgcac atagttgcct ttgtatctct gtatgaaata aaaggtcatt | 7200 |
| tgttcatgtt aaaaaaaaa | 7219 |

<210> SEQ ID NO 18
<211> LENGTH: 1354
<212> TYPE: DNA
<213> ORGANISM: Homo sapiens

<400> SEQUENCE: 18

| | |
|---|---|
| gcagtgcccg actccgcagg agcgccaggg cggctcctgc tcttcctgga ctccctgaag | 60 |
| aggcgtttgt cgaaatgtcc acagaaggag gatttggtgg tactagccgc agtgatgccc | 120 |
| agcaaagcct aaagtccttc tggcttcggg tcatggaaga aatctggaat ttagcagtga | 180 |

```
aagatttctg aatgcaggaa ctcccactgg ctcgtattaa gaagattatg aaactggatg      240
aagatgtgaa gatgatcagt gcagaggccc ctgtgctctt tgccagggca gcccagattt      300
tttatcacag agttgactct tcgagcctgg attcacacag aggataacaa ctgccggact      360
tatgtcgcca tggcaattac gaaatttgat caattggatt ttctcatcga tattgttcta      420
agagatgaac tgaaacctcc aaagtgtcag gaggaggtgc tgcagtctgt aactcctgct      480
gagccagtcc aatactattt cacgctggct cagcagccca ccgcccgtcc aagtccaggg      540
acagcagcaa ggccagacca ccgccagctc catgaccacc atgcagcctg gcagatcat       600 catcgcacag cttcagcagg gccagaccac gcccgtgacg acgcaggttg agaaggtca       660 gcaggtgcag attgtccagg cccagccaca gggtcaagcc cagtaggccc agagtggtac      720
tggatggacc gtgcaggtga tgtagcagat cctcactaac acaggagaga tccagcagat      780
cccggtgcag ctgaaggctg ccagctgca gtgtatccgc ttagcccagt ctgtatcagg       840
cacccacgtt ctgcagggac agatccgac acttgccacc agcgctcaac cgattacaca      900
gacagaggtc cagcaaagac agcagtagtt cagccagttc acagatggac agcagctcta     960
ccagatccag caagtatcca tacctgcggg ccaggacctg cccagcccat gttttccag      1020 tcagtcaacc agccctctga tgggcaggcc ccccgggtga ctggcggctg agggccggag    1080
ctggcaaggc cgaggacact caacacaatt tttgccgtac agcccaggt catgaacaca     1140 gccttcttcc ccagaggacc cggccgacct cagctcctcc tgcaggctag gacaatggcg    1200
cactaggcct catgcctggg ggccgagatt ctccaacaga aagatgcaat attttttgtt    1260
tccttttttc tccaaggaat caatatttca atatgttgag ctgtgtgtcc aatgctatga    1320
aattaaaata ttaaatcaca aaaaaaaaaa aaaa                                 1354
```

<210> SEQ ID NO 19
<211> LENGTH: 3653
<212> TYPE: DNA
<213> ORGANISM: Homo sapiens

<400> SEQUENCE: 19

```
aatgaatcca actactgtcc ttgtcctctc ctctctaggt ttgtggagac tgaattccac       60
aaacctaggg acagggcact ctctaggggc aagtcaactc tcaattatag tgagggcagg     120
ttccccagtt gccagcctac accctggcca gccacccaag ggaatacctg ctgctgctaa     180
ggcagtcaat gttgggaggg tcagggaagg ggagaggaag tagctgagtg tagagattat     240
ccaggctttc cttcccgtcc tctgtacaga aaggcagaca tacactgact cctgaagtgc     300
cccaggatca tagttggttc ttcttagggg gagggagtga aacggtggcc ttgctccaat     360
tccaggcctc tggagaaagg agtgctcaac tggagagtct cagaacccttt tacagtactt    420 cagcaggccc agcacccaac cttccccacc ataccctgc cctgggaatg cccccttacca     480 cagtggcttc cattcctgac atttgaacca gctcctgcac ttgaaggaca aggcagccac     540
tgggcagctc cggaggcgg gaggcgtgac tccttcatat caggccatct ggaggagcac     600
cagatttccc tcttgtgaaa caaccccca cagtggggat ttaatggtca ccacacaagc      660
cccaaaaaac caggccctgc agagccatga cttcacaggg gagaaaacca gcccaagagg    720
ctgccctcac ccaacactta gctctaagtc cagactctta aaggttctgt taaagatctg     780
cggccaggcg cagtggctca catctgtaat cccagcactt tggaggccg aggtgggcgg     840 atcacgaggt caggagagcg agaccatcct ggctaacaca gtgaagccct gtctctacta     900
```

```
aaaatacaaa aaattagcca ggtgtggtgg cgggcacctg tagtaccagc tacttgggag    960
gctgaggcag gagaatggcg tgaacccagg aggcagagct tgcagtgagc cgagatcacg   1020
ccactgcact ccaacctggg tgacagagcg agactccgtc tcaaaaaaaa aaaaaaaaa   1080
aaaagatttg cctagtgagc cttggccaacc caagagcctt cctgggctct caggtttctt   1140
gaggcaaaac ttctaaagat gcaaatagaa tccttggtag ctacaaagct catctagcca   1200
aattataagt actatccaag cccaggattc attcttgaag atgagatgta aaagcactgc   1260
tgggcccttg caaagggaga gatcagagaa aataggagaa cgaacaccag ctcatgccaa   1320
tctcagtctc atgagctaca gagaaaaaga gccaaaaaag tttatcctgg ctcagccacc   1380
ttctggcttt gtagctacag gcaagttatt taacttttct gaatgttggt ttttccatct   1440
ggaaaaagga gacaggaaaa gctgccactg gaggctacct taagggtcaa tgagtgaaat   1500
ggggttgagt gcttaatgaa ctgttaaaac atgacacaga tgggtgaggt gacatctgac   1560
tgctcttcac agcagtcctt gcatggtgag cagatgcaat cagtgtgctc gttcattcac   1620
ttgttcatca aacaccaaca gtaccccactt gtgccaggcc ttgtgctggg caccgtaggg   1680
gctatggaag gagtaagaca cagtcatgct ctcaaggaac tcgctgtcca gcagagtgat   1740
aggacatgaa tacatacttc tagcaaaggc tgagtagcat taggcaggtg gccagatgag   1800
gtcagagctc tggccctagt gccctgtagt aagttgcgag ggagtaggaa atgaagacaa   1860
aacagcaaga gcacaggtcc agcacaagaa ggtgaaggac atggaaagag gagcagagca   1920
tgataaagct acaaaagtag ggggcaagtc atgaggtccg ggtcactggg gagccctgga   1980
caggctctga atgggagata gactagactg acaaagcagc tctttctgga gacctcctgt   2040
ggagggtccc ctcttctacc cttgggagac gaggtgtcat tcacttcacg atacacatgg   2100
ggaaaggaag ttggacaggg gaaggcactt gtctaaggtc actcagtggt catgccagtg   2160
caaagcaccc aaagcctggt ccaggtcctg ccacctcctg cgtgggctcc atcttctcgg   2220
ctcagttcaa gcctttatta tcagagtccc tctgtgtgcc aggctctgtg ctgaatgtcc   2280
gtgtcggcca caaattgcac taacggtgct tactgccact tcctctccga ccttacctcc   2340
aaagacccag ccgggcctaa ccctcacaca cagccagagg aatccttccc aaacacagtt   2400
aatcacatcg ctcatccgtt taaaactggc ttactagagc caacacagga taaaatccac   2460
aatcagtccc aaacccatct ttctctgccg tctctagacc acattcactg agcaccaagg   2520
cctgcacgct tcgcagccag ccctcctgct ctccccttg ccctccagcc acactggccc   2580
tcaacccccca acactgggcc cacctctgag ccctgcatca acaccagca ccccttcgc   2640
cgagctcatt cttcatcatt cctcagagct cagcttaagc atcaccttcc ttccctgcga   2700
cagggtcagg tccttttcctg tgcgctccgc agcaccctgc ctgtccctcg agtcctcgc   2760
gagaggaact agataactgt gatccccgcg cacagcacgg tgtctgccta ggacacagtg   2820
agcgcttcaa cgcgctgaac taaacgaatg aaggggaaca ccaactcagc tgtcaccccc   2880
gccccaagt gtcactggct agaagatctt ccccggttc gccggcagca ccggtgggtc   2940
ttgtcacctc tgcgccccgc agccctccgg aggctgcagt tgctgtctgc tgacaggcgt   3000
cccctcagga gaacgggagc tcctccgcg cagggcctg ctcagcaccc ctggtccgg   3060
gggcccccac ggaggccgcc gcgctcagtg aaactttgcc gcgcgcagca gtggccggag   3120
acccgcgcgg accctctccc cgcggggacc cgccagggcg agtcgcccct ccccgcggc   3180
agacgacccg acctgggcca aggtcggcca agtgctcgcc gctgcccag cggcccttgg   3240
acccacagga cccggacccg agtgcgcgga agcctccgag ccgcggccag gtctcagaat   3300
```

-continued

| | |
|---|---|
| gcgcggcggg gcagcccggc ccgtcaagca gcgaagccga aactagaagc ctgaggtctg | 3360 |
| gcttggtcac tgtttgctgg ggaactccga cgagcaacta cccttcgggg actcagtttc | 3420 |
| ccccgggcca agtgagacgg acagctgcgg ctcccgcgag aactcgcgcg ggaacaggag | 3480 |
| ctgcgggctc cgcacagcgc ccggcacgta gacccagtct actaacgggc tggaaggtcg | 3540 |
| cgctcccgcc tccgcgcctc cctagaacct ttctcacctc aagctcgggc tcccggactc | 3600 |
| tctcacctca cggcccctcc ttccaccttg ggccgcccag cctcaaccgc cct | 3653 |

<210> SEQ ID NO 20
<211> LENGTH: 1538
<212> TYPE: DNA
<213> ORGANISM: Homo sapiens

<400> SEQUENCE: 20

| | |
|---|---|
| ggctacgcaa gaccttcagt tccggattag gaggccccgc cccccggccc gagggagggg | 60 |
| cggagagacc cgctcctgcg acttagggcg atgccacctt aaagggcttg acctcctcga | 120 |
| agccagaact gcggaagagg atggagaaag aaacgctaga tagacccagg attcgaaccc | 180 |
| acaacagctt ggatgcaaag ctcattttga attctgaaga gctgggagtt tagcagtgga | 240 |
| cgaccaaaca aaaaatacc agaagacggt gaaagcagca gctggaaatg agagaaaaat | 300 |
| taagaaatag aaaatgctgt tcatgtatt agggagtgca catctttaaa gagaagtgaa | 360 |
| gaacctttt ggctaggcgc tttctgggga ccttggcagt tatcaacaag tcactctgaa | 420 |
| actaacagaa ggtgaggagg gagtaatcca gaaggaaac tgccattttt gctagggcaa | 480 |
| gaaagtagac ctagcaatgc aatgccatca aggagttagc tggctctagc gttctccgaa | 540 |
| ctttgcaact cattttatat tacattgtct gcgtcaagaa atttcaagta aatgccttga | 600 |
| gatttatat gtataaaatg tagtctctgg ccaggcgggg tggctcacgc ctgtaatccc | 660 |
| agcactttgg gaggctgagg cgagtagatc acgatgtcag gagatcaaga ccatcctggc | 720 |
| taacatggtg aaaccccgtc tctactaaaa aatacaaaaa attagccggg catgatggtg | 780 |
| ggcgcctgta gtcccagcta ctcgggaggc tgagacagga gaatggtgtg aacccgggag | 840 |
| gcagagcttg cagtgagccg agatcgcgcc actgcactcc agcctgggcg acagagcgag | 900 |
| actccgtctc aaaaaaaaaa aaaaaaaaaa aagtctcaga agaagtgtca agttgactaa | 960 |
| atgatttta agtcccttcc actctactat atcacaataa tttcccctat tttacctat | 1020 |
| ttaattttca caacaaccct gcagcctgta agtaggtgac tcctccatgg tcagcaggtg | 1080 |
| gtcagtggtc gaactatta ggactatctg atgctctttc ctctgctcac cattgcaata | 1140 |
| caatgagaaa atgcaaatg aatctaagta cagtgttctc tgggaatatg aagatagaac | 1200 |
| taaaactgc ctgagagatc agggcaggct tctagaaagt tgtgtctaac tagtcttgag | 1260 |
| gtttacataa accacaccag gctgatggga ctgggaaggg cccactaagc agtgagacca | 1320 |
| ttcccttttg gagagtcctt gcatcccctc ccagatttcc tctttgaggg gaaggtgaga | 1380 |
| gaggaggtaa aaggggtgag gaatggagaa taactcattc tggttcttgt ttccccttttt | 1440 |
| ccacataaaa gtatatttgt cttgtgttcc ataccagt ccatactgat gtgatggtgt | 1500 |
| ttttttatgct tccttttgaa taaacatttc attcttaa | 1538 |

<210> SEQ ID NO 21
<211> LENGTH: 3285
<212> TYPE: DNA
<213> ORGANISM: Homo sapiens

<400> SEQUENCE: 21

```
ggtcagtttc tggtcacatg attttcttct cgggctgcaa acaaagggaa gcctgcaaca      60
agttaagctg aagaccgaag caagagctgg ttcaggtggc agccacagca gcctcaggga     120
cctcagcaac tatggcctcc tgcccagact ctgataatag ctgggtgctt gctggctccg     180
agagcctgcc agtggagaca ctgggcccgg catccaggat ggacccagaa tctgagagag     240
ccctgcaggc ccctcacagc ccctccaaga cagatgggaa agaattagct gggaccatgg     300
atggagaagg gacgctcttc cagactgaaa gccctcagtc tggcagcatt ctaacagagg     360
agactgaggt caagggcacc ctggaaggtg atgtttgtgg tgtggagcct cctggcccag     420
gagacacagt agtccaggga gacctgcagg agaccaccgt ggtgacaggc ctgggaccag     480
acacacagga cctggaaggc cagagccctc acagagcct gccttcaacc cccaaagcag      540
cttggatcag ggaggagggc cgctgctcca gcagtgacga tgacaccgac gtggacatgg     600
agggtctgcg gagacggcgg ggccgggagg ccggcccacc tcagcccatg gtgcccctgg     660
ctgtggagaa ccaggctggg ggtgagggtg caggcgggga gctgggcatc tccctcaaca     720
tgtgcctcct tggggccctg gttctgcttg gctgggggt cctcctcttc tcaggtggcc     780
tctcagagtc tgagactggg cccatggagg aagtggagcg gcaggtcctc ccagaccccg     840
aggtgctgga agctgtgggg gacaggcagg atgggctaag gaacagctg caggccccag      900
tgcctcctga cagtgtcccc agcctgcaaa acatgggtct tctgctggac aagctggcca     960
aggagaacca ggacatccgg ctgctgcagg cccagctgca ggcccaaaag gaagagcttc    1020
agagcctgat gcaccagccc aaagggctag aggaggagaa tgcccagctc cgggggggctc   1080
tgcagcaggg cgaagccttc agcgggctc tggagtcaga gctgcagcag ctgcgggccc     1140
ggctccaggg gctggaggcc gactgtgtcc ggggcccaga tggggtgtgc ctcagtgggg    1200
gtagaggccc acagggtgac aaggccatca gggagcaagg cccccagggag caggagccag    1260
aactcagctt cctgaagcag aaggaacagc tggaggctga ggcacaggca ttaaggcaag    1320
agttagagag gcagcgacgg ctgctggggt ctgtacagca ggatctggag aggagcttgc    1380
aggatgccag ccgcggggac ccagctcatg ctggcttggc tgagctgggc cacagattgg    1440
cccagaaact gcagggcctg agaactgggg ccaggaccc tggggtctct gccaatgcct    1500
caaaggcctg gcaccagaag tcccacttcc agaattctag ggagtggagt ggaaaggaaa    1560
agtggtggga tgggcagaga gaccggaagg ctgagcactg gaaacataag aaggaagaat    1620
ctggccggga aaggaagaag aactggggag gtcaggagga cagggagcca gcaggaaggt    1680
ggaaggaggg caggccaagg gtggaggagt cggggagcaa gaaggagggc aagcgacagg    1740
gcccgaagga accccaagg aaaagtggta gcttccactc ctctggagaa agcagaagc      1800
aacctcggtg gagggaaggg actaaggaca gccatgaccc cctgccatcc tgggcagagc    1860
tgttgaggcc caagtaccgg gcaccccagg gctgctcagg tgtggacgag tgtgcccggc    1920
aggagggcct gactttcttt ggcacagagc tagcccagt gcggcaacag gagctggcct    1980
ctctgctaag aacatacttg gcacggctgc cctgggctgg gcagctgacc aaggagctac    2040
ccctctcacc tgctttcttt ggtgaggatg gcatcttccg tcatgaccgc ctccgcttcc    2100
gggattttgt ggatgccctg gaggacagct tggaggaggt ggctgtgcaa cagacaggtg    2160
atgatgatga agtagatgac tttgaggact tcatcttcag ccacttcttt ggagacaaag    2220
cactgaagaa gaggtcaggg aagaaggaca agcactcaca gagcccaaga gctgcggggc    2280
ccagggaggg gcacagccat agccaccacc accaccaccg gggctgacac cctgccccac    2340
```

```
agggaatggc cttggcctgg cccagcccaa gatcccagcg ttatctaact cctggagggt    2400
ggactctgtc ctggcttgtt tggtgtcctc agatatcttt cacacagtag agcaaaatca    2460
ccagccctgc actgatgtca ctttatgtag aaaaaggcct tagctggacc tgcgttgccg    2520
tctatgcaaa tgcatgcaaa tactccaggc cctgggatgt gggcttgtgt tttgtcactg    2580
tgaaggggga gatgggagag gagcctgttt tggggtgggg tctgggaaag gcaatctgat    2640
tctgaagcta aagagctttc atcctcttga gtgtatgtcc ccatagtggg cccccttgacc   2700 cacatgctga ccggtgcctt gggatttgac tagagttgct ggctcgaggc ccagcacgag    2760
gacttaccct ggggttttgt taggtttgga agcagctgtc cctagggggt gaagtccccc    2820
cccttttttt ttttaccccct gcttctccca cggcttcacc tccctatgtg aactgtagac   2880
tcagatccca ataaagtgct gttgcagcta tgatgctagg tggtttctaa gcacagggga    2940
caccccacac cccctgcctg aatggatggg tccatcccag gcactggtac ttgccccctt    3000
gttctgtatc ccccttttgcc cttgccttgc ccttccaaca aacccctaggc ccttgagaag   3060 ctgatacttc tccttttgct cacagctgcc ttggccccac ccctgggaga tgtagcaaat    3120
tgagtgtggg ttttggagtc tgagcctcag gctcaaatcc aggccaagtg atcttgggca    3180
agttaatctc tgggaacttt gggtttctta tcctcaaaaa aggcgatgga agggctgggg    3240
aagtgattaa ataaaagcaa cgcaagaaaa aaaaaaaaa aaaaa    3285

<210> SEQ ID NO 22
<211> LENGTH: 1176
<212> TYPE: DNA
<213> ORGANISM: Homo sapiens

<400> SEQUENCE: 22
aatagtgatt aggaaacctt gaagcctgcc caacgatcgt gggcaggagg tggtttctgg      60
tttgttgggg cgtgtgtatg tgtatttggg gggactgaag ggtacgtggg gcgaaacaaa     120
accggccatg gcagcagcgg aggaggagga cgggggcccc gaagggccaa atcgcgagcg     180
gggcggggcg ggcgcgacct tcgaatgtaa tatatgtttg gagactgctc gggaagctgt     240
ggtcagtgtg tgtggccacc tgtactgttg gccatgtctt catcagtggc tggagacacg     300
gccagaacgg caagagtgtc cagtatgtaa agctgggatc agcagagaga aggttgtccc     360
gctttatggg cgagggagcc agaagcccca ggatcccaga ttaaaaactc caccccgccc     420
ccagggccag agaccagctc cggagagcag aggggggattc cagccatttg gtgataccgg    480
gggcttccac ttctcatttg gtgttggtgc tttttcccttt ggctttttca ccaccgtctt    540
caatgcccat gagcctttcc gccggggtac aggtgtggat ctgggacagg gtcacccagc    600
ctccagctgg caggattccc tcttcctgtt tctcgccatc ttcttctttt tttggctgct    660
cagtatttga gctatgtctg cttcctgccc acctccagcc agagaagaat cagtattgag    720
ggtccctgct gacccttccg tactcctgga ccccccttgac ccctctatttt ctgttggcta   780 aggccagccc tggacattgt ccaggaaggc ctggggagga ggagtgaagt ctgtgcatag    840
atgggagagc cttctgctca gaggctcact cagtaacgtt gtttaattct ctgccctggg    900
gaaggaggat ggattgagag aatgtctttc tcctctccta agtctttgct ttccctgatt    960
tcttgatttg atcttcaaag gtgggcaaag ttccctctga ctcttccccc actccccatc    1020
ttactgattt aatttaattt ttcactcccc agagtctaat atggattctg actcttaagt    1080
gcttccgccc cctcactacc tcctttaata caaattcaat aaaaaaggtg aaatataaaa   1140
```
aaaaaaaaaa aaaaaaaaa aaaaaaaaaa aaaaaa                               1176

<210> SEQ ID NO 23
<211> LENGTH: 5565
<212> TYPE: DNA
<213> ORGANISM: Homo sapiens

<400> SEQUENCE: 23

```
ctcctgcacg gcgagtgctg gagcacgacg taccgctcgc tcggtcaggg cgcccctcc     60 gcccgcctcc tgcttcctcc tccgctgcct gccgccgccg cctccaccat tgtataatgc    120
tcggggcgcg caggcagaga acggcggagt cttagcttca gcctcgcctg ctgcccgctc    180
cccggcgcca ccctcgggcc cctggagcgg ggcactccgc atggagcggg agtagctgag    240
gagtgggcgg aaaccctcc tgatgcgtta gttcccaggt ggagctgcat gtgatatatg     300
ttgggtaaag gaggaaaacg gaagtttgat gagcatgaag atgggctgga aggcaaaatc    360
gtgtctccct gtgacggtcc atccaaggtg tcttacacct tacagcgcca gactatcttc    420
aacatttccc ttatgaaact ctataaccac aggcccctga cagagcccag cttgcaaaag    480
accgttttaa ttaacaacat gttgaggcgg atccaggagg aactcaaaca ggaaggcagc    540
ctgaggccca tgttcacccc ctcctcccag cccaccaccg agcccagcga cagctaccga    600
gaggccccgc cggccttcag ccacctggcg tccccgtcct cccacccctg cgacctcgga    660
agcactacgc ccctggaggc ctgcctcacc ccggcctcac tgctcgagga cgacgatgac    720
acgttttgca cctcccaggc catgcagccc acggctccca ccaaactgtc acctccagcc    780
ctcttgccag aaaaggacag tttctcctct gccttggacg agatcgagga gctctgtccc    840
acatctacct ccacagaggc ggccacggct gcgactgaca gtgtgaaagg gacctccagc    900
gaggctggca cccagaaact cgacggtcct caagagagcc gcgcagatga ctcaaaactg    960
atggactctc tgcctgggaa ttttgaaata cgacgtcca cgggtttcct gacagacttg    1020
accctggatg catcctgtt tgctgacatt gatacgtcca tgtatgattt tgaccctgc    1080 acttcctcat cagggacagc ctcaaaaatg gcccctgtgt ctgccgacga cctcctcaaa    1140
actctggctc cttacagcag tcagcctgtc accccaagtc agcctttcaa aatggacctc    1200
acagagctgg accacatcat ggaggtgctt gttgggtcct aagacccagg gacccagcga    1260
ctatgcccac ccagaccca gagcgttccc ataaccctga cagttctcca cactgtgcat    1320
gcacccttgc ttgccttttt cagagaaaaa gaaaatttta caacaggatc acactagttt    1380
ttgctttgag cagagttgga gtgccttcat ccaagtatga ccactttaa tacacttttt    1440 tgagtggttc ctcagagacc tactaccctg gtataggaaa gaatccattt gaagacaatg    1500
ttgcaatgtt gaatgacaaa aataaacagt tcaagtgaag cacaaggatt aagttggaaa    1560
agctgtaaat tgcatgtgca tatttgtcta tttttctat aagttttatt gcaagaggta    1620
aagaagaaaa ctatatatat atatcttatt tagataatct cagtaccttt tctggcattt    1680
ttgccctgta taggttgact tggcaattcg gccttttag aggcattaac tactcctcgt    1740
aagtgttgca tttacatggc tgtttagaaa actgctgccc aaatttattt tatattttttg   1800 tacagattct gcagtttatg atattgtttt tctaaaaaca aatgctgttt atacatatga    1860
gatagctatt tgataggat ttgctcacat agttcctgca aacttcagat gtacaagttg     1920
cacttgtact tttatagagt tgtaatgttt tatatgtgta tggtgcaaga gaaaattgga    1980
tcaaatcaat ctgcagttga tgtccccaaa tgcaaacaca ggcacacaca tgcacacacc    2040
cataaacaca cacacagtgc tttaagaaag ggccaggtga tatcacaccc aaatttcaca    2100
```

```
agcactgacc ccctggcacc aacacccgcc agtactgtga cttccaaagc cagagccaca    2160
tgtgctcatc aaacttgcat taagcagttg gcgggagatg gctgtggagc tgggggttta    2220
agtgatggtt ctcttttgct ccctcttttg agggtaaagc tactgtcttt cttaagagtg    2280
tatttatgcc aagtttgcgc ttttaattgt ttttattttg ttttttaatg aaaacccaga    2340
tctttccttt ttggcataat ttttatgatg acctgaaatt ttacatccga acaaaatttt    2400
acatccgaaa agcaaccaac ttcttcatgg aactcagccc tgttgcaatg cttagggccc    2460
ttaaagaaga aaatctcccc agaaggcatc catcatgttg cttaattgtc ttctgcagct    2520
tcctttccct agagctttcc ctgtgttgct aagagctgaa aatggcatct tcgtgatcac    2580
cacagtgagc ttggctcgcc tcggccggcc cgggatgcac tcttacaaca tgtgtgactc    2640
ttgaacctgg agttcatcac attacgtcac agcttccat ctggttgctt tcctgagtca    2700
gctacttcac acttgtcaag gctgttttac cccaaaactc agacaggact ttctatgcat    2760
gttttccctc ctccccccaa ttccccccccc catcaccttta tctcccagga cacacttgag    2820
aagtagcttt ttattcctag tggtgtacat ttaattttaa aaaggttgca atgtatcatg    2880
cttgttgccg aaactgttta tggccttctt gtttcagttt tttctttttct tccaatggta    2940 ctttagctgt tgagtgcagg ttacaaccta tattgttatg cagatggctt ctttaggaat    3000
aacttttata tttatttaaa aattttttaaa ttatgggatg ttttgttgtt gttgttgtct    3060
ttgttgttgg tcatttgtca atattcagtc accaattctg ctcacttctt gccatggata    3120
aaattgggtc tttctggcta attaaaaaag acaactttat aaaatggcac tttaagcaag    3180
ccatagttag ttttattttt gtaatgcaca tggcaaagca aagacgtttg tgatgaagga    3240
actgctcatc taagcaaaag atttgagtat gatatgataa aggctttcta cattctaatt    3300 tacttttttcc ccccacttga atgtgtttta aaggctaatt atcagctcag tagagcagtg    3360
agaaactgat caaattgcac ttgttctcct acaagcaacc tccacgcaga cacctcgtac    3420
tgctacaggt gtgtcatttc ctttaatagg accagggacc atgtaactga ggtgagggtt    3480
gtagtagatg cttccagtgt cagtatgcct gttaatttta agagcttccc tttcttgcag    3540
agaacaagtc tgcccagatt ccatgctttc tataactgga ggacctggca aacctgccgc    3600
atgctgcaca catctaccta cgtacacata tacaatagta ttgatgattc tgaacaataa    3660
cagggtaaaa cagttggttt gccattgtta aaaactgatt tacagtaact tacaacaact    3720
gtacttttgt tggattagca aatcatgtgt ttaaacaaat cccatatgtt gggcaacagt    3780
tcaaataagc acgagaagt gttgcccaaa cttggttctc tgactcttat gtatttgtaa    3840
ggctgggctt caaaatcaaa acaaaaaccc caaaaacagc aggcaaatgc ttttttaactc    3900 tgacaccgtt gccataaatc cctgatactc aaagtctaac aagaaagaca tggaaaatta    3960
gcagcccatt ttcagaaaga tcaaaatgat ctagggttct aattgctttt gcatcctatt    4020
cttacaaagt gatgtcccaa cagggaacag taggagctgg agtgggatct ccaagtccca    4080
gtttgagtgt gggatgtgct tccagcagtg ccttcccttt atgaaagaca tcacatggca    4140
tccagggcca gcaggcagc ttgaggtgcc tttacgagaa aaccgagctg gggctgggag    4200
aggacagtta ttgacactga tgtgcaatga agtgacaaga tgagagcaga atcgtaagag    4260
ctttgaattt gaagtgagtt ttttcccccc cataagttat ttattccttt tttctgtgta    4320
aatatattta ttttactgtg gagcgctaac atctggatcg taacatgtgc agaatgtatg    4380
gtaggaatgt attctcttgt aggaatgtaa atctgtatta aagggggtc caagccaggc    4440
```

| | | |
|---|---|---|
| ccccaggtct tctcattgta tgcacagtcc gcattcattt ttactcttct ctaatatggg | 4500 | |
| tctatttgaa atatgcaaaa ggtatgagga atgttttaat acctccaaat ttttaagaaa | 4560 | |
| agcatcaaag ggttgatatt ttttaaagtt tttttagtag cactttctct ggatgacaga | 4620 | |
| aggagcaacc acatgggcac ccttgttcat accaaaggt gagcagtggc cagagcctcc | 4680 | |
| tctgcacctc tcgagtgtct ttaccaattg agcttttat cgccatagcc ccttggagtg | 4740 | |
| ccccagctgc cctgaggtca atcaaggaaa atttcttaat gaaataagct ccaaagagcc | 4800 | |
| aaagtatcaa cttacagatc gttttaaag cttaaattta tgaaccacct ttgtggtaaa | 4860 | |
| caatgaatta tgaataccgc agggcagcct tcttaaatga caaatgtaaa aaaaaaaaaa | 4920 | |
| aaaaagactc tacttcgtgc agcaattgct actctatacg aattgtctta atttgaaaac | 4980 | |
| cttgctgtta caaattggac ctttatacat tttctgaaaa caatgaaaag agtatattta | 5040 | |
| accttttctg gctgtaaatg gttaccttcc tgtaactgcc ccgcacctgg aggcatggag | 5100 | |
| ttgtgtgcat cctgcttatg tacaattgtt ttcagtgttt ctaagaatga gtctgaatgg | 5160 | |
| ttcttgaaaa ttagccagga tcaaatgcta ttgcagacaa agccaataaa aagttggact | 5220 | |
| tcttttgggg ataacaagtt ttggaagaga aatgcaggcc atatgtgcgc atgaccgaga | 5280 | |
| ttttgaaaaa agatgtacat agtgacatgt ttggtgcatg ttttttgagg agggcttttg | 5340 | |
| tcaaaaagga ggtataacct ttcccccaca gacctgagag ctgtgccttt tctatgcaat | 5400 | |
| attacagacg ttcatcgga acccagatgg ctgtattcac atgtaggttt gggctgtaat | 5460 | |
| ctaaacaatt ggacagatta aatgtacatg gaaatgagca gtcttacttt tgtagtttta | 5520 | |
| tattatacaa taaacagtta aaagatgaaa aaaaaaaaaa aaaaa | 5565 | |

<210> SEQ ID NO 24
<211> LENGTH: 1201
<212> TYPE: DNA
<213> ORGANISM: Homo sapiens

<400> SEQUENCE: 24

| | | |
|---|---|---|
| taccacctca ggagagttcc agggaagaac cccacccgca ctccaatgag gtcacaatgg | 60 | |
| ctggagctct gaggggccca ggctccctga gccaggagga gaggagaaag tccaaggaaa | 120 | |
| gatggctggc agtcaccct acttcaacct gcctgactcc acacacccat cgccgccctc | 180 | |
| cgctccaccc agcctccgct ggcaccagcg ctgccagccc tctggtgcca ccaatggcct | 240 | |
| gctggtggcc ctgctgggtg ggggcctgcc tgctggcttc gtgggccccc tttctcgtat | 300 | |
| ggcttaccag ggttccaacc tgccctcgct ggagctgctc atctgtcgat gcctcttcca | 360 | |
| cctccctatt gccctgctac ttaaactgcg tggcgacccc cttctgggac tcctgacat | 420 | |
| ccgaggctgg gcctgcttct gtgccctgct caacgtcctc agcattggat gtgcctacag | 480 | |
| tgcagttcag gtggtgcccg ctggcaacgc tgccactgtt cgcaaaggtt cttccaccgt | 540 | |
| atgctccgct gtcctcaccc tctgccttga gagccagggt ctcggtggct acgagtggtg | 600 | |
| tggactgttg ggcagcatcc taggactaat catcattctg ggacctggac tctggacact | 660 | |
| acaggagggg accacaggtg tctacaccac cctgggctat gtgcaggctt tcctgggagg | 720 | |
| cctgcgctgt tccctggggc ttctggtcta tcgttctctg cactttccct cctgcctccc | 780 | |
| aacagtggcc ttcctatctg gcttggtggg gctgctgggc tgtgtgccag gcctctttgt | 840 | |
| gctgcagacc cccgtgttgc ccagtgacct cctgagttgg agttgtgtgg gggcagaggg | 900 | |
| gatcctcgcg ttggtctcct tcacatgtgt gggctatgcg gtcaccaagg cccaccctgc | 960 | |
| cctggtgtgc gctgtcctgc attccgaggt ggttgtggcc cttatactgc agtattatat | 1020 | |

```
gctccatgag actgtggcac tttctgacat catgggggca ggggttgtgc tgggcagcat    1080
tgccatcatt acagcccgga acctcagctg tgagaggaca gggaaggtgg aggagtgaga    1140
tagaacttgg gagcccgggg gttgggaggg acagggataa ataaagacaa agactgaaga    1200
c                                                                    1201

<210> SEQ ID NO 25
<211> LENGTH: 6335
<212> TYPE: DNA
<213> ORGANISM: Homo sapiens

<400> SEQUENCE: 25
agtgctgagg gagcaaagtt cattttctcg ggtaggagaa gatgattctc ttgcaacacg      60
tgcggattgt gacaaaatct ttcattaaca aggggagttt cggtgaagtg gaggtttggg     120
gaaaggcgag gaagtcggtc tggagcaagc aagcaaagtg cggaagctgt actgggattc     180
ttctagaaag tggggtggga aaggagctag ggagggcgtg tggagggacg agatctgtgt     240
cagaacgtgc gtgtgagcgg atacaaaacc cgagagaggc gtgagcagcg ctgtgtttgc     300
gagcgggagc gaggggcgcc ggctggggtg tgtgctcctg agctcttcag aaaccaggct     360
gctttcagga acattgctgt ggattcccag ggcctattcc actagaagca agatggctga     420
actcaatact catgtgaatg tcaaggaaaa gatctatgca gttagatcag ttgttcccaa     480
caaaagcaat aatgaaatag tcctggtgct ccaacagttt gattttaatg tggataaagc     540
cgtgcaagcc tttgtggatg gcagtgcaat tcaagttcta aaagaatgga atatgacagg     600
aaaaaagaag aacaataaaa gaaaagaag caagtccaag cagcatcaag caacaaaga     660 tgctaaagac aaggtggaga ggcctgaggc agggcccctg cagccgcagc caccacagat     720
tcaaaacggc cccatgaatg gctgcgagaa ggacagctcg tccacagatt ctgctaacga     780
aaaaccagcc cttatccctc gtgagaaaaa gatctcgata cttgaggaac cttcaaaggc     840
acttcgtggg gtcacagaag gcaacagact actgcaacag aaactatcct tagatgggaa     900
ccccaaacct atacatggaa caacagagag gtcagatggc ctacagtggt cagctgagca     960
gccttgtaac ccaagcaagc ctaaggcaaa acatctcct gttaagtcca ataccctgc     1020 agctcatctt gaaataaagc cagatgagtt ggcaaagaaa agaggcccaa atattgagaa    1080
atcagtgaag gatttgcaac gctgcaccgt ttctctaact agatatcgcg tcatgattaa    1140
ggaagaagtg gatagttccg tgaagaagat caaagctgcc tttgctgaat tacacaactg    1200
catcattgac aaagaagttt cattaatggc agaaatggat aaagttaaag aagaagccat    1260
ggaaatcctg actgctcgtc agaagaaagc agaagaacta agagactca ctgaccttgc     1320 cagtcagatg gcagagatgc agctggccga actcagggca gaaattaagc actttgtcag    1380
cgagcgtaaa tatgacgagg agctcgggaa agctgcccgg ttttcctgtg acatcgaaca    1440
gctgaaggcc caaatcatgc tctgcggaga aattacacat ccaaagaaca actattcctc    1500
aagaactccc tgcagctccc tgctgcctct gctgaatgcg cacgcagcaa cctctgggaa    1560
acagagtaac ttttcccgaa aatcatccac tcacaataag ccctctgaag gcaaagcggc    1620
aaaccccaaa atggtgagca gtctccccag caccgccgac ccctctcacc agaccatgcc    1680
ggccaacaag cagaatggat cttctaacca agacggaga tttaatccac agtatcataa    1740
caacaggcta atgggcctg ccaagtcgca gggcagtggg aatgaagccg agccactggg    1800
aaagggcaac agccgccacg aacacagaag acagccgcac aacggcttcc ggcccaaaaa    1860
```

```
caaaggcggt gccaaaaatc aagaggcttc cttggggatg aagaccccg  aggcccggc      1920 ccattctgaa aagccccggc gaaggcagca cgctgcagac acctcggagg ccaggccctt     1980
ccggggtagt gtcggtaggg tttcacagtg caatctctgc cccacgagaa tagaagtttc     2040
cacagatgca gcagttctct cagtcccggc tgtgacgttg gtggcctgag ctaggaggaa     2100
aaagagcagt tttcactcag ttttggttcc ctgcccgagg tgctgaccca attcgctgcc     2160
aaaagagtgt caatcagaat atacaaatcc cgtatggttg tgtcatcctc tcttaatcat     2220
ttttactaat tctaataatc agctctagct tgcttcataa ttttcatggc tttgcttgat     2280
ctgttgatgc tttctctcat caagactttg cagcatttta gccaggcagt atttactcat     2340
tattaggaaa atcaagatgt ggctgaagat cagaggctca gttagcaacc tgtgttgtag     2400
cagtgatgtc agtccattga ttgtctttag agagttaatg ttacaaaaaa gaattcttaa     2460
taatcagaca aacatgatct gctgaggaca catgcgcttt tgtagaattt aacatctggt     2520 gttttttctga aaaatatat atacatatat tgctttattt gaaacaaatt aaaatatgct    2580
gcatttgaca cctggctagt ttcttttatt gatacccacc tagttattga atgtactgtt     2640
tagtgctttc aaaaaaaact ttagagacta gaggttgtgg tgcaaagctg tgtacaataa     2700
atactgtttc tgttgagaca agtactcttt caggaaaata tatatatgcc ctttcaatta    2760
gattacacaa atagatggat atgcaccctg atcatcttag acacaccatg tggcagttgg     2820
gcagttggaa acattggttg caagtactac aaacctcagc tgagcctagc ttcaacaata    2880
agaatttatt ggttcagtga gtgaaaagtc cagttggtcc aatttgatca ggatttcagc    2940
tcccatctct ttttttttt tctttttttct ttttcttttt ttgagacagt cttgctttgt     3000
cacccaggtg gagtgcaatg gcatgatctc ggctcactgc aacctccgcc tcctgggttc    3060
aagccattct cctgcccggc cttccgagta gctgggatta caggcatgtg ccaccacgcc     3120
ctgctaattt ttatattat agtacagaca ggatttcacc atgttgtcca ggctggtctc    3180
aaacccctga cctcaggtga tccacctgct ttggcctccg aaactgccgg aattacaggc    3240
atgagccacc gtacccggcc agctcccatc tcttaattat cttagctctc ctttcctcct     3300 tggggttgaca ttgcattcag aattgtggca aagggccacc atgctcttaa gactcaagtc    3360
tattttccac actgtccaga ggagagaagt tatcctagta gcttctacac agagcaagtg    3420
tctttctcag aaatcccagc aaaggtcttg cataccattg ctggtaggcc tgtctcttaa    3480
accaatcatg aaagggggga gagaagtgaa tgggatgaac taatttgcat agactaatta     3540
gagcccaccc ctggagcctg ggtgtggcca tcttcccaga gttcctgagc tagatggaga    3600
aggggtactt ctcagaaagg gaaaatggat acccaatggc ccaaacccaa aatagcccca    3660
gttcccctaa ctttgactac agggcagtcc agtttgggtg ccgcttccgt tgcactcaca     3720
tgtcctacat atctgttgac tactcacaag tgcaaatgct tattctcaac tcaacattaa    3780
cattttttct ggcaacccag gttcactggt tctcttccac agagcggccc tgagcagctg    3840
agcctgcaag ccacgcaagc atctgttct tcttttgcca agtacaggag gatgtttgct      3900
ctctctgtag agagcttct gaggtctctg ggtgtaccca gagatttaat agaaattctt    3960
aacgttaagt cacattccag gaaggaagga agagttgttc gttcaaataa gaaagataaa     4020
tgttcggcac tgtaggccct gtttacccca tctgaggccc tgaattcata tattacaaga    4080
cggaaggatt ttgcacagtt ttttatgtag caagattttg ctcaccactg aaaaatgtca    4140
gtgtaaatgt gaccgcttta aagatgagtc aagtaattct tggaacaggg aaaaaaatga    4200
atttgccagg tcaggagttc acctgccttt gtcagagttg aacccaacca ctcttgacct    4260
```

```
cgactcactc ccttagggtt aagaaagccc aaacacattc ctgagcacag agcaaacact      4320
cccatgtcac tgaaaagaaa caaaagaatg ctaaaaagtg ctcagacctg atcacatttt      4380
ttccaatatt ttttccttt tttttttttt tttgagacag ggtcttgctc tatcacctag       4440
gctggagtgc atgttttga dacagggtct tgctctatca cctaggctgg agtgcatgat      4500
catggctcac tatagccttg aactcctggg ctcaagccat cctcagcctc ccaagttgcg      4560
aggactacag gtgtgcacca caacgtccca gctactttt aaattttag tagaaacgag        4620 gtctcactat ggtgcccaga ctggtctcga actccggagc tcaagtgatc ttcctgcttt      4680
ggcctcccaa agtgttagaa ttacaggcat gagccacctc gcctggctgg ttttgccttt     4740
tcttatagac cctgggcatg taagcattta ttagtttgca tttttgaaac agtaatttca      4800
atattttagt gccaatgtca ggccgcttaa acactgtatt acatatcttc atctgtctgg      4860
tggaactatt ggtgtgatcc tagagaactg agtcctattc tgccattcat ttaaagtgtt      4920
ttaaactcta atctctctac ttaatgcaca gtagtcagat tattctctta aacatttgcc      4980
tagtagaggt taaaatagtt taatccttat gaagatggaa taacttcaaa ctcacattgt      5040
ggcacttaga tcttccacca agacttcatc cgtgaaatcc acacctccct gttgggttcc      5100
caattacatt ccaaatttac atttcttttg agaatctctg catactccag ctctgtcctg      5160
ttgatcctat tctagaagtg cttaatgcag caagacacag aaagtaaaac gcaaattgct      5220
gcaaaattca ccctcagtgg aggactagaa acacaacatg tccaatttaa agctcagttc      5280
acaagcagtt caattctgct ggcatcagaa aaggagattc taattaaaca ttcttaggga      5340
aggacatcaa atgaggttaa tgggaaacgt taccagatta aaagcagttt tttgacaaag      5400
taacagattt ggaaattctg actctctgaa agccttgatt tgaacctcaa acttgatttc      5460
accatgagaa gtggggatca agggcctgcg cagttctttt cctaaatcga ttcggtgctc      5520 cccacccga cgcaggcaca ggtccgcaac cagatagga gatgcctgaa tttcaggcta      5580
cctttgacaa agctttcttc ctccctccct cccttgcac gctgcatccc acgctgcctg      5640
cttaaagcgc cctcatgtgt ctacagatgg taaaacgttt atttctcaac agacattcca      5700
gtgatagcat ccaatgacct atgtaacggc acccttttt gctgtacgcg tttttgaga      5760 tggagtctcg ctctgtcgcc caggctggag tgcagtggcg cggtctcggc tcactgcaag      5820
ctccgcctcc cgggttcacg ccattctcct gcctcagcct cccgagtagc tgggactaca      5880
ggcacccgcc accacacctg ctaattttt tgtatttta gtagatacag ggtttcaccg      5940
tgttagccag gatggttttg atctcctgac ctcgtgatcc acccccctcg gcctcccaaa     6000
gtgctgggat tacaggggtg agccactgcg cccggcccca gtcacttgtt cttaagtttc      6060
ttaagcaaac tataaaatag caaaagacca aaaaaaagg aaaaaaagca gttcgcctaa       6120
tacattgttc cagcatttcc ttgaaagtac tgagccatct caattgctct gattttgtga      6180
gaaaattatg aagagttgca aagtcccagt gattctcttg ttacttagct aagaatttga      6240
aatgtaattt aaatactatt ctttacaatc cattataagg atttttaaaat cttttgcctt    6300 ctttaataaa ttctaacaaa gaaaaaaaaa aaaaa                                 6335
```

<210> SEQ ID NO 26
<211> LENGTH: 3572
<212> TYPE: DNA
<213> ORGANISM: Homo sapiens

<400> SEQUENCE: 26

```
agagccgagg ccaggctgcc ctcgaagcgg ggcggggcga agcggggcgg ggccgagcag      60
ggcggggcgg gggcttgagg tgattcccaa gccgcgggc ggctccggtg gtgcggggaa      120
accgaaagtg ggcggcggcc gcggcggggc ccctggcgga gacggcggca ggagctgggc     180
ccagagacgc ggggacgggc cgtgggcccc cggaacgaga ttacctgcta tgccatggcc     240
tgcacagaaa ctgcaagaat tgctcagctt gtggctcgtc aaaggagttc taaaaggaaa    300
accgggcgtc aagttaattg tcagatgaga gtgaagaaaa ccatgccatt ttttctagaa    360
ggaaaaccaa agcaaccct cagacaacca ggatttgctt caaattttc tgttggcaaa     420
aaacctaatc cagcaccgtt aagagacaaa ggaaactctg ttggagttaa gcctgatgct    480
gaaatgtctc cttatatgct acacacaact cttggaaatg aagcattcaa agacattcca    540
gtgcaaaggc atgtgaccat gtccaccaac aacaggttta gcccaaaggc gtcccttcaa    600
ccacctttgc agatgcatct ctcaagaacc tctactaagg aaatgagtga taatttaaat    660
cagactgttg aaaacccaa tgtcaagcct cctgcctctt acacttataa aatggatgag    720
gttcaaaatc gcataaagga aatactaaac aagcataaca atggcatttg gatatctaag    780
cttccacatt tttacaaaga gttatataaa gaagaccttta atcaaggaat tttacaacag    840
tttgaacact ggcctcatat ttgcacggtg gagaaaccctt gcagtggtgg ccaagattta    900
cttctttatc cagctaagag aaaagcagctt ttgagaagtg aactggatac tgagaaagta    960
cctctatccc cactacctgg tcccaaacaa acaccaccgt tgaaagggtg tccaacagtt   1020
atggcaggag actttaaaga aaaagtggca gacctgctgg tgaaatacac aagtggcctt   1080
tgggccagtg cacttccgaa agcatttgag gaaatgtaca agtgaaatt ccctgaggat    1140
gccttaaaaa atcttgcctc actttctgat gtatgcagca tagactacat ttctggaaat   1200
ccccagaagg ccattctcta tgctaaactt ccattgccca ctgacaaaat ccaaaaggat   1260
gcagggcaag cacatggtga taatgatatc aaggctatgg ttgaacaaga gtatttgcag   1320
gtagaagaaa gcattgctga aagtgctaat accttttatgg aggacataac agttcctcct   1380
ttaatgattc caactgaagc atcaccatct gtattggtgg ttgaactgag caacacaaat   1440
gaagtggtta tcaggtatgt gggcaaagac tattctgctg ctcaggaatt aatggaagat   1500
gagatgaagg aatattacag taagaatcct aagatcacac cagtccaggc tgtgaatgtt   1560
gggcagttgc tggccgtaaa tgccgaggag gacgcctggt tacgggcaca ggtcatctca   1620
acagaagaga acaaaataaa ggtatgctat gttgactatg gttttagtga aaatgttgaa   1680
aaaagcaaag catacaaatt aaacccgaag ttttgttcac tctcatttca agctacaaaa   1740
tgtaagcttg caggcttgga agtcctaagc gatgaccctg atctagtgaa ggtggttgaa   1800
tctttaactt gtgaaagat ctttgcagtg gaaatacttg acaaagctga cattccactt   1860
gttgttctgt acgatacctc aggagaagat gatatcaata tcaatgccac ctgcttgaag   1920
gctatatgtg acaagtcact agaggttcac ctgcaggttg acgccatgta cacaaatgtc   1980
aaagtaacta atatttgctc tgatgggaca ctctactgcc aggtgccttg taagggtctg   2040
aacaagctca gtgaccttct acgtaagata gaggactact tccattgcaa gcacatgacc   2100
tctgagtgct tgtttcatt accttctgt gggaaaatct gcctcttcca ttgcaaagga   2160
aaatggttac gagtagagat cacaaatgtt cacagcagcc gggctcttga tgttcagttc   2220
ctggactctg gcactgtgac atctgtaaaa gtgtcagagc tcaggaaat tccacctcgg   2280
tttctacaag aaatgattgc aataccacct caggccatta agtgctgttt agcagatctt   2340
ccacaatcta ttggcatgtg gacaccagat gcagtgctgt ggttaagaga ttctgttttg   2400
```

-continued

```
aattgctcgg actgtagcat taaggttaca aaagtggatg aaaccagagg gatcgcacat    2460
gtttatttat ttaccccctaa gaacttccct gaccctcatc gcagtattaa tcgccagatt    2520
acaaatgcag acttgtggaa gcatcagaag gatgtgtttt tgagtgccat atccagtgga    2580
gctgactctc ccaacagcaa aaatggcaac atgcccatgt cgggcaacac tggagagaat    2640
ttcagaaaga acctcacaga tgtcatcaaa aagtccatgg tggaccatac gagcgctttc    2700
tccacagagg aactgccacc tcctgtccac ttatcaaagc caggggaaca catggatgtg    2760
tatgtgcctg tggcctgtca cccaggctac ttcgtcatcc agccttggca ggagatacat    2820
aagttggaag ttctgatgga agagatgatt ctatattaca gcgtgtctga agagcgccac    2880
atagcagtgg agaaagacca agtgtatgct gcaaaagtgg aaaataagtg gcacagggtg    2940
cttttaaaag gaatcctgac caatggactg gtatctgtgt atgagctgga ttatggcaaa    3000
cacgaattag tcaacataag aaaagtacag cccctagtgg acatgttccg aaagctgccc    3060
ttccaagcag tcacagctca acttgcagga gtgaagtgca accagtggtc tgaggaggct    3120
tctatggtgt ttcgaaatca tgtggagaag aaacctctgg tggcactggt gcagacagtc    3180
attgaaaatg ctaacccttg ggaccggaaa gtagtggtct acttagtgga cacatcgttg    3240
ccagacaccg ataccctggat tcatgatttt atgtcagagt atctgataga gctttcaaaa    3300
gttaattaat gactgcctct gaaaccttga caactaattc agattttta gcaataacaa    3360 aatgtagtag gcttaaaaaa aatcttaact ctgctacatg gctctgactg ctgtggggga    3420
ttgaaaagaa tatgcttatg tttgatgaaa gatatttaac aagttttgtt ttaacagagt    3480
tgacttttca agaaaattg tacttgaatt attactataa tattagaata aaaatgttta    3540
tcaatataaa aaaaaaaaa aaaaaaaaa aa                                    3572
```

<210> SEQ ID NO 27
<211> LENGTH: 4476
<212> TYPE: DNA
<213> ORGANISM: Homo sapiens

<400> SEQUENCE: 27

```
agcagagaga acacacgtcc ttgcggaagt gacggcagtt ccgagtccag tgggggcggt      60
gggagcgatg agggtctgag acggtgggag cggttgtgtg aagatggaga cattccatac     120
accaagcttg ggtgatgagg aatttgaaat cccaccatc tccttggatt ctgatccctc      180
attggctgtc tcagatgtgg ttggccactt tgatgacctg cagaccctt cctcttcaca      240 ggatggcagt tttcagccc agtatggggt ccagacattg gacatgcctg tgggcatgac      300
ccatggcttg atggagcagg gcgggggggct cctgagtggg ggcttgacca tggacttgga    360
ccactctata ggaactcagt atagtgccaa cccacctgtt acaattgatg taccaatgac    420
agacatgaca tctggcttga tggggcatag ccagttgacc accattgatc agtcagaact    480
gagttcccag ctgggtttga gcctaggggg tggcaccatc ctgccacctg cccagtcacc    540
tgaagatcgt ctttcaacca ccccttcacc tactagttca cttcacgagg atggtgttga    600
ggatttccgg aggcaacttc ccagccagaa gacagtcgtg gtggaagcag ggaaaaagca    660
gaaggcccca aagaagagaa aaaagaaaga tcctaatgaa cctcagaaac cagtttcagc    720 atatgccttta ttcttttcgtg atacacaggc tgccatcaag ggacagaatc ctaatgccac    780
ttttggtgag gtttcaaaaa ttgtggcctc catgtgggat agtcttggag aggagcaaaa    840
acaggtatat aagaggaaaa ctgaggctgc caagaaagag tatctgaagg cactggctgc    900
```

```
ttacaaagac aaccaggagt gtcaggccac tgtggaaaca gtggaattgg atccagcacc    960
accatcacaa actccttctc cacctcctat ggctactgtt gacccagcat ctccagcacc   1020
agcttcaata gagcccsctg ccctgtcccc atccattgtt gttaactcca cccttcatc   1080
ctatgtggca aaccaggcat cttctggagc tggggtcag cccaatatca ccaagttgat   1140
tattaccaaa caaatgttgc cctcttctat tactatgtct caaggaggga tggttactgt   1200
tatcccagcc acagtggtga cctcccgggg gctccaacta ggccaaacca gtacagctac   1260
tatccagccc agtcaacaag cccagattgt cactcggtca gtgttgcagg cagcagcagc   1320
tgctgctgct gctgcttcta tgcaactgcc tccaccccga ctacagcccc tccattaca    1380
acagatgcca cagcccccga ctcagcagca agttaccatt ctgcagcagc ctcctccact   1440
ccaggccatg caacagcctc cacctcagaa agttcgaatc aatttacagc aacagcctcc   1500
tcctctgcag atcaagagtg tgcctctacc cactttgaaa atgcagacta ccttagtccc   1560
accaactgtg gaaagtagtc ctgagcggcc tatgaacaac agccctgagg cccatacagt   1620
ggaggcacct tctcctgaga ctatctgtga atgatcaca gatgtagttc ctgaggttga    1680
gtctccttct cagatggatg ttgaattggt gagtgggtct cctgtggcac tctcaccccca  1740
gcctcgatgt gtgaggtctg gttgtgagaa ccctcccatt gtgagtaagg actgggacaa   1800
tgaatactgc agcaatgagt gtgtggtgaa gcactgcagg gatgtattct tggcctgggt   1860
agcctctaga aattcaaaca cagtggtgtt tgtgaaatag tccttcctgt tctccaagcc   1920
agtgaagagt tatctgctgg gaaagtgtcc aagagcctgt ttttgaaaca caagctgggc   1980
ttctggtagt gcctcatcac aacccatgat ggctgttcat gtttcacccc ttttcttcct   2040
tcagcagagg ccaggctatg gagcagggcc actgaatttg ctgtaatctg gagatgcttt   2100
ttactttcaa ccataagcgg taatagcaga ggaaagggtg aagggagtct gggcaagcaa   2160
agcatagaga tggtgggtg gtggtggggt tgaagaaact tgttggtata attgtcatag    2220
gacttgccta aaatattatt aaaattacgg gagtgtactc agctttgagc ctaggagaaa   2280
atgccactgt gtgcatccat tttaaagggt ccctcataa aaaaatgtta ttccccatta    2340
tcacatcagt acactgcttt gaaaacaaaa cttttcaaca tgggcatact gggctacatg   2400
gaaaatgaca tcacccagga gtgatttctc tttatatata ttatttctgc agttaccatc   2460
cttatctgag ttatcacagt tcatgaatct aagaggcgga actctacatc attagtaaga   2520
ggttccacca aagtctaaag ttgtattcac ttgtgtttga tgaactatct ttaaaagacc   2580
ataggtctat cattatttct tagacataat ctaaagaaaa acagactaga gaagccacct   2640
ggttgtaaca gaataagcag aagtttacag catgatagtc caagtggtga taactttaaa   2700
taaaactcaa atttttactg tttgtagaca ggaatgctgt cctagagaac ctcctcctca   2760
accagctacg tacatagttt tatcctatgc attcctgttt tctgtgtgtt ttttgttttt    2820
tttttttttt tttttttttg agacagagtc tcgctctgtc acccaggctg gagtgcagtg   2880
gtgcgacctc agctcactga aacctctgcc tcccgggttc aagcgattct cctgcatcag   2940
cctcccgagt agctaggatt acaggcgccc gccactacgc ccagctaatt tgtggtattt   3000
ttagtagaga cagggtttca ccatgttggc caggctggtc tcgaactcct gacctcatga   3060
tccgcccgcc ttgacctccc aaagtgctgg gattacaggc atgagccacc gcacccagcc   3120
tgcattcctg ttttttttaat ggttttggag ggtagcagta gagatggggt ctcactatgt   3180
tgcccagtct agtcttgaac tcctgggcta cagttaccct cctacctcgg cttcccaaag   3240
tgctcggatt acaggtgtga gccactgtgc ctagcctata atgatcattt taatgtttcc   3300
```

```
catgcactca tttagtttga accttcacag caacccaatg aggtaatact cccatttcac    3360
atataatact gagagatgag ttgcacaaga ttatacactg ttaagtagca gagccagaat    3420
ggacttcaga atcccaacta caatacaaat gtttatttaa ataaagaaga aagctattgt    3480
acaaatatca ctcttcaggt ttagcttaca gagccatggc tatggattct tagctctgta    3540
aggaagtgct tctataaatt cttaggttta gagatgatac catctgggta cctttgcttg    3600
aaccgtgcaa ccacatctgg gtctagtagg tggatcccat ccagttggtt tccaagggtg    3660
atcctgaaac agtgtaaaag gaggggcaaa ccagaaatcc tggaattaga gggtttaata    3720
ttgttaaaaa atgcatacca aatgaagact gcctatcatc atatcaaata tgccaattct    3780
aaaaagagct taacattaga atagtatatg gtagaattac tagttcagaa ttggcataga    3840
ttctggtgtt aaaatagact ggatctgtat tatctgaggg ttagtaacta atgcttagcc    3900
aggcctgctt cacagagttg ctaccaggga gtattctttg gataagcaaa atgctagcag    3960
catgtgtttt aagctctgtt aaggggtgaa agatgtaatt attgacagat taaatagata    4020
acttcgtaac caccaggggg cagattcaat acatcacaga atggctgagg aagatccttg    4080
ggttgtgaag agagtagaaa ccctagggag cagtgctttt gggtcctaga acctgttgag    4140
tttctaatga atatttgtag aatctcataa aacagtttaa atacaagctt aagtggctta    4200
tgaatcctgt gaagctcatt tatggactag tgtaaaacaa tgtgaagctc tactaagttc    4260
tgtccttaat cataaataat agccccttga ggactagcct gttctctggt caccttacca    4320
gttgggttgc acattgtgtg gtcgtccaaa taactcaatc ttgcgagtgc aggagatag    4380 tctttcaatc atgccataga tttcatctgg tttatgactg gtggaacgaa cctaggaaat    4440
aaaaactagc tgcttttaa gttacacaag aaaaaa                              4476
```

<210> SEQ ID NO 28
<211> LENGTH: 4814
<212> TYPE: DNA
<213> ORGANISM: Homo sapiens

<400> SEQUENCE: 28

```
cttcgtgcca cgtcaccgcc tgcgtcgctt ccggaggcgc agcgggcgat gacgtagagg     60
gacgtgccct ctatatgagg ttggggagcg gctgagtcgg ccttttccgc ccgctccccc    120 ctcccccccga gcgccgctcc ggctgcaccg cgctcgctcc gagtttcagg ctcgtgctaa    180
gctagcgccg tcgtcgtctc ccttcagtcg ccatcatgat tatctaccgg gacctcatca    240
gccacgatga gatgttctcc gacatctaca agatccggga gatcgcggac gggttgtgcc    300
tggaggtgga ggggaagatg gtcagtagga cagaaggtaa cattgatgac tcgctcattg    360
gtggaaatgc ctccgctgaa ggccccgagg gcgaaggtac cgaaagcaca gtaatcactg    420
gtgtcgatat tgtcatgaac catcacctgc aggaaacaag tttcacaaaa gaagcctaca    480
agaagtacat caaagattac atgaaatcaa tcaagggaa acttgaagaa cagagaccag    540
aaagagtaaa acctttatg acaggggctg cagaacaaat caagcacatc cttgctaatt    600
tcaaaaacta ccagttcttt attggtgaaa acatgaatcc agatggcatg ttgctctat    660 tggactaccg tgaggatggt gtgacccat atatgatttt ctttaaggat ggtttagaaa    720
tggaaaaatg tgatgcaaaa gaaagaaatc cctgcgcttt ctgtctgtct ttgtggcggc    780
ccagattgaa ttggggaata catctttagc ctggaaatgt aggctgcatg ttaatggtaa    840
tgtaactttt gcagtgtaat gtttgaaaaa tattaatgta gttttgctt ttacagtaac    900
```

```
aaatgtggca attattttgg atctatcacc tgtcatcata actggcttct gcttgtcatc    960
cacacaacac caggacttaa gacaaatggg actgatgtca tcttgagctc ttcatttatt   1020
ttgactgtga tttatttgga gtggaggcat tgttttttaag aaaaacatgt catgtaggtt   1080
gtctaaaaat aaaatgcatt taaactcatt tgagagaatg ccttttagtt taatgcatat   1140
ttaaactaaa ttgatcctgt agtgttcctg gagaagctag agcctgattg taggctacta   1200
ctcatcaatt aacttctaca gtggagacta cttctgggac tggaatataa aaaagaatca   1260
aaggttctga ttttgagttg caataaaggg aaagaccatg ctcatagcag tgccaacatc   1320
tgaagtgtgg agccttaccc atttcatcac ctacaacgga agtagttaac tggaagagat   1380
taccaagaga ataaaagag actcattcag tggaagcaac tttgtctcag cttatttcac   1440
ataaagagag cgaagtcttt tgggatgaat gttaattaaa ctccctggta actagaacag   1500
ggactggcaa actagcctat ctgaccacct gttttgtaca cttaaggtg gttggttgcc    1560
tttttaaatg gttgagggga aagaatacc ttgtgggata tggaatttaa gttcgagtcc    1620
agttttattg gaacgtggct atgcttattc atttatggat tgactgtggc tgttgtcagt   1680
gcatgagcag agttgtgtct aacagactag agcctgcaag tttgccagcc cctgatttaa   1740
aagatgaagg tacacagaat gtgggctggc tggtgggcaa aggggtaaaa atgttctcta   1800
tattgtatct gaaagatgg ggtgtctgaa taagaaaatg catctatttg acagacctgg    1860
agcagttgct atctgctgct atggttcca ccacagatgc aagaagaaca tgtccttgcg    1920
cttccgtct gtctaattgt ggcagctgag attgaataga ggaatacagg aggaaaaaaa    1980
gcgggaagag tttttgaggc aggtcggtca cccaggcttg tagtgcagtg cacaagcaa    2040
ctcactgcat tctctgcatc ctgtgctcaa gccatttttcc cacctcagtc tcactagttg   2100
ctgggactgc aggcatgcac ccctatgccc agctaatttt tgtagagacc gagtatcgct   2160
tagttgccca gggtggtctc aactcctggg ctcaaggaga tctgcccacc tcagcctccc   2220
aaagtgcagg cctagcctgg gaggggaatt ttcaaaacgt gagttttggg aaatagtcta   2280
tcagccttac ctggttgatt acacttgtaa agaaagatt aaaagcaggc cagtgactct    2340
ggtctgcttg aacatgtgaa tgtagtggtt tgagcaatct ggagtttgcc ctagtgtcaa   2400
attccagact gtccatagtg tccaaaacct gaggcagata ctaatgttaa ccccagcac    2460
cccgtgattg gaaacaaacc taaatacgta ttgggaactt aatagcaatt ttaagcattc   2520
tgatagattt tttgtaggga tggggtcatg ccatgtggcc caggctggtc tgaaaactct   2580
ggcctcaagt gatctcaagc tttggccttc taaagtgttg ggattacagg tgtgaggcat   2640
tgcacctggc ttagcgttct gatttgacat tgtaatgaaa agtgtgagtc tcatctacag   2700
ggccttttgt cctctgaaat gatagcagga agggaattt caggcagtgg tcaaagctgg    2760
ggaaaccagg atagtgaaga aggccttgag gtgagagatg aagctaatt ggtgaactag    2820
ccttggaagc ctgaaacaga caagtagcaa ttcagagact ttgtgggctc cactgctcca   2880
acttgttttg aagattttca gttctgcaga agaggtattt ccccagttgt cctttcagtg   2940
ctcttagctg ttttcccaac atccagatcc aatcaaggct gggacatagc attttatcat   3000
gtctatttaa gtcagaagtg atgaaccca gctgtttacc tcatggtaaa cctttgaaga    3060
ttccaggtag aatcttctca gactttgaag actgtctcat tttatatctt tttctcgtta   3120
ttcctagggt caagacgttt tgggcaagaa taaggatgtg aacatcagaa agctcataac   3180
attttgtttt tgatgctaag tttaacaaag gcatgcttta gtagcctgtg ggccctaggg   3240
tttgttaaag tgtggagaac aactgagtgg agcaagagga cttttctagg aaggtccttg   3300
```

```
taatgtgaca tttgaaaaca aatgaaggtg tggaagtagg ccatgtggat atcaggacaa   3360
accattccag gccaagacaa cagcagttag tctggagtgt gatgtgttct gggaaaaaag   3420
tggccacttt gctaacccaa gaagacagga agggttgtaa agcagtggga gtgtgcaagg   3480
aaggaagacc agacctcaag gaaaccacag gcgctctgag cagaagagtt acatgatatg   3540
actcaaattt ttaaaggatc actttggctg ccaggtggca gggtaaaagc atagaataat   3600
tgtgtataat gtgttttttaa ggcaaagata gtggcttagt ctagggtagt agactgaggt   3660
ggtaggaaat gaagatagag acaacaggat atgctggtgg gtgaggatgg atttaatgtt   3720
gatacaagta ttttggtctg agcgtttgga agaaagttgg cactgaggtg ggaagtcgag   3780
tttagttttg ttagttttgg atgtgttaag tttgagatgc tgattcttca gagaagtcta   3840
agctggagaa ctatatagag agtggaaaga taacaataga cattgaaagc catgatacag   3900
gataaggtca tttggagaga ggatagactg cattccaaca tgagattggt tgacaaagag   3960
aaaccaacaa aggtaattaa gaggtgctcc cactgcactt gtactcagaa ggctgaggta   4020
ggattgttag aggccagcct gggcaccaca gggagacccc atctctaaaa tttagccagg   4080
aaccatggct catgcctgta gccccaggaa tttgggaggc tgagtgggga ggatcgcttg   4140
aggtcaggag tttgagacca gcctgggcaa catagggaga cctaaaaaaa ttaattgggc   4200
atctgtagtc ccagctactc aggcggctga gctgagagga tggcttgagt ccgagagatt   4260
gagggtgcag tgagctgtga tcataccact gcactccagc ctgggcggca gtgagacact   4320
atctgaaaaa agtttaaaaa ttttaaaaaa gaaggaactg cccctgaggt aagaaccaag   4380
ggagggcctc ccagaggtca ggtggaaaaa gttttaggaa ggaggaagta gtcaacaggg   4440
ttacctgttg caaagtactt aagtaatatg aggcctgata gtggtaaact tgactaccgt   4500
tggatttcac tagtgggaaa ggaagtctaa ttaaaatgca ctcaagagac taacagtcgc   4560
aggcatgaaa tacaatacag gtacatggtt ttttattatg tgtgcatctg cttcagtaat   4620
aggtgtgaat tactcatttg gatcattagg agtttcaaaa tctagttaaa tgactagatt   4680
tttgttgatg taaattctgt cattctgaac tgcagggatt gtcagtaact taactgcaaa   4740
ctaaactggt gataattatg gtaaaattgc aagacgagca ataaatctca accaacttga   4800
gagaacactg ataa                                                    4814
```

<210> SEQ ID NO 29
<211> LENGTH: 2914
<212> TYPE: DNA
<213> ORGANISM: Homo sapiens

<400> SEQUENCE: 29

```
gatttcagtt gaaagatgtg tttttgtgag tagagcaccg cagaagaact gaagactgtt     60
gtgtgctccc cgcagaaggg gctaccatga tcctttcctc ctataacacc atccagtcgg    120
ttttctgttg ctgctgttgc tgttcagtgc agaagcgaca aatgagaaca cagataagcc    180
tgagcacaga tgaagagctt ccagaaaaat acacccagcg tcgcaggccg tggctcagcc    240
aattgtcaaa taagaagcaa tccaacacgg gccgtgtgca gccgtcaaaa cgaaagccac    300
tgcctcccct cccaccctct gaggttgctg aagagaagat ccaagtcaag gcactttatg    360
attttctgcc cagagaaccc tgtaatttag ccttaaggag agcagaagaa tacctgatac    420
tggagaaata caatcctcac tggtggaagg caagagaccg tttggggaat gaaggcttaa    480
tcccaagcaa ctatgtgact gaaaacaaaa taactaattt agaaatatat gagtggtacc    540
```

```
atagaaacat taccagaaat caggcagaac atctattgag acaagagtct aaagaaggtg      600
catttattgt cagagattca agacatttag gatcctacac aatttccgta tttatgggag      660
ctagaagaag tacggaggct gccataaaac attatcagat aaaaaagaat gactcaggac      720
agtggtatgt ggctgaaaga cacgcctttc aatcaatccc tgagttaatc tggtatcacc      780
agcacaatgc agccggtctc atgactcgtc tccgatatcc agttgggctg atgggcagtt      840
gtttaccagc cacagctggg tttagctacg aaaagtggga gatagatcca tctgagttgg      900
cttttataaa ggagattgga agcggtcagt ttggagtggt ccatttaggt gaatggcggt      960
cacatatcca ggtagctatc aaggccatca atgaaggctc catgtctgaa gaggatttca     1020
ttgaagaggc caaagtgatg atgaaattat ctcattcaaa gctagtgcaa ctttatggag     1080
tctgtataca gcggaagccc ctttacattg tgacagagtt catggaaaat ggctgcctgc     1140
ttaactatct cagggagaat aaaggaaagc ttaggaagga aatgctactg agtgtatgcc     1200
aggatatatg tgaaggaatg gaatatctgc agaggaatgg ctatattcat agggatttgg     1260
cggcaaggaa ttgtttggtc agttcaacat gcatagtaaa aatttcagac tttggaatga     1320
caaggtacgt tttggatgat gagtatgtca gttcttttgg agccaagttc ccaatcaagt     1380
ggtcccctcc tgaagttttt cttttcaata agtacagcag taaatctgat gtctggtcat     1440
ttggagtttt aatgtgggaa gtttttacag aaggaaaaat gccttttgaa aataagtcaa     1500
atttgcaagt cgtggaagct atttctgaag gcttcaggct atatcgccct cacctggcac     1560
caatgtccat atatgaagtc atgtacagct gctggcatga gaaacctgaa ggccgcccta     1620
catttgccga gctgctgcgg gctgtcacag agattgcgga aacctggtga ccggaaacag     1680
aatgccaacc caaagagtca tcttgcaaaa ctgtcattta ttgtgaatat cttcaccata     1740
tggggtcact tatggtgaat atctttcttc agagttgctg actcttgaaa acagtgcaaa     1800
gatcacagtt tttaaaagtt ttaaaaattt aagaatattc acacaatcgt ttttctatgt     1860
gtgagaggga tttgcacact cttattttc tgtaaaatat ttcacatccc aaatgtgaag     1920
aagtgaaaaa gacttcgcag cagtcttcat tgtggtgctc ttcatgatca tagccccagg     1980
aacccttgag gttcttcttc acaaggctga gagtgcttcc ttcttgaaga cgagtgacat     2040
tcatcacttc agtgatccat gcatagaata tgaaaataaa ttcttccaac tcatgggata     2100
aaggggactc ccttgaagaa tttcatgttt tgggctgta tagctcttta cagaaaatgc     2160 accttttataa atcacatgaa tgttagtatt ctggaaatgt cttttgttaa tataatcttc     2220
ccatgttatt taacaaattg ttttttgcaca tatctgatta tattgaaagc agttttttgc     2280
attcgagttt taaacactgt tataaaatgt agccaaagct caccttttgaa cagatcccgg     2340 tgacattcta tttccaggaa aatccggaac ctgattttag ttctgtgatt ttacactttt     2400
tacatgtgag attggacagt tcagaggcc ttattttgtc atactaagtg tctcctgtaa      2460
ttttcaggaa gatgatttgt tcttcccaga agaggagaca aaagcaagat agccaaatgt     2520
gacatcaagc tccattgttt cggaaatcca ggattttgaa ttcgagatga acaaccagc     2580 aatcacagtt aaatcttaac tttgcctgca ctctttgtag gaatgatcag aaatttatct     2640
ttatcattct gagtgcttca ggagtacaat aggaagaaag atactggaga aagcactaat     2700
gtaatcacca tgaagtctga caacaggagc ccattatttg cgtactgtcc caccctgtat     2760
catggttctc tgggaacaag ctttatgatt ctcattagag tttatttgtt gattgtcagt     2820
agttgcgact tttaaattat atttcccca ctcaaagaat ggtatcttta tatatcaatg      2880
acattcaata aatgtgtatt atttctaatg agaa                                 2914
```

<210> SEQ ID NO 30
<211> LENGTH: 2741
<212> TYPE: DNA
<213> ORGANISM: Homo sapiens

<400> SEQUENCE: 30

```
attaaataag agaaaaaagc ataaaaggag taggcttttt tggcagatac tgttatatgg      60
gatggacagg aggggaagac atgaaaatca actaaaatga aatacataaa aaatcagtaa     120
agagcctgct tacgaaagtg gaaaaacaac agctgggcgg ggtcgcaggg tggcaaacgt     180
acgcgggcac gtgcacgtgc ttttggggcc gacagacgcg ccagttgcct aggcgcatgc     240
gtctggctat cccagaagca cctgcgcctt ccggctcgtg ctttcctcag tctcgcgcct     300
ttctctgcag ctcgcgcctt tctctgcagc tcgcgccttt ctctgcagct cgcgcctttc     360
tctgcagctc gcgcctttct ctgcagctcg ccccttcctc tgcagctcgc cccttcctct     420
gcagctccca cctcactccc ctcagcgttc tttttcccac ggtcttcccg ttgccgctaa     480
cctaactaac tctcagccat ggcctccaac gaagatttct ccatcacaca agacctggag     540
atcccggcag atattgtgga gctccacgac atcaatgtgg agccccttcc tatggaggac     600
attccgacgg aaagcgtcca gtacgaggat gtggatggca attggatcta cggtggccac     660
aaccatccgc cattgatggt gttgcagccg ctcttcacga acacgggcta tggcgaccac     720
gaccaggaaa tgcttatgtt gcagacacaa gaggaagtgg tgggctattg cgactcagac     780
aaccagctag gcaacgactt ggaggaccag ttggccctcc cggatagcat tgaagacgag     840
cacttccaga tgaccctggc ctctctgtcg gcctcggcgg catcaacatc aacatcaacc     900
cagagccgca gcaaaagcc cagcaaaaag cccagcggca agagtgccac cagcactgag     960
gccaacccgg caggcagcag ctccagcctg gcacgagga agtgggagca aagcaaatg    1020
caggtcaaaa cgctggaggg tgagttttcc gtgactatgt ggtcccctaa cgataacaat    1080
gaccaagggg cagtgggtga aggccaggct gaaaacccac ctgattattc cgagtacttg    1140
aaagggaaga aacttcctcc tggggggtta ccaggcattg atctctcaga tcctaaacag    1200
ctggcagaat ttactaaagt gaagcccaaa aggtccaaag gagaacctcc caaaacagtc    1260
ccttgctctt atagcggctg cgaaaagatg ttccgggatt acgccgccat gagaaaacat    1320
ctccacatcc acgggcccag agtccacgta tgtgcagaat gtggcaaagc ttttcttgag    1380
agctcaaagc tgagacgaca ccagctggtc cacaccggcg agaagccctt tcagtgcaca    1440
ttcgaaggct gcgggaaacg cttttccctt gatttcaatt tgcgcacaca cttgcgcatc    1500
cacaccggcg ataagccctt cgtgtgcccc ttcgatgttt gcaacaggaa gttcgctcag    1560
tcaaccaacc tgaaacccca catattaacg catgtgaaga ccaaaaacaa cccgtgaaaa    1620
ggagaagacc cctctcagac ttgggaatta tcttccagga ctgcggtagg gaataaatat    1680
gcctctcaaa gctttgtatg ttgtttctaa gagttttaaa aaaaaatgaa tcctgcacat    1740
ttaaggttcg tgttttgtta gagtagtaaa aatagaattt aaacgttttt aaaaaggtaa    1800
accttgacat aagataatag tgctaagatg ccatagcttg ttctgtaact atttttgtaa    1860
agtttggtcc caacaggaga aaaattcgta gacttcacat caagagacgg ttcttacaaa    1920
ctgtttaaaa tgggactttt cacattctta gaaataggaa gttcatttat tgtttacaat    1980
gttttttaaa aacttgttaa aaaattcaaa gtgttcatgt ttatactttt aggaatatgc    2040
ttaataagtc tatgtatggt ttttctggag gttgataact ttgggaaaga tttactttaa    2100
```

| | |
|---|---|
| aagagtgaac aattatatgc atacgtgaag tattttcctg cttaaaaaag ttatataggt | 2160 |
| gttatttgtt ttaatcttgg ttgtagtctt ggatgttaac acatcttgca ttttagctgt | 2220 |
| attaggtcat gtagtattga tattaggtga tttaatagta ctagtttaaa cctattttag | 2280 |
| tcattttatt ttccccaaaa tactaccaga tgctgttgtt tagtgtaatt tctttgcctg | 2340 |
| ttcagttaaa gtagtgcttg cttgtagaat atattgtgta tatgttgact ttaacactta | 2400 |
| agaagtacat cctgtgtaat agaaaaagca aaataaaaca cctcttctaa agaaggaaaa | 2460 |
| aagtagtttg cctatatcag tacagaagtt agaactaaag aaaaggggga gggtgctact | 2520 |
| ggcatctggt gagtggaggg agatcaggaa tgccactaaa catcctacaa tgcacagaca | 2580 |
| gccccacgaa acacataatt atttggctaa aatgccaata gtgtcaggtg caggggctca | 2640 |
| ggcctgtaat gtcaacactt tgggaggccg aggtgggtgg atcgtttgag ctcaggaatt | 2700 |
| gaacatcagc ctgggcaaca tggcataact cggtctctac c | 2741 |

<210> SEQ ID NO 31
<211> LENGTH: 6137
<212> TYPE: DNA
<213> ORGANISM: Homo sapiens

<400> SEQUENCE: 31

| | |
|---|---|
| gtcttttgtc cctcggcgga caccgtttgc cagccaaagc tatgtctgcg cgctcaccga | 60 |
| cttcataggg tgccgaattc tttttttccc aggcttgcca tggctagtcg aggggctcgg | 120 |
| cagcgcctga agggcagcgg ggccagcagt ggggatacgg ccccggctgc ggacaagctg | 180 |
| cgggagctgc tgggcagccg agaggcgggc ggcgcggagc accggaccga gttatctggg | 240 |
| aacaaagcag gacaagtctg ggcacctgaa ggatctactg ctttcaagtg tctgctttca | 300 |
| gcaaggttat gtgctgctct cctgagcaac atctctgact gtgatgaaac attcaactac | 360 |
| tgggagccaa cacactacct catctatggg gaagggtttc agacttggga atattcccca | 420 |
| gcatatgcca ttcgctccta tgcttacctg ttgcttcatg cctggccagc tgcatttcat | 480 |
| gcaagaattc tacaaactaa taagattctt gtgttttact ttttgcgatg tcttctggct | 540 |
| tttgtgagct gtatttgtga actttacttt tacaaggctg tgtgcaagaa gtttgggttg | 600 |
| cacgtgagtc gaatgatgct agccttcttg gttctcagca ctggcatgtt ttgctcatca | 660 |
| tcagcattcc ttcctagtag cttctgtatg tacactacgt tgatagccat gactggatgg | 720 |
| tatatggaca agacttccat tgctgtgctg ggagtagcag ctggggctat cttaggctgg | 780 |
| ccattcagtg cagctcttgg tttacccatt gcctttgatt tgctggtcat gaaacacagg | 840 |
| tggaagagtt tctttcattg gtcgctgatg gccctcatac tatttctggt gcctgtggtg | 900 |
| gtcattgaca gctactatta tgggaagttg gtgattgcac cactcaacat tgttttgtat | 960 |
| aatgtctttta ctcctcatgg acctgatctt tatggtacag aaccctggta tttctattta | 1020 |
| attaatggat ttctgaattt caatgtagcc tttgctttgg ctctcctagt cctaccactg | 1080 |
| acttctctta tggaatacct gctgcagaga tttcatgttc agaatttagg ccacccgtat | 1140 |
| tggcttacct tggctccaat gtatatttgg tttataattt tcttcatcca gcctcacaaa | 1200 |
| gaggagagat ttcttttccc tgtgtatcca cttatatgtc tctgtggcgc tgtggctctc | 1260 |
| tctgcacttc agaaatgtta ccactttgtg tttcaacgat atcgcctgga gcactatact | 1320 |
| gtgacatcga attggctgga attaggaact gtcttcctgt ttgggctctt gtcatttttct | 1380 |
| cgctctgtgg cactgttcag aggatatcac gggccccttg atttgtatcc agaatttttac | 1440 |
| cgaattgcta cagacccaac catccacact gtcccagaag gcagacctgt gaatgtctgt | 1500 |

```
gtgggaaaag agtggtatcg atttcccagc agcttccttc ttcctgacaa ttggcagctt    1560
cagttcattc catcagagtt cagaggtcag ttaccaaaac cttttgcaga aggacctctg    1620
gccacccgga ttgttcctac tgacatgaat gaccagaatc tagaagagcc atccagatat    1680
attgatatca gtaaatgcca ttatttagtg gatttggaca ccatgagaga aacacccgg     1740 gagccaaaat attcatccaa taaagaagaa tggatcagct tggcctatag accattcctt    1800
gatgcttcta gatcttcaaa gctgctgcgg gcattctatg tccccttcct gtcagatcag    1860
tatacagtgt acgtaaacta caccatcctc aaaccccgga agcaaagca aatcaggaag     1920 aaaagtggag gttagcaaca cacctgtggc cccaaaggac aaccatcttg ttaactattg    1980
attccagtga cctgactccc tgcaagtcat cgcctgtaac atttgtaata aggtcttct     2040 gacatgaata ctggaatctg ggtgctctgg gctagtcaaa gtctatttca aagtctaatc    2100
aaagtcacat ttgctccctg tgtgtgtctc tgttctgcat gtaaactttt tgcagctagg    2160
cagagaaagg ccctaaagca cagatagata tattgctcca catctcattg ttttcctct    2220 gttcaattat ttactagacc ggagaagagc agaaccaact tacaggaaga attgaaaatc    2280
ctggtactgg atggctgtga taagctgttc tccacactct ggcctggcat ctgagaacta    2340
gcaagcctct cttaggccat atgggcttct ccaccaaagc tgtttggcag ctcctagcag    2400
accttcttat tgaaatcctc atgctgaaaa tgaacacagc ctagttgcca acccacatgt    2460
ccttttcacc tccagcaaga ctaagcttct ttaaagcact tcacaggact aggaccctgt    2520
cctggagcta tctcaggaaa aaggtgacca tttgaggaac tgtgacctaa ttttattata    2580
atgatgcctc taattttcat ttcctttaca accaactgta actataaggt tgtattgctt    2640
ttttgttcag tttagcatg ctatttttg aattctagac tcctccatgt gaagatatca     2700
acagacaaaa ctacaactgt ataggacata tttggagaaa attctatcaa ttgatacatt    2760
tggatgacat cacatttta agtaatgtaa tctgaggcca ttgctgagga aattaagaat     2820
tttccttttt ttttaaccac ccccagtgaa aaggatcagt gtatatttat agcacctatt    2880
ttttagttct gtctgttgtg aggcacatcc tgcatgggc acttctagtc aaataggcaa     2940
tgataaggac ctaattaaaa tgtgataagt gtatactatt actttaaaag cctttacagt    3000
cagtacttca gttacaagg cactttcaca gcatctcgtt tgatcctcac agtcacaaca     3060
tgtggtagac aaggcaggtg attttatcc ccatttaca gataaggaa caggctgcgg      3120 gtggggagtg agggaggta agatagtta gttgcctaag gtcacacagc cagtaagtaa     3180
tagagctggg actggaaccc aggtttcctt actctcatct attgctcctc catattcctc    3240
actcaaccat gaaaacatta cttgaaagga ctgatgaggt taaccagaga cctaactgat    3300
attgtaactt tctattttaa ggaagaattg tgtctgtatt tgagttcttt ggagcctcca    3360
gtctgcctgt gtgttagacc agcacagcag tgctgtgtga tgcagcctga cctgtggcag    3420
gaaagtagtg cttctgttg gaagtcatgt tcttttgcag ccacacagga tccaaatatc     3480
agtactattc ctgtagtcaa tctggggtca cattataggt gccttatttc cctaagggta    3540
actgatctga atatctgcaa ataggatgaa tctatttttc agaagttcca tctttcattt    3600 ttctttttt ttttgagaca gagtctcatt ctgtcgccca tgctggagtg cagtggcgcg     3660
atctcggctc gctgcaacct ctgcctccca ggttgaagca attctcatgc ctcagccacc    3720
cgagtagctg ggattacagg catgcgccat catgcccagc taatttatgt attttttagta   3780 gagttggagt ttcaccatgt tggccaggct ggtcttggac tcctgacctc aggtcatcca    3840
```

```
cccgcctcag cctcccaaag tgctggtatt acaggcgtga gccaccgcac ccagccccat      3900
ctttcatttt caaagagaag ggcattctaa taggaactgg tgccaagaga aagaaaaga      3960
agtgataaca gaagaaatgg ctagttacaa tattaaaaag ctcctctttg agatctcctc      4020
tgcaggaata tcagagacgg agttgaagcg ctggagaggt aataggtcta gacagtacag      4080
aacaataact ggggagtgtg tgaggataga ctgggctccc ccttgcttga aagatctctg      4140
gcatttaatt ctcaattctt gattactatt ttccagtgta aaactagcac atatgatctg      4200
actacaggac agagaatttt aagtgaaaca tttgccttac ttgcagtaat aatgtgctgt      4260
tcttcacagt agctaaggcc ctctatgttt cccagaggta aataagaatc caggaatgga      4320
ggtccatctg tgatgaatgg cttttttcta atcaaagtag tataatgctg ttttatctgt      4380
tttgtcatct tgttttttt tttttttaaa aaacaaaac cttaattata atatagcgca       4440
aagaaaggcc aggactgatg cagggattcc ttggaaatat cagttcctat cacttttaaa      4500
acctgatttt ggatctctct gttctatgta tgtctttagt gagagcacaa tacatggcag      4560
aacgctgtgc caaatgttat aggtaaggaa tatagaaatg aatgttttt gttgtgaagg       4620
tgttttcatg tgatattta taaacacatt ttaaaaaatc tccatcactt tttagtatag       4680
gaaggatagc tttgcctggg aaaaacagtt tcaacacacc tgctcagagt agcagttctc      4740
cctcaaaaaa gcagtgttca gcctgcactg actgttctgc ttgccaaaag gaggaagcat      4800
gcaagatact tatttctcca tagattgtgg agtatagagg gatgtgggac tacagattat      4860
tattttttt ccccgagaca gagtcttgct ctgtcgccca ggttggaaca caatggcacg       4920
acctcagctc actgcaacct ctgtctcccg ggttcaagca attctcctgc ttcagcctcc      4980
tgagtagctg ggattacagg cacacaccac caccgcactc agctaatttt tgtattttta      5040
gtagaggtgg ggttttacca tgttggccag gctggtctta aactcctgac cttgtaatca      5100
tcccgcctcg gcctcctaaa gtgctaggat tacaggcatg agccaccgca cccggcccag      5160
ataattttta atagcctttg atcatggggt gagtgaggga gtaggtatac ttggcaaatg      5220
catggttctc tgatttctag ctctaaagca gccttatctg aatccccaaa tcttgtgatg      5280
ctgagtacca ttactgaacc agtctgcacg gtaggcatct gctaccaaaa tttacctcct      5340
acctggtagg tgtcatctga taagaaagaa gacaggttat tttaattttt tgagataatc      5400
acagaaaatt gcagcccata ctctttatta ccgaattcaa gtttggaaat agaccctttg      5460
ttttaaatca tgatgggtct ttatcccaat catttatctg ggtcattttt ccaactttgg      5520
agttctagga aagaaccttg aaaacctgat atgattctgc agcatgaggt ctacggtgac      5580
catttgggca aagctccagt ggcaatcatt tattgtgttt tgcatttcct gggatttatt      5640
gaaataagaa ttcactgtga ttatgtagtc ttctggctag tatcaggcag ctctgctttt      5700
aatttggtta attttatttt ctctgaagag ggagaagagg tacaatttaa tcttggcctc      5760
cacaagcata ttaaagctca cgtgttaatc agtgcattct tatgctccta cattaaatgc      5820
cttgggtaaa tggataaatg gacatgtgcc cagctttaat ttttttgca acagaaagat       5880
cagacttccg tatggcatcg ttggatttca gaggctttct ggtgtatctg taaatctgaa      5940
tgttgccttc tgccagtctg tataaccagg tgattcatgc tgcaaatgaa atcaggaagc      6000
agtaaagtgt taaagcaaga gtattgtcca attcacttgt cttcctgatc cttgtacttt      6060
atttcacgtg tcggtgttta cattacatac ttatatttcc tgtgaaagaa agagttaaat      6120
aaattgtagc agtttga                                                    6137
```

<210> SEQ ID NO 32
<211> LENGTH: 3531
<212> TYPE: DNA
<213> ORGANISM: Homo sapiens

<400> SEQUENCE: 32

| | | | | | |
|---|---|---|---|---|---|
| agcggagcgc | caggcagcgc | ggagcggagg | ccaggcccac | agccgctccg | cctcccggcc | 60 |
| cgcagatccc | cgacggccgc | accgcgggct | cctctggccc | gcaagaacac | gtgcatggcg | 120 |
| tcctggggaa | ggcgctgagt | gcggagtcgc | ggcgccgcac | gcggcaccat | ggccctggag | 180 |
| caggcgctgc | aggcggcgcg | gcagggcgag | ctggacgtgc | tgaggtcgct | gcacgccgca | 240 |
| ggcctcctgg | ggccctcgct | gcgcgacccg | ctggacgcgc | tgcccgtgca | ccacgcggcc | 300 |
| cgcgctggga | agctgcactg | tctgcgcttc | ctggtggagg | aagccgccct | cccgccgcg | 360 |
| gcccgcgccc | gcaacggcgc | cacaccggcc | cacgacgcct | ccgccaccgg | ccacctcgcc | 420 |
| tgcctgcagt | ggctgctgtc | gcagggcggc | tgcagagtgc | aggacaaaga | caattctggt | 480 |
| gccacagtct | tgcatctggc | tgcccgcttc | ggccaccccg | aggtggtgaa | ctggctcttg | 540 |
| catcatggcg | gtggggaccc | caccgcggcc | acagacatgg | gcgccctgcc | tatccactac | 600 |
| gctgccgcca | aaggagactt | cccctccctg | aggcttctcg | tcgagcacta | ccctgaggga | 660 |
| gtgaatgccc | aaaccaagaa | cggtgccacg | cccctgtacc | tggcgtgcca | ggagggccac | 720 |
| ctggaggtga | cccagtacct | ggtgcaggaa | tgcggcgcag | acccgcacgc | gcgcgcccac | 780 |
| gacggcatga | ccccgctgca | cgccgcggcg | cagatgggcc | acagcccagt | catcgtgtgg | 840 |
| ttggtgagct | gcaccgacgt | gagcctgtcc | gagcaggaca | agacggcgc | caccgccatg | 900 |
| cacttcgcgg | cgagccgcgg | ccacaccaag | gtgctcagct | ggctgctgct | gcacggcggg | 960 |
| gagatctcgg | ctgacctgtg | ggcgggacc | ccgctgcacg | acgccgccga | gaacggggag | 1020 |
| ctagagtgct | gccagatcct | ggtagtgaac | ggcgcggagc | tggacgtccg | cgaccgcgac | 1080 |
| gggtacacgg | ccgccgacct | gtcggacttc | aacggccaca | gccactgcac | ccgctacctg | 1140 |
| cgcacggtgg | agaacctgag | cgtggagcac | cgcgtgcttt | cccgggatcc | atccgcagag | 1200 |
| ctggaggcta | agcagccgga | ttcaggcatg | tcctcaccca | ataccacggt | gtcggtccag | 1260 |
| ccgctgaact | ttgacctcag | ctcgcctacc | agcaccctct | ccaactacga | ctcctgctcc | 1320 |
| tccagccact | ccagcatcaa | gggccagcac | cctccatgtg | ggctttccag | cgctagagct | 1380 |
| gcagacatac | agagctacat | ggacatgctg | aacccggagc | tgggcctgcc | tcggggcacg | 1440 |
| attgggaagc | ccacaccccc | accacccca | cccagcttcc | cccgccacc | cccgcccca | 1500 |
| ggcacccaac | tgcccccacc | cccacctggc | tacccagctc | ccaagcctcc | tgtaggacca | 1560 |
| caggcagctg | acatctacat | gcagaccaag | aacaaactcc | gccacgtgga | gacagaggcc | 1620 |
| ctcaagaagg | agctgagctc | ctgtgacggc | cacgacgggc | tgcggaggca | ggactccagc | 1680 |
| cgcaagcccc | gcgccttcag | caagcagccc | agcacggggg | actactaccg | gcagctgggc | 1740 |
| cgctgccccg | gcgagacgct | ggccgcacgc | ccgggcatgg | cgcacagcga | ggaggtgcgt | 1800 |
| gcccgccagc | ccgcgcgcgc | cggctgcccg | cgcctcggcc | ctgccgcccg | cggctcactc | 1860 |
| gaaggcccct | ccgctcccc | gcaggcggcg | ctgcttcctg | ggaaccatgt | tcctaacggc | 1920 |
| tgcgccgcga | ccccaaggc | gtccagggag | ctgccaccgc | cgccccacc | gccgcgccg | 1980 |
| ccctgccgg | aggccgcgag | ttcgccaccg | ccggccccgc | ctctgcccct | cgagagcgct | 2040 |
| ggccctggct | gcgggcagcg | ccgctcctcc | tcgtccaccg | gcagcaccaa | gtctttcaac | 2100 |
| atgatgtccc | cgacgggcga | caactcggag | ctactggctg | agattaaggc | aggcaagagc | 2160 |

| | |
|---|---|
| ctgaagccga cgccccagag caaggggctg accacagtgt tctcaggcat cgggcagccg | 2220 |
| gccttccagc ccgattcgcc gctgccttct gtgtcacctg cactgtcacc agtccggagc | 2280 |
| cccacaccgc cagctgcggg gtttcagccg ctgctcaatg gaagcttggt tcccgtgccg | 2340 |
| cccactactc ctgcgccggg agtgcagctg gacgtggagg ctctcatccc cacgcacgat | 2400 |
| gagcagggcc ggcccatccc cgagtggaag cgccaggtga tggtgcgcaa gatgcagctg | 2460 |
| aagatgcagg aggaggagga gcagaggcgg aaggaggagg aggaggaggc ccggctggcc | 2520 |
| agcatgcccg cctggaggcg ggacctcctg cggaagaagc tggaagaaga gagggagcag | 2580 |
| aagcggaaag aggaggagcg acagaagcag gaggagctgc ggcgggagaa ggaacagtca | 2640 |
| gagaagctgc ggacgctggg ctacgatgag agcaagctgg cgccctggca gcgacaggtc | 2700 |
| atcctgaaga aggggggacat cgctaagtac tagaggccgc agactcctgt ccgcagcctc | 2760 |
| gcagctccgt ggggccctcc gccccagccc cagccagcca ggccctggtg aaaggctgg | 2820 |
| gagccgcaca gccctcccct cctgcgctgg aaaccctccc tgaccccac cctggccccc | 2880 |
| cgtatcccca gcccttggca acactggagt gcacacgccg ccacggttgc ccagaaaaag | 2940 |
| tgcccaagct gctgacgcaa acaacaacaa atgctgctta tttgcatgcc gacttacata | 3000 |
| tatttgcatg ttcgttgact atcaaagagt gcagagctct ccccagcccc gtgggtggtg | 3060 |
| actttgttttt cctgcggggc tcagccccct ccaggatgca gccccctccc ccgcaccccg | 3120 |
| gaaccggcgt cgctggcgca tcctgggtgg aggcaggccc cgagctcggg gaaggggttt | 3180 |
| tcccttcctc tctgacccag atctgcgcgc ggcctagccc gggcctcatt tcttatcccc | 3240 |
| gccaagggtt tcctctcagt catttgttta ccagaaacat gaaaactgcc tgtctggccg | 3300 |
| ggccgcactt gtggccccg ggaccccacc tctggcccca cctccctcaa gtctgcgccc | 3360 |
| cgtccccagc cagacccact cgctgccggg acccttcac tgccccggtg gagtgaatag | 3420 |
| aggatgaggg gccctgaccc tgtgtctcca actgctgcac cccatcccga ccctgtctcc | 3480 |
| gccacctcgc agccccatta aagcgctctc atctgggctc cggttcactc a | 3531 |

<210> SEQ ID NO 33
<211> LENGTH: 2272
<212> TYPE: DNA
<213> ORGANISM: Homo sapiens

<400> SEQUENCE: 33

| | |
|---|---|
| ttgggcggtg gaccgcccct cggccccggg gtaggctgac acgggagggt cctcagctaa | 60 |
| agccaaaagc agatcaaagt ggtgggactc gcgtcgcggc cgcggagacg tgaagctctc | 120 |
| gaggctcctc ccgctgcggg tcggcgctcg ccctcgctct cctcgccctc cgccccggcc | 180 |
| ccggccccgc gcccgccatg gagaagactg agctgatcca gaaggccaag ctggccgagc | 240 |
| aggccgagcg ctacgacgac atggccacct gcatgaaggc agtgaccgag cagggcgccg | 300 |
| agctgtccaa cgaggagcgc aacctgctct cgtggcccta caagaacgtg gtcgggggcc | 360 |
| gcaggtccgc ctggagggtc atctctagca tcgagcagaa gaccgacacc tccgacaaga | 420 |
| agttgcagct gattaaggac tatcgggaga agtggagtc cgagctgaga tccatctgca | 480 |
| ccacggtgct ggaattgttg gataaatatt taatagccaa tgcaactaat ccagagagta | 540 |
| aggtcttcta tctgaaaatg aagggtgatt acttccggta ccttgctgaa gttgcgtgtg | 600 |
| gtgatgatcg aaaacaaacg atagataatt cccaaggagc ttaccaagag gcatttgata | 660 |
| taagcaagaa agagatgcaa cccacacacc caatccgcct ggggcttgct cttaactttt | 720 |
| ctgtatttta ctatgagatt cttaataacc cagagcttgc ctgcacgctg gctaaaacgg | 780 |

```
cttttgatga ggccattgct gaacttgata cactgaatga agactcatac aaagacagca      840
ccctcatcat gcagttgctt agagacaacc taacactttg acatcagac agtgcaggag       900 aagaatgtga tgcggcagaa ggggctgaaa actaaatcca tacagggtgt catccttctt      960
tccttcaaga aaccttttta cacatctcca ttccttattc cacttggatt tcctatagca     1020
aagaaaccca ttcatgtgta tggaatcaac tgtttatagt cttttcacac tgcagctttg     1080
ggaaaacttc attccttgat ttgtgtttgt cttggccttc ctggtgtgca gtactgctgt     1140
agaaaagtat taatagcttc atttcatata aacataagta actcccaaac acttatgtag     1200
aggactaaaa atgtatctgg tatttaagta atctgaacca gttctgcaag tgactgtgtt     1260
ttgtattact gtgaaaataa gaaaatgtag ttaattacaa tttaaagagt attccacata     1320
acttcttaat ttctacattc cctcccttac tcttcggggg tttcctttca gtaagcaact     1380
tttccatgct cttaatgtat tcctttttag taggaatccg gaagtattag attgaatgga     1440
aaagcacttg ccatctctgt ctaggggtca caaattgaaa tggctcctgt atcacatacg     1500
gaggtcttgt gtatctgtgg caacagggag tttccttatt cactctttat ttgctgctgt     1560
ttaagttgcc aacctcccct cccaataaaa attcacttac acctcctgcc tttgtagttc     1620
tggtattcac tttactatgt gatagaagta gcatgttgct gccagaatac aagcattgct     1680
tttggcaaat taaagtgcat gtcatttctt aatacactag aaaggggaaa taaattaaag     1740
tacacaagtc caagtctaaa actttagtac ttttccatgc agatttgtgc acatgtgaga     1800
gggtgtccag tttgtctagt gattgttatt tagagagttg gaccactatt gtgtgttgct     1860
aatcattgac tgtagtccca aaaaagcctt gtgaaaatgt tatgccctat gtaacagcag     1920
agtaacataa aataaagta catttttataa accatttact atggctttgt aacaattgca     1980
tacccatatt ttaagggaca ggtgaattta ctactttcta aagtttattg atacttccct     2040
tttatgtaaa atgtagtagt gatacctata tttccacatt gtgcattgtg acacacttgt     2100
ctagggatgc ctggaagtgt ataaaattgg actgcatttc ttagagtgtt ttactataga     2160
tcagtctcat gggccatctc ttcctcagat gtaaatgata tctggttaag tgttatatgg     2220
aataaagtgg acatttttaaa actagcaaag ttaaaaaaaa aaaaaaaaa aa             2272
```

<210> SEQ ID NO 34
<211> LENGTH: 4510
<212> TYPE: DNA
<213> ORGANISM: Homo sapiens

<400> SEQUENCE: 34

```
gcagagggggg cggagagcgc ccccgggggc ggggcacgca agtgacggcg gcgcgggtgg       60
tggagcgctg ggcggccagg ctccctggct ggccggtttg ggcgtctggg ccgtgaaggt      120
gggacctcct gttccgggcc gcaagtttcc ctctccagcc gcccgccgtt cgtagcatgt      180
cccccagaac tcggggagcg caggcaggac aggcttagag aagacgcggt ccccagcgct      240
tgggccacgg acgtcccacc ccgctcctct gtcgctggag aaccgccggg ccgagccact      300
gggagaagca ggccagagcc ttccaggggc tccggcccgt ggaccccgagg aggatgagct     360 ggcttttttcc cctgaccaag agcgcctcct cctccgcggc tgggtccccc ggtggcctca    420
ccagcctcca gcagcagaag cagcgcctga tcgagtccct ccggaactca cactccagat    480
tgcttcctcc acagtttcct caggaaaaac cagtgatcag tgtttatcca ccaatacgac    540
atcacttaat ggataaacaa ggagtgtatg ttacctctcc attagtaaac aattttacaa     600
```

```
tgcactcaga tcttggaaaa attattcaga gtctgttgga tgagttttgg aagaatcctc    660
cagttttagc tcctacttca acagcatttc cttatctata cagtaaccca agtgggatgt    720
ctccttatgc ttctcagggt tttccatttc ttcctccata tcctccacaa gaagcaaaca    780
ggagtatcac ttctttatct gttgctgaca ctgtttcttc ttcaacaaca agtcatacca    840
cagccaagcc tgccgctcct tcatttggtg tcctttcaaa tctgccatta cccattccca    900
cagtggatgc ttcaataccg acaagccaaa atggttttgg gtacaagatg ccagatgtcc    960
ctgatgcatt tccagaactc tcagaactaa gtgtgtcaca actcacagat atgaatgaac   1020
aagaggaggt attactagaa cagtttctga ctttgcctca actaaaacaa attattaccg   1080
acaaagatga cttagtaaaa agtattgagg aactagcaag aaaaaatctc cttttggagc   1140
ccagcttgga agccaaaaga caaactgttt tagataagta tgaattactt acacagatga   1200
agtccacttt cgaaaagaag atgcaaaggc agcatgaact tagtgagagc tgtagtgcaa   1260
gtgcccttca ggcaagattg aaagtagctg cacatgaagc tgaggaagaa tctgataata   1320
ttgcagaaga cttcttggag ggaaagatgg aaatagatga ttttctcagt agcttcatgg   1380
aaaagagaac aatttgccac tgtagaagag ccaaggaaga gaaacttcag caggcgatag   1440
caatgcacag ccaatttcat gctccactat agattttcct ggaaacatga actgccaaga   1500
gaggaatggg acacaaaacc aaacactgtt ttatatttat ggtttgcaaa ctggcatttc   1560
atcagtggct aaattcacag atatcctata tagattgtat acagaactga gactgatttt   1620
gtaccgatta aatgattgc tatgatcttt gagaaatttt tctgcactat ttgcactgaa   1680
atgtttattt attgttgata aattgtatca tatttaagtt ccactgctgt tcctcttacc   1740
ttgattaaat gcctatgcat gtacttttag ctagttttta atatttata aaacttcatt   1800 taaatttgta ttttttaactt gaagttccat ttctttatca aggatggtat ttagattttt   1860
ttcctcttaa cctttttttca aaactatttt tcaactgtga ggaaacccctt attttctttt  1920 ctttgtggat aaaactttca aaagcaattt aagatattca tagtgttagg aaacaccaaa   1980
cctgcctatg tgccatctca caaagaaac ttttaatacc tacaataaat caaaagaata    2040
aaccagctgt tctatatat tgtttcattt ttaaaactaa agatgcattt aagaagcaat    2100
acaagtaaat attttaccta ataggaaaaa aaaagttgc ctttcattta aaccattcca    2160
acagaaattc ttatgctaat ttaaaacata tatatatctg gtaggtttgt ggttggatag   2220
gttttctaaa ttcctaatgt taaaaacaat ctttatgtta atatacacta aatctataca   2280 caaaaaagt cagtgaactt ttctgacctt tactgtgagt tacctttttcc taagaggaaa   2340 gctatagtaa taagtaaaat ttaatttta ggcaatcctg atttttaatg aatttaattg    2400
agtgttcttg tatactacat tgagcagttt gcttctatac cgtgtcacaa aattcatgta   2460
tttcttgaga agccctaaaa gctcataaag gaaaatgccg tgaactatgt agctcaggct   2520
tggtaaggtg ccatctaaat tacaaaacaa actaatgcat aattttgctt aaatttcatc   2580
ccagtatgat tgtcttccca acaccagcat atagtataga ttgtctgtct tttttatatt   2640
ttttagttct tcctgtacat gttttttggca ataaagttat aggaagaaca aaattatttt   2700
gttagaatta aaacatgctt aatatttagt ctgtttgtgg agggcaggta ttcacgtgga   2760
ctgagataca atgttggata cagaaaataa ctttcattgt cttcctgaca ctgtgctaag   2820
gacatgctgt taaagcttca aagtgaccag atgaggaagg aataattaat tattactcct   2880
gatttgtaga taactgaggt aagagtgttt caaatttatg atagtctttt gggtattcag   2940
aaacctttcc ttatactgca ctggccacca gagcttaatt ttcccagcag ttacagcaat   3000
```

```
gggagataga acagtctcaa tcttttgcca accatcaggt tcctagaaac caggtaggtg    3060
tatcccataa caagggagga gcataccaca gcccctcatt tgattaattc atttgatcta    3120
tctatgttat taagtaccta ctaggaataa ggcattgtgg aaatactata caaagataaa    3180
cattgtttag atgcttatct actttccttt tcaccagaaa aacagaaaaa aaagaaacat    3240
tttcttacag agtaaaaatg ttctacataa tcacatgagt agttcatctc agtgtttttt    3300
attctttaaa gttgaactat cccagtttca ttctatacca ttcattggat aaccttgtta    3360
caacccagtc atgaaacaga gcagtgtgat cagttatctg catttaacaa atagacaaat    3420
cagtttacat aaaggttatg tatgtcaccc acgatgaaaa gaatctgcat ttgaatatgc    3480
ccgtatgaat gtgggttctg ttttttgcaac agagattaag tgaccatttt ttctaatttt    3540
atggctatat attttcttca taaaaattgg tcacatcgga gaagcagtgc cacaggaaaa    3600
atgaaatgca tgtgaaagtt tgtattctga ttttacaaga tgagatagaa atcagaatta    3660
aagaggaata cttaggagtt actaggctaa tcagtgtacg aatttgtcat aggtagagat    3720
ttaaaggtta atatcttaaa atagaagaaa attctaaatc aatcaatcag tgagatataa    3780
actaaacaga cccacttcaa agttgaaaga aatttctagg cataaattga gactaggaaa    3840
tttatatcag aatagagggt gcttgacaca tatatatgct taaattgaag gacagctcag    3900
attcattttt aggagaagaa agtaaactaa tgtgctctta aagaataaaa atttattcta    3960
tggtttctgt ctctgatcat caccttccat tctataaaaa gctcagttac tgatttgctg    4020
ggtcatggtc aaaattctta cctatttatt tcatatcaac tttaaaaaat aaattacttg    4080
cattctatat attactaatt gggaagtaat atgcctcaaa tcagttttat actggattat    4140
tccctatgct ttaaaccact gctctcaata aaacacttcc tgattaatgt ttgattatta    4200 gatatttag tcttgttggg gatattttag tcttgttggg ttagccatgc tctgaagaat    4260
ctgtgaaagt acagtaaagt tttaataagc aataaatgta accttttata taaatctcag    4320
tgctaggtta acttctaata agcagacgaa catgttacat aaattataat gtctgtcttg    4380
taaaaaagtt gagggggacta aaagtttatg actctgatat ggaagttgtc atattaaaaa    4440
actacatttt aaaacatcaa atatttatac tatttgcttt tcaaataaaa gcatagtgct    4500
gtttggcata                                                           4510
```

<210> SEQ ID NO 35
<211> LENGTH: 11062
<212> TYPE: DNA
<213> ORGANISM: Homo sapiens

<400> SEQUENCE: 35

```
gcagatcggg agcggtgccg agaaaaattt ccttactaga tgacatttca tcgcaatgtc      60
cgatcgtttg gggcaaatta ccaagggcaa ggatgggaaa agcaagtact cgactctcag     120
cctgtttgat aagtataaag gaaaatcagt agacgcgatt agatcctcag ttattcctag     180
acatggctta cagagtcttg ggaaagttgc tgcagcccgg cgcatgccac cgcctgcaaa     240
cctgccaagc ttgaagtctg aaaacaaagg aaacgacccc aacatcgtga tagtaccccaa    300 ggacgggacg ggatgggcaa acaagcagga tcagcaagac ccaaagagtt ccagtgcgac     360
ggcctctcag ccgccggagt cgctgccgca gccgggtttg cagaaatctg tctccaattt     420
gcagaaaccg acacagtcaa tcagtcagga gaatacaaat tcagtgccag gtggaccaaa     480
gtcatgggca cagctgaatg gaaagccagt aggacacgaa ggtggtttaa ggggctcaag     540
```

```
ccgactgtta tccttctctc ccgaggaatt tccgacgctg aaagcagctg gagggcagga    600
caaggctggc aaagaaaagg gcgtcttaga tctgtcgtat gggccaggac caagcctccg    660
ccctcagaat gtgacaagct ggagggaggg cggtgggcga cacataattt ctgccacgtc    720
tctgagcacc tccccaactg agctgggcag caggaactcg agtacgggag atggagcccc    780
ctcctcggca tgtaccagcg attctaagga cccctctctc cgcccggctc agcctgtccg    840
aaaagggggct tcacagttca tgggaaatgt ataccaccca cctacatacc atgacatgct    900
tcctgctttt atgtgttcgc cgaagtcatc agaaaaccag ggtacagtgg aacgaggctc    960
ttttcccctt cctcagctcc gccttgaacc tcgagttcct tttagacagt tccagatgaa   1020
tgaccaagac ggaaaagaaa acaggctggg attgtctcgc ccactccgcc cactaaggca   1080
gctggtggag cgggcaccac ggcccaccat tatcaatgcg gaaaacctga agggccttga   1140
cgatctggac gccgatgccg atgatggctg gcaggcctc catgaagaag tggactattc    1200
tgagaaactg aagttcagtg atgatgaaga ggaggaagaa gttgtgaagg acggcaggcc   1260
aaagtggaac agttgggacc ctaggaggca gcggcagttg tcaatgagct ctgcagacag   1320
tgcggacgct aagcggactc gagaggaagg gaaggactgg gctgaagcag tgggtgcgtc   1380
ccgtgtggtc cgaaaggcgc cagaccctca gccaccgccc aggaagcttc atggctgggc   1440
accaggccct gactaccaga agtcatcaat gggcagcatg ttccggcaac agtccatcga   1500
ggacaaggag gacaagcccc caccaaggca gaagttcatt cagtcagaga tgtccgaggc   1560
ggtggagcga gcccgaaagc cgggaagaa agaggagcgc cgagcccggg aggagaggct   1620
ggccgcctgt gctgccaaac tcaagcagct ggaccagaag tgtaagcagg cacgaaaggc   1680
aggtgaggcc cggaagcagg cagagaagga agtgccctgg tctccaagtg ctgagaaggc   1740
atctccccag gaaaacggcc ctgctgtcca caaaggctcc ccagaattcc ctgcccaaga   1800
gaccccacc acattcccag aagaggcacc cacagtgtcc ccagcagtgg cacagagcaa   1860
cagcagtgag gaagaggcca gagaggctgg gtcccctgca caggagttca gtatcagaa   1920
gtcccttcct ccccgattcc agcgccagca gcagcaacaa cagcaggagc agctgtacaa   1980
gatgcagcac tggcagccgg tgtacccccc gccgtcccac cccagcgca cctttacccc   2040
acaccacccc cagatgttgg gcttcgatcc caggtggatg atgatgcctt cctacatgga   2100
cccacgtatc acgcccactc ggaccccggt ggacttctac ccctccgccc tgcatccctc   2160
aggactgatg aagcccatga tgccccagga gtccctcaat gggacaggct gtcgctctga   2220
ggatcagaac tgtgtgcccc cactccaaga aagaaaagtg accccatcg actcaccccc   2280
tgtgtggagc ccagagggct acatggcact gcagagcaag ggctacccgc tcccgcaccc   2340
gaagtcgagt gacaccttgg ctatggacat gcgtgtcagg aatgaaagct ctttctctgc   2400
ctcactcgga agggcagggg gcgtaagtgc tcagcgcgat ctctttgagg agagagggga   2460
ggagtacttg agtgcttttg acaagaaggc ccaagcagac tttgacagct gtatctcttc   2520
tcaaagaata ggccaggagc ttttgtttcc accccaagaa aatgttcagg atgcaggtgc   2580
tcctgggggt cacacccaaa acctcaggtg ttccccattg gagcctgact tgtcccaga   2640
tgagaaaaag ccagagtgtg gcagttggga tgttagccac cagccagaga ccgctgacac   2700
agcccatggt gttgagcggg agacaccccg ggaggggacg gcctttaaca tctcctcctg   2760
ggacaagaac gggagcccca acaaacagcc atcctcggag cctgaatgga ctcccgagcc   2820
ccggagctcc agcagccagc acccggagca gacgggcagg acccgaggt cgggaccat    2880
caagaaacca gtcctgaaag ccctcaaggt ggaagacaag gagaaggagc ttgagaagat   2940
```

-continued taagcaggag ctaggggagg agagtacccg gctggccaag gagaaggagc agagccccac 3000
ggcagaaaag gatgaggacg aagagaacga tgcctctctg gccaactcct ccaccaccac 3060
tttggaggac aaaggccctg gccatgccac ttttggccgc gaggccacca aatttgaaga 3120
ggaggagaaa cctgacaagg cctgggaagc cagaccccca cgagagtcca gcgatgttcc 3180
ccccatgaag agaaataact ggatctttat tgatgaggag caagcctttg ggtcagaggg 3240
acaggcccgg ggccggggcc gtggtttcag agagttcact tttcgtggtc ggcctgctgg 3300
cggaaatggg agcggcctct gtggtggggg ggtcctgggg gcccgcagca tctactgcag 3360
cagtcagcgc agcggccgtg gccggggcct gcgagagttt gcgcggccag aggactgccc 3420
cagagccaag ccccgacgga gagttgccag tgagacccat agcgagggct cagagtatga 3480
agaacttccc aagcgccgcc ggcagagggg ctccgagaac gggaatgaag gctcgctcct 3540
ggagagggag gagagcacct tgaagaaggg cgactgcaga gattcttggc ggtccaacaa 3600
ggggtgctct gaggaccaca gcggtctaga tgccaagagc cgaggccctc gggcctttgg 3660
gcgagccctc cctccccggc tgagcaattg cgggtatgga cggagaacct tcgtctccaa 3720
agagtcaccc cactggcaga gcaaaagtcc aggcagctct tggcaggaat atggcccttc 3780
cgacacatgc ggatcccggc gacctacaga cagagactat gtcccagatt cctacagaca 3840
ccctgacgca tttggtggcc ggggctttga ggacagccgc gcggaggaca agagatcctt 3900
cttccaagat gaacacgtgg cagattctga aaatgcagag aaccggccct tcaggagaag 3960
gcgcccccca cgccaagata agccccctcg attccggcgc ctccggcaag agcgggagtc 4020
cctgggcctg tggggacccg aggaggagcc ccacctgctg gcaggtcagt ggccaggcag 4080
gcccaaactg tgttctgggg acaagagtgg cactgtgggc cgcaggtccc ctgagctctc 4140
ctaccagaac tcctccgatc acgccaatga ggagtgggag acggcctccg aaagcagcga 4200
cttcagcgag cggcgggagc ggcgggaagg ccctgggtcc gagcccgact cccaggtgga 4260
tggtggcctg tcgggggcta gtttgggtga gaagaaggag ctggccaaga ggagcttctc 4320
cagtcagaga cccgtggttg acagacagag ccgaaagctg gagccgggag ggtttgggga 4380
gaagcccgtt aggccaggtg gtggtgacac ctcccctcgc tatgagagcc aacagaatgg 4440
gacgcctttg aaagtgaaaa gatccccaga cgaggccttg cctggaggtc ttagtggctg 4500
cagcagtggg agtggccact cccctatgc cctggagcgg gcagcccatg ccagtgctga 4560
ccttcccgaa gcctccagta aaaaggcaga gaaggaggcc aagttggctg ctccgagggc 4620
aggtgaacag ggagaggcca tgaaacagtt tgacctgaac tatggaagtg ccatcattga 4680
aaattgcggg tccagccccg gggaggagag tgaggtgggt tctatggtgg gcgaaggctt 4740
catcgaagtc ctgaccaaga agcagcgccg cctgctggag gaagagagaa gaaagaagga 4800
gcaggccgtg caggtgcctg tcaaaggtcg aggcctttcc tcccgtattc ctcctcgatt 4860
tgcaaaaaag cagaacaact tatgtctgga gcaaggtgac gtgaccgtgc ctggcagcag 4920
cctgggcact gagatctggg agagcagcag ccaggctctc cctgtgcagg ccccagccaa 4980
cgactcctgg aggaaagctg tcactgcctt cagcagcacc gagactggct ctgcggagca 5040
gggttttaag agcagccagg gagatagtgg cgttgacttg agtgccgagt ctcgggagtc 5100
gtctgcgacc tcctcgcagc gcagctcccc atatgggact ctgaagccag aggagatgag 5160
cgggcccggc ctggcggaac ccaaggccga cagccacaag gagcaggctc caaagccatc 5220
tgagcagaag gattcagaac aaggctctgg acagagcaag gagcacagac caggacccat 5280


```
cggcaacgag cgttctctga aaaacagaaa gggctcggag ggggccgagc ggctgcaagg    5340
ggctgtcgtc ccgcctgtta acggggtgga gattcacgtg gactccgtgc tgcctgtgcc    5400
acccattgaa tttggagtca gtccaaaaga ctccgatttc agcttgccac ctggttctgc    5460
ctctggtcct actgggagtc cagttgttaa acttcaggat gccttggcca gtaatgcagg    5520
gttaacacag agtatcccca tcctgcggcg ggaccatcac atccagaggg ccatcggtct    5580
ctccccaatg tccttcccca ccgccgacct tactctgaag atggagtctg cgcgcaaggc    5640
ttgggaaaac tcccccagtt tgccggagca gagctctcca ggcggcgctg gctcaggcat    5700
ccagcctcca tcctctgtgg gtgcctccag cggggtcaac tacagctcct tcggtggagt    5760
gtccatgcca cccatgcctg tggcctctgt agcaccttct gcttctatgc caggcagcca    5820
cctcccgccc ctgtacctgg atggccatgt gtttgcaagt cagccccggc tggttcctca    5880
aacgatacct cagcagcaga gttaccaaca ggccgccgct gcccagcaga tcccgatctc    5940
ccttcacaca tctctgcagg cacaagctca gcttggactg aggggtgggc ttcctgtgtc    6000
ccagtcccag gagatcttca gctccttgca gcccttcaga tctcaggtgt acatgcaccc    6060
cagcctgtca ccgcccagca ccatgatcct ctctgggggc acagccttga agcctccata    6120
ctcggcgttc ccaggcatgc agcccttgga gatggtgaag ccgcagtctg gctcacccta    6180
ccagcccatg agcgggaacc aagccctggt ctacgagggc cagctcagcc aggctgctgg    6240
cctgggtgcc tcccagatgt ggactccca gctcccacag ctgaccatgc cactgcctcg    6300
gtacggctcc gggcagcagc cactgatcct gccccagtct attcagctgc cacctgggca    6360
gagcctctcc gttggggccc cccgaaggat tcctccgccc gggtcccagc cgccagtcct    6420
gaacaccagc agagagccct ctcagatgga gatgaaaggc ttccactttg ccgacagtaa    6480
acagaatgtc ccttcaggag gccccgtgcc atcgccacag acctacaggc ctagctctgc    6540
tagccccagt gggaagccct ctggatcagc agttaacatg ggctctgtgc agggacacta    6600
cgtgcaacag gcaaaacaac gagtggatga gaaacccagc ctgggagccg tgaagctgca    6660
ggaggccccc tcggctgcct cccagatgaa gcgaaccgga gcgatcaagc ctcgggctgt    6720
caaagtggag gagagtaagg cctgacagtg cctggctgcc acctcgcctc tccctactga    6780
ggacggtgcc gccatgcggc ctcgacacag ccgacactcg ggagcctcac cagatccacc    6840
gtccaaatgc gtggcccaga ctgagagacc tccctcctct ccactcccga agctccgtt    6900 gtcaaccagc ttgcacccgt ggatatatgg cattgacccg cttgctttga tacgaaacaa    6960
aaaagcagac gactccttca tcccatctgc tcctaccgtg actgtggagt gacgcctcct    7020
gtgcagtgca gatttgccct ccctgcctcc tccctgtcct gccgcgcagc cagggcgcct    7080
tctcagcagt gcttccggcc cagccgccca tccctaggca cagtgatttg gcagcagggt    7140
cattttactt tgaggctttt tgttttaaaa tgtagccaag ttttttacaa aggggaaagg    7200
aaaagaaaac aaaaacgcaa gctccatgtg tatagctgaa cttttatatg tttcttgcca    7260 gccctccgc tcccttccat ctctagcctc tgtcctgttt agtttgatac gtcactgcag    7320
taccttaaga ggtgactctt aagaatgcat cccctcctga ttcctcagct ggttcaccct    7380
tgaggttatt tgcaaaaaga aaaggaggtt cttgagggca ccgattgcga gcattctggt    7440
gcctggctcc ccgcctggga agcgatgggg tgctcagagc agcaggcagg ttgggggagg    7500
gggggggtca tagttgggtt ccagctcctg gcttgatgag cccagggcgc ttacaggcag    7560
cccatgaagt tgatgacagt tttagcatga gaatcacaca gggtccctgt cctgggctcc    7620
tctaaagcca gtggatgtgc tgggcaccag agacaaatca tggagatggc tgctggtggc    7680
```

```
tcccaggttg gcccagatgg ggtgagctga cataccacag gcccatccca ggccccgtgg    7740
gctctgcttc tggggctcca taccctgccc tgcaggggtg ctgtgttttt cacacatttc    7800
tttccctgaa gccttctgta acctgtcatt ttccttcctt cctcttccgg agcctgctgc    7860
tttctctgga cctgtctcca cctcccacac agctcatcgt gaacaccact tggtgatgga    7920
gggagtggac ccgtgtgtgg tccccaagtg aggccactgg gagtttgtcc ttttcctcct    7980
ttgcttcact cccagcagca gacccaggtt gtcaggacag gagggcctga gctaagcagt    8040
aggcatcagt ctcgtttgtc ttcagacggc gggggcaggt ccagggtgag gctgggtgga    8100
gggctgacca aggtccaaag ggcctgcgca gcctccggga gggcagcttc tccagccaga    8160
ggcttgtgtg agccatcgtg tgctgggctt gttttttaagt aagaaacaag gaaatcactc    8220
cagattctgt cattccaagg aaagggaagg ggacagttca ggtttctcag ctgttcttag    8280
gggtcactga gcgtctacct cctcctccag aggaggctgg ctcagaacac ctagaggagg    8340
gggccgggga tgcaccccc accagaggct gccttcagcg tctcacgggt gcaggacagc    8400
gctcaggctt gggctctaag ctctgtgtct agtgtagaac atggggaagg agcatcttag    8460
gaactgctga agtaacttct tactgctctc acaattctaa ggaagcggga gaacggcctc    8520
ctaccaacag cgcccacccc agagctgcct gggaaagggc agttttactg aaaggtgctt    8580
tactgttcac ctgcatcttt cagcagctcc cctcctgccc tcacctggtc ttttccctct    8640
ttatcccaag cctttatgct tgagtccctt ccccaggggc tgcccacccg acagttccag    8700
gcattcccta cctgagcttc ttgtctgctt ttccttctcc cactgcaagc ggctgcttgt    8760
ggggcctggg atgagccctc tctgtcccca ccggccctcc ttgccaagcc attcctgggt    8820
gagttcaggc ctgcgggagc cacacattca tctccacctg gacacttgag ccgcatggcc    8880 agaccctcc cacctgatgc ggtggtgcgt gtgatttgtc aaaagaaagc cttctggatg    8940
ctgttaagat gtaccttcca ggtgaacctg gtatcagacc cacagtactt gctgtttgag    9000
aaaaaataaa aacaaaaagg tcacctgttc tccagcccct ttctcttacc tggtatttcc    9060
ttcctttctc ctcccccacc ccaaataaaa aaacaaaaaa cactagaatt tatttatatg    9120
tattgatgtt gtaggtctag gtgaaaaaaa aagaagtaaa tgtttcactg ctctatttat    9180
atataatgtc tgaattaatt ctgtgcagga aaggccagga aattgcatgt gaagttcggt    9240
gcagtcacca cctgtgtgtg acctgagctg cagtctcttc gctgagatgc aggttttaaa    9300
tgagacttgg ggggctgagg gcaggcctca ggcctcccag cgccccaacc cctccttggt    9360
ctaatgaaat gcagttctta gtgcagagat gttttaaggt gcaatatatc tcttcctttc    9420
ccgtggtttt agagccaagc tcaaggtagt aggacgtagg gtcttatttt gttttcaaac    9480
ccccatcctc agagcgcaga tacatgcaga ggcttctgcc aggataccac ggggccttag    9540
tgggaacagg tggagaccag cacttccctt tcctgctgct gaggtaggga ttgggggtc    9600 agaacccact cactttttgcc tgttaaagtt gccctcctga cgctggcagc tctgccttgg    9660
tcactgggga tgcggctcgt tgctcagcca ccagtggcct tgcggtattg tccaccatcc    9720
actagagtgg gatgaagtcc agagtgtggg tatacatctc agatgcccat ctacccactg    9780
gggacttcaa tgccagctgc atttggtttg gttttcttaa ctgttggctt ctccccacag    9840
cgttttttgt ttttttttaa acattcatat tgttttcaaa cttggaattc atagacactc    9900
tggctctagg ttccttaagg gggaaaacaa aagatgactt tatttcacat tcaagaaaat    9960
cagttcagtt ccaaagctgt ggtccttcca gccacttcta gggacactgg ggaaccttgt   10020
```

| | |
|---|---|
| taaacgttga catcagtgct ctccagccgt gctgtcaccc tcctatcttc tggatctgcc | 10080 |
| ttcgcgatgg tcagtgacag cttctggaag ctgagcacac acaggtgcac agccatgctg | 10140 |
| tggtctggcc tgctacggca gcatggcagc tctggtggag ccttctccct tgccatttgg | 10200 |
| ttcccctgtg ccaagtagct gcaggctgcc cctcaaatct tcatttgtcc cttttcactt | 10260 |
| cctgcagaac aagcctgggt tagagggtct gctggaaatg gcctttgaag accaaggata | 10320 |
| ccaggatgtg tgcactctgt cgtgttctgt gatgaatggg aaacgtaggc ttccagaaag | 10380 |
| ccagctctct tctgaaatgt gacggaccta agcaggaagt catccaggac aggagtggct | 10440 |
| cagtgttggg gatggacgct gtcgcccagc catgctccac cagggccacc aatgtgtagt | 10500 |
| tggctggtgg tcttcgggca tgtgagacct gctcttcact gtttccaccc cacttggtgg | 10560 |
| cctccaggat ggtagtggca ccctcagagc cccatcttca gcatgttctg aagcctcaga | 10620 |
| gtggaaattc ctgctaaggc tctgtgtgga cgcctttctc ccgtgatcta aagggacac | 10680 |
| tgtactcaag cttttgacct catgccttgt gtagtaaaaa aggatttggg ggttttgttt | 10740 |
| ggttcctgag agggttgtgt tttgtttttg tttcctttg tttatgtttt ggcctttcct | 10800 |
| ctttgtcttt ccatgtagac cagatatttg aaagggcaga cgatggctag aggtgtaatg | 10860 |
| tgcagcttgt ttatacggta ttttgggaaa cttaccttgg atgggaaatc gaatcgtgga | 10920 |
| ttcaccaggc cggtgctggc acactcaccc tcgcccttc cctccggttc agtacctatt | 10980 |
| gtttctcctt tcaaatatgt gattgtacta gctctttcca tatgaaagaa ttctccttat | 11040 |
| ttaaataaaa aaagtttaaa aa | 11062 |

<210> SEQ ID NO 36
<211> LENGTH: 7689
<212> TYPE: DNA
<213> ORGANISM: Homo sapiens

<400> SEQUENCE: 36

| | |
|---|---|
| tcccacagtg cctggcccag aagccttgct aaatatttga acaggattgc ccaatacttt | 60 |
| tctgctgtga gaatgtaaga tggatccaga agagcaggag ctcttaaatg attacagata | 120 |
| cagaagctac tcttcagtga ttgaaaaggc tttgagaaat tttgagtcct cgagtgaatg | 180 |
| ggcggatctc atatcttcac ttggcaaact caacaaggct cttcagagta acctgaggta | 240 |
| ctccttgttg ccaagacggc tcctcatcag caaaagatta gctcagtgtt tgcaccctgc | 300 |
| cctgcccagt ggtgtccact aaaagctct ggaaacctac gagattatct ttaaaatcgt | 360 |
| ggggaccaaa tggctggcca aggacttgtt tctgtacagc tgcgggttat ttcctctcct | 420 |
| ggcacacgcg gcggtgtcgg tgaggccggt gctgctcacc ctgtacgaga agtacttcct | 480 |
| cccactgcag aagctgctcc tgcccagtct gcaggcctc atcgtgggcc tgctgcccgg | 540 |
| ccttgaagag ggctccgaga tctccgacag aacggatgct ctgctcctga ctgtcgct | 600 |
| ggtggttggc aaagaggtgt tttacaccgc cctctggggg agcgtcctgg ccagcccgtc | 660 |
| catccgcctc cctgcctcag tcttcgtggt gggccacatc aacagggatg cccccggccg | 720 |
| ggagcagaag tacatgctgg ggaccaatca ccaactcacg gtgaagtctt tgcgtgcctc | 780 |
| cctgttggac tcaaatgttc ttgtgcaaag aaataatctg gaaatcgttc tgttttctt | 840 |
| cccattttat acctgtctgg attccaatga gagagccatc cccctcctca gatctgacat | 900 |
| cgtgcgcatt ctctcagccc ccacccgac cctactgaga agggacatgt ccctgaacag | 960 |
| aagactgtat gcatggttac taggctcaga cataaaagga aataccgttg tgccagaatc | 1020 |
| tgaaatctca aattcttatg aagaccagtc gtcttatttt tttgaaaaat actccaagga | 1080 |

```
tcttttagtt gagggtttgg ctgagatatt gcatcagaag ttcatagatg ctgacgtgga   1140
ggaacgccat catgcatacc tgaagccttt tcgcgtcctc atcagtctgc ttgacaagcc   1200
agaaataggg cctcaagtgg ttgggaattt gtttctcgaa gtcatcaggg cctttattc    1260
ttactgcaga gatgcccttg gctctgatct taaacttagc tacacccaga gtggaaattc   1320
gctgataagt gcaatcaagg aaaacagaaa tgcctctgag attgtcaaaa cggtaaattt   1380
gctgataact tctctaagca cagactttct ctgggattat atgacaaggt gtttgagga    1440
atgctttaga ccagtgaagc agcgttacag cgtgaggaac agcgtcagcc ctcccccac    1500
ggtctcggag ctctgcgccc tcctggtctt cctgctggat gtcattcctt tggaacttta   1560
ctctgaggtg caaacccagt atctccctca ggtgctcggc tgcctggtgc agcctcttgc   1620
tgaggacatg gaggccttaa gtttacctga actcacgcat gccttgaaga cgtgtttcaa   1680
ggtgctcagc aaagtccaga tgcctccttc ctacctcgac acggagtcca ccagcggaac   1740
ctcgagtcca gtaaaaggtg aaaacggcaa ataattttg gaaacaaagg cagtgattcc    1800
cggtgacgaa gatgcttcgt tccccctct gaagtctgag gacagtggga tcgggctcag    1860
tgcctcgtca ccggagctct ctgagcactt gagggttcct cgagtttctc tggaaaggga   1920
cgacgtttgg aagaagggcg ggagcatgca gaggacgttt ctttgcatcc aagagctaat   1980
cgccaacttt gccagcaaga acattttttgg agtacagctg acagcgtcag gagaagaaag   2040
caagtccgag gagcctgcag ggaagaggga cagggatggg acgcagagcc tggcagccaa   2100
tgattccagc aggaagaact cttgggagcc caagcccatc actgtgcctc agttcaagca   2160
gatgctgtca gacttgttca cagcacgagg gtctccattc aagacaaaaa gttcagagtc   2220
accatcgtct tcgcccagca gccctgccag gaaaaacggg ggagaatggg atgttgagaa   2280
ggtggtcatt gacctggggg gttccaggga ggaacgcagg gaggcctttg ccgccgcctg   2340
ccacctgctg ctggattgtg ccactttccc tgtctacctg tccgaggaag agaccgagca   2400
gctctgtgca acgctcttcc agctgccagg agccggtgat tccagttttc catcttggct   2460
gaagtccctc atgactattt gctgctgtgt gactgactgc tacctccaga acgtggccat   2520
ttccactctg ctggaagtga taaaccattc ccagtccctg gcgcttgtca ttgaagacaa   2580
gatgaaacgc tataagagct ctggacacaa ccctttttt ggcaagctgc agatggtgac    2640
ggttcctccc attgctccag ggatattgaa agtcattgca gagaaaacag atttctatca   2700
gagggtggct cgtgtgcttt ggaatcagct gaacaaagag acccgggagc atcacgtcac   2760
ctgcgtagaa ttgttctacc ggctgcactg cctggcccct acggccaaca tctgcgagga   2820
catcatctgc catgccctcc tggaccctga caagggaaca aggctggaag ctctgtttag   2880
attttccgtg atctggcatc tgacaagaga gatccaaggc agtcgagtaa catctcacaa   2940
tcgctccttt gataggtcct tgtttgtcgt gctggacagc ctggcctgca cggatggtgc   3000
catcggtgcg gcagcccagg gctggctggt cgtgcgctc tccctcgggg acgtggctcg    3060
catcctcgaa cccgtgctcc tgctgctgct gcagccaaaa acccagagaa cctccatcca   3120
ctgcctcaag caggagaact cggccgatga cttgcaccgt tggtttaaca ggaagaaaac   3180
ctctttcaga gaggcatgcg cagtgcccga gcctcaggag agcggctctg aagagcacct   3240
gcctctgagc cagttcacca cagtggaccg tgaagccatt tgggccgaag tggagaagga   3300
gcccgagaag tacccgctgc gaggcgagct gagcgaggaa gagctgccct actacgtgga   3360
gcttccagac aggacggccc acggcgcccc ggacagcagc gagcacaccg agtctgcaga   3420
```

-continued

| | |
|---|---|
| tacaagctcc tgccacacgg acagcgagaa cacgtcctcc ttctcctccc cttcccacga | 3480 |
| cctgcaggag ctgagcaacg aagagaactg ctgtgcaccc atccccatgg ggggcagggc | 3540 |
| gtaccccaag cgctcggccc tgctggcggc cttccagtca gaaagcttca aggctggggc | 3600 |
| caagttaagc ctggtgcggg tggactcgga caagacgcag gcttctgagt cgttctccag | 3660 |
| cgacgaggag gcggacttgg agctccaggc cctcaccaca tccaggctgc taaagcagca | 3720 |
| gcgggaaagg caggaggccg tcgaggcctt gttcaagcac atcctgctct acctgcagcc | 3780 |
| ctacgactct cggcgggtcc tctatgcctt ctcggtgctg gaggctgtgc tcaaaaccaa | 3840 |
| ccctaaggaa ttcatcgagg ctgtgtccag gactagcatg gataccagct ccaccgcgca | 3900 |
| cctcaacctc atctccaacc tcctcgctcg ccaccaggag gccctcattg ccagagttt | 3960 |
| ctacggaaag ctccagaccc aggtcccaa cgtgtgcccc cactctctgc tcctggagct | 4020 |
| gctcacctac ctctgcctga gcttcctgcg ctcctactac ccttgctatt tgaaggtctc | 4080 |
| gcaccgagac attctcggca accgggacgt gcaggtcaaa agtgtcgagg ttttgatcag | 4140 |
| gataatgatg cagctggtct cagtggccaa gtcttcggaa gggaagaacg tggagttcat | 4200 |
| ccacagcttg ctgcagaggt gcaaagttca ggagtttgtc ctgctctccc tgtcggcgtc | 4260 |
| catgtacacg agccagaagc gctacgggct ggccaccgcc caccacggca gggccctgcc | 4320 |
| agaggacagc ctctttgagg agagtctcat taacttgggt caggaccaga tctggagtga | 4380 |
| gcacccgctg cagattgagc tgctgaagct gctgcaggtg ctgattgtct tggaacacca | 4440 |
| cctgggtcgg gcccatgagg aggcggaaaa ccagcccgac ctgtcccggg agtggcagag | 4500 |
| agccctgaac ttcagcagg ccatcagcgc cctgcagtac gtgcagcccc accccctcac | 4560 |
| ctcccagggt cttctggtct ctgcggtggt gaggggtctg cagcccgcct acggttacgg | 4620 |
| catgcatccg gcctgggtga gcttggtcac gcattccttg ccctacttcg gaaagtccct | 4680 |
| gggctggacg gtgacaccct tgttgtccca gatttgcaaa aacttggatg acttggtcaa | 4740 |
| gcagtatgaa agcgaatctg tgaagctctc tgtcagcaca acctccaaga gggaaaacat | 4800 |
| ttctccagat tatccactca cccttctaga aggtctaacg accattagtc attttgtct | 4860 |
| tttggaacaa gccaaccaaa acaaaaagac catggctgca ggtgatcctg ccaacttgag | 4920 |
| gaatgccaga aatgccattt tggaagagct gcctcgaact gttaacacca tggcccttct | 4980 |
| ctggaatgtt ctcagaaagg aggagactca aaagagacct gtcgatctcc taggggccac | 5040 |
| gaagggatcc tcttccgttt actttaaaac caccaaaacc ataagacaaa aaattttaga | 5100 |
| cttcttaaac cccttgacgg cccatcttgg ggttcagttg acagcggctg ttgcggcagt | 5160 |
| gtggagcaga aagaaagccc agcgtcacag taagatgaag attatcccaa cggcaagtgc | 5220 |
| atcccagcta acccttgtcg acttggtgtg tgcactcagc accctgcaga ctgacacgct | 5280 |
| gctgcacctg gtgaaggagg tggtgaagag gccaccccaa gtcaaagggg gtgatgagaa | 5340 |
| atcgccccta gtggacattc ctgtgttgca gttttgctat gcttttctcc aaaggctccc | 5400 |
| agtaccagcc ttgcaagaga acttttcttc actgttggga gtattgaaag agtctgtaca | 5460 |
| gttgaatcta gccccacctg ggtatttttct gcttctcagc atgctgaatg actttgtaac | 5520 |
| aagaactccc aacctggaaa acaagaagga ccaaaaagac ctgcaggaaa tcactcagaa | 5580 |
| aatcctagaa gctgtgggga acattgccgg ctcttccttg gagcaaacca gctggctaag | 5640 |
| cagaaacctg gaagtgaagg cccaacctca ggcctctcta aagaatctg atgctgagga | 5700 |
| ggacctgtat gatgctgctg cagcttcagc aatggtgtct tcatccgccc cgtcggtgta | 5760 |
| cagcgtgcaa gccctctctc tcctggcaga ggtactggct tccctcctgg acatggttta | 5820 |

```
tcgaagtgat gagaaggaga aagctgtgcc gttaatctcc cgtctgcttt actatgtttt    5880
tccatactta cgcaaccaca gtgcctacaa tgctcccagc ttccgggctg gcgctcagct    5940
gctgagctcc ctgagtggct atgcctacac aaagcgagcc tggaggaagg aggtcctgga    6000
gctgtttctc gaccccgctt tctttcagat ggatacttcc tgtgttcatt ggaagtccat    6060
tattgaccat cttttgactc atgagaaaac aatgtttaag gatttaatga acatgcagag    6120
cagttctttg aaactattct caagttttga acagaaagcc atgctgttaa agcgccaggc    6180
ttttgctgtc ttcagtggag aacttgatca ataccacctt taccttccac tgatacaaga    6240
acgcctgaca gacaatctca gagttggaca gacatcccata gttgctgctc agatgtttct    6300
ttttttcaga gttttgctgc taagaatatc tcctcaacat ttgacttcat tgtggccaat    6360
aatggtctct gaattgattc agacattcac acagcttgaa aagatctaa aagatgaaga     6420 tgagtcattg agaagcacca acaaagtaaa cagaacgaaa gtttcagtcc cggatgcaaa    6480
tggaccctca gtgggggaga taccccagag tgaactcatc ttgtatttat cagcttgcaa    6540
attcttggac acagcgcttt cttttccacc tgacaagatg ccattatttc aaatttatag    6600
gtgggcattt attccagaag tggacacaga ggggcctgcc ttcctgtcgg atgtagagga    6660
gaatcaccaa gaatgcaaac cccacactgt caggattcta gaacttctaa aattaaagtt    6720
tggggaaatc agtagctctg atgagatcac catgaagagt gaattcccgc ttctgcgcca    6780
acattctgtt tccagcatca ggcagttgat gccattcttc atgactctaa atggtgcatt    6840
taagacccag agacagctgc ctgctgatag cccaggaact ccattcttgg actttcctgt    6900
cacagatagc ccaaggatct taaaacaact ggaagaatgc atcgaatatg attttctgga    6960
acatccagaa tgttaaccat gtgagagaga atatgtttaa tccatgtatt ggtactttac    7020
tgaaaaccag gttatattct aaagaagaaa gaaggcagga tagtgctttt gaacaagcct    7080
atttccattt tgaaagtaga tttcaggcta ggtgcggtgg ctcacacctg taatctcagc    7140
actttgggag gccaaggcag gcagatcact tgaggtcagg agttcgagac cagcctgacc    7200
aacatggtga ccctgtctct actaaaaaa tacaaaaatt agctgggtgt ggtggcggcg    7260
cctgtaatcc cagctacttg ggaggctaag gcatgagaat tgcttgaacc caggaggtgg    7320
aggctgcagt gagccgagat cacgacactg cactccagct gtgtgacaga atgagaccat    7380
ctccaaaaaa aaaaaaagt agatttcaga taatttactg ttcagcaaca ggacacacct    7440
ccctaaatgc cttgtaatat atttgaatct gattctgcat ttcttcctca atttatgtaa    7500
tgaaaataaa attaatatat catctaacag tagcacaaaa tttgtaatat gaagtaaagt    7560
atgaagataa tgaagaagtt gttttctttg ttgaagcagt tatatgggtc tttctcagta    7620
tatttctctt ttctctaaaa gtttaaactt attaaagaa tgttattttt aacctttcaa     7680
aaaaaaaa                                                             7689
```

<210> SEQ ID NO 37
<211> LENGTH: 1138
<212> TYPE: DNA
<213> ORGANISM: Homo sapiens

<400> SEQUENCE: 37

```
gctctggccg gccccggcga ttggtcaccg cccgctaggg gacagccctg gcctcctctg      60
attggcaagc gctggccacc tccccacacc ccttgcgaac gctcccctag tggagaaaag     120
gagtagctat tagccaattc ggcagggccc gcttttttaga agcttgattt cctttgaaga    180
```

```
tgaaagacta gcggaagctc tgcctctttc cccagtgggc gagggaactc ggggcgattg     240
gctgggaact gtatccaccc aaatgtcacc gatttcttcc tatgcaggaa atgagcagac     300
ccatcaataa gaaatttctc agcctggccg aaaatggttg gccccacgaa gccacgacaa     360
ctggaggcaa agagggttgc tcaacgcccc gcctcattgg aaaaccaaat cagatctggg     420
acctatatag cgtggcggag gcggggcgat gattgtcgcg ctcgcaccca ctgcagctgc     480
gcacagtcgc atttctttcc ccgcccctga gaccctgcag caccatctgt catggcggct     540
gggctgtttg gtttgagcgc tcgccgtctt ttggcggcag cggcgacgcg agggctcccg     600
gccgcccgcg tccgctggga atctagcttc tccaggactg tggtcgcccc gtccgctgtg     660
gcgggaaagc ggcccccaga accgaccaca ccgtggcaag aggacccaga acccgaggac     720
gaaaacttgt atgagaagaa cccagactcc catggttatg acaaggaccc cgttttggac     780
gtctggaaca tgcgacttgt cttcttcttt ggcgtctcca tcatcctggt ccttggcagc     840
acctttgtgg cctatctgcc tgactacagg tgcacagggt gtccaagagc gtgggatggg     900
atgaaagagt ggtcccgccg cgaagctgag aggcttgtga ataccgaga ggccaatggc     960 cttcccatca tggaatccaa ctgcttcgac cccagcaaga tccagctgcc agaggatgag    1020
tgaccagttg ctaagtgggg ctcaagaagc accgccttcc ccacccctg cctgccattc     1080 tgacctcttc tcagagcacc taattaaagg ggctgaaagt ctgaaaaaaa aaaaaaaa     1138

<210> SEQ ID NO 38
<211> LENGTH: 1377
<212> TYPE: DNA
<213> ORGANISM: Homo sapiens

<400> SEQUENCE: 38
atgctaaaac taatcgtccc aacaattata ttactaccac tgacatgact ttccaaaaaa      60
cacataattt gaatcaacac aaccaccac agcctaatta ttagcatcat ccctctacta     120
ttttttaacc aaatcaacaa caacctattt agctgttccc aaccttttc ctccgacccc     180 ctaacaaccc ccctcctaat actaactacc tgactcctac ccctcacaat catggcaagc     240
caacgccact tatccagtga accactatca cgaaaaaaac tctacctctc tatactaatc     300
tccctacaaa tctccttaat tataacattc acagccacag aactaatcat atttatatc     360 ttcttcgaaa ccacacttat ccccaccttg gctatcatca cccgatgagg caaccagcca     420
gaacgcctga acgcaggcac atacttccta ttctacaccc tagtaggctc ccttccccta     480
ctcatcgcac taatttacac tcacaacacc ctaggctcac taaacattct actactcact     540
ctcactgccc aagaactatc aaactcctga gccaacaact aatatgact agcttacaca     600 atagctttta tagtaaagat acctctttac ggactccact tatgactccc taaagcccat     660
gtcgaagccc ccatcgctgg gtcaatagta cttgccgcag tactcttaaa actaggcggc     720
tatggtataa tacgcctcac actcattctc aaccccctga caaaacacat agcctacccc     780
ttccttgtac tatccctatg aggcataatt ataacaagct ccatctgcct acgacaaaca     840
gacctaaaat cgctcattgc atactcttca atcagccaca tagccctcgt agtaacagcc     900
attctcatcc aaaccccctg aagcttcacc ggcgcagtca ttctcataat cgcccacggg     960
cttacatcct cattactatt ctgcctagca aactcaaact acgaacgcac tcacagtcgc    1020
atcataatcc tctctcaagg acttcaaact actcccact aatagctttt tgatgacttc    1080
tagcaagcct cgctaacctc gccttacccc ccactattaa cctactggga gaactctctg    1140
tgctagtaac cacgttctcc tgatcaaata tcactctcct acttacagga ctcaacatac    1200
```

-continued

| | |
|---|---|
| tagtcacagc cctatactcc ctctacatat ttaccacaac acaatggggc tcactcaccc | 1260 |
| accacattaa caacataaaa ccctcattca cacgagaaaa caccctcatg ttcatacacc | 1320 |
| tatcccccat tctcctccta tccctcaacc ccgacatcat taccgggttt tcctctt | 1377 |

<210> SEQ ID NO 39
<211> LENGTH: 1779
<212> TYPE: DNA
<213> ORGANISM: Homo sapiens

<400> SEQUENCE: 39

| | |
|---|---|
| cggcgtgccc tggggcggcg cgggcgcagg ggcgcgtgcg cggcgggctg tcgttggctg | 60 |
| gagcagcggc tgcgcgggtc gcggtgctgt gaggtctgcg ggcgctggca aatccggccc | 120 |
| aggatgtaga gctggcagtg cctgacggcg cgtctgacgc ggagttgggt ggggtagaga | 180 |
| gtaggggcg gtagtcgggg gtggtgggag aaggaggagg cggcgaatca cttataaatg | 240 |
| gcgccgaagc aggacccgaa gcctaaattc caggaggttg ggatgaatgg gttccggaga | 300 |
| gcagagtact caaatacgtg gacaccaatt tgcagaaaca gcgagaactt caaaaagcca | 360 |
| atcaggagca gtatgcagag gggaagatga gagggctgc cccaggaaag aagacatctg | 420 |
| gtctgcaaca gaaaatgtt gaagtgaaaa cgaaaaagaa caaacagaaa acacctggaa | 480 |
| atggagatgg tggcagtacc agtgagaccc ctcagcctcc tcggaagaaa agggcccggg | 540 |
| tagatcctac tgttgaaaat gaggaaacat tcatgaacag agttgaagtt aaagtaaaga | 600 |
| ttcctgaaga gctaaaaccg tggccttgttg atgactggga cttaattacc aggcaaaaac | 660 |
| agctcttta tcttcctgcc aagaagaatg tggattccat tcttgaggat tatgcaaatt | 720 |
| acaagaaatc tcgtggaaac acagataata aggagtatgc ggttaatgaa gttgtggcag | 780 |
| ggataaaaga atacttcaac gtaatgttgg gtacccagct actctataaa tttgagagac | 840 |
| cacagtatgc tgaaattctt gcagatcatc ccgatgcacc catgtcccag gtgtatggag | 900 |
| cgccacatct cctgagatta tttgtacgaa ttggagcaat gttggcttat acacctctgg | 960 |
| atgagaagag ccttgcttta ttactcaatt atcttcacga tttcctaaag tacctggcaa | 1020 |
| agaattctgc aactttgttc agtgccagcg attatgaagt ggctcctcct gagtaccatc | 1080 |
| ggaaagctgt gtgagaggca ctctcactca cttatgtttg gatctccgta aacacatttt | 1140 |
| tgttcttagt ctatctcttg tacaaacgat gtgctttgaa gatgttagtg tataacaatt | 1200 |
| gatgtttgtt ttctgtttga ttttaaacag agaaaaaata aaggggggta atagctcctt | 1260 |
| ttttcttctt tctttttttt tttcatttca aaattgctgc cagtgttttc aatgatggac | 1320 |
| aacagaggga tatgctgtag agtgtttat tgcctagttg acaaagctgc ttttgaatgc | 1380 |
| tggtggttct attcctttga cactacgcac ttttataata catgttaatg ctatatgaca | 1440 |
| aaatgctctg attcctagtg ccaaaggttc aattcagtgt atataactga acacactcat | 1500 |
| ccatttgtgc ttttgttttt ttttatggtg cttaaagtaa agagcccatc ctttgcaagt | 1560 |
| catccatgtt gttacttagg cattttatct tggctcaaat tgttgaagaa tggtggcttg | 1620 |
| tttcatggtt tttgtatttg tgtctaatgc acgttttaac atgatagacg caatgcattg | 1680 |
| tgtagctagt tttctggaaa agtcaatctt ttaggaattg ttttttcagat cttcaataaa | 1740 |
| ttttttcttt aaatttcaaa gaacaaaaaa aaaaaaaaa | 1779 |

<210> SEQ ID NO 40
<211> LENGTH: 7827
<212> TYPE: DNA

<213> ORGANISM: Homo sapiens

<400> SEQUENCE: 40

```
gtagtcttga cgtgagctag ctggcatggc ggcctgcatt gcagcggggc actgggctgc    60
aatgggccta ggccggagtt tccaagccgc caggactctg ctcccccgc cggcctctat    120
cgcctgcagg gtccacgcgg ggcctgtccg gcagcagagc actgggcctt ccgagcccgg   180
tgcgttccaa ccgccgccga aaccggtcat cgtggacaag caccgccccg tggaaccgga   240
acgcaggttc ttgagtcctg aattcattcc tcgaagggga agaacagatc ctctgaaatt   300
tcaaatagaa agaaaagata tgttagaaag gagaaaagta ctccacattc cagagttcta   360
tgttggaagt attcttcgtg ttactacagc tgacccatat gccagtggaa aaatcagcca   420
gtttctgggg atttgcattc agagatcagg aagaggactt ggagctactt tcatccttag   480
gaatgttatc gaaggacaag gtgtcgagat ttgctttgaa ctttataatc ctcgggtcca   540
ggagattcag gtggtcaaat tagagaaacg gctggatgat agcttgctat acttacgaga   600
tgcccttcct gaatatagca cttttgatgt gaatatgaag ccagtagtac aagagcctaa   660
ccaaaaagtt cctgttaatg agctgaaagt aaaaatgaag cctaagccct ggtctaaacg   720
ctgggaacgt ccaaatttta atattaaagg aatcagattt gatctttgtt taactgaaca   780
gcaaatgaaa aagctcagaa gtggaatca gccatggctt gaatttgata tgatgaggga   840
atatgatact tcaaaaattg aagctgcaat atggaaggaa attgaagcgt cgaaaaggtc   900
ttgattctga gaatgaattt ggttagttgc agaagataca ttggctctaa gaggatatat   960
tttgagacca atttaatttc atttataaga acatagtaat taagtgaact aagcattcat  1020
tgttttatta atacttttt tctaaaataa aacttgtaca ccagtttatt actctaaaaa  1080
gagaattaca catgccaaat ggaccaatgt ccatttgctt attggaggca aagctacaat  1140
agaagtcaga gcatcaccag aatggtcttt aatgagcatg gaacctgagc aaagggaata  1200
ggtgggatga atttttttt taattgtgaa acaattcata agcacaatat gatttacaga  1260
ataataaaca ttcatgtacc cactatcagg ttaagaaata gaacatttat taatatgtag  1320
gaatgttaag aaataaaaca tttaataaga tctcagaaga ctccagtaaa tctgcaattg  1380
tatctctctc cttttaaat gtaaatatca tcttgacttg ttaattattc ccttgcattt   1440
cttttagttt actgccaaca catatattct tcaacaatat atttaatttt gaaaaacctg  1500
aaaaaaaaaa cctgttagca agtataaagg ggcagtatta ctattattgc atgaaggctt  1560
caagggaaac gttacagtct ttgggtcata gtctggcttc agcttcctct gagagtttac  1620
agaggccaat tttgagcaaa ttcatggcta aggttatgag tgagttctgc taaacagaag  1680
gctcaccaca aggtatctgg caggattata ctgggtagct ggatgttgca gaaatgtggt  1740
tagaggaagt aaactgtttt ttgatgctca cagcatgatg aatcaaactc tgtatcttag  1800
gattaggtta aaacaatacc tttggtatga tatgagtgtt gttgctgatc catgcagcat  1860
ggattggaaa gctgggtat aagcacacat gctaagaaa acatgtaat ttggtccata   1920
ctcacctgga tatactgttc ctcaggttaa aaaatacagt actatcctaa atcttgaagg  1980
caactctcag cctatccatt gagttacctt cagatctgcc ctctggttcc tagctgtctt  2040
gggactaact tctttcctgc gctcagctgt tttctggatt ccatgttttc cattttattg  2100
agtactaact tgttttgctg cagcacatcc tttggtagct tctagaggaa gtttgtgtgg  2160
aggtaaaatt tttgagacct tgcatgtctc atgtttgatt gatactttat acgtttaggt  2220
aggaggtaat tttccttcag gactttaaaa atattgttgc tccatttct ttgtttctat   2280
```

| | | | | | |
|---|---|---|---|---|---|
| tgttgtattg | agaaatccaa | tgccattttg | atttccccat | cataaatttc | atgatgatgt | 2340 |
| gtcttggtgt | gggtctatat | ttatccattg | tattgggttt | taggtgaacc | cttccagata | 2400 |
| gtaactcatt | tctgtcagtt | ctgggaaaca | cttagcattg | gttgatgatt | tattctctgc | 2460 |
| tgctttgttc | tcccaactat | tatttggatg | ttggatatcc | agcactgggt | atctattttc | 2520 |
| ttacctccct | cccttgaccc | cagtctctgt | tttttagctc | tttagctcaa | tcttccaact | 2580 |
| ctttgctatt | gtattttaaa | atcttaagac | cccttcttga | tttgtagaag | ttccttttct | 2640 |
| tacaaccaaa | aagcctttat | ctatggattt | gttcacagat | aaggggtatt | caatatagtg | 2700 |
| tattttttt | tcatttaaaa | ttgtttgcgc | atctatttcc | tccaaatttc | tttctgtatt | 2760 |
| tattttttgt | tgtctatatt | tcagactttt | ccaggatatc | tgataatctt | tggctgtctt | 2820 |
| cttatggttg | aaagagggac | taaaaagctt | ggaaagcctt | tgggttgtgg | aaggggctg | 2880 |
| tctttaggat | tatctgaatg | ggctttttg | ggagtcccct | cctccacatg | aatattttgg | 2940 |
| ttttgtcaga | ttccctagaa | tagaggcttc | caatctcctt | cctggagggg | tctgtccagg | 3000 |
| aaggagattg | tctaggggtc | tgtcagacag | cagctttcag | ctacttcctt | gatcttttc | 3060 |
| actaatgatt | atatagtcat | ctaactactg | tcaacaagta | atagatatcc | tatccttcac | 3120 |
| ttgtttagat | tatttgctga | gataacctct | caaaagaacc | tctcaaaata | aaaggttaac | 3180 |
| aagagcctat | atcttatatt | tttcttctct | ttatcttgtt | agaagatagc | tattaaaacc | 3240 |
| tgttctttt | ctgtcttgat | aaacacactt | caatcttggt | agaatggtag | atgggacagt | 3300 |
| atattttagg | acctaaagct | ctgcaaatgt | atgatcagct | tgtaagtaca | ggtgctcaaa | 3360 |
| aacatgtaaa | caatcatgct | ttttactctg | taggaatatc | tttaaaattc | ttgtgaattt | 3420 |
| ttccccagaa | gtaaagcaaa | tcttccccca | gaaataaaat | taaatgtgca | taatctaaag | 3480 |
| ctttttttt | ttattgtggt | aggatatata | tataaaacat | aatttgccat | tgtaaacatt | 3540 |
| ttaaatttac | aagtcagagg | cattaattac | atcacaatgt | tgtgaaatta | ttactactat | 3600 |
| ttccaaaatt | ttctcatcac | cccaaactga | aactctgtaa | ctgttgagca | ataacctcat | 3660 |
| tcctgtatct | ctcccaaccc | caggtaacct | caaatctttc | tttttatctt | tgagacaagg | 3720 |
| tctcattcta | tcactcaggt | aggagtgcag | tggtgtgatc | atagctcatt | gcagcctcaa | 3780 |
| aatcctgggc | tcaagcaatc | ctccttgagt | agctaagact | ataggcacac | attaactgcg | 3840 |
| cctggctgat | tttgttttt | gtagagatgt | ggtcttgcta | tgtttcccat | gctggtcttg | 3900 |
| agttcctggc | ctcaagcagt | ccttaagatt | catccatgtt | gtggcatgtg | tcagaatttc | 3960 |
| atttgttttt | atgactaaat | aatattccat | tgtatgtata | tacattttgt | tcatccatct | 4020 |
| tctgatgaac | actgggatat | gtctacctt | tggctattgt | gaataatgct | gcagtaaaca | 4080 |
| ttgacataac | aagtatgtat | ttgattgcct | gtttctaagt | tcttttgggt | atacatcttg | 4140 |
| agtagaattg | ctagataatg | tcatgtttta | tttctcttgt | gatttcttct | tcgatcccct | 4200 |
| ggttgagtgt | gttaatttct | acatgtttat | gaatttccca | ctgttttttt | gttattgatt | 4260 |
| tccaagttca | ttccattgtg | attagagaag | atacttagta | tgattttaat | gttttgaga | 4320 |
| attggtgtgt | ggcctgatag | atggtctgtc | ctggagaatg | ttcctcatac | acttgagcaa | 4380 |
| aatatttatc | atgctattgt | tgactgtagt | tttctatatg | tctcttaggt | caaggtggtt | 4440 |
| tacaatgtgt | taaggttctc | ttttttaaa | aaaattttg | cacagagtat | ctttttctat | 4500 |
| gtgttccatg | tatttgtgtc | tttggagcta | tagtctcttg | tagacagcat | atcactatct | 4560 |
| tgttttgttt | tgttttttct | gtccattctg | ccaatttctg | cctttttgatt | ggaaaattta | 4620 |

```
atccatttgc atttaaagta attaaggaag gactttcttc taccatttaa cacttcttct    4680
atatgtcata tactttttg gcccctcatt tcctcttat ggccttcttt tctgtttttt      4740
tgtagtgaac tagtctgatt ctctttccac tcccctttgt gtatatttgt tagatgtttt    4800
atttgtggtt gctatgggga ttatagttaa catcctacac ttaaaacaat ctaatttaaa    4860
ctgataccaa tttaccttca atagcataca aaatctctac tcctgtaaag ctctgcccct    4920
gccccctta tgttattgat ggcacaaatt gcctaataaa taatttatag ttatttgtat     4980
gagtttgtct tttaaatcat ttaggaaata aaaagtggag ttagaaaaca gtatgatagt    5040
aatactgact tttatatttg tcaatatatt tatcttattt tggatcctta tttcattata    5100
tagatttgag ttactgtcta gtgcccttcc atttcggccc aaaggattcc cttatgcatt    5160
tcttgcaggg caagtctaat tgtaataaac tccctcagct tttgttttat ctgagaatgt    5220
cttgatttct cccttatttt tgatggataa ttttgccaga tacatgaatt tttggtaaca    5280
gtattttct ttcagcactt taaatatgtc atcccactac cttctgactt catggtttct     5340
catgagatat tagatgttat aaaatttgag gattcctcat tcttgatgag tcagttctgt    5400
cttattgctt ttcggatttg ctcagctttt gtcttttgac agtttgatta taacgcggct    5460
cagtgtgggt ctctgagttt atcccactta gagtttgttg agtttcttgg agtcatagat    5520
ttatgtcttt tatcaaattt tggacatatt tggctattat ttcttcaatt tttttcactg    5580
cttctttctt ttccttctga atattctta atgtatatgt tggtctgttt gatgctgtct     5640
caccagtttc ttaggctgtg ttctcttttg ttcctcagac ttgattattg cagttgccct    5700
tcttttatt tttttcaagt ttgttgattc ttctccctgt tcagatcaac tgttgaactc     5760
ctctagtgaa tttatttcag ttactgtact tttcagctcc aagatttatc tttggttcct    5820
ttttataacg tctgtgtctt tattgatatt ctcattttgt tcatatgtct ctttcttcct    5880
ttagttctt gtccatgttt tcctttagct ctttgggctt atttaagaca attgtttaaa     5940
gtctttgcat agtaagtcca atgtctgtgt tcttcaggg atggttttca ttattttgtt    6000
ttcaatgagc catactttcc tgtgtctttg tatgctgtct ttttgttgtt gaaaactgta    6060
tgtttgaaca tcataacgtg gtggccctga aaatcagata ttccccccctt cctgagagtt    6120
agttttattt ttattattga agattgtagc agtctattgc tacatgtgca gtcatttcca    6180
aactattttt gcaaagactg tattccttct gtgtgtcatc actgaagtct ctgttcctta    6240
gtttgtgttt aatagtttga catagatttc cttgaaagga gttaaaacta gcagaaaaat    6300
ctctctccca gtcttccag tctttgtaga ttggttctgt gctgggcttt tccattaata     6360
cttagccagg cttgtactga gcctaacaat caggcccaaa agcgtagggt cttttgcagat   6420
cttgtctgag catgcttctt gctgtgtatg cacgtagttt tctaaatctc cctgtatgtg    6480
ctgttgaata ttctaatttc ccaaagaaac tcctttgcag cttttctca cagaacatag     6540
atggtttttt ggatatcttg accatagtct ttcgacccag tgtttgcgg ttgttagttc     6600
accttacact ttttcaagc attgcctact gcttacgatg agtgctctgt caatccttta    6660
agtagcccca gacaggctac cagagactta acaagaatt tgtaagttct gctcagcttc     6720
ctctagaaat ggggatcagg gtccaagaca gaatgcagtt gctgatttca agactgctgc    6780
aacaccaggg agcttgtggg ggaagggcaa gcagaaatgt cacaaagctt tcttgccatt    6840
ttaaagttgc ctgttcttga ctcagcattt gcttcattgc tataaacttt ttactgtttt    6900
tcagagttct gataaaattg gctatgcctg ttcctgcttt aaaaaatata tatatatttt    6960
ttagggattg gggtctcact atactgacca ggctggtctt gaacttctgg cctcaagcca    7020
```

| | |
|---|---|
| tcctctcatt tcagcttccc aaagtgctgc aattacacgc gtgaaccacc acacccagcc | 7080 |
| cctgcttgtt tttcaatgtg cctactccac catgttgctc aagtatgtat attttctaaa | 7140 |
| ctaccttgta gtgttgtgat gggaaataaa tccctgagcc ttttgaataa ctcagagaga | 7200 |
| tcaaaaactt agtttatcct attcgaagga ttagaaaaat gatatatctt tcactttttc | 7260 |
| agggataggc tcctcattag aaggctccta tgtgccgatg ctgtacaaga catttcattt | 7320 |
| ctcttaatgt ttacaacaag cttgttgcca aggctgatct tgaactcctg gcctcaaacg | 7380 |
| atcctcccag ctcagtctca caaagtgttg ggatgtctgg ccaactaatg actatcttaa | 7440 |
| ctcttgtgtt tcaatgttta tgccttcttt tatcttgact gattgtatga ctatgtcttc | 7500 |
| tagaacaatg ttgaacagaa atggtgagag cagacatcct tgctttaata tttcaccatt | 7560 |
| atatatgatg ttaggtatag attttctca cagatgcctt ttatcagatt gaggaattta | 7620 |
| tattcctact ttgccgaaag gttttgtag tatgaggggg tgctgaattt tgtcaaacac | 7680 |
| tttttcggta ataattgaga tgattggttc tgcagtcatc gagatgtgga ttttctcctt | 7740 |
| tattctgttc gtgagtgatt acactggttg actaatgtta aaacaacctt actttccagg | 7800 |
| aataaaccct attatctttt ttataca | 7827 |

<210> SEQ ID NO 41
<211> LENGTH: 1821
<212> TYPE: DNA
<213> ORGANISM: Homo sapiens

<400> SEQUENCE: 41

| | |
|---|---|
| tgcgggtacg gacagcgcat gagcttatgt tgagggcgga gcccagacca gcccttcgtc | 60 |
| ctatcctgcc cttccagcac ctctcagccg taacttaaac tacacttccc agaagcctcc | 120 |
| tcagccaggg acttccgttg tcgtcagcgg aagcggtgac agatcatccc aggccacaca | 180 |
| gaggccggct tggtcactat ggaggagata ggcatcttgg tggagaaggc tcaggatgag | 240 |
| atcccagcac tgtccgtgtc ccggccccag accggcctgt ccttcctggg ccctgagcct | 300 |
| gaggacctgg aggacctgta cagccgctac aaggaggagg tgaagcgaat ccaaagcatc | 360 |
| ccgctggtca tcggacaatt tctggaggct gtggatcaga atacagccat cgtgggctct | 420 |
| accacaggct ccaactatta tgtgcgcatc ctgagcacca tcgatcggga gctgctcaag | 480 |
| cccaacgcct cagtggccct ccacaagcac agcaatgcac tggtggacgt gctgcccccc | 540 |
| gaagccgaca gcagcatcat gatgctcacc tcagaccaga agccagatgt gatgtacgcg | 600 |
| gacatcggag gcatggacat ccagaagcag gaggtgcggg aggccgtgga gctcccgctc | 660 |
| acgcatttcg agctctacaa gcagatcggc atcgatcccc ccgaggcgt cctcatgtat | 720 |
| ggcccacctg gctgtgggaa gaccatgttg gcaaaggcgg tggcacatca cacaacagct | 780 |
| gcattcatcc gggtcgtggg ctcggagttt gtacagaagt atctgggtga ggccccccgc | 840 |
| atggtccggg atgtgttccg cctggccaag gagaatgcac ctgccatcat cttcatagac | 900 |
| gagattgatg ccatcgccac caagagattc gatgctcaga caggggccga cagggaggtt | 960 |
| cagaggatcc tgctggagct gctgaatcag atggatggat ttgatcagaa tgtcaatgtc | 1020 |
| aaggtaatca tggccacaaa cagagcagac acctgatc cggccctgct acggccagga | 1080 |
| cggctggacc gtaaaattga atttccactt cctgaccgcc gccagaagag attgattttc | 1140 |
| tccactatca ctagcaagat gaacctctct gaggaggttg acttggaaga ctatgtggcc | 1200 |
| cggccagata agatttcagg agctgatatt aactccatct gtcaggagag tggaatgttg | 1260 |

```
gctgtccgtg aaaaccgcta cattgtcctg gccaaggact tcgagaaagc atacaagact      1320
gtcatcaaga aggacgagca ggagcatgag ttttacaagt gacccttccc ttccctccac      1380
cacaccactc aggggctggg gcttctctcg caccccagc acctctgtcc caaaacctca       1440 ttccctttt tctttaccca ggattggttt cttcaataaa tagataagat cgaatccatt       1500
taatttcttc ttagaagttt aactcctttg gagaatgtgg gccttgaata ggatcctctg      1560
ggtccctctt aatctgacag atgagcagac gaggtgcatg gcctgggttg cagcttgaga      1620
gaaccaaaat attcaaacca gatgacttcc aaaatgtggg gaagggatg gaaaatgaac       1680 ctgagatgga gtccttaatc acgggataaa gccctgtgca tctccctcat ttcctacagg      1740
taaaagacag taagaaatt caggtcacag gccttgggag ttcataggaa ggagatgtcc       1800
agtgctgtcc agtagaactt t                                                 1821
```

<210> SEQ ID NO 42
<211> LENGTH: 5159
<212> TYPE: DNA
<213> ORGANISM: Homo sapiens

<400> SEQUENCE: 42

```
ggtcccggaa gtgcgccagt cgtaccttcg cggccgcaac tcgctcggcc gccgccatct       60
tgcgagctcg tcgtactgac cgagcgggga ggctgtcttg aggcggcacc gctcaccgac      120
accgaggcgg actggcagcc ctgagcgtcg cagtcatgcc ggccggaccc gtgcaggcgg      180 tgccccgcc gccgcccgtg cccacggagc ccaaacagcc cacagaagaa gaagcatctt      240
caaaggagga ttctgcacct tctaagccag ttgtgggat tatttaccct cctccagagg       300
tcagaaatat tgttgacaag actgccagct tgtggccag aaacgggcct gaatttgaag       360
ctaggatccg acagaacgag atcaacaacc ccaagttcaa ctttctgaac cccaatgacc      420
cttaccatgc ctactaccgc cacaaggtca gcgagttcaa ggaagggaag gctcaggagc      480
cgtccgccgc catccccaag gtcatgcagc agcagcagca gaccacccag cagcagctgc      540
cccagaaggt ccaagcccaa gtaatccaag agaccatcgt gcccaaagag cctcctcctg      600
agtttgagtt cattgctgat cctccctcta tctcagcctt cgacttggat gtggtgaagc      660
tgacggctca gtttgtggcc aggaatgggc gccagtttct gacccagctg atgcagaaag      720
agcagcgcaa ctaccagttt gactttctcc gcccacagca cagcctcttc aactacttca      780
cgaagctagt ggaacagtac accaagatct tgattccacc caaggtttta ttttcaaagc      840
tcaagaaaga ggctgaaaac ccccgagaag ttttggatca ggtgtgttac cgagtggaat      900
gggccaaatt ccaggaacgt gagaggaaga aggaagaaga ggagaaggag aaggagcggg      960
tggcctatgc tcagatcgac tggcatgatt tgtggtggt ggaaacagtg gacttccaac     1020
ccaatgagca agggaacttc cctccccca ccacgccaga ggagctgggg gcccgaatcc     1080
tcattcagga gcgctatgaa aagtttgggg agagtgagga agttgagatg gaggtcgagt     1140
ctgatgagga ggatgacaaa caggagaagg cggaggagcc tccttcccag ctggaccagg     1200
acacccaagt acaagatatg gatgagggtt cagatgatga agaagaaggg cagaaagtgc     1260
ccccaccccc agagacaccc atgcctccac ctctgccccc aactccagac caagtcattg     1320
tccgcaagga ttatgatccc aaagcctcca gcccttgcc tccagccct gctccagatg      1380 agtatcttgt gtccccccatt actggggaga agatccccgc cagcaaaatg caggaacaca     1440
tgcgcattgg acttcttgac cctcgctggc tggagcagcg ggatcgctcc atccgtgaga     1500
agcagagcga tgatgaggtg tacgcaccag gtctggatat tgagagcagc ttgaagcagt     1560
```

```
tggctgagcg gcgtactgac atcttcggtg tagaggaaac agccattggt aagaagatcg    1620
gtgaggagga gatccagaag ccagaggaaa aggtgacctg ggatggccac tcaggcagca    1680
tggcccggac ccagcaggct gcccaggcca acatcaccct ccaggagcag attgaggcca    1740
ttcacaaggc caaaggcctg gtgccagagg atgacactaa agagaagatt ggccccagca    1800
agcccaatga aatccctcaa cagccaccgc caccatcttc agccaccaac atccccagct    1860
cggctccacc catcacttca gtgccccgac cacccacaat gccacctcca gttcgtacta    1920
cagttgtctc cgcagtaccc gtcatgcccc ggcccccaat ggcatctgtg gtccggctgc    1980
ccccaggctc agtgatcgcc cccatgccgc ccatcatcca cgcgcccaga atcaacgtgg    2040
tgcccatgcc tccctcggcc cctcctatta tggcccccg cccacccccc atgattgtgc     2100
caacagcctt tgtgcctgct ccacctgtgg cacctgtccc agctccagcc caatgccc      2160 ctgtgcatcc cccacctccc atggaagatg agcccacctc caaaaaactg aagacagagg    2220
acagcctcat gccagaggag gagttcctgc gcagaaacaa gggtccagtg tccatcaaag    2280
tccaggtgcc caacatgcag gataagacgg aatggaaact gaatgggcag gtgctggtct    2340
tcaccctccc actcacggac caggtctctg tcattaaggt gaagattcat gaagccacag    2400
gcatgcctgc agggaaacag aagctacagt atgagggtat cttcatcaaa gattccaact    2460
cactggctta ctacaacatg gccaatggcg cagtcatcca cctggccctc aaggagagag    2520
gcgggaggaa gaagtagaca agaggaacct gctgtcaagt ccctgccatt tgcctctcc     2580 tgtctcccac cccctgcccc agacccagga gccccctga ggctttgcct tgcctgcata     2640
tttgtttcgc tcttactcag tttgggaatt caaattgtcc tgcagaggtt cattcccctg    2700
acccttcccc cacattggta agagtagctg ggttttctaa gccactctct ggaatctctt    2760
tgtgttaggg tctcgatttg aggacattca tttcttcagc agcccattag caactgagag    2820
cccagggatg tcctacagga tagtttcata gtgacaggtg gcacttggct aatagaatat    2880
ggctgatatt gtcattaatc attttgtacc ttgacatggg ttgtctaata aaactcggac    2940
ccttcttgtg aaatcagtta aataagactt gtctcggtca cctgtgccct gtccagactc    3000
gaggcagtgg taacactgca cagtgctatg tggcttctct ttgaggattt ttgggttttg    3060
taactaaatt cttgctgccc tcatacttt tatgtattag aatcatattc gtattgccct     3120
tttaaaacat tgggatcctc caaaggcctg ccccatgtat ttaacagtaa tacaggaagc    3180
atggcaggca ccatgcaaac caaggatgga tggtgcagtc cctgtgtcag tgggcggtgg    3240
tttcctgctg gcctggaatc actcatcacc tgattgattg gctctgtggt cctgggcagg    3300
tgcctcatag gtgtgtggat atgatgacgt ttctttaaaa tgtatgtatt taacaaatac    3360
ttaattgtat taaggtcatg taccaaggat ttgataaagt ttaaataatt tactctctac    3420
ttttatccat tttatccatt ttaactcatg taatcctcat gtgagtattc ctgtttaaca    3480
cttgagtaaa ctgaggcaca gagaacataa gttgcatgcc atagtcacac actgtgaaag    3540
tgaaaagaga atgtgtgcaa aacacgtcac agtcctggtt tctgagtaaa ggcaggctgt    3600
tatctttaga atcaagctat cacagggaga taggcaatgc tgtgggtgtt ggaggaaggt    3660
gagagcctgt tgctaacaat ttcctggttt taaagctaag gctgatttta ttgggaagat    3720
ctcacatgtg tgtggcccct gagagttccc agtgcctttt atttgcagtc cttccatttg    3780
gacctcctag ctgccccatc aggtcatctc cagggctcag aggggtgaga ccatttccca    3840
aggtcacaga accagctctc tagtcaccac cctgcctctc cctctcaccc agagtcagta    3900
```

```
ccagttttat ggctttatta caaactgctg ggtccctccc attttcaact tgattgatgg    3960
gatgtcatcc cttatcctgt ctgacatttg cctctggcct ggttgctaga agtttgcccc    4020
aggggcaaga gttgaaattt ggcttcctga ggtgggcttt gtggtttgcg tccctaaagt    4080
gagcccacta ctggttgctt gtccatggcc aacaccagaa atcccctgag cactacctgg    4140
gtctcattcc aagaaggaag agggtcagga gacctgggga gtctcatatt ccaagttctt    4200
ctttctttct gggagcagtg ggcagttcat ggtgttaggg cactcacccc cacagactgg    4260
caaaccctgc aggacttccg tggctgaggc tgtgaccgga ggccaggaat gccgttgggt    4320
ggattgtgag tgaatgggcc ctttgagctg ccctctagag agcaaatcca gtttcctgga    4380
gctcctgaat gaatatctgt actggctcgc tcagatgcag aagctccatt gaccatgagg    4440
ccttgtgaac atcagtggcc acaggcccag tgtgctgctt ggcactgcac tagtttagga    4500
cctgcagcat gtaggtagcg tcctagtgtt tataatacaa agctgctctg cacagctttt    4560
ctgattcttc ttgcaatctc ctgaggatta tctgccccat ttttaaaacg aggtggaata    4620
cccaaggtca tgtagccagt gagtgctctg gaaagcaaaa gcagctcatc ccttcctggg    4680
gaccacactg ctctgctcca ccagaccaca ctatgaaata ggaataagtg ctcctgttgc    4740
aggactgctg ggaaaacagg tggtgtggga cttaagtcac cataattttg aagacttgca    4800
tgcagagggc tccaggaatt gtagacatta aggaatttca ctttcagttc tacccactac    4860
ttaagtactt gtcatgtact cttagaggag gccagtaatg atcagaacca ttttactttA    4920
aaattaataa tattgtatta gagaatatat taaatggtta tattgggtta tgttaggata    4980
tatacttgaa tggaaataca tgtactatta gcaatcatat ttcatttatc cctgtaatta    5040
gacaagaaag cataatatag ctctactcat gggtacacat accagtgtat aagattttta    5100
gaagtttact ttttaaaaat aaaagcaaaa tgtaagatct taaaaaaaaa aaaaaaaa     5159
```

<210> SEQ ID NO 43
<211> LENGTH: 5416
<212> TYPE: DNA
<213> ORGANISM: Homo sapiens

<400> SEQUENCE: 43

```
agtgggccgc catgttgtcg gagtgaaagg taaggggag cgagagcgcc agagagagaa      60
gatcgggggg ctgaaatcca tcttcatcct accgctccgc ccgtgttggt ggaatgagcg    120
ttgcatgtgt cttgaagaga aaagcagtgc tttggcagga ctctttcagc ccccacctga    180
aacatcaccc tcaagaacca gctaatccca acatgcctgt tgttttgaca tctggaacag    240
ggtcgcaagc gcagccacaa ccagctgcaa atcaggctct tgcagctggg actcactcca    300
gccctgtccc aggatctata ggagttgcag gccgttccca ggacgacgct atggtggact    360
acttctttca gaggcagcat ggtgagcagc ttggggagg aggaagtgga ggaggcggct    420
ataataatag caaacatcga tggcctactg gggataacat tcatgcagaa catcaggtgc    480
gttccatgga tgaactgaat catgattttc aagcacttgc tctggaggga agagcgatgg    540
gagagcagct cttgccaggt aaaaagtttt gggaaacaga tgaatccagc aaagatggac    600
caaaaggaat attcctgggt gatcaatggc gagacagtgc ctggggaaca tcagatcatt    660
cagtttccca gccaatcatg gtgcagagaa gacctggtca gagtttccat gtgaacagtg    720
aggtcaattc tgtactgtcc ccacgatcgg agagtggggg actaggcgtt agcatggtgg    780
agtatgtgtt gagctcatcc ccgggcgatt cctgtctaag aaaaggagga tttgccccaa    840
gggatgcaga cagtgatgaa aacgacaaag gtgaaaagaa gaacaagggt acgtttgatg    900
```

-continued

```
gagataagct aggagatttg aaggaggagg gtgatgtgat ggacaagacc aatggtttac    960
cagtgcagaa tgggattgat gcagacgtca aagattttag ccgtacccct ggtaattgcc   1020
agaactctgc taatgaagtg gatcttctgg gtccaaacca gaatggttct gagggcttag   1080
cccagctgac cagcaccaat ggtgccaagc ctgtggagga tttctccaac atggagtccc   1140
agagtgtccc cttggacccc atggaacatg tgggcatgga gcctcttcag tttgattatt   1200
caggcacgca ggtacctgtg gactcagcag cagcaactgt gggacttttt gactacaatt   1260
ctcaacaaca gctgttccaa agacctaatg cgcttgctgt ccagcagttg acagctgctc   1320
agcagcagca gtatgcactg gcagctgctc atcagccgca catcggttta gctcccgctg   1380
cgtttgtccc caatccatac atcatcagcg ctgctccccc agggacggac ccctacacag   1440
ctggattggc tgcagcagcg cactaggcca gctgtgtggt ccctcaccag tattatggag   1500
ttactccctg gggagtctac cctgccagtc ttttccagca gcaagctgcc gctgccgctg   1560
cagcaactaa ttcagctaat caacagacca ccccacaggc tcagcaagga cagcagcagg   1620
ttctccgtgg aggagccagc caacgtcctt tgaccccaaa ccagaaccag cagggacagc   1680
aaacggatcc ccttgtggca gctgcagcag tgaattctgc ccttgcattt ggacaaggtc   1740
tggcagcagg catgccaggt tatccggtgt tggctcctgc tgcttactat gaccaaactg   1800
gtgcccttgt agtgaatgca ggcgcgagaa atggtcttgg agctcctgtt cgacttgtag   1860
ctcctgcccc agtcatcatt agttcctcag ctgcacaagc agctgttgca gcagccgcag   1920
cttcagcaaa tggagcagct ggtggtcttg ctggaacaac aaatggacca tttcgccctt   1980
taggaacaca gcagcctcag ccccagcccc agcagcagcc caataacaac ctggcatcca   2040
gttctttcta cggcaacaac tctctgaaca gcaattcaca gagcagctcc ctcttctccc   2100
agggctctgc ccagcctgcc aacacatcct tgggattcgg aagtagcagt tctctcggcg   2160
ccacctgggg atccgccctt ggagggtttg aacagcagt tgcaaactcc aacactggca   2220
gtggctcccg ccgtgactcc ctgactggca gcagtgacct ttataagagg acatcgagca   2280
gcttgacccc cattggacac agttttata acggccttag cttttcctcc tctcctggac   2340
ccgtgggcat gcctctccct agtcaggac caggacattc acagacacca cctccttccc   2400
tctcttcaca tggatcctct tcaagcttaa acctgggagg actcacgaat ggcagtggaa   2460
gatacatctc tgctgctcca ggcgctgaag ccaagtaccg cagtgcaagc agcgcctcca   2520
gcctcttcag cccgagcagc actcttttct cttcctctcg tttgcgatat ggaatgtctg   2580
atgtcatgcc ttctggcagg agcaggcttt tggaagattt tcgaaacaac cggtaccccca   2640 atttacaact gcgggagatt gctggacata taatggaatt tccaagac cagcatgggt   2700 ccagattcat tcagctgaaa ctggagcgtg ccacaccagc tgagcgccag cttgtcttca   2760
atgaaatcct ccaggctgcc taccaactca tggtggatgt gtttggtaat tacgtcattc   2820
agaagttctt tgaatttggc agtcttgaac agaagctggc tttggcagaa cggattcgag   2880
gccacgtcct gtcattggca ctacagatgt atggctgccg tgttatccag aaagctcttg   2940 agttttattcc ttcagaccag caggtaatta atgagatggt tcgggaacta gatggccatg   3000
tcttgaagtg tgtgaaagat cagaatggca atcacgtggt tcagaaatgc attgaatgtg   3060
tacagcccca gtctttgcaa tttatcatcg atgcgtttaa gggacaggta tttgccttat   3120
ccacacatcc ttatgctgc cgagtgattc agagaatcct ggagcactgt ctccctgacc   3180
agacactccc tattttagag gagcttcacc agcacacaga gcagcttgta caggatcaat   3240
```

```
atggaaatta tgtaatccaa catgtactgg agcacggtcg tcctgaggat aaaagcaaaa    3300
ttgtagcaga atccgaggc aatgtacttg tattgagtca gcacaaattt gcaagcaatg    3360
ttgtggagaa gtgtgttact cacgcctcac gtacggagcg cgctgtgctc atcgatgagg    3420
tgtgcaccat gaacgacggt ccccacagtg ccttatacac catgatgaag gaccagtatg    3480
ccaactacgt ggtccagaag atgattgacg tggcggagcc aggccagcgg aagatcgtca    3540
tgcataagat ccggcccac atcgcaactc ttcgtaagta cacctatggc aagcacattc    3600
tggccaagct ggagaagtac tacatgaaga acggtgttga cttagggccc atctgtggcc    3660
cccctaatgg tatcatctga ggcagtgtca cccgctgttc cctcattccc gctgacctca    3720
ctggcccact ggcaaatcca accagcaacc agaaatgttc tagtgtagag tctgagacgg    3780
gcaagtggtt gctccaggat tactccctcc tccaaaaaag gaatcaaatc cacgagtgga    3840
aaagcctttg taaatttaat tttattacac ataacatgta ctatttttt taattgacta    3900 attgccctgc tgttttactg gtgtatagga tacttgtaca taggtaacca atgtacatgg    3960
gaggccacat attttgttca ctgttgtatc tatatttcac atgtggaaac tttcagggtg    4020
gttggtttaa caaaaaaaaa aagctttaaa aaaaaagaa aaaaaggaaa aggttttag    4080 ctcatttgcc tggccggcaa gttttgcaaa tagctcttcc ccacctcctc attttagtaa    4140
aaaacaaaca aaaacaaaaa aacctgagaa gtttgaattg tagttaaatg accccaaact    4200
ggcatttaac actgttttata aaaatatat atatatatat atatatatat aatgaaaaag    4260
gtttcagagt tgctaaagct tcagtttgtg acattaagtt tatgaaattc taaaaaatgc    4320
cttttttgga gactatatta tgctgaagaa ggctgttcgt gaggaggaga tgcgagcacc    4380
cagaacgtct tttgaggctg ggcgggtgtg attgtttact gcctactgga ttttttcta    4440 ttaacattga aaggtaaaat ctgattattt agcatgagaa aaaaaaatcc aactctgctt    4500
ttggtcttgc ttctataaat atatagtgta tacttggtgt agactttgca tatatacaaa    4560
tttgtagtat tttcttgttt tgatgtctaa tctgtatcta taatgtaccc tagtagtcga    4620
acatactttt gattgtacaa ttgtacattt gtatacctgt aatgtaaatg tggagaagtt    4680
tgaatcaaca taaacacgtt ttttggtaag aaaagagaat tagccagccc tgtgcattca    4740
gtgtatattc tcacctttta tggtcgtagc atatagtgtt gtatattgta aattgtaatt    4800
tcaaccagaa gtaaattttt ttcttttgaa ggaataaatg ttctttatac agcctagtta    4860
atgtttaaaa agaaaaaaat agcttggttt tatttgtcat ctagtctcaa gtatagcgag    4920
attcttccta aatgttattc aagattgagt tctcactagt gttttttaa tcctaaaaaa    4980 gtaatgtttt gattttgtga cagtcaaaag gacgtgcaaa agtctagcct tgcccgagct    5040
ttccttacaa tcagaccccc tctcaccttg taaagtgtga atcgcccttc ccttttgtac    5100
agaagatgaa ctgtattttg cattttgtct acttgtaagt gaatgtaaca tactgtcaat    5160
tttccttgtt tgaatataga attgtaacac tacacggtgt acatttccag agccttgtgt    5220
atatttccaa tgaactttt tgcaagcaca cttgtaacca tatgtgtata attaacaaac    5280
ctgtgtatgc ttatgcctgg gcaactattt tttgtaactc ttgtgtagat tgtctctaaa    5340
caatgtgtga tctttatttt gaaaaataca gaactttgga atctgaaaaa aaaaaaaaa    5400 aaaaaaaaaa aaaaaa                                                    5416
```

<210> SEQ ID NO 44
<211> LENGTH: 1940
<212> TYPE: DNA
<213> ORGANISM: Homo sapiens

<400> SEQUENCE: 44

```
gagtgagcgg cgcggggcca atcagcgtgc gccgttccga aagttgcctt ttatggctcg      60
agcggccgcg gcggcgccct ataaaaccca gcggcgcgac gcgccaccac cgccgagacc     120
gcgtccgccc cgccgagcaca gagcctcgcc tttgccgatc cgccgcccgt ccacacccgc    180
cgccagctca ccatggatga tgatatcgcc gcgctcgtcg tcgacaacgg ctccggcatg     240
tgcaaggccg gcttcgcggg cgacgatgcc ccccgggccg tcttcccctc catcgtgggg     300
cgccccaggc accagggcgt gatggtgggc atgggtcaga aggattccta tgtgggcgac     360
gaggcccaga gcaagagagg catcctcacc ctgaagtacc ccatcgagca cggcatcgtc     420
accaactggg acgacatgga gaaaatctgg caccacacct tctacaatga gctgcgtgtg     480
gctcccgagg agcaccccgt gctgctgacc gaggcccccc tgaacccaa ggccaaccgc      540
gagaagatga cccagatcat gtttgagacc ttcaacaccc cagccatgta cgttgctatc     600
caggctgtgc tatccctgta cgcctctggc cgtaccactg gcatcgtgat ggactccggt     660
gacggggtca cccacactgt gcccatctac gaggggtatg ccctcccca tgccatcctg     720
cgtctggacc tggctggccg ggacctgact gactacctca tgaagatcct caccgagcgc    780
ggctacagct tcaccaccac ggccgagcgg gaaatcgtgc gtgacattaa ggagaagctg     840
tgctacgtcg ccctggactt cgagcaagag atggccacgg ctgcttccag ctcctccctg    900
gagaagagct acgagctgcc tgacggccag gtcatcacca ttggcaatga gcggttccgc     960
tgccctgagg cactcttcca gccttccttc ctgggcatgg agtcctgtgg catccacgaa    1020
actaccttca actccatcat gaagtgtgac gtggacatcc gcaaagacct gtacgccaac    1080
acagtgctgt ctggcggcac caccatgtac cctggcattg ccgacaggat gcagaaggag    1140
atcactgccc tggcacccag cacaatgaag atcaagatca ttgctcctcc tgagcgcaag    1200
tactccgtgt ggatcggcgg ctccatcctg gcctcgctgt ccaccttcca gcagatgtgg    1260
atcagcaagc aggagtatga cgagtccggc ccctccatcg tccaccgcaa atgcttctag    1320
gcggactatg acttagttgc gttacacccct ttcttgacaa aacctaactt gcgcagaaaa    1380
caagatgaga ttggcatggc tttatttgtt tttttttgttt tgttttggtt ttttttttt    1440
ttttggcttg actcaggatt taaaaactgg aacggtgaag gtgacagcag tcggttggag    1500
cgagcatccc ccaaagttca caatgtggcc gaggactttg attgcacatt gttgtttttt    1560
taatagtcat tccaaatatg agatgcgttg ttacaggaag tcccttgcca tcctaaaagc    1620
cacccccactt ctctctaagg agaatggccc agtcctctcc caagtccaca caggggaggt   1680
gatagcattg ctttcgtgta aattatgtaa tgcaaaattt ttttaatctt cgccttaata    1740
cttttttatt ttgtttttatt ttgaatgatg agccttcgtg ccccccttc cccttttt     1800
gtccccccaac ttgagatgta tgaaggcttt tggtctccct gggagtgggt ggaggcagcc   1860
agggcttacc tgtacactga cttgagacca gttgaataaa agtgcacacc ttaaaaatga   1920
ggaaaaaaaa aaaaaaaaaa                                                1940
```

<210> SEQ ID NO 45
<211> LENGTH: 1309
<212> TYPE: DNA
<213> ORGANISM: Homo sapiens

<400> SEQUENCE: 45

```
gctctctgct cctcctgttc gacagtcagc cgcatcttct tttgcgtcgc cagccgagcc      60
```

| | |
|---|---|
| acatcgctca gacaccatgg ggaaggtgaa ggtcggagtc aacggatttg gtcgtattgg | 120 |
| gcgcctggtc accagggctg cttttaactc tggtaaagtg gatattgttg ccatcaatga | 180 |
| ccccttcatt gacctcaact acatggttta catgttccaa tatgattcca cccatggcaa | 240 |
| attccatggc accgtcaagg ctgagaacgg gaagcttgtc atcaatggaa atcccatcac | 300 |
| catcttccag gagcgagatc cctccaaaat caagtggggc gatgctggcg ctgagtacgt | 360 |
| cgtggagtcc actggcgtct tcaccaccat ggagaaggct ggggctcatt tgcaggggga | 420 |
| agccaaaagg gtcatcatct ctgcccctc tgctgatgcc cccatgttcg tcatgggtgt | 480 |
| gaaccatgag aagtatgaca acagcctcaa gatcatcagc aatgcctcct gcaccaccaa | 540 |
| ctgcttagca cccctggcca aggtcatcca tgacaacttt ggtatcgtgg aaggactcat | 600 |
| gaccacagtc catgccatca ctgccaccca aagactgtg gatggcccct ccgggaaact | 660 |
| gtggcgtgat ggccgcgggg ctctccagaa catcatccct gcctctactg cgctgccaa | 720 |
| ggctgtgggc aaggtcatcc ctgagctgaa cgggaagctc actggcatgg ccttccgtgt | 780 |
| ccccactgcc aacgtgtcag tggtggacct gacctgccgt ctagaaaaac ctgccaaata | 840 |
| tgatgacatc aagaaggtgg tgaagcaggc gtcggagggc cccctcaagg gcatcctggg | 900 |
| ctacactgag caccaggtgg tctcctctga cttcaacagc gacacccact cctccacctt | 960 |
| tgacgctggg gctggcattg ccctcaacga ccactttgtc aagctcattt cctggtatga | 1020 |
| caacgaattt ggctacagca cagggtggt ggacctcatg gcccacatgg cctccaagga | 1080 |
| gtaagacccc tggaccacca gccccagcaa gagcacaaga ggaagagaga ccctcact | 1140 |
| gctggggagt ccctgccaca ctcagtcccc caccacactg aatctcccct cctcacagtt | 1200 |
| gccatgtaga ccccttgaag aggggagggg cctagggagc cgcaccttgt catgtaccat | 1260 |
| caataaagta ccctgtgctc aaccagttaa aaaaaaaaaa aaaaaaaaa | 1309 |

<210> SEQ ID NO 46
<211> LENGTH: 2321
<212> TYPE: DNA
<213> ORGANISM: Homo sapiens

<400> SEQUENCE: 46

| | |
|---|---|
| gtcctcaacc aagatggcgc ggatggcttc aggcgcatca cgacaccggc gcgtcacgcg | 60 |
| acccgcccta cgggcacctc ccgcgctttt cttagcgccg cagacggtgg ccgagcgggg | 120 |
| gaccgggaag catggcccgg gggtcggcgg ttgcctgggc ggcgctcggg ccgttgttgt | 180 |
| ggggctgcgc gctggggctg cagggcggga tgctgtaccc ccaggagagc ccgtcgcggg | 240 |
| agtgcaagga gctggacggc ctctggagct ccgcgccga cttctctgac aaccgacgcc | 300 |
| ggggcttcga ggagcagtgg taccggcggc cgctgtggga gtcaggcccc accgtggaca | 360 |
| tgccagttcc ctccagcttc aatgacatca gccaggactg gcgtctgcgg cattttgtcg | 420 |
| gctgggtgtg gtacgaacgg gagtgatcc tgccggagcg atggacccag gacctgcgca | 480 |
| caagagtggt gctgaggatt ggcagtgccc attcctatgc catcgtgtgg gtgaatgggg | 540 |
| tcgacacgct agagcatgag gggggctacc tccccttcga ggccgacatc agcaacctgg | 600 |
| tccaggtggg gccctgccc tccggctccg aatcactat cgccatcaac aacacactca | 660 |
| cccccaccac cctgccacca gggaccatcc aatacctgac tgacacctcc aagtatccca | 720 |
| agggttactt tgtccagaac acatatttg acttttcaa ctacgctgga ctgcagcggt | 780 |
| ctgtacttct gtacacgaca cccaccacct acatcgatga catcaccgtc accaccagcg | 840 |
| tggagcaaga cagtgggctg gtgaattacc agatctctgt caagggcagt aacctgttca | 900 |

```
agttggaagt gcgtcttttg gatgcagaaa acaaagtcgt ggcgaatggg actgggaccc      960
agggccaact taaggtgcca ggtgtcagcc tctggtggcc gtacctgatg cacgaacgcc     1020
ctgcctatct gtattcattg gaggtgcagc tgactgcaca gacgtcactg gggcctgtgt     1080
ctgacttcta cacactccct gtggggatcc gcactgtggc tgtcaccaag agccagttcc     1140
tcatcaatgg gaaacctttc tatttccacg tgtcaacaa gcatgaggat gcggacatcc      1200
gagggaaggg cttcgactgg ccgctgctgg tgaaggactt caacctgctt cgctggcttg     1260
gtgccaacgc tttccgtacc agccactacc cctatgcaga ggaagtgatg cagatgtgtg     1320
accgctatgg gattgtggtc atcgatgagt gtcccggcgt gggcctggcg ctgccgcagt     1380
tcttcaacaa cgtttctctg catcaccaca tgcaggtgat ggaagaagtg gtgcgtaggg     1440
acaagaacca ccccgcggtc gtgatgtggt ctgtggccaa cgagcctgcg tcccacctag     1500
aatctgctgg ctactacttg aagatggtga tcgctcacac caaatccttg gaccccctccc    1560
ggcctgtgac ctttgtgagc aactctaact atgcagcaga caaggggggct ccgtatgtgg    1620
atgtgatctg tttgaacagc tactactctt ggtatcacga ctacgggcac ctggagttga    1680
ttcagctgca gctggccacc cagtttgaga actggtataa gaagtatcag aagcccatta    1740
ttcagagcga gtatggagca gaaacgattg cagggtttca ccaggatcca cctctgatgt    1800
tcactgaaga gtaccagaaa agtctgctag agcagtacca tctgggtctg gatcaaaaac    1860
gcagaaaata cgtggttgga gagctcattt ggaattttgc cgatttcatg actgaacagt    1920
caccgacgag agtgctgggg aataaaaagg ggatcttcac tcggcagaga caaccaaaaa    1980
gtgcagcgtt cctttttgcga gagagatact ggaagattgc caatgaaacc aggtatcccc   2040
actcagtagc caagtcacaa tgtttggaaa acagcctgtt tacttgagca agactgatac    2100
cacctgcgtg tcccttcctc cccgagtcag ggcgacttcc acagcagcag aacaagtgcc    2160
tcctggactg ttcacggcag accagaacgt ttctggcctg ggttttgtgg tcatctattc    2220
tagcagggaa cactaaaggt ggaaataaaa gattttctat tatggaaata agagttggc     2280
atgaaagtgg ctactgaaaa aaaaaaaaaa aaaaaaaaa a                         2321
```

<210> SEQ ID NO 47
<211> LENGTH: 1229
<212> TYPE: DNA
<213> ORGANISM: Homo sapiens

<400> SEQUENCE: 47

```
gtctgacggg cgatggcgca gccaatagac aggagcgcta tccgcggttt ctgattggct      60
actttgttcg cattataaaa ggcacgcgcg ggcgcgaggc ccttctctcg ccaggcgtcc     120
tcgtggaagt gacatcgtct ttaaaccctg cgtggcaatc cctgacgcac cgccgtgatg     180
cccagggaag acagggcgac ctggaagtcc aactacttcc ttaagatcat ccaactattg     240
gatgattatc cgaaatgttt cattgtggga gcagacaatg tgggctccaa gcagatgcag    300
cagatccgca tgtcccttcg cgggaaggct gtggtgctga tgggcaagaa caccatgatg    360
cgcaaggcca tccgagggca cctggaaaac aacccagctc tggagaaact gctgcctcat    420
atccggggga atgtgggctt tgtgttcacc aaggaggacc tcactgagat cagggacatg    480
ttgctggcca ataaggtgcc agctgctgcc cgtgctggtg ccattgcccc atgtgaagtc    540
actgtgccag cccagaacac tggtctcggg cccgagaaga cctcctttttt ccaggcttta   600
ggtatcacca ctaaaatctc caggggcacc attgaaatcc tgagtgatgt gcagctgatc    660
```

| | |
|---|---|
| aagactggag acaaagtggg agccagcgaa gccacgctgc tgaacatgct caacatctcc | 720 |
| cccttctcct ttgggctggt catccagcag gtgttcgaca atggcagcat ctacaaccct | 780 |
| gaagtgcttg atatcacaga ggaaactctg cattctcgct tcctggaggg tgtccgcaat | 840 |
| gttgccagtg tctgtctgca gattggctac ccaactgttg catcagtacc ccattctatc | 900 |
| atcaacgggt acaaacgagt cctggccttg tctgtggaga cggattacac cttcccactt | 960 |
| gctgaaaagg tcaaggcctt cttggctgat ccatctgcct ttgtggctgc tgcccctgtg | 1020 |
| gctgctgcca ccacagctgc tcctgctgct gctgcagccc cagctaaggt tgaagccaag | 1080 |
| gaagagtcgg aggagtcgga cgaggatatg ggatttggtc tctttgacta atcaccaaaa | 1140 |
| agcaaccaac ttagccagtt ttatttgcaa acaaggaaa taaaggctta cttctttaaa | 1200 |
| aagtaaaaaa aaaaaaaaaa aaaaaaaaa | 1229 |

<210> SEQ ID NO 48
<211> LENGTH: 5234
<212> TYPE: DNA
<213> ORGANISM: Homo sapiens

<400> SEQUENCE: 48

| | |
|---|---|
| agagcgtcgg gatatcgggt ggcggctcgg gacggaggac gcgctagtgt gagtgcgggc | 60 |
| ttctagaact acaccgaccc tcgtgtcctc ccttcatcct gcggggctgg ctggagcggc | 120 |
| cgctccggtg ctgtccagca gccatagggg accgcacggg gagcgggaaa gcggtcgcgg | 180 |
| ccccaggcgg ggcggccggg atggagcggg gccgcgagcc tgtggggaag gggctgtggc | 240 |
| ggcgcctcga gcggctgcag gttcttctgt gtggcagttc agaatgatgg atcaagctag | 300 |
| atcagcattc tctaacttgt ttggtggaga accattgtca tatacccggt tcagcctggc | 360 |
| tcggcaagta gatggcgata acagtcatgt ggagatgaaa cttgctgtag atgaagaaga | 420 |
| aaatgctgac aataacacaa aggccaatgt cacaaaacca aaaggtgta gtggaagtat | 480 |
| ctgctatggg actattgctg tgatcgtctt tttcttgatt ggatttatga ttggctactt | 540 |
| gggctattgt aaaggggtag aaccaaaaac tgagtgtgag agactggcag gaaccgagtc | 600 |
| tccagtgagg gaggagccag agaggactt ccctgcagca cgtcgcttat attgggatga | 660 |
| cctgaagaga aagttgtcgg agaaactgga cagcacagac ttcaccggca ccatcaagct | 720 |
| gctgaatgaa aattcatatg tccctcgtga ggctggatct caaaaagatg aaaatcttgc | 780 |
| gttgtatgtt gaaaatcaat tcgtgaatt taaactcagc aaagtctggc gtgatcaaca | 840 |
| ttttgttaag attcaggtca agacagcgc tcaaaactcg gtgatcatag ttgataagaa | 900 |
| cggtagactt gtttacctgg tggagaatcc tgggggttat gtggcgtata gtaaggctgc | 960 |
| aacagttact ggtaaactgg tccatgctaa ttttggtact aaaaaagatt ttgaggattt | 1020 |
| atacactcct gtgaatggat ctatagtgat tgtcagagca gggaaaatca cctttgcaga | 1080 |
| aaaggttgca aatgctgaaa gcttaaatgc aattggtgtg ttgatataca tggaccagac | 1140 |
| taaatttccc attgttaacg cagaactttc attctttgga catgctcatc tggggacagg | 1200 |
| tgacccttac acacctggat tcccttcctt caatcacact cagtttccac catctccggtc | 1260 |
| atcaggattg cctaatatac ctgtccagac aatctccaga gctgctgcag aaaagctgtt | 1320 |
| tgggaatatg aaggagact gtccctctga ctggaaaaca gactctacat gtaggatggt | 1380 |
| aacctcagaa agcaagaatg tgaagctcac tgtgagcaat gtgctgaaag agataaaaat | 1440 |
| tcttaacatc tttggagtta ttaaaggctt tgtagaacca gatcactatg ttgtagttgg | 1500 |
| ggcccagaga gatgcatggg gccctggagc tgcaaaatcc ggtgtaggca cagctctcct | 1560 |

```
attgaaactt gcccagatgt tctcagatat ggtcttaaaa gatgggtttc agcccagcag   1620
aagcattatc tttgccagtt ggagtgctgg agactttgga tcggttggtg ccactgaatg   1680
gctagaggga tacctttcgt ccctgcattt aaaggctttc acttatatta atctggataa   1740
agcggttctt ggtaccagca acttcaaggt ttctgccagc ccactgttgt atacgcttat   1800
tgagaaaaca atgcaaaatg tgaagcatcc ggttactggg caatttctat atcaggacag   1860
caactgggcc agcaaagttg agaaactcac tttagacaat gctgctttcc ctttccttgc   1920
atattctgga atcccagcag tttctttctg ttttgcgag acacagatt atccttattt      1980 gggtaccacc atggacacct ataaggaact gattgagagg attcctgagt tgaacaaagt   2040
ggcacgagca gctgcagagg tcgctggtca gttcgtgatt aaactaaccc atgatgttga   2100
attgaacctg gactatgaga ggtacaacag ccaactgctt tcatttgtga gggatctgaa   2160
ccaatacaga gcagacataa aggaaatggg cctgagttta cagtggctgt attctgctcg   2220
tggagacttc ttccgtgcta cttccagact aacaacagat ttcgggaatg ctgagaaaac   2280
agacagattt gtcatgaaga aactcaatga tcgtgtcatg agagtggagt atcacttcct   2340
ctctccctac gtatctccaa aagagtctcc tttccgacat gtcttctggg gctccggctc   2400
tcacacgctg ccagctttac tggagaactt gaaactgcgt aaacaaaata acggtgcttt   2460
taatgaaacg ctgttcagaa accagttggc tctagctact tggactattc agggagctgc   2520
aaatgccctc tctggtgacg tttgggacat tgacaatgag ttttaaatgt gatacccata   2580
gcttccatga aacagcagg gtagtctggt ttctagactt gtgctgatcg tgctaaattt    2640
tcagtagggc tacaaaacct gatgttaaaa ttccatccca tcatcttggt actactagat   2700
gtctttaggc agcagctttt aatacagggt agataacctg tacttcaagt taaagtgaat   2760
aaccacttaa aaaatgtcca tgatggaata ttcccctatc tctagaattt taagtgcttt   2820
gtaatgggaa ctgcctcttt cctgttgttg ttaatgaaaa tgtcagaaac cagttatgtg   2880
aatgatctct ctgaatccta agggctggtc tctgctgaag gttgtaagtg gtcgcttact   2940
ttgagtgatc ctccaacttc atttgatgct aaatagagag ataccaggttg aaagaccttc   3000 tccaaatgag atctaagcct ttccataagg aatgtagctg gtttcctcat tcctgaaaga   3060
aacagttaac tttcagaaga gatgggcttg ttttcttgcc aatgaggtct gaaatggagg   3120
tccttctgct ggataaaatg aggttcaact gttgattgca ggaataaggc cttaatatgt   3180
taacctcagt gtcatttatg aaaagagggg accagaagcc aaagacttag tatattttct   3240
tttcctctgt cccttccccc ataagcctcc atttagttct tgttatttt tgtttcttcc     3300 aaagcacatt gaaagagaac cagtttcagg tgtttagttg cagactcagt ttgtcagact   3360
ttaaagaata atatgctgcc aaattttggc caaagtgtta atcttagggg agagcttcct   3420
gtccttttgg cactgagata tttattgttt atttatcagt gacagagttc actataaatg   3480
gtgttttttt aatagaatat aattatcgga agcagtgcct tccataatta tgacagttat   3540
actgtcggtt ttttttaaat aaaagcagca tctgctaata aaacccaaca gatactggaa   3600
gttttgcatt tatggtcaac acttaagggt tttagaaaac agccgtcagc caaatgtaat   3660
tgaataaagt tgaagctaag attagagat gaattaaatt taattagggg ttgctaagaa    3720
gcgagcactg accagataag aatgctggtt ttcctaaatg cagtgaattg tgaccaagtt   3780
ataaatcaat gtcacttaaa ggctgtggta gtactcctgc aaaatttat agctcagttt     3840 atccaaggtg taactctaat tcccattttg caaaatttcc agtaccttg tcacaatcct     3900
```

| aacacattat cgggagcagt gtcttccata atgtataaag aacaaggtag ttttttaccta | 3960 |
| ccacagtgtc tgtatcggag acagtgatct ccatatgtta cactaagggt gtaagtaatt | 4020 |
| atcgggaaca gtgtttccca taattttctt catgcaatga catcttcaaa gcttgaagat | 4080 |
| cgttagtatc taacatgtat cccaactcct ataattccct atcttttagt tttagttgca | 4140 |
| gaaacatttt gtggtcatta agcattgggt gggtaaattc aaccactgta aaatgaaatt | 4200 |
| actacaaaat ttgaaattta gcttgggttt tgttaccttt tatggtttct ccaggtcctc | 4260 |
| tacttaatga gatagtagca tacatttata atgtttgcta ttgacaagtc attttaactt | 4320 |
| tatcacatta tttgcatgtt acctcctata aacttagtgc ggacaagttt taatccagaa | 4380 |
| ttgacctttt gacttaaagc agagggactt tgtatagaag gtttgggggc tgtggggaag | 4440 |
| gagagtcccc tgaaggtctg acacgtctgc ctacccattc gtggtgatca attaaatgta | 4500 |
| ggtatgaata agttcgaagc tccgtgagtg aaccatcatt ataaacgtga tgatcagctg | 4560 |
| tttgtcatag ggcagttgga aacggcctcc tagggaaaag ttcatagggt ctcttcaggt | 4620 |
| tcttagtgtc acttacctag atttacagcc tcacttgaat gtgtcactac tcacagtctc | 4680 |
| tttaatcttc agttttatct ttaatctcct cttttatctt ggactgacat ttagcgtagc | 4740 |
| taagtgaaaa ggtcatagct gagattcctg gttcgggtgt tacgcacacg tacttaaatg | 4800 |
| aaagcatgtg gcatgttcat cgtataacac aatatgaata cagggcatgc attttgcagc | 4860 |
| agtgagtctc ttcagaaaac ccttttctac agttagggtt gagttacttc ctatcaagcc | 4920 |
| agtacgtgct aacaggctca atattcctga tgaaatatc agactagtga caagctcctg | 4980 |
| gtcttgagat gtcttctcgt taaggagatg ggccttttgg aggtaaagga taaaatgaat | 5040 |
| gagttctgtc atgattcact attctagaac ttgcatgacc tttactgtgt tagctctttg | 5100 |
| aatgttcttg aaattttaga ctttctttgt aaacaaatga tatgtcctta tcattgtata | 5160 |
| aaagctgtta tgtgcaacag tgtggagatt ccttgtctga tttaataaaa tacttaaaca | 5220 |
| ctgaaaaaaa aaaa | 5234 |

<210> SEQ ID NO 49
<211> LENGTH: 1869
<212> TYPE: DNA
<213> ORGANISM: Homo sapiens

<400> SEQUENCE: 49

| tacctggttg atcctgccag tagcatatgc ttgtctcaaa gattaagcca tgcatgtcta | 60 |
| agtacgcacg gccggtacag tgaaactgcg aatggctcat taaatcagtt atggttcctt | 120 |
| tggtcgctcg ctcctctccc acttggataa ctgtggtaat tctagagcta atacatgccg | 180 |
| acgggcgctg accccttcg cggggggat gcgtgcattt atcagatcaa aaccaacccg | 240 |
| gtcagcccct ctccggcccc ggccgggggg cgggcgccgg cggctttggt gactctagat | 300 |
| aacctcgggc cgatcgcacg ccccccgtgg cggcgacgac ccattcgaac gtctgcccta | 360 |
| tcaactttcg atggtagtcg ccgtgcctac catggtgacc acgggtgacg gggaatcagg | 420 |
| gttcgattcc ggagagggag cctgagaaac ggctaccaca tccaaggaag gcagcaggcg | 480 |
| cgcaaattac ccactcccga cccggggagg tagtgacgaa aataacaat acaggactct | 540 |
| ttcgaggccc tgtaattgga atgagtccac tttaaatcct ttaacgagga tccattggag | 600 |
| ggcaagtctg gtgccagcag ccgcggtaat tccagctcca atagcgtata ttaaagttgc | 660 |
| tgcagttaaa aagctcgtag ttggatcttg ggagcgggcg gcggtccgc cgcgaggcga | 720 |
| gccaccgccc gtccccgccc cttgcctctc ggcgccccct cgatgctctt agctgagtgt | 780 |

```
cccgcgggc  ccgaagcgtt  tactttgaaa  aaattagagt  gttcaaagca  ggcccgagcc    840
gcctggatac  cgcagctagg  aataatggaa  taggaccgcg  gttctatttt  gttggttttc    900
ggaactgagg  ccatgattaa  gagggacggc  cgggggcatt  cgtattgcgc  cgctagaggt    960
gaaattcttg  gaccggcgca  agacggacca  gagcgaaagc  atttgccaag  aatgttttca   1020
ttaatcaaga  acgaaagtcg  gaggttcgaa  gacgatcaga  taccgtcgta  gttccgacca   1080
taaacgatgc  cgaccggcga  tgcggcggcg  ttattcccat  gacccgccgg  gcagcttccg   1140
ggaaaccaaa  gtctttgggt  tccgggggga  gtatggttgc  aaagctgaaa  cttaaaggaa   1200 ttgacgaag  ggcaccacca  ggagtggagc  ctgcggctta  atttgactca  acacgggaaa   1260
cctcacccgg  cccggacacg  acaggattg  acagattgat  agctctttct  cgattccgtg   1320
ggtggtggtg  catggccgtt  cttagttggt  ggagcgattt  gtctggttaa  ttccgataac   1380
gaacgagact  ctggcatgct  aactagttac  gcgaccccg  agcggtcggc  gtccccaac    1440 ttcttagagg  gacaagtggc  gttcagccac  ccgagattga  gcaataacag  gtctgtgatg   1500
cccttagatg  tccggggctg  cacgcgcgct  acactgactg  gctcagcgtg  tgcctaccct   1560
acgccggcag  gcgcgggtaa  cccgttgaac  cccattcgtg  atgggggatcg  gggattgcaa   1620 ttattcccca  tgaacgagga  attcccagta  agtgcgggtc  ataagcttgc  gttgattaag   1680
tccctgccct  ttgtacacac  cgcccgtcgc  tactaccgat  tggatggttt  agtgaggccc   1740
tcggatcggc  cccgccgggg  tcggcccacg  gccctggcgg  agcgctgaga  agacggtcga   1800
acttgactat  ctagaggaag  taaaagtcgt  aacaaggttt  ccgtaggtga  acctgcggaa   1860
ggatcatta                                                               1869

<210> SEQ ID NO 50
<211> LENGTH: 2288
<212> TYPE: DNA
<213> ORGANISM: Homo sapiens

<400> SEQUENCE: 50
ggggccgaac  gtggtataaa  aggggcggga  ggccaggctc  gtgccgtttt  gcagacgcca    60
ccgccgagga  aaaccgtgta  ctattagcca  tggtcaaccc  caccgtgttc  ttcgacattg   120
ccgtcgacgg  cgagcccttg  ggccgcgtct  cctttgagct  gtttgcagac  aaggtcccaa   180
agacagcaga  aaattttcgt  gctctgagca  ctggagagaa  aggatttggt  tataaggggtt   240 cctgctttca  cagaattatt  ccagggttta  tgtgtcaggg  tggtgacttc  acacgccata   300
atggcactgg  tggcaagtcc  atctatgggg  agaaatttga  agatgagaac  ttcatcctaa   360
agcatacggg  tcctggcatc  ttgtccatgg  caaatgctgg  acccaacaca  aatggttccc   420 agttttcat  ctgcactgcc  aagactgagt  ggttggatgg  caagcatgtg  gtgtttggca   480
aagtgaaaga  aggcatgaat  attgtggagg  ccatggagcg  ctttgggtcc  aggaatggca   540
agaccagcaa  gaagatcacc  attgctgact  gtggacaact  cgaataagtt  tgacttgtgt   600
tttatcttaa  ccaccagatc  attccttctg  tagctcagga  gcacccct  ccaccccatt   660 tgctcgcagt  atcctagaat  ctttgtgctc  tcgctgcagt  tccctttggg  ttccatgttt   720
tccttgttcc  ctcccatgcc  tagctggatt  gcagagttaa  gttatgatt  atgaaataaa   780 aactaaataa  caattgtcct  cgtttgagtt  aagagtgttg  atgtaggctt  tattttaagc   840
agtaatgggt  tacttctgaa  acatcacttg  tttgcttaat  tctacacagt  acttagattt   900
tttttacttt  ccagtcccag  gaagtgtcaa  tgtttgttga  gtggaatatt  gaaaatgtag   960
```

```
gcagcaactg ggcatggtgg ctcactgtct gtaatgtatt acctgaggca gaagaccacc      1020
tgagggtagg agtcaagatc agcctgggca acatagtgag acgctgtctc tacaaaaaat      1080
aattagcctg gcctggtggt gcatgcctag tcctagctga tctggaggct gacgtgggag      1140
gattgcttga gcctagagtg agctattatc atgccactgt acagcctggg tgttcacaga      1200
tcttgtgtct caaaggtagg cagaggcagg aaaagcaagg agccagaatt aagaggttgg      1260
gtcagtctgc agtgagttca tgcatttaga ggtgttcttc aagatgacta atgtcaaaaa      1320
ttgagacatc tgttgcggtt tttttttttt tttttccccc tggaatgcag tggcgtgatc      1380
tcagctcact gcagcctccg cctcctgggt tcaagtgatt ctagtgcctc agcctcctga      1440
gtagctggga taatgggcgt gtgccaccat gcccagctaa ttttttgtatt tttagtatag      1500 atggggtttc atcattttga ccaggctggt ctcaaactct tgacctcagc tgatgcgcct      1560
gccttggcct cccaaactgc tgagattaca gatgtgagcc accgcaccct acctcatttt      1620
ctgtaacaaa gctaagcttg aacactgttg atgttcttga gggaagcata ttgggcttta      1680
ggctgtaggt caagtttata catcttaatt atggtggaat tccatatgtag agtctaaaaa      1740 gccaggtact tggtgctaca gtcagtctcc ctgcagaggg ttaaggcgca gactacctgc      1800
agtgaggagg tactgcttgt agcatataga gcctctccct agctttggtt atggaggctt      1860
tgaggttttg caaacctgac caatttaagc cataagatct ggtcaaaggg atacccttcc      1920
cactaaggac ttggtttctc aggaaattat atgtacagtg cttgctggca gttagatgtc      1980
aggacaatct aagctgagaa aaccccttct ctgcccacct taacagacct ctagggttct      2040
taacccagca atcaagtttg cctatcctag aggtggcgga tttgatcatt tggtgtgttg      2100
ggcaattttt gttttactgt ctggttcctt ctgcgtgaat taccaccacc accacttgtg      2160
catctcagtc ttgtgtgttg tctggttacg tattccctgg gtgataccat tcaatgtctt      2220
aatgtacttg tggctcagac ctgagtgcaa ggtggaaata aacatcaaac atcttttcat      2280
tatccccta                                                              2288

<210> SEQ ID NO 51
<211> LENGTH: 2439
<212> TYPE: DNA
<213> ORGANISM: Homo sapiens

<400> SEQUENCE: 51
gagagcagcg gccgggaagg ggcggtgcgg gaggcggggt gtggggcggt agtgtgggcc        60
ctgttcctgc ccgcgcggtg ttccgcattc tgcaagcctc cggagcgcac gtcggcagtc       120
ggctccctcg ttgaccgaat caccgacctc tctccccagc tgtatttcca aaatgtcgct       180
ttctaacaag ctgacgctgg acaagctgga cgttaaaggg aagcgggtcg ttatgagagt       240
cgacttcaat gttcctatga agaacaacca gataacaaac aaccagagga ttaaggctgc       300
tgtcccaagc atcaaattct gcttggacaa tggagccaag tcggtagtcc ttatgagcca       360
cctaggccgg cctgatggtg tgcccatgcc tgacaagtac tccttagagc cagttgctgt       420
agaactcaaa tctctgctgg gcaaggatgt tctgttcttg aaggactgtg taggcccaga       480
agtggagaaa gcctgtgcca acccagctgc tgggtctgtc atcctgctgg agaacctccg       540 cttttcatgtg gaggaagaag ggaagggaaa agatgcttct gggaacaagg ttaaagccga       600
gccagccaaa atagaagctt tccgagcttc actttccaag ctaggggatg tctatgtcaa       660
tgatgctttt ggcactgctc acagagccca cagctccatg gtaggagtca atctgccaca       720
gaaggctggt gggttttttga tgaagaagga gctgaactac tttgcaaagg ccttggagag       780
```

```
cccagagcga ccccttcctgg ccatcctggg cggagctaaa gttgcagaca agatccagct    840
catcaataat atgctggaca aagtcaatga gatgattatt ggtggtggaa tggcttttac    900
cttccttaag gtgctcaaca acatggagat tggcacttct ctgtttgatg aagagggagc    960
caagattgtc aaagacctaa tgtccaaagc tgagaagaat ggtgtgaaga ttaccttgcc   1020
tgttgacttt gtcactgctg acaagtttga tgagaatgcc aagactggcc aagccactgt   1080
ggcttctggc atacctgctg ctggatgggc cttggactgt ggtcctgaaa gcagcaagaa   1140
gtatgctgag gctgtcactc gggctaagca gattgtgtgg aatggtcctg tgggggtatt   1200
tgaatgggaa gcttttgccc ggggaaccaa agctctcatg gatgaggtgg tgaaagccac   1260
ttctaggggc tgcatcacca tcataggtgg tggagacact gccacttgct gtgccaaatg   1320
gaacacggag gataaagtca gccatgtgag cactgggggt ggtgccagtt tggagctcct   1380
ggaaggtaaa gtccttcctg gggtggatgc tctcagcaat atttagtact ttcctgcctt   1440
ttagttcctg tgcacagccc ctaagtcaac ttagcatttt ctgcatctcc acttggcatt   1500
agctaaaacc ttccatgtca agattcagct agtggccaag agatgcagtg ccaggaaccc   1560
ttaaacagtt gcacagcatc tcagctcatc ttcactgcac cctggatttg catacattct   1620
tcaagatccc atttgaattt tttagtgact aaaccattgt gcattctaga gtgcatatat   1680
ttatattttg cctgttaaaa agaaagtgag cagtgttagc ttagttctct tttgatgtag   1740
gttattatga ttagctttgt cactgtttca ctactcagca tggaaacaag atgaaattcc   1800
atttgtaggt agtgagacaa aattgatgat ccattaagta aacaataaaa gtgtccattg   1860
aaaccgtgat tttttttttt ttcctgtcat actttgttag gaagggtgag aatagaatct   1920
tgaggaacgg atcagatgtc tatattgctg aatgcaagaa gtggggcagc agcagtggag   1980
agatgggaca attagataaa tgtccattct ttatcaaggg cctactttat ggcagacatt   2040
gtgctagtgc ttttattcta acttttattt ttatcagtta cacatgatca aatttaaaa    2100
agtcaaggct tataacaaaa aagccccagc ccattcctcc cattcaagat tcccactccc   2160
cagaggtgac cactttcaac tcttgagttt tcaggtata tacctccatg tttctaagta    2220
atatgcttat attgttcact tcttttttttt ttatttttta aagaaatcta tttcatacca   2280
tggaggaagg ctctgttcca catatatttc cacttcttca ttctctcggt atagttttgt   2340
cacaattata gattagatca aaagtctaca taactaatac agctgagcta tgtagtatgc   2400
tatgattaaa tttacttatg taaaaaaaaa aaaaaaaa                           2439

<210> SEQ ID NO 52
<211> LENGTH: 1196
<212> TYPE: DNA
<213> ORGANISM: Homo sapiens

<400> SEQUENCE: 52
cacttctgcc gcccctgttt caagggataa gaaaccctgc gacaaaacct cctcctttc      60
caagcggctg ccgaagatgg cggaggtgca ggtcctggtg cttgatggtc gaggccatct    120
cctgggccgc ctggcggcca tcgtggctaa acaggtactg ctgggccgga aggtggtggt    180
cgtacgctgt gaaggcatca acatttctgg caatttctac agaaacaagt tgaagtacct    240
ggctttcctc cgcaagcgga tgaacaccaa ccccttcccga ggcccctacc acttccgggc    300
ccccagccga atcttctggc ggaccgtgcg aggtatgctg cccacacaaaa ccaagcgagg    360
ccaggccgct ctggaccgtc tcaaggtgtt tgacggcatc ccaccgccct acgacaagaa    420
```

| aaagcggatg gtggttcctg ctgccctcaa ggtcgtgcgt ctgaagccta caagaaagtt | 480 |
| tgcctatctg gggcgcctgg ctcacgaggt tggctggaag taccaggcag tgacagccac | 540 |
| cctggaggag aagaggaaag agaaagccaa gatccactac cggaagaaga aacagctcat | 600 |
| gaggctacgg aaacaggccg agaagaacgt ggagaagaaa attgacaaat acacagaggt | 660 |
| cctcaagacc cacggactcc tggtctgagc ccaataaaga ctgttaattc ctcatgcgtt | 720 |
| gcctgccctt cctccattgt tgccctgaa tgtacgggac ccaggggcag cagcagtcca | 780 |
| ggtgccacag gcagccctgg gacataggaa gctgggagca aggaaagggt cttagtcact | 840 |
| gcctcccgaa gttgcttgaa agcactcgga gaattgtgca ggtgtcattt atctatgacc | 900 |
| aataggaaga gcaaccagtt actatgagtg aagggagcc agaagactga ttggagggcc | 960 |
| ctatcttgtg agtggggcat ctgttggact ttccacctgg tcatatactc tgcagctgtt | 1020 |
| agaatgtgca agcacttggg gacagcatga gcttgctgtt gtacacaggg tatttctaga | 1080 |
| agcagaaata gactgggaag atgcacaacc aaggggttac aggcatcgcc catgctcctc | 1140 |
| acctgtattt tgtaatcaga aataaattgc ttttaaagaa aaaaaaaaa aaaaaa | 1196 |

<210> SEQ ID NO 53
<211> LENGTH: 987
<212> TYPE: DNA
<213> ORGANISM: Homo sapiens

<400> SEQUENCE: 53

| aatataagtg gaggcgtcgc gctggcgggc attcctgaag ctgacagcat tcgggccgag | 60 |
| atgtctcgct ccgtggcctt agctgtgctc gcgctactct ctctttctgg cctggaggct | 120 |
| atccagcgta ctccaaagat tcaggtttac tcacgtcatc cagcagagaa tggaaagtca | 180 |
| aatttcctga attgctatgt gtctgggttt catccatccg acattgaagt tgacttactg | 240 |
| aagaatggag agagaattga aaaagtggag cattcagact tgtctttcag caaggactgg | 300 |
| tctttctatc tcttgtacta cactgaattc accccccactg aaaaagatga gtatgcctgc | 360 |
| cgtgtgaacc atgtgacttt gtcacagccc aagatagtta agtgggatcg agacatgtaa | 420 |
| gcagcatcat ggaggtttga agatgccgca tttggattgg atgaattcca aattctgctt | 480 |
| gcttgctttt taatattgat atgcttatac acttacactt tatgcacaaa atgtagggtt | 540 |
| ataataatgt taacatggac atgatcttct ttataattct actttgagtg ctgtctccat | 600 |
| gtttgatgta tctgagcagg ttgctccaca ggtagctcta ggagggctgg caacttagag | 660 |
| gtggggagca gagaattctc ttatccaaca tcaacatctt ggtcagattt gaactcttca | 720 |
| atctcttgca ctcaaagctt gttaagatag ttaagcgtgc ataagttaac ttccaattta | 780 |
| catactctgc ttagaatttg ggggaaaatt tagaaatata attgacagga ttattggaaa | 840 |
| tttgttataa tgaatgaaac attttgtcat ataagattca tatttacttc ttatacattt | 900 |
| gataaagtaa ggcatggttg tggttaatct ggtttatttt tgttccacaa gttaaataaa | 960 |
| tcataaaact tgatgtgtta tctctta | 987 |

<210> SEQ ID NO 54
<211> LENGTH: 3003
<212> TYPE: DNA
<213> ORGANISM: Homo sapiens

<400> SEQUENCE: 54

| ctttctcctt cccctctctc cgggctcccg tcccggctca tcaccggcc tgtggcccac | 60 |
| tcccaccgcc agctggaacc ctggggacta cgacgtccct caaaccttgc ttctaggaga | 120 |

| | |
|---|---|
| taaaaagaac atccagtcat ggataaaaat gagctggttc agaaggccaa actggccgag | 180 |
| caggctgagc gatatgatga catggcagcc tgcatgaagt ctgtaactga gcaaggagct | 240 |
| gaattatcca atgaggagag gaatcttctc tcagttgctt ataaaatgt tgtaggagcc | 300 |
| cgtaggtcat cttggagggt cgtctcaagt attgaacaaa agacgaagg tgctgagaaa | 360 |
| aaacagcaga tggctcgaga atacagagag aaaattgaga cggagctaag agatatctgc | 420 |
| aatgatgtac tgtctctttt ggaaaagttc ttgatcccca atgcttcaca agcagagagc | 480 |
| aaagtcttct atttgaaaat gaaggagat tactaccgtt acttggctga ggttgccgct | 540 |
| ggtgatgaca agaaagggat tgtcgatcag tcacaacaag cataccaaga agcttttgaa | 600 |
| atcagcaaaa aggaaatgca accaacacat cctatcagac tgggtctggc ccttaacttc | 660 |
| tctgtgttct attatgagat tctgaactcc ccagagaaag cctgctctct tgcaaagaca | 720 |
| gcttttgatg aagccattgc tgaacttgat acattaagtg aagagtcata caaagacagc | 780 |
| acgctaataa tgcaattact gagagacaac ttgacattgt ggacatcgga tacccaagga | 840 |
| gacgaagctg aagcaggaga aggaggggaa aattaaccgg ccttccaact tttgtctgcc | 900 |
| tcattctaaa atttacacag tagaccattt gtcatccatg ctgtcccaca aatagttttt | 960 |
| tgtttacgat ttatgacagg tttatgttac ttctatttga atttctatat ttcccatgtg | 1020 |
| gtttttatgt ttaatattag gggagtagag ccagttaaca tttagggagt tatctgtttt | 1080 |
| catcttgagg tggccaatat ggggatgtgg aattttata caagttataa gtgtttggca | 1140 |
| tagtactttt ggtacattgt ggcttcaaaa gggccagtgt aaaactgctt ccatgtctaa | 1200 |
| gcaaagaaaa ctgcctacat actggtttgt cctggcgggg aataaaaggg atcattggtt | 1260 |
| ccagtcacag gtgtagtaat tgtgggtact ttaaggtttg gagcacttac aaggctgtgg | 1320 |
| tagaatcata ccccatggat accacatatt aaaccatgta tatctgtgga atactcaatg | 1380 |
| tgtacacctt tgactacagc tgcagaagtg ttcctttaga caaagttgtg acccatttta | 1440 |
| ctctggataa gggcagaaac ggttcacatt ccattatttg taaagttacc tgctgttagc | 1500 |
| tttcattatt tttgctacac tcatttatt tgtatttaaa tgtttaggc aacctaagaa | 1560 |
| caaatgtaaa agtaaagatg caggaaaaat gaattgcttg gtattcatta cttcatgtat | 1620 |
| atcaagcaca gcagtaaaac aaaaacccat gtatttaact tttttttagg attttttgctt | 1680 |
| ttgtgatttt tttttttttg atacttgcct aacatgcatg tgctgtaaaa atagttaaca | 1740 |
| gggaaataac ttgagatgat ggctagcttt gtttaatgtc ttatgaaatt ttcatgaaca | 1800 |
| atccaagcat aattgttaag aacacgtgta ttaaattcat gtaagtggaa taaaagtttt | 1860 |
| atgaatggac ttttcaacta ctttctctac agcttttcat gtaaattagt cttggttctg | 1920 |
| aaacttctct aaaggaaatt gtacattttt tgaaatttat tccttattcc ctcttggcag | 1980 |
| ctaatgggct cttaccaagt ttaaacacaa aatttatcat aacaaaaata ctactaatat | 2040 |
| aactactgtt tccatgtccc atgatcccct ctcttcctcc ccaccctgaa aaaatgagt | 2100 |
| tcctattttt tctgggagag ggggggattg attagaaaaa aatgtagtgt gttccattta | 2160 |
| aaattttggc atatggcatt ttctaactta ggaagccaca atgttcttgg cccatcatga | 2220 |
| cattgggtag cattaactgt aagttttgtg cttccaaatc acttttggt ttttaagaat | 2280 |
| ttcttgatac tcttatagcc tgccttcaat tttgatcctt tattctttct atttgtcagg | 2340 |
| tgcacaagat taccttcctg ttttagcctt ctgtcttgtc accaaccatt cttacttggt | 2400 |
| ggccatgtac ttggaaaaag gccgcatgat ctttctggct ccactcagtg tctaaggcac | 2460 |

| | |
|---|---:|
| cctgcttcct ttgcttgcat cccacagact atttccctca tcctatttac tgcagcaaat | 2520 |
| ctctccttag ttgatgagac tgtgtttatc tccctttaaa accctaccta tcctgaatgg | 2580 |
| tctgtcattg tctgccttta aaatccttcc tctttcttcc ccctctattc tctaaataat | 2640 |
| gatggggcta agttataccc aaagctcact ttacaaaata tttcctcagt actttgcaga | 2700 |
| aaacaccaaa caaaaatgcc attttaaaaa aggtgtattt tttcttttag aatgtaagct | 2760 |
| cctcaagagc agggacaatg ttttctgtat gttctattgt gcctagtaca ctgtaaatgc | 2820 |
| tcaataaata ttgatgatgg gaggcagtga gtcttgatga taagggtgag aaactgaaat | 2880 |
| cccaaacact gttttgttgc ttgttttatt atgacctcag attaaattgg gaaatattgg | 2940 |
| ccctttttgaa taattgtccc aaatattaca ttcaaataaa agtgcaatgg agaaaaaaaa | 3000 |
| aaa | 3003 |

<210> SEQ ID NO 55
<211> LENGTH: 2803
<212> TYPE: DNA
<213> ORGANISM: Homo sapiens

<400> SEQUENCE: 55

| | |
|---|---:|
| actgcagccc cgctcgactc cggcgtggtg cgcaggcgcg gtatcccccc tcccccgcca | 60 |
| gctcgacccc ggtgtggtgc gcaggcgcag tctgcgcagg gactggcggg actgcgcggc | 120 |
| ggcaacagca gacatgtcgg gggtccgggg cctgtcgcgg ctgctgagcg ctcggcgcct | 180 |
| ggcgctggcc aaggcgtggc caacagtgtt gcaaacagga acccgaggtt ttcacttcac | 240 |
| tgttgatggg aacaagaggg catctgctaa agtttcagat tccatttctg ctcagtatcc | 300 |
| agtagtggat catgaatttg atgcagtggt ggtaggcgct ggaggggcag gcttgcgagc | 360 |
| tgcatttggc ctttctgagg cagggtttaa tacagcatgt gttaccaagc tgtttcctac | 420 |
| caggtcacac actgttgcag cacagggagg aatcaatgct gctctgggga acatggagga | 480 |
| ggacaactgg aggtggcatt ctacgacac cgtgaagggc tccgactggc tgggggacca | 540 |
| ggatgccatc cactacatga cggagcaggc ccccgccgcc gtggtcgagc tagaaaatta | 600 |
| tggcatgccg tttagcagaa ctgaagatgg gaagatttat cagcgtgcat ttggtggaca | 660 |
| gagcctcaag tttggaaagg cgggcaggc ccatcggtgc tgctgtgtgg ctgatcggac | 720 |
| tggccactcg ctattgcaca ccttatatgg aaggtctctg cgatatgata ccagctattt | 780 |
| tgtggagtat tttgccttgg atctcctgat ggagaatggg gagtgccgtg gtgtcatcgc | 840 |
| actgtgcata gaggacgggt ccatccatcg cataagagca aagaacactg ttgttgccac | 900 |
| aggaggctac gggcgcacct acttcagctg cacgtctgcc cacaccagca ctggcgacgg | 960 |
| cacggccatg atcaccaggg caggccttcc ttgccaggac ctagagtttg ttcagttcca | 1020 |
| ccctacaggc atatatggtg ctggttgtct cattacggaa ggatgtcgtg gagagggagg | 1080 |
| cattctcatt aacagtcaag gcgaaaggtt tatggagcga tacgcccctg tcgcgaagga | 1140 |
| cctggcgtct agagatgtgg tgtctcggtc catgactctg gagatccgag aaggaagagg | 1200 |
| ctgtggccct gagaaagatc acgtctacct gcagctgcac cacctacctc cagagcagct | 1260 |
| ggccacgcgc ctgcctggca tttcagagac agccatgatc ttcgctggcg tggacgtcac | 1320 |
| gaaggagccg atccctgtcc tccccaccgt gcattataac atgggcggca ttcccaccaa | 1380 |
| ctacaagggg caggtcctga ggcacgtgaa tggccaggat cagattgtgc ccggcctgta | 1440 |
| cgcctgtggg gaggccgcct gtgcctcggt acatggtgcc aaccgcctcg gggcaaactc | 1500 |
| gctcttggac ctggttgtct ttggtcgggc atgtgccctg agcatcgaag agtcatgcag | 1560 |

```
gcctggagat aaagtccctc caattaaacc aaacgctggg gaagaatctg tcatgaatct      1620
tgacaaattg agatttgctg atggaagcat aagaacatcg gaactgcgac tcagcatgca      1680
gaagtcaatg caaaatcatg ctgccgtgtt ccgtgtggga agcgtgttgc aagaaggttg      1740
tgggaaaatc agcaagctct atggagacct aaagcacctg aagacgttcg accggggaat      1800
ggtctggaac acggacctgg tggagaccct ggagctgcag aacctgatgc tgtgtgcgct      1860
gcagaccatc tacggagcag aggcacggaa ggagtcacgg ggcgcgcatg ccagggaaga      1920
ctacaaggtg cggattgatg agtacgatta ctccaagccc atccaggggc aacagaagaa      1980 gcccttgag gagcactgga ggaagcacac cctgtcctat gtggacgttg gcactgggaa       2040
ggtcactctg gaatatagac ccgtgatcga caaaactttg aacgaggctg actgtgccac      2100
cgtcccgcca gccattcgct cctactgatg agacaagatg tggtgatgac agaatcagct      2160
tttgtaatta tgtataatag ctcatgcatg tgtccatgtc ataactgtct tcatacgctt      2220
ctgcactctg gggaagaagg agtacattga agggagattg gcacctagtg gctgggagct      2280
tgccaggaac ccagtggcca gggagcgtgg cacttacctt tgtcccttgc ttcattcttg      2340
tgagatgata aaactgggca cagctcttaa ataaaatata aatgaacaaa ctttcttta      2400 tttccaaatc catttgaaat attttactgt tgtgacttta gtcatatttg ttgacctaaa      2460
aatcaaatgt aatctttgta ttgtgttaca tcaaaatcca gatattttgt atagtttctt      2520 ttttctttt ctttctttt ttttttttga gacaggatcg gtgcagtagt acaatcacag        2580
ctcactgcag cctcaaactc ctgggcagct caggtgatct tcctgactca gccttctgag      2640
tagttggggc tacaggtgtg caccaccatg cccagctcat ttattttgta attgtaggga      2700
cagggtctca ctgtgttgcc taggctggtc tcaagtgatc ctccctcctt ggcctcccaa      2760
ggtgctggaa ttataggtgt gaacaaacca aaaaaaaaa aaa                         2803

<210> SEQ ID NO 56
<211> LENGTH: 1435
<212> TYPE: DNA
<213> ORGANISM: Homo sapiens

<400> SEQUENCE: 56
ggcggggcct gcttctcctc agcttcaggc ggctgcgacg agccctcagg cgaacctctc        60
ggctttcccg cgcggcgccg cctcttgctg cgcctccgcc tcctcctctg ctccgccacc       120
ggcttcctcc tcctgagcag tcagcccgcg cgccggccgg ctccgttatg gcgacccgca       180
gccctggcgt cgtgattagt gatgatgaac caggttatga ccttgattta ttttgcatac       240
ctaatcatta tgctgaggat ttggaagggg tgtttattcc tcatggacta attatggaca       300
ggactgaacg tcttgctcga gatgtgatga aggagatggg aggccatcac attgtagccc       360
tctgtgtgct caaggggggc tataaattct ttgctgacct gctggattac atcaaagcac       420
tgaatagaaa tagtgataga tccattccta tgactgtaga ttttatcaga ctgaagagct       480
attgtaatga ccagtcaaca ggggacataa agtaattgg tggagatgat ctctcaactt        540 taactgaaa gaatgtcttg attgtggaag atataattga cactggcaaa acaatgcaga       600
ctttgctttc cttggtcagg cagtataatc aaagatggt caaggtcgca agcttgctgg        660
tgaaaaggac cccacgaagt gttggatata agccagactt tgttggattt gaaattccag       720
acaagtttgt tgtaggatat gcccttgact ataatgaata cttcagggat ttgaatcatg       780
tttgtgtcat tagtgaaact ggaaaagcaa aatacaaagc ctaagatgag agttcaagtt       840
```

```
gagtttggaa acatctggag tcctattgac atcgccagta aaattatcaa tgttctagtt    900
ctgtggccat ctgcttagta gagcttttg catgtatctt ctaagaattt tatctgtttt     960
gtactttaga aatgtcagtt gctgcattcc taaactgttt atttgcacta tgagcctata   1020
gactatcagt tcccttggg cggattgttg tttaacttgt aaatgaaaaa attctcttaa    1080
accacagcac tattgagtga aacattgaac tcatatctgt aagaaataaa gagaagatat   1140 attagtttt taattggtat tttaattttt atatatgcag gaaagaatag aagtgattga    1200
atattgttaa ttataccacc gtgtgttaga aaagtaagaa gcagtcaatt ttcacatcaa   1260
agacagcatc taagaagttt tgttctgtcc tggaattatt ttagtagtgt ttcagtaatg   1320
ttgactgtat tttccaactt gttcaaatta ttaccagtga atctttgtca gcagttccct   1380
tttaaatgca aatcaataaa ttcccaaaaa tttaaaaaaa aaaaaaaaaa aaaaa        1435
```